US012735418B2

(12) United States Patent
Baba et al.

(10) Patent No.: US 12,735,418 B2
(45) Date of Patent: Sep. 15, 2026

(54) CONDENSED RING COMPOUNDS THAT INHIBIT H-PGDS

(71) Applicant: SATO PHARMACEUTICAL CO., LTD., Tokyo (JP)

(72) Inventors: Motoaki Baba, Tokyo (JP); Takuma Okui, Tokyo (JP); Yoshiki Itoh, Tokyo (JP)

(73) Assignee: SATO PHARMACEUTICAL CO., LTD., Tokyo (JP)

( * ) Notice: Subject to any disclaimer, the term of this patent is extended or adjusted under 35 U.S.C. 154(b) by 541 days.

(21) Appl. No.: 18/002,232

(22) PCT Filed: Jun. 18, 2021

(86) PCT No.: PCT/JP2021/023271

§ 371 (c)(1),
(2) Date: Dec. 16, 2022

(87) PCT Pub. No.: WO2021/256569

PCT Pub. Date: Dec. 23, 2021

(65) Prior Publication Data

US 2023/0339937 A1 Oct. 26, 2023

(30) Foreign Application Priority Data

Jun. 19, 2020 (JP) ................................ 2020-106254

(51) Int. Cl.

| | |
|---|---|
| *C07D 471/04* | (2006.01) |
| *C07D 491/048* | (2006.01) |
| *C07D 495/04* | (2006.01) |

(52) U.S. Cl.

CPC ....... *C07D 471/04* (2013.01); *C07D 491/048* (2013.01); *C07D 495/04* (2013.01)

(58) Field of Classification Search

CPC . C07D 495/04; C07D 471/04; C07D 491/048

See application file for complete search history.

(56) References Cited

U.S. PATENT DOCUMENTS

| | | | | |
|---|---|---|---|---|
| 8,865,714 | B2 * | 10/2014 | Urade | A61P 9/10 514/254.01 |
| 2009/0281098 | A1 | 11/2009 | Urade et al. | |
| 2011/0319413 | A1 | 12/2011 | Urade et al. | |
| 2012/0309760 | A1 | 12/2012 | Urade et al. | |
| 2013/0165438 | A1 | 6/2013 | Urade et al. | |
| 2014/0128394 | A1 | 5/2014 | Urade et al. | |
| 2021/0161908 | A1 * | 6/2021 | Inada | A61K 31/5377 |
| 2025/0074906 | A1 * | 3/2025 | Baba | A61P 9/10 |

FOREIGN PATENT DOCUMENTS

| | | | |
|---|---|---|---|
| JP | 2007-051121 | A | 3/2007 |
| JP | 2013-014520 | A | 1/2013 |
| WO | 2005/094805 | A1 | 10/2005 |
| WO | 2007/007778 | A1 | 1/2007 |
| WO | 2007/041634 | A1 | 4/2007 |
| WO | 2008/075172 | A2 | 6/2008 |
| WO | 2008/104869 | A1 | 9/2008 |
| WO | 2008/121670 | A1 | 10/2008 |
| WO | 2009/153720 | A1 | 12/2009 |
| WO | 2009/153721 | A1 | 12/2009 |

(Continued)

OTHER PUBLICATIONS

Nagalla, "The Efficacy Of Prostaglandin Synthase Inhibition On Attenuating Pressure Overload Induced Cardiac Remodeling" Electronic Theses and Dissertations 724, University of Mississippi, pp. 1-92, downloaded from egrove.olemiss.edu/etd (Year: 2014).*

Rittchen et al., "Therapeutic Potential of Hematopoietic Prostaglandin D2 Synthase in Allergic Inflammation" Cells vol. 8 p. 619, doi: 10.3390/cells8060619 (Year: 2019).*

Mutius et al., "Primary prevention of asthma: from risk and protective factors to targeted strategies for prevention" The Lancet vol. 396 pp. 854-866, DOI:10.1016/S0140-6736(20)31861-4 (Year: 2020).*

Zhang et al., "Myoediting: Toward Prevention of Muscular Dystrophy by Therapeutic Genome Editing" Physiol Rev vol. 98 pp. 1205-1240, doi:10.1152/physrev.00046.2017 (Year: 2018).*

(Continued)

*Primary Examiner* — Andrea Olson

(74) *Attorney, Agent, or Firm* — Studebaker Brackett PLLC

(57) ABSTRACT

The present invention provides a compound having a hematopoietic prostaglandin D synthase (H-PGDS) inhibitory activity and being useful for preventing or treating a disease involving the enzyme, and a pharmaceutical composition comprising the compound. Specifically, the present invention provides a compound represented by Formula (I) below or a pharmaceutically acceptable salt thereof:

(I)

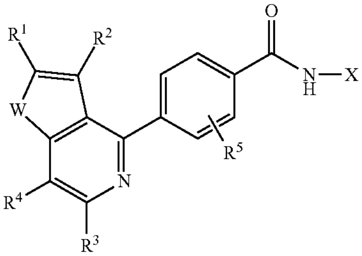

[wherein $R^1$ represents a hydrogen atom and the like, $R^2$ represents a hydrogen atom and the like, $R^3$ represents a hydrogen atom and the like, $R^4$ represents a hydrogen atom and the like, $R^5$ represents a hydrogen atom and the like, W represents an oxygen atom and the like, and X represents a $C_{1-6}$ alkyl group and the like.]

28 Claims, No Drawings

(56) References Cited

FOREIGN PATENT DOCUMENTS

| | | | | |
|---|---|---|---|---|
| WO | 2010/033977 A2 | | 3/2010 | |
| WO | 2010/104024 A1 | | 9/2010 | |
| WO | 2011/044307 A1 | | 4/2011 | |
| WO | WO-2011052628 A1 | * | 5/2011 | ........... A61K 31/702 |
| WO | 2011/090062 A1 | | 7/2011 | |
| WO | 2011/150457 A2 | | 12/2011 | |
| WO | 2012/033069 A1 | | 3/2012 | |
| WO | 2017/103851 A1 | | 6/2017 | |
| WO | 2017/209272 A1 | | 12/2017 | |
| WO | 2018/069863 A1 | | 4/2018 | |
| WO | 2018/229629 A1 | | 12/2018 | |
| WO | 2019/116256 A1 | | 6/2019 | |
| WO | 2019/203296 A1 | | 10/2019 | |
| WO | 2020/095215 A1 | | 5/2020 | |

OTHER PUBLICATIONS

Alpizar-Rodriguez et al., "Is the prevention of rheumatoid arthritis possible?" Clinical Rheumatology vol. 39 pp. 1383-1389, DOI:10.1007/s10067-020-04927-6 (Year: 2020).*

Caldwell et al., "Prospects for the Primary Preventionof Myocardial Infarction and Stroke" Journal of Cardiovascular Pharmacology and Therapeutics vol. 24 No. 3 pp. 207-214, DOI: 10.1177/1074248418817344 (Year: 2019).*

Marks et al., "Prevention of asthma during the first 5 years of life: A randomized controlled trial" J Allergy Clin Immunol vol. 118 pp. 53-61, doi:10.1016/j.jaci.2006.04.004 (Year: 2006).*

Mohri et al., "Inhibition of Prostaglandin D Synthase Suppresses Muscular Necrosis" The American Journal of Pathology vol. 174 No. 5 pp. 1735-1744, DOI:10.2353/ajpath.2009.080709 (Year: 2009).*

Velica et al., "Prostaglandin D2 inhibits C2C12 Myogenesis" Molecular and Cellular Endocrinology vol. 309 pp. 71-78, DOI:10.1016/j.mce.2010.023 (Year: 2010).*

Redensek et al., "Expression and Detrimental Role of Hematopoietic Prostaglandin D Synthase in Spinal Cord Contusion Injury" Glia vol. 59 pp. 603-614, DOI:10.1002/glia.21128 (Year: 2011).*

Nabe et al., "Inhibition of hematopoietic prostaglandin D synthase improves allergic nasal blockage in guinea pigs" Prostaglandins and other lipid mediators vol. 95 pp. 27-34, DOI:10.1018/j.prostaglandins.2011.05.001 (Year: 2011).*

Okinaga et al., "Induction of hematopoietic prostaglandin D synthase in hyalinated necrotic muscle fibers: its implication in grouped necrosis" Acta Neuropathol, vol. 104 pp. 377-384, DOI:10.1007/s00401-002-0567-z (Year: 2002).*

Folia Pharmacol Jpn vol. 123 pp. 5-13 (Year: 2004).*

Kamani et al., "Role of Prostaglandin D2 for delayed wound healing in Sterptozotocin-induced diabetic mice" (3rd Annual Meeting of the Japanese Pharmacological Society, Session ID:93_3P-339 (Year: 2020).*

International Preliminary Report On Patentability (Chapter I) and Written Opinion of the International Searching Authority issued in PCT/JP2021/023271; issued Dec. 13, 2022.

John I. Trujillo et al.; "Investigation of the Binding Pocket of Human Hematopoietic Prostaglandin (PG) D2 Synthase (hH-PGDS): A Tale of Two Waters"; Bioorganic & Medicinal Chemistry Letters; vol. 22; Elsevier Ltd.; Apr. 13, 2012; pp. 3795-3799.

Angelika N. Christ et al.; "Development and Characterization of New Inhibitors of the Human and Mouse Hematopoietic Prostaglandin D2 Synthases"; Journal of Medicinal Chemistry Article; vol. 53, No. 15; American Chemical Society; Jul. 20, 2010; pp. 5536-5548.

Kirk L. Olson et al.; "Novel Amide and Imidazole Compounds as Potent Hematopoietic Prostaglandin D2 Synthase Inhibitors"; Bioorganic & Medicinal Chemistry Letters; vol. 34, 127759; Elsevier Ltd.; Dec. 29, 2020; pp. 1-6.

International Search Report issued in PCT/JP2021/023271; mailed Aug. 3, 2021.

* cited by examiner

CONDENSED RING COMPOUNDS THAT INHIBIT H-PGDS

TECHNICAL FIELD

The present invention relates to a condensed ring compound that inhibits H-PGDS and is useful in the pharmaceutical field. Specifically, the present invention relates to a condensed ring compound having a hematopoietic prostaglandin D synthase inhibitory activity and being useful for preventing or treating a disease involving the enzyme, a pharmaceutical composition comprising the compound, and an inhibitor of the enzyme.

BACKGROUND ART

Prostaglandin D synthase is an enzyme that converts prostaglandin $H_2$, which is a common intermediate of various prostaglandins, into prostaglandin $D_2$.

Among prostaglandin D synthases, hematopoietic prostaglandin D synthase (hematopoetic PGD synthase, H-PGDS) distributed in mast cells, Th2 lymphocytes and the like is known to be involved in various diseases (for example, allergic diseases, inflammatory diseases, neuromuscular related diseases, and ischemic diseases) via the production of prostaglandin $D_2$.

Therefore, attempts have been made to develop pharmaceutical compounds that treat the various diseases by inhibiting H-PGDS (Patent Literatures 1 to 23 and Non-Patent Literatures 1 to 3).

CITATION LIST

Patent Literature

Patent Literature 1: WO 2019/203296
Patent Literature 2: JP 2013-14520 A
Patent Literature 3: WO 2012/033069
Patent Literature 4: WO 2011/090062
Patent Literature 5: WO 2010/104024
Patent Literature 6: WO 2007/007778
Patent Literature 7: JP 2007-51121 A
Patent Literature 8: WO 2020/095215
Patent Literature 9: WO 2019/116256
Patent Literature 10: WO 2018/229629
Patent Literature 11: WO 2018/069863
Patent Literature 12: WO 2017/103851
Patent Literature 13: WO 2011/044307
Patent Literature 14: WO 2008/121670
Patent Literature 15: WO 2007/041634
Patent Literature 16: WO 2011/150457
Patent Literature 17: WO 2010/033977
Patent Literature 18: WO 2009/153721
Patent Literature 19: WO 2009/153720
Patent Literature 20: WO 2008/104869
Patent Literature 21: WO 2008/075172
Patent Literature 22: WO 2005/094805
Patent Literature 23: WO 2017/209272

Non Patent Literature

Non Patent Literature 1: Bioorg. Med. Chem. Lett. 2012, 22, 3795-3799
Non Patent Literature 2: J. Med. Chem. 2010, 53, 5536-5548
Non Patent Literature 3: Bioorg. Med. Chem. Lett. 2021, 34, 127759

SUMMARY OF INVENTION

Technical Problem

An object of the present invention is to provide a novel condensed ring compound having an excellent H-PGDS inhibitory activity and being useful for treating and preventing a disease involving H-PGDS.

Solution to Problem

In order to solve the above problem, the present inventors have extensively synthesized and studied novel compounds, and as a result, have found that a condensed ring compound represented by Formula (I) below has excellent H-PGDS inhibitory activity, and have completed the present invention.

Therefore, the present invention relates to a compound represented by Formula (I):

(I)

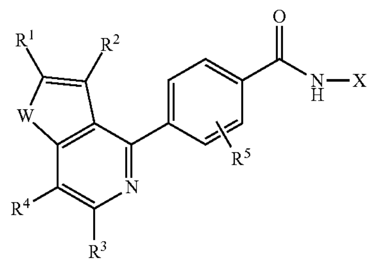

[wherein $R^1$ represents a hydrogen atom, a halogen atom, or a $C_{1-6}$ alkyl group;

$R^2$ represents a hydrogen atom, a halogen atom, a cyano group, a hydroxy group, a carbamoyl group, a $C_{1-6}$ alkyl group, a halo $C_{1-6}$ alkyl group, a hydroxy $C_{1-6}$ alkyl group, or a $C_{1-6}$ alkoxy group;

$R^3$ represents a hydrogen atom, a halogen atom, a cyano group, a hydroxy group, an amino group, a carbamoyl group, a sulfamoyl group, a carboxy group, a Chi-6 alkyl group, a $C_{2-6}$ alkenyl group, a halo $C_{1-6}$ alkyl group, a hydroxy $C_{1-6}$ alkyl group, a $C_{2-7}$ alkanoyl group, a $C_{1-6}$ alkylsulfonyl group, a $C_{1-6}$ alkoxy group, a halo $C_{1-6}$ alkoxy group, a $C_{1-6}$ alkylsulfonyloxy group, a halo $C_{1-6}$ alkylsulfonyloxy group, a mono $C_{1-6}$ alkylamino group, a di $C_{1-6}$ alkylamino group, a mono $C_{2-7}$ alkanoylamino group, a ($C_{2-7}$ alkanoyl) $C_{1-6}$ alkylamino group, a di $C_{2-7}$ alkanoylamino group, a mono $C_{1-6}$ alkylsulfonylamino group, a mono $C_{1-6}$ alkylcarbamoyl group, a di $C_{1-6}$ alkylcarbamoyl group, a mono $C_{1-6}$ alkylsulfamoyl group, a di $C_{1-6}$ alkylsulfamoyl group, a $C_{3-6}$ cycloalkyl group, a cyclic ether group, a cyclic amino group, or a halo cyclic amino group;

$R^4$ represents a hydrogen atom, a halogen atom, a cyano group, a hydroxy group, an amino group, a carbamoyl group, a sulfamoyl group, a carboxy group, a $C_{1-6}$ alkyl group, a $C_{2-6}$ alkenyl group, a halo $C_{1-6}$ alkyl group, a hydroxy $C_{1-6}$ alkyl group, a $C_{1-6}$ alkoxy group, a halo $C_{1-6}$ alkoxy group, a mono $C_{1-6}$ alkylamino group, or a di $C_{1-6}$ alkylamino group;

$R^5$ represents a hydrogen atom, a halogen atom, a cyano group, a hydroxy group, a $C_{1-6}$ alkyl group, a halo $C_{1-6}$ alkyl group, or a hydroxy $C_{1-6}$ alkyl group;

W represents an oxygen atom, a sulfur atom, or a group represented by General Formula: —N($R^6$)—;

$R^6$ represents a hydrogen atom or a $C_{1-6}$ alkyl group; and

X represents a $C_{1-6}$ alkyl group, a $C_{2-6}$ alkenyl group, a halo $C_{1-6}$ alkyl group, a hydroxy $C_{1-6}$ alkyl group, a ($C_{1-6}$ alkoxy) $C_{1-6}$ alkyl group, a (halo $C_{1-6}$ alkoxy) $C_{1-6}$ alkyl group, an amino $C_{1-6}$ alkyl group, a (mono $C_{1-6}$ alkylamino) $C_{1-6}$ alkyl group, a (di $C_{1-6}$ alkylamino) $C_{1-6}$ alkyl group, a carbamoyl $C_{1-6}$ alkyl group, a (mono $C_{1-6}$ alkylcarbamoyl) $C_{1-6}$ alkyl group, a (di $C_{1-6}$ alkylcarbamoyl) $C_{1-6}$ alkyl group, a sulfamoyl $C_{1-6}$ alkyl group, a (mono $C_{1-6}$ alkylsulfamoyl) $C_{1-6}$ alkyl group, a (di $C_{1-6}$ alkylsulfamoyl) $C_{1-6}$ alkyl group, or a group represented by General Formula (II):

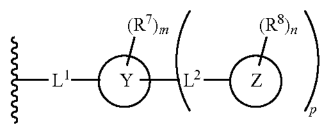

(wherein the wavy line represents the point of attachment to the nitrogen atom, $L^1$ represents a single bond, a $C_{1-6}$ alkanediyl group, or a hydroxy $C_{1-6}$ alkanediyl group;

ring Y represents a $C_{6-10}$ aryl group, a heteroaryl group, a $C_{3-10}$ cycloalkyl group, or a 4- to 10-membered heterocyclyl group (wherein the $C_{3-10}$ cycloalkyl group and the 4- to 10-membered heterocyclyl group are optionally condensed with a benzene ring or a heteroaryl ring to form a condensed ring group, or optionally form a bicyclo ring group or a spiro ring group);

each $R^7$ independently represents a halogen atom, a cyano group, a hydroxy group, a sulfanyl group, an amino group, a carbamoyl group, a sulfamoyl group, a carboxy group, a formyl group, an imino group, an azide group, a hydrazino group, a nitro group, a $C_{1-6}$ alkyl group, a $C_{2-6}$ alkenyl group, a halo $C_{1-6}$ alkyl group, a hydroxy $C_{1-6}$ alkyl group, a ($C_{1-6}$ alkoxy) $C_{1-6}$ alkyl group, a $C_{2-7}$ alkanoyl group, a $C_{1-6}$ alkylsulfonyl group, a $C_{1-6}$ alkoxy group, a halo $C_{1-6}$ alkoxy group, a hydroxy $C_{1-6}$ alkoxy group, a $C_{1-6}$ alkylthio group, a mono $C_{1-6}$ alkylamino group, a di $C_{1-6}$ alkylamino group, a mono (halo $C_{1-6}$ alkyl)amino group, a $C_{2-7}$ alkoxycarbonyl group, a mono $C_{1-6}$ alkylcarbamoyl group, a di $C_{1-6}$ alkylcarbamoyl group, a $C_{1-6}$ alkylsulfonyloxy group, a halo $C_{1-6}$ alkylsulfonyloxy group, a mono $C_{1-6}$ alkylsulfamoyl group, a di $C_{1-6}$ alkylsulfamoyl group, a mono $C_{2-7}$ alkanoylamino group, a ($C_{2-7}$ alkanoyl) $C_{1-6}$ alkylamino group, a di $C_{2-7}$ alkanoylamino group, a mono $C_{1-6}$ alkylsulfonylamino group, a mono ($C_{2-7}$ alkoxycarbonyl)amino group, a $C_{3-6}$ cycloalkyl group, a cyclic ether group, a cyclic amino group, a halo cyclic amino group, or an oxo group;

$L^2$ represents a single bond, a $C_{1-6}$ alkanediyl group, a hydroxy $C_{1-6}$ alkanediyl group, a carbonyl group, or a sulfonyl group;

ring Z represents a phenyl group, a heteroaryl group, or a 4- to 10-membered heterocyclyl group (the 4- to 10-membered heterocyclyl group is optionally condensed with a benzene ring or a heteroaryl ring to form a condensed ring group, or optionally forms a bicyclo ring group or a spiro ring group);

each $R^8$ independently represents a halogen atom, a cyano group, a hydroxy group, a sulfanyl group, an amino group, a carbamoyl group, a sulfamoyl group, a carboxy group, a $C_{1-6}$ alkyl group, a $C_{2-6}$ alkenyl group, a halo $C_{1-6}$ alkyl group, a hydroxy $C_{1-6}$ alkyl group, a ($C_{1-6}$ alkoxy) $C_{1-6}$ alkyl group, a $C_{2-7}$ alkanoyl group, a $C_{1-6}$ alkylsulfonyl group, a $C_{1-6}$ alkoxy group, a halo $C_{1-6}$ alkoxy group, a mono $C_{1-6}$ alkylamino group, a di $C_{1-6}$ alkylamino group, a $C_{2-7}$ alkoxycarbonyl group, a mono $C_{1-6}$ alkylcarbamoyl group, a di $C_{1-6}$ alkylcarbamoyl group, a $C_{1-6}$ alkylsulfonyloxy group, a halo $C_{1-6}$ alkylsulfonyloxy group, a mono $C_{1-6}$ alkylsulfamoyl group, a di $C_{1-6}$ alkylsulfamoyl group, a mono $C_{2-7}$ alkanoylamino group, a ($C_{2-7}$ alkanoyl) $C_{1-6}$ alkylamino group, a di $C_{2-7}$ alkanoylamino group, a mono $C_{1-6}$ alkylsulfonylamino group, a mono ($C_{2-7}$ alkoxycarbonyl)amino group, a $C_{3-6}$ cycloalkyl group, a cyclic ether group, a cyclic amino group, a halo cyclic amino group, or an oxo group;

m represents 0, 1, 2, or 3;

n represents 0, 1, or 2; and p represents 0 or 1.)]

or a pharmaceutically acceptable salt thereof (hereinafter, also referred to as "compound of the present invention").

Further, the compound of the present invention also includes a compound represented by Formula (I) in which $R^7$ is an oxetanylamino group, a hydroxyhalo $C_{1-6}$ alkyl group, a halo $C_{2-7}$ alkanoyl group, a hydroxy $C_{2-7}$ alkanoyl group, a hydroxy $C_{3-6}$ cycloalkyl group, a (hydroxy $C_{3-6}$ cycloalkyl) $C_{1-6}$ alkoxy group, or a $C_{3-6}$ cycloalkylcarbonyl group, and $R^8$ is a morpholinocarbonyl group.

Further, the present invention relates to a pharmaceutical composition comprising the compound of the present invention, particularly a pharmaceutical composition for use in the treatment or prevention of a disease involving H-PGDS.

Further, the present invention relates to an H-PGDS inhibitor comprising the compound of the present invention.

Advantageous Effects of Invention

The compound of the present invention has excellent H-PGDS inhibitory activity as shown in Examples described later, and thus is useful as a therapeutic agent or a preventive agent for a disease involving H-PGDS.

DESCRIPTION OF EMBODIMENTS

Hereinafter, the definitions of the terms used to specify the compound of the present invention will be described.

Examples of the "halogen atom" in Formula (I) (Formula (II) and Formula (III) in Formula (I) are included. The same applies hereinafter.) include a fluorine atom, a chlorine atom, a bromine atom, and an iodine atom.

The "$C_{1-6}$ alkyl group" in Formula (I) means a linear or branched alkyl group having 1 to 6 carbon atoms, and examples thereof include a methyl group, an ethyl group, a propyl group, an isopropyl group, a butyl group, an isobutyl group, a sec-butyl group, a tert-butyl group, a pentyl group, an isopentyl group, a neopentyl group, a 1,1-dimethylpropyl group, a 1-methylbutyl group, a 2-methylbutyl group, a 1,2-dimethylpropyl group, a 1-ethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, and a 1,2,2-trimethylpropyl group.

The "halo $C_{1-6}$ alkyl group" in Formula (I) means the "$C_{1-6}$ alkyl group" in which any substitutable positions are substituted with 1 or 2 or more, preferably 1 to 5, same or different "halogen atoms" above, and examples thereof include a fluoromethyl group, a difluoromethyl group, a trifluoromethyl group, a 2-fluoroethyl group, a 1,2-difluoroethyl group, a 2,2,2-trifluoroethyl group, a 2,2,3,3,3-pentafluoropropyl group, a chloromethyl group, a 2-chloroethyl group, a 1,2-dichloroethyl group, a bromomethyl group, and an iodomethyl group.

The "hydroxy $C_{1-6}$ alkyl group" in Formula (I) means the "$C_{1-6}$ alkyl group" in which any substitutable positions are substituted with 1 or 2 or more, preferably 1 or 2 hydroxy groups, and examples thereof include a hydroxymethyl group, a 1-hydroxyethyl group, a 1-hydroxypropyl group, a 2-hydroxyethyl group, a 2-hydroxypropyl group, a 2-hydroxy-1-methylethyl group, a 1-hydroxy-1-methylethyl group, a 1,2-dihydroxyethyl group, and a 3-hydroxypropyl group.

The "hydroxyhalo $C_{1-6}$ alkyl group" in Formula (I) means the "halo $C_{1-6}$ alkyl group" in which any substitutable positions are substituted with 1 or 2 or more, preferably 1 or 2 hydroxy groups, and examples thereof include a 2,2,2-trifluoro-1-hydroxyethyl group and a 2-hydroxy-1,1-difluoroethyl group.

The "$C_{1-6}$ alkoxy group" in Formula (I) means a group in which a hydrogen atom of a hydroxy group is substituted with the "$C_{1-6}$ alkyl group", and examples thereof include a methoxy group, an ethoxy group, a propoxy group, an isopropoxy group, a butoxy group, a sec-butoxy group, a tert-butoxy group, a pentyloxy group, an isopentyloxy group, a hexyloxy group, and an isohexyloxy group.

The "$C_{2-6}$ alkenyl group" in Formula (I) means a linear or branched alkenyl group having 2 to 6 carbon atoms, and examples thereof include a vinyl group, a 1-propenyl group, an allyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group, and a 4-pentenyl group.

The "$C_{2-7}$ alkanoyl group" in Formula (I) means a group in which the "$C_{1-6}$ alkyl group" and a carbonyl group are bonded, that is, an alkanoyl group having 2 to 7 carbon atoms, and examples thereof include an acetyl group, a propanoyl group, a butanoyl group, a 2-methylpropanoyl group, a pentanoyl group, a 3-methylbutanoyl group, and a 2,2-dimethylpropanoyl group.

The "halo $C_{2-7}$ alkanoyl group" in Formula (I) means the "$C_{2-7}$ alkanoyl group" in which any substitutable positions are substituted with 1 or 2 or more, preferably 1 to 5, same or different "halogen atoms" above, and examples thereof include a 3,3,3-trifluoropropanoyl group.

The "hydroxy $C_{2-7}$ alkanoyl group" in Formula (I) means the "$C_{2-7}$ alkanoyl group" in which any substitutable positions are substituted with 1 or 2 or more, preferably 1 or 2 hydroxy groups, and examples thereof include a 2-hydroxy-2-methylpropanoyl group.

The "$C_{1-6}$ alkylsulfonyl group" in Formula (I) means a group in which the "$C_{1-6}$ alkyl group" and a sulfonyl group are bonded, and examples thereof include a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group, and an isohexylsulfonyl group.

The "halo $C_{1-6}$ alkoxy group" in Formula (I) means a group in which a hydrogen atom of a hydroxy group is substituted with the "halo $C_{1-6}$ alkyl group", and examples thereof include a fluoromethoxy group, a difluoromethoxy group, a trifluoromethoxy group, a 2-fluoroethoxy group, a 1,2-difluoroethoxy group, a 2,2,2-trifluoroethoxy group, a chloromethoxy group, a 2-chloroethoxy group, a 1,2-dichloroethoxy group, a bromomethoxy group, and an iodomethoxy group.

The "$C_{1-6}$ alkylsulfonyloxy group" in Formula (I) means a group in which a hydrogen atom of a hydroxy group is substituted with the "$C_{1-6}$ alkylsulfonyl group", and examples thereof include a methylsulfonyloxy group, an ethylsulfonyloxy group, a propylsulfonyloxy group, and an isopropylsulfonyloxy group.

The "halo $C_{1-6}$ alkylsulfonyloxy group" in Formula (I) means the "$C_{1-6}$ alkylsulfonyloxy group" in which any substitutable positions are substituted with 1 or 2 or more, preferably 1 to 3, same or different "halogen atoms" above, and examples thereof include a fluoromethylsulfonyloxy group, a difluoromethylsulfonyloxy group, a trifluoromethylsulfonyloxy group, and a 2,2,2-trifluoroethylsulfonyloxy group.

The "mono $C_{1-6}$ alkylamino group" in Formula (I) means a group in which one hydrogen atom of an amino group is substituted with the "$C_{1-6}$ alkyl group", and examples thereof include a methylamino group, an ethylamino group, a propylamino group, an isopropylamino group, a butylamino group, a sec-butylamino group, and a tert-butylamino group.

The "di $C_{1-6}$ alkylamino group" in Formula (I) means a group in which two hydrogen atoms of an amino group are substituted with the same or different "$C_{1-6}$ alkyl group" above, and examples thereof include a dimethylamino group, a diethylamino group, a dipropylamino group, a diisopropylamino group, a dibutylamino group, a diisobutylamino group, a dipentylamino group, a dihexylamino group, an N-ethyl-N-methylamino group, an N-methyl-N-propylamino group, an N-butyl-N-methylamino group, an N-methyl-N-pentylamino group, and an N-hexyl-N-methylamino group.

The "mono $C_{2-7}$ alkanoylamino group" in Formula (I) means a group in which one hydrogen atom of an amino group is substituted with the "$C_{2-7}$ alkanoyl group", and examples thereof include an acetylamino group, a propanoylamino group, a butanoylamino group, a 2-methylpropanoylamino group, a pentanoylamino group, a 3-methylbutanoylamino group, and a 2,2-dimethylpropanoylamino group.

The "($C_{2-7}$ alkanoyl) $C_{1-6}$ alkylamino group" in Formula (I) means a group in which a hydrogen atom bonded to a nitrogen atom of the "mono $C_{1-6}$ alkylamino group" is substituted with the "$C_{2-7}$ alkanoyl group", and examples thereof include an N-acetyl-N-methylamino group, an N-methyl-N-propanoylamino group, an N-butanoyl-N-methylamino group, an N-methyl-N-pentanoylamino group, an N-acetyl-N-ethylamino group, and an N-acetyl-N-propylamino group.

The "di $C_{2-7}$ alkanoylamino group" in Formula (I) means a group in which two hydrogen atoms of an amino group are substituted with the same or different "$C_{2-7}$ alkanoyl group" above, and examples thereof include a diacetylamino group, a dipropanoylamino group, and an N-acetyl-N-propanoylamino group.

The "mono $C_{1-6}$ alkylsulfonylamino group" in Formula (I) means a group in which one hydrogen atom of an amino group is substituted with the "$C_{1-6}$ alkylsulfonyl group", and examples thereof include a methylsulfonylamino group, an ethylsulfonylamino group, a propylsulfonylamino group, an isopropylsulfonylamino group, a butylsulfonylamino group, a sec-butylsulfonylamino group, and a tert-butylsulfonylamino group.

The "mono $C_{1-6}$ alkylcarbamoyl group" in Formula (I) means a group in which one hydrogen atom of a carbamoyl group is substituted with the "$C_{1-6}$ alkyl group", and examples thereof include a methylcarbamoyl group, an ethylcarbamoyl group, a propylcarbamoyl group, an isopropylcarbamoyl group, a butylcarbamoyl group, a sec-butylcarbamoyl group, and a tert-butylcarbamoyl group.

The "di $C_{1-6}$ alkylcarbamoyl group" in Formula (I) means a group in which two hydrogen atoms of a carbamoyl group are substituted with the same or different "$C_{1-6}$ alkyl group" above, and examples thereof include a dimethylcarbamoyl group, a diethylcarbamoyl group, a dipropylcarbamoyl group, a diisopropylcarbamoyl group, and an N-ethyl-N-methylcarbamoyl group.

The "mono $C_{1-6}$ alkylsulfamoyl group" in Formula (I) means a group in which one hydrogen atom of a sulfamoyl group is substituted with the "$C_{1-6}$ alkyl group", and examples thereof include a methylsulfamoyl group, an ethylsulfamoyl group, a propylsulfamoyl group, an isopropylsulfamoyl group, a butylsulfamoyl group, a sec-butylsulfamoyl group, and a tert-butylsulfamoyl group.

The "di $C_{1-6}$ alkylsulfamoyl group" in Formula (I) means a group in which two hydrogen atoms of a sulfamoyl group are substituted with the same or different "$C_{1-6}$ alkyl group" above, and examples thereof include a dimethylsulfamoyl group, a diethylsulfamoyl group, a dipropylsulfamoyl group, a diisopropylsulfamoyl group, and an N-ethyl-N-methylsulfamoyl group.

The "$C_{3-6}$ cycloalkyl group" in Formula (I) means a 3- to 6-membered aliphatic cyclic group, and examples thereof include a cyclopropyl group, a cyclobutyl group, a cyclopentyl group, and a cyclohexyl group.

The "hydroxy $C_{3-6}$ cycloalkyl group" in Formula (I) means the "$C_{3-6}$ cycloalkyl group" in which any substitutable positions are substituted with 1 or 2 or more, preferably 1 or 2 hydroxy groups, and examples thereof include a 1-hydroxycyclopropyl group, a 2-hydroxycyclopropyl group, and a 1-hydroxycyclobutyl group.

The "(hydroxy $C_{3-6}$ cycloalkyl) $C_{1-6}$ alkoxy group" in Formula (I) means the "$C_{1-6}$ alkoxy group" in which any substitutable positions are substituted with 1 or 2 or more, preferably 1 "hydroxy $C_{3-6}$ cycloalkyl group" above, and examples thereof include a (1-hydroxycyclopropyl)methoxy group, a (2-hydroxycyclopropyl)methoxy group, and a (1-hydroxycyclobutyl)methoxy group.

The "$C_{3-6}$ cycloalkylcarbonyl group" in Formula (I) means a group in which the "$C_{3-6}$ cycloalkyl" and a carbonyl group are bonded, and examples thereof include a cyclopropylcarbonyl group, a cyclobutylcarbonyl group, a cyclopentylcarbonyl group, and a cyclohexylcarbonyl group.

The "cyclic ether group" in Formula (I) means a group in which carbon atoms that constitute the ring of the "$C_{3-6}$ cycloalkyl group" are substituted with 1 or 2 oxygen atoms, and examples thereof include an oxiranyl group, an oxetanyl group, an oxolanyl group, a dioxolanyl group, an oxanyl group, and a dioxanyl group.

The "cyclic amino group" in Formula (I) means a group in which carbon atoms that constitute the ring of the "$C_{3-6}$ cycloalkyl group" are substituted with 1 or 2 nitrogen atoms and a bonding hand is present on the nitrogen atom, and examples thereof include an azetidin-1-yl group, a pyrrolidin-1-yl group, a piperidin-1-yl group, and a piperazin-1-yl group.

The "halo cyclic amino group" in Formula (I) means the "cyclic amino group" in which any substitutable positions are substituted with 1 or 2 or more, preferably 1 to 5, same or different "halogen atoms" above, and examples thereof include a 3-fluoroazetidin-1-yl group, a 3,3-difluoroazetidin-1-yl group, a 3,3-difluoropyrrolidin-1-yl group, a 3,3,4,4-tetrafluoropyrrolidin-1-yl group, and a 3,3-difluoropiperidin-1-yl group.

The "($C_{1-6}$ alkoxy) $C_{1-6}$ alkyl group" in Formula (I) means the "$C_{1-6}$ alkyl group" in which any substitutable positions are substituted with 1 or 2 or more, preferably 1 or 2, same or different "$C_{1-6}$ alkoxy groups" above, and examples thereof include a methoxymethyl group, an ethoxymethyl group, a 1-methoxyethyl group, a 1-ethoxyethyl group, a 2-methoxyethyl group, a 2-ethoxyethyl group, a 1-methoxy-1-methylethyl group, a 1,2-dimethoxyethyl group, and a 3-methoxypropyl group.

The "(halo $C_{1-6}$ alkoxy) $C_{1-6}$ alkyl group" in Formula (I) means the "$C_{1-6}$ alkyl group" in which any substitutable positions are substituted with 1 or 2 or more, preferably 1 or 2, same or different "halo $C_{1-6}$ alkoxy groups" above, and examples thereof include a fluoromethoxymethyl group, a difluoromethoxymethyl group, a trifluoromethoxymethyl group, a 1-(fluoromethoxy)ethyl group, a 1-(difluoromethoxy)ethyl group, a 1-(trifluoromethoxy)ethyl group, a 2-(fluoromethoxy)ethyl group, a 2-(difluoromethoxy)ethyl group, a 2-(trifluoromethoxy)ethyl group, a chloromethoxymethyl group, and a bromomethoxymethyl group.

The "amino $C_{1-6}$ alkyl group" in Formula (I) means the "$C_{1-6}$ alkyl group" in which any substitutable positions are substituted with 1 or 2 or more, preferably 1 or 2 amino groups, and examples thereof include an aminomethyl group, a 1-aminoethyl group, a 1-aminopropyl group, a 2-aminoethyl group, a 2-aminopropyl group, a 2-amino-1-methylethyl group, a 1-amino-1-methylethyl group, a 1,2-diaminoethyl group, and a 3-aminopropyl group.

The "(mono $C_{1-6}$ alkylamino) $C_{1-6}$ alkyl group" in Formula (I) means the "$C_{1-6}$ alkyl group" in which any substitutable positions are substituted with 1 or 2 or more, preferably 1 "mono $C_{1-6}$ alkylamino group" above, and examples thereof include a methylaminomethyl group, an ethylaminomethyl group, a propylaminomethyl group, an isopropylaminomethyl group, a 1-(methylamino)ethyl group, a 2-(methylamino)ethyl group, and a 2-(isopropylamino)ethyl group.

The "(di $C_{1-6}$ alkylamino) $C_{1-6}$ alkyl group" in Formula (I) means the "$C_{1-6}$ alkyl group" in which any substitutable positions are substituted with 1 or 2 or more, preferably 1 "di $C_{1-6}$ alkylamino group" above, and examples thereof include a dimethylaminomethyl group, a diethylaminomethyl group, a dipropylaminomethyl group, a diisopropylaminomethyl group, a 1-(diisopropylamino)ethyl group, a 2-(diisopropylamino)ethyl group, a (N-ethyl-N-methylamino)methyl group, a 1-(N-ethyl-N-methylamino)ethyl group, and a 2-(N-ethyl-N-methylamino)ethyl group.

The "carbamoyl $C_{1-6}$ alkyl group" in Formula (I) means the "$C_{1-6}$ alkyl group" in which any substitutable positions are substituted with 1 or 2 or more, preferably 1 carbamoyl group, and examples thereof include a carbamoylmethyl group, a 1-carbamoylethyl group, a 1-carbamoylpropyl group, a 2-carbamoylethyl group, a 2-carbamoylpropyl group, a 2-carbamoyl-1-methylethyl group, a 1-carbamoyl-1-methylethyl group, and a 3-carbamoylpropyl group.

The "(mono $C_{1-6}$ alkylcarbamoyl) $C_{1-6}$ alkyl group" in Formula (I) means the "$C_{1-6}$ alkyl group" in which any substitutable positions are substituted with 1 or 2 or more, preferably 1 "mono $C_{1-6}$ alkylcarbamoyl group" above, and examples thereof include a methylcarbamoylmethyl group, an ethylcarbamoylmethyl group, a propylcarbamoylmethyl group, an isopropylcarbamoylmethyl group, a 1-(methylcarbamoyl)ethyl group, a 2-(methylcarbamoyl)ethyl group, a 1-(ethylcarbamoyl)ethyl group, and a 2-(ethylcarbamoyl) ethyl group.

The "(di $C_{1-6}$ alkylcarbamoyl) $C_{1-6}$ alkyl group" in Formula (I) means the "$C_{1-6}$ alkyl group" in which any substitutable positions are substituted with 1 or 2 or more, preferably 1 "di $C_{1-6}$ alkylcarbamoyl group" above, and examples thereof include a dimethylcarbamoylmethyl group, a diethylcarbamoylmethyl group, a dipropylcarbamoylmethyl group, a diisopropylcarbamoylmethyl group, a 1-(dimethylcarbamoyl)ethyl group, a 2-(dimethylcarbamoyl)ethyl group, a (N-ethyl-N-methylcarbamoyl)methyl group, a 1-(N-ethyl-N-methylcarbamoyl)ethyl group, and a 2-(N-ethyl-N-methylcarbamoyl)ethyl group.

The "sulfamoyl $C_{1-6}$ alkyl group" in Formula (I) means the "$C_{1-6}$ alkyl group" in which any substitutable positions are substituted with 1 or 2 or more, preferably 1 sulfamoyl group, and examples thereof include a sulfamoylmethyl group, a 1-sulfamoylethyl group, a 1-sulfamoylpropyl group, a 2-sulfamoylethyl group, a 2-sulfamoylpropyl group, a 2-sulfamoyl-1-methylethyl group, a 1-sulfamoyl-1-methylethyl group, and a 3-sulfamoylpropyl group.

The "(mono $C_{1-6}$ alkylsulfamoyl) $C_{1-6}$ alkyl group" in Formula (I) means the "$C_{1-6}$ alkyl group" in which any substitutable positions are substituted with 1 or 2 or more, preferably 1 "mono $C_{1-6}$ alkylsulfamoyl group" above, and examples thereof include a methylsulfamoylmethyl group, an ethylsulfamoylmethyl group, a propylsulfamoylmethyl group, an isopropylsulfamoylmethyl group, a 1-(methylsulfamoyl)ethyl group, a 2-(methylsulfamoyl)ethyl group, a 1-(ethylsulfamoyl)ethyl group, and a 2-(ethylsulfamoyl) ethyl group.

The "(di $C_{1-6}$ alkylsulfamoyl) $C_{1-6}$ alkyl group" in Formula (I) means the "$C_{1-6}$ alkyl group" in which any substitutable positions are substituted with 1 or 2 or more, preferably 1 "di $C_{1-6}$ alkylsulfamoyl group" above, and examples thereof include a dimethylsulfamoylmethyl group, a diethylsulfamoylmethyl group, a dipropylsulfamoylmethyl group, a diisopropylsulfamoylmethyl group, a 1-(dimethylsulfamoyl)ethyl group, a 2-(dimethylsulfamoyl)ethyl group, a (N-ethyl-N-methylsulfamoyl)methyl group, a 1-(N-ethyl-N-methylsulfamoyl)ethyl group, and a 2-(N-ethyl-N-methylsulfamoyl)ethyl group.

The "$C_{1-6}$ alkanediyl group" in Formula (I) means a divalent group obtained by removing one hydrogen atom from the "$C_{1-6}$ alkyl group", and examples thereof include a methylene group, an ethane-1,1-diyl group, an ethane-1,2-diyl group, a propane-1,1-diyl group, a propane-1,2-diyl group, a propane-2,2-diyl group, and a propane-1,3-diyl group.

The "hydroxy $C_{1-6}$ alkanediyl group" in Formula (I) means the "$C_{1-6}$ alkanediyl group" in which any substitutable positions are substituted with 1 or 2 or more, preferably 1 or 2 hydroxy groups, and examples thereof include a hydroxymethylene group, a 1-hydroxyethane-1,1-diyl group, a 2-hydroxyethane-1,1-diyl group, a 1-hydroxyethane-1,2-diyl group, a 2-hydroxyethane-1,2-diyl group, a 1,2-dihydroxyethane-1,1-diyl group, and a 1,2-dihydroxyethane-1,2-diyl group.

The "$C_{6-10}$ aryl group" in Formula (I) means an aromatic hydrocarbon group having 6 to 10 carbon atoms, and examples thereof include a phenyl group and a naphthyl group.

The "heteroaryl group" in Formula (I) means a 5- or 6-membered monocyclic ring containing 1 or 2 or more, preferably 1 to 4 heteroatoms selected identically or differently from the group consisting of an oxygen atom, a nitrogen atom, and a sulfur atom, or a bicyclic ring in which the monocyclic ring is condensed with a benzene ring or a pyridine ring, and examples thereof include a pyrrolyl group, a furyl group, a thienyl group, an imidazolyl group, a pyrazolyl group, a thiazolyl group, an isothiazolyl group, an oxazolyl group, an isoxazolyl group, a triazolyl group, a tetrazolyl group, a 1,2,3-oxadiazolyl group, a 1,2,4-oxadiazolyl group, a 1,3,4-oxadiazolyl group, a 1,2,5-oxadiazolyl group, a 1,2,3-thiadiazolyl group, a 1,2,4-thiadiazolyl group, a 1,3,4-thiadiazolyl group, a 1,2,5-thiadiazolyl group, a pyridyl group, a pyrazinyl group, a pyrimidinyl group, a pyridazinyl group, a 1,2,4-triazinyl group, a 1,3,5-triazinyl group, an indolyl group, an isoindolyl group, a benzofuranyl group, a benzothienyl group, a benzimidazolyl group, a benzoxazolyl group, a benzisoxazolyl group, a benzothiazolyl group, a benzisothiazolyl group, an indazolyl group, an imidazopyridyl group, a purinyl group, a quinolyl group, a quinolizinyl group, an isoquinolyl group, a phthalazinyl group, a naphthyridinyl group, a quinoxalinyl group, a quinazolinyl group, a cinnolinyl group, a pteridinyl group, and a pyrido[3,2-b]pyridyl group.

The "$C_{3-10}$ cycloalkyl group" in Formula (I) means a 3- to 10-membered aliphatic cyclic group, and examples thereof include a cyclopropyl group, a cyclobutyl group, a cyclopentyl group, a cyclohexyl group, a cycloheptyl group, and a cyclooctyl group.

The "$C_{3-10}$ cycloalkyl group" may be condensed with a benzene ring or a heteroaryl ring to form a condensed ring group, and examples of such a condensed ring group include an indan-1-yl group, an indan-2-yl group, a 1,2,3,4-tetrahydronaphthalen-1-yl group, and a 1,2,3,4-tetrahydronaphthalen-2-yl group.

Further, the "$C_{3-10}$ cycloalkyl group" may form a bicyclo ring group or a spiro ring group, and examples of such a cyclic group include a bicyclo[2.2.1]heptyl group, a bicyclo[2.2.2]octyl group, a bicyclo[3.2.1]octyl group, a spiro[2.3]hexyl group, a spiro[3.3]heptyl group, a spiro[2.5]octyl group, and a spiro[3.4]octyl group.

The "4- to 10-membered heterocyclyl group" in Formula (I) means an aliphatic cyclic group having 4 to 10 atoms constituting the ring and containing 1 or 2 or more, preferably 1 to 3 heteroatoms identically or differently selected from the group consisting of a nitrogen atom, an oxygen atom, and a sulfur atom, and examples thereof include an azetidinyl group, a pyrrolidinyl group, a piperidinyl group, an azepanyl group, an oxetanyl group, an oxolanyl group, an oxanyl group, a pyrazolidinyl group, an imidazolidinyl group, an oxazolidinyl group, an isoxazolidinyl group, a thiazolidinyl group, an isothiazolidinyl group, a dioxolanyl group, a dioxanyl group, a morpholinyl group, a piperazinyl group, and a thiomorpholinyl group.

The "4- to 10-membered heterocyclyl group" may be condensed with a benzene ring or a heteroaryl ring to form a condensed ring group, and examples of such a condensed ring group include a group represented by the following formula (in the formula, the wavy line represents the point of attachment).

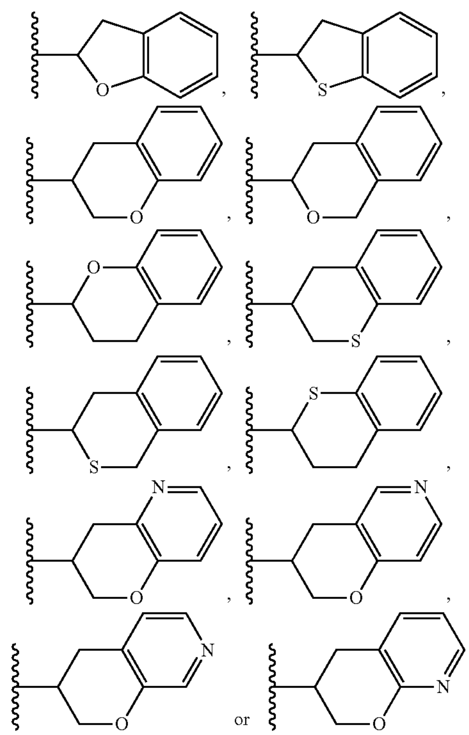

Further, the "4- to 10-membered heterocyclyl group" may form a bicyclo ring group or a spiro ring group, and examples of such a cyclic group include a 2-azabicyclo[2.2.1]heptyl group, a 1-azabicyclo[2.2.2]octyl group, a 2-azabicyclo[2.2.2]octyl group, a 2-azaspiro[3.3]heptyl group, a 2-azaspiro[3.4]octyl group, and a 2-oxaspiro[3.5]nonyl group.

The "4- to 10-membered nitrogen-containing heterocyclyl group" in General Formula (III) means, among the "4- to 10-membered heterocyclyl group", an aliphatic cyclic group containing 1 or 2 or more, preferably 1 nitrogen atom in atoms that constitute the ring, and bonded to $L^2$ of Formula (I) via the nitrogen atom, and examples thereof include an azetidinyl group, a pyrrolidinyl group, a piperidinyl group, an azepanyl group, and a 2-azaspiro[3.3]heptyl group.

The "hydroxy $C_{1-6}$ alkoxy group" in Formula (I) means the "$C_{1-6}$ alkoxy group" in which any substitutable positions are substituted with 1 or 2 or more, preferably 1 or 2 hydroxy groups, and examples thereof include a 2-hydroxyethoxy group, a 2-hydroxypropoxy group, a 3-hydroxypropoxy group, and a 2-hydroxy-2-methylpropoxy group.

The "$C_{1-6}$ alkylthio group" in Formula (I) means a group in which a hydrogen atom of a sulfanyl group is substituted with the "$C_{1-6}$ alkyl group", and examples thereof include a methylthio group, an ethylthio group, a propylthio group, an isopropylthio group, a butylthio group, a sec-butylthio group, an isobutylthio group, a tert-butylthio group, a pentylthio group, an isopentylthio group, a hexylthio group, and an isohexylthio group.

The "mono (halo $C_{1-6}$ alkyl)amino group" in Formula (I) means a group in which one hydrogen atom of an amino group is substituted with the "halo $C_{1-6}$ alkyl group", and examples thereof include a 2-fluoroethylamino group, a 2,2-difluoroethylamino group, a 2,2,2-trifluoroethylamino group, and a 2,2,3,3,3-pentafluoropropylamino group.

The "$C_{2-7}$ alkoxycarbonyl group" in Formula (I) means a group in which the "$C_{1-6}$ alkoxy group" and a carbonyl group are bonded, that is, an alkoxycarbonyl group having 2 to 7 carbon atoms, and examples thereof include a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, and a pentyloxycarbonyl group.

The "mono ($C_{2-7}$ alkoxycarbonyl)amino group" in Formula (I) means a group in which one hydrogen atom of an amino group is substituted with the "$C_{2-7}$ alkoxycarbonyl group", and examples thereof include a methoxycarbonylamino group, an ethoxycarbonylamino group, a propoxycarbonylamino group, an isopropoxycarbonylamino group, a butoxycarbonylamino group, an isobutoxycarbonylamino group, a tert-butoxycarbonylamino group, and a pentyloxycarbonylamino group.

The "oxo group" in Formula (I) means an oxygen atom bonded via a double bond (=O). Therefore, when an oxo group is bonded to a carbon atom, the oxo group forms a carbonyl group together with the carbon atom, when one oxo group is bonded to a sulfur atom, the oxo group forms a sulfinyl group together with the sulfur atom, and when two oxo groups are bonded to a sulfur atom, the oxo groups form a sulfonyl group together with the sulfur atom. Examples of the cyclic group in which an oxo group is bonded to a carbon atom that constitutes a ring include a 2-oxopyrrolidin-3-yl group, a 2-oxopiperidin-4-yl group, a 6-oxo-1,6-dihydropyridin-2-yl group, a 1-methyl-6-oxo-1,6-dihydropyridin-2-yl group, a 6-oxo-1,6-dihydropyrimidin-2-yl group, and a 1-methyl-6-oxo-1,6-dihydropyrimidin-2-yl group. Examples of the cyclic group in which an oxo group is bonded to a sulfur atom that constitutes a ring include a 1,1-dioxoisothiazolidin-5-yl group and a 1,1-dioxothiomorpholin-4-yl group.

The "any substitutable position" means a site of a substitutable hydrogen atom on a carbon atom, a nitrogen atom, an oxygen atom, and/or a sulfur atom, the substitution of the hydrogen atom being chemically acceptable, and the substitution resulting in a stable compound.

Each group that constitutes Formula (I) will be described in detail.

$R^1$ in Formula (I) represents a hydrogen atom, a halogen atom, or a $C_{1-6}$ alkyl group, and is preferably a hydrogen atom.

The halogen atom of $R^1$ is preferably a fluorine atom or a chlorine atom.

The $C_{1-6}$ alkyl group of $R^1$ is preferably a methyl group or an ethyl group.

$R^2$ in Formula (I) represents a hydrogen atom, a halogen atom, a cyano group, a hydroxy group, a carbamoyl group, a $C_{1-6}$ alkyl group, a halo $C_{1-6}$ alkyl group, a hydroxy $C_{1-6}$ alkyl group, or a $C_{1-6}$ alkoxy group, and is preferably a hydrogen atom, a halogen atom, or a $C_{1-6}$ alkyl group.

The halogen atom of $R^2$ is preferably a fluorine atom or a chlorine atom.

The $C_{1-6}$ alkyl group of $R^2$ is preferably a methyl group or an ethyl group.

The halo $C_{1-6}$ alkyl group of $R^2$ is preferably a trifluoromethyl group or a 2,2,2-trifluoroethyl group.

The hydroxy $C_{1-6}$ alkyl group of $R^2$ is preferably a hydroxymethyl group or a 1-hydroxyethyl group.

The $C_{1-6}$ alkoxy group of $R^2$ is preferably a methoxy group or an ethoxy group.

$R^3$ in Formula (I) represents a hydrogen atom, a halogen atom, a cyano group, a hydroxy group, an amino group, a carbamoyl group, a sulfamoyl group, a carboxy group, a $C_{1-6}$ alkyl group, a $C_{2-6}$ alkenyl group, a halo $C_{1-6}$ alkyl group, a hydroxy $C_{1-6}$ alkyl group, a $C_{2-7}$ alkanoyl group, a $C_{1-6}$ alkylsulfonyl group, a $C_{1-6}$ alkoxy group, a halo $C_{1-6}$ alkoxy group, a $C_{1-6}$ alkylsulfonyloxy group, a halo $C_{1-6}$ alkylsulfonyloxy group, a mono $C_{1-6}$ alkylamino group, a di $C_{1-6}$ alkylamino group, a mono $C_{2-7}$ alkanoylamino group, a ($C_{2-7}$ alkanoyl) $C_{1-6}$ alkylamino group, a di $C_{2-7}$ alkanoylamino group, a mono $C_{1-6}$ alkylsulfonylamino group, a mono $C_{1-6}$ alkylcarbamoyl group, a di $C_{1-6}$ alkylcarbamoyl group, a mono $C_{1-6}$ alkylsulfamoyl group, a di $C_{1-6}$ alkylsulfamoyl group, a $C_{3-6}$ cycloalkyl group, a cyclic ether group, a cyclic amino group, or a halo cyclic amino group, and is preferably a hydrogen atom, a halogen atom, or a $C_{1-6}$ alkyl group.

The $C_{1-6}$ alkyl group of $R^3$ is preferably a methyl group or an ethyl group.

The $C_{2-6}$ alkenyl group of $R^3$ is preferably a vinyl group or an allyl group.

The halo $C_{1-6}$ alkyl group of $R^3$ is preferably a trifluoromethyl group or a 2,2,2-trifluoroethyl group.

The hydroxy $C_{1-6}$ alkyl group of $R^3$ is preferably a hydroxymethyl group or a 1-hydroxyethyl group.

The $C_{2-7}$ alkanoyl group of $R^3$ is preferably an acetyl group or a propanoyl group.

The $C_{1-6}$ alkylsulfonyl group of $R^3$ is preferably a methylsulfonyl group or an ethylsulfonyl group.

The $C_{1-6}$ alkoxy group of $R^3$ is preferably a methoxy group or an ethoxy group.

The halo $C_{1-6}$ alkoxy group of $R^3$ is preferably a difluoromethoxy group or a trifluoromethoxy group.

The $C_{1-6}$ alkylsulfonyloxy group of $R^3$ is preferably a methylsulfonyloxy group or an ethylsulfonyloxy group.

The halo $C_{1-6}$ alkylsulfonyloxy group of $R^3$ is preferably a trifluoromethylsulfonyloxy group or a 2,2,2-trifluoroethylsulfonyloxy group.

The mono $C_{1-6}$ alkylamino group of $R^3$ is preferably a methylamino group or an ethylamino group.

The di $C_{1-6}$ alkylamino group of $R^3$ is preferably a dimethylamino group or an N-ethyl-N-methylamino group.

The mono $C_{2-7}$ alkanoylamino group of $R^3$ is preferably an acetylamino group or a propanoylamino group.

The ($C_{2-7}$ alkanoyl) $C_{1-6}$ alkylamino group of $R^3$ is preferably an N-acetyl-N-methylamino group or an N-acetyl-N-ethylamino group.

The di $C_{2-7}$ alkanoylamino group of $R^3$ is preferably a diacetylamino group or a dipropanoylamino group.

The mono $C_{1-6}$ alkylsulfonylamino group of $R^3$ is preferably a methylsulfonylamino group or an ethylsulfonylamino group.

The mono $C_{1-6}$ alkylcarbamoyl group of $R^3$ is preferably a methylcarbamoyl group or an ethylcarbamoyl group.

The di $C_{1-6}$ alkylcarbamoyl group of $R^3$ is preferably a dimethylcarbamoyl group or an N-ethyl-N-methylcarbamoyl group.

The mono $C_{1-6}$ alkylsulfamoyl group of $R^3$ is preferably a methylsulfamoyl group or an ethylsulfamoyl group.

The di $C_{1-6}$ alkylsulfamoyl group of $R^3$ is preferably a dimethylsulfamoyl group or an N-ethyl-N-methylsulfamoyl group.

The $C_{3-6}$ cycloalkyl group of $R^3$ is preferably a cyclopropyl group or a cyclobutyl group.

The cyclic ether group of $R^3$ is preferably an oxetanyl group or an oxolanyl group.

The cyclic amino group of $R^3$ is preferably an azetidin-1-yl group or a pyrrolidin-1-yl group.

The halo cyclic amino group of $R^3$ is preferably a 3,3-difluoroazetidin-1-yl group or a 3,3-difluoropyrrolidin-1-yl group.

$R^4$ in Formula (I) represents a hydrogen atom, a halogen atom, a cyano group, a hydroxy group, an amino group, a carbamoyl group, a sulfamoyl group, a carboxy group, a $C_{1-6}$ alkyl group, a $C_{2-6}$ alkenyl group, a halo $C_{1-6}$ alkyl group, a hydroxy $C_{1-6}$ alkyl group, a $C_{1-6}$ alkoxy group, a halo $C_{1-6}$ alkoxy group, a mono $C_{1-6}$ alkylamino group, or a di $C_{1-6}$ alkylamino group, and is preferably a hydrogen atom, a halogen atom, or a $C_{1-6}$ alkyl group.

The $C_{1-6}$ alkyl group of $R^4$ is preferably a methyl group or an ethyl group.

The $C_{2-6}$ alkenyl group of $R^4$ is preferably a vinyl group or an allyl group.

The halo $C_{1-6}$ alkyl group of $R^4$ is preferably a trifluoromethyl group or a 2,2,2-trifluoroethyl group.

The hydroxy $C_{1-6}$ alkyl group of $R^4$ is preferably a hydroxymethyl group or a 1-hydroxyethyl group.

The $C_{1-6}$ alkoxy group of $R^4$ is preferably a methoxy group or an ethoxy group.

The halo $C_{1-6}$ alkoxy group of $R^4$ is preferably a difluoromethoxy group or a trifluoromethoxy group.

The mono $C_{1-6}$ alkylamino group of $R^4$ is preferably a methylamino group or an ethylamino group.

The di $C_{1-6}$ alkylamino group of $R^4$ is preferably a dimethylamino group or an N-ethyl-N-methylamino group.

$R^5$ in Formula (I) represents a hydrogen atom, a halogen atom, a cyano group, a hydroxy group, a $C_{1-6}$ alkyl group, a halo $C_{1-6}$ alkyl group, or a hydroxy $C_{1-6}$ alkyl group, and is preferably a hydrogen atom or a fluorine atom.

The halogen atom of $R^5$ is preferably a fluorine atom or a chlorine atom.

The $C_{1-6}$ alkyl group of $R^5$ is preferably a methyl group or an ethyl group.

The halo $C_{1-6}$ alkyl group of $R^5$ is preferably a trifluoromethyl group or a 2,2,2-trifluoroethyl group.

The hydroxy $C_{1-6}$ alkyl group of $R^5$ is preferably a hydroxymethyl group or a 1-hydroxyethyl group.

W in Formula (I) represents an oxygen atom, a sulfur atom, or a group represented by General Formula: $—N(R^6)—$($R^6$ represents a hydrogen atom or a $C_{1-6}$ alkyl group), and is preferably an oxygen atom or General Formula: $—N(R^6)—$ (wherein $R^6$ is as defined above), and more preferably an oxygen atom or —NH—.

The $C_{1-6}$ alkyl group of $R^6$ is preferably a methyl group or an ethyl group.

X in Formula (I) is a $C_{1-6}$ alkyl group, a $C_{2-6}$ alkenyl group, a halo $C_{1-6}$ alkyl group, a hydroxy $C_{1-6}$ alkyl group, a ($C_{1-6}$ alkoxy) $C_{1-6}$ alkyl group, a (halo $C_{1-6}$ alkoxy) $C_{1-6}$ alkyl group, an amino $C_{1-6}$ alkyl group, a (mono $C_{1-6}$ alkylamino) $C_{1-6}$ alkyl group, a (di $C_{1-6}$ alkylamino) $C_{1-6}$ alkyl group, a carbamoyl $C_{1-6}$ alkyl group, a (mono $C_{1-6}$ alkylcarbamoyl) $C_{1-6}$ alkyl group, a (di $C_{1-6}$ alkylcarbamoyl) $C_{1-6}$ alkyl group, a sulfamoyl $C_{1-6}$ alkyl group, a (mono $C_{1-6}$ alkylsulfamoyl) $C_{1-6}$ alkyl group, a (di $C_{1-6}$ alkylsulfamoyl) $C_{1-6}$ alkyl group, or a group represented by General Formula (II):

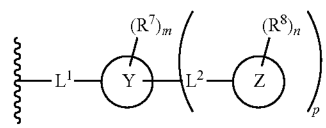

(wherein the wavy line represents the point of attachment to the nitrogen atom, $L^1$ represents a single bond, a $C_{1-6}$ alkanediyl group, or a hydroxy $C_{1-6}$ alkanediyl group;

ring Y represents a $C_{6-10}$ aryl group, a heteroaryl group, a $C_{3-10}$ cycloalkyl group (the $C_{3-10}$ cycloalkyl group is optionally condensed with a benzene ring or a heteroaryl ring to form a condensed ring group, or optionally forms a bicyclo ring group or a spiro ring group) or a 4-10 membered heterocyclyl group (the 4- to 10-membered heterocyclyl group is optionally condensed with a benzene ring or a heteroaryl ring to form a condensed ring group, or optionally forms a bicyclo ring group or a spiro ring group);

each $R^7$ independently represents a halogen atom, a cyano group, a hydroxy group, a sulfanyl group, an amino group, a carbamoyl group, a sulfamoyl group, a carboxy group, a formyl group, an imino group, an azide group, a hydrazino group, a nitro group, a $C_{1-6}$ alkyl group, a $C_{2-6}$ alkenyl group, a halo $C_{1-6}$ alkyl group, a hydroxy $C_{1-6}$ alkyl group, a ($C_{1-6}$ alkoxy) $C_{1-6}$ alkyl group, a $C_{2-7}$ alkanoyl group, a $C_{1-6}$ alkylsulfonyl group, a $C_{1-6}$ alkoxy group, a halo $C_{1-6}$ alkoxy group, a hydroxy $C_{1-6}$ alkoxy group, a $C_{1-6}$ alkylthio group, a mono $C_{1-6}$ alkylamino group, a di $C_{1-6}$ alkylamino group, a mono (halo $C_{1-6}$ alkyl)amino group, a $C_{2-7}$ alkoxycarbonyl group, a mono $C_{1-6}$ alkylcarbamoyl group, a di $C_{1-6}$ alkylcarbamoyl group, a $C_{1-6}$ alkylsulfonyloxy group, a halo $C_{1-6}$ alkylsulfonyloxy group, a mono $C_{1-6}$ alkylsulfamoyl group, a di $C_{1-6}$ alkylsulfamoyl group, a mono $C_{2-7}$ alkanoylamino group, a ($C_{2-7}$ alkanoyl) $C_{1-6}$ alkylamino group, a di $C_{2-7}$ alkanoylamino group, a mono $C_{1-6}$ alkylsulfonylamino group, a mono ($C_{2-7}$ alkoxycarbonyl)amino group, a $C_{3-6}$ cycloalkyl group, a cyclic ether group, a cyclic amino group, a halo cyclic amino group, or an oxo group;

$L^2$ represents a single bond, a $C_{1-6}$ alkanediyl group, a hydroxy $C_{1-6}$ alkanediyl group, a carbonyl group, or a sulfonyl group;

ring Z represents a phenyl group, a heteroaryl group, or a 4- to 10-membered heterocyclyl group (the 4- to 10-membered heterocyclyl group is optionally condensed with a benzene ring or a heteroaryl ring to form a condensed ring group, or optionally forms a bicyclo ring group or a spiro ring group);

each $R^8$ independently represents a halogen atom, a cyano group, a hydroxy group, a sulfanyl group, an amino group, a carbamoyl group, a sulfamoyl group, a carboxy group, a $C_{1-6}$ alkyl group, a $C_{2-6}$ alkenyl group, a halo $C_{1-6}$ alkyl group, a hydroxy $C_{1-6}$ alkyl group, a ($C_{1-6}$ alkoxy) $C_{1-6}$ alkyl group, a $C_{2-7}$ alkanoyl group, a $C_{1-6}$ alkylsulfonyl group, a $C_{1-6}$ alkoxy group, a halo $C_{1-6}$ alkoxy group, a mono $C_{1-6}$ alkylamino group, a di $C_{1-6}$ alkylamino group, a $C_{2-7}$ alkoxycarbonyl group, a mono $C_{1-6}$ alkylcarbamoyl group, a di $C_{1-6}$ alkylcarbamoyl group, a $C_{1-6}$ alkylsulfonyloxy group, a halo $C_{1-6}$ alkylsulfonyloxy group, a mono $C_{1-6}$ alkylsulfamoyl group, a di $C_{1-6}$ alkylsulfamoyl group, a mono $C_{2-7}$ alkanoylamino group, a mono $C_{1-6}$ alkylsulfonylamino group, a mono ($C_{2-7}$ alkoxycarbonyl)amino group, a $C_{3-6}$ cycloalkyl group, a cyclic ether group, a cyclic amino group, a halo cyclic amino group, or an oxo group;

m represents 0, 1, 2, or 3;

n represents 0, 1, or 2; and p represents 0 or 1.).

The $C_{1-6}$ alkyl group of X is preferably a butyl group or a hexyl group.

The $C_{2-6}$ alkenyl group of X is preferably a vinyl group or an allyl group.

The halo $C_{1-6}$ alkyl group of X is preferably a 2,2,2-trifluoroethyl group or a 2,2,3,3,3-pentafluoropropyl group.

The hydroxy $C_{1-6}$ alkyl group of X is preferably a 3-hydroxypropyl group or a 2-hydroxypropyl group.

The ($C_{1-6}$ alkoxy) $C_{1-6}$ alkyl group of X is preferably a 3-methoxypropyl group or a 2-ethoxyethyl group.

The (halo $C_{1-6}$ alkoxy) $C_{1-6}$ alkyl group of X is preferably a 2-(difluoromethoxy) ethyl group or a 2-(trifluoromethoxy) ethyl group.

The amino $C_{1-6}$ alkyl group of X is preferably a 2-aminoethyl group or a 2-aminopropyl group.

The (mono $C_{1-6}$ alkylamino) $C_{1-6}$ alkyl group of X is preferably a 2-(methylamino)ethyl group or a 2-(isopropylamino)ethyl group.

The (di $C_{1-6}$ alkylamino) $C_{1-6}$ alkyl group of X is preferably a 2-(diisopropylamino)ethyl group or a 2-(N-ethyl-N-methylamino)ethyl group.

The carbamoyl $C_{1-6}$ alkyl group of X is preferably a 2-carbamoylethyl group or a 2-carbamoylpropyl group.

The (mono $C_{1-6}$ alkylcarbamoyl) $C_{1-6}$ alkyl group of X is preferably a 2-(methylcarbamoyl)ethyl group or a 2-(ethylcarbamoyl)ethyl group.

The (di $C_{1-6}$ alkylcarbamoyl) $C_{1-6}$ alkyl group of X is preferably a 2-(dimethylcarbamoyl)ethyl group or a 2-(N-ethyl-N-methylcarbamoyl)ethyl group.

The sulfamoyl $C_{1-6}$ alkyl group of X is preferably a 2-sulfamoylethyl group or a 2-sulfamoylpropyl group.

The (mono $C_{1-6}$ alkylsulfamoyl) $C_{1-6}$ alkyl group of X is preferably a 2-(methylsulfamoyl)ethyl group or a 2-(ethylsulfamoyl)ethyl group.

The (di $C_{1-6}$ alkylsulfamoyl) $C_{1-6}$ alkyl group of X is preferably a 2-(dimethylsulfamoyl)ethyl group or a 2-(N-ethyl-N-methylsulfamoyl)ethyl group.

The $C_{1-6}$ alkanediyl group of $L^1$ is preferably a methylene group or a propane-1,3-diyl group.

The hydroxy $C_{1-6}$ alkanediyl group of $L^1$ is preferably a 2-hydroxyethane-1,1-diyl group or a 2-hydroxyethane-1,2-diyl group.

$L^1$ is preferably a single bond or a methylene group.

The $C_{6-10}$ aryl group of ring Y is preferably a phenyl group or a naphthyl group.

The heteroaryl group of ring Y is preferably a pyrazolyl group or a pyridyl group.

The $C_{3-10}$ cycloalkyl group of ring Y is preferably a cyclohexyl group, an indan-1-yl group, or a spiro[3.3]heptyl group.

The 4- to 10-membered heterocyclyl group of ring Y is preferably a 4- to 10-membered nitrogen-containing heterocyclyl group or a condensed heterocyclyl group obtained by condensing a 4- to 10-membered heterocyclyl group and a benzene ring or a heteroaryl ring.

Ring Y is preferably a group represented by General Formula (III):

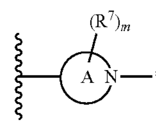

(wherein the wavy line represents the point of attachment to $L^1$,

* represents the point of attachment to $L^2$, $R^7$ and m are as defined above, and ring A is a 4- to 10-membered nitrogen-containing heterocyclyl group); and ring Y is more preferably a group represented by General Formula:

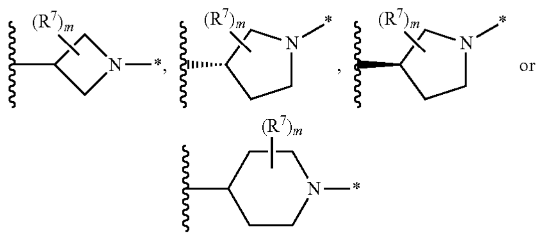

(wherein the wavy line represents the point of attachment to $L^1$,

* represents the point of attachment to $L^2$, and $R^7$ and m are as described above).

Preferable examples of the ring Y include a condensed heterocyclyl group obtained by condensing a 4- to 10-membered heterocyclyl group and a benzene ring or a heteroaryl ring; and more preferable examples of the ring Y include a ring represented by General Formula:

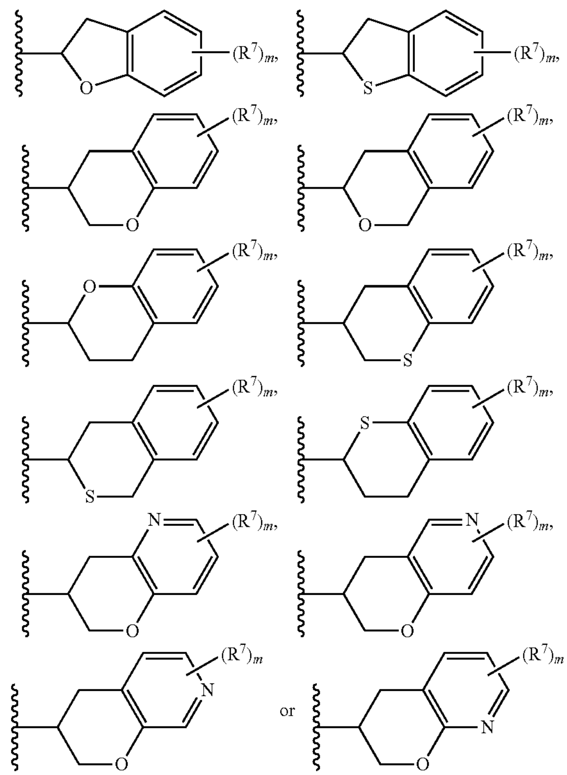

(wherein the wavy line represents the point of attachment to $L^1$, and $R^7$ and m are as described above).

The halogen atom of $R^7$ is preferably a fluorine atom or a chlorine atom.

The $C_{1-6}$ alkyl group of $R^7$ is preferably a methyl group or an ethyl group.

The $C_{2-6}$ alkenyl group of $R^7$ is preferably a vinyl group or an allyl group.

The halo $C_{1-6}$ alkyl group of $R^7$ is preferably a trifluoromethyl group or a 2,2,2-trifluoroethyl group.

The hydroxy $C_{1-6}$ alkyl group of $R^7$ is preferably a hydroxymethyl group or a 1-hydroxy-1-methylethyl group.

The ($C_{1-6}$ alkoxy) $C_{1-6}$ alkyl group of $R^7$ is preferably a 2-methoxyethyl group or a 2-ethoxyethyl group.

The $C_{2-7}$ alkanoyl group of $R^7$ is preferably an acetyl group or a propanoyl group.

The $C_{1-6}$ alkylsulfonyl group of $R^7$ is preferably a methylsulfonyl group or an ethylsulfonyl group.

The $C_{1-6}$ alkoxy group of $R^7$ is preferably a methoxy group or an ethoxy group.

The halo $C_{1-6}$ alkoxy group of $R^7$ is preferably a difluoromethoxy group or a trifluoromethoxy group.

The hydroxy $C_{1-6}$ alkoxy group of $R^7$ is preferably a 2-hydroxyethoxy group or a 2-hydroxy-2-methylpropoxy group.

The $C_{1-6}$ alkylthio group of $R^7$ is preferably a methylthio group or an ethylthio group.

The mono $C_{1-6}$ alkylamino group of $R^7$ is preferably a methylamino group or an ethylamino group.

The di $C_{1-6}$ alkylamino group of $R^7$ is preferably a dimethylamino group or an N-ethyl-N-methylamino group.

The mono (halo $C_{1-6}$ alkyl)amino group of $R^7$ is preferably a 2,2-difluoroethylamino group or a 2,2,2-trifluoroethylamino group.

The $C_{2-7}$ alkoxycarbonyl group of $R^7$ is preferably a methoxycarbonyl group or an ethoxycarbonyl group.

The mono $C_{1-6}$ alkylcarbamoyl group of $R^7$ is preferably a methylcarbamoyl group or an ethylcarbamoyl group.

The di $C_{1-6}$ alkylcarbamoyl group of $R^7$ is preferably a dimethylcarbamoyl group or an N-ethyl-N-methylcarbamoyl group.

The $C_{1-6}$ alkylsulfonyloxy group of $R^7$ is preferably a methylsulfonyloxy group or an ethylsulfonyloxy group.

The halo $C_{1-6}$ alkylsulfonyloxy group of $R^7$ is preferably a trifluoromethylsulfonyloxy group or a 2,2,2-trifluoroethylsulfonyloxy group.

The mono $C_{1-6}$ alkylsulfamoyl group of $R^7$ is preferably a methylsulfamoyl group or an ethylsulfamoyl group.

The di $C_{1-6}$ alkylsulfamoyl group of $R^7$ is preferably a dimethylsulfamoyl group or an N-ethyl-N-methylsulfamoyl group.

The mono $C_{2-7}$ alkanoylamino group of $R^7$ is preferably an acetylamino group or a propanoylamino group.

The ($C_{2-7}$ alkanoyl) $C_{1-6}$ alkylamino group of $R^7$ is preferably an N-acetyl-N-methylamino group or an N-acetyl-N-ethylamino group.

The di $C_{2-7}$ alkanoylamino group of $R^7$ is preferably a diacetylamino group or a dipropanoylamino group.

The mono $C_{1-6}$ alkylsulfonylamino group of $R^7$ is preferably a methylsulfonylamino group or an ethylsulfonylamino group.

The mono ($C_{2-7}$ alkoxycarbonyl)amino group of $R^7$ is preferably a methoxycarbonylamino group or a tert-butoxycarbonylamino group.

The $C_{3-6}$ cycloalkyl group of $R^7$ is preferably a cyclopropyl group or a cyclobutyl group.

The cyclic ether group of $R^7$ is preferably an oxetanyl group or an oxolanyl group.

The cyclic amino group of $R^7$ is preferably an azetidin-1-yl group or a pyrrolidin-1-yl group.

The halo cyclic amino group of $R^7$ is preferably a 3,3-difluoroazetidin-1-yl group or a 3,3-difluoropyrrolidin-1-yl group.

The cyclic group in which an oxo group is bonded to a carbon atom that constitutes a ring of $R^7$ is preferably a 2-oxopyrrolidin-3-yl group or a 2-oxopiperidin-4-yl group.

The cyclic group in which an oxo group is bonded to a sulfur atom that constitutes a ring of $R^7$ is preferably a 1,1-dioxoisothiazolidin-5-yl group or a 1,1-dioxothiomorpholin-4-yl group.

The $C_{1-6}$ alkanediyl group of $L^2$ is preferably a methylene group or an ethane-1,2-diyl group.

The hydroxy $C_{1-6}$ alkanediyl group of $L^2$ is preferably a hydroxymethylene group or a 1-hydroxyethane-1,1-diyl group.

The heteroaryl group of ring Z is preferably a tetrazolyl group or a pyrimidinyl group.

The 4- to 10-membered heterocyclyl group of ring z is preferably a pyrrolidinyl group or an isothiazolidinyl group.

Ring Z is preferably a phenyl group or a heteroaryl group (preferably a 5- or 6-membered nitrogen-containing heteroaryl group), more preferably a group represented by General Formula:

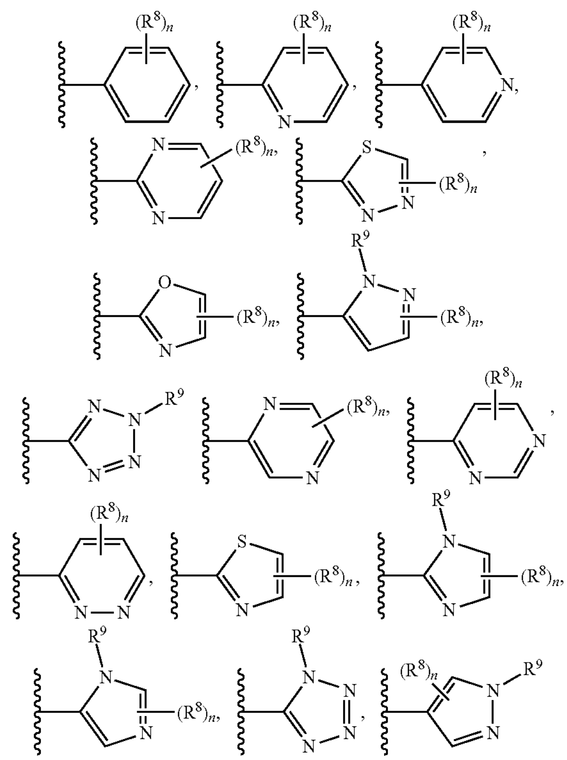

(wherein the wavy line represents the point of attachment to $L^2$, $R^8$ and n are as defined above, $R^9$ is a $C_{1-6}$ alkyl group, a halo $C_{1-6}$ alkyl group, a hydroxy $C_{1-6}$ alkyl group, a ($C_{1-6}$ alkoxy) $C_{1-6}$ alkyl group, or a $C_{3-6}$ cycloalkyl group).

The halogen atom of $R^8$ is preferably a fluorine atom or a chlorine atom.

The $C_{1-6}$ alkyl group of $R^8$ is preferably a methyl group or an ethyl group.

The $C_{2-6}$ alkenyl group of $R^8$ is preferably a vinyl group or an allyl group.

The halo $C_{1-6}$ alkyl group of $R^8$ is preferably a trifluoromethyl group or a 2,2,2-trifluoroethyl group.

The hydroxy $C_{1-6}$ alkyl group of $R^8$ is preferably a hydroxymethyl group or a 1-hydroxy-1-methylethyl group.

The ($C_{1-6}$ alkoxy) $C_{1-6}$ alkyl group of $R^8$ is preferably a methoxymethyl group or an ethoxymethyl group.

The $C_{2-7}$ alkanoyl group of $R^8$ is preferably an acetyl group or a propanoyl group.

The $C_{1-6}$ alkylsulfonyl group of $R^8$ is preferably a methylsulfonyl group or an ethylsulfonyl group.

The $C_{1-6}$ alkoxy group of $R^8$ is preferably a methoxy group or an ethoxy group.

The halo $C_{1-6}$ alkoxy group of $R^8$ is preferably a difluoromethoxy group or a trifluoromethoxy group.

The mono $C_{1-6}$ alkylamino group of $R^8$ is preferably a methylamino group or an ethylamino group.

The di $C_{1-6}$ alkylamino group of $R^8$ is preferably a dimethylamino group or an N-ethyl-N-methylamino group.

The $C_{2-7}$ alkoxycarbonyl group of $R^8$ is preferably a methoxycarbonyl group or an ethoxycarbonyl group.

The mono $C_{1-6}$ alkylcarbamoyl group of $R^8$ is preferably a methylcarbamoyl group or an ethylcarbamoyl group.

The di $C_{1-6}$ alkylcarbamoyl group of $R^8$ is preferably a dimethylcarbamoyl group or an N-ethyl-N-methylcarbamoyl group.

The $C_{1-6}$ alkylsulfonyloxy group of $R^8$ is preferably a methylsulfonyloxy group or an ethylsulfonyloxy group.

The halo $C_{1-6}$ alkylsulfonyloxy group of $R^8$ is preferably a trifluoromethylsulfonyloxy group or a 2,2,2-trifluoroethylsulfonyloxy group.

The mono $C_{1-6}$ alkylsulfamoyl group of $R^8$ is preferably a methylsulfamoyl group or an ethylsulfamoyl group.

The di $C_{1-6}$ alkylsulfamoyl group of $R^8$ is preferably a dimethylsulfamoyl group or an N-ethyl-N-methylsulfamoyl group.

The mono $C_{2-7}$ alkanoylamino group of $R^8$ is preferably an acetylamino group or a propanoylamino group.

The ($C_{2-7}$ alkanoyl) $C_{1-6}$ alkylamino group of $R^8$ is preferably an N-acetyl-N-methylamino group or an N-acetyl-N-ethylamino group.

The di $C_{2-7}$ alkanoylamino group of $R^8$ is preferably a diacetylamino group or a dipropanoylamino group.

The mono $C_{1-6}$ alkylsulfonylamino group of $R^8$ is preferably a methylsulfonylamino group or an ethylsulfonylamino group.

The mono ($C_{2-7}$ alkoxycarbonyl)amino group of $R^8$ is preferably a methoxycarbonylamino group or a tert-butoxycarbonylamino group.

The $C_{3-6}$ cycloalkyl group of $R^8$ is preferably a cyclopropyl group or a cyclobutyl group.

The cyclic ether group of $R^8$ is preferably an oxetanyl group or an oxolanyl group.

The cyclic amino group of $R^8$ is preferably an azetidin-1-yl group or a pyrrolidin-1-yl group.

The halo cyclic amino group of $R^8$ is preferably a 3,3-difluoroazetidin-1-yl group or a 3,3-difluoropyrrolidin-1-yl group.

m is preferably 0 when p is 1, and m is preferably 1 or 2 when p is 0.

n is preferably 0 or 1.

In one aspect of the present invention, X is preferably a group represented by General Formula (II).

In one aspect of the present invention, the group represented by General Formula (II) is preferably one in which p is 1 and ring Y is one represented by General Formula (III):

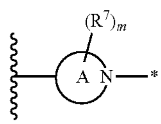

(wherein
the wavy line represents the point of attachment to $L^1$
* represents the point of attachment to $L^2$,
$R^7$ and m are as defined above, and
ring A is a 4- to 10-membered nitrogen-containing heterocyclyl group),
and is more preferably one in which, further, m is 0, or $L^2$ is a single bond.

In one aspect of the present invention, the group represented by General Formula (II) is preferably one in which p is 1 and ring Y is one represented by General Formula:

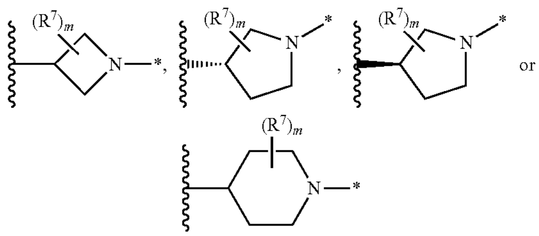

(wherein
the wavy line represents the point of attachment to $L^1$,
* represents the point of attachment to $L^2$, and
$R^7$ and m are as defined above),
and is more preferably one in which, further, m is 0, or $L^2$ is a single bond.

In one aspect of the present invention, the group represented by General Formula (II) is preferably one in which p is 1 and ring Z is a phenyl group or a heteroaryl group.

In one aspect of the present invention, the group represented by General Formula (II) is preferably a group in which p is 1 and ring Z is a phenyl group or a 5- or 6-membered nitrogen-containing heteroaryl group.

In one aspect of the present invention, the group represented by General Formula (II) is preferably one in which p is 1 and ring Z is one represented by General Formula:

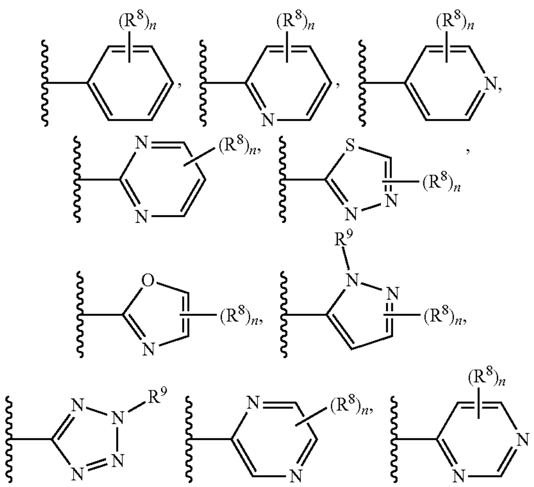

-continued

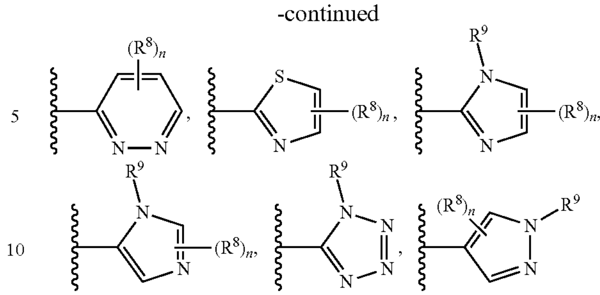

(wherein
the wavy line represents the point of attachment to $L^2$,
$R^8$ and n are as defined above, and
$R^9$ is a $C_{1-6}$ alkyl group, a halo $C_{1-6}$ alkyl group, a hydroxy $C_{1-6}$ alkyl group, a ($C_{1-6}$ alkoxy) $C_{1-6}$ alkyl group, or a $C_{3-6}$ cycloalkyl group. $R^9$ is an option of $R^8$ when $R^8$ is bonded via a nitrogen atom that constitutes ring Z.

The $C_{1-6}$ alkyl group of $R^9$ is preferably a methyl group or an ethyl group.

The halo $C_{1-6}$ alkyl group of $R^9$ is preferably a 2,2,2-trifluoroethyl group or a 2,2,3,3,3-pentafluoropropyl group.

The hydroxy $C_{1-6}$ alkyl group of $R^9$ is preferably a 2-hydroxyethyl group or a 3-hydroxypropyl group.

The ($C_{1-6}$ alkoxy) $C_{1-6}$ alkyl group of $R^9$ is preferably a 2-methoxyethyl group or a 2-ethoxyethyl group.

The $C_{3-6}$ cycloalkyl group of $R^9$ is preferably a cyclopropyl group or a cyclobutyl group.

In one aspect of the present invention, the group represented by General Formula (II) is preferably one in which p is 0, and ring Y is a $C_{3-10}$ cycloalkyl group (the $C_{3-10}$ cycloalkyl group is optionally condensed with a benzene ring or a heteroaryl ring to form a condensed ring group, or optionally forms a bicyclo ring group or a spiro ring group), or a 4- to 10-membered heterocyclyl group (the 4- to 10-membered heterocyclyl group is optionally condensed with a benzene ring or a heteroaryl ring to form a condensed ring group, or optionally forms a bicycle ring group or a spiro ring group.).

In one aspect of the present invention, the group represented by General Formula (II) is preferably one in which p is 0, and ring Y is a $C_{3-10}$ cycloalkyl group (the $C_{3-10}$ cycloalkyl group is optionally condensed with a benzene ring or a heteroaryl ring to form a condensed ring group, or optionally forms a bicyclo ring group or a spiro ring group).

In one aspect of the present invention, the group represented by General Formula (II) is preferably one in which p is 0, and ring Y is a condensed heterocyclyl group obtained by condensing a 4- to 10-membered heterocyclyl group and a benzene ring or a heteroaryl ring.

In one aspect of the present invention, the group represented by General Formula (II) is preferably one in which p is 0 and ring Y is a group represented by General Formula:

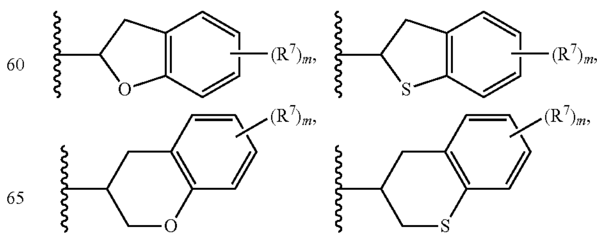

-continued

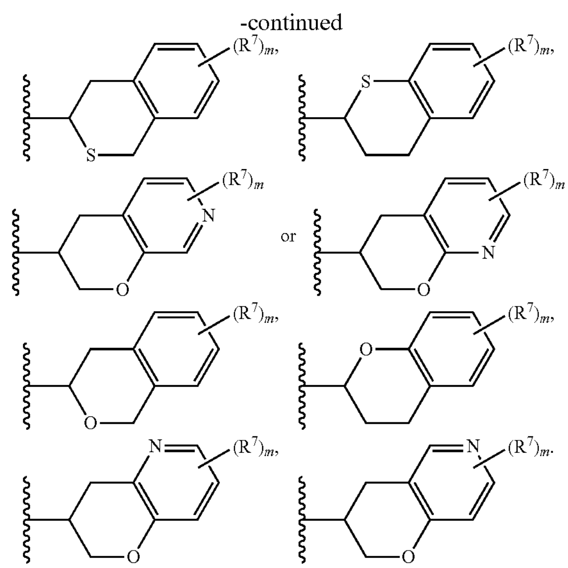

or (wherein the wavy line represents the point of attachment to $L^1$, and $R^7$ and m are as defined above).

In one aspect of the present invention, the group represented by General Formula (II) is preferably one in which $L^1$ is a methylene group, p is 0, and ring Y is a group represented by General Formula:

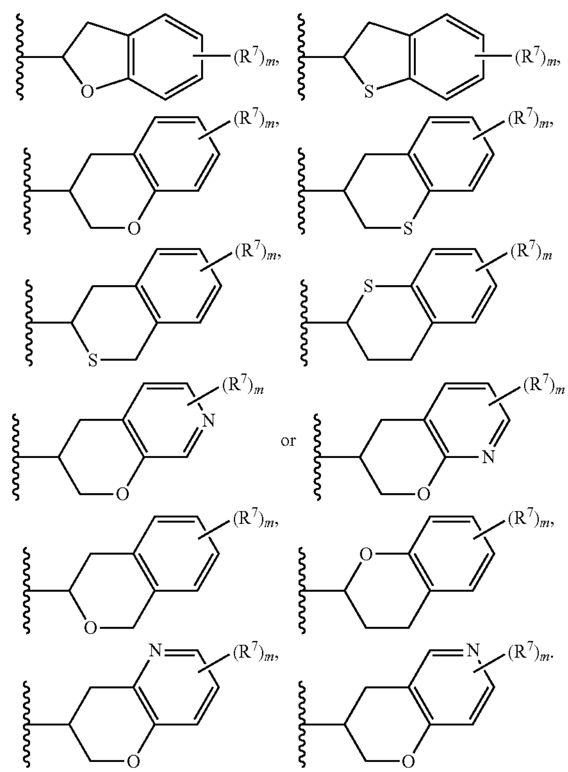

or (wherein the wavy line represents the point of attachment to $L^1$, and $R^7$ and m are as defined above).

In one aspect of the present invention, the group represented by General Formula (II) is preferably one in which p is 0 and ring Y is a group represented by General Formula:

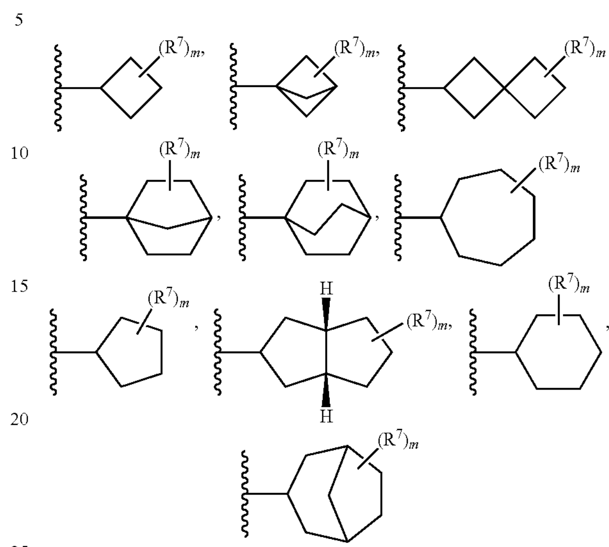

(wherein the wavy line represents the point of attachment to $L^1$, and $R^7$ and m are as defined above).

Specific examples of the compound of the present invention include those described in Examples, and among them, the following compounds (1) to (49) are preferable.

(1) N-[trans-4-(2-hydroxypropan-2-yl)cyclohexyl]-4-(1H-pyrrolo[3,2-c]pyridin-4-yl)benzamide;

(2) N-[trans-4-(2-hydroxypropan-2-yl)cyclohexyl]-4-(thieno[3,2-c]pyridin-4-yl)benzamide;

(3) 4-(furo[3,2-c]pyridin-4-yl)-N-[trans-4-(2-hydroxy-2-methylpropoxy)cyclohexyl]benzamide;

(4) 4-(furo[3,2-c]pyridin-4-yl)-N-[1-(1-methyl-1H-tetrazol-5-yl)piperidin-4-yl]benzamide;

(5) 4-(furo[3,2-c]pyridin-4-yl)-N-{trans-4-[(2,2,2-trifluoroethyl)amino]cyclohexyl}benzamide;

(6) 4-(furo[3,2-c]pyridin-4-yl)-N-[trans-4-(2-hydroxypropan-2-yl)cyclohexyl]benzamide;

(7) 3-fluoro-4-(furo[3,2-c]pyridin-4-yl)-N-[trans-4-(2-hydroxypropan-2-yl)cyclohexyl]benzamide;

(8) N-[trans-4-(2-hydroxypropan-2-yl)cyclohexyl]-4-(6-methylfuro[3,2-c]pyridin-4-yl)benzamide;

(9) N-[trans-4-(2-hydroxypropan-2-yl)cyclohexyl]-4-(7-methylfuro[3,2-c]pyridin-4-yl)benzamide;

(10) 4-(furo[3,2-c]pyridin-4-yl)-N-[1-(pyrimidin-2-yl)piperidin-4-yl]benzamide;

(11) 4-(furo[3,2-c]pyridin-4-yl)-N-[1-(2,2,2-trifluoroethyl)piperidin-4-yl]benzamide;

(12) (S)-4-(furo[3,2-c]pyridin-4-yl)-N-[1-(pyrimidin-2-yl)pyrrolidin-3-yl]benzamide;

(13) (S)-4-(furo[3,2-c]pyridin-4-yl)-N-{1-[5-(hydroxymethyl)pyrimidin-2-yl]pyrrolidin-3-yl}benzamide;

(14) N-(chroman-3-ylmethyl)-4-(furo[3,2-c]pyridin-4-yl)benzamide;

(15) 4-(furo[3,2-c]pyridin-4-yl)-N-(1-propionylpiperidin-4-yl)benzamide;

(16) N-[1-(cyclopropanecarbonyl)piperidin-4-yl]-4-(furo[3,2-c]pyridin-4-yl)benzamide;

(17) 4-(furo[3,2-c]pyridin-4-yl)-N-[1-(oxetan-3-yl)piperidin-4-yl]benzamide;

(18) N-[1-(1,3,4-thiadiazol-2-yl)piperidin-4-yl]-4-(furo[3,2-c]pyridin-4-yl)benzamide;
(19) 4-(furo[3,2-c]pyridin-4-yl)-N-[1-(2-hydroxy-2-methylpropanoyl)piperidin-4-yl]benzamide;
(20) 4-(furo[3,2-c]pyridin-4-yl)-N-(trans-4-hydroxycyclohexyl)benzamide;
(21) 4-(furo[3,2-c]pyridin-4-yl)-N-[trans-4-(1-hydroxycyclopropyl)cyclohexyl]benzamide;
(22) 4-(furo[3,2-c]pyridin-4-yl)-N-{trans-4-[(1-hydroxycyclopropyl)methoxy]cyclohexyl}benzamide;
(23) 4-(furo[3,2-c]pyridin-4-yl)-N-(trans-4-hydroxy-4-methylcyclohexyl)benzamide;
(24) 4-(furo[3,2-c]pyridin-4-yl)-N-(4-hydroxybicyclo[2.2.2]octan-1-yl)benzamide;
(25) 4-(furo[3,2-c]pyridin-4-yl)-N-[trans-4-(methoxy-$d_3$)cyclohexyl]benzamide;
(26) 4-(furo[3,2-c]pyridin-4-yl)-N-(trans-4-isopropoxycyclohexyl)benzamide;
(27) N-{trans-4-[(2,2-difluoroethyl)amino]cyclohexyl}-4-(furo[3,2-c]pyridin-4-yl)benzamide;
(28) 4-(furo[3,2-c]pyridin-4-yl)-N-[trans-4-(oxetane-3-ylamino)cyclohexyl]benzamide;
(29) 4-[6-(hydroxymethyl)furo[3,2-c]pyridin-4-yl]-N-[trans-4-(2-hydroxypropan-2-yl)cyclohexyl]benzamide;
(30) 4-[6-(hydroxymethyl-$d_2$)furo[3,2-c]pyridin-4-yl]-N-[trans-4-(2-hydroxypropan-2-yl)cyclohexyl]benzamide;
(31) 3-fluoro-4-(furo[3,2-c]pyridin-4-yl)-N-[trans-4-(2-hydroxy-2-methylpropoxy)cyclohexyl]benzamide;
(32) N-[trans-4-(1-hydroxycyclopropyl)cyclohexyl]-4-(6-methylfuro[3,2-c]pyridin-4-yl)benzamide;
(33) N-[1-(pyrimidin-2-yl)piperidin-4-yl]-4-(1H-pyrrolo[3,2-c]pyridin-4-yl)benzamide;
(34) N-(trans-4-hydroxycyclohexyl)-4-(1H-pyrrolo[3,2-c]pyridin-4-yl)benzamide;
(35) N-[trans-4-(2-hydroxypropan-2-yl)cyclohexyl]-4-(6-methyl-1H-pyrrolo[3,2-c]pyridin-4-yl)benzamide;
(36) N-[trans-4-(2-hydroxypropan-2-yl)cyclohexyl]-4-(7-methyl-1H-pyrrolo[3,2-c]pyridin-4-yl)benzamide;
(37) 3-fluoro-N-[trans-4-(2-hydroxypropan-2-yl)cyclohexyl]-4-(1H-pyrrolo[3,2-c]pyridin-4-yl)benzamide;
(38) N-[trans-4-(2-hydroxy-2-methylpropoxy)cyclohexyl]-4-(6-methylfuro[3,2-c]pyridin-4-yl)benzamide;
(39) N-(4-hydroxybicyclo[2.2.2]octan-1-yl)-4-(6-methylfuro[3,2-c]pyridin-4-yl)benzamide;
(40) N-(trans-4-hydroxy-4-methylcyclohexyl)-4-(6-methylfuro[3,2-c]pyridin-4-yl)benzamide;
(41) 3-fluoro-4-(furo[3,2-c]pyridin-4-yl)-N-(4-hydroxybicyclo[2.2.2]octan-1-yl)benzamide;
(42) 3-fluoro-4-(furo[3,2-c]pyridin-4-yl)-N-(trans-4-hydroxy-4-methylcyclohexyl)benzamide;
(43) 3-fluoro-4-(furo[3,2-c]pyridin-4-yl)-N-{trans-4-[(1-hydroxycyclopropyl)methoxy]cyclohexyl}benzamide;
(44) 4-(furo[3,2-c]pyridin-4-yl)-N-[cis-4-(2-hydroxy-2-methylpropoxy)cyclohexyl]benzamide;
(45) 4-(furo[3,2-c]pyridin-4-yl)-N-(4-hydroxybicyclo[2.2.1]heptan-1-yl)benzamide;
(46) N-(4-cyanobicyclo[2.2.2]octan-1-yl)-4-(furo[3,2-c]pyridin-4-yl)benzamide;
(47) 4-[4-(furo[3,2-c]pyridin-4-yl)benzamide]bicyclo[2.2.2]octane-1-carboxamide;
(48) 4-(furo[3,2-c]pyridin-4-yl)-N-{cis-4-[(1-hydroxycyclopropyl)methoxy]cyclohexyl}benzamide; and
(49) 4-(furo[3,2-c]pyridin-4-yl)-N-[cis-4-(2-hydroxypropan-2-yl)cyclohexyl]benzamide.

The compound of Formula (I) may have a chiral center, a chiral axis, and a chiral plane.

The compound of Formula (I) may be produced as racemates, racemic mixtures, and individual diastereomers.

The compound of Formula (I) includes all possible isomers, including optical isomers, and mixtures thereof.

The compound of Formula (I) may exist as tautomers. Even when only one tautomeric structure is depicted herein, both tautomeric forms are included in the invention.

The compound of Formula (I) includes isotopologues in which 1 or 2 or more atoms in the molecule are substituted with an isotope thereof. In the present specification, an isotope means an atom having the same atomic number and a different mass number. Therefore, "substitution with an isotope" in the present specification means substitution with an atom having the same atomic number but having a mass number different from that normally existing in nature.

For example, the hydrogen atom that constitutes the compound of Formula (I) may be substituted with $^{2}H$ (D) or $^{3}H$ (T), and similarly, the carbon atom that constitutes Formula (I) may be substituted with $^{11}C$, $^{13}C$, or $^{14}C$. Isotopologues substituted with stable isotopes such as $^{2}H$ (D) are useful as therapeutic advantages may be obtained due to higher metabolic stability. On the other hand, isotopologues substituted with radioisotopes such as $^{3}H$ (T) and $^{14}C$ are useful in drug and/or substrate tissue distribution studies. These isotopologues can be prepared by the methods disclosed herein or similar methods using appropriate reagents containing the corresponding isotopes.

The "pharmaceutically acceptable salt" of the compound of Formula (I) is not particularly limited as long as it is pharmaceutically acceptable. Examples thereof include a base addition salt of a carboxyl group, a hydroxy group, or an acidic heteroaryl group when the compound of Formula (I) has a carboxyl group, a hydroxy group, or an acidic heteroaryl group (tetrazolyl group and the like), and an acid addition salt of an amino group or a basic heteroaryl group when the compound of Formula (I) has an amino group or a basic heteroaryl group.

Examples of the base addition salt include alkali metal salts (for example, sodium salts and potassium salts); alkaline earth metal salts (for example, calcium salts and magnesium salts); ammonium salts; and organic amine salts (for example, trimethylamine salts, triethylamine salts, dicyclohexylamine salts, ethanolamine salts, diethanolamine salts, triethanolamine salts, procaine salts, and N,N'-dibenzylethylenediamine salts).

Examples of the acid addition salt include inorganic acid salts (for example, hydrochlorides, sulfates, nitrates, phosphates, and perchlorates); organic acid salts (for example, maleates, fumarates, tartrates, citrates, ascorbates, and trifluoroacetates); and sulfonates (for example, methanesulfonates, isethionates, benzenesulfonates, p-toluenesulfonates).

The "pharmaceutically acceptable salt" can be produced according to a method used in the field of organic synthesis. For example, the pharmaceutically acceptable salt can be produced by neutralizing and titrating a solution of a free form of the compound of Formula (I) with an alkaline solution or an acidic solution.

The "pharmaceutically acceptable salt" also includes solvates with pharmaceutically acceptable solvents such as water and ethanol.

The production method of the compound of the present invention will be specifically described, but the production method is not limited thereto. The reaction order can be appropriately changed, and the reaction may be performed starting from a step considered to be rational.

A substituent transformation (interconversion or further modification of a substituent) step may be inserted between each step.

When a reactive functional group is present, protection/deprotection may be performed. As the protecting group and the method for protection/deprotection, those used in the field of organic synthesis can be used. For example, a method described in the literature [See Protective Groups in Organic Synthesis, 3 rd edition, T. W. Greene, John Wiley & Sons (1999)] or a method similar thereto can be appropriately used. The protection/deprotection can be performed any number of times in any step as necessary.

Unless otherwise specified, a free compound is used for convenience in the following production methods, but a salt of the free compound can also be used for production.

In order to promote the progress of the reaction, reagents other than the mentioned reagents may be appropriately used. If necessary, microwave irradiation may be used for heating in each reaction.

Raw material compounds whose production method is not described are commercially available, or can be easily prepared by combining known synthesis reactions.

The compound obtained in each step may be isolated and purified according to conventional means (crystallization, recrystallization, column chromatography, preparative HPLC, and the like), but the reaction may proceed to the next step without isolation or purification.

Production Method 1: Production Method of Compound of Formula (I) (1)

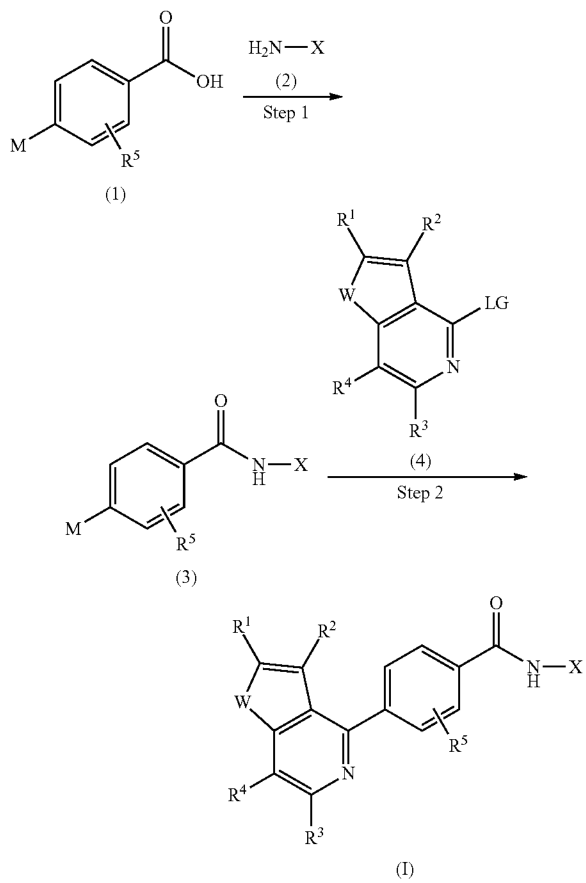

(1)

(3)

(I)

(wherein $R^1$, $R^2$, $R^3$, $R^4$, $R^5$, W, and X are as defined above,

M is a boronic acid, a boronate ester, a trifluoroborate salt, a cyclic triolborate salt or the like, LG represents a leaving group such as a halogen atom and a trifluoromethanesulfonyloxy group.)

Step 1:

A compound of Formula (1) (hereinafter, also referred to as "compound (1)") and a compound of Formula (2) (hereinafter, also referred to as "compound (2)") are reacted in the presence of a condensing agent to give a compound of Formula (3) (hereinafter, also referred to as "compound (3)").

Examples of the compound (1) include a boronic acid (1a), a boronate ester (1b), a trifluoroborate salt (1c), and a cyclic triolborate salt (1d) shown below.

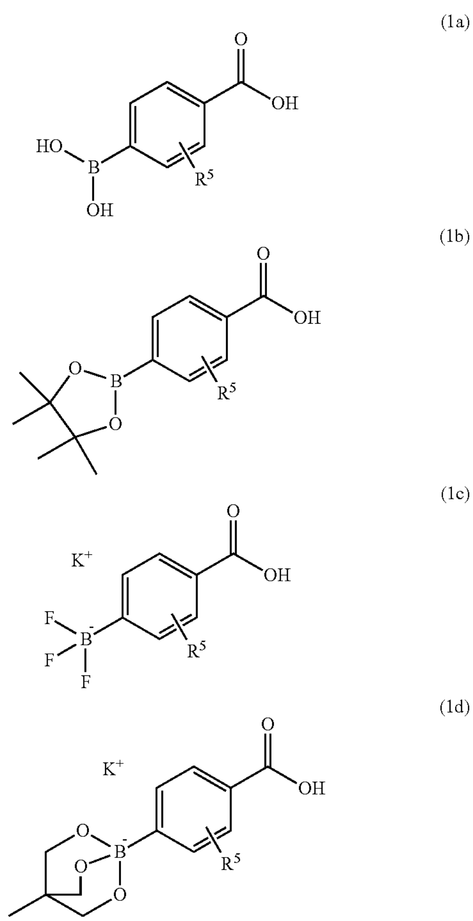

(1a)

(1b)

(1c)

(1d)

As the compound (2), a commercially available product can be used, but the compound (2) may be produced by appropriately combining a known method, a method described in Examples, and a method similar thereto as necessary.

Examples of the condensing agent include N,N'-dicyclohexylcarbodiimide (DCC), 1-ethyl-3-(3-dimethylaminopropyl) carbodiimide hydrochloride (EDC), N,N'-carbonyldiimidazole (CDI), diphenylphosphate azide (DPPA), (1-cyano-2-ethoxy-2-oxoethylideneaminooxy)dimethylaminomorpholinocarbenium hexafluorophosphate (COMU), and O-(7-azabenzotriazol-1-yl)-N,N,N',N'-tetramethyluronium hexafluorophosphate (HATU).

In step 1, a base may be used as necessary. Examples of the base include N,N-diisopropylethylamine, triethylamine, sodium carbonate, potassium carbonate, cesium carbonate, sodium bicarbonate, tripotassium phosphate, potassium fluoride, cesium fluoride, potassium tert-butoxide, lithium hydroxide, sodium hydroxide, and potassium hydroxide, and N,N-diisopropylethylamine and triethylamine are particularly preferable.

The reaction solvent is not particularly limited as long as the reaction solvent does not interfere with the reaction, examples thereof include N,N-dimethylformamide, N,N-dimethylacetamide, N-methylpyrrolidone, tetrahydrofuran, 1,4-dioxane, dichloromethane, chloroform, dimethylsulfoxide, acetonitrile, ethyl acetate, toluene, methanol, ethanol, and water, and N,N-dimethylformamide, N,N-dimethylacetamide, N-methylpyrrolidone, dichloromethane, and chloroform are particularly preferable.

The amount used of the compound (2) is usually 1 to 3 mol, and preferably 1 to 2 mol relative to 1 mol of the compound (1).

The amount used of the base is usually 1 to 10 mol, and preferably 1 to 3 mol relative to 1 mol of the compound (1).

The reaction temperature is usually 0° C. to 100° C., and preferably 0° C. to 60° C.

The reaction time is usually 10 minutes to 24 hours, and preferably 30 minutes to 5 hours.

Step 2:

A compound (3) and a compound of Formula (4) (hereinafter, also referred to as "compound (4)") are subjected to a coupling reaction in the presence of a palladium catalyst and a base to give a compound of Formula (I).

As the compound (4), a commercially available product can be used, but the compound (4) may be produced by appropriately combining a known method, a method described in Examples, and a method similar thereto as necessary.

Examples of the palladium catalyst include tetrakis(triphenylphosphine)palladium (0), palladium (II) acetate, tris(dibenzylideneacetone)dipalladium (0), [1,1'-bis(diphenylphosphino)ferrocene]dichloropalladium (II), [1,1'-bis(diphenylphosphino)ferrocene]dichloropalladium (II) dichloromethane complex, [1,3-bis(2,6-diisopropylphenyl)imidazol-2-ylidene]chloro[3-phenylallyl]palladium (II), and [1,3-bis(2,6-diisopropylphenyl)-4,5-dihydroimidazol-2-ylidene]chloro[3-phenylallyl]palladium (II).

In step 2, a phosphine ligand may be used as necessary. Examples of the phosphine ligand include triphenylphosphine, tris(2-methylphenyl)phosphine, tri (2-furyl)phosphine, tri-tert-butylphosphine, (4-dimethylaminophenyl)di-tert-butylphosphine (Amphos), 2-[di(tert-butyl)phosphino]-1,1'-biphenyl (JohnPhos), 2-[di(tert-butyl)phosphino]-2'-N,N-dimethylamino-1,1'-biphenyl (tBuDavePhos), 2-(dicyclohexylphosphino)-1,1'-biphenyl (CyJohnPhos), 2-(dicyclohexylphosphino)-2'-N,N-dimethylamino-1,1'-biphenyl (DavePhos), 2-dicyclohexylphosphino-2',6'-dimethoxybiphenyl (SPhos), 2-dicyclohexylphosphino-2 ', 4', 6'-triisopropylbiphenyl (XPhos), and 4,5-bis(diphenylphosphino)-9,9-dimethylxanthene (Xantphos).

Examples of the base include sodium carbonate, potassium carbonate, cesium carbonate, sodium bicarbonate, tripotassium phosphate, potassium fluoride, cesium fluoride, potassium tert-butoxide, lithium hydroxide, sodium hydroxide, potassium hydroxide, N,N-diisopropylethylamine, and triethylamine.

The reaction solvent is not particularly limited as long as the reaction solvent does not interfere with the reaction, and examples thereof include tetrahydrofuran, 1,4-dioxane, 1,2-dimethoxyethane, toluene, methanol, ethanol, acetonitrile, and water.

The reaction solvent may be a single solvent or a mixed solvent of 2 or more kinds.

Examples of the mixed solvent include a combination of methanol and water, a combination of ethanol and water, a combination of toluene and water, and a combination of 1,4-dioxane and water.

The amount used of the compound (3) is usually 1 to 3 mol, and preferably 1 to 2 mol relative to 1 mol of the compound (4).

The amount used of the palladium catalyst is usually 0.01 to 0.5 mol, and preferably 0.03 to 0.2 mol relative to 1 mol of the compound (4).

The amount used of the base is usually 1 to 10 mol, and preferably 1 to 3 mol relative to 1 mol of the compound (4).

The reaction temperature is usually 20° C. to 160° C., and preferably 20° C. to 120° C.

The reaction time is usually 10 minutes to 24 hours, and preferably 30 minutes to 5 hours.

Production method 2: production method of compound of Formula (I) (2)

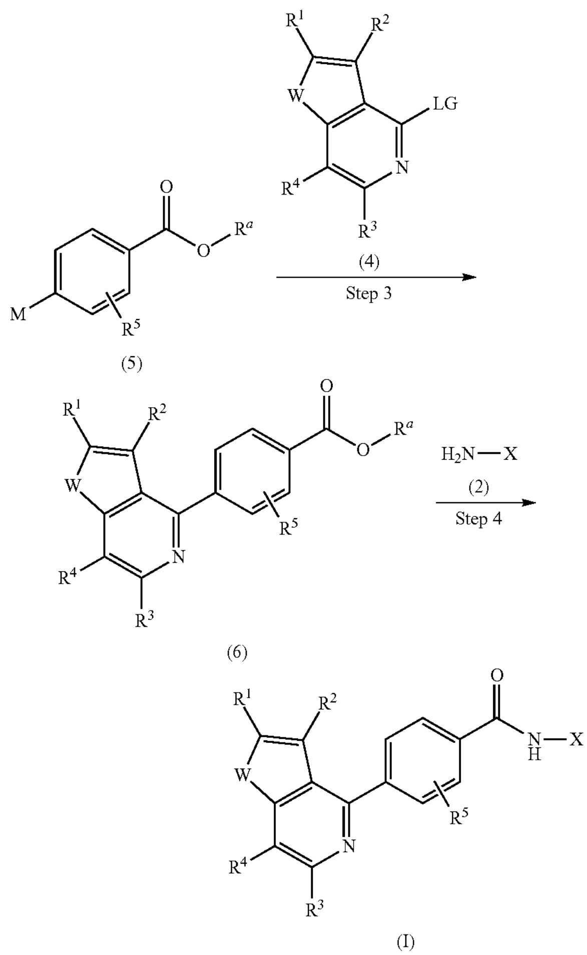

(5)

(6)

(I)

(wherein $R^1$, $R^2$, $R^3$, $R^4$, $R^5$, W, and X are as defined above,

M is a boronic acid, a boronate ester, a trifluoroborate salt, a cyclic triolborate salt or the like, LG is a leaving group such as a halogen atom and a trifluoromethanesulfonyloxy group, and $R^a$ represents a $C_{1-6}$ alkyl group.)

Step 3:

A compound of Formula (5) (hereinafter, also referred to as "compound (5)") and a compound (4) are subjected to a coupling reaction in the presence of a palladium catalyst and a base to give a compound of Formula (6) (hereinafter, also referred to as "compound (6)").

Examples of the compound (5) include a boronic acid (5a), a boronate ester (5b), a trifluoroborate salt (5c), and a cyclic triolborate salt (5d) shown below.

(5a)

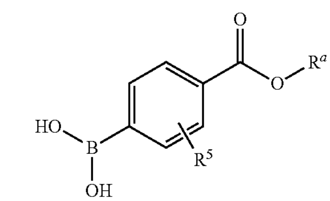

(5b)

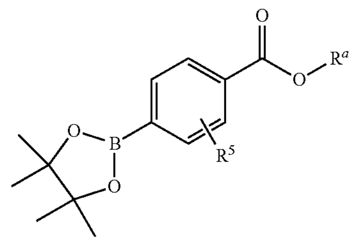

(5c)

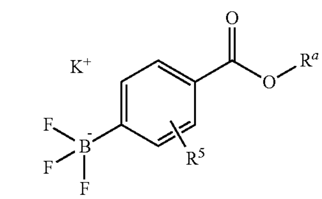

(5d)

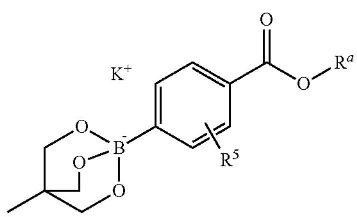

As the compound (4), a commercially available product can be used, but the compound (4) may be produced by appropriately combining a known method, a method described in Examples, and a method similar thereto as necessary.

Examples of the palladium catalyst include tetrakis(triphenylphosphine)palladium (0), palladium (II) acetate, tris(dibenzylideneacetone)dipalladium (0), [1,1'-bis(diphenylphosphino)ferrocene]dichloropalladium (II), [1,1'-bis(diphenylphosphino)ferrocene]dichloropalladium (II) dichloromethane complex, [1,3-bis(2,6-diisopropylphenyl)imidazol-2-ylidene]chloro[3-phenylallyl]palladium (II), and [1,3-bis(2,6-diisopropylphenyl)-4,5-dihydroimidazol-2-ylidene]chloro[3-phenylallyl]palladium (II).

In step 3, a phosphine ligand may be used as necessary. Examples of the phosphine ligand include triphenylphosphine, tris(2-methylphenyl)phosphine, tri (2-furyl)phosphine, tri-tert-butylphosphine, (4-dimethylaminophenyl)di-tert-butylphosphine (Amphos), 2-[di(tert-butyl)phosphino]-1,1'-biphenyl (JohnPhos), 2-[di(tert-butyl)phosphino]-2'-N,N-dimethylamino-1,1'-biphenyl (tBuDavePhos), 2-(dicyclohexylphosphino)-1,1'-biphenyl (CyJohnPhos), 2-(dicyclohexylphosphino)-2'-N,N-dimethylamino-1,1'-biphenyl (DavePhos), 2-dicyclohexylphosphino-2',6'-dimethoxybiphenyl (SPhos), 2-dicyclohexylphosphino-2',4',6'-triisopropylbiphenyl (XPhos), and 4,5-bis(diphenylphosphino)-9,9-dimethylxanthene (Xantphos).

Examples of the base include sodium carbonate, potassium carbonate, cesium carbonate, sodium bicarbonate, tripotassium phosphate, potassium fluoride, cesium fluoride, potassium tert-butoxide, lithium hydroxide, sodium hydroxide, potassium hydroxide, N,N-diisopropylethylamine, and triethylamine.

The reaction solvent is not particularly limited as long as the reaction solvent does not interfere with the reaction, and examples thereof include tetrahydrofuran, 1,4-dioxane, 1,2-dimethoxyethane, toluene, methanol, ethanol, acetonitrile, and water.

The reaction solvent may be a single solvent or a mixed solvent of 2 or more kinds.

Examples of the mixed solvent include a combination of methanol and water, a combination of ethanol and water, a combination of toluene and water, and a combination of 1,4-dioxane and water.

The amount used of the compound (5) is usually 1 to 3 mol, and preferably 1 to 2 mol relative to 1 mol of the compound (4).

The amount used of the palladium catalyst is usually 0.01 to 0.5 mol, and preferably 0.03 to 0.2 mol relative to 1 mol of the compound (4).

The amount used of the base is usually 1 to 10 mol, and preferably 1 to 3 mol relative to 1 mol of the compound (4).

The reaction temperature is usually 20° C. to 160° C., and preferably 20° C. to 120° C.

The reaction time is usually 10 minutes to 24 hours, and preferably 30 minutes to 5 hours.

Step 4:

The compound (6) is amidated with the compound (2) in the presence of a base catalyst to give a compound of Formula (I).

As the compound (2), a commercially available product can be used, but the compound (2) may be produced by appropriately combining a known method, a method described in Examples, and a method similar thereto as necessary.

Examples of the base catalyst include 1,5,7-triazabicyclo[4.4.0]dec-5-ene, 1,8-diazabicyclo[5.4.0]-7-undecene (DBU), and sodium methoxide.

The reaction solvent is not particularly limited as long as the reaction solvent does not interfere with the reaction, and examples thereof include toluene, 2-methyltetrahydrofuran, tetrahydrofuran, 1,2-dimethoxyethane, 1,4-dioxane, dichloromethane, chloroform, ethyl acetate, acetonitrile, and dimethyl sulfoxide, and toluene, 2-methyltetrahydrofuran, and tetrahydrofuran are particularly preferable.

The amount used of the compound (2) is usually 1 to 20 mol, and preferably 1 to 10 mol relative to 1 mol of the compound (6).

The amount used of the base catalyst is usually 0.01 to 1 mol, and preferably 0.1 to 0.6 mol relative to 1 mol of the compound (6).

The reaction temperature is usually 20° C. to 160° C., and preferably 40° C. to 110° C.

The reaction time is usually 1 hour to 48 hours, and preferably 5 hours to 48 hours.

Production method 3: production method of compound of Formula (I) (3)

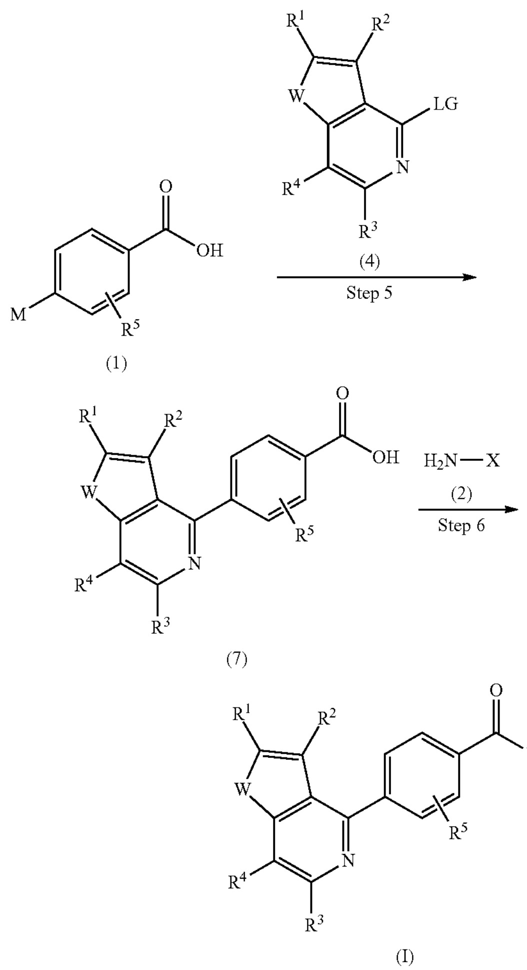

(1) (4) (7) (2) (7) (I)

(wherein $R^1$, $R^2$, $R^3$, $R^4$, $R^5$, W, and X are as defined above,

M is a boronic acid, a boronate ester, a trifluoroborate salt, a cyclic triolborate salt or the like, LG represents a leaving group such as a halogen atom and a trifluoromethanesulfonyloxy group.)

Step 5:

According to the method of step 2 in production method 1, the compound (1) and the compound (4) are subjected to a coupling reaction in the presence of a palladium catalyst and a base to give a compound of Formula (7) (hereinafter, also referred to as "compound (7)").

Step 6:

According to the method of step 1 in production method 1, the compound (7) and the compound (2) are reacted in the presence of a condensing agent to give a compound of Formula (I).

Production Method 4: Production Method of Compound of Formula (7)

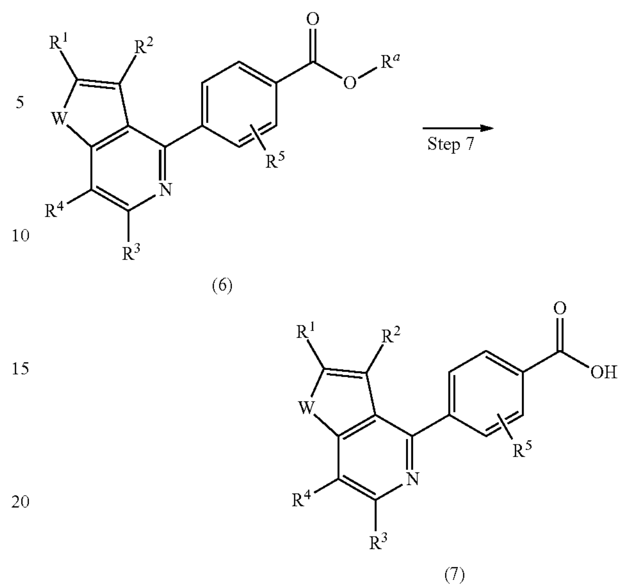

(6) (7)

(wherein $R^1$, $R^2$, $R^3$, $R^4$, $R^5$, and W are as defined above, and $R^a$ represents a $C_{1-6}$ alkyl group.)

Step 7:

The compound (6) is hydrolyzed in the presence of a base to give the compound (7).

Examples of the base include lithium hydroxide, sodium hydroxide, and potassium hydroxide.

The reaction solvent is not particularly limited as long as the reaction solvent does not interfere with the reaction, and examples thereof include methanol, ethanol, 1-propanol, 2-propanol, 1-butanol, 2-butanol, tert-butanol, and water, and methanol, ethanol, and water are preferable.

The reaction solvent may be a single solvent or a mixed solvent of 2 or more kinds.

Examples of the mixed solvent include a combination of methanol and water and a combination of ethanol and water.

The amount used of the base is usually 1 mol to large excess relative to 1 mol of the compound (6).

The reaction temperature is usually 0° C. to 160° C., and preferably 0° C. to 130° C.

The reaction time is usually 0.5 hours to 48 hours, and preferably 10 minutes to 5 hours.

Production method 5: production method of compound of Formula (12)

The compound of Formula (12) corresponds to a compound in which X is a group of General Formula (II) (wherein $L^1$ is a single bond, ring Y is a group of General Formula (III), $L^2$ is a single bond, and p is 1) in Formula (I).

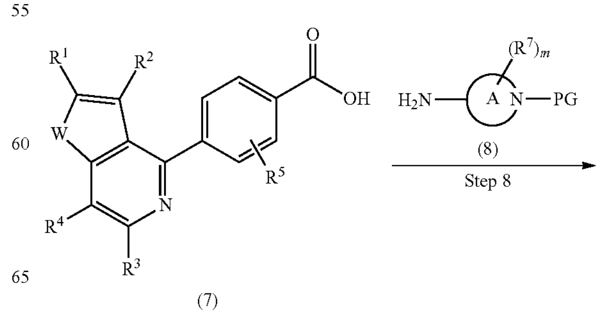

(7) (8)

-continued

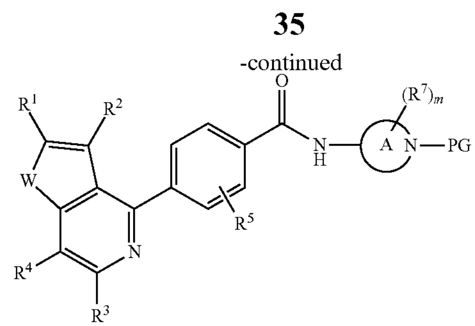

Step 9

(9)

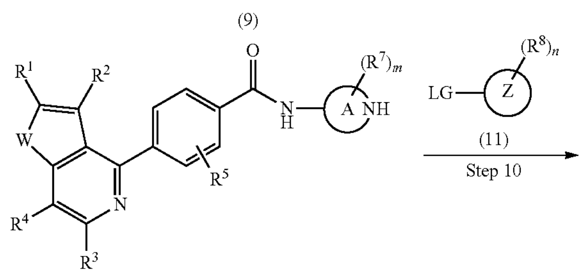

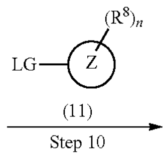

(10)

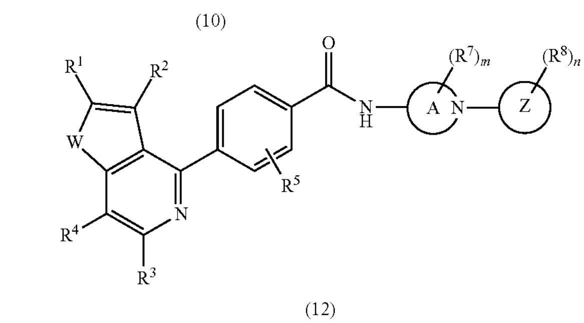

(12)

(wherein $R^1$, $R^2$, $R^3$, $R^4$, $R^5$, $R^7$, $R^8$, ring A, ring Z, m, and n are as defined above, PG is a protecting group for an amine, and LG represents a leaving group such as a halogen atom and a trifluoromethanesulfonyloxy group.)

Step 8:

According to the method of step 1 in production method 1, the compound (7) and a compound of Formula (8) (hereinafter, also referred to as "compound (8)") are reacted in the presence of a condensing agent to give a compound of Formula (9) (hereinafter, also referred to as "compound (9)").

Examples of the compound (8) include azetidine (8a), pyrrolidine (8b-1), pyrrolidine (8b-2), and piperidine (8c) shown below.

(8a)

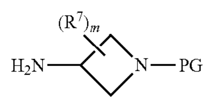

(8b-1)

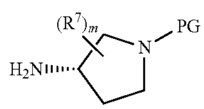

(8b-2)

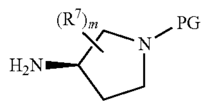

-continued (8c)

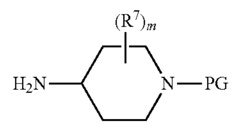

PG (protecting group for an amine) is not particularly limited as long as the PG has the function, and examples thereof include a benzyl group, a 4-methoxybenzyl group, a 2,4-dimethoxybenzyl group, a 3,4-dimethoxybenzyl group, a trityl group, a methoxycarbonyl group, an ethoxycarbonyl group, a propyloxycarbonyl group, a tert-butoxycarbonyl group, and a benzyloxycarbonyl group, and a tert-butoxycarbonyl group and a 4-methoxybenzyl group are particularly preferable.

Step 9:

The compound (9) is deprotected under acidic or hydrogenation conditions to give a compound of Formula (10) (hereinafter, also referred to as "compound (10)").

Deprotection Under Acidic Conditions

Examples of the acid used under acidic conditions include hydrogen chloride, hydrochloric acid, sulfuric acid, trifluoroacetic acid, acetic acid, formic acid, p-toluenesulfonic acid, methanesulfonic acid, and pyridinium p-toluenesulfonate.

The reaction solvent is not particularly limited as long as the reaction solvent does not interfere with the reaction, and examples thereof include tetrahydrofuran, 1,4-dioxane, dichloromethane, chloroform, acetonitrile, ethyl acetate, toluene, and water.

The amount used of the acid is usually 0.01 mol to large excess relative to 1 mol of the compound (9).

The reaction temperature is usually 0° C. to 100° C., and preferably 0° C. to 40° C.

The reaction time is usually 10 minutes to 24 hours, and preferably 10 minutes to 5 hours.

Deprotection Under Hydrogenation Conditions

A catalyst is used under hydrogenation conditions. Examples of the catalyst include 5% palladium-activated carbon, 10% palladium-activated carbon, 20% palladium hydroxide-activated carbon, Raney nickel, platinum, and platinum oxide.

The reaction solvent is not particularly limited as long as the reaction solvent does not interfere with the reaction, and examples thereof include methanol, ethanol, 1-propanol, 2-propanol, tetrahydrofuran, 1,4-dioxane, toluene, and ethyl acetate.

The amount used of the catalyst is usually 0.01 to 1 mol, and preferably 0.05 to 0.2 mol relative to 1 mol of the compound (9).

The reaction temperature is usually 0° C. to 100° C., and preferably 10° C. to 40° C.

The reaction time is usually 10 minutes to 24 hours, and preferably 30 minutes to 5 hours.

Step 10:

The compound (10) and a compound of Formula (11) (hereinafter, also referred to as "compound (11)") are reacted in the presence of a base to give a compound (12).

Examples of the compound (11) include pyridine (11a), pyridine (11b), pyrimidine (11c), pyrazine (11d), pyrimidine (11e), pyridazine (11f), thiazole (11g), thiadiazole (11h), oxazole (11i), pyrazole (11j), imidazole (11k), imidazole (11l), tetrazole (11m), pyrazole (11n), and tetrazole (11o) shown below.

(11a)

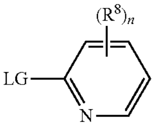

(11b)

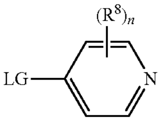

(11c)

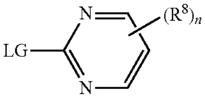

(11d)

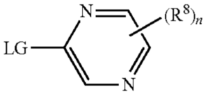

(11e)

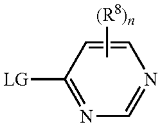

(11f)

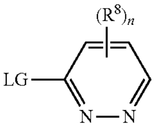

(11g)

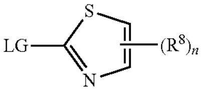

(11h)

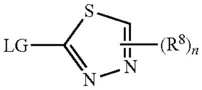

(11i)

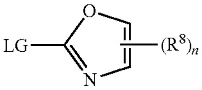

(11j)

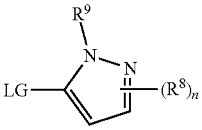

(11k)

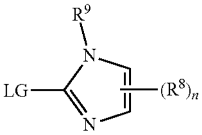

(11l)

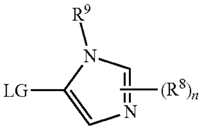

-continued (11m)

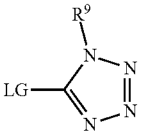

(11n)

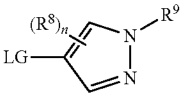

(11o)

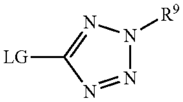

Examples of the base include N,N-diisopropylethylamine, triethylamine, sodium carbonate, potassium carbonate, cesium carbonate, sodium bicarbonate, tripotassium phosphate, potassium fluoride, cesium fluoride, sodium tert-butoxide, potassium tert-butoxide, lithium hydroxide, sodium hydroxide, potassium hydroxide, sodium hydride, and potassium hydride.

The reaction solvent is not particularly limited as long as the reaction solvent does not interfere with the reaction, examples thereof include N,N-dimethylformamide, N,N-dimethylacetamide, N-methylpyrrolidone, tetrahydrofuran, 1,4-dioxane, dichloromethane, chloroform, dimethylsulfoxide, acetonitrile, ethyl acetate, toluene, methanol, ethanol, and water, and N,N-dimethylformamide, N,N-dimethylacetamide, N-methylpyrrolidone, and dimethylsulfoxide are particularly preferable.

The amount used of the compound (11) is usually 1 to 3 mol, and preferably 1 to 2 mol relative to 1 mol of the compound (10).

The amount used of the base is usually 1 to 10 mol, and preferably 1 to 3 mol relative to 1 mol of the compound (10).

The reaction temperature is usually 0° C. to 200° C., and preferably 0° C. to 160° C.

The reaction time is usually 10 minutes to 24 hours, and preferably 30 minutes to 10 hours.

Production method 6: production method of compound of Formula (14)

The compound of Formula (14) corresponds to a compound in which X is a group of General Formula (II) (wherein $L^1$ is a single bond, ring Y is a group of General Formula (III), $L^2$ is a single bond, and p is 1) in Formula (I).

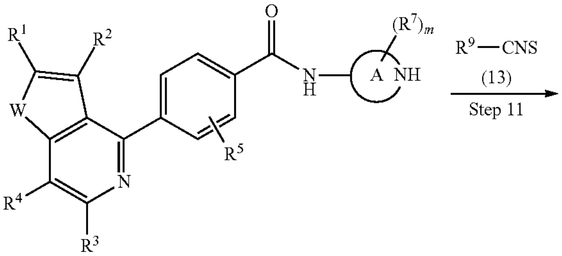

(10)

-continued

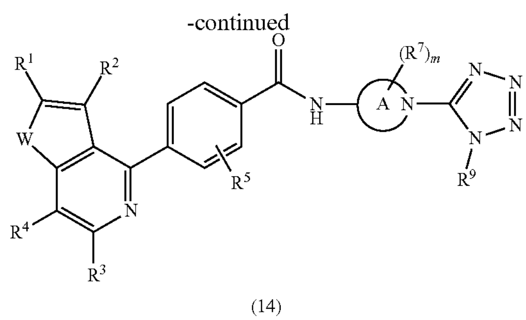

(14)

(wherein $R^1$, $R^2$, $R^3$, $R^4$, $R^5$, $R^7$, $R^9$, ring A, and m are as defined above.)

Step 11:

A thiourea intermediate produced by reaction of the compound (10) and a compound of Formula (13) (hereinafter, also referred to as "compound (13)") is reacted with an alkylating agent to obtain an S-alkylisothiourea intermediate, which is then reacted with sodium azide to give a compound of Formula (14) (hereinafter, also referred to as "compound (14)").

As the compound (13), a commercially available product can be used, but the compound (13) may be produced by a known method or a method similar thereto.

Examples of the alkylating agent include 1,3-propane sultone, 1,4-butane sultone, methyl iodide, ethyl iodide, dimethyl sulfate, and diethyl sulfate, and 1,3-propane sultone is particularly preferable. When 1,3-propane sultone is used as the alkylating agent, it is preferable to inactivate excessive 1,3-propane sultone by addition of a base and then perform a reaction with sodium azide.

Examples of the base include triethylamine, N,N-diisopropylethylamine, and pyridine, and triethylamine is particularly preferable.

The alkylating agent and the base may be added simultaneously.

The reaction solvent is not particularly limited as long as the reaction solvent does not interfere with the reaction, examples thereof include acetonitrile, N,N-dimethylformamide, N,N-dimethylacetamide, N-methylpyrrolidone, dimethylsulfoxide, tetrahydrofuran, 1,4-dioxane, ethyl acetate, and toluene, and acetonitrile, N,N-dimethylformamide, N,N-dimethylacetamide, and N-methylpyrrolidone are particularly preferable.

The amount used of the compound (13) is usually 1 to 3 mol, and preferably 1 to 2 mol relative to 1 mol of the compound (10).

The amount used of the alkylating agent is usually 1 to 5 mol, and preferably 1 to 3 mol relative to 1 mol of the compound (10).

The amount used of the base is usually 1 to 10 mol, and preferably 1 to 6 mol relative to 1 mol of the compound (10).

The amount used of the sodium azide is usually 1 to 20 mol, and preferably 1 to 12 mol relative to 1 mol of the compound (10).

The reaction temperature after addition of the compound (13) is usually 20° C. to 160° C. and preferably 100° C., the reaction temperature after addition of the alkylating agent is usually 20° C. to 160° C. and preferably 100° C., the reaction temperature after addition of the base is usually 20° C. to 160° C. and preferably 100° C., and the reaction temperature after addition of sodium azide is usually 20° C. to 160° C. and preferably 50° C. to 100° C.

The reaction time after addition of the compound (13) is usually 10 minutes to 24 hours and preferably 30 minutes to 8 hours, the reaction time after addition of the alkylating agent is usually 10 minutes to 72 hours and preferably 1 hour to 16 hours, the reaction time after addition of the base is usually 5 minutes to 1 hour and preferably 30 minutes to 1 hour, and the reaction time after addition of sodium azide is usually 10 minutes to 72 hours and preferably 1 hour to 12 hours.

A pharmaceutical composition and an H-PGDS inhibitor comprising the compound of the present invention will be described.

"H-PGDS" refers to hematopoietic prostaglandin D synthase (hematopoietic PGD synthase).

"Inhibiting H-PGDS" refers to deleting or decreasing the activity of H-PGDS as prostaglandin D synthase, for example, inhibiting the activity of H-PGDS under the conditions described in Example 222 described later.

The "H-PGDS inhibitor" refers to an agent for inhibiting H-PGDS.

The "pharmaceutical composition for treating or preventing a disease involving H-PGDS" refers to a pharmaceutical composition for treating or preventing a disease involving H-PGDS by inhibiting H-PGDS.

Examples of the "disease involving H-PGDS" include asthma, chronic obstructive pulmonary disease, allergic rhinitis, sinusitis, eosinophilic pneumonia, atherosclerosis, rheumatoid arthritis, cystic fibrosis, actinic keratosis, chronic urticaria, dermatitis, muscular dystrophy, sarcopenia, disuse muscle atrophy, muscle damage, wounds, dermatomyositis, amyotrophic lateral sclerosis, cerebral infarction, myocardial infarction, ischemic bowel disease, ischemic renal disease, ischemic stomach disease, ischemic liver disease, diabetic ischemic limb, and Buerger's disease.

The pharmaceutical composition and inhibitor of the present invention can be provided as a preparation.

The "preparation" may contain a pharmaceutically acceptable carrier together with the compound of the present invention.

The preparation can be produced using preparation techniques commonly used in the pharmaceutical field.

Examples of the "pharmaceutically acceptable carrier" include solvents (for example, purified water, ethanol, propylene glycol, macrogol, sesame oil, corn oil, and olive oil), excipients (for example, lactose, white sugar, D-mannitol, starch, corn starch, crystalline cellulose, and light anhydrous silicic acid), disintegrants (for example, starch, carboxymethyl cellulose, calcium carboxymethyl cellulose, sodium carboxymethyl starch, and L-hydroxypropyl cellulose), binders (for example, crystalline cellulose, white sugar, D-mannitol, dextrin, hydroxypropyl cellulose, hydroxypropyl methylcellulose, polyvinylpyrrolidone, starch, sucrose, gelatin, methylcellulose, and sodium carboxymethylcellulose), lubricants (for example, magnesium stearate, calcium stearate, talc, and colloidal silica), wetting agents (for example, propylene glycol monostearate, sorbitan monooleate, diethylene glycol monolaurate, and polyoxyethylene lauryl ether), antioxidants (for example, sodium sulfite, potassium sulfite, ascorbic acid, and α-tocopherol), suspending agents (stearyl triethanolamine, sodium lauryl sulfate, lauryl aminopropionic acid, lecithin, benzalkonium chloride, benzethonium chloride, glycerin monostearate, polyvinyl alcohol, polyvinyl pyrrolidone, sodium carboxymethyl cellulose, methyl cellulose, hydroxymethyl cellulose, hydroxyethyl cellulose, and hydroxypropyl cellulose), preservatives (for example, ethyl parahydroxybenzoate, chlorobutanol, benzyl alcohol, sodium dehydroacetate, sorbic acid, and potassium sorbate), buffers (for example, sodium hydrogen phosphate, sodium acetate, sodium carbonate, and sodium citrate), and solubilizers (for example, propylene glycol, D-mannitol, benzyl benzoate, ethanol, triethanolamine, sodium carbonate, and sodium citrate).

The preparation can be present in a variety of dosage forms depending on the use. The preparation may be solid or liquid. The preparation may be an oral preparation or an external preparation. Examples of the preparation include tablets, capsules, powders, granules, liquids, suppositories, ointments, injections, and drops.

The content of the compound of the present invention in the preparation can be appropriately selected depending on the use. For example, in the case of an oral preparation, 0.1 to 100% by mass, preferably 5 to 98% by mass of the compound of the present invention can be compounded as an active ingredient in the total mass of the formulation.

The preparation may contain an agent other than the compound of the present invention (hereinafter, also referred to as "concomitant drug"). The concomitant drug can be appropriately selected according to the use.

"Concomitant" means that multiple active ingredients are used in combination. Examples of the concomitant include use as a compounding agent, use as a kit, and an embodiment in which each active ingredient is separately administered in the same or different administration routes.

EXAMPLES

Hereinafter, the present invention will be described more specifically with reference to Examples, but the present invention is not limited to these Examples.

As the various reagents used in Examples, commercial products were used unless otherwise specified.

In Examples, room temperature means 1° C. to 40° C.

In silica gel column chromatography, unless otherwise specified, Biotage (registered trademark) SNAP Ultra Silica Cartridge or SNAP KP-Sil Cartridge (Biotage), or CHROMATOREX (registered trademark) Q-PACK SI, Q-PACK NH, or Q-PACK $CO_2H$ (FUJI SILYSIA CHEMICAL LTD.) was used as a column, and ethyl acetate/n-hexane, methanol/chloroform, or methanol/ethyl acetate was used as a mobile phase.

In reversed-phase silica gel column chromatography, Biotage (registered trademark) SNAP Ultra C18 Cartridge (Biotage) was used as a column, and a 0.1% aqueous trifluoroacetic acid solution and a 0.1% trifluoroacetic acid acetonitrile solution were used as mobile phases.

In reverse-phase preparative liquid chromatography, YMC-Actus Triart C18 (YMC) was used as a column, and a 0.1% aqueous trifluoroacetic acid solution and a 0.1% trifluoroacetic acid acetonitrile solution were used as mobile phases.

In preparative thin layer chromatography, PLC Silica gel 60 F254 (Merck) was used as a TLC (silica gel plate).

$^1$H-NMR was measured using ECZ400S (400 MHz, JEOL Ltd.). The chemical shifts of the NMR data were described in parts per million (ppm, δ) based on the residual protons in the deuterated solvent used.

The mass spectrum was measured by electrospray ionization (ESI) using ACQUITY (registered trademark) SQD (Waters). As ESI-MS data, found values were described. In the case of a salt, a molecular ion peak of a free form is usually observed.

The microwave reaction was performed using Initiator (registered trademark) (Biotage).

The meanings of the abbreviations are shown below.

s: singlet d: doublet t: triplet q: quartet dd: double doublet m: multiplet br: broad $CDCl_3$: deuterated chloroform $CD_3OD$: deuterated methanol DMSO-$d_6$: deuterated dimethyl sulfoxide DIPEA: N,N-diisopropylethylamine DMF: N,N-dimethylformamide DMSO: dimethyl sulfoxide EDC: 1-ethyl-3-(3-dimethylaminopropyl) carbodiimide hydrochloride NMP: N-methylpyrrolidone $PdCl_2$(dppf): [1,1'-bis(diphenylphosphino)ferrocene]dichloropalladium (II)

$PdCl_2$(dppf)·$CH_2Cl_2$: [1,1'-bis(diphenylphosphino)ferrocene]dichloropalladium (II) dichloromethane complex Pd $(PPh_3)_4$: tetrakis(triphenylphosphine)palladium (0)

THF: tetrahydrofuran

Example 1

Synthesis of N-methyl-4-(1H-pyrrolo[3,2-c]pyridin-4-yl)benzamide [1] (Hereinafter, Referred to as a Compound [1])

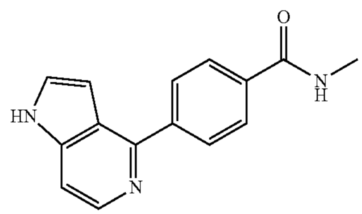 [SMILES: CNC(=O)c1ccc(-c2nccc3[nH]ccc23)cc1]

To a solution of 4-chloro-1H-pyrrolo[3,2-c]pyridine (76 mg) in ethanol (1.0 mL)/water (1.0 mL) were added N-methyl-4-(4,4,5,5-tetramethyl-1,3,2-dioxaborolan-2-yl) benzamide (116 mg), potassium carbonate (90 mg), and [1,3-bis(2,6-diisopropylphenyl)-4,5-dihydroimidazol-2-ylidene]chloro[3-phenylallyl]palladium (II) (13 mg) at room temperature, and the mixture was stirred at 80° C. for 3 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (78 mg) as a white solid.

$^1$H-NMR (400 MHz, DMSO-$d_6$) δ: 11.70 (br, 1H), 8.59-8.45 (m, 1H), 8.28 (d, J=5.9 Hz, 1H), 8.08 (d, J=8.7 Hz, 2H), 7.97 (d, J=8.2 Hz, 2H), 7.56-7.54 (m, 1H), 7.41 (dd, J=5.9, 0.9 Hz, 1H), 6.81-6.79 (m, 1H), 2.81 (d, J=4.6 Hz, 3H).

ESI-MS: 252.2 [M+H]$^+$

Example 2

Synthesis of N-[trans-4-(2-hydroxypropan-2-yl)cyclohexyl]-4-(1H-pyrrolo[3,2-c]pyridin-4-yl)benzamide [2] (Hereinafter, Referred to as a Compound [2])

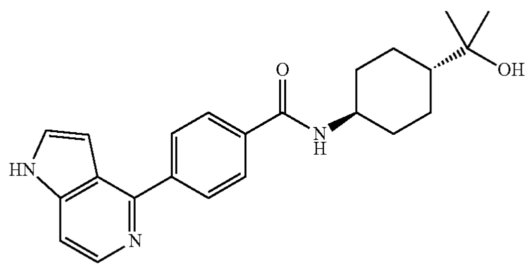 [SMILES: CC(C)(O)[C@H]1CC[C@H](NC(=O)c2ccc(-c3nccc4[nH]ccc34)cc2)CC1]

(1) Synthesis of N-[trans-4-(2-hydroxypropan-2-yl)cyclohexyl]-4-(4,4,5,5-tetramethyl-1,3,2-dioxaborolan-2-yl)benzamide [2-1] (Hereinafter, Referred to as a Compound [2-1])

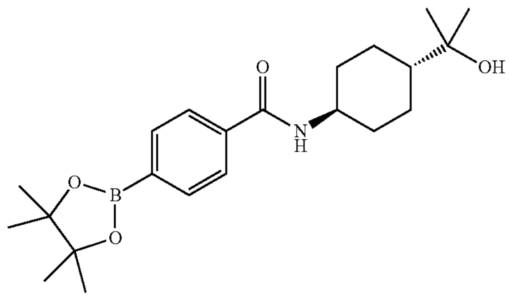 [SMILES: CC1(C)OB(c2ccc(C(=O)N[C@H]3CC[C@H](C(C)(C)O)CC3)cc2)OC1(C)C]

To a solution of 4-(4,4,5,5-tetramethyl-1,3,2-dioxaborolan-2-yl)benzoic acid (2.44 g) in DMF (33 mL) were added DIPEA (1.84 mL) and (1-cyano-2-ethoxy-2-oxoethylideneaminooxy)dimethylaminomorpholinocarbenium hexafluorophosphate (4.63 g) at room temperature, and the mixture was stirred at room temperature for 5 minutes. To the reaction mixture was added 2-(trans-4-aminocyclohexyl)propan-2-ol (2.01 g) at room temperature, and the mixture was stirred at room temperature for 30 minutes. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was suspended in ethyl acetate/n-hexane and the solid was collected by filtration to give the title compound (2.54 g) as a white solid.

$^1$H-NMR (400 MHz, $CDCl_3$) δ: 7.85 (d, J=8.2 Hz, 2H), 7.72 (d, J=7.8 Hz, 2H), 5.92 (d, J=8.2 Hz, 1H), 4.01-3.84 (m, 1H), 2.27-2.09 (m, 2H), 2.03-1.84 (m, 2H), 1.45-1.11 (m, 23H).

ESI-MS: 388.5 [M+H]$^+$ (2) Synthesis of N-[trans-4-(2-hydroxypropan-2-yl)cyclohexyl]-4-(1H-pyrrolo[3,2-c]pyridin-4-yl)benzamide [2]

To a solution of 4-chloro-1H-pyrrolo[3,2-c]pyridine (770 mg) in ethanol (12.5 mL)/water (12.5 mL) were added the compound [2-1] (2.54 g), potassium carbonate (906 mg), and [1,3-bis(2,6-diisopropylphenyl)imidazol-2-ylidene]chloro[3-phenylallyl]palladium (II) (163 mg) at room temperature, and the mixture was stirred at 100° C. for 2 hours under an argon atmosphere. To the reaction mixture was added water, and the resulting solid was collected by filtration. The obtained solid was dissolved in a chloroform (400 mL)/methanol (200 mL) solution, and the solution was injected into a column packed with a strongly acidic cation exchange resin (H form) (DOWEX™ 50WX2, 50-100 mesh). The column was washed with chloroform/methanol (2/1 by volume) solution and eluted with 2 M ammonia/methanol solution. The eluate was concentrated under reduced pressure, and the obtained residue was purified by silica gel column chromatography to give the title compound (984 mg) as a white solid.

$^1$H-NMR (400 MHz, DMSO-$d_6$) δ: 11.70 (br, 1H), 8.36-8.20 (m, 2H), 8.07 (d, J=8.2 Hz, 2H), 7.98 (d, J=8.2 Hz, 2H), 7.55 (d, J=3.2 Hz, 1H), 7.41 (d, J=5.5 Hz, 1H), 6.79 (d, J=2.7 Hz, 1H), 4.04 (s, 1H), 3.81-3.65 (m, 1H), 2.00-1.74 (m, 4H), 1.41-1.25 (m, 2H), 1.24-0.96 (m, 9H).

ESI-MS: 378.4 [M+H]$^+$

Example 3

Synthesis of N-[trans-4-(hydroxymethyl)cyclohexyl]-4-(1H-pyrrolo[3,2-c]pyridin-4-yl)benzamide [3] (Hereinafter, Referred to as a Compound [3])

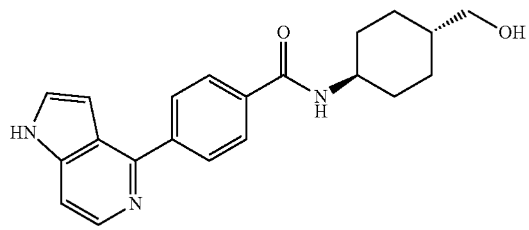 [SMILES: O=C(N[C@H]1CC[C@H](CO)CC1)c1ccc(-c2nccc3[nH]ccc23)cc1]

The title compound was synthesized according to the method in Example 2.

$^1$H-NMR (400 MHz, DMSO-$d_6$) δ: 11.69 (br, 1H), 8.37-8.21 (m, 2H), 8.06 (d, J=8.2 Hz, 2H), 7.98 (d, J=7.8 Hz, 2H), 7.57-7.54 (m, 1H), 7.41 (d, J=6.4 Hz, 1H), 6.86-6.72 (m, 1H), 4.40 (t, J=5.3 Hz, 1H), 3.84-3.67 (m, 1H), 3.23 (dd, J=5.7, 5.7 Hz, 2H), 1.95-1.69 (m, 4H), 1.44-1.19 (m, 3H), 1.08-0.88 (m, 2H).

ESI-MS: 350.3 [M+H]$^+$

Example 4

Synthesis of N-[trans-4-(2-hydroxypropan-2-yl)cyclohexyl]-4-(1-methyl-1H-pyrrolo[3,2-c]pyridin-4-yl)benzamide [4] (Hereinafter, Referred to as a Compound [4])

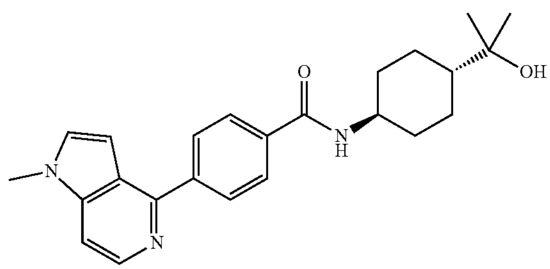 [SMILES: Cn1ccc2c(-c3ccc(C(=O)N[C@H]4CC[C@H](C(C)(C)O)CC4)cc3)nccc21]

To a solution of 4-chloro-1-methyl-1H-pyrrolo[3,2-c]pyridine (14 mg) in 1,4-dioxane (1.3 mL)/water (0.30 mL) were added the compound [2-1] (30 mg), tripotassium phosphate (33 mg), and $PdCl_2$(dppf) (5.7 mg) at room temperature, and the mixture was stirred at 130° C. for 30 minutes using a microwave reactor. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (9.0 mg) as a white solid.

$^1$H-NMR (400 MHz, DMSO-$d_6$) δ: 8.34 (d, J=5.5 Hz, 1H), 8.28 (d, J=7.8 Hz, 1H), 8.05 (d, J=8.2 Hz, 2H), 7.97 (d, J=8.2 Hz, 2H), 7.54 (d, J=3.7 Hz, 1H), 7.51 (d, J=5.9 Hz, 1H), 6.79 (d, J=2.7 Hz, 1H), 4.04 (s, 1H), 3.85 (s, 3H), 3.79-3.64 (m, 1H), 1.96-1.74 (m, 4H), 1.41-1.25 (m, 2H), 1.24-0.95 (m, 9H).

ESI-MS: 392.2 $[M+H]^+$

Example 5

Synthesis of N-cyclohexyl-4-(1H-pyrrolo[3,2-c]pyridin-4-yl)benzamide [5] (Hereinafter, Referred to as a Compound [5])

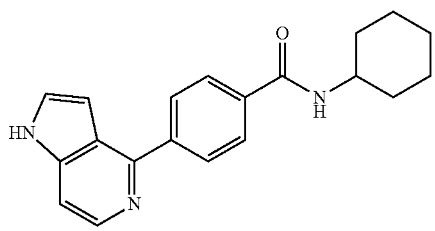 [SMILES: O=C(NC1CCCCC1)c1ccc(-c2nccc3[nH]ccc23)cc1]

(1) Synthesis of ethyl 4-(1H-pyrrolo[3,2-c]pyridin-4-yl)benzoate [5-1] (Hereinafter, Referred to as a Compound [5-1])

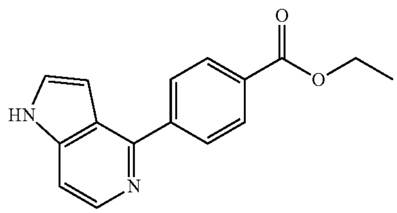 [SMILES: CCOC(=O)c1ccc(-c2nccc3[nH]ccc23)cc1]

To a solution of 4-chloro-1H-pyrrolo[3,2-c]pyridine (839 mg) in ethanol (5.5 mL)/water (5.5 mL) were added 4-(ethoxycarbonyl)phenylboronic acid (1.39 g), potassium carbonate (988 mg), and [1,3-bis(2,6-diisopropylphenyl)-4,5-dihydroimidazol-2-ylidene]chloro[3-phenylallyl]palladium (II) (143 mg) at room temperature, and the mixture was stirred at 100° C. for 3 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (1.19 g) as a white solid.

$^1$H-NMR (400 MHz, $CDCl_3$) δ: 9.14 (br, 1H), 8.45 (d, J=5.9 Hz, 1H), 8.20 (d, J=8.2 Hz, 2H), 8.08 (d, J=7.8 Hz, 2H), 7.39-7.28 (m, 2H), 6.91-6.77 (m, 1H), 4.42 (q, J=7.2 Hz, 2H), 1.43 (t, J=7.1 Hz, 3H).

ESI-MS: 267.3 $[M+H]^+$ (2) Synthesis of N-cyclohexyl-4-(1H-pyrrolo[3,2-c]pyridin-4-yl)benzamide [5]

To a solution of the compound [5-1] (40) mg) in toluene (0.30 mL) were added 1,5,7-triazabicyclo[4.4.0]dec-5-ene (6.3 mg) and cyclohexylamine (86 μL) at room temperature, and the mixture was stirred at 80° C. for 31 hours. To the reaction mixture was added chloroform, and the mixture was purified by silica gel column chromatography to give the title compound (9.4 mg) as a white solid.

$^1$H-NMR (400 MHz, DMSO-$d_6$) δ: 11.71 (br, 1H), 8.37-8.20 (m, 2H), 8.06 (d, J=8.2 Hz, 2H), 7.98 (d, J=8.7 Hz, 2H), 7.55 (d, J=2.7 Hz, 1H), 7.41 (d, J=5.5 Hz, 1H), 6.79 (d, J=3.2 Hz, 1H), 3.87-3.71 (m, 1H), 1.93-1.66 (m, 4H), 1.65-1.57 (m, 1H), 1.42-1.06 (m, 5H).

ESI-MS: 320.4 $[M+H]^+$

Examples 6 to 58

Each compound of Examples 6 to 58 shown in the following Tables was synthesized according to the method shown in step (2) in Example 5. The structure, name, and ESI-MS of the compound of each Example are shown in the following Tables.

TABLE 1-1

| Example | Structure | Name | ESI-MS |
|---|---|---|---|
| 6 | 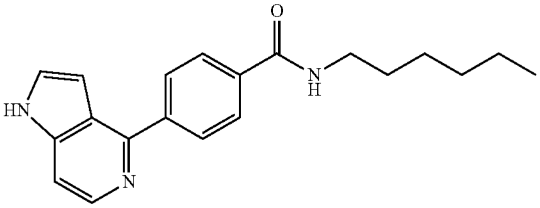 [SMILES: CCCCCCNC(=O)c1ccc(-c2nccc3[nH]ccc23)cc1] | N-hexyl-4-(1H-pyrrolo[3,2-c]pyridin-4-yl)benzamide | 322.4 $[M + H]^+$ |
| 7 | 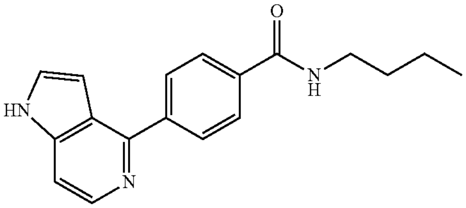 [SMILES: CCCCNC(=O)c1ccc(-c2nccc3[nH]ccc23)cc1] | N-butyl-4-(1H-pyrrolo[3,2-c]pyridin-4-yl)benzamide | 294.3 $[M + H]^+$ |
| 8 | 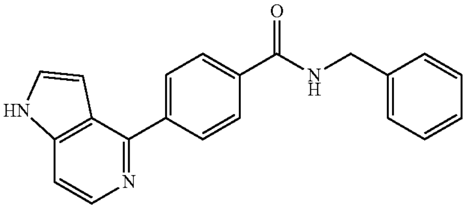 [SMILES: O=C(NCc1ccccc1)c1ccc(-c2nccc3[nH]ccc23)cc1] | N-benzyl-4-(1H-pyrrolo[3,2-c]pyridin-4-yl)benzamide | 328.3 $[M + H]^+$ |
| 9 | 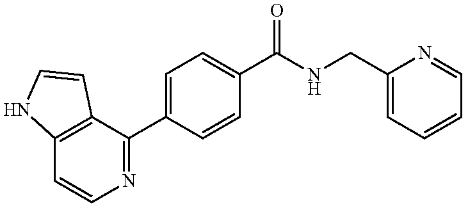 [SMILES: O=C(NCc1ccccn1)c1ccc(-c2nccc3[nH]ccc23)cc1] | (N-(pyridin-2-ylmethyl)-4-(1H-pyrrolo[3,2-c]pyridin-4-yl)benzamide | 329.3 $[M + H]^+$ |
| 10 | 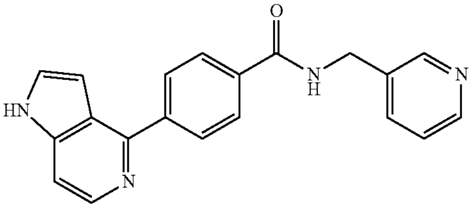 [SMILES: O=C(NCc1cccnc1)c1ccc(-c2nccc3[nH]ccc23)cc1] | N-(pyridin-3-ylmethyl)-4-(1H-pyrrolo[3,2-c]pyridin-4-yl)benzamide | 329.3 $[M + H]^+$ |

TABLE 1-2

| | | | |
|---|---|---|---|
| 11 | 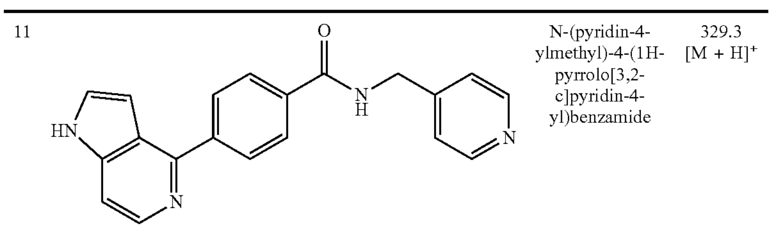 | N-(pyridin-4-ylmethyl)-4-(1H-pyrrolo[3,2-c]pyridin-4-yl)benzamide | 329.3 $[M + H]^+$ |

TABLE 1-2-continued
| | | | |
|---|---|---|---|
| 12 | 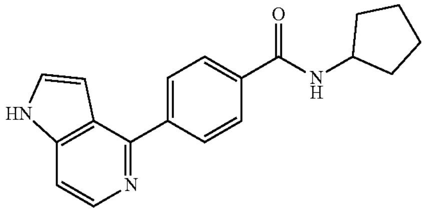 [SMILES: O=C(NC1CCCC1)c1ccc(-c2nccc3[nH]ccc23)cc1] | N-cyclopenthyl-4-(1H-pyrrolo[3,2-c]pyridin-4-yl)benzamide | 306.3 $[M + H]^+$ |
| 13 | 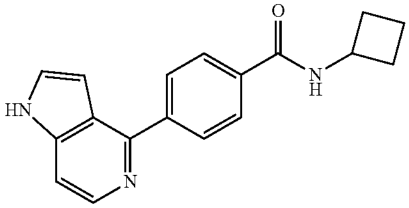 [SMILES: O=C(NC1CCC1)c1ccc(-c2nccc3[nH]ccc23)cc1] | N-cyclobutyl-4-(1H-pyrrolo[3,2-c]pyridin-4-yl)benzamide | 292.3 $[M + H]^+$ |
| 14 | 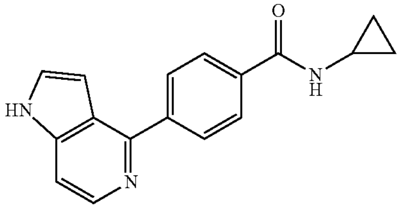 [SMILES: O=C(NC1CC1)c1ccc(-c2nccc3[nH]ccc23)cc1] | N-cyclopropyl-4-(1H-pyrrolo [3,2-c]pyridin-4-yl)benzamide | 278.3 $[M + H]^+$ |
| 15 | 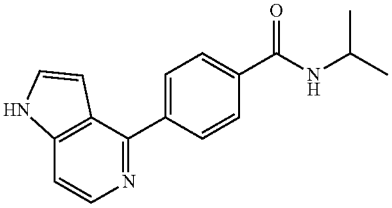 [SMILES: CC(C)NC(=O)c1ccc(-c2nccc3[nH]ccc23)cc1] | N-isopropyl-4-(1H-pyrrolo[3,2-c]pyridin-4-yl)benzamide | 280.3 $[M + H]^+$ |
TABLE 1-3
| | | | |
|---|---|---|---|
| 16 | 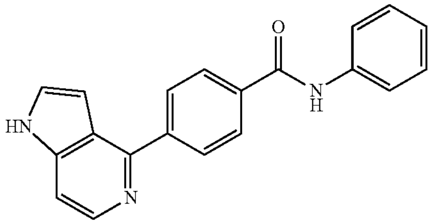 [SMILES: O=C(Nc1ccccc1)c1ccc(-c2nccc3[nH]ccc23)cc1] | N-phenyl-4-(1H-pyrrolo[3,2-c]pyridin-4-yl)benzamide | 314.3 $[M + H]^+$ |
| 17 | 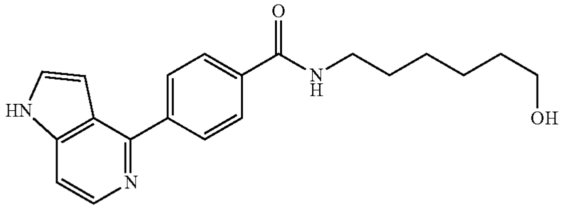 [SMILES: O=C(NCCCCCCO)c1ccc(-c2nccc3[nH]ccc23)cc1] | N-(6-hydroxyhexyl)-4-(1H-pyrrolo[3,2-c]pyridin-4-yl)benzamide | 338.4 $[M + H]^+$ |

TABLE 1-3-continued

| | | | |
|---|---|---|---|
| 18 | 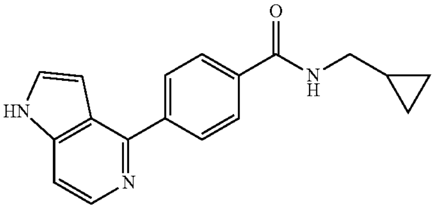 [SMILES: O=C(NCC1CC1)c1ccc(-c2nccc3[nH]ccc23)cc1] | N-(cyclopropyl-methyl)-4-(1H-pyrrolo[3,2-c]pyridin-4-yl)benzamide | 292.3 $[M + H]^+$ |
| 19 | 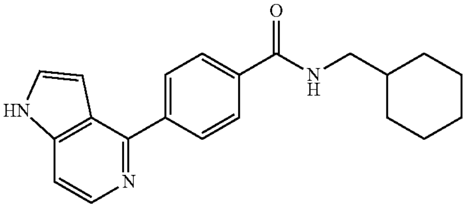 [SMILES: O=C(NCC1CCCCC1)c1ccc(-c2nccc3[nH]ccc23)cc1] | N-(cyclohexyl-methyl)-4-(1H-pyrrolo[3,2-c]pyridin-4-yl)benzamide | 334.4 $[M + H]^+$ |
| 20 | 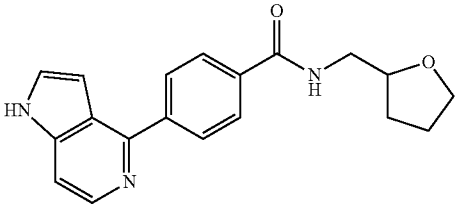 [SMILES: O=C(NCC1CCCO1)c1ccc(-c2nccc3[nH]ccc23)cc1] | 4-(1H-pyrrolo[3,2-c]pyridin-4-yl)-N-[(tetrahydrofuran-2-yl)methyl] benzamide | 322.3 $[M + H]^+$ |

TABLE 1-4

| | | | |
|---|---|---|---|
| 21 | 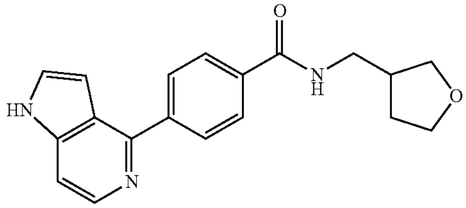 [SMILES: O=C(NCC1CCOC1)c1ccc(-c2nccc3[nH]ccc23)cc1] | 4-(1H-pyrrolo[3,2-c]pyridin-4-yl)-N-[(tetrahydrofuran-3-yl)methyl] benzamide | 322.4 $[M + H]^+$ |
| 22 | 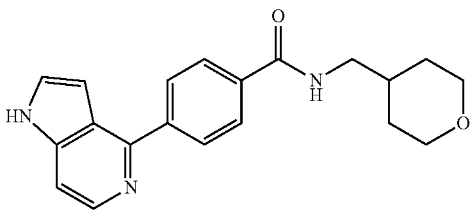 | 4-(1H-pyrrolo[3,2-c]pyridin-4-yl)-N-[(tetrahydro-2H-pyran-4-yl)methyl] benzamide | 336.3 $[M + H]^+$ |
| 23 | 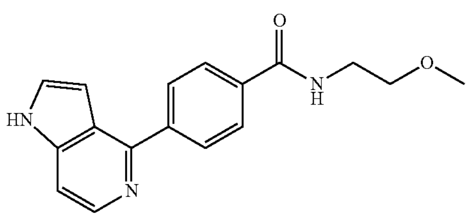 [SMILES: COCCNC(=O)c1ccc(-c2nccc3[nH]ccc23)cc1] | N-(2-methoxyethyl)-4-(1H-pyrrolo[3,2-c]pyridin-4-yl)benzamide | 296.3 $[M + H]^+$ |
| 24 | 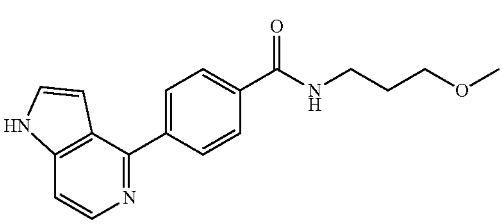 | N-(3-methoxypropyl)-4-(1H-pyrrolo[3,2-c]pyridin-4-yl)benzamide | 310.3 $[M + H]^+$ |

TABLE 1-4-continued

| | | | |
|---|---|---|---|
| 25 | 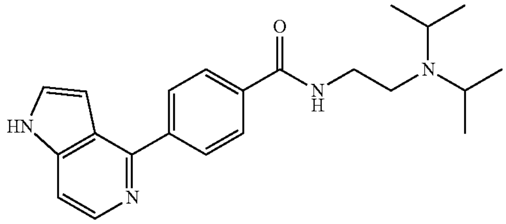 [SMILES: CC(C)N(CCNC(=O)c1ccc(-c2nccc3[nH]ccc23)cc1)C(C)C] | N-[2-(diisopropylamino)ethyl]-4-(1H-pyrrolo[3,2-c]pyridin-4-yl)benzamide | 365.4 $[M + H]^+$ |

TABLE 1-5

| | | | |
|---|---|---|---|
| 26 | 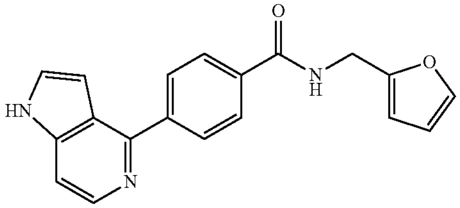 [SMILES: O=C(NCc1ccco1)c1ccc(-c2nccc3[nH]ccc23)cc1] | N-(furan-2-ylmethyl)-4-(1H-pyrrolo[3,2-c]pyridin-4-yl)benzamide | 318.3 $[M + H]^+$ |
| 27 | 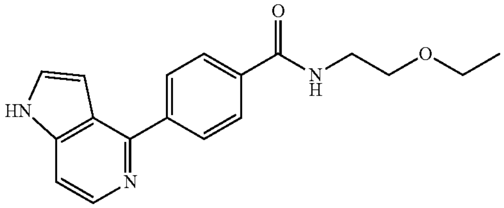 [SMILES: CCOCCNC(=O)c1ccc(-c2nccc3[nH]ccc23)cc1] | N-(2-ethoxyethyl)-4-(1H-pyrrolo[3,2-c]pyridin-4-yl)benzamide | 310.3 $[M + H]^+$ |
| 28 | 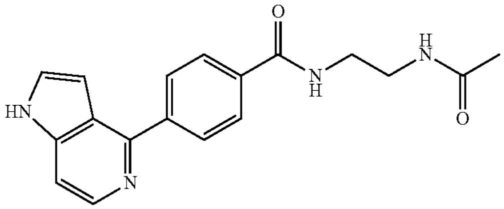 [SMILES: CC(=O)NCCNC(=O)c1ccc(-c2nccc3[nH]ccc23)cc1] | N-(2-acetamidoethyl)-4-(1H-pyrrolo[3,2-c]pyridin-4-yl)benzamide | 323.3 $[M + H]^+$ |
| 29 | 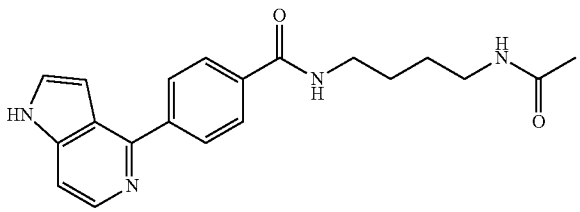 [SMILES: CC(=O)NCCCCNC(=O)c1ccc(-c2nccc3[nH]ccc23)cc1] | N-(4-acetamidobutyl)-4-(1H-pyrrolo[3,2-c]pyridin-4-yl)benzamide | 351.4 $[M + H]^+$ |
| 30 | 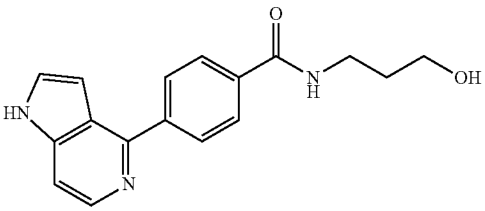 [SMILES: O=C(NCCCO)c1ccc(-c2nccc3[nH]ccc23)cc1] | N-(3-hydroxypropyl)-4-(1H-pyrrolo[3,2-c]pyridin-4-yl)benzamide | 296.2 $[M + H]^+$ |

TABLE 1-6

| | | | |
|---|---|---|---|
| 31 | 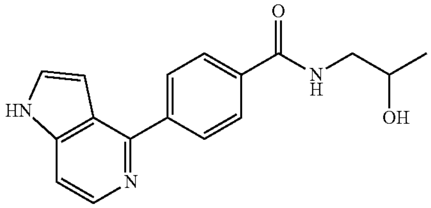 [SMILES: CC(O)CNC(=O)c1ccc(-c2nccc3[nH]ccc23)cc1] | N-(2-hydroxypropyl)-4-(1H-pyrrolo[3,2-c]pyridin-4-yl)benzamide | 296.2 $[M + H]^+$ |
| 32 | 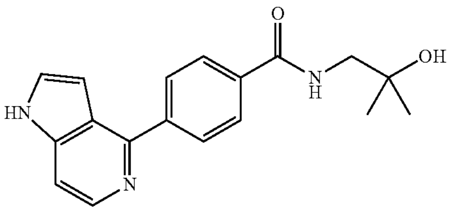 [SMILES: CC(C)(O)CNC(=O)c1ccc(-c2nccc3[nH]ccc23)cc1] | N-(2-hydroxy-2-methylpropyl)-4-(1H-pyrrolo[3,2-c]pyridin-4-yl)benzamide | 310.3 $[M + H]^+$ |
| 33 | 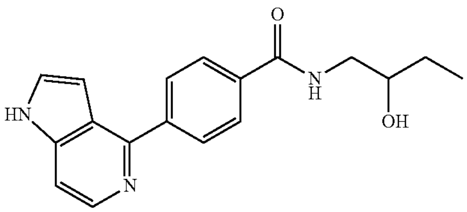 [SMILES: CCC(O)CNC(=O)c1ccc(-c2nccc3[nH]ccc23)cc1] | N-(2-hydroxybutyl)-4-(1H-pyrrolo[3,2-c]pyridin-4-yl)benzamide | 310.1 $[M + H]^+$ |
| 34 | 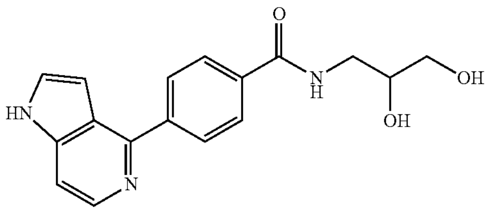 [SMILES: O=C(NCC(O)CO)c1ccc(-c2nccc3[nH]ccc23)cc1] | N-(2,3-dihydroxypropyl)-4-(1H-pyrrolo[3,2-c]pyridin-4-yl)benzamide | 312.3 $[M + H]^+$ |
| 35 | 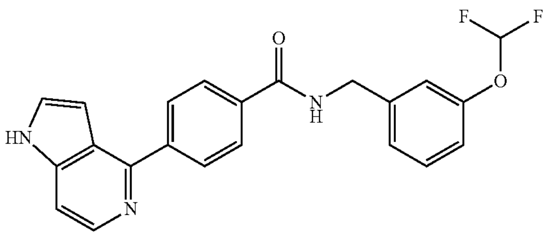 [SMILES: O=C(NCc1cccc(OC(F)F)c1)c1ccc(-c2nccc3[nH]ccc23)cc1] | N-[3-(difluoromethoxy)benzyl]-4-(1H-pyrrolo[3,2-c]pyridin-4-yl)benzamide | 394.3 $[M + H]^+$ |

TABLE 1-7

| | | | |
|---|---|---|---|
| 36 | 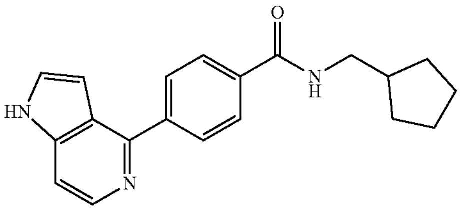 [SMILES: O=C(NCC1CCCC1)c1ccc(-c2nccc3[nH]ccc23)cc1] | N-(cyclopenthyl-methyl)-4-(1H-pyrrolo[3,2-c]pyridin-4-yl)benzamide | 320.3 $[M + H]^+$ |

TABLE 1-7-continued

| | | | |
|---|---|---|---|
| 37 | 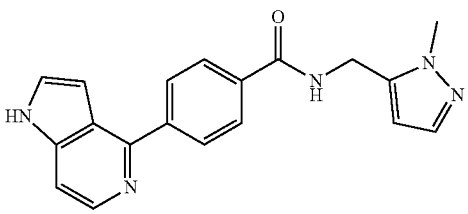 [SMILES: Cn1nccc1CNC(=O)c1ccc(-c2nccc3[nH]ccc23)cc1] | N-[(1-methyl-1H-pyrazol-5-yl)methyl]-4-(1H-pyrrolo[3,2-c]pyridin-4-yl)benzamide | 332.3 $[M + H]^+$ |
| 38 | 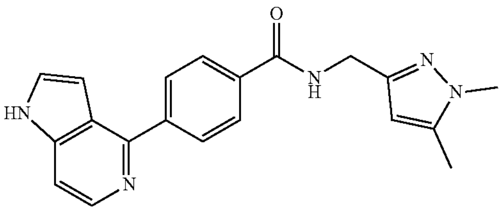 [SMILES: Cc1cc(CNC(=O)c2ccc(-c3nccc4[nH]ccc34)cc2)nn1C] | N-[(1,5-dimethyl-1H-pyrazol-3-yl)methyl]-4-(1H-pyrrolo[3,2-c]pyridin-4-yl)benzamide | 346.4 $[M + H]^+$ |
| 39 | 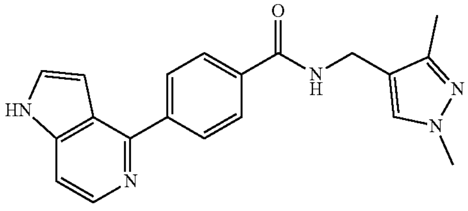 [SMILES: Cc1nn(C)cc1CNC(=O)c1ccc(-c2nccc3[nH]ccc23)cc1] | N-[(1,3-dimethyl-1H-pyrazol-4-yl)methyl]-4-(1H-pyrrolo[3,2-c]pyridin-4-yl)benzamide | 346.4 $[M + H]^+$ |
| 40 | 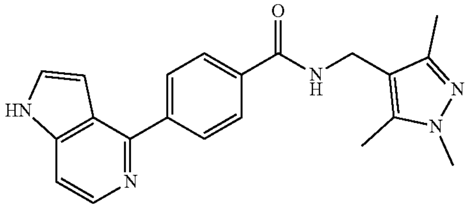 [SMILES: Cc1nn(C)c(C)c1CNC(=O)c1ccc(-c2nccc3[nH]ccc23)cc1] | 4-(1H-pyrrolo[3,2-c]pyridin-4-yl)-N-[(1,3,5-trimethyl-1H-pyrazol-4-yl)methyl] benzamide | 360.4 $[M + H]^+$ |

TABLE 1-8

| | | | |
|---|---|---|---|
| 41 | 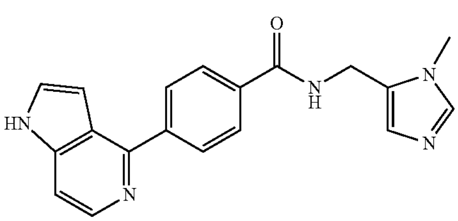 [SMILES: Cn1cncc1CNC(=O)c1ccc(-c2nccc3[nH]ccc23)cc1] | N-[(1-methyl-1H-imidazol-5-yl)methyl]-4-(1H-pyrrolo[3,2-c]pyridin-4-yl)benzamide | 332.3 $[M + H]^+$ |
| 42 | 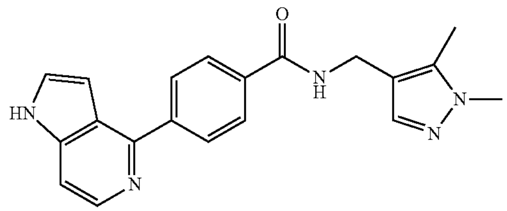 [SMILES: Cc1c(CNC(=O)c2ccc(-c3nccc4[nH]ccc34)cc2)cnn1C] | N-[(1,5-dimethyl-1H-pyrazol-4-yl)methyl]-4-(1H-pyrrolo[3,2-c]pyridin-4-yl)benzamide | 346.3 $[M + H]^+$ |

TABLE 1-8-continued

| | | | |
|---|---|---|---|
| 43 | 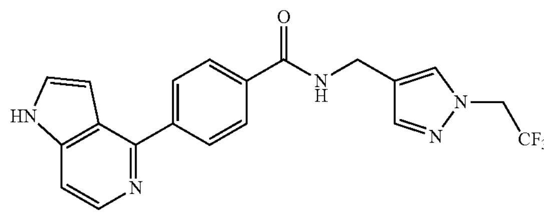 [SMILES: O=C(NCc1cnn(CC(F)(F)F)c1)c1ccc(-c2nccc3[nH]ccc23)cc1] | 4-(1H-pyrrolo[3,2-c]pyridin-4-yl)-N-{[1-(2,2,2-trifluoroethyl)-1H-pyrazol-4-yl]methyl}benzamide | 400.3 [M + H]+ |
| 44 | 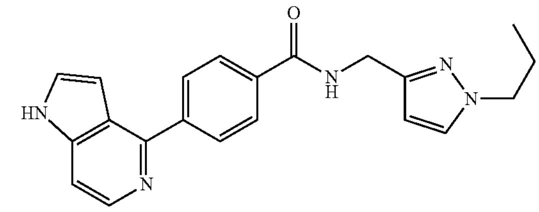 [SMILES: CCCn1ccc(CNC(=O)c2ccc(-c3nccc4[nH]ccc34)cc2)n1] | N-[(1-propyl-1H-pyrazol-3-yl)methyl]-4-(1H-pyrrolo[3,2-c]pyridin-4-yl)benzamide | 360.3 [M + H]+ |
| 45 | 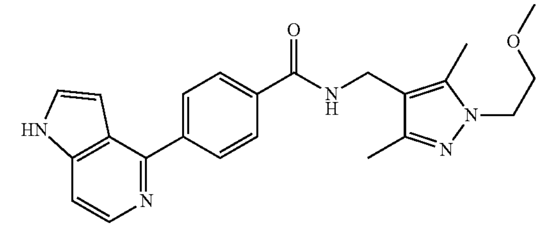 [SMILES: COCCn1nc(C)c(CNC(=O)c2ccc(-c3nccc4[nH]ccc34)cc2)c1C] | N-{[1-(2-methoxyethyl)-3,5-dimethyl-1H-pyrazol-4-yl]methyl}-4-(1H-pyrrolo[3,2-c]pyridin-4-yl)benzamide | 404.3 [M + H]+ |

TABLE 1-9

| | | | |
|---|---|---|---|
| 46 | 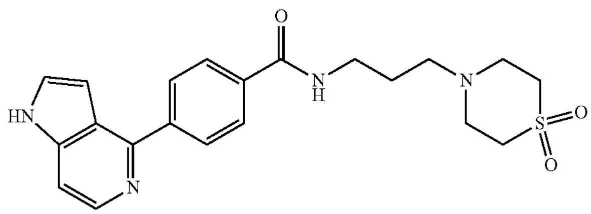 [SMILES: O=C(NCCCN1CCS(=O)(=O)CC1)c1ccc(-c2nccc3[nH]ccc23)cc1] | N-[3-(1,1-dioxidothio-morpholino)-propyl]-4-(1H-pyrrolo[3,2-c]pyridin-4-yl)benzamide | 413.3 [M + H]+ |
| 47 | 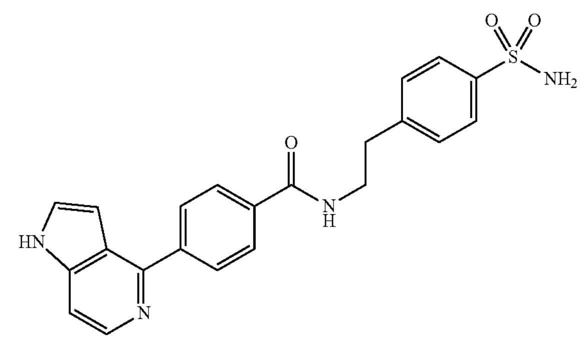 [SMILES: NS(=O)(=O)c1ccc(CCNC(=O)c2ccc(-c3nccc4[nH]ccc34)cc2)cc1] | 4-(1H-pyrrolo[3,2-c]pyridin-4-yl)-N-(4-sulfamoylphenethyl)benzamide | 421.3 [M + H]+ |
| 48 | 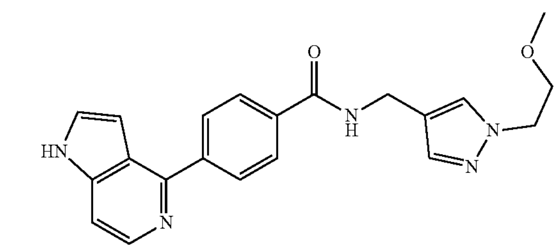 [SMILES: COCCn1cc(CNC(=O)c2ccc(-c3nccc4[nH]ccc34)cc2)cn1] | N-{[1-(2-methoxyethyl)-1H-pyrazol-4-yl]methyl}-4-(1H-pyrrolo[3,2-c]pyridin-4-yl)benzamide | 376.3 [M + H]+ |

TABLE 1-9-continued

| | | | |
|---|---|---|---|
| 49 | 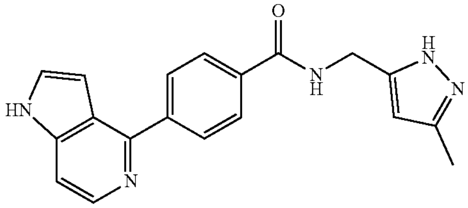 [SMILES: Cc1cc(CNC(=O)c2ccc(-c3nccc4[nH]ccc34)cc2)[nH]n1] | N-[(3-methyl-1H-pyrazol-5-yl)methyl]-4-(1H-pyrrolo[3,2-c]pyridin-4-yl)benzamide | 332.3 $[M + H]^+$ |
| 50 | 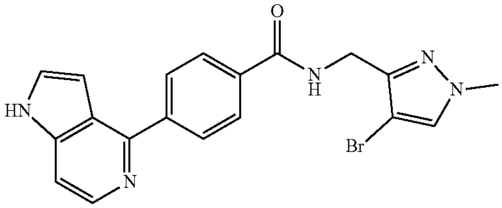 [SMILES: Cn1cc(Br)c(CNC(=O)c2ccc(-c3nccc4[nH]ccc34)cc2)n1] | N-[(4-bromo-1-methyl-1H-pyrazol-3-yl)methyl]-4-(1H-pyrrolo[3,2-c]pyridin-4-yl)benzamide | 410.1 $[M + H]^+$ |

TABLE 1-10

| | | | |
|---|---|---|---|
| 51 | 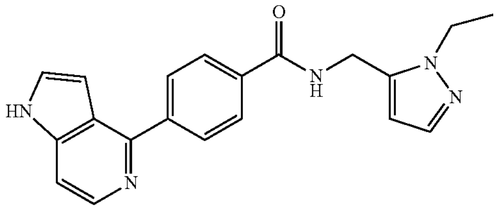 [SMILES: CCn1nccc1CNC(=O)c1ccc(-c2nccc3[nH]ccc23)cc1] | N-[(1-ethyl-1H-pyrazol-5-yl)methyl]-4-(1H-pyrrolo[3,2-c]pyridin-4-yl)benzamide | 346.3 $[M + H]^+$ |
| 52 | 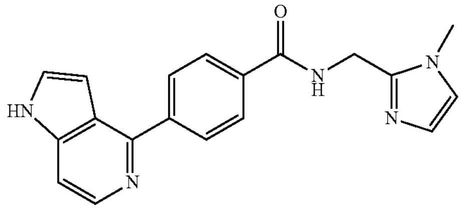 [SMILES: Cn1ccnc1CNC(=O)c1ccc(-c2nccc3[nH]ccc23)cc1] | N-[(1-methyl-1H-imidazol-2-yl)methyl]-4-(1H-pyrrolo[3,2-c]pyridin-4-yl)benzamide | 332.3 $[M + H]^+$ |
| 53 | 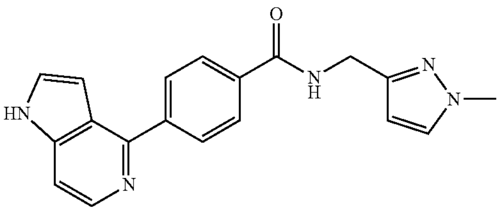 [SMILES: Cn1ccc(CNC(=O)c2ccc(-c3nccc4[nH]ccc34)cc2)n1] | N-[(1-methyl-1H-pyrazol-3-yl)methyl]-4-(1H-pyrrolo[3,2-c]pyridin-4-yl)benzamide | 332.3 $[M + H]^+$ |
| 54 | 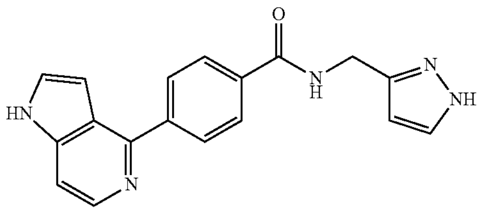 [SMILES: O=C(NCc1cc[nH]n1)c1ccc(-c2nccc3[nH]ccc23)cc1] | N-[(1H-pyrazol-3-yl)methyl]-4-(1H-pyrrolo[3,2-c]pyridin-4-yl)benzamide | 318.2 $[M + H]^+$ |

TABLE 1-10-continued

| | | | |
|---|---|---|---|
| 55 | 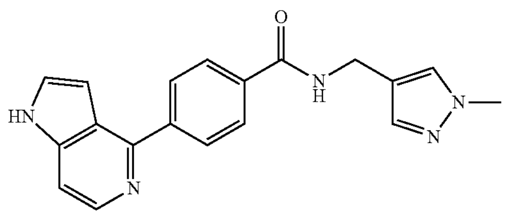 [SMILES: Cn1cc(CNC(=O)c2ccc(-c3nccc4[nH]ccc34)cc2)cn1] | N-[(1-methyl-1H-pyrazol-4-yl)methyl]-4-(1H-pyrrolo[3,2-c]pyridin-4-yl)benzamide | 332.2 $[M + H]^+$ |

TABLE 1-11

| | | | |
|---|---|---|---|
| 56 | 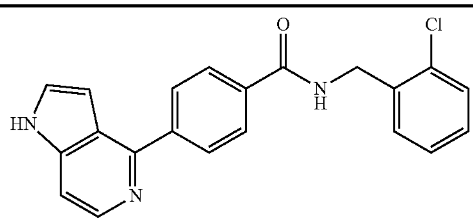 | N-(2-chlorobenzyl)-4-(1H-pyrrolo[3,2-c]pyridin-4-yl)benzamide | 362.2 $[M + H]^+$ |
| 57 | 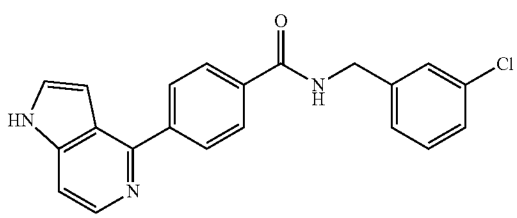 [SMILES: O=C(NCc1cccc(Cl)c1)c1ccc(-c2nccc3[nH]ccc23)cc1] | N-(3-chlorobenzyl)-4-(1H-pyrrolo[3,2-c]pyridin-4-yl)benzamide | 362.2 $[M + H]^+$ |
| 58 | 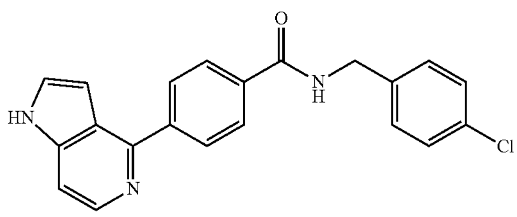 [SMILES: O=C(NCc1ccc(Cl)cc1)c1ccc(-c2nccc3[nH]ccc23)cc1] | N-(4-chlorobenzyl)-4-(1H-pyrrolo[3,2-c]pyridin-4-yl)benzamide | 362.2 $[M + H]^+$ |

Example 59

Synthesis of N-benzyl-4-(thieno[3,2-c]pyridin-4-yl) benzamide [59] (Hereinafter, Referred to as a Compound [59])

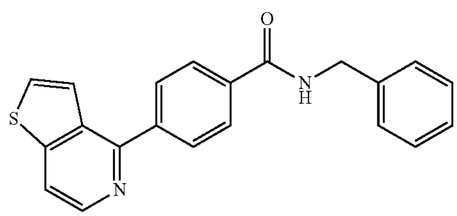 [SMILES: O=C(NCc1ccccc1)c1ccc(-c2nccc3sccc23)cc1]

(1) Synthesis of ethyl 4-(thieno[3,2-c]pyridin-4-yl) benzoate [59-1] (Hereinafter, Referred to as a Compound [59-1])

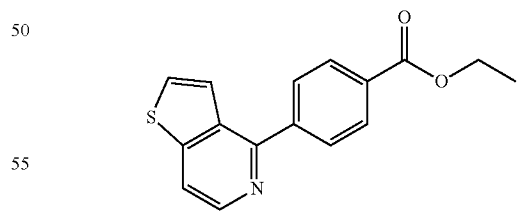

To a solution of 4-chlorothieno[3,2-c]pyridine (509 mg) in ethanol (3.0 mL)/water (3.0 mL) were added 4-(ethoxycarbonyl)phenylboronic acid (757 mg), potassium carbonate (539 mg), and [1,3-bis(2,6-diisopropylphenyl)-4,5-dihydroimidazol-2-ylidene]chloro[3-phenylallyl]palladium (II) (78.0 mg) at room temperature, and the mixture was stirred at 100° C. for 2 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (741 mg) as a yellow white solid.

$^1$H-NMR (400 MHz, $CDCl_3$) δ: 8.58 (d, J=5.5 Hz, 1H), 8.21 (d, J=8.7 Hz, 2H), 7.92 (d, J=8.2 Hz, 2H), 7.84 (dd, J=5.5, 0.9 Hz, 1H), 7.59 (dd, J=5.5, 0.9 Hz, 1H), 7.54 (d, J=5.5 Hz, 1H), 4.43 (q, J=7.2 Hz, 2H), 1.44 (t, J=7.1 Hz, 3H).

ESI-MS: 284.5 [M+H]$^+$ (2) Synthesis of N-benzyl-4-(thieno[3,2-c]pyridin-4-yl)benzamide [59]

To a solution of the compound [59-1] (28 mg) in toluene (0.20 mL) were added 1,5,7-triazabicyclo[4.4.0]dec-5-ene (4.2 mg) and benzylamine (55 μL) at room temperature, and the mixture was stirred at 80° C. for 21 hours. To the reaction mixture was added ethyl acetate, and the mixture was purified by silica gel column chromatography to give the title compound (31 mg) as a white solid.

$^1$H-NMR (400 MHz, DMSO-$d_6$) δ: 9.19 (t, J=5.9 Hz, 1H), 8.54 (d, J=5.5 Hz, 1H), 8.12 (d, J=5.5 Hz, 1H), 8.07 (d, J=8.2 Hz, 2H), 8.01-7.85 (m, 3H), 7.66 (d, J=5.0 Hz, 1H), 7.42-7.29 (m, 4H), 7.29-7.18 (m, 1H), 4.52 (d, J=5.9 Hz, 2H).

ESI-MS: 345.2 [M+H]$^+$

Example 60

Synthesis of N-(pyridin-4-ylmethyl)-4-(thieno[3,2-c]pyridin-4-yl)benzamide [60] (Hereinafter, Referred to as a Compound [60])

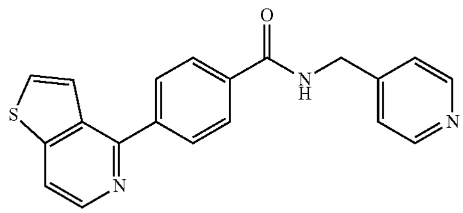 [SMILES: O=C(NCc1ccncc1)c1ccc(-c2nccc3sccc23)cc1]

To a solution of the compound [59-1] (28 mg) in toluene (0.20 mL) were added 1,5,7-triazabicyclo[4.4.0]dec-5-ene (4.2 mg) and 4-picolylamine (51 μL) at room temperature, and the mixture was stirred at 80° C. for 21 hours. To the reaction mixture was added ethyl acetate, and the mixture was purified by silica gel column chromatography to give the title compound (31 mg) as a white solid.

ESI-MS: 346.2 [M+H]$^+$

Example 61

Synthesis of N-(2-hydroxypropyl)-4-(thieno[3,2-c]pyridin-4-yl)benzamide [61] (Hereinafter, Referred to as a Compound [61])

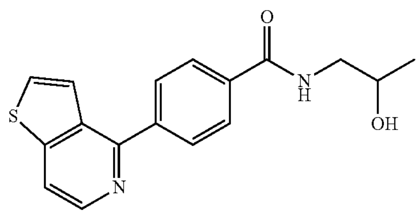 [SMILES: CC(O)CNC(=O)c1ccc(-c2nccc3sccc23)cc1]

To a solution of the compound [59-1] (28 mg) in toluene (0.20 mL) were added 1,5,7-triazabicyclo[4.4.0]dec-5-ene (4.2 mg) and 1-amino-2-propanol (39 μL) at room temperature, and the mixture was stirred at 80° C. for 21 hours. To the reaction mixture was added ethyl acetate, and the mixture was purified by silica gel column chromatography to give the title compound (24 mg) as a white solid.

ESI-MS: 313.2 [M+H]$^+$

Example 62

Synthesis of N-[2-(diisopropylamino)ethyl]-4-(thieno[3,2-c]pyridin-4-yl)benzamide dihydrochloride [62] (Hereinafter, Referred to as a Compound [62])

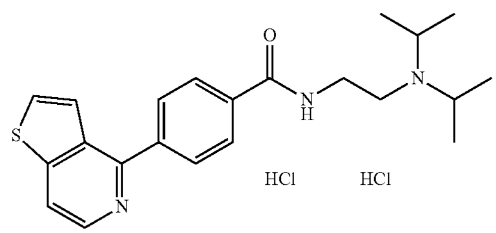 [SMILES: CC(C)N(CCNC(=O)c1ccc(-c2nccc3sccc23)cc1)C(C)C ; Cl ; Cl]

To a solution of the compound [59-1] (28 mg) in toluene (0.20 mL) were added 1,5,7-triazabicyclo[4.4.0]dec-5-ene (4.2 mg) and N,N-diisopropylethylenediamine (87 μL) at room temperature, and the mixture was stirred at 80° C. for 21 hours. To the reaction mixture was added ethyl acetate, and the mixture was purified by silica gel column chromatography. To the obtained oil was added a solution of 4 M hydrogen chloride in ethyl acetate, and the resulting solid was collected by filtration to give the title compound (20 mg) as a white solid.

ESI-MS: 382.3 [M+H]$^+$

Example 63

Synthesis of N-[trans-4-(2-hydroxypropan-2-yl)cyclohexyl]-4-(thieno[3,2-c]pyridin-4-yl)benzamide [63] (Hereinafter, Referred to as a Compound [63])

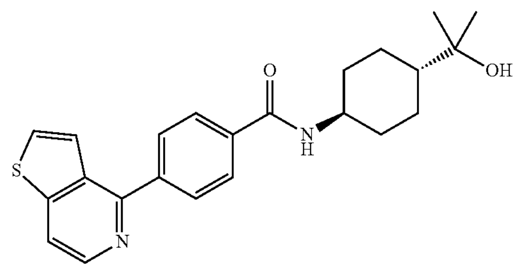 [SMILES: CC(C)(O)[C@H]1CC[C@H](NC(=O)c2ccc(-c3nccc4sccc34)cc2)CC1]

To a solution of 4-chlorothieno[3,2-c]pyridine (58.0 mg) in ethanol (0.8 mL)/water (0.8 mL) were added the compound [2-1] (120 mg), potassium carbonate (56.0 mg), and [1,3-bis(2,6-diisopropylphenyl)-4,5-dihydroimidazol-2-ylidene]chloro[3-phenylallyl]palladium (II) (10.0 mg) at room temperature, and the mixture was stirred at 80° C. for 1 hour under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (105 mg) as a white solid.

$^1$H-NMR (400 MHz, DMSO-$d_6$) δ: 8.54 (d, J=5.5 Hz, 1H), 8.32 (d, J=8.2 Hz, 1H), 8.12 (dd, J=5.5, 0.9 Hz, 1H), 8.01 (d, J=8.2 Hz, 2H), 7.96 (d, J=5.5 Hz, 1H), 7.90 (d, J=8.2 Hz, 2H), 7.70-7.61 (m, 1H), 4.04 (s, 1H), 3.85-3.65 (m, 1H), 1.96-1.72 (m, 4H), 1.42-1.25 (m, 2H), 1.24-0.93 (m, 9H).

ESI-MS: 395.3 [M+H]$^+$

Example 64

Synthesis of 4-(furo[3,2-c]pyridin-4-yl)-N-[trans-4-(2-hydroxy-2-methylpropoxy)cyclohexyl]benzamide [64] (Hereinafter, Referred to as a Compound [64])

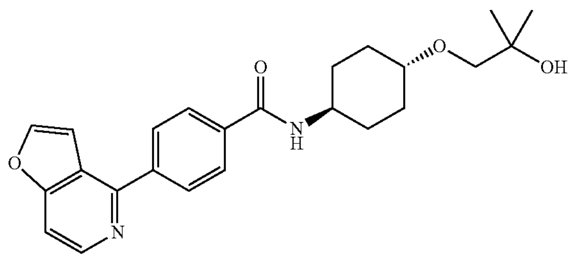 [SMILES: CC(C)(O)CO[C@H]1CC[C@H](NC(=O)c2ccc(-c3nccc4occc34)cc2)CC1]

(1) Synthesis of trans-4-(dibenzylamino)cyclohexan-1-ol [64-1] (Hereinafter, Referred to as a Compound [64-1])

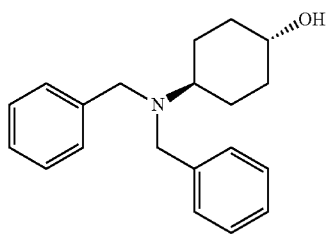 [SMILES: O[C@H]1CC[C@H](N(Cc2ccccc2)Cc2ccccc2)CC1]

To a solution of trans-4-aminocyclohexan-1-ol (3.00 g) in ethanol (50.0 mL) were added benzyl bromide (6.80 mL) and sodium bicarbonate (8.75 g) at room temperature, and the mixture was stirred at 80° C. for 45 minutes. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (2.00 g) as a white solid.

$^1$H-NMR (400 MHz, $CDCl_3$) δ: 7.37-7.35 (m, 4H), 7.30-3.57-3.52-7.26 (m, 4H), 7.22-7.18 (m, 2H), 3.64 (s, 4H), (m, 1H), 2.56-2.48 (m, 1H), 2.14-1.97 (m, 2H), 1.94-1.88 (m, 2H), 1.48-1.38 (m, 2H), 1.23-1.14 (m, 2H).

ESI-MS: 296.3 [M+H]$^+$ (2) Synthesis of tert-butyl 2-{[trans-4-(dibenzylamino)cyclohexyl]oxy}acetate [64-2] (Hereinafter, Referred to as a Compound [64-2])

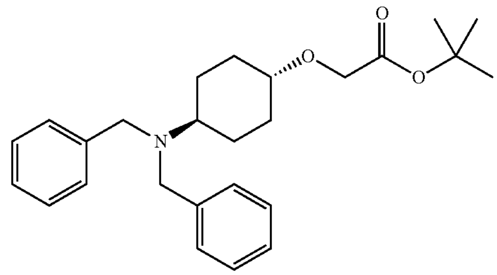 [SMILES: CC(C)(C)OC(=O)CO[C@H]1CC[C@H](N(Cc2ccccc2)Cc2ccccc2)CC1]

To a solution of the compound [64-1] (2.0 g) in DMF (13 mL) were added 60% sodium hydride (320 mg) and tert-butyl bromoacetate (1.5 mL) at room temperature, and the mixture was stirred at 55° C. for 2 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (700 mg) as a yellow oil.

$^1$H-NMR (400 MHz, $CDCl_3$) δ: 7.36-7.34 (m, 4H), 7.30-7.26 (m, 4H), 7.21-7.18 (m, 2H), 3.96 (s, 2H), 3.60 (s, 4H), 3.27-3.20 (m, 1H), 2.56-2.49 (m, 1H), 2.10-2.07 (m, 2H), 1.93-1.90 (m, 2H), 1.46-1.43 (m, 13H).

ESI-MS: 410.4 [M+H]$^+$ (3) Synthesis of 1-{[trans-4-(dibenzylamino)cyclohexyl]oxy}-2-methylpropan-2-ol [64-3] (Hereinafter, Referred to as a Compound [64-3])

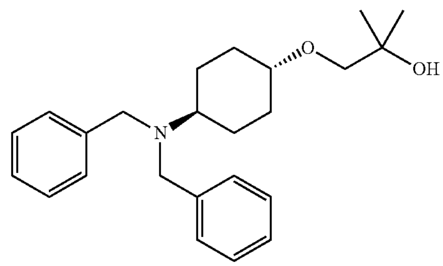 [SMILES: CC(C)(O)CO[C@H]1CC[C@H](N(Cc2ccccc2)Cc2ccccc2)CC1]

To a solution of the compound [64-2] (700 mg) in THE (3.40 mL) was added a solution of 3 M methylmagnesium bromide in diethyl ether (1.70 mL) at 0° C., and the mixture was stirred at room temperature for 3 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (285 mg) as a yellow oil.

$^1$H-NMR (400 MHz, $CDCl_3$) δ: 7.37-7.35 (m, 4H), 7.31-7.27 (m, 4H), 7.22-7.19 (m, 2H), 3.61 (s, 4H), 3.24 (s, 2H), 3.22-3.15 (m, 1H), 2.56-2.50 (m, 1H), 2.08-2.04 (m, 2H), 1.93-1.90 (m, 2H), 1.40-1.31 (m, 2H), 1.20-1.10 (m, 8H).

ESI-MS: 368.4 [M+H]$^+$ (4) Synthesis of 1-[(trans-4-aminocyclohexyl)oxy]-2-methylpropan-2-ol [64-4] (Hereinafter, Referred to as a Compound [64-4])

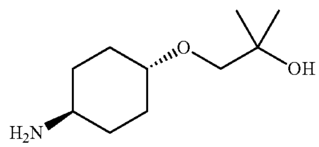

To a solution of the compound [64-3] (285 mg) in ethanol (1.50 mL) was added 20% palladium hydroxide-activated carbon (21.0 mg) at room temperature, and the mixture was stirred at room temperature for 4 hours under a hydrogen atmosphere. The reaction mixture was filtered and concentrated under reduced pressure to give the title compound (140 mg) as a black oil.

$^{1}$H-NMR (400 MHz, $CDCl_3$) δ: 3.27-3.21 (m, 3H), 2.74-2.68 (m, 1H), 2.03-1.99 (m, 2H), 1.89-1.86 (m, 2H), 1.34-1.08 (m, 10H).

ESI-MS: 188.3 $[M+H]^+$ (5) Synthesis of ethyl 4-(furo[3,2-c]pyridin-4-yl) benzoate [64-5] (Hereinafter, Referred to as a Compound [64-5])

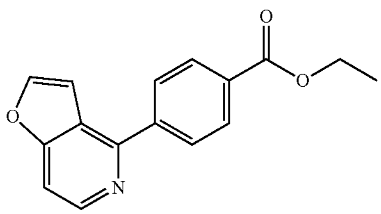 [SMILES: CCOC(=O)c1ccc(-c2nccc3occc23)cc1]

To a solution of 4-chlorofuro[3,2-c]pyridine (2.00 g) in ethanol (13.0 mL)/water (13.0 mL) were added 4-(ethoxycarbonyl)phenylboronic acid (2.65 g), potassium carbonate (2.36 g), and [1,3-bis(2,6-diisopropylphenyl)-4,5-dihydroimidazol-2-ylidene]chloro[3-phenylallyl]palladium (II) (84.0 mg) at room temperature, and the mixture was stirred at 100° C. for 3 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (3.20 g) as a white solid.

$^{1}$H-NMR (400 MHz, $CDCl_3$) δ: 8.62 (d, J=5.5 Hz, 1H), 8.24-8.18 (m, 2H), 8.05-8.03 (m, 2H), 7.74 (d, J=2.3 Hz, 1H), 7.48 (dd, J=5.9, 0.9 Hz, 1H), 7.08-7.07 (m, 1H), 3H), 4.43 (q, J=7.2 Hz, 2H), 1.44 (t, J=7.1 Hz, ESI-MS: 268.3 $[M+H]^+$ (6) Synthesis of 4-(furo[3,2-c]pyridin-4-yl)-N-[trans-4-(2-hydroxy-2-methylpropoxy)cyclohexyl] benzamide [64]

To a solution of the compound [64-5] (20 mg) in toluene (150 μL) were added 1,5,7-triazabicyclo[4.4.0]dec-5-ene (3.2 mg) and the compound [64-4] (71 mg) at room temperature, and the mixture was stirred at 80° C. for 24 hours. To the reaction mixture was added chloroform, and the mixture was purified by silica gel column chromatography to give the title compound (4.2 mg) as a brown solid.

$^{1}$H-NMR (400 MHz, DMSO-$d_6$) δ: 8.59 (d, J=5.5 Hz, 1H), 8.33 (d, J=7.8 Hz, 1H), 8.24 (d, J=2.7 Hz, 1H), 8.08 (dd, J=6.9, 1.8 Hz, 2H), 8.03-7.98 (m, 2H), 7.73 (d, J=5.5 Hz, 1H), 7.37-7.36 (m, 1H), 3.86-3.72 (m, 1H), 3.16-3.11 (m, 3H), 2.03-2.01 (m, 2H), 1.90-1.87 (m, 2H), 1.46-1.34 (m, 2H), 1.31-1.20 (m, 2H), 1.06 (s, 6H).

ESI-MS: 409.4 $[M+H]^+$

Examples 65 to 97

Each compound of Examples 65 to 97 shown in the following Tables was synthesized according to the method shown in step (6) in Example 64. The structure, name, and ESI-MS of the compound of each Example are shown in the following Tables.

TABLE 2-1

| Example | Structure | Name | ESI-MS |
|---|---|---|---|
| 65 | 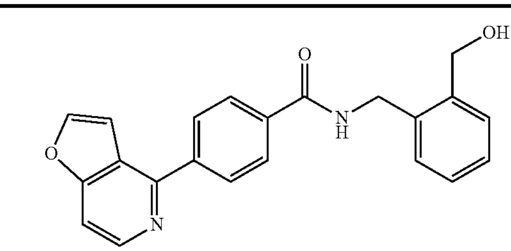 | 4-(furo[3,2-c]pyridin-4-yl)-N-[2-(hydroxymethyl) benzyl]benzamide | 359.2 $[M + H]^+$ |
| 66 | 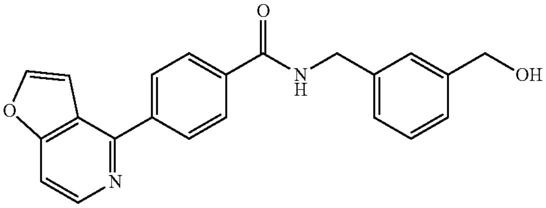 [SMILES: O=C(NCc1cccc(CO)c1)c1ccc(-c2nccc3occc23)cc1] | 4-(furo[3,2-c]pyridin-4-yl)-N-[3-(hydroxymethyl) benzyl]benzamide | 369.2 $[M + H]^+$ |

TABLE 2-1-continued

| Example | Structure | Name | ESI-MS |
|---|---|---|---|
| 67 | 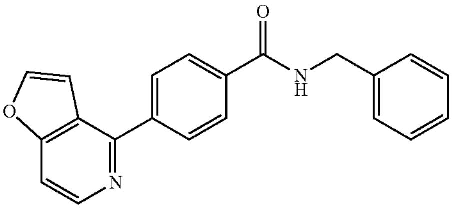 [SMILES: O=C(NCc1ccccc1)c1ccc(-c2nccc3occc23)cc1] | N-benzyl-4-(furo[3,2-c]pyridin-4-yl)benzamide | 329.2 $[M + H]^+$ |
| 68 | 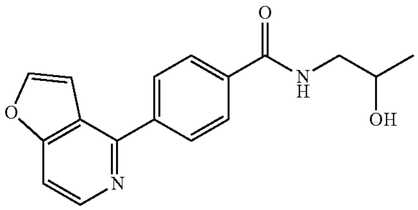 [SMILES: CC(O)CNC(=O)c1ccc(-c2nccc3occc23)cc1] | 4-(furo[3,2-c]pyridin-4-yl)-N-(2-hydroxypropyl) benzamide | 297.2 $[M + H]^+$ |
| 69 | 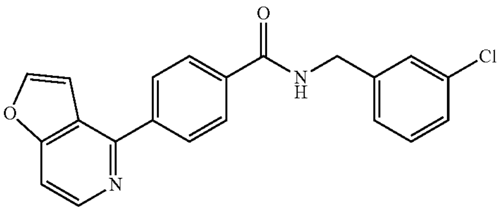 [SMILES: O=C(NCc1cccc(Cl)c1)c1ccc(-c2nccc3occc23)cc1] | N-(3-chlorobenzyl)-4-(furo[3,2-c]pyridin-4-yl)benzamide | 363.2 $[M + H]^+$ |

TABLE 2-2

| | | | |
|---|---|---|---|
| 70 | 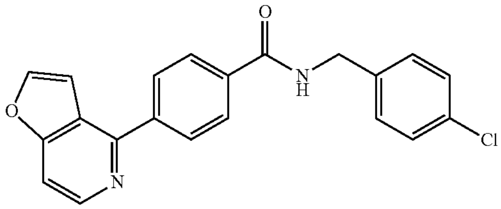 [SMILES: O=C(NCc1ccc(Cl)cc1)c1ccc(-c2nccc3occc23)cc1] | N-(4-chlorobenzyl)-4-(furo[3,2-c]pyridin-4-yl)benzamide | 363.2 $[M + H]^+$ |
| 71 | 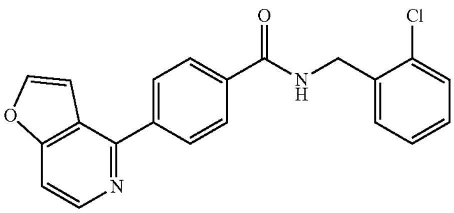 [SMILES: O=C(NCc1ccccc1Cl)c1ccc(-c2nccc3occc23)cc1] | N-(2-chlorobenzyl)-4-(furo[3,2-c]pyridin-4-yl)benzamide | 363.2 $[M + H]^+$ |
| 72 | 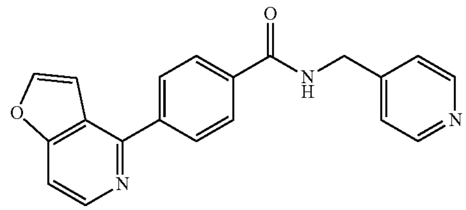 [SMILES: O=C(NCc1ccncc1)c1ccc(-c2nccc3occc23)cc1] | 4-(furo[3,2-c]pyridin-4-yl)-N-(pyridin-4-ylmethyl) benzamide | 330.2 $[M + H]^+$ |

TABLE 2-2-continued
| | | | |
|---|---|---|---|
| 73 | 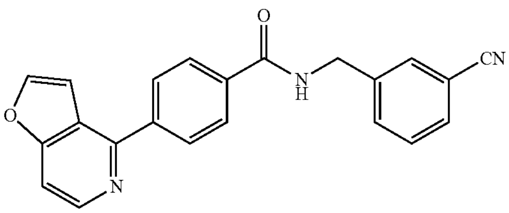 [SMILES: N#Cc1cccc(CNC(=O)c2ccc(-c3nccc4occc34)cc2)c1] | N-(3-cyanobenzyl)-4-(furo[3,2-c]pyridin-4-yl)benzamide | 354.2 $[M + H]^+$ |
| 74 | 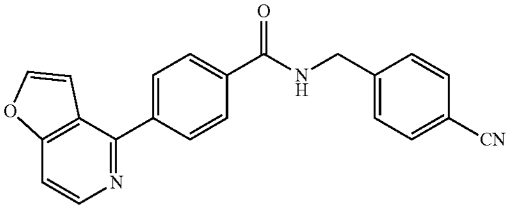 [SMILES: N#Cc1ccc(CNC(=O)c2ccc(-c3nccc4occc34)cc2)cc1] | N-(4-cyanobenzyl)-4-(furo[3,2-c]pyridin-4-yl)benzamide | 354.2 $[M + H]^+$ |
TABLE 2-3
| | | | |
|---|---|---|---|
| 75 | 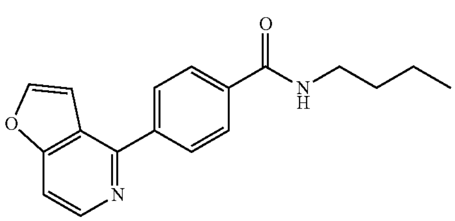 | N-butyl-4-(furo[3,2-c]pyridin-4-yl)benzamide | 295.2 $[M + H]^+$ |
| 76 | 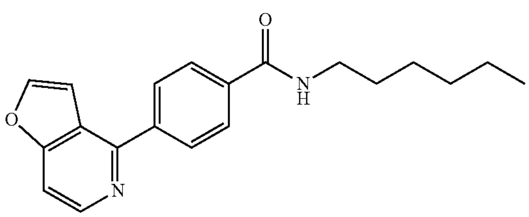 [SMILES: CCCCCCNC(=O)c1ccc(-c2nccc3occc23)cc1] | 4-(furo[3,2-c]pyridin-4-yl)-N-hexylbenzamide | 323.3 $[M + H]^+$ |
| 77 | 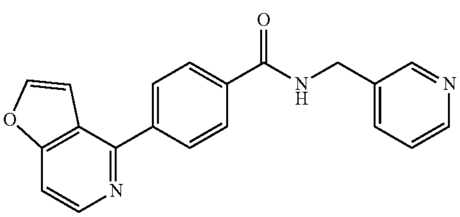 [SMILES: O=C(NCc1cccnc1)c1ccc(-c2nccc3occc23)cc1] | 4-(furo[3,2-c]pyridin-4-yl)-N-(pyridin-3-ylmethyl) benzamide | 330.2 $[M + H]^+$ |
| 78 | 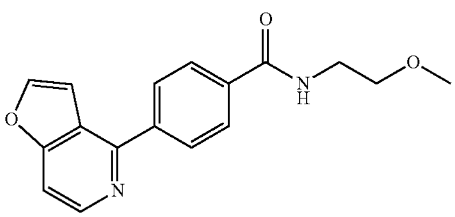 [SMILES: COCCNC(=O)c1ccc(-c2nccc3occc23)cc1] | 4-(furo[3,2-c]pyridin-4-yl)-N-(2-methoxyethyl) benzamide | 297.2 $[M + H]^+$ |

TABLE 2-3-continued

| | | | |
|---|---|---|---|
| 79 | 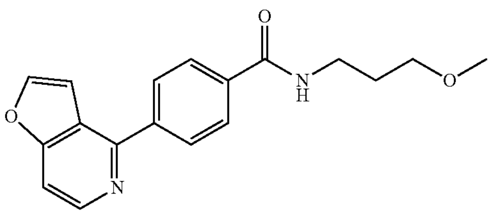 [SMILES: COCCCNC(=O)c1ccc(-c2nccc3occc23)cc1] | 4-(furo[3,2-c]pyridin-4-yl)-N-(3-methoxypropyl) benzamide | 311.2 [M + H]$^+$ |

TABLE 2-4

| | | | |
|---|---|---|---|
| 80 | 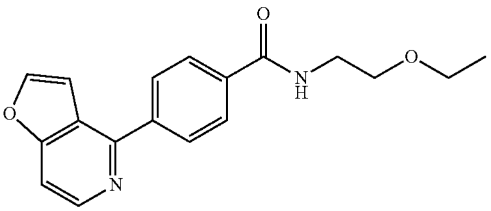 [SMILES: CCOCCNC(=O)c1ccc(-c2nccc3occc23)cc1] | N-(2-ethoxyethyl)-4-(furo[3,2-c]pyridin-4-yl)benzamide | 311.2 [M + H]$^+$ |
| 81 | 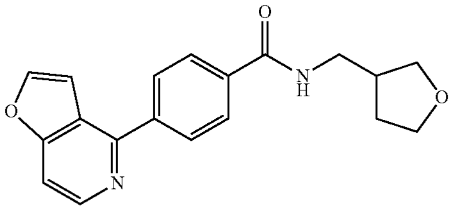 [SMILES: O=C(NCC1CCOC1)c1ccc(-c2nccc3occc23)cc1] | 4-(furo[3,2-c]pyridin-4-yl)-N-[(tetrahydrofuran-3-yl)methyl] benzamide | 323.2 [M + H]$^+$ |
| 82 | 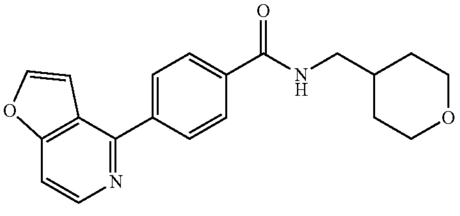 [SMILES: O=C(NCC1CCOCC1)c1ccc(-c2nccc3occc23)cc1] | 4-(furo[3,2-c]pyridin-4-yl)-N-[(tetrahydro-2H-pyran-4-yl)methyl] benzamide | 337.3 [M + H]$^+$ |
| 83 | 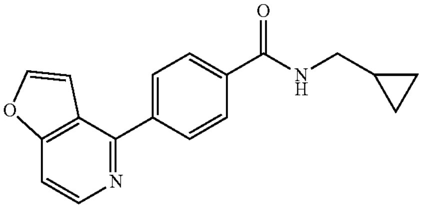 [SMILES: O=C(NCC1CC1)c1ccc(-c2nccc3occc23)cc1] | N-(cyclopropyl-methyl)-4-(furo[3,2-c]pyridin-4-yl)benzamide | 293.2 [M + H]$^+$ |
| 84 | 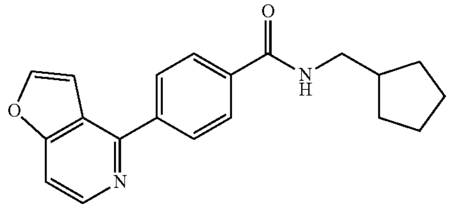 [SMILES: O=C(NCC1CCCC1)c1ccc(-c2nccc3occc23)cc1] | N-(cyclopenthyl-methyl)-4-(furo[3,2-c]pyridin-4-yl)benzamide | 321.2 [M + H]$^+$ |

TABLE 2-5
| | | | |
|---|---|---|---|
| 85 | 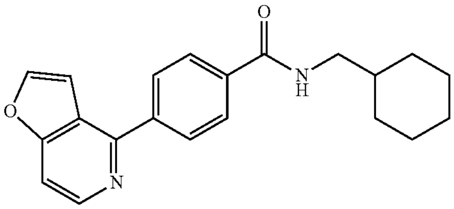 [SMILES: O=C(NCC1CCCCC1)c1ccc(-c2nccc3occc23)cc1] | N-(cyclohexyl-methyl)-4-(furo[3,2-c]pyridin-4-yl)benzamide | 335.2 $[M + H]^+$ |
| 86 | 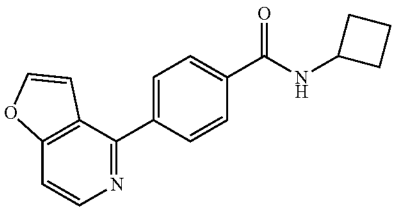 [SMILES: O=C(NC1CCC1)c1ccc(-c2nccc3occc23)cc1] | N-cyclobutyl-4-(furo[3,2-c]pyridin-4-yl)benzamide | 293.2 $[M + H]^+$ |
| 87 | 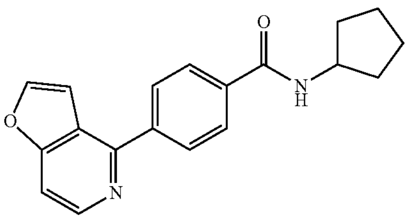 [SMILES: O=C(NC1CCCC1)c1ccc(-c2nccc3occc23)cc1] | N-cyclopenthyl-4-(furo[3,2-c]pyridin-4-yl)benzamide | 307.2 $[M + H]^+$ |
| 88 | 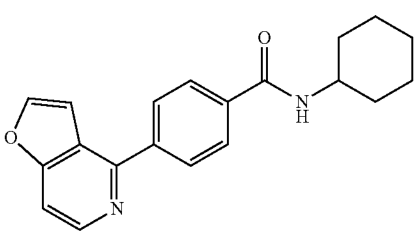 [SMILES: O=C(NC1CCCCC1)c1ccc(-c2nccc3occc23)cc1] | N-cyclohexyl-4-(furo[3,2-c]pyridin-4-yl)benzamide | 321.2 $[M + H]^+$ |
| 89 | 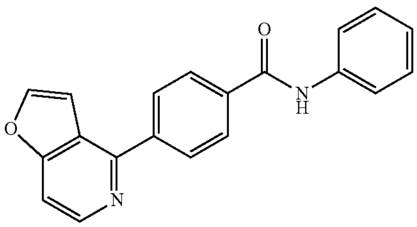 | 4-(furo[3,2-c]pyridin-4-yl)-N-phenylbenzamide | 315.2 $[M + H]^+$ |
TABLE 2-6
| | | | |
|---|---|---|---|
| 90 | 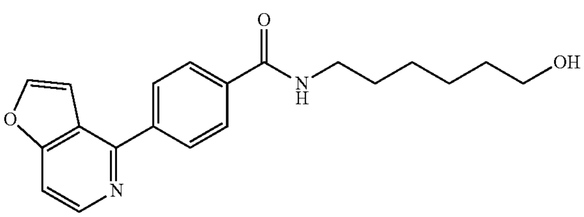 [SMILES: O=C(NCCCCCCO)c1ccc(-c2nccc3occc23)cc1] | 4-(furo[3,2-c]pyridin-4-yl)-N-(6-hydroxyhexyl) benzamide | 339.3 $[M + H]^+$ |

TABLE 2-6-continued
| | | | |
|---|---|---|---|
| 91 | 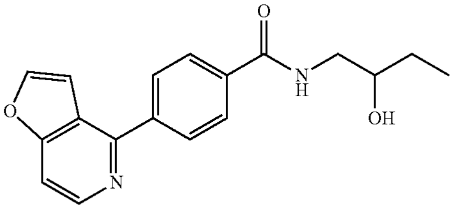 [SMILES: CCC(O)CNC(=O)c1ccc(-c2nccc3occc23)cc1] | 4-(furo[3,2-c]pyridin-4-yl)-N-(2-hydroxybutyl) benzamide | 311.2 $[M + H]^+$ |
| 92 | 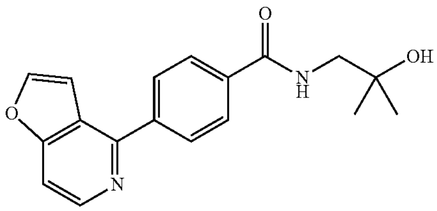 [SMILES: CC(C)(O)CNC(=O)c1ccc(-c2nccc3occc23)cc1] | 4-(furo[3,2-c]pyridin-4-yl)-N-(2-hydroxy-2-methylpropyl) benzamide | 311.2 $[M + H]^+$ |
| 93 | 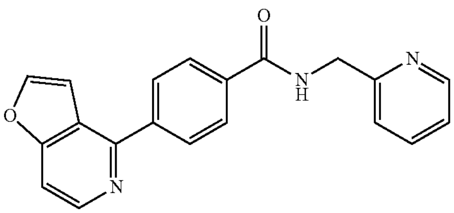 [SMILES: O=C(NCc1ccccn1)c1ccc(-c2nccc3occc23)cc1] | 4-(furo[3,2-c]pyridin-4-yl)-N-(pyridin-2-ylmethyl) benzamide | 330.2 $[M + H]^+$ |
| 94 | 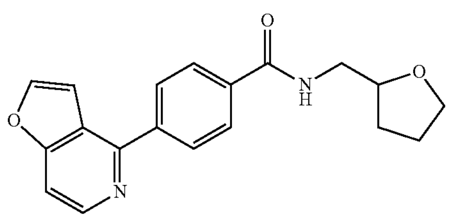 [SMILES: O=C(NCC1CCCO1)c1ccc(-c2nccc3occc23)cc1] | 4-(furo[3,2-c]pyridin-4-yl)-N-[(tetrahydro-furan-2-yl) methyl] benzamide | 323.2 $[M + H]^+$ |
TABLE 2-7
| | | | |
|---|---|---|---|
| 95 | 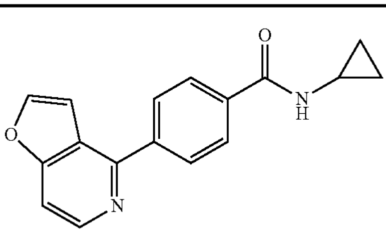 | N-cyclopropyl-4-(furo[3,2-c]pyridin-4-yl)benzamide | 279.2 $[M + H]^+$ |
| 96 | 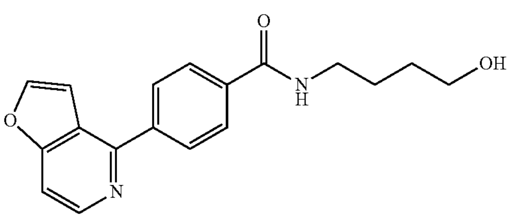 [SMILES: O=C(NCCCCO)c1ccc(-c2nccc3occc23)cc1] | 4-(furo[3,2-c]pyridin-4-yl)-N-(4-hydroxybutyl) benzamide | 311.2 $[M + H]^+$ |

TABLE 2-7-continued

| | | | |
|---|---|---|---|
| 97 | 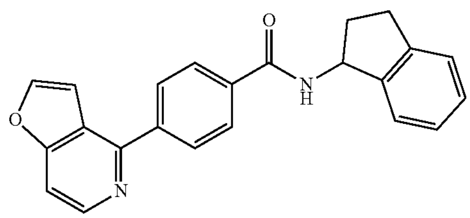 [SMILES: O=C(NC1CCc2ccccc21)c1ccc(-c2nccc3occc23)cc1] | N-(2,3-dihydro-1H-inden-1-yl)-4-(furo[3,2-c]pyridin-4-yl)benzamide | 355.2 [M + H]$^+$ |

Example 98

Synthesis of N-[2-(diisopropylamino)ethyl]-4-(furo[3,2-c]pyridin-4-yl)benzamide Dihydrochloride [98] (Hereinafter, Referred to as a Compound [98])

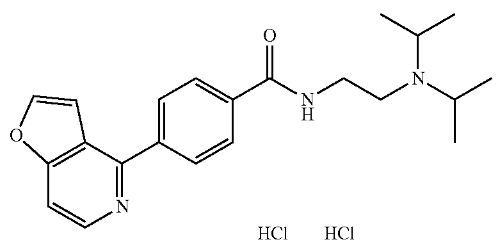 [SMILES: CC(C)N(CCNC(=O)c1ccc(-c2nccc3occc23)cc1)C(C)C ; Cl ; Cl]

HCl HCl

To a solution of the compound [64-5] (150 mg) in toluene (1.12 mL) were added 1,5,7-triazabicyclo[4.4.0]dec-5-ene (23.4 mg) and N,N-diisopropylethylenediamine (488 μL) at room temperature, and the mixture was stirred at 80° C. for 24 hours. To the reaction mixture was added chloroform, and the mixture was purified by silica gel column chromatography. To the obtained oil was added a solution of 4 M hydrogen chloride in ethyl acetate, and the resulting solid was collected by filtration to give the title compound (154 mg) as a yellow solid.

ESI-MS: 366.3 [M+H]$^+$

Example 99

Synthesis of 4-(furo[3,2-c]pyridin-4-yl)-N-[1-(1-methyl-1H-tetrazol-5-yl)piperidin-4-yl]benzamide [99] (Hereinafter, Referred to as a Compound [99])

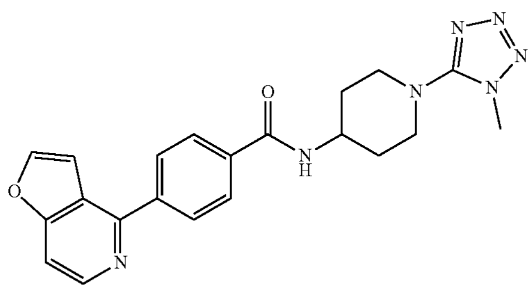 [SMILES: Cn1nnnc1N1CCC(NC(=O)c2ccc(-c3nccc4occc34)cc2)CC1]

(1) Synthesis of 4-(furo[3,2-c]pyridin-4-yl)benzoic acid [99-1] (Hereinafter, Referred to as a Compound [99-1])

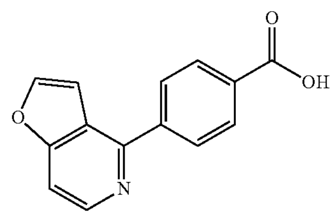 [SMILES: O=C(O)c1ccc(-c2nccc3occc23)cc1]

To a solution of the compound [64-5] (3.50 g) in methanol (44.0 mL) was added a 2 M aqueous sodium hydroxide solution (33.0 mL) at room temperature, and the mixture was stirred at 100° C. for 10 minutes. To the reaction mixture was added 2 M Hydrochloric acid (33.0 mL), and the resulting solid was collected by filtration and dried at 40° C. under reduced pressure to give the title compound (3.42 g) as a gray solid.

$^1$H-NMR (400 MHz, DMSO-$d_6$) δ: 8.72-8.66 (m, 1H), 8.43-8.36 (m, 1H), 8.17-8.12 (m, 4H), 8.02-7.91 (m, 1H), 7.49-7.45 (m, 1H).

ESI-MS: 240.3 [M+H]$^+$ (2) Synthesis of 4-(furo[3,2-c]pyridin-4-yl)-N-[1-(1-methyl-1H-tetrazol-5-yl)piperidin-4-yl]benzamide [99]

To a solution of the compound [99-1] (10.0 mg) in DMF (150 μL) were added DIPEA (8.00 μL), (1-cyano-2-ethoxy-2-oxoethylideneaminooxy)dimethylaminomorpholinocarbenium hexafluorophosphate (20.0 mg), and 1-(1-methyl-1H-1,2,3,4-tetrazol-5-yl)piperidin-4-amine dihydrochloride (14.0 mg) at room temperature, and the mixture was stirred at room temperature for 22 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (13.0 mg) as a pink solid.

$^1$H-NMR (400 MHz, $CD_3OD$) δ: 8.53 (d, J=5.5 Hz, 1H), 8.04-7.99 (m, 5H), 7.63 (d, J=5.9 Hz, 1H), 7.20 (d, J=2.3 Hz, 1H), 4.22-4.14 (m, 1H), 3.94 (s, 3H), 3.76-3.73 (m, 2H), 3.25-3.18 (m, 2H), 2.13-2.09 (m, 2H), 1.92-1.82 (m, 2H).

ESI-MS: 404.4 [M+H]$^+$

Examples 100 to 117

Each compound of Examples 100 to 117 shown in the following Tables was synthesized according to the method shown in step (2) in Example 99. The structure, name, and ESI-MS of the compound of each Example are shown in the following Tables.

TABLE 3-1

| Example | Structure | Name | ESI-MS |
|---|---|---|---|
| 100 | 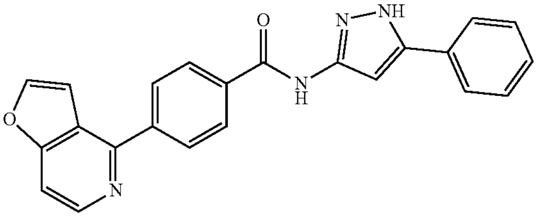 [SMILES: O=C(Nc1cc(-c2ccccc2)[nH]n1)c1ccc(-c2nccc3occc23)cc1] | 4-(furo[3,2-c]pyridin-4-yl)-N-(5-phenyl-1H-pyrazol-3-yl)benzamide | 381.3 $[M + H]^+$ |
| 101 | 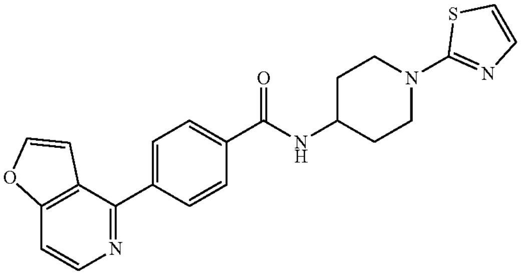 [SMILES: O=C(NC1CCN(c2nccs2)CC1)c1ccc(-c2nccc3occc23)cc1] | 4-(furo[3,2-c]pyridin-4-yl)-N-[1-(thiazol-2-yl)piperidin-4-yl]benzamide | 405.3 $[M + H]^+$ |
| 102 | 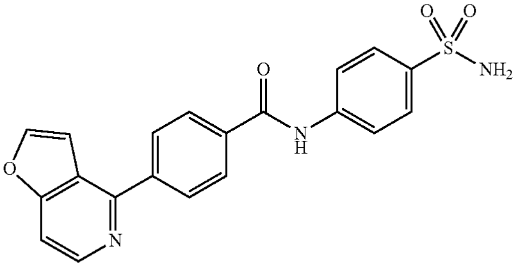 [SMILES: NS(=O)(=O)c1ccc(NC(=O)c2ccc(-c3nccc4occc34)cc2)cc1] | 4-(furo[3,2-c]pyridin-4-yl)-N-(4-sulfamoylphenyl) benzamide | 394.3 $[M + H]^+$ |
| 103 | 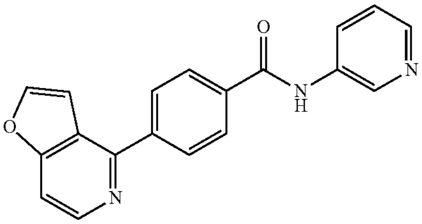 | 4-(furo[3,2-c]pyridin-4-yl)-N-(pyridin-3-yl)benzamide | 316.3 $[M + H]^+$ |
| 104 | 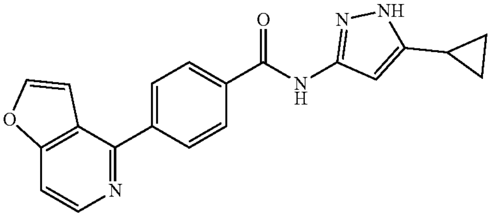 [SMILES: O=C(Nc1cc(C2CC2)[nH]n1)c1ccc(-c2nccc3occc23)cc1] | N-(5-cyclopropyl-1H-pyrazol-3-yl)-4-(furo[3,2-c]pyridin-4-yl)benzamide | 345.3 $[M + H]^+$ |

TABLE 3-2
| | | | |
|---|---|---|---|
| 105 | 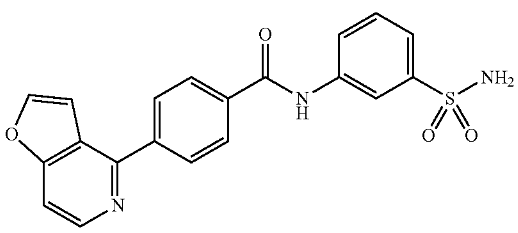 [SMILES: NS(=O)(=O)c1cccc(NC(=O)c2ccc(-c3nccc4occc34)cc2)c1] | 4-(furo[3,2-c]pyridin-4-yl)-N-(3-sulfamoylphenyl) benzamide | 394.3 [M + H]+ |
| 106 | 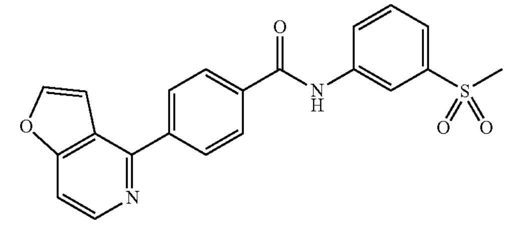 [SMILES: CS(=O)(=O)c1cccc(NC(=O)c2ccc(-c3nccc4occc34)cc2)c1] | 4-(furo[3,2-c]pyridin-4-yl)-N-[3-(methylsulfonyl) phenyl]benzamide | 393.3 [M + H]+ |
| 107 | 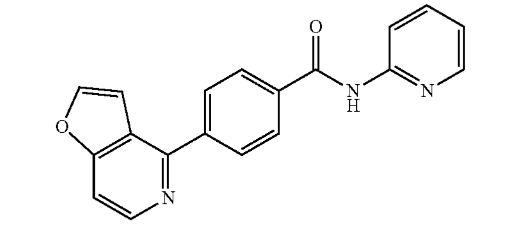 [SMILES: O=C(Nc1ccccn1)c1ccc(-c2nccc3occc23)cc1] | 4-(furo[3,2-c]pyridin-4-yl)-N-(pyridin-2-yl)benzamide | 316.3 [M + H]+ |
| 108 | 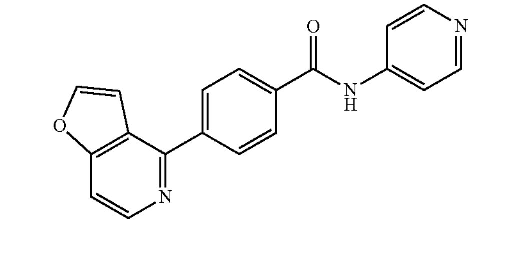 [SMILES: O=C(Nc1ccncc1)c1ccc(-c2nccc3occc23)cc1] | 4-(furo[3,2-c]pyridin-4-yl)-N-(pyridin-4-yl)benzamide | 316.3 [M + H]+ |
| 109 | 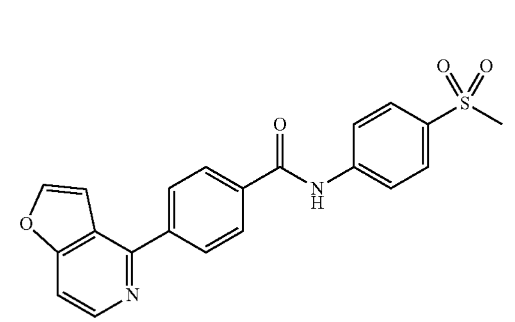 [SMILES: CS(=O)(=O)c1ccc(NC(=O)c2ccc(-c3nccc4occc34)cc2)cc1] | 4-(furo[3,2-c]pyridin-4-yl)-N-[4-(methylsulfonyl) phenyl]benzamide | 393.3 [M + H]+ |
TABLE 3-3
| | | | |
|---|---|---|---|
| 110 | 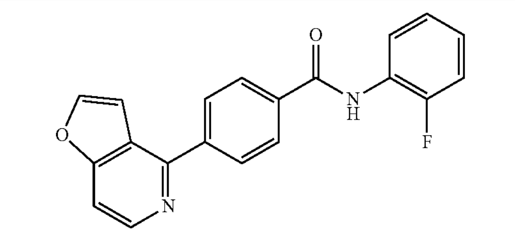 [SMILES: O=C(Nc1ccccc1F)c1ccc(-c2nccc3occc23)cc1] | N-(2-fluorophenyl)-4-(furo[3,2-c]pyridin-4-yl)benzamide | 333.3 [M + H]+ |

TABLE 3-3-continued
| | | | |
|---|---|---|---|
| 111 | 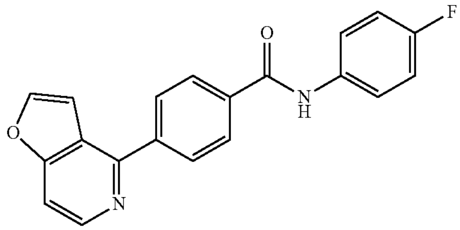 [SMILES: O=C(Nc1ccc(F)cc1)c1ccc(-c2nccc3occc23)cc1] | N-(4-fluorophenyl)-4-(furo[3,2-c]pyridin-4-yl)benzamide | 333.3 $[M + H]^+$ |
| 112 | 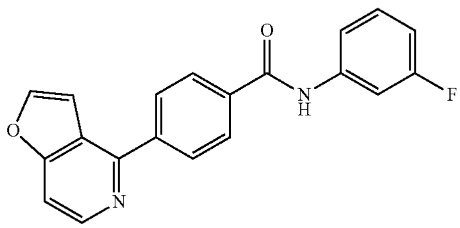 [SMILES: O=C(Nc1cccc(F)c1)c1ccc(-c2nccc3occc23)cc1] | N-(3-fluorophenyl)-4-(furo[3,2-c]pyridin-4-yl)benzamide | 333.3 $[M + H]^+$ |
| 113 | 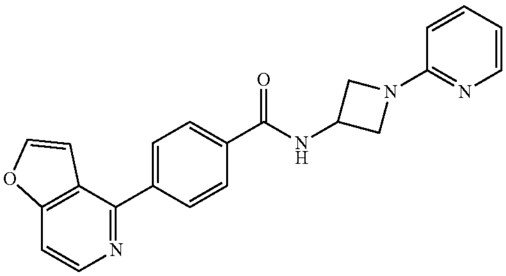 | 4-(furo[3,2-c]pyridin-4-yl)-N-[1-(pyridin-2-yl)azetidin-3-yl]benzamide | 371.4 $[M + H]^+$ |
| 114 | 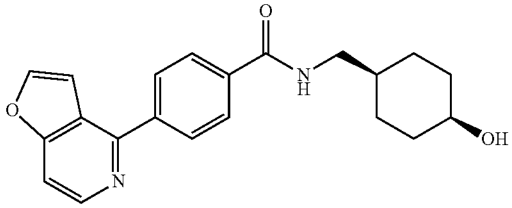 [SMILES: O=C(NC[C@H]1CC[C@@H](O)CC1)c1ccc(-c2nccc3occc23)cc1] | 4-(furo[3,2-c]pyridin-4-yl)-N-[(cis-4-hydroxycyclohexyl)methyl]benzamide | 351.4 $[M + H]^+$ |
TABLE 3-4
| | | | |
|---|---|---|---|
| 115 | 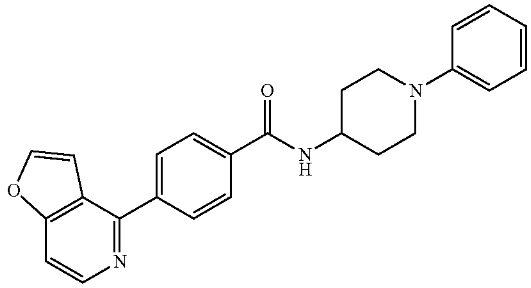 [SMILES: O=C(NC1CCN(c2ccccc2)CC1)c1ccc(-c2nccc3occc23)cc1] | 4-(furo[3,2-c]pyridin-4-yl)-N-(1-phenylpiperidin-4-yl)benzamide | 398.5 $[M + H]^+$ |

TABLE 3-4-continued

| | | | |
|---|---|---|---|
| 116 | 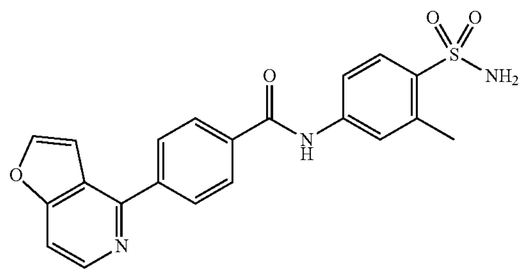 | 4-(furo[3,2-c]pyridin-4-yl)-N-(3-methyl-4-sulfamoylphenyl) benzamide | 408.4 [M + H]+ |
| 117 | 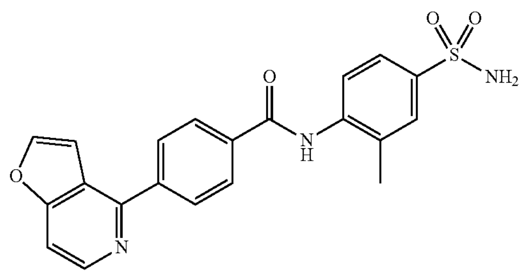 | 4-(furo[3,2-c]pyridin-4-yl)-N-(2-methyl-4-sulfamoylphenyl) benzamide | 408.4 [M + H]+ |

Example 118

Synthesis of 4-(furo[3,2-c]pyridin-4-yl)-N-[1-(pyridin-2-yl)piperidin-4-yl]benzamide [118] (Hereinafter, Referred to as a Compound [118])

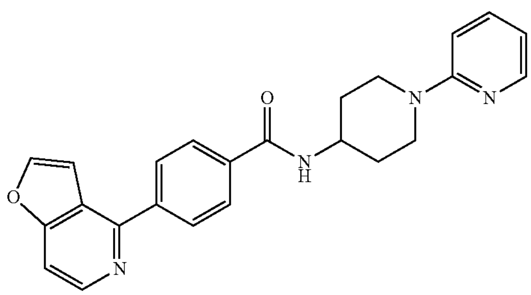 [SMILES: O=C(NC1CCN(c2ccccn2)CC1)c1ccc(-c2nccc3occc23)cc1]

To a solution of the compound [99-1] (20.0 mg) in DMF (300 μL) were added DIPEA (16.0 μL), (1-cyano-2-ethoxy-2-oxoethylideneaminooxy)dimethylaminomorpholinocarbenium hexafluorophosphate (40.0 mg), and 1-(pyridin-2-yl)piperidin-4-amine (19.4 mg) at room temperature, and the mixture was stirred at room temperature for 24 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (13.0 mg) as a yellow solid.

$^1$H-NMR (400 MHz, DMSO-$d_6$) δ: 8.55 (d, J=5.5 Hz, 1H), 8.39 (d, J=8.2 Hz, 1H), 8.21 (d, J=2.3 Hz, 1H), 8.10-8.03 (m, 3H), 7.99 (dd, J=6.9, 1.8 Hz, 2H), 7.69 (dd, J=5.9, 0.9 Hz, 1H), 7.57-7.43 (m, 1H), 7.34-7.33 (m, 1H), 6.85 (d, J=8.7 Hz, 1H), 6.57 (dd, J=6.6, 4.8 Hz, 1H), 4.31-4.28 (m, 2H), 4.16-4.07 (m, 1H), 2.95-2.89 (m, 2H), 1.85-1.83 (m, 2H), 1.58-1.49 (m, 2H).

ESI-MS: 399.4 $[M+H]^+$

Example 119

Synthesis of 4-(furo[3,2-c]pyridin-4-yl)-N-{trans-4-[(2,2,2-trifluoroethyl)amino]cyclohexyl}benzamide [119] (Hereinafter, Referred to as a Compound [119])

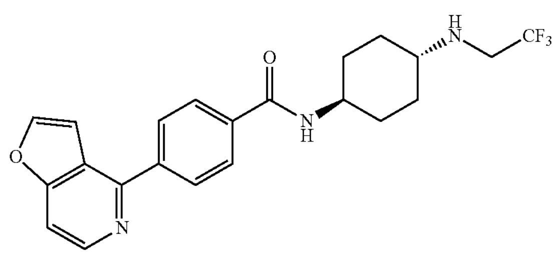 [SMILES: O=C(N[C@H]1CC[C@H](NCC(F)(F)F)CC1)c1ccc(-c2nccc3occc23)cc1]

(1) Synthesis of benzyl{trans-4-[(2,2,2-trifluoroethyl)amino]cyclohexyl}carbamate [119-1] (Hereinafter, Referred to as a Compound [119-1])

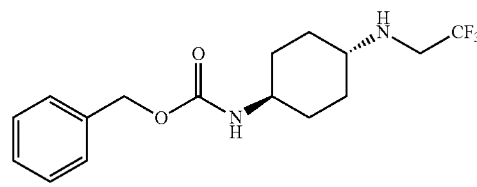 [SMILES: O=C(N[C@H]1CC[C@H](NCC(F)(F)F)CC1)OCc1ccccc1]

To a solution of trans-1,4-cyclohexanediamine (228 mg) in water (2.00 mL)/1,4-dioxane (18.0 mL) were added potassium carbonate (553 mg) and benzyl chloroformate (284 μL) at 0° C., and the mixture was stirred at room temperature for 19 hours. The reaction mixture was concentrated under reduced pressure, water was added to the obtained residue, and the mixture was extracted with chloroform. The organic layer was dried over anhydrous sodium sulfate and concentrated under reduced pressure. To a solution of the obtained residue in 1,4-dioxane (6.30 mL) were added DIPEA (220 μL) and 2,2,2-trifluoroethyl trifluoromethanesulfonate (91.0 μL) at room temperature, and the mixture was stirred at room temperature for 19 hours. The reaction mixture was concentrated under reduced pressure, water was added to the obtained residue, and the mixture was extracted with chloroform. The organic layer was dried over anhydrous sodium sulfate and concentrated under reduced pressure. The obtained residue was purified by silica gel column chromatography to give the title compound (132 mg) as a white solid.

$^1$H-NMR (400 MHz, $CDCl_3$) δ: 7.36-7.30 (m, 5H), 5.08 (s, 2H), 4.58-4.57 (m, 1H), 3.48-3.47 (m, 1H), 3.19 (q, J=9.6 Hz, 2H), 2.04-1.94 (m, 4H), 1.29-1.10 (m, 4H).

ESI-MS: 331.3 $[M+H]^+$ (2) Synthesis of 4-(furo[3,2-c]pyridin-4-yl)-N-{trans-4-[(2,2,2-trifluoroethyl)amino]cyclohexyl}benzamide [119]

To a solution of the compound [119-1] (117 mg) in ethanol (1.20 mL) was added 10% palladium-activated carbon (19.0 mg) at room temperature, and the mixture was stirred at room temperature for 23 hours under a hydrogen atmosphere. The reaction mixture was filtered and concentrated under reduced pressure. To a solution of the obtained residue in DMF (300 μL) were added DIPEA (16.0 μL), (1-cyano-2-ethoxy-2-oxoethylideneaminooxy)dimethylaminomorpholinocarbenium hexafluorophosphate (40.0 mg), and the compound [99-1] (20.0 mg) at room temperature, and the mixture was stirred at room temperature for 21 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (4.50 mg) as a pink solid.

$^1$H-NMR (400 MHz, DMSO-$d_6$) δ: 8.58 (d, J=5.5 Hz, 1H), 8.33 (d, J=8.2 Hz, 1H), 8.24 (d, J=2.3 Hz, 1H), 8.08 (dd, J=6.9, 1.8 Hz, 2H), 8.04-7.94 (m, 2H), 7.72 (dd, J=5.7, 1.1 Hz, 1H), 7.36-7.35 (m, 1H), 3.86-3.68 (m, 1H), 3.29-3.19 (m, 2H), 2.41-2.39 (m, 1H), 2.23-2.18 (m, 1H), 1.94-1.84 (m, 4H), 1.42-1.32 (m, 2H), 1.16-1.06 (m, 2H).

ESI-MS: 418.4 $[M+H]^+$

Example 120

Synthesis of 4-(furo[3,2-c]pyridin-4-yl)-N-[trans-4-(hydroxymethyl)cyclohexyl]benzamide [120] (Hereinafter, Referred to as a Compound [120])

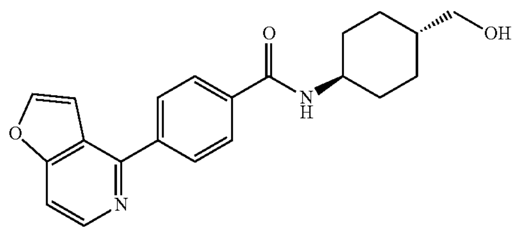 [SMILES: O=C(N[C@H]1CC[C@H](CO)CC1)c1ccc(-c2nccc3occc23)cc1]

To a solution of the compound [99-1] (191 mg) in DMF (3.20 mL) were added DIPEA (150 μL), (1-cyano-2-ethoxy-2-oxoethylideneaminooxy)dimethylaminomorpholinocarbenium hexafluorophosphate (377 mg), and (trans-4-aminocyclohexyl)methanol (134 mg) at room temperature, and the mixture was stirred at room temperature for 17 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (280 mg) as a yellow solid.

$^1$H-NMR (400 MHz, DMSO-$d_6$) δ: 8.59 (d, J=5.5 Hz, 1H), 8.34 (d, J=7.8 Hz, 1H), 8.25 (d, J=2.3 Hz, 1H), 8.08 (dd, J=6.4, 1.8 Hz, 2H), 8.02-8.00 (m, 2H), 7.74 (d, J=5.9 Hz, 1H), 7.37-7.36 (m, 1H), 3.79-3.71 (m, 1H), 3.24-3.22 (m, 2H), 1.89-1.87 (m, 2H), 1.80-1.77 (m, 2H), 1.40-1.31 (m, 3H), 1.03-0.94 (m, 2H).

ESI-MS: 351.3 $[M+H]^+$

Example 121

Synthesis of 4-(furo[3,2-c]pyridin-4-yl)-N-[trans-4-(1-hydroxyethyl)cyclohexyl]benzamide [121] (Hereinafter, Referred to as a Compound [121])

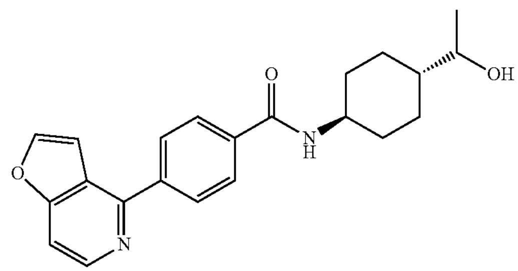 [SMILES: CC(O)[C@H]1CC[C@H](NC(=O)c2ccc(-c3nccc4occc34)cc2)CC1]

To a solution of the compound [120] (250 mg) in dichloromethane (2.40 mL) was added 1,1,1-triacetoxy-1,1-dihydro-1,2-benziodoxol-3 (1H)-one (Dess-Martin periodinane) (394 mg) at room temperature, and the mixture was stirred at room temperature for 3 hours. To the reaction mixture was added water, and the mixture was extracted with chloroform. The organic layer was dried over anhydrous sodium sulfate and concentrated under reduced pressure. To a solution of the obtained residue in THF (3.00 mL) was added a solution of 3 M methylmagnesium bromide in diethyl ether (880 μL) at 0° C., and the mixture was stirred at room temperature for 2 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (47.0 mg) as a pink solid.

$^1$H-NMR (400 MHz, DMSO-$d_6$) δ: 8.56 (d, J=5.9 Hz, 1H), 8.33-8.27 (m, 1H), 8.21 (d, J=2.3 Hz, 1H), 8.09-8.03 (m, 2H), 8.01-7.95 (m, 2H), 7.69 (dd, J=5.8, 1.0 Hz, 1H), 7.34-7.33 (m, 1H), 4.28-4.27 (m, 1H), 3.75-3.66 (m, 1H), 3.35-3.33 (m, 1H), 1.90-1.67 (m, 4H), 1.36-1.02 (m, 8H).

ESI-MS: 365.3 $[M+H]^+$

Example 122

Synthesis of 4-(furo[3,2-c]pyridin-4-yl)-N-[6-(2-hydroxypropan-2-yl)spiro[3.3]heptan-2-yl]benzamide [122] (Hereinafter, Referred to as a Compound [122])

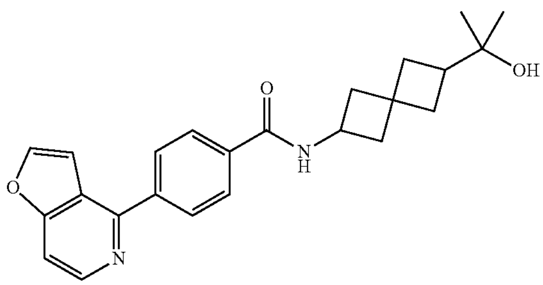 [SMILES: CC(C)(O)C1CC2(CC(NC(=O)c3ccc(-c4nccc5occc45)cc3)C2)C1]

(1) Synthesis of methyl 6-(dibenzylamino)spiro[3.3]heptane-2-carboxylate [122-1] (Hereinafter, Referred to as a Compound [122-1])

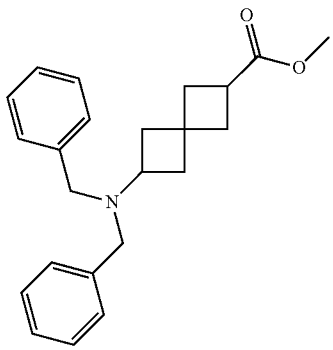 [SMILES: COC(=O)C1CC2(C1)CC(N(Cc1ccccc1)Cc1ccccc1)C2]

To a solution of methyl 6-oxospiro[3.3]heptane-2-carboxylate (1.00 g) in THF (50.0 mL) was added dibenzylamine (1.17 mL) at room temperature, and the mixture was stirred at room temperature for 2 hours. To the reaction mixture were added sodium triacetoxyborohydride (1.90 g) and acetic acid (34.0 μL) at room temperature, and the mixture was stirred at room temperature for 19 hours. To the reaction mixture was added a saturated aqueous sodium bicarbonate solution, and the mixture was extracted with ethyl acetate. The obtained residue was purified by silica gel column chromatography to give the title compound (530 mg) as a yellow oil.

ESI-MS: 351.3 $[M+H]^+$ (2) Synthesis of 2-[6-(dibenzylamino)spiro[3.3]heptan-2-yl]propan-2-ol [122-2] (Hereinafter, Referred to as a Compound [122-2])

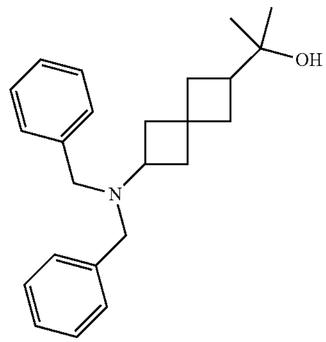 [SMILES: CC(C)(O)C1CC2(CC(N(Cc3ccccc3)Cc3ccccc3)C2)C1]

To a solution of the compound [122-1] (530 mg) in diethyl ether (20.0 mL) was added a solution of 3 M methylmagnesium bromide in diethyl ether (6.06 mL) at 0° C., and the mixture was stirred at room temperature for 3 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (306 mg) as a white solid.

ESI-MS: 351.4 $[M+H]^+$ (3) Synthesis of 2-(6-aminospiro[3.3]heptan-2-yl)propan-2-ol [122-3] (Hereinafter, Referred to as a Compound [122-3])

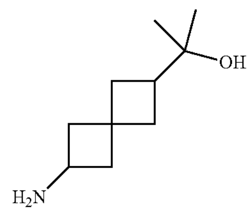

To a solution of the compound [122-2] (306 mg) in ethanol (2.00 mL) was added 20% palladium hydroxide-activated carbon (30.0 mg) at room temperature, and the mixture was stirred at room temperature for 5 hours under a hydrogen atmosphere. The reaction mixture was filtered and concentrated under reduced pressure to give the title compound (142 mg) as a brown oil.

ESI-MS: 170.3 $[M+H]^+$ (4) Synthesis of 4-(furo[3,2-c]pyridin-4-yl)-N-[6-(2-hydroxypropan-2-yl)spiro[3.3]heptan-2-yl]benzamide [112]

To a solution of the compound [99-1] (20 mg) in DMF (0.30 mL) were added DIPEA (16 μL), (1-cyano-2-ethoxy-2-oxoethylideneaminooxy)dimethylaminomorpholinocarbenium hexafluorophosphate (40 mg), and the compound [122-3] (18 mg) at room temperature, and the mixture was stirred at room temperature for 22 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (8.2 mg) as a yellow solid.

$^1$H-NMR (400 MHz, DMSO-$d_6$) δ: 8.64 (d, J=5.9 Hz, 1H), 8.56-8.51 (m, 1H), 8.22-8.20 (m, 1H), 8.11-8.02 (m, 2H), 8.01-7.94 (m, 2H), 7.70-7.69 (m, 1H), 7.34-7.33 (m, 1H), 4.32-4.26 (m, 1H), 3.96 (s, 1H), 2.42-2.37 (m, 1H), 2.12-2.06 (m, 4H), 1.99-1.88 (m, 4H), 0.94 (s, 3H), 0.92 (s, 3H).

ESI-MS: 391.4 $[M+H]^+$

Example 123

Synthesis of 4-(furo[3,2-c]pyridin-4-yl)-N-[1-(pyridin-4-yl)piperidin-4-yl]benzamide [123] (Hereinafter, Referred to as a Compound [123])

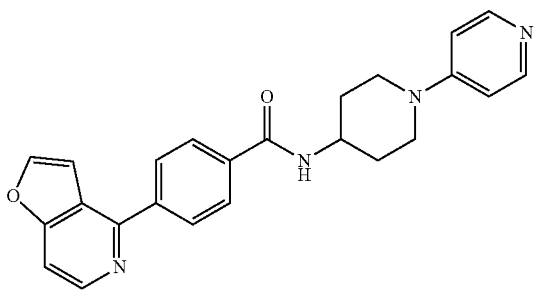 [SMILES: O=C(NC1CCN(c2ccncc2)CC1)c1ccc(-c2nccc3occc23)cc1]

To a solution of the compound [99-1] (35 mg) in DMF (0.50 mL) were added DIPEA (85 μL), (1-cyano-2-ethoxy-2-oxoethylideneaminooxy)dimethylaminomorpholinocarbenium hexafluorophosphate (56 mg), and 4-amino-1-(pyridin-4-yl)piperidine dihydrochloride (20 mg) at room temperature, and the mixture was stirred at room temperature for 2 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (10 mg) as a yellow solid.

$^1$H-NMR (400 MHz, DMSO-$d_6$) δ: 8.55 (d, J=5.5 Hz, 1H), 8.40 (d, J=7.8 Hz, 1H), 8.21 (d, J=2.3 Hz, 1H), 8.11 (d, J=6.4 Hz, 2H), 8.06 (d, J=8.7 Hz, 2H), 7.99 (d, J=8.2 Hz, 2H), 7.73-7.65 (m, 1H), 7.33 (d, J=1.1 Hz, 1H), 6.82 (d, J=6.9 Hz, 2H), 4.13-4.03 (m, 1H), 3.99-3.96 (m, 2H), 3.00-2.94 (m, 2H), 1.91-1.78 (m, 2H), 1.60-1.51 (m, 2H).

ESI-MS: 399.3 $[M+H]^+$

Example 124

Synthesis of 4-(furo[3,2-c]pyridin-4-yl)-N-[trans-4-(2-hydroxypropan-2-yl)cyclohexyl]benzamide [124] (Hereinafter, Referred to as a Compound [124])

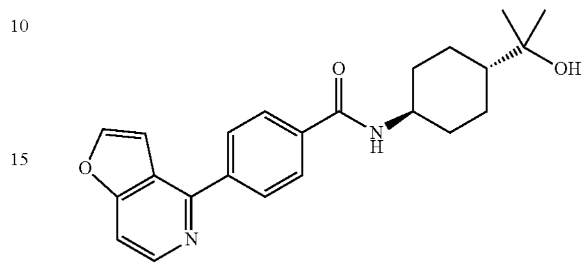

To a solution of 4-chlorofuro[3,2-c]pyridine (336 mg) in ethanol (5.20 mL)/water (5.20 mL) were added the compound [2-1] (808 mg), potassium carbonate (375 mg), and [1,3-bis(2,6-diisopropylphenyl)-4,5-dihydroimidazol-2-ylidene]chloro[3-phenylallyl]palladium (II) (54.2 mg) at room temperature, and the mixture was stirred at 80° C. for 6 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (588 mg) as a white solid.

$^1$H-NMR (400 MHz, DMSO-$d_6$) δ: 8.58 (d, J=5.5 Hz, 1H), 8.32 (d, J=7.8 Hz, 1H), 8.23 (d, J=2.3 Hz, 1H), 8.08 (d, J=8.7 Hz, 2H), 8.01 (d, J=8.7 Hz, 2H), 7.72 (d, J=5.5 Hz, 1H), 7.39-7.33 (m, 1H), 4.04 (s, 1H), 3.81-3.66 (m, 1H), 2.00-1.70 (m, 4H), 1.47-1.25 (m, 2H), 1.24-0.92 (m, 9H).

ESI-MS: 379.4 $[M+H]^+$

Example 125

Synthesis of 3-fluoro-4-(furo[3,2-c]pyridin-4-yl)-N-[trans-4-(2-hydroxypropan-2-yl)cyclohexyl]benzamide [125] (Hereinafter, Referred to as a Compound [125])

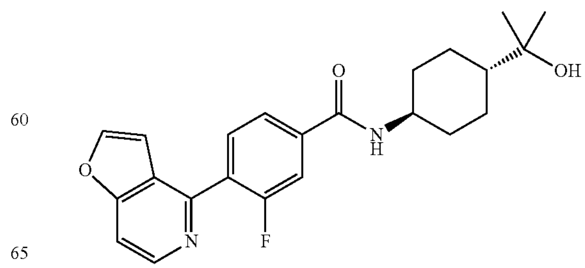

(1) Synthesis of methyl 3-fluoro-4-(furo[3,2-c]pyridin-4-yl)benzoate [125-1] (Hereinafter, Referred to as a Compound [125-1])

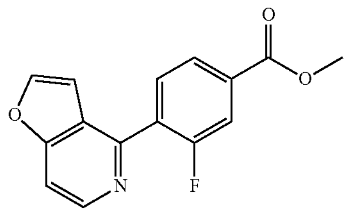 [SMILES: COC(=O)c1ccc(-c2nccc3occc23)c(F)c1]

To a solution of 4-chlorofuro[3,2-c]pyridine (154 mg) in methanol (1.65 mL)/water (1.65 mL) were added 2-fluoro-4-(methoxycarbonyl)phenylboronic acid (257 mg), potassium carbonate (180 mg), and [1,3-bis(2,6-diisopropylphenyl)-4,5-dihydroimidazol-2-ylidene]chloro[3-phenylallyl] palladium (II) (26.0 mg) at room temperature, and the mixture was stirred at 80° C. for 1 hour under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (242 mg) as a light yellow solid.

$^1$H-NMR (400 MHz, $CDCl_3$) δ: 8.64 (d, J=5.5 Hz, 1H), 7.99 (dd, J=8.0, 1.6 Hz, 1H), 7.94-7.85 (m, 2H), 7.71 (d, J=2.3 Hz, 1H), 7.52 (dd, J=5.9, 0.9 Hz, 1H), 6.89-6.80 (m, 1H), 3.98 (s, 3H).

ESI-MS: 272.2 [M+H]$^+$ (2) Synthesis of 3-fluoro-4-(furo[3,2-c]pyridin-4-yl) benzoic acid [125-2] (Hereinafter, Referred to as a Compound [125-2])

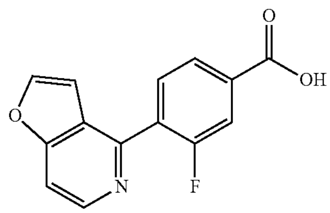 [SMILES: O=C(O)c1ccc(-c2nccc3occc23)c(F)c1]

To a solution of the compound [125-1] (242 mg) in methanol (8.8 mL) was added a 2 M aqueous sodium hydroxide solution (4.4 mL) at room temperature, and the mixture was stirred at 60° C. for 20 minutes. The reaction mixture was concentrated under reduced pressure and 2 M hydrochloric acid was added. The resulting solid was collected by filtration, washed with water, and then dried under reduced pressure to give the title compound (191 mg) as a gray solid.

$^1$H-NMR (400 MHz, DMSO-$d_6$) δ: 8.62 (d, J=5.5 Hz, 1H), 8.19 (d, J=2.3 Hz, 1H), 7.93 (dd, J=8.2, 1.4 Hz, 1H), 7.90-7.81 (m, 2H), 7.79 (dd, J=5.9, 0.9 Hz, 1H), 7.08-6.94 (m, 1H).

ESI-MS: 258.2 [M+H]$^+$ (3) Synthesis of 3-fluoro-4-(furo[3,2-c]pyridin-4-yl)-N-[trans-4-(2-hydroxypropan-2-yl)cyclohexyl] benzamide [125]

To a solution of the compound [125-2] (51 mg) in DMF (1.0 mL) were added DIPEA (37 μL) and (1-cyano-2-ethoxy-2-oxoethylideneaminooxy)dimethylaminomorpholinocarbenium hexafluorophosphate (94 mg) at room temperature, and the mixture was stirred at room temperature for 5 minutes. To the reaction mixture was added 2-(trans-4-aminocyclohexyl) propan-2-ol (41 mg) at room temperature, and the mixture was stirred at room temperature for 22 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (65 mg) as a white solid.

$^1$H-NMR (400 MHz, DMSO-$d_6$) δ: 8.61 (d, J=5.5 Hz, 1H), 8.40 (d, J=7.8 Hz, 1H), 8.18 (d, J=2.3 Hz, 1H), 7.91-7.75 (m, 4H), 7.01-6.90 (m, 1H), 4.03 (s, 1H), 3.85-3.64 (m, 1H), 1.99-1.73 (m, 4H), 1.40-1.24 (m, 2H), 1.25-0.92 (m, 9H).

ESI-MS: 397.4 [M+H]$^+$

Example 126

Synthesis of 2-fluoro-4-(furo[3,2-c]pyridin-4-yl)-N-[trans-4-(2-hydroxypropan-2-yl)cyclohexyl]benzamide [126] (Hereinafter, Referred to as a Compound [126])

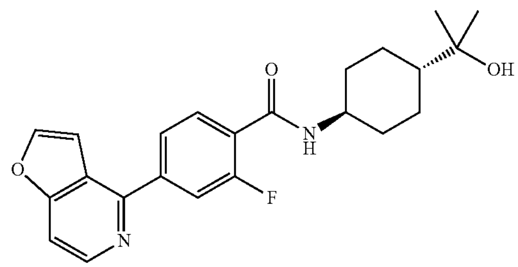 [SMILES: CC(C)(O)[C@H]1CC[C@H](NC(=O)c2ccc(-c3nccc4occc34)cc2F)CC1]

(1) Synthesis of methyl 2-fluoro-4-(furo[3,2-c]pyridin-4-yl)benzoate [126-1] (Hereinafter, Referred to as a Compound [126-1])

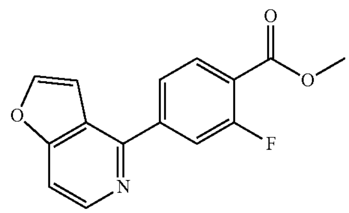 [SMILES: COC(=O)c1ccc(-c2nccc3occc23)cc1F]

To a solution of 4-chlorofuro[3,2-c]pyridine (154 mg) in methanol (1.65 mL)/water (1.65 mL) were added 3-fluoro-4-(methoxycarbonyl)phenylboronic acid (257 mg), potassium carbonate (180 mg), and [1,3-bis(2,6-diisopropylphenyl)-4,5-dihydroimidazol-2-ylidene]chloro[3-phenylallyl] palladium (II) (26.0 mg) at room temperature, and the mixture was stirred at 80° C. for 2 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (208 mg) as a light yellow solid.

ESI-MS: 272.2 [M+H]$^+$ (2) Synthesis of 2-fluoro-4-(furo[3,2-c]pyridin-4-yl) benzoic Acid [126-2] (Hereinafter, Referred to as a Compound [126-2])

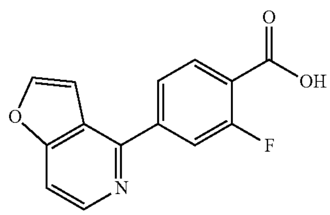 [SMILES: O=C(O)c1ccc(-c2nccc3occc23)cc1F]

To a solution of the compound [126-1] (208 mg) in methanol (7.6 mL) was added a 2 M aqueous sodium hydroxide solution (3.8 mL) at room temperature, and the mixture was stirred at 60° C. for 1 hour. The reaction mixture was concentrated under reduced pressure and 2 M hydrochloric acid was added. The resulting solid was collected by filtration, washed with water, and then dried under reduced pressure to give the title compound (111 mg) as a gray solid.

ESI-MS: 258.2 [M+H]$^+$ (3) Synthesis of 2-fluoro-4-(furo[3,2-c]pyridin-4-yl)-N-[trans-4-(2-hydroxypropan-2-yl)cyclohexyl] benzamide [126]

To a solution of the compound [126-2] (51 mg) in DMF (1.0 mL) were added DIPEA (37 μL) and (1-cyano-2-ethoxy-2-oxoethylideneaminooxy)dimethylaminomorpholinocarbenium hexafluorophosphate (94 mg) at room temperature, and the mixture was stirred at room temperature for 5 minutes. To the reaction mixture was added 2-(trans-4-aminocyclohexyl) propan-2-ol (41 mg) at room temperature, and the mixture was stirred at room temperature for 22 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (74 mg) as a yellow solid.

$^1$H-NMR (400 MHz, DMSO-$d_6$) δ: 8.59 (d, J=5.5 Hz, 1H), 8.31-8.20 (m, 2H), 7.91 (dd, J=8.0, 1.6 Hz, 1H), 7.84 (dd, J=11.4, 1.4 Hz, 1H), 7.75 (dd, J=5.5, 0.9 Hz, 1H), 7.70 (t, J=7.5 Hz, 1H), 7.45-7.35 (m, 1H), 4.03 (s, 1H), 3.75-3.61 (m, 1H), 2.00-1.73 (m, 4H), 1.36-0.93 (m, 11H).

ESI-MS: 397.4 [M+H]$^+$

Example 127

Synthesis of N-[trans-4-(2-hydroxypropan-2-yl) cyclohexyl]-4-(6-methylfuro[3,2-c]pyridin-4-yl) benzamide [127] (Hereinafter, Referred to as a Compound [127])

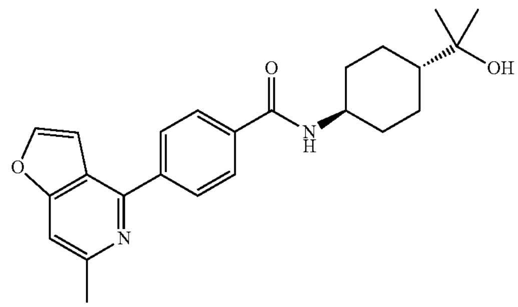 [SMILES: Cc1cc2occc2c(-c2ccc(C(=O)N[C@H]3CC[C@H](C(C)(C)O)CC3)cc2)n1]

(1) Synthesis of 3-hydroxy-6-methyl-3,5-dihydrofuro[3,2-c]pyridin-4 (2H)-one [127-1] (Hereinafter, Referred to as a Compound [127-1])

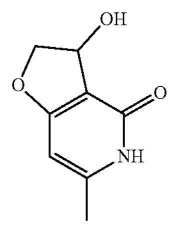

To a solution of 2,4-dihydroxy-6-methylpyridine (528 mg) in acetone (42 mL) was added potassium carbonate (1.75 g) at room temperature, and the mixture was stirred at room temperature for 15 minutes. To the reaction mixture was added a 40% aqueous chloroacetaldehyde solution (4.15 mL) at room temperature, and the mixture was stirred at room temperature for 2 hours. The reaction mixture was concentrated under reduced pressure and water was added. The resulting solid was collected by filtration and dried under reduced pressure to give the title compound (267 mg) as a brown solid.

$^1$H-NMR (400 MHz, DMSO-$d_6$) δ: 11.10 (br, 1H), 5.81 (s, 1H), 5.28 (d, J=5.9 Hz, 1H), 5.06-5.01 (m, 1H), 4.44 (dd, J=10.5, 6.4 Hz, 1H), 4.23 (dd, J=10.3, 2.1 Hz, 1H), 2.13 (s, 3H).

ESI-MS: 168.2 [M+H]$^+$ (2) Synthesis of 4-chloro-6-methylfuro[3,2-c]pyridine [127-2] (Hereinafter, Referred to as a Compound [127-2])

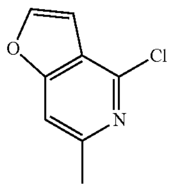

To the compound [127-1] (266 mg) was added phosphoryl chloride (4.00 mL) at room temperature, and the mixture was stirred at room temperature for 30 minutes. Then, the reaction mixture was stirred at 100° C. for 3 hours. The reaction mixture was poured into an ice-cold saturated aqueous sodium bicarbonate solution and extracted with ethyl acetate. The organic layer was dried over anhydrous sodium sulfate and concentrated under reduced pressure. The obtained residue was purified by silica gel column chromatography to give the title compound (152 mg) as a light yellow solid.

$^1$H-NMR (400 MHz, $CDCl_3$) δ: 7.61 (d, J=2.3 Hz, 1H), 7.23 (s, 1H), 6.83 (dd, J=2.3, 0.9 Hz, 1H), 2.63 (s, 3H).

ESI-MS: 168.1 $[M+H]^+$ (3) Synthesis of N-[trans-4-(2-hydroxypropan-2-yl)cyclohexyl]-4-(6-methylfuro[3,2-c]pyridin-4-yl)benzamide [127]

To a solution of the compound [127-2] (37 mg) in ethanol (1.0 mL)/water (1.0 mL) were added the compound [2-1] (78 mg), potassium carbonate (36 mg), and [1,3-bis(2,6-diisopropylphenyl)-4,5-dihydroimidazol-2-ylidene]chloro[3-phenylallyl]palladium (II) (6.5 mg) at room temperature, and the mixture was stirred at 80° C. for 3 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (60 mg) as a white solid.

$^1$H-NMR (400 MHz, DMSO-$d_6$) δ: 8.31 (d, J=7.8 Hz, 1H), 8.13 (d, J=2.3 Hz, 1H), 8.05 (d, J=8.2 Hz, 2H), 7.99 (d, J=8.7 Hz, 2H), 7.56 (s, 1H), 7.28 (d, J=1.4 Hz, 1H), 4.04 (s, 1H), 3.80-3.65 (m, 1H), 2.64 (s, 3H), 1.95-1.76 (m, 4H), 1.41-1.26 (m, 2H), 1.23-0.95 (m, 9H).

ESI-MS: 393.4 $[M+H]^+$

Example 128

Synthesis of N-[trans-4-(2-hydroxypropan-2-yl)cyclohexyl]-4-(2-methylfuro[3,2-c]pyridin-4-yl)benzamide [128] (Hereinafter, Referred to as a Compound [128])

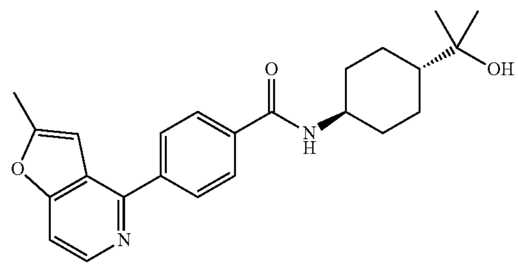 [SMILES: Cc1cc2c(-c3ccc(C(=O)N[C@H]4CC[C@H](C(C)(C)O)CC4)cc3)nccc2o1]

To a solution of 4-chloro-2-methylfuro[3,2-c]pyridine (37 mg) in ethanol (1.0 mL)/water (1.0 mL) were added the compound [2-1] (78 mg), potassium carbonate (36 mg), and [1,3-bis(2,6-diisopropylphenyl)-4,5-dihydroimidazol-2-ylidene]chloro[3-phenylallyl]palladium (II) (6.5 mg) at room temperature, and the mixture was stirred at 80° C. for 2 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (55 mg) as a white solid.

$^1$H-NMR (400 MHz, DMSO-$d_6$) δ: 8.50 (d, J=5.5 Hz, 1H), 8.30 (d, J=8.2 Hz, 1H), 8.05 (d, J=8.2 Hz, 2H), 7.99 (d, J=8.2 Hz, 2H), 7.60 (dd, J=5.5, 0.9 Hz, 1H), 7.04-6.96 (m, 1H), 4.04 (s, 1H), 3.81-3.64 (m, 1H), 2.52 (d, J=0.9 Hz, 3H), 1.96-1.75 (m, 4H), 1.40-1.25 (m, 2H), 1.24-0.92 (m, 9H).

ESI-MS: 393.4 $[M+H]^+$

Example 129

Synthesis of N-[trans-4-(2-hydroxypropan-2-yl)cyclohexyl]-4-(7-methylfuro[3,2-c]pyridin-4-yl)benzamide [129] (Hereinafter, Referred to as a Compound [129])

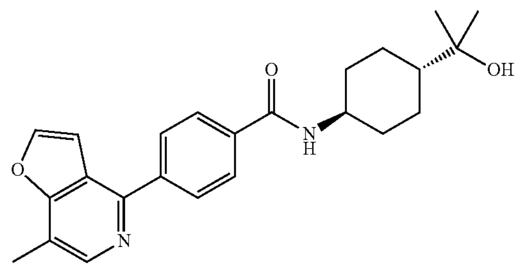 [SMILES: Cc1cnc(-c2ccc(C(=O)N[C@H]3CC[C@H](C(C)(C)O)CC3)cc2)c2ccoc12]

(1) Synthesis of 4-chloro-7-methylfuro[3,2-c]pyridine [129-1] (Hereinafter, Referred to as a Compound [129-1])

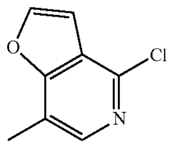

To a solution of 7-bromo-4-chlorofuro[3,2-c]pyridine (116 mg) in 1,4-dioxane (2.0 mL) were added cesium carbonate (163 mg), $PdCl_2$(dppf) (36.6 mg), and 2,4,6-trimethylboroxine (70.0 μL) at room temperature, and the mixture was stirred at 100° C. for 3 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (40.2 mg) as a white solid.

$^1$H-NMR (400 MHz, $CDCl_3$) δ: 8.07 (s, 1H), 7.69 (d, J=2.3 Hz, 1H), 6.87 (d, J=2.3 Hz, 1H), 2.49 (s, 3H).

ESI-MS: 168.2 $[M+H]^+$ (2) Synthesis of N-[trans-4-(2-hydroxypropan-2-yl)cyclohexyl]-4-(7-methylfuro[3,2-c]pyridin-4-yl)benzamide [129]

To a solution of the compound [129-1] (37 mg) in ethanol (1.0 mL)/water (1.0 mL) were added the compound [2-1] (78 mg), potassium carbonate (36 mg), and [1,3-bis(2,6-diisopropylphenyl)-4,5-dihydroimidazol-2-ylidene]chloro[3-phenylallyl]palladium (II) (6.5 mg) at room temperature, and the mixture was stirred at 80° C. for 1 hour under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (48 mg) as a white solid.

$^1$H-NMR (400 MHz, DMSO-$d_6$) δ: 8.42 (s, 1H), 8.30 (d, J=8.2 Hz, 1H), 8.23 (d, J=2.3 Hz, 1H), 8.05 (d, J=8.7 Hz, 2H), 7.99 (d, J=8.7 Hz, 2H), 7.35 (d, J=2.3 Hz, 1H), 4.04 (s, 1H), 3.82-3.59 (m, 1H), 2.51 (s, 3H), 2.01-1.64 (m, 4H), 1.45-1.25 (m, 2H), 1.25-0.93 (m, 9H).

ESI-MS: 393.4 $[M+H]^+$

Example 130

Synthesis of N-[trans-4-(2-hydroxypropan-2-yl)cyclohexyl]-4-(3-methylfuro[3,2-c]pyridin-4-yl)benzamide [130] (Hereinafter, Referred to as a Compound [130])

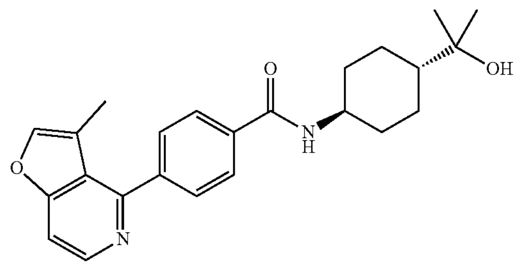 [SMILES: Cc1coc2ccnc(-c3ccc(C(=O)N[C@H]4CC[C@H](C(C)(C)O)CC4)cc3)c12]

(1) Synthesis of 4-chloro-3-methylfuro[3,2-c]pyridine [130-1] (Hereinafter, Referred to as a Compound [130-1])

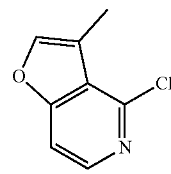

To a solution of 3-bromo-4-chlorofuro[3,2-c]pyridine (41.6 mg) in 1,4-dioxane (3.6 mL) were added cesium carbonate (70.0 mg), $PdCl_2(dppf)\cdot CH_2Cl_2$ (14.6 mg), and 2,4,6-trimethylboroxine (30.0 μL) at room temperature, and the mixture was stirred at 100° C. for 2 hours under an argon atmosphere. $PdCl_2(dppf)\cdot CH_2Cl_2$ (7.3 mg) and 2,4,6-trimethylboroxine (30.0 μL) were added at room temperature, and the mixture was stirred at 100° C. for 4 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (14.1 mg) as a yellow solid.

ESI-MS: 168.2 $[M+H]^+$ (2) Synthesis of N-[trans-4-(2-hydroxypropan-2-yl)cyclohexyl]-4-(3-methylfuro[3,2-c]pyridin-4-yl)benzamide [130]

To a solution of the compound [130-1] (20 mg) in ethanol (0.60 mL)/water (0.60 mL) were added the compound [2-1] (45 mg), potassium carbonate (21 mg), and [1,3-bis(2,6-diisopropylphenyl)-4,5-dihydroimidazol-2-ylidene]chloro[3-phenylallyl]palladium (II) (4.9 mg) at room temperature, and the mixture was stirred at 80° C. for 1 hour under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (18 mg) as a white solid.

$^{1}$H-NMR (400 MHz, DMSO-$d_6$) δ: 8.51 (d, J=5.5 Hz, 1H), 8.30 (d, J=7.8 Hz, 1H), 8.03-7.91 (m, 3H), 7.75-7.60 (m, 3H), 4.02 (s, 1H), 3.80-3.66 (m, 1H), 1.96-1.76 (m, 7H), 1.41-1.25 (m, 2H), 1.24-0.96 (m, 9H).

ESI-MS: 393.5 $[M+H]^+$

Example 131

Synthesis of 3-chloro-4-(furo[3,2-c]pyridin-4-yl)-N-[trans-4-(2-hydroxypropan-2-yl)cyclohexyl]benzamide [131] (Hereinafter, Referred to as a Compound [131])

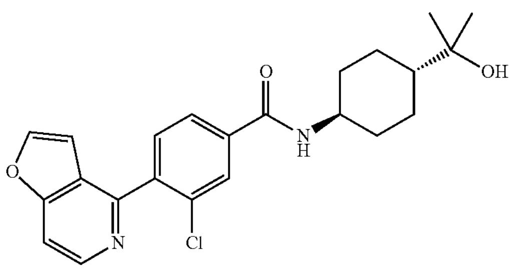

(1) Synthesis of methyl 3-chloro-4-(furo[3,2-c]pyridin-4-yl)benzoate [131-1] (Hereinafter, Referred to as a Compound [131-1])

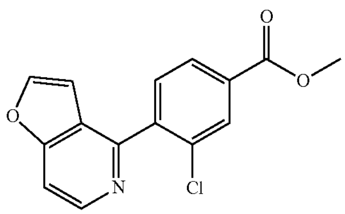 [SMILES: COC(=O)c1ccc(-c2nccc3occc23)c(Cl)c1]

To a solution of 4-chlorofuro[3,2-c]pyridine (154 mg) in 1,4-dioxane (4.0 mL)/water (1.0 mL) were added 2-chloro-4-(methoxycarbonyl)phenylboronic acid (279 mg), tripotassium phosphate (425 mg), and $PdCl_2$(dppf) (73.2 mg) at room temperature, and the mixture was stirred at 100° C. for 30 minutes under an argon atmosphere. To the reaction mixture was added water, and the mixture was extracted with ethyl acetate. The organic layer was dried over anhydrous sodium sulfate and concentrated under reduced pressure. The obtained residue was purified by reversed-phase silica gel column chromatography to give the title compound (103 mg) as a white solid.

ESI-MS: 288.2 $[M+H]^+$ (2) Synthesis of 3-chloro-4-(furo[3,2-c]pyridin-4-yl) benzoic acid [131-2] (Hereinafter, Referred to as a Compound [131-2])

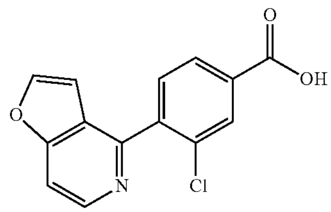 [SMILES: O=C(O)c1ccc(-c2nccc3occc23)c(Cl)c1]

To a solution of the compound [131-1] (31 mg) in methanol (2.2 mL) was added a 2 M aqueous sodium hydroxide solution (1.1 mL) at room temperature, and the mixture was stirred at room temperature for 2 hours. The reaction mixture was concentrated under reduced pressure and 1 M hydrochloric acid was added. The resulting solid was collected by filtration, washed with water, and then dried under reduced pressure to give the title compound (28 mg) as a white solid.

ESI-MS: 274.2 $[M+H]^+$ (3) Synthesis of 3-chloro-4-(furo[3,2-c]pyridin-4-yl)-N-[trans-4-(2-hydroxypropan-2-yl)cyclohexyl] benzamide [131]

To a solution of the compound [131-2] (28 mg) in DMF (1.0 mL) were added DIPEA (19 μL) and (1-cyano-2-ethoxy-2-oxoethylideneaminooxy)dimethylaminomorpholinocarbenium hexafluorophosphate (47 mg) at room temperature, and the mixture was stirred at room temperature for 5 minutes. To the reaction mixture was added 2-(trans-4-aminocyclohexyl) propan-2-ol (21 mg) at room temperature, and the mixture was stirred at room temperature for 4 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (31 mg) as a white solid.

$^{1}$H-NMR (400 MHz, DMSO-$d_6$) δ: 8.58 (d, J=5.9 Hz, 1H), 8.45 (d, J=8.2 Hz, 1H), 8.16 (d, J=2.3 Hz, 1H), 8.08 (d, J=1.8 Hz, 1H), 7.95 (dd, J=7.8, 1.8 Hz, 1H), 7.80-7.74 (m, 1H), 7.63 (d, J=7.8 Hz, 1H), 6.85-6.79 (m, 1H), 4.04 (s, 1H), 3.79-3.66 (m, 1H), 2.03-1.74 (m, 4H), 1.39-1.25 (m, 2H), 1.24-0.94 (m, 9H).

ESI-MS: 413.4 $[M+H]^+$

Example 132

Synthesis of 4-(furo[3,2-c]pyridin-4-yl)-N-[trans-4-(2-hydroxypropan-2-yl)cyclohexyl]-3-methylbenzamide [132] (Hereinafter, Referred to as a Compound [132])

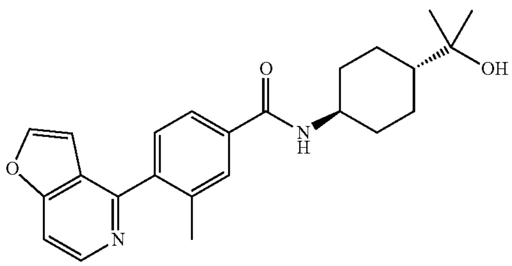 [SMILES: Cc1cc(C(=O)N[C@H]2CC[C@H](C(C)(C)O)CC2)ccc1-c1nccc2occc12]

(1) Synthesis of methyl 4-(furo[3,2-c]pyridin-4-yl)-3-methylbenzoate [132-1] (Hereinafter, Referred to as a Compound [132-1])

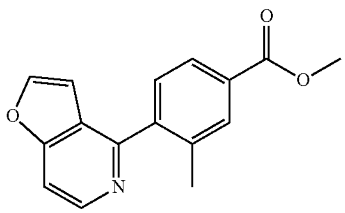 [SMILES: COC(=O)c1ccc(-c2nccc3occc23)c(C)c1]

To a solution of 4-chlorofuro[3,2-c]pyridine (154 mg) in methanol (2.5 mL)/water (2.5 mL) were added methyl 3-methyl-4-(4,4,5,5-tetramethyl-1,3,2-dioxaborolan-2-yl) benzoate (359 mg), potassium carbonate (180) mg), and [1,3-bis(2,6-diisopropylphenyl)-4,5-dihydroimidazol-2-ylidene]chloro[3-phenylallyl]palladium (II) (26.0 mg) at room temperature, and the mixture was stirred at 80° C. for 1 hour under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (272 mg) as a yellow solid.

ESI-MS: 268.1 $[M+H]^+$ (2) Synthesis of 4-(furo[3,2-c]pyridin-4-yl)-N-[trans-4-(2-hydroxypropan-2-yl)cyclohexyl]-3-methylbenzamide [132]

The title compound was synthesized from the compound [132-1] according to the methods of steps (2) and (3) in Example 131.

$^1$H-NMR (400 MHz, DMSO-$d_6$) δ: 8.55 (d, J=5.5 Hz, 1H), 8.25 (d, J=7.8 Hz, 1H), 8.14 (d, J=2.3 Hz, 1H), 7.84 (s, 1H), 7.78 (dd, J=7.8, 1.4 Hz, 1H), 7.71 (dd, J=5.9, 0.9 Hz, 1H), 7.45 (d, J=7.8 Hz, 1H), 6.83-6.77 (m, 1H), 4.04 (s, 1H), 3.79-3.65 (m, 1H), 2.27 (s, 3H), 1.96-1.77 (m, 4H), 1.40-1.24 (m, 2H), 1.23-0.97 (m, 9H).

ESI-MS: 393.4 $[M+H]^+$

Example 133

Synthesis of 3-cyano-4-(furo[3,2-c]pyridin-4-yl)-N-[trans-4-(2-hydroxypropan-2-yl)cyclohexyl] [133] (Hereinafter, Referred to as a Compound [133])

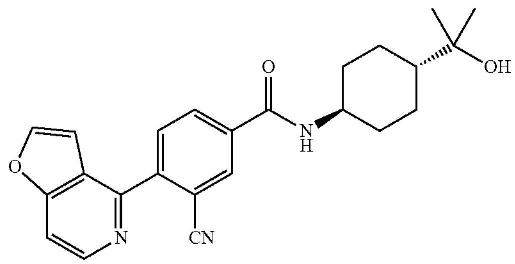

(1) Synthesis of methyl 3-cyano-4-(furo[3,2-c]pyridin-4-yl)benzoate [133-1] (Hereinafter, Referred to as a Compound [133-1])

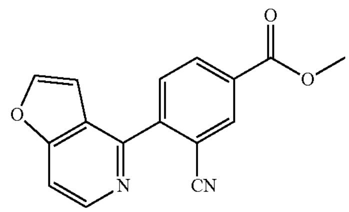

To a solution of 4-chlorofuro[3,2-c]pyridine (41 mg) in 1,2-dimethoxyethane (2.6 mL) were added methyl 3-cyano-4-(4,4,5,5-tetramethyl-1,3,2-dioxaborolan-2-yl benzoate (83 mg), cesium fluoride (88 mg), and bis[di-tert-butyl (4-dimethylaminophenyl)phosphine]dichloropalladium (II) (9.3 mg) at room temperature, and the mixture was stirred at 100° C. for 1 hour under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (34 mg) as a yellow white solid.

ESI-MS: 279.3 $[M+H]^+$ (2) Synthesis of 3-cyano-4-(furo[3,2-c]pyridin-4-yl)-N-[trans-4-(2-hydroxypropan-2-yl)cyclohexyl] benzamide [133]

The title compound was synthesized from the compound [133-1] according to the methods of steps (2) and (3) in Example 131.

$^1$H-NMR (400 MHz, DMSO-$d_6$) δ: 8.64 (d, J=5.5 Hz, 1H), 8.54 (d, J=7.8 Hz, 1H), 8.47 (d, J=1.8 Hz, 1H), 8.32-8.22 (m, 2H), 7.98 (d, J=8.2 Hz, 1H), 7.84 (d, J=5.5 Hz, 1H), 7.14 (d, J=1.8 Hz, 1H), 4.05 (s, 1H), 3.80-3.66 (m, 1H), 2.03-1.76 (m, 4H), 1.39-1.25 (m, 2H), 1.24-0.93 (m, 9H).

ESI-MS: 404.4 $[M+H]^+$

Example 134

Synthesis of 4-(furo[3,2-c]pyridin-4-yl)-3-hydroxy-N-[trans-4-(2-hydroxypropan-2-yl)cyclohexyl] [134] (Hereinafter, Referred to as a Compound [134])

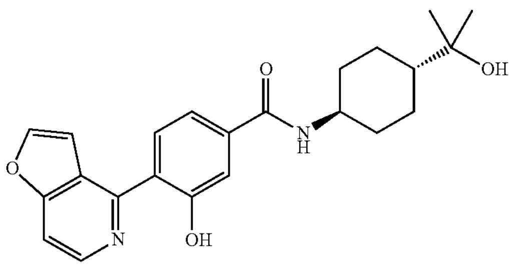 [SMILES: CC(C)(O)[C@H]1CC[C@H](NC(=O)c2ccc(-c3nccc4occc34)c(O)c2)CC1]

(1) Synthesis of methyl 4-(furo[3,2-c]pyridin-4-yl)-3-methoxybenzoate [134-1] (Hereinafter, Referred to as a Compound [134-1])

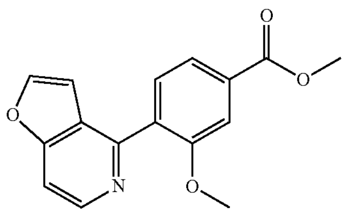 [SMILES: COC(=O)c1ccc(-c2nccc3occc23)c(OC)c1]

To a solution of 4-chlorofuro[3,2-c]pyridine (76.8 mg) in methanol (1.25 mL)/water (1.25 mL) were added 2-methoxy-4-(methoxycarbonyl)phenylboronic acid (137 mg), potassium carbonate (89.8 mg), and [1,3-bis(2,6-diisopropylphenyl)-4,5-dihydroimidazol-2-ylidene]chloro[3-phenylallyl]palladium (II) (13.0 mg) at room temperature, and the mixture was stirred at 80° C. for 30 minutes under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (117 mg) as a yellow white solid.

ESI-MS: 284.3 $[M+H]^+$ (2) Synthesis of methyl 4-(furo[3,2-c]pyridin-4-yl)-3-hydroxybenzoate [134-2] (Hereinafter, Referred to as a Compound [134-2])

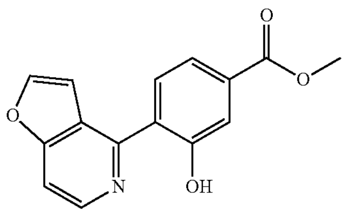

To a solution of the compound [134-1] (56 mg) in dichloromethane (1.0 mL) was added a solution of 1 M boron tribromide in dichloromethane (989 μL) at 0° C. under an argon atmosphere, and the mixture was stirred at 0° C. for 3 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (10 mg) as a yellow solid.

ESI-MS: 270.3 $[M+H]^+$ (3) Synthesis of 4-(furo[3,2-c]pyridin-4-yl)-3-hydroxy-N-[trans-4-(2-hydroxypropan-2-yl)cyclohexyl]benzamide [134]

The title compound was synthesized from the compound [134-2] according to the methods of steps (2) and (3) in Example 131.

$^1$H-NMR (400 MHz, DMSO-$d_6$) δ: 8.57 (d, J=5.9 Hz, 1H), 8.33 (d, J=2.3 Hz, 1H), 8.27 (d, J=8.2 Hz, 1H), 8.12 (d, J=8.2 Hz, 1H), 7.86-7.80 (m, 1H), 7.64-7.55 (m, 1H), 7.49-7.40 (m, 2H), 4.03 (s, 1H), 3.77-3.62 (m, 1H), 1.94-1.76 (m, 4H), 1.39-0.98 (m, 11H).

ESI-MS: 395.4 $[M+H]^+$

Example 135

Synthesis of 4-[7-(hydroxymethyl)furo[3,2-c]pyridin-4-yl]-N-[trans-4-(2-hydroxypropan-2-yl)cyclohexyl]benzamide [135] (Hereinafter, Referred to as a Compound [135])

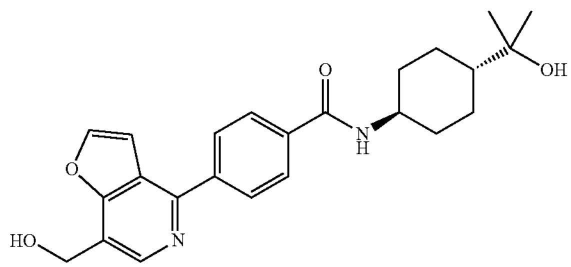 [SMILES: CC(C)(O)[C@H]1CC[C@H](NC(=O)c2ccc(-c3ncc(CO)c4occc34)cc2)CC1]

(1) Synthesis of 4-chlorofuro[3,2-c]pyridin-7-carbaldehyde [135-1] (Hereinafter, Referred to as a Compound [135-1])

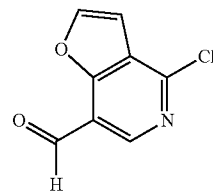 [SMILES: O=Cc1cnc(Cl)c2ccoc12]

To a solution of 7-bromo-4-chlorofuro[3,2-c]pyridine (233 mg) in THF (5.0 mL) was added a solution of 1.3 M isopropylmagnesium chloride-lithium chloride complex in THE (1.15 mL) at room temperature under an argon atmosphere, and the mixture was stirred at room temperature for 20 minutes. Then, N-formylpiperidine (222 μL) was added at room temperature, and the mixture was stirred at room temperature for 30 minutes. 1 M hydrochloric acid was added to the reaction mixture, then a saturated aqueous sodium bicarbonate solution was added thereto, and the mixture was extracted with ethyl acetate. The organic layer was dried over anhydrous sodium sulfate and concentrated under reduced pressure. The obtained residue was purified by silica gel column chromatography to give the title compound (155 mg) as a white solid.

$^1$H-NMR (400 MHz, $CDCl_3$) δ: 10.40 (s, 1H), 8.75 (s, 1H), 7.87 (d, J=2.3 Hz, 1H), 7.01 (d, J=1.8 Hz, 1H).

ESI-MS: 182.2 $[M+H]^+$ (2) Synthesis of 4-(7-formylfuro[3,2-c]pyridin-4-yl)-N-[trans-4-(2-hydroxypropan-2-yl)cyclohexyl]benzamide [135-2] (Hereinafter, Referred to as a Compound [135-2])

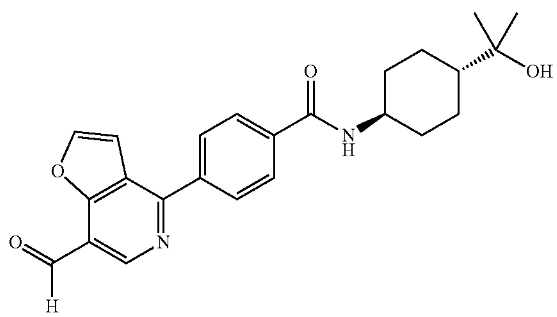 [SMILES: CC(C)(O)[C@H]1CC[C@H](NC(=O)c2ccc(-c3ncc(C=O)c4occc34)cc2)CC1]

To a solution of the compound [135-1] (72.6 mg) in 1,4-dioxane (3.2 mL)/water (0.8 mL) were added the compound [2-1] (155 mg), tripotassium phosphate (170 mg), and $PdCl_2(dppf)\cdot CH_2Cl_2$ (16.3 mg) at room temperature, and the mixture was stirred at 100° C. for 15 minutes under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (139 mg) as a white solid.

$^1$H-NMR (400 MHz, DMSO-$d_6$) δ: 10.37 (s, 1H), 9.08 (s, 1H), 8.41 (d, J=2.3 Hz, 1H), 8.37 (d, J=7.8 Hz, 1H), 8.16 (d, J=8.7 Hz, 2H), 8.04 (d, J=8.7 Hz, 2H), 7.50 (d, J=2.3 Hz, 1H), 4.04 (s, 1H), 3.80-3.66 (m, 1H), 1.97-1.71 (m, 4H), 1.42-1.26 (m, 2H), 1.24-0.94 (m, 9H).

ESI-MS: 407.4 $[M+H]^+$ (3) Synthesis of 4-[7-(hydroxymethyl)furo[3,2-c]pyridin-4-yl]-N-[trans-4-(2-hydroxypropan-2-yl)cyclohexyl]benzamide [135]

To a solution of the compound [135-2] (20 mg) in methanol (1.0 mL) was added sodium borohydride (5.7 mg) at room temperature, and the mixture was stirred at room temperature for 20 minutes. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (17 mg) as a white solid.

$^1$H-NMR (400 MHz, DMSO-$d_6$) δ: 8.55 (s, 1H), 8.31 (d, J=8.2 Hz, 1H), 8.24 (d, J=2.3 Hz, 1H), 8.07 (d, J=8.7 Hz, 2H), 8.00 (d, J=8.2 Hz, 2H), 7.36 (d, J=2.3 Hz, 1H), 5.46 (br, 1H), 4.86 (d, J=3.7 Hz, 2H), 4.04 (s, 1H), 3.79-3.65 (m, 1H), 1.96-1.75 (m, 4H), 1.43-1.24 (m, 2H), 1.24-0.96 (m, 9H).

ESI-MS: 409.4 $[M+H]^+$

Example 136

Synthesis of 4-(7-fluorofuro[3,2-c]pyridin-4-yl)-N-[trans-4-(2-hydroxypropan-2-yl)cyclohexyl]benzamide [136] (Hereinafter, Referred to as a Compound [136])

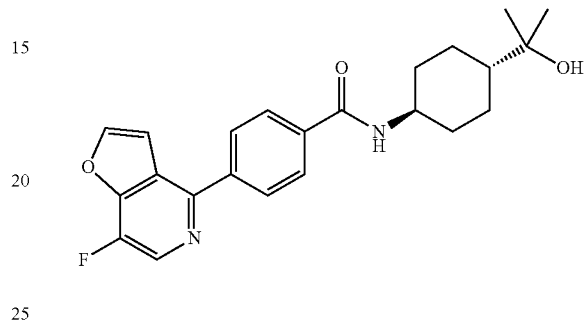

(1) Synthesis of 4-chloro-7-fluorofuro[3,2-c]pyridine [136-1] (Hereinafter, Referred to as a Compound [136-1])

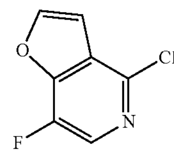 [SMILES: Fc1cnc(Cl)c2ccoc12]

To a solution of 7-bromo-4-chlorofuro[3,2-c]pyridine (47 mg) in THF (0.50 mL) was added a solution of 1.3 M isopropylmagnesium chloride-lithium chloride complex in THE (0.23 mL) at 0° C. under an argon atmosphere, and the mixture was stirred at room temperature for 40 minutes. The reaction mixture was concentrated under reduced pressure, dichloromethane (0.50 mL) was added at room temperature, and the mixture was cooled to 0° C. A solution of N-fluorobenzenesulfonimide (95 mg) in dichloromethane (0.50 mL) was then added at 0° C., and the mixture was stirred at room temperature for 2 hours. To the reaction mixture was added chloroform, and the mixture was purified by silica gel column chromatography to give the title compound (5.7 mg) as a white solid.

$^1$H-NMR (400 MHz, $CDCl_3$) δ: 8.18 (d, J=2.3 Hz, 1H), 7.76 (d, J=2.3 Hz, 1H), 6.94 (dd, J=2.5, 2.5 Hz, 1H).

(2) Synthesis of 4-(7-fluorofuro[3,2-c]pyridin-4-yl)-N-[trans-4-(2-hydroxypropan-2-yl)cyclohexyl]benzamide [136]

To a solution of the compound [136-1] (5.5 mg) in ethanol (0.50 mL)/water (0.50 mL) were added the compound [2-1] (12 mg), potassium carbonate (5.8 mg), and [1,3-bis(2,6-diisopropylphenyl)-4,5-dihydroimidazol-2-ylidene]chloro[3-phenylallyl]palladium (II) (1.0 mg) at room temperature, and the mixture was stirred at 80° C. for 1 hour under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (7.4 mg) as a white solid.

$^1$H-NMR (400 MHz, DMSO-$d_6$) δ: 8.64 (d, J=1.8 Hz, 1H), 8.36 (d, J=2.3 Hz, 1H), 8.32 (d, J=8.2 Hz, 1H), 8.09-7.95 (m, 4H), 7.47 (dd, J=2.5, 2.5 Hz, 1H), 4.04 (s, 1H), 3.79-3.66 (m, 1H), 1.96-1.76 (m, 4H), 1.43-1.25 (m, 2H), 1.24-0.92 (m, 9H).

ESI-MS: 397.4 [M+H]$^+$

Example 137

Synthesis of N-[trans-4-(2-hydroxypropan-2-yl) cyclohexyl]-4-(7-vinylfuro[3,2-c]pyridin-4-yl)benzamide [137] (Hereinafter, Referred to as a Compound [137])

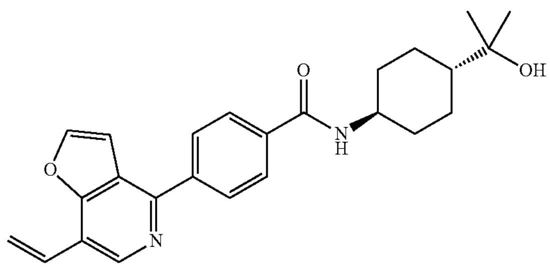 [SMILES: C=Cc1cnc(-c2ccc(C(=O)N[C@H]3CC[C@H](C(C)(C)O)CC3)cc2)c2ccoc12]

To a solution of methyltriphenylphosphonium bromide (237 mg) in THF (2.7 mL) was added potassium tert-butoxide (74.5 mg) at room temperature, and the mixture was stirred at room temperature for 5 minutes. Then, to the reaction mixture was added a solution of the compound [135-2] (54.0 mg) in THF (1.8 mL) at room temperature, and the mixture was stirred at room temperature for 3 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (29.1 mg) as a white solid.

$^1$H-NMR (400 MHz, DMSO-$d_6$) δ: 8.65 (s, 1H), 8.36-8.27 (m, 2H), 8.08 (d, J=8.7 Hz, 2H), 8.00 (d, J=8.2 Hz, 2H), 7.40 (d, J=2.3 Hz, 1H), 7.00 (dd, J=17.8, 11.9 Hz, 1H), 6.38 (dd, J=17.8, 0.9 Hz, 1H), 5.70 (dd, J=11.4, 0.9 Hz, 1H), 4.04 (s, 1H), 3.79-3.66 (m, 1H), 1.95-1.76 (m, 4H), 1.39-1.26 (m, 2H), 1.23-0.99 (m, 9H).

ESI-MS: 405.3 [M+H]$^+$

Example 138

Synthesis of 4-(7-ethylfuro[3,2-c]pyridin-4-yl)-N-[trans-4-(2-hydroxypropan-2-yl)cyclohexyl]benzamide [138] (Hereinafter, Referred to as a Compound [138])

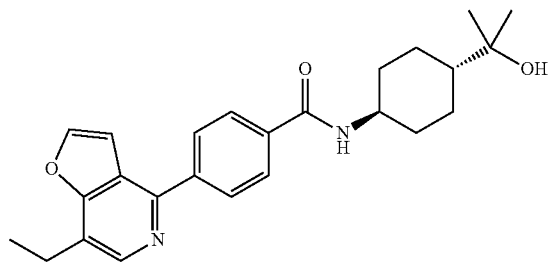 [SMILES: CCc1cnc(-c2ccc(C(=O)N[C@H]3CC[C@H](C(C)(C)O)CC3)cc2)c2ccoc12]

To a solution of the compound [137] (15 mg) in methanol (1.0 mL) was added 5% palladium-activated carbon (15 mg) at room temperature, and the mixture was stirred at room temperature for 1 hour under a hydrogen atmosphere. The insoluble matter was filtered and concentrated under reduced pressure. The obtained residue was purified by reversed-phase silica gel column chromatography to give the title compound (7.2 mg) as a white solid.

$^1$H-NMR (400 MHz, DMSO-$d_6$) δ: 8.44 (s, 1H), 8.30 (d, J=7.8 Hz, 1H), 8.23 (d, J=2.3 Hz, 1H), 8.05 (d, J=8.2 Hz, 2H), 7.99 (d, J=8.7 Hz, 2H), 7.34 (d, J=2.3 Hz, 1H), 4.04 (s, 1H), 3.83-3.65 (m, 1H), 2.94 (q, J=7.6 Hz, 2H), 1.96-1.76 (m, 4H), 1.42-1.25 (m, 5H), 1.24-0.90 (m, 9H).

ESI-MS: 407.4 [M+H]$^+$

Example 139

Synthesis of 4-(7-cyanofuro[3,2-c]pyridin-4-yl)-N-[trans-4-(2-hydroxypropan-2-yl)cyclohexyl]benzamide [139] (Hereinafter, Referred to as a Compound [139])

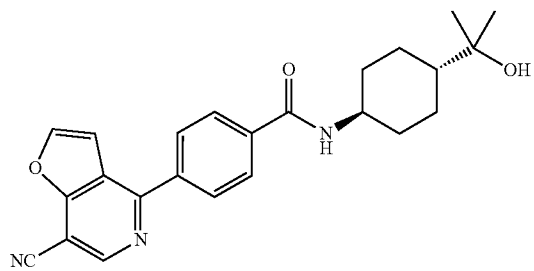 [SMILES: CC(C)(O)[C@H]1CC[C@H](NC(=O)c2ccc(-c3ncc(C#N)c4occc34)cc2)CC1]

(1) Synthesis of 4-chlorofuro[3,2-c]pyridin-7-carbonitrile [139-1] (Hereinafter, Referred to as a Compound [139-1])

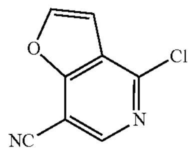 [SMILES: N#Cc1cnc(Cl)c2ccoc12]

To a solution of the compound [135-1] (54.5 mg) in DMF (1.0 mL) were added hydroxylamine hydrochloride (31.3 mg) and triethylamine (62.7 μL) at room temperature, and the mixture was stirred at room temperature for 5 minutes. Then, a solution of 1.7 M propylphosphonic anhydride in ethyl acetate (265 μL) was added at room temperature, and the mixture was stirred at 100° C. for 7 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (45.9 mg) as a white solid.

ESI-MS: 179.2 $[M+H]^+$ (2) Synthesis of 4-(7-cyanofuro[3,2-c]pyridin-4-yl)-N-[trans-4-(2-hydroxypropan-2-yl)cyclohexyl]benzamide [139]

To a solution of the compound [139-1] (44.6 mg) in ethanol (1.25 mL)/water (1.25 mL) were added the compound [2-1] (96.8 mg), potassium carbonate (44.9 mg), and [1,3-bis(2,6-diisopropylphenyl)-4,5-dihydroimidazol-2-ylidene]chloro[3-phenylallyl]palladium (II) (8.1 mg) at room temperature, and the mixture was stirred at 80° C. for 2 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (60.4 mg) as a white solid.

ESI-MS: 404.3 $[M+H]^+$

Example 140

Synthesis of 4-(4-{[trans-4-(2-hydroxypropan-2-yl)cyclohexyl]carbamoyl}phenyl)furo[3,2-c]pyridine-7-carboxamide [140] (Hereinafter, Referred to as a Compound [140])

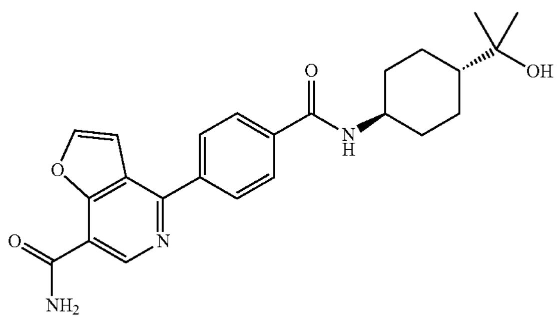 [SMILES: CC(C)(O)[C@H]1CC[C@H](NC(=O)c2ccc(-c3ncc(C(N)=O)c4occc34)cc2)CC1]

To a solution of the compound [139] (19.6 mg) in tert-butanol (972 μL) was added potassium tert-butoxide (81.8 mg) at room temperature, and the mixture was stirred at 40° C. for 4 hours under an argon atmosphere. To the reaction mixture was added water, and the mixture was extracted with ethyl acetate. The organic layer was concentrated under reduced pressure, and ethanol and water were added to the obtained residue. The solid was collected by filtration, washed with water, and then dried under reduced pressure to give the title compound (17.1 mg) as a white solid.

ESI-MS: 422.3 $[M+H]^+$

Example 141

Synthesis of 4-[7-(1-hydroxyethyl)furo[3,2-c]pyridin-4-yl]-N-[trans-4-(2-hydroxypropan-2-yl)cyclohexyl]benzamide [141] (Hereinafter, Referred to as a Compound [141])

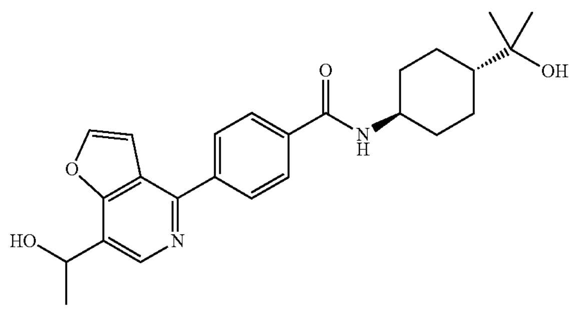 [SMILES: CC(O)c1cnc(-c2ccc(C(=O)N[C@H]3CC[C@H](C(C)(C)O)CC3)cc2)c2ccoc12]

(1) Synthesis of 1-(4-chlorofuro[3,2-c]pyridin-7-yl)ethan-1-ol [141-1] (Hereinafter, Referred to as a Compound [141-1])

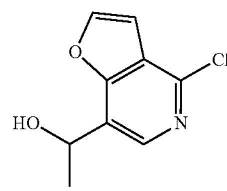

To a solution of the compound [135-1] (10.7 mg) in THF (1.2 mL) was added a solution of 3 M methylmagnesium chloride in THF (39 μL) at 0° C. under an argon atmosphere, and the mixture was stirred at 0° C. for 10 minutes. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (9.4 mg) as a colorless oil.

ESI-MS: 198.2 $[M+H]^+$ (2) Synthesis of 4-[7-(1-hydroxyethyl)furo[3,2-c]pyridin-4-yl]-N-[trans-4-(2-hydroxypropan-2-yl)cyclohexyl]benzamide [141]

To a solution of the compound [141-1] (9.4 mg) in ethanol (0.48 mL)/water (0.48 mL) were added the compound [2-1]

(18 mg), potassium carbonate (8.6 mg), and [1,3-bis(2,6-diisopropylphenyl)-4,5-dihydroimidazol-2-ylidene]chloro [3-phenylallyl]palladium (II) (1.6 mg) at room temperature, and the mixture was stirred at 80° C. for 3 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (16 mg) as a white solid.

$^1$H-NMR (400 MHz, DMSO-$d_6$) δ: 8.59 (s, 1H), 8.30 (d, J=8.2 Hz, 1H), 8.23 (d, J=2.3 Hz, 1H), 8.05 (d, J=8.7 Hz, 2H), 7.99 (d, J=8.7 Hz, 2H), 7.34 (d, J=2.3 Hz, 1H), 5.54 (d, J=4.6 Hz, 1H), 5.31-5.19 (m, 1H), 4.03 (s, 1H), 3.80-3.65 (m, 1H), 1.96-1.77 (m, 4H), 1.54 (d, J=6.4 Hz, 3H), 1.40-1.25 (m, 2H), 1.24-0.92 (m, 9H).

ESI-MS: 423.3 [M+H]$^+$

Example 142

Synthesis of 4-(furo[3,2-c]pyridin-4-yl)-N-(piperidin-4-yl)benzamide [142] (Hereinafter, Referred to as a Compound [142])

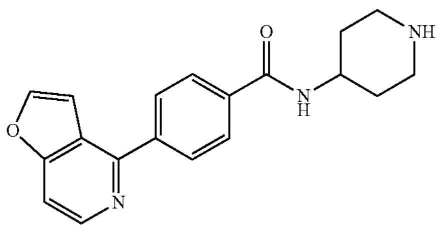 [SMILES: O=C(NC1CCNCC1)c1ccc(-c2nccc3occc23)cc1]

To a solution of the compound [99-1] (500 mg) in DMF (7.00 mL) were added DIPEA (392 μL), (1-cyano-2-ethoxy-2-oxoethylideneaminooxy)dimethylaminomorpholinocarbenium hexafluorophosphate (986 mg), and tert-butyl 4-aminopiperidine-1-carboxylate (461 mg) at room temperature, and the mixture was stirred at room temperature for 16 hours. To the reaction mixture was added a saturated aqueous sodium bicarbonate solution, and the mixture was extracted with ethyl acetate. The organic layer was dried over anhydrous sodium sulfate and concentrated under reduced pressure. To a solution of the obtained residue in dichloromethane (20.0 mL) was added trifluoroacetic acid (14.0 mL) at room temperature, and the mixture was stirred at room temperature for 30 minutes. To the reaction mixture was added a 5 M aqueous sodium hydroxide solution at 0° C., and the mixture was extracted with ethyl acetate. The organic layer was dried over anhydrous sodium sulfate and concentrated under reduced pressure. The obtained residue was purified by silica gel column chromatography to give the title compound (420 mg) as a white solid.

$^1$H-NMR (400 MHz, DMSO-$d_6$) δ: 8.59 (dd, J=5.7, 2.1 Hz, 1H), 8.37 (d, J=7.8 Hz, 1H), 8.24-8.23 (m, 1H), 8.12-8.05 (m, 2H), 8.04-7.98 (m, 2H), 7.72 (d, J=5.9 Hz, 1H), 7.37-7.35 (m, 1H), 3.88-3.80 (m, 1H), 3.31-3.30 (m, 2H), 2.97-2.94 (m, 2H), 1.76-1.72 (m, 2H), 2.05 (br, 1H), 1.47-1.39 (m, 2H).

ESI-MS: 322.4 [M+H]$^+$

Example 143

Synthesis of 4-(furo[3,2-c]pyridin-4-yl)-N-[1-(pyrimidin-2-yl)piperidin-4-yl]benzamide [143] (Hereinafter, Referred to as a Compound [143])

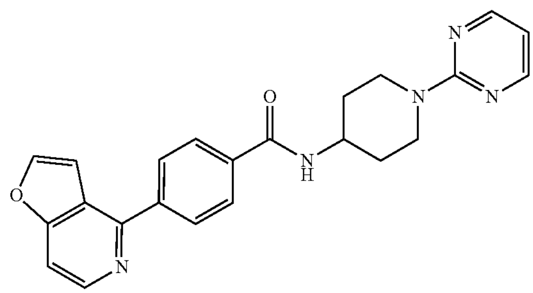 [SMILES: O=C(NC1CCN(c2ncccn2)CC1)c1ccc(-c2nccc3occc23)cc1]

To a solution of the compound [142] (2010 mg) in NMP (300 μL) were added potassium carbonate (77.0 mg) and 2-chloropyrimidine (32.0 mg) at room temperature, and the mixture was stirred at 140° C. for 4 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (14.0 mg) as a white solid.

$^1$H-NMR (400 MHz, DMSO-$d_6$) δ: 8.58 (d, J=5.5 Hz, 1H), 8.41 (d, J=7.3 Hz, 1H), 8.36 (d, J=5.0 Hz, 2H), 8.24 (d, J=2.3 Hz, 1H), 8.09 (d, J=8.2 Hz, 2H), 8.01 (d, J=8.2 Hz, 2H), 7.72 (dd, J=5.5, 0.9 Hz, 1H), 7.36 (d, J=2.3 Hz, 1H), 6.61 (t, J=4.8 Hz, 1H), 4.67-4.64 (m, 2H), 4.19-4.11 (m, 1H), 3.06-3.00 (m, 2H), 1.91-1.87 (m, 2H), 1.55-1.46 (m, 2H).

ESI-MS: 400.4 [M+H]$^+$

Examples 144 to 170

Each compound of Examples 144 to 170 shown in the following Tables was synthesized according to the method shown in Example 143. The structure, name, and ESI-MS of the compound of each Example are shown in the following Tables.

TABLE 4-1
| Example | Structure | Name | ESI-MS |
|---|---|---|---|
| 144 | 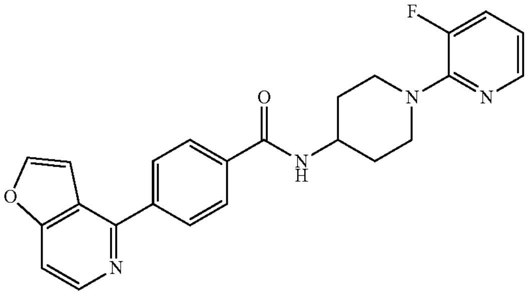 [SMILES: O=C(NC1CCN(c2ncccc2F)CC1)c1ccc(-c2nccc3occc23)cc1] | N-[1-(3-fluoropyridin-2-yl)piperidin-4-yl]-4-(furo[3,2-c]pyridin-4-yl)benzamide | 417.4 [M + H]+ |
| 145 | 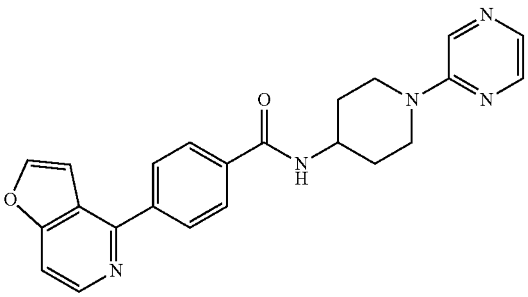 [SMILES: O=C(NC1CCN(c2cnccn2)CC1)c1ccc(-c2nccc3occc23)cc1] | 4-(furo[3,2-c]pyridin-4-yl)-N-[1-(pyrazin-2-yl)piperidin-4-yl]benzamide | 400.4 [M + H]+ |
| 146 | 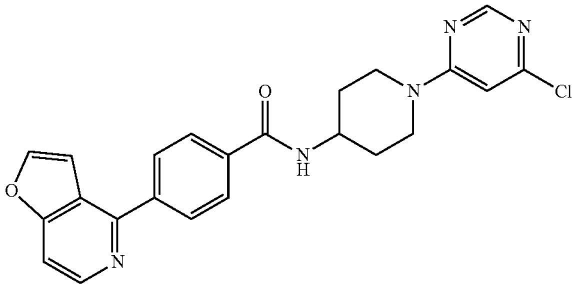 [SMILES: O=C(NC1CCN(c2cc(Cl)ncn2)CC1)c1ccc(-c2nccc3occc23)cc1] | N-[1-(6-chloropyrimidin-4-yl)piperidin-4-yl]-4-(furo[3,2-c]pyridin-4-yl)benzamide | 434.4 [M + H]+ |
| 147 | 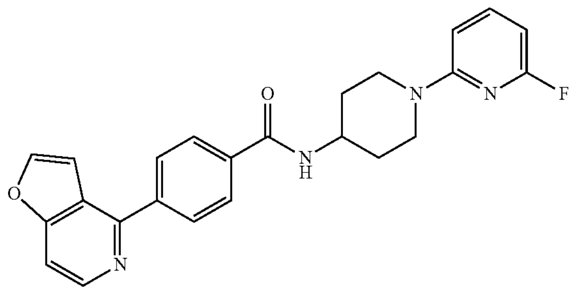 [SMILES: O=C(NC1CCN(c2cccc(F)n2)CC1)c1ccc(-c2nccc3occc23)cc1] | N-[1-(6-fluoropyridin-2-yl)piperidin-4-yl]-4-(furo[3,2-c]pyridin-4-yl)benzamide | 417.4 [M + H]+ |
| 148 | 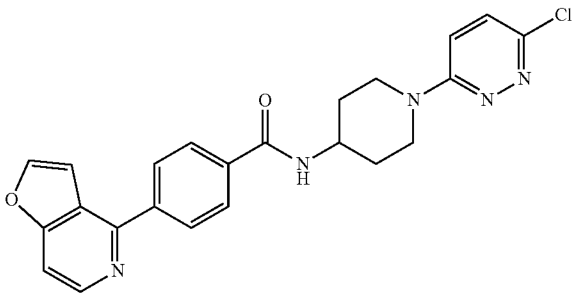 [SMILES: O=C(NC1CCN(c2ccc(Cl)nn2)CC1)c1ccc(-c2nccc3occc23)cc1] | N-[1-(6-chloropyridazin-3-yl)piperidin-4-yl]-4-(furo[3,2-c]pyridin-4-yl)benzamide | 434.4 [M + H]+ |

TABLE 4-2
| | | | |
|---|---|---|---|
| 149 | 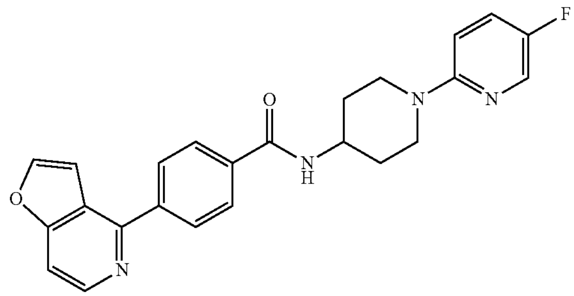 [SMILES: O=C(NC1CCN(c2ccc(F)cn2)CC1)c1ccc(-c2nccc3occc23)cc1] | N-[1-(5-fluoropyridin-2-yl)piperidin-4-yl]-4-(furo[3,2-c]pyridin-4-yl)benzamide | 417.4 $[M + H]^+$ |
| 150 | 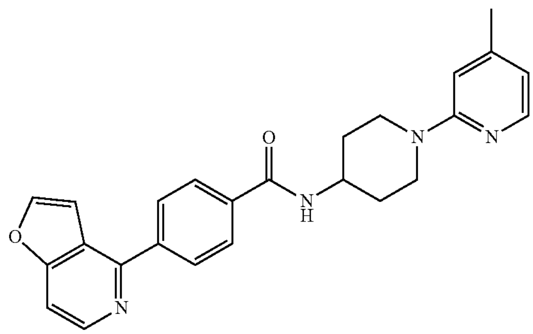 [SMILES: Cc1ccnc(N2CCC(NC(=O)c3ccc(-c4nccc5occc45)cc3)CC2)c1] | 4-(furo[3,2-c]pyridin-4-yl)-N-[1-(4-methylpyridin-2-yl)piperidin-4-yl]benzamide | 413.4 $[M + H]^+$ |
| 151 | 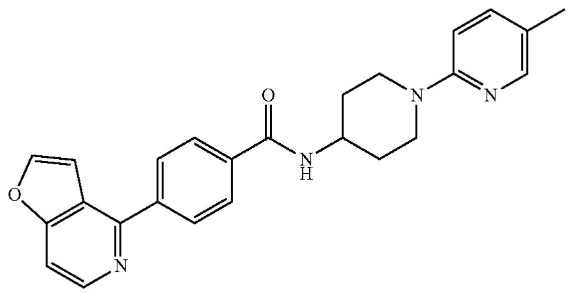 [SMILES: Cc1ccc(N2CCC(NC(=O)c3ccc(-c4nccc5occc45)cc3)CC2)nc1] | 4-(furo[3,2-c]pyridin-4-yl)-N-[1-(5-methylpyridin-2-yl)piperidin-4-yl]benzamide | 413.4 $[M + H]^+$ |
| 152 | 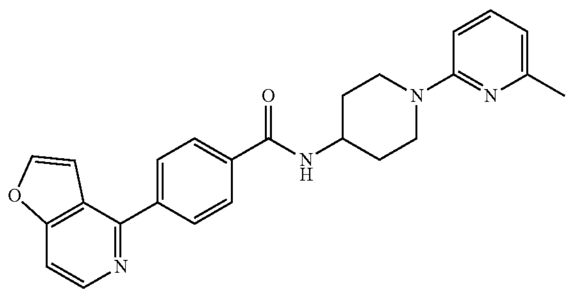 [SMILES: Cc1cccc(N2CCC(NC(=O)c3ccc(-c4nccc5occc45)cc3)CC2)n1] | 4-(furo[3,2-c]pyridin-4-yl)-N-[1-(6-methylpyridin-2-yl)piperidin-4-yl]benzamide | 413.4 $[M + H]^+$ |
| 153 | 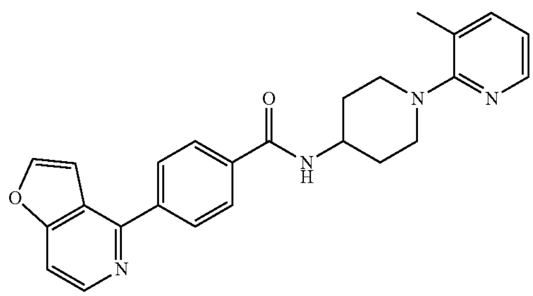 [SMILES: Cc1cccnc1N1CCC(NC(=O)c2ccc(-c3nccc4occc34)cc2)CC1] | 4-(furo[3,2-c]pyridin-4-yl)-N-[1-(3-methylpyridin-2-yl)piperidin-4-yl]benzamide | 413.4 $[M + H]^+$ |

TABLE 4-3

| | | | |
|---|---|---|---|
| 154 | 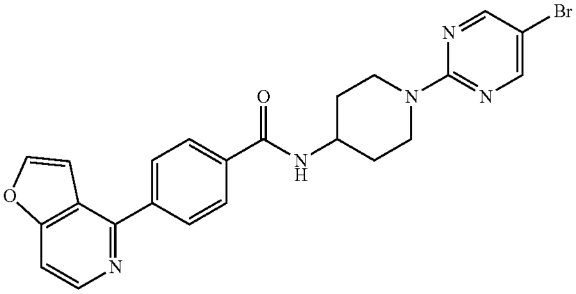 [SMILES: O=C(NC1CCN(c2ncc(Br)cn2)CC1)c1ccc(-c2nccc3occc23)cc1] | N-[1-(5-bromopyrimidin-2-yl)piperidin-4-yl]-4-(furo[3,2-c]pyridin-4-yl)benzamide | 478.3 $[M + H]^+$ |
| 155 | 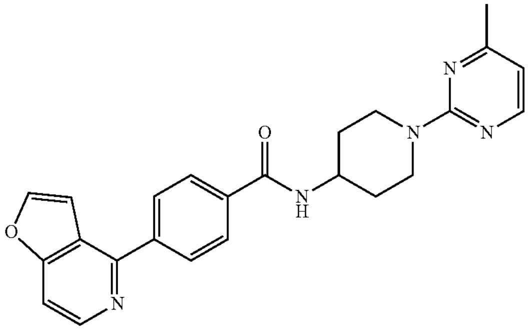 [SMILES: Cc1ccnc(N2CCC(NC(=O)c3ccc(-c4nccc5occc45)cc3)CC2)n1] | 4-(furo[3,2-c]pyridin-4-yl)-N-[1-(4-methylpyrimidin-2-yl)piperidin-4-yl]benzamide | 414.4 $[M + H]^+$ |
| 156 | 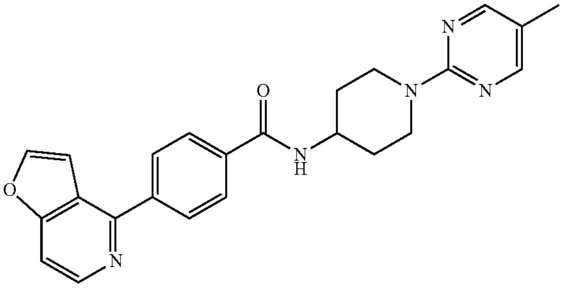 [SMILES: Cc1cnc(N2CCC(NC(=O)c3ccc(-c4nccc5occc45)cc3)CC2)nc1] | 4-(furo[3,2-c]pyridin-4-yl)-N-[1-(5-methylpyrimidin-2-yl)piperidin-4-yl]benzamide | 414.5 $[M + H]^+$ |
| 157 | 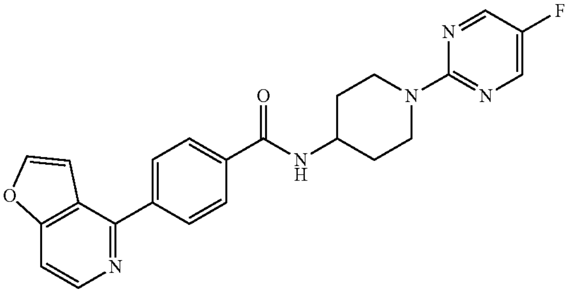 [SMILES: O=C(NC1CCN(c2ncc(F)cn2)CC1)c1ccc(-c2nccc3occc23)cc1] | N-[1-(5-fluoropyrimidin-2-yl)piperidin-4-yl]-4-(furo[3,2-c]pyridin-4-yl)benzamide | 418.4 $[M + H]^+$ |
| 158 | 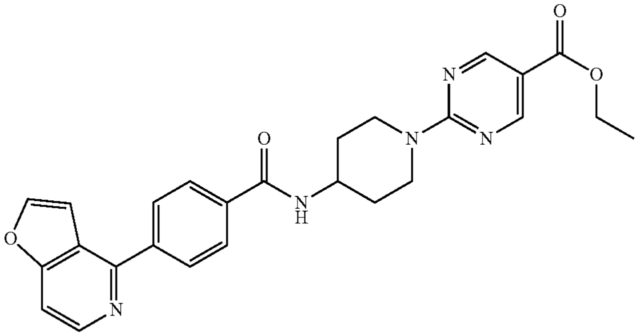 [SMILES: CCOC(=O)c1cnc(N2CCC(NC(=O)c3ccc(-c4nccc5occc45)cc3)CC2)nc1] | Ethyl 2-{4-[4-(furo[3,2-c]pyridin-4-yl)benzamide]piperidin-1-yl}pyrimidine-5-carboxylate | 472.5 $[M + H]^+$ |

TABLE 4-4
| | | | |
|---|---|---|---|
| 159 | 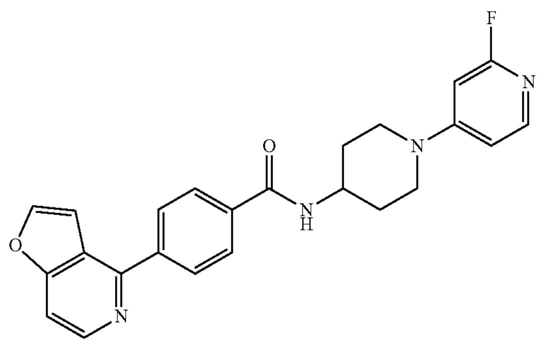 [SMILES: O=C(NC1CCN(c2ccnc(F)c2)CC1)c1ccc(-c2nccc3occc23)cc1] | N-[1-(2-fluoropyridin-4-yl)piperidin-4-yl]-4-(furo[3,2-c]pyridin-4-yl)benzamide | 417.4 $[M + H]^+$ |
| 160 | 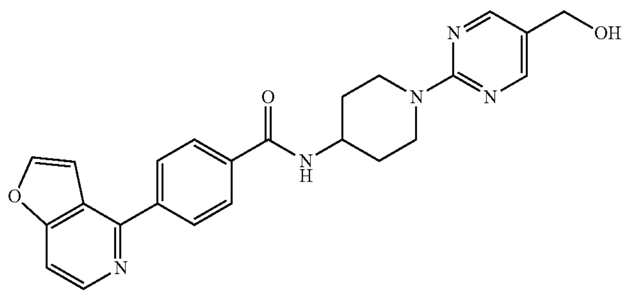 [SMILES: O=C(NC1CCN(c2ncc(CO)cn2)CC1)c1ccc(-c2nccc3occc23)cc1] | 4-(furo[3,2-c]pyridin-4-yl)-N-{1-[5-(hydroxymethyl) pyrimidin-2-yl]piperidin-4-yl}benzamide | 430.4 $[M + H]^+$ |
| 161 | 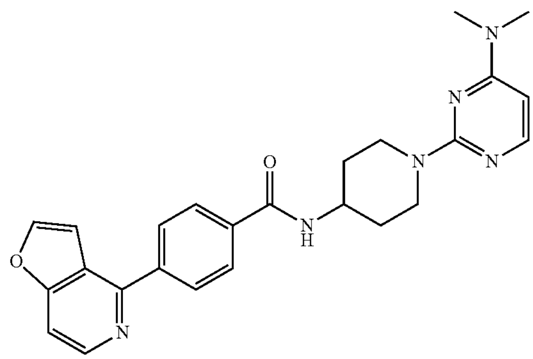 [SMILES: CN(C)c1ccnc(N2CCC(NC(=O)c3ccc(-c4nccc5occc45)cc3)CC2)n1] | N-{1-[4-(dimethylamino) pyrimidin-2-yl]piperidin-4-yl}-4-(furo[3,2-c]pyridin-4-yl)benzamide | 443.5 $[M + H]^+$ |
| 162 | 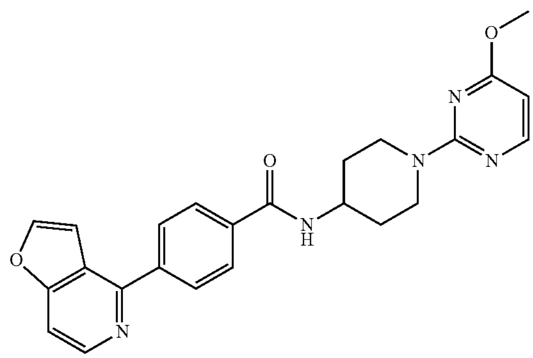 [SMILES: COc1ccnc(N2CCC(NC(=O)c3ccc(-c4nccc5occc45)cc3)CC2)n1] | 4-(furo[3,2-c]pyridin-4-yl)-N-[1-(4-methoxypyrimidin-2-yl)piperidin-4-yl]benzamide | 430.4 $[M + H]^+$ |

TABLE 4-4-continued
| | | | |
|---|---|---|---|
| 163 | 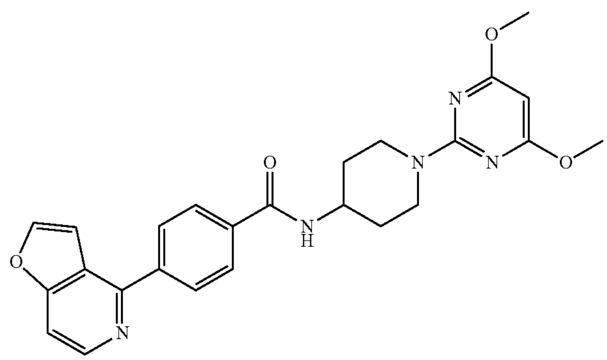 [SMILES: COc1cc(OC)nc(N2CCC(NC(=O)c3ccc(-c4nccc5occc45)cc3)CC2)n1] | N-[1-(4,6-dimethoxypyrimidin-2-yl)piperidin-4-yl]-4-(furo[3,2-c]pyridin-4-yl)]benzamide | 460.5 [M + H]$^+$ |
TABLE 4-5
| | | | |
|---|---|---|---|
| 164 | 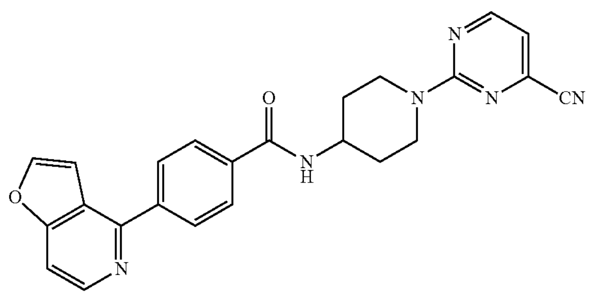 [SMILES: N#Cc1ccnc(N2CCC(NC(=O)c3ccc(-c4nccc5occc45)cc3)CC2)n1] | N-[1-(4-cyanopyrimidin-2-yl)piperidin-4-yl]-4-(furo[3,2-c]pyridin-4-yl)benzamide | 425.4 [M + H]$^+$ |
| 165 | 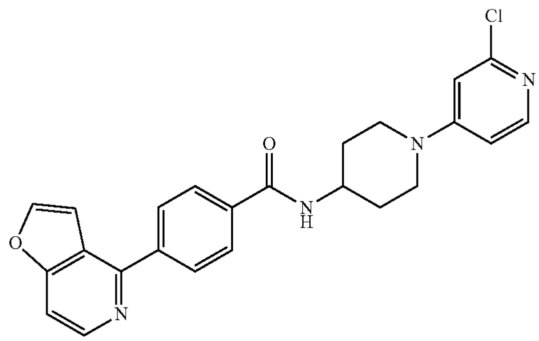 [SMILES: O=C(NC1CCN(c2ccnc(Cl)c2)CC1)c1ccc(-c2nccc3occc23)cc1] | N-[1-(2-chloropyridin-4-yl)piperidin-4-yl]-4-(furo[3,2-c]pyridin-4-yl)benzamide | 433.4 [M + H]$^+$ |
| 166 | 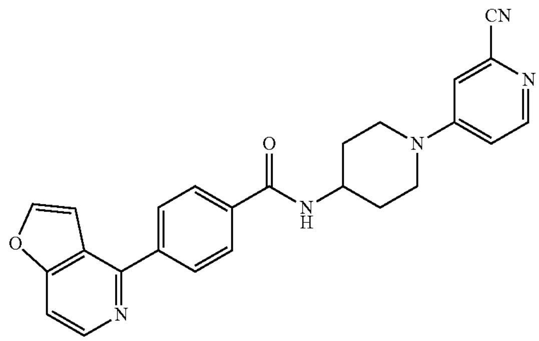 [SMILES: N#Cc1cc(N2CCC(NC(=O)c3ccc(-c4nccc5occc45)cc3)CC2)ccn1] | N-[1-(2-cyanopyridin-4-yl)piperidin-4-yl]-4-(furo[3,2-c]pyridin-4-yl)benzamide | 424.4 [M + H]$^+$ |

TABLE 4-5-continued
| | | | |
|---|---|---|---|
| 167 | 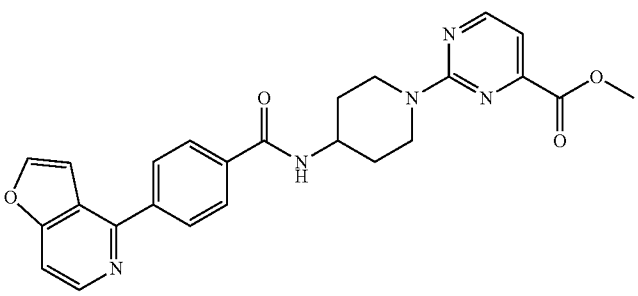 [SMILES: COC(=O)c1ccnc(N2CCC(NC(=O)c3ccc(-c4nccc5occc45)cc3)CC2)n1] | Methyl 2-{4-[4-(furo[3,2-c]pyridin-4-yl)benzamide]piperidin-1-yl}pyrimidine-4-carboxylate | 458.3 [M + H]$^+$ |
| 168 | 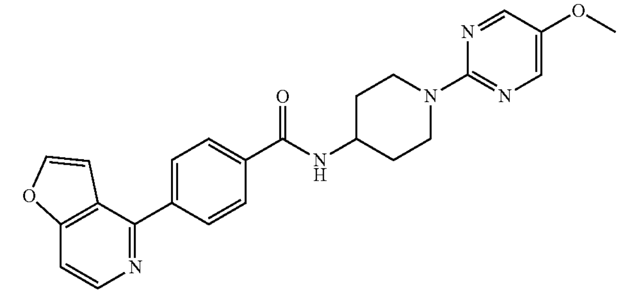 [SMILES: COc1cnc(N2CCC(NC(=O)c3ccc(-c4nccc5occc45)cc3)CC2)nc1] | 4-(furo[3,2-c]pyridin-4-yl)-N-[1-(5-methoxypyrimidin-2-yl)piperidin-4-yl]benzamide | 430.3 [M + H]$^+$ |
TABLE 4-6
| | | | |
|---|---|---|---|
| 169 | 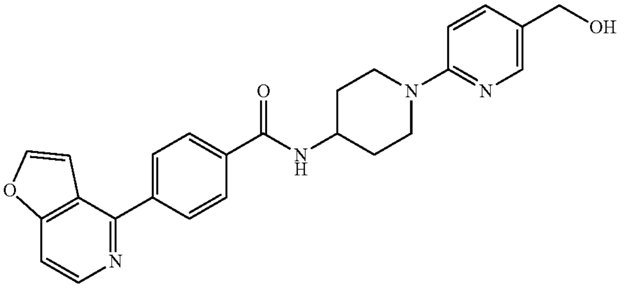 [SMILES: O=C(NC1CCN(c2ccc(CO)cn2)CC1)c1ccc(-c2nccc3occc23)cc1] | 4-(furo[3,2-c]pyridin-4-yl)-N-{1-[5-(hydroxymethyl)pyridin-2-yl]piperidin-4-yl}benzamide | 429.3 [M + H]$^+$ |
| 170 | 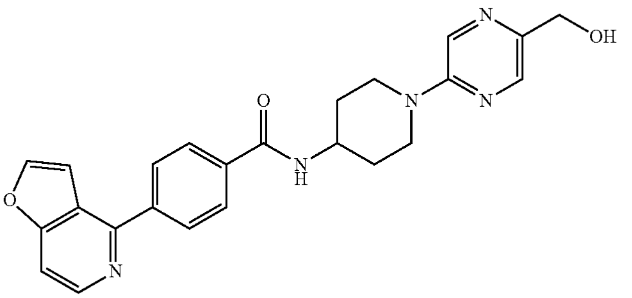 [SMILES: O=C(NC1CCN(c2cnc(CO)cn2)CC1)c1ccc(-c2nccc3occc23)cc1] | 4-(furo[3,2-c]pyridin-4-yl)-N-{1-[5-(hydroxymethyl)pyrazin-2-yl]piperidin-4-yl}benzamide | 430.4 [M + H]$^+$ |

Example 171

Synthesis of 4-(furo[3,2-c]pyridin-4-yl)-N-[1-(pyrimidin-4-yl)piperidin-4-yl]benzamide [171] (Hereinafter, Referred to as a Compound [171])

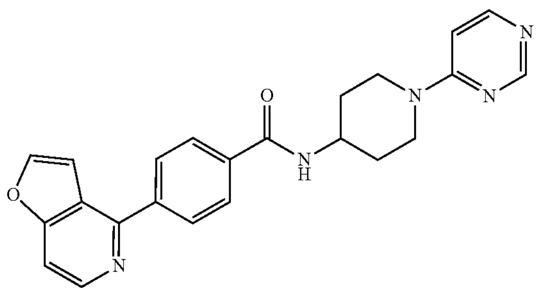 [SMILES: O=C(NC1CCN(c2ccncn2)CC1)c1ccc(-c2nccc3occc23)cc1]

To a solution of the compound [146] (20 mg) in ethanol (0.50 mL) was added 10% palladium-activated carbon (2.0 mg) at room temperature, and the mixture was stirred at room temperature for 23 hours under a hydrogen atmosphere. The reaction mixture was filtered and concentrated under reduced pressure. The obtained residue was purified by silica gel column chromatography to give the title compound (2.1 mg) as a white solid.

ESI-MS: 400.5 $[M+H]^+$

Example 172

Synthesis of 4-(furo[3,2-c]pyridin-4-yl)-N-[1-(6-oxo-1,6-dihydropyridin-2-yl)piperidin-4-yl]benzamide [172] (Hereinafter, Referred to as a Compound [172])

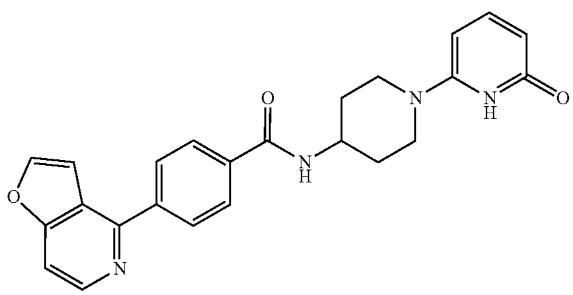

To a solution of the compound [147] (10 mg) in 1,4-dioxane (0.20 mL) was added 5 M hydrochloric acid (0.20 mL) at room temperature, and the mixture was stirred at room temperature for 23 hours. To the reaction mixture was added a 5 M aqueous sodium hydroxide solution, and the mixture was extracted with chloroform. The organic layer was dried over anhydrous sodium sulfate and concentrated under reduced pressure. The obtained residue was purified by silica gel column chromatography to give the title compound (2.1 mg) as a white solid.

$^1$H-NMR (400 MHz, $CD_3OD$) δ: 8.53 (d, J=5.5 Hz, 1H), 8.01-7.99 (m, 5H), 7.63 (d, J=5.9 Hz, 1H), 7.44 (t, J=8.2 Hz, 1H), 7.19-7.18 (m, 1H), 5.90-5.88 (m, 2H), 4.18-4.14 (m, 1H), 3.92-3.89 (m, 2H), 3.06-3.01 (m, 2H), 2.18-2.06 (m, 2H), 1.79-1.74 (m, 2H).

ESI-MS: 415.4 $[M+H]^+$

Example 173

Synthesis of N-[1-(5-cyanopyrimidin-2-yl)piperidin-4-yl]-4-(furo[3,2-c]pyridin-4-yl)benzamide [173] (Hereinafter, Referred to as a Compound [173])

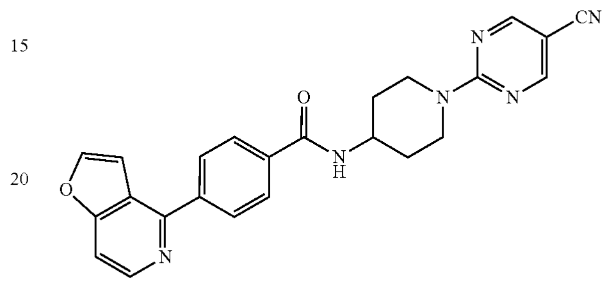

To a solution of the compound [154] (13.4 mg) in DMF (0.60 mL) were added zinc cyanide (6.6 mg) and Pd $(PPh_3)_4$ (6.5 mg) at room temperature, and the mixture was stirred at 120° C. for 30 minutes using a microwave reactor under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (5.6 mg) as a white solid.

ESI-MS: 425.4 $[M+H]^+$

Example 174

Synthesis of 2-{4-[4-(furo[3,2-c]pyridin-4-yl)benzamide]piperidin-1-yl}pyrimidine-5-carboxamide [174] (Hereinafter, Referred to as a Compound [174])

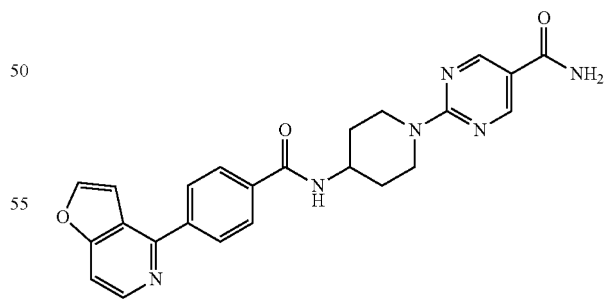

To a solution of the compound [173] (14.6 mg) in tert-butanol (0.60 mL) was added potassium tert-butoxide (93.0 mg) at room temperature, and the mixture was stirred at 80° C. for 2 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (5.5 mg) as a white solid.

ESI-MS: 443.4 $[M+H]^+$

Example 175

Synthesis of 2-{4-[4-(furo[3,2-c]pyridin-4-yl)benzamide]piperidin-1-yl}pyrimidine-4-carboxamide [175] (Hereinafter, Referred to as a Compound [175])

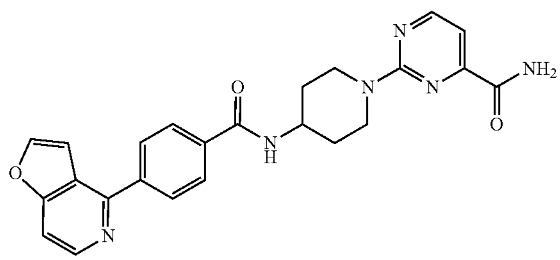 [SMILES: NC(=O)c1ccnc(N2CCC(NC(=O)c3ccc(-c4nccc5occc45)cc3)CC2)n1]

To a solution of the compound [164] (10.6 mg) in tert-butanol (0.50 mL) was added potassium tert-butoxide (67.0 mg) at room temperature, and the mixture was stirred at 80° C. for 3 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (3.8 mg) as a white solid.

ESI-MS: 443.4 $[M+H]^+$

Example 176

Synthesis of 4-{4-[4-(furo[3,2-c]pyridin-4-yl)benzamide]piperidin-1-yl}picolinamide [176] (Hereinafter, Referred to as a Compound [176])

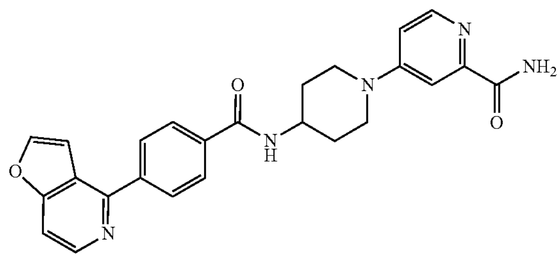 [SMILES: NC(=O)c1cc(N2CCC(NC(=O)c3ccc(-c4nccc5occc45)cc3)CC2)ccn1]

To a solution of the compound [166] (7.8 mg) in tert-butanol (0.40 mL) was added potassium tert-butoxide (50 mg) at room temperature, and the mixture was stirred at 80° C. for 3 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (5.4 mg) as a white solid.

ESI-MS: 442.4 $[M+H]^+$

Example 177

Synthesis of 4-(furo[3,2-c]pyridin-4-yl)-N-[1-(5-sulfamoylpyrimidin-2-yl)piperidin-4-yl]benzamide [177] (Hereinafter, Referred to as a Compound [177])

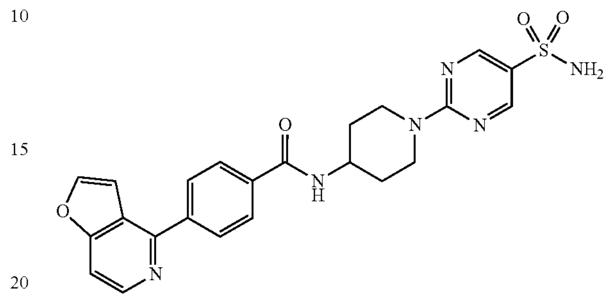

(1) Synthesis of N-(1-{5-[N-(tert-butyl) sulfamoyl]pyrimidin-2-yl}piperidin-4-yl)-4-(furo[3,2-c]pyridin-4-yl)benzamide [177-1] (Hereinafter, Referred to as a Compound [177-1])

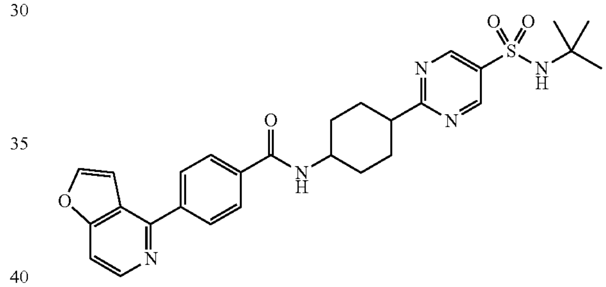

To a solution of 2-chloropyrimidine-5-sulfonyl chloride (100 mg) in THF (1.50 mL) was added tert-butylamine (60.0 μL) at 0° C., and the mixture was stirred at room temperature for 1 hour. The reaction mixture was concentrated under reduced pressure. To a solution of the obtained residue in DMSO (150 μL) were added potassium carbonate (10.0 mg) and the compound [142] (10.0 mg) at room temperature, and the mixture was stirred at 140° C. for 4 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (9.6 mg) as a white solid.

ESI-MS: 535.3 $[M+H]^+$ (2) Synthesis of 4-(furo[3,2-c]pyridin-4-yl)-N-[1-(5-sulfamoylpyrimidin-2-yl)piperidin-4-yl]benzamide [177]

To a solution of the compound [177-1] (9.60 mg) in ethyl acetate (200 μL) was added trifluoroacetic acid (200 μL) at room temperature, and the mixture was stirred at 80° C. for 2 hours. To the reaction mixture was added a saturated aqueous sodium bicarbonate solution, and the mixture was extracted with chloroform. The organic layer was dried over anhydrous sodium sulfate and concentrated under reduced pressure. The obtained residue was purified by silica gel column chromatography to give the title compound (0.73 mg) as a white solid.

ESI-MS: 479.4 [M+H]$^+$

Example 178

Synthesis of N-{1-[4-(azetidin-1-yl)pyrimidin-2-yl]piperidin-4-yl}-4-(furo[3,2-c]pyridin-4-yl)benzamide [178] (Hereinafter, Referred to as a Compound [178])

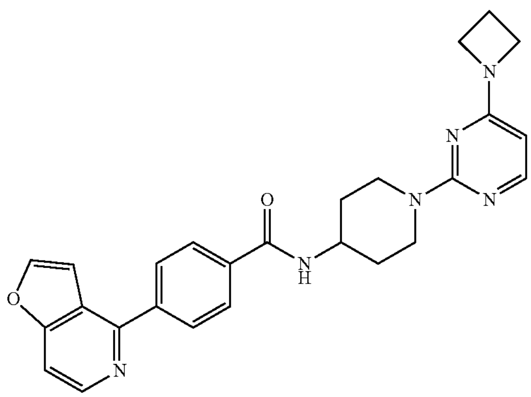 [SMILES: O=C(NC1CCN(c2nccc(N3CCC3)n2)CC1)c1ccc(-c2nccc3occc23)cc1]

(1) Synthesis of 4-(azetidin-1-yl)-2-chloropyrimidine [178-1] (Hereinafter, Referred to as a Compound [178-1])

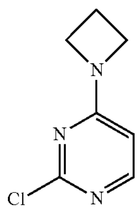 [SMILES: Clc1nccc(N2CCC2)n1]

To a solution of 2,4-dichloropyrimidine (100 mg) in THF (1.00 mL) were added cesium carbonate (437 mg) and azetidine hydrochloride (69.0 mg) at room temperature, and the mixture was stirred at 60° C. for 19 hours. To the sodium reaction mixture was added a saturated aqueous bicarbonate solution, and the mixture was extracted with chloroform. The organic layer was dried over anhydrous sodium sulfate and concentrated under reduced pressure. The obtained residue was purified by silica gel column chromatography to give the title compound (15.5 mg) as a white solid.

ESI-MS: 170.2 [M+H]$^+$ (2) Synthesis of N-{1-[4-(azetidin-1-yl)pyrimidin-2-yl]piperidin-4-yl}-4-(furo[3,2-c]pyridin-4-yl)benzamide [178]

To a solution of the compound [142] (27.0 mg) in NMP (300 μL) were added cesium carbonate (59.0 mg) and the compound [178-1] (15.5 mg) at room temperature, and the mixture was stirred at 140° C. for 4 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (12.2 mg) as a yellow solid.

ESI-MS: 455.4 [M+H]$^+$

Example 179

Synthesis of 4-(furo[3,2-c]pyridin-4-yl)-N-[1-(6-oxo-1,6-dihydropyrimidin-2-yl)piperidin-4-yl]benzamide [179] (Hereinafter, Referred to as a Compound [179])

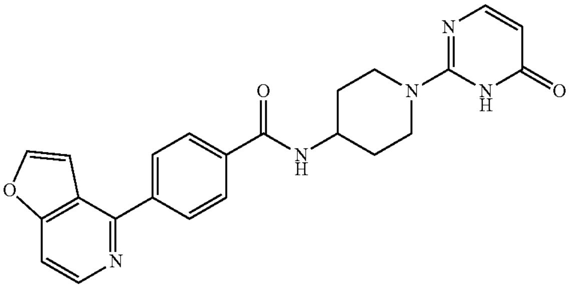 [SMILES: O=C(NC1CCN(c2nccc(=O)[nH]2)CC1)c1ccc(-c2nccc3occc23)cc1]

(1) Synthesis of 2-chloropyrimidin-4(3H)-one [179-1] (Hereinafter, Referred to as a Compound [179-1])

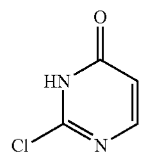

To 2,4-dichloropyrimidine (1.00 g) was added a 5 M aqueous sodium hydroxide solution (2.68 mL) at room temperature, and the mixture was stirred at 80° C. for 4 hours. To the reaction mixture was added 5 M hydrochloric acid, and the mixture was extracted with ethyl acetate. The organic layer was dried over anhydrous sodium sulfate and concentrated under reduced pressure. The obtained residue was purified by silica gel column chromatography to give the title compound (780 mg) as a yellow solid.

ESI-MS: 131.1 [M+H]$^+$ (2) Synthesis of 4-(furo[3,2-c]pyridin-4-yl)-N-[1-(6-oxo-1,6-dihydropyrimidin-2-yl)piperidin-4-yl]benzamide [179]

To a solution of the compound [142] (20 mg) in NMP (0.30 mL) were added potassium carbonate (56 mg) and the compound [179-1] (23 mg) at room temperature, and the mixture was stirred at 140° C. for 17 hours. To the reaction mixture was added 1 M hydrochloric acid, and the mixture was extracted with chloroform. The organic layer was dried over anhydrous sodium sulfate and concentrated under reduced pressure. The obtained residue was purified by silica gel column chromatography to give the title compound (7.5 mg) as a yellow solid.

ESI-MS: 416.4 $[M+H]^+$

Example 180

Synthesis of 4-(furo[3,2-c]pyridin-4-yl)-N-[1-(2,2,2-trifluoroethyl)piperidin-4-yl]benzamide [180] (Hereinafter, Referred to as a Compound [180])

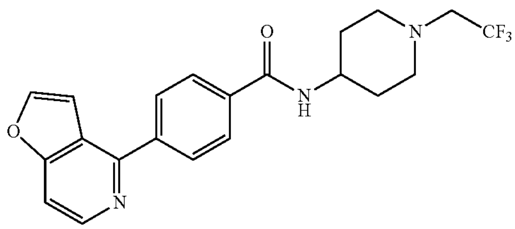 [SMILES: O=C(NC1CCN(CC(F)(F)F)CC1)c1ccc(-c2nccc3occc23)cc1]

To a solution of the compound [142] (10 mg) in 1,4-dioxane (0.30 mL) were added DIPEA (16 μL) and 2,2,2-trifluoroethyl trifluoromethanesulfonate (5.4 μL) at room temperature, and the mixture was stirred at room temperature for 16 hours. The reaction mixture was concentrated under reduced pressure, and the obtained residue was purified by silica gel column chromatography to give the title compound (8.5 mg) as a white solid.

$^1$H-NMR (400 MHz, DMSO-$d_6$) δ: 8.59 (d, J=5.5 Hz, 1H), 8.38 (d, J=7.8 Hz, 1H), 8.24 (d, J=2.3 Hz, 1H), 8.14-8.06 (m, 2H), 8.01 (dd, J=6.6, 2.1 Hz, 2H), 7.72 (dd, J=5.5, 0.9 Hz, 1H), 7.37-7.36 (m, 1H), 3.84-3.77 (m, 1H), 3.17 (q, J=10.2 Hz, 2H), 2.96-2.93 (m, 2H), 2.47-2.39 (m, 2H), 1.84-1.78 (m, 2H), 1.66-1.56 (m, 2H).

ESI-MS: 404.4 $[M+H]^+$

Example 181

Synthesis of 4-(furo[3,2-c]pyridin-4-yl)-N-[1-(4-methyl-6-oxo-1,6-dihydropyrimidin-2-yl)piperidin-4-yl]benzamide [181] (Hereinafter, Referred to as a Compound [181])

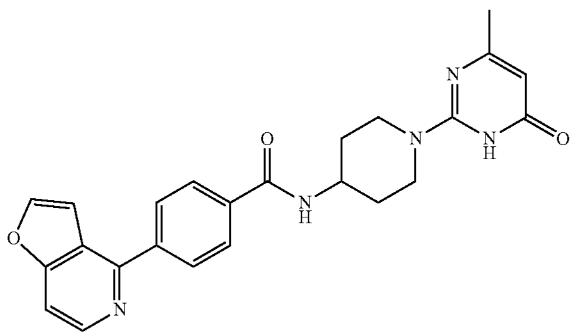 [SMILES: Cc1cc(=O)[nH]c(N2CCC(NC(=O)c3ccc(-c4nccc5occc45)cc3)CC2)n1]

(1) Synthesis of 2-chloro-6-methylpyrimidin-4(3H)-one trifluoroacetate [181-1] (Hereinafter, Referred to as a Compound [181-1])

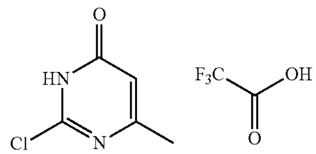

To 2,4-dichloro-6-methylpyrimidine (155 mg) was added a 5 M aqueous sodium hydroxide solution (536 μL) at room temperature, and the mixture was stirred at 80° C. for 4 hours. The reaction mixture was purified by reversed-phase silica gel column chromatography to give the title compound (89.3 mg) as a yellow solid.

ESI-MS: 145.3 $[M+H]^+$ (2) Synthesis of 4-(furo[3,2-c]pyridin-4-yl)-N-[1-(4-methyl-6-oxo-1,6-dihydropyrimidin-2-yl)piperidin-4-yl]benzamide [181]

To a solution of the compound [142] (20 mg) in NMP (0.3 mL) were added potassium carbonate (25 mg) and the compound [181-1] (18 mg) at room temperature, and the mixture was stirred at 140° C. for 4 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (7.8 mg) as a white solid.

ESI-MS: 430.4 $[M+H]^+$

Example 182

Synthesis of N-[1-(5-bromo-6-oxo-1,6-dihydropyrimidin-2-yl)piperidin-4-yl]-4-(furo[3,2-c]pyridin-4-yl)benzamide [182] (Hereinafter, Referred to as a Compound [182])

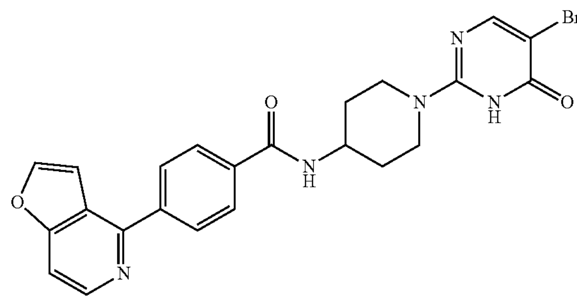 [SMILES: O=C(NC1CCN(c2ncc(Br)c(=O)[nH]2)CC1)c1ccc(-c2nccc3occc23)cc1]

(1) Synthesis of 5-bromo-2-chloropyrimidin-4 (3H)-one [182-1] (Hereinafter, Referred to as a Compound [182-1])

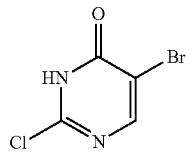

To 5-bromo-2,4-dichloropyrimidine (5.0 g) was added a 5 M aqueous sodium hydroxide solution (8.8 mL) at room temperature, and the mixture was stirred at 80° C. for 3 hours. To the reaction mixture was added 1 M hydrochloric acid, and the mixture was extracted with chloroform. The organic layer was dried over anhydrous sodium sulfate and concentrated under reduced pressure. The obtained residue was suspended in chloroform/n-hexane and the solid was collected by filtration to give the title compound (2.2 g) as a yellow solid.

ESI-MS: 209.1 $[M+H]^+$ (2) Synthesis of N-[1-(5-bromo-6-oxo-1,6-dihydropyrimidin-2-yl)piperidin-4-yl]-4-(furo[3,2-c]pyridin-4-yl)benzamide [182]

To a solution of the compound [142] (20 mg) in NMP (0.30 mL) were added potassium carbonate (25 mg) and the compound [182-1] (18 mg) at room temperature, and the mixture was stirred at 140° C. for 4 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (7.8 mg) as a white solid.

ESI-MS: 494.4 $[M+H]^+$

Example 183

Synthesis of 4-(furo[3,2-c]pyridin-4-yl)-N-[1-(1-methyl-6-oxo-1,6-dihydropyrimidin-2-yl)piperidin-4-yl]benzamide [183] (Hereinafter, Referred to as a Compound [183])

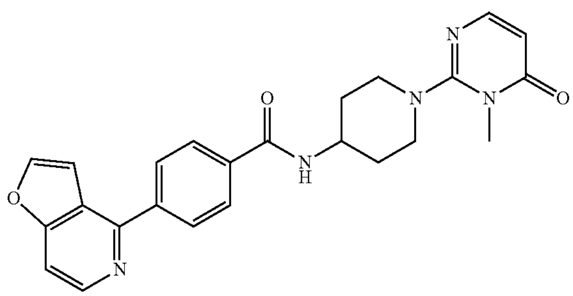 [SMILES: Cn1c(N2CCC(NC(=O)c3ccc(-c4nccc5occc45)cc3)CC2)nccc1=O]

(1) Synthesis of 2-chloro-3-methylpyrimidine-4 (3H)-one [183-1] (Hereinafter, Referred to as a Compound [183-1])

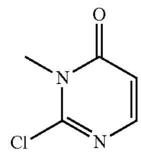

To a solution of the [179-1] (680 mg) in 1,4-dioxane (11.0 mL) was added potassium tert-butoxide (1.14 g) at room temperature, and the mixture was stirred at room temperature for 10 minutes. To the reaction mixture was added iodomethane (2.06 mL) at room temperature, and the mixture was stirred at 80° C. for 6 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (32.0 mg) as a white solid.

$^1$H-NMR (400 MHz, $CDCl_3$) δ: 7.69 (d, J=6.9 Hz, 1H), 6.37 (d, J=6.4 Hz, 1H), 3.64 (s, 3H).

(2) Synthesis of 4-(furo[3,2-c]pyridin-4-yl)-N-[1-(1-methyl-6-oxo-1,6-dihydropyrimidin-2-yl)piperidin-4-yl]benzamide [183]

To a solution of the compound [142] (59 mg) in NMP (0.6 mL) were added potassium carbonate (76 mg) and the compound [183-1] (32 mg) at room temperature, and the mixture was stirred at 120° C. for 3 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (62 mg) as a yellow solid.

$^1$H-NMR (400 MHz, DMSO-$d_6$) δ: 8.59 (d, J=5.9 Hz, 1H), 8.50 (d, J=7.3 Hz, 1H), 8.24 (d, J=2.3 Hz, 1H), 8.10 (d, J=8.7 Hz, 2H), 8.04 (d, J=8.7 Hz, 2H), 7.73 (d, J=6.4 Hz, 2H), 7.37-7.36 (m, 1H), 6.00 (d, J=6.4 Hz, 1H), 4.15-3.99 (m, 1H), 3.61-3.58 (m, 2H), 3.37 (s, 3H), 2.99-2.93 (m, 2H), 1.93-1.91 (m, 2H), 1.79-1.70 (m, 2H).

ESI-MS: 430.4 $[M+H]^+$

Example 184

Synthesis of 4-(furo[3,2-c]pyridin-4-yl)-N-[1-(1-methyl-6-oxo-1,6-dihydropyridin-2-yl)piperidin-4-yl]benzamide [184] (Hereinafter, Referred to as a Compound [184])

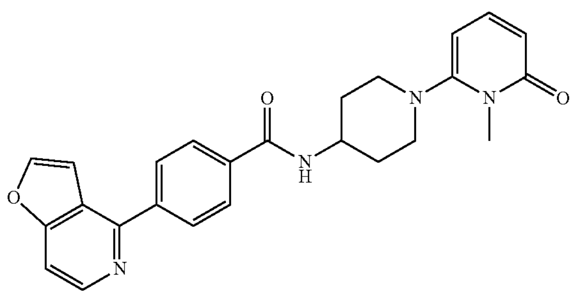 [SMILES: Cn1c(N2CCC(NC(=O)c3ccc(-c4nccc5occc45)cc3)CC2)cccc1=O]

To a solution of 2,6-difluoropyridine (1.00 g) in tert-butanol (29.0 mL) was added potassium tert-butoxide (2.90 g) at room temperature, and the mixture was stirred at room temperature for 2 hours. To the reaction mixture was added formic acid (992 μL) at room temperature, and the mixture was stirred at room temperature for 20 hours. To the reaction mixture was added water, and the mixture was extracted with ethyl acetate. The organic layer was dried over anhydrous sodium sulfate and concentrated under reduced pressure to give a crude product (340 mg). To a solution of the crude product (100 mg) in 1,4-dioxane (3.00 mL) was added potassium tert-butoxide (300 mg) at room temperature, and the mixture was stirred at room temperature for 20 minutes. To the reaction mixture was added iodomethane (550 μL) at room temperature, and the mixture was stirred at 80° C. for 1 hour. To the reaction mixture was added water, and the mixture was extracted with ethyl acetate. The organic layer was dried over anhydrous sodium sulfate and concentrated under reduced pressure. To a solution of the obtained residue in NMP (0.30 mL) were added potassium carbonate (25.0 mg) and the compound (20.0 mg) at room temperature, and the mixture was stirred at 120° C. for 3 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (3.2 mg) as a brown solid.

$^1$H-NMR (400 MHz, DMSO-$d_6$) δ: 8.59 (d, J=5.3 Hz, 1H), 8.51 (d, J=7.8 Hz, 1H), 8.24 (d, J=2.3 Hz, 1H), 8.15-8.08 (m, 2H), 8.04 (dd, J=6.4, 1.8 Hz, 2H), 7.73 (dd, J=5.9, 0.9 Hz, 1H), 7.42-7.30 (m, 2H), 6.09 (dd, J=9.1, 0.9 Hz, 1H), 5.86 (dd, J=7.3, 0.9 Hz, 1H), 4.04-4.00 (m, 1H), 3.40 (s, 3H), 3.21-3.19 (m, 2H), 2.78-2.72 (m, 2H), 1.98-1.94 (m, 2H), 1.85-1.68 (m, 2H).

ESI-MS: 429.4 [M+H]$^+$

Example 185

Synthesis of 4-(furo[3,2-c]pyridin-4-yl)-N-{1-[5-(2-hydroxypropan-2-yl)pyrimidin-2-yl]piperidin-4-yl}benzamide [185] (Hereinafter, Referred to as a Compound [185])

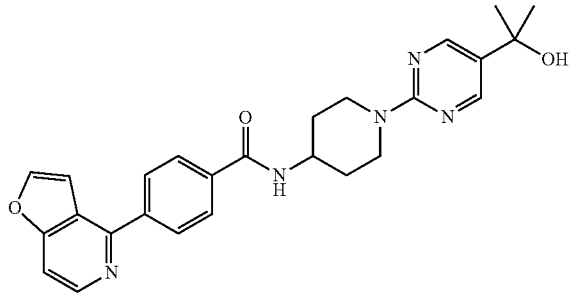 [SMILES: CC(C)(O)c1cnc(N2CCC(NC(=O)c3ccc(-c4nccc5occc45)cc3)CC2)nc1]

(1) Synthesis of 2-(2-chloropyrimidin-5-yl) propan-2-ol [185-1] (Hereinafter, Referred to as a Compound [185-1])

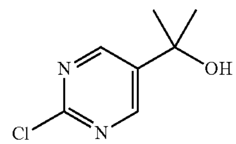

To a solution of ethyl 2-chloropyrimidine-5-carboxylate (100 mg) in THF (1.78 mL) was added a solution of 3 M methylmagnesium bromide in diethyl ether (533 μL) at 0° C., and the mixture was stirred at 40° C. for 2 hours. To the reaction mixture was added a saturated aqueous ammonium chloride solution, and the mixture was extracted with ethyl acetate. The organic layer was dried over anhydrous sodium sulfate and concentrated under reduced pressure. The obtained residue was purified by silica gel column chromatography to give the title compound (25.4 mg) as a white solid.

ESI-MS: 173.2 [M+H]$^+$ (2) Synthesis of 4-(furo[3,2-c]pyridin-4-yl)-N-{1-[5-(2-hydroxypropan-2-yl)pyrimidin-2-yl]piperidin-4-yl}benzamide [185]

To a solution of the compound [142] (19 mg) in NMP (0.30 mL) were added potassium carbonate (25 mg) and the compound [185-1] (10 mg) at room temperature, and the mixture was stirred at 120° C. for 1 hour. To the reaction mixture was added water, and the mixture was extracted with chloroform. The organic layer was dried over anhydrous sodium sulfate and concentrated under reduced pressure. The obtained residue was purified by silica gel column chromatography to give the title compound (8.2 mg) as a white solid.

ESI-MS: 458.5 [M+H]$^+$

Example 186

Synthesis of N-(1-acetylpiperidin-4-yl)-4-(furo[3,2-c]pyridin-4-yl)benzamide [186] (Hereinafter, Referred to as a Compound [186])

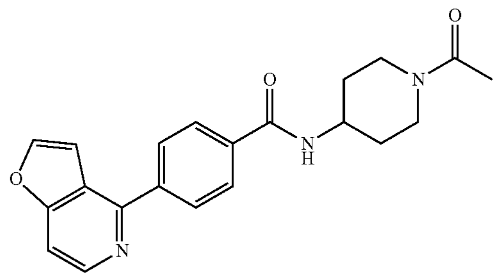 [SMILES: CC(=O)N1CCC(NC(=O)c2ccc(-c3nccc4occc34)cc2)CC1]

To a solution of the compound [142] (20 mg) in NMP (0.30 mL) were added cesium carbonate (60 mg) and acetyl chloride (3.9 μL) at room temperature, and the mixture was stirred at 120° C. for 14 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (10 mg) as a white solid.

$^1$H-NMR (400 MHz, DMSO-$d_6$) δ: 8.59 (dd, J=5.5, 1.4 Hz, 1H), 8.50-8.38 (m, 1H), 8.24 (d, J=2.3 Hz, 1H), 8.10 (d, J=6.9 Hz, 2H), 8.06-7.98 (m, 2H), 7.73 (d, J=5.5 Hz, 1H), 7.37-7.35 (m, 1H), 4.34-4.31 (m, 1H), 4.20-3.97 (m, 1H), 3.84-3.80 (m, 1H), 3.16-3.09 (m, 1H), 2.80-2.61 (m, 1H), 2.02 (s, 3H), 1.85-1.80 (m, 2H), 1.58-1.32 (m, 2H).

ESI-MS: 364.3 [M+H]$^+$

Example 187

Synthesis of 4-(furo[3,2-c]pyridin-4-yl)-N-{1-[4-(hydroxymethyl)pyrimidin-2-yl]piperidin-4-yl}benzamide [187] (Hereinafter, Referred to as a Compound [187])

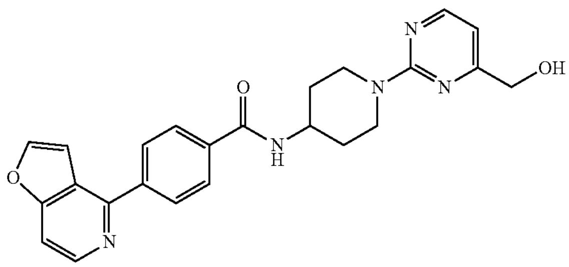 [SMILES: O=C(NC1CCN(c2nccc(CO)n2)CC1)c1ccc(-c2nccc3occc23)cc1]

To a solution of the compound [167] (15 mg) in THE (0.40 mL) was added sodium borohydride (12 mg) at 0° C., and the mixture was stirred at room temperature for 17 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (10 mg) as a white solid.

ESI-MS: 430.3 [M+H]$^+$

Example 188

Synthesis of N-{1-[5-(N-acetylacetamide)pyrimidin-2-yl]piperidin-4-yl}-4-(furo[3,2-c]pyridin-4-yl)benzamide [188] (Hereinafter, Referred to as a Compound [188])

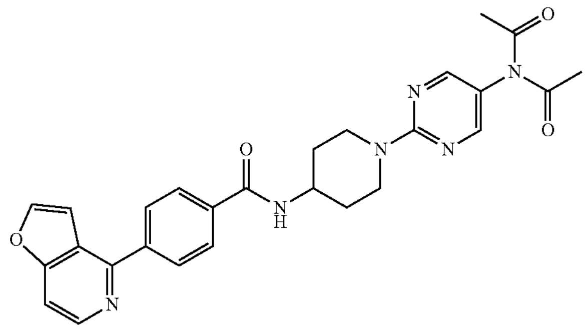 [SMILES: CC(=O)N(C(C)=O)c1cnc(N2CCC(NC(=O)c3ccc(-c4nccc5occc45)cc3)CC2)nc1]

(1) Synthesis of 4-(furo[3,2-c]pyridin-4-yl)-N-[1-(5-nitropyrimidin-2-yl)piperidin-4-yl]benzamide [188-1] (Hereinafter, Referred to as a Compound [188-1])

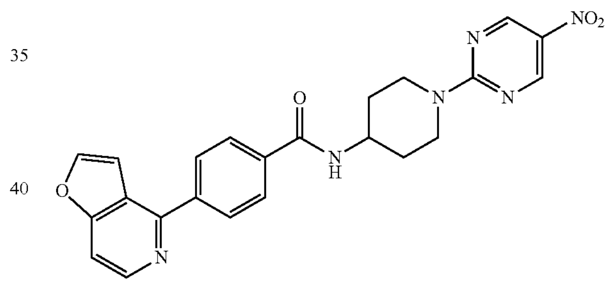

To a solution of the compound [142] (40.0 mg) in NMP (370 L) were added potassium carbonate (77.0 mg) and 2-chloro-5-nitropyrimidine (27.0 mg) at room temperature, and the mixture was stirred at 120° C. for 1 hour. To the reaction mixture was added water, and the mixture was extracted with chloroform. The organic layer was dried over anhydrous sodium sulfate and concentrated under reduced pressure. The obtained residue was purified by silica gel column chromatography to give the title compound (28.6 mg) as a yellow solid.

ESI-MS: 445.3 [M+H]$^+$ (2) Synthesis of N-{1-[5-(N-acetylacetamide)pyrimidin-2-yl]piperidin-4-yl}-4-(furo[3,2-c]pyridin-4-yl)benzamide [188]

To a solution of the compound [188-1] (24 mg) in ethanol (0.40 mL)/water (0.40 mL) were added iron (15 mg) and ammonium chloride (29 mg) at room temperature, and the mixture was stirred at 80° C. for 4 hours. The reaction mixture was filtered and concentrated under reduced pressure to give a crude product (51 mg). To a solution of the obtained crude product (20 mg) in dichloromethane (0.50 mL) were added triethylamine (20 µL) and acetyl chloride (17 µL) at room temperature, and the mixture was stirred at room temperature for 2 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (2.1 mg) as a white solid.

ESI-MS: 499.3 $[M+H]^+$

Example 189

Synthesis of N-[1-(5-acetamidopyrimidin-2-yl)piperidin-4-yl]-4-(furo[3,2-c]pyridin-4-yl)benzamide [189] (Hereinafter, Referred to as a Compound [189])

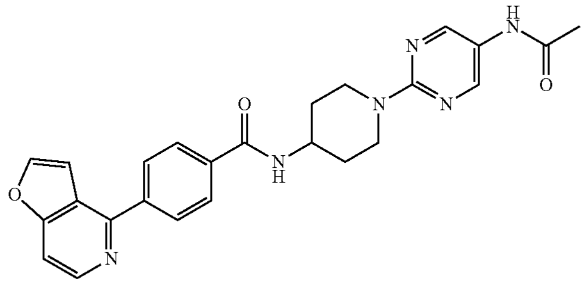 [SMILES: CC(=O)Nc1cnc(N2CCC(NC(=O)c3ccc(-c4nccc5occc45)cc3)CC2)nc1]

To a solution of the compound [188-1] (24 mg) in ethanol (0.40 mL)/water (0.40 mL) were added iron (15 mg) and ammonium chloride (29 mg) at room temperature, and the mixture was stirred at 80° C. for 4 hours. The reaction mixture was filtered and concentrated under reduced pressure to give a crude product (51 mg). To a solution of the obtained crude product (30 mg) in dichloromethane (0.30 mL) were added triethylamine (30 µL) and acetyl chloride (6.7 µL) at room temperature, and the mixture was stirred at room temperature for 4 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (6.4 mg) as a white solid.

ESI-MS: 457.3 $[M+H]^+$

Example 190

Synthesis of 4-(furo[3,2-c]pyridin-4-yl)-N-[1-(pyridazin-3-yl)piperidin-4-yl]benzamide [190] (Hereinafter, Referred to as a Compound [190])

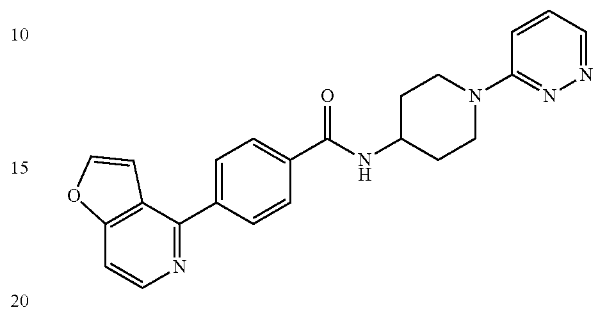

To a solution of the compound [99-1] (20 mg) in dichloromethane (0.30 mL) were added 4-dimethylaminopyridine (11 mg), EDC (17 mg), and 1-(pyridazin-3-yl)piperidin-4-amine (16 mg) at room temperature, and the mixture was stirred at room temperature for 2 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (12 mg) as a yellow solid.

$^1$H-NMR (400 MHz, DMSO-$d_6$) δ: 8.58 (d, J=5.5 Hz, 1H), 8.53-8.52 (m, 1H), 8.43 (d, J=8.2 Hz, 1H), 8.24 (d, J=2.3 Hz, 1H), 8.12-8.06 (m, 2H), 8.05-7.99 (m, 2H), 7.72 (dd, J=5.5, 0.9 Hz, 1H), 7.38-7.29 (m, 3H), 4.42-4.39 (m, 2H), 4.18-4.15 (m, 1H), 3.09-3.04 (m, 2H), 1.92-1.90 (m, 2H), 1.64-1.55 (m, 2H).

ESI-MS: 400.4 $[M+H]^+$

Example 191

Synthesis of (S)-4-(furo[3,2-c]pyridin-4-yl)-N-[1-(pyrimidin-2-yl)pyrrolidin-3-yl]benzamide [191] (Hereinafter, Referred to as a Compound [191])

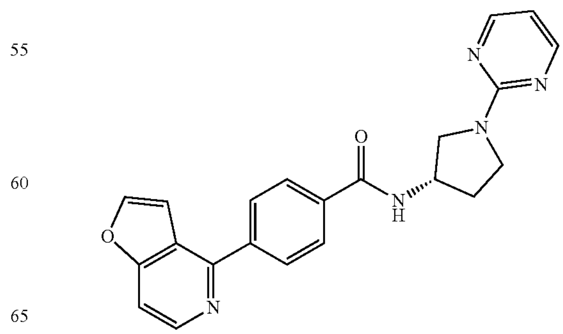

(1) Synthesis of tert-butyl(S)-3-[4-(furo[3,2-c]pyridin-4-yl)benzamide]pyrrolidine-1-carboxylate [191-1] (Hereinafter, Referred to as a Compound [191-1])

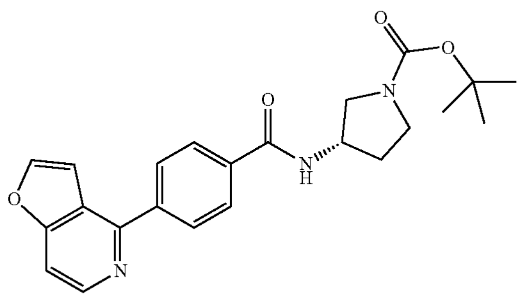 [SMILES: CC(C)(C)OC(=O)N1CC[C@H](NC(=O)c2ccc(-c3nccc4occc34)cc2)C1]

To a solution of the compound [99-1] (520 mg) in dichloromethane (4.00 mL) were added 4-dimethylaminopyridine (279 mg), EDC (437 mg), and tert-butyl(S)-3-aminopyrrolidine-1-carboxylate (432 μL) at room temperature, and the mixture was stirred at room temperature for 3 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (810 mg) as a yellow oil.

$^1$H-NMR (400 MHz, DMSO-$d_6$) δ: 8.67-8.65 (m, 1H), 8.60-8.58 (m, 1H), 8.25-8.23 (m, 1H), 8.10 (d, J=4.6 Hz, 2H), 8.04-8.02 (m, 2H), 7.74-7.72 (m, 1H), 7.37-7.35 (m, 1H), 4.48-4.42 (m, 1H), 3.57-3.42 (m, 3H), 3.23-3.20 (m, 1H), 2.15-2.07 (m, 1H), 1.97-1.91 (m, 1H), 1.40 (s, 9H).

ESI-MS: 408.4 [M+H]$^+$ (2) Synthesis of (S)-4-(furo[3,2-c]pyridin-4-yl)-N-(pyrrolidin-3-yl)benzamide dihydrochloride [191-2] (Hereinafter, Referred to as a Compound [191-2])

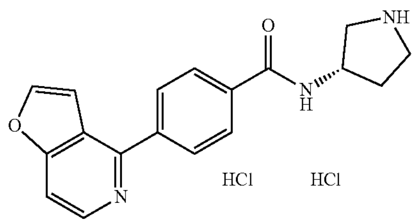 [SMILES: O=C(N[C@H]1CCNC1)c1ccc(-c2nccc3occc23)cc1 ; Cl ; Cl]

To a solution of the compound [191-1] (794 mg) in ethyl acetate (3.25 mL) was added a solution of 4 M hydrogen chloride in ethyl acetate (3.25 mL) at room temperature, and the mixture was stirred at room temperature for 15 minutes. The reaction mixture was concentrated under reduced pressure to give the title compound (540 mg) as a white solid.

$^1$H-NMR (400 MHz, DMSO-$d_6$) δ: 9.19 (br, 2H), 8.91-8.86 (m, 1H), 8.66-8.64 (m, 1H), 8.39-8.28 (m, 1H), 8.19-8.04 (m, 4H), 7.98-7.79 (m, 1H), 7.38-7.37 (m, 1H), 4.56-4.55 (m, 1H), 3.40-3.21 (m, 4H), 2.23-2.15 (m, 1H), 2.05-1.99 (m, 1H).

ESI-MS: 308.3 [M+H]$^+$ (3) Synthesis of (S)-4-(furo[3,2-c]pyridin-4-yl)-N-[1-(pyrimidin-2-yl)pyrrolidin-3-yl]benzamide [191]

To a solution of the compound [191-2] (20.0 mg) in NMP (300 μL) were added potassium carbonate (26.0 mg) and 2-chloropyrimidine (11.0 mg) at room temperature, and the mixture was stirred at 140° C. for 4 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (9.6 mg) as a yellow solid.

$^1$H-NMR (400 MHz, DMSO-$d_6$) δ: 8.76 (d, J=6.9 Hz, 1H), 8.59 (d, J=5.5 Hz, 1H), 8.34 (d, J=4.6 Hz, 2H), 8.24 (d, J=2.5 Hz, 1H), 8.11-8.08 (m, 2H), 8.05-8.03 (m, 2H), 7.73-7.72 (m, 1H), 7.36-7.35 (m, 1H), 6.61-6.59 (m, 1H), 4.63-4.59 (m, 1H), 3.83-3.53 (m, 4H), 2.29-2.22 (m, 1H), 2.29-2.04 (m, 1H).

ESI-MS: 386.4 [M+H]$^+$

Example 192

Synthesis of (R)-4-(furo[3,2-c]pyridin-4-yl)-N-[1-(pyrimidin-2-yl)pyrrolidin-3-yl]benzamide [192] (Hereinafter, Referred to as a Compound [192])

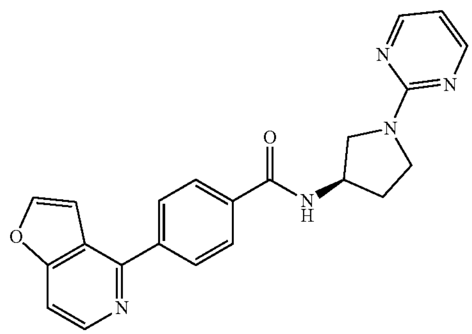 [SMILES: O=C(N[C@@H]1CCN(c2ncccn2)C1)c1ccc(-c2nccc3occc23)cc1]

(1) Synthesis of tert-butyl (R)-3-[4-(furo[3,2-c]pyridin-4-yl)benzamide]pyrrolidine-1-carboxylate [192-1] (Hereinafter, Referred to as a Compound [192-1])

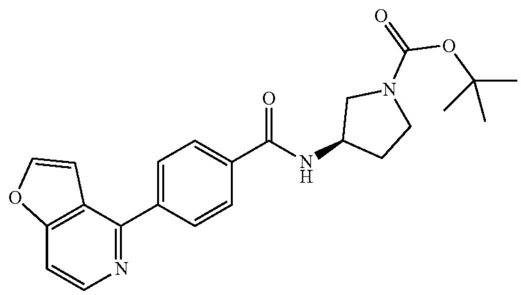 [SMILES: CC(C)(C)OC(=O)N1CC[C@@H](NC(=O)c2ccc(-c3nccc4occc34)cc2)C1]

To a solution of the compound [99-1] (100 mg) in dichloromethane (0.80 mL) were added 4-dimethylaminopyridine (54 mg), EDC (84 mg), and tert-butyl (S)-3-aminopyrrolidine-1-carboxylate (83 μL) at room temperature, and the mixture was stirred at room temperature for 3 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (160 mg) as a yellow oil.

ESI-MS: 408.4 $[M+H]^+$ (2) Synthesis of (R)-4-(furo[3,2-c]pyridin-4-yl)-N-[1-(pyrimidin-2-yl)pyrrolidin-3-yl]benzamide [192]

The title compound (4.2 mg) was synthesized from the compound [192-1] according to the methods of steps (2) and (3) in Example 191 as a yellow solid.

ESI-MS: 386.4 $[M+H]^+$

Example 193

Synthesis of (S)-4-(furo[3,2-c]pyridin-4-yl)-N-{1-[5-(hydroxymethyl)pyrimidin-2-yl]pyrrolidin-3-yl}benzamide [193] (Hereinafter, Referred to as a Compound [193])

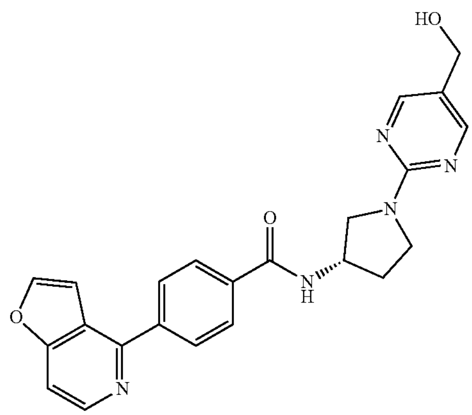 [SMILES: O=C(N[C@H]1CCN(c2ncc(CO)cn2)C1)c1ccc(-c2nccc3occc23)cc1]

To a solution of the compound [191-2] (13.5 mg) in NMP (150 μL) were added potassium carbonate (17.7 mg) and (2-chloropyrimidin-5-yl)methanol (11.0 mg) at room temperature, and the mixture was stirred at 120° C. for 1 hour. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (8.0 mg) as a yellow solid.

$^1$H-NMR (400 MHz, DMSO-$d_6$) δ: 8.73 (d, J=6.4 Hz, 1H), 8.56 (d, J=5.5 Hz, 1H), 8.28 (d, J=4.6 Hz, 2H), 8.21 (d, J=2.3 Hz, 1H), 8.07 (d, J=8.7 Hz, 2H), 8.01 (d, J=8.2 Hz, 2H), 7.70 (dd, J=5.5, 0.9 Hz, 1H), 7.35-7.34 (m, 1H), 5.01 (t, J=5.5 Hz, 1H), 4.64-4.57 (m, 1H), 4.32-4.30 (m, 2H), 3.84-3.80 (m, 1H), 3.72-3.66 (m, 1H), 3.60-3.50 (m, 2H), 2.30-2.22 (m, 1H), 2.12-2.04 (m, 1H).

ESI-MS: 416.4 $[M+H]^+$

Examples 194 to 197

Each compound of Examples 194 to 197 shown in the following Tables was synthesized according to the method shown in Example 193. The structure, name, and ESI-MS of the compound of each Example are shown in the following Tables.

TABLE 5

| Example | Structure | Name | ESI-MS |
| --- | --- | --- | --- |
| 194 | 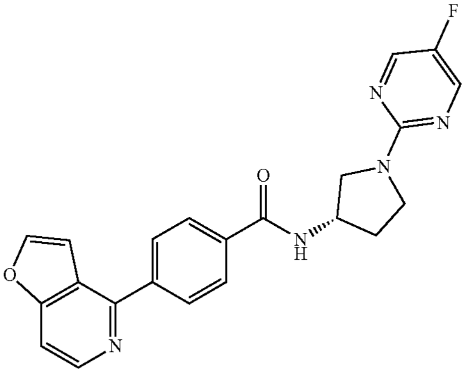 [SMILES: O=C(N[C@H]1CCN(c2ncc(F)cn2)C1)c1ccc(-c2nccc3occc23)cc1] | (S)-N-[1-(5-fluoropyrimidin-2-yl)pyrrolidin-3-yl]-4-(furo[3,2-c]pyridin-4-yl)benzamide | 404.4 $[M + H]^+$ |

TABLE 5-continued
| Example | Structure | Name | ESI-MS |
|---|---|---|---|
| 195 | 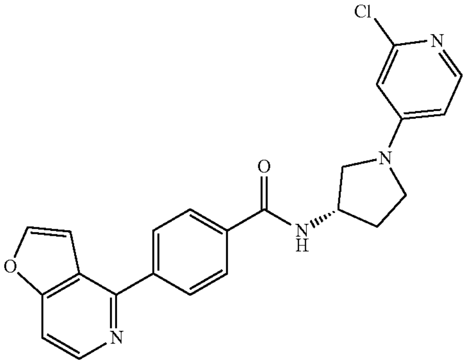 | (S)-N-[1-(2-chloropyridin-4-yl)pyrrolidin-3-yl]-4-(furo[3,2-c]pyridin-4-yl)benzamide | 419.3 $[M + H]^+$ |
| 196 | 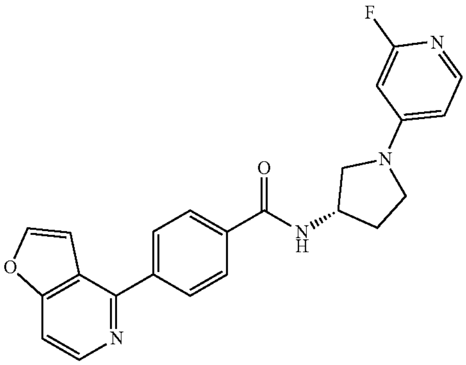 | (S)-N-[1-(2-fluoropyridin-4-yl)pyrrolidin-3-yl]-4-(furo[3,2-c]pyridin-4-yl)benzamide | 403.3 $[M + H]^+$ |
| 197 | 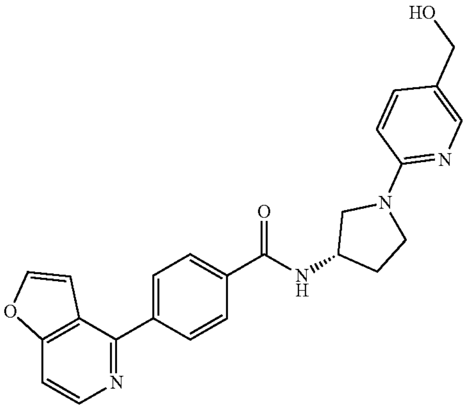 [SMILES: O=C(N[C@H]1CCN(c2ccc(CO)cn2)C1)c1ccc(-c2nccc3occc23)cc1] | (S)-4-(furo[3,2-c]pyridin-4-yl)-N-{1-[5-(hydroxymethyl)pyridin-2-yl]pyrrolidin-3-yl}benzamide | 415.2 $[M + H]^+$ |

Example 198

Synthesis of (S)-4-(furo[3,2-c]pyridin-4-yl)-N-{1-[5-(hydroxymethyl) pyrazin-2-yl]pyrrolidin-3-yl}benzamide [198] (Hereinafter, Referred to as a Compound [198])

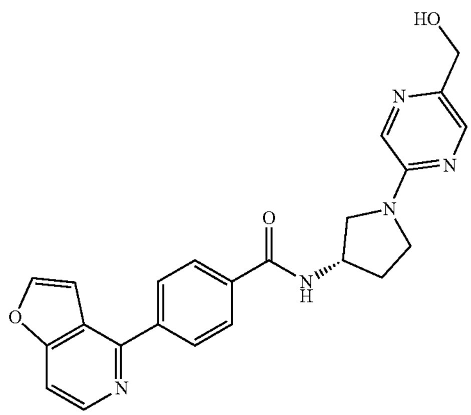 [SMILES: O=C(N[C@H]1CCN(c2cnc(CO)cn2)C1)c1ccc(-c2nccc3occc23)cc1]

To a solution of the compound [191-2] (20 mg) in NMP (0.50 mL) were added cesium carbonate (94 mg) and (5-chloropyrazin-2-yl)methanol (13 mg) at room temperature, and the mixture was stirred at 120° C. for 23 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (5.2 mg) as a white solid.

ESI-MS: 416.4 $[M+H]^+$

Example 199

Synthesis of (S)-4-(furo[3,2-c]pyridin-4-yl)-N-[1-(2,2,2-trifluoroethyl)pyrrolidin-3-yl]benzamide [199] (Hereinafter, Referred to as a Compound [199])

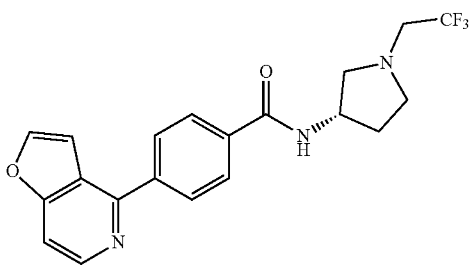 [SMILES: O=C(N[C@H]1CCN(CC(F)(F)F)C1)c1ccc(-c2nccc3occc23)cc1]

To a solution of the compound [191-2] (20 mg) in 1,4-dioxane (0.30 mL) were added DIPEA (15 L) and 2,2,2-trifluoroethyl trifluoromethanesulfonate (6.3 μL) at room temperature, and the mixture was stirred at room temperature for 5 hours. The reaction mixture was filtered and concentrated under reduced pressure. The obtained residue was purified by silica gel column chromatography to give the title compound (2.1 mg) as a white solid.

ESI-MS: 390.3 $[M+H]^+$

Example 200

Synthesis of (S)-4-(furo[3,2-c]pyridin-4-yl)-N-{1-[5-(2-hydroxypropan-2-yl)pyrimidin-2-yl]pyrrolidin-3-yl}benzamide [200] (Hereinafter, Referred to as a Compound [200])

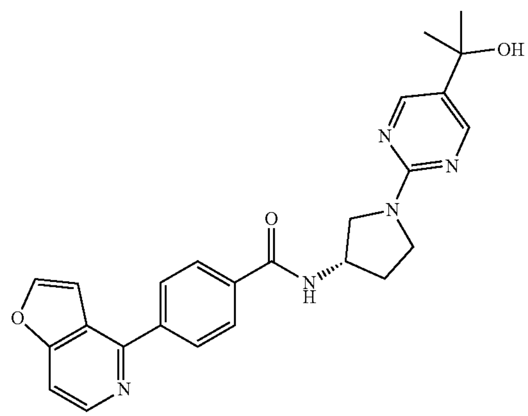 [SMILES: CC(C)(O)c1cnc(N2CC[C@H](NC(=O)c3ccc(-c4nccc5occc45)cc3)C2)nc1]

(1) Synthesis of ethyl (S)-2-{3-[4-(furo[3,2-c]pyridin-4-yl)benzamide]pyrrolidin-1-yl}pyrimidine-5-carboxylate [200-1] (Hereinafter, Referred to as a Compound [200-1])

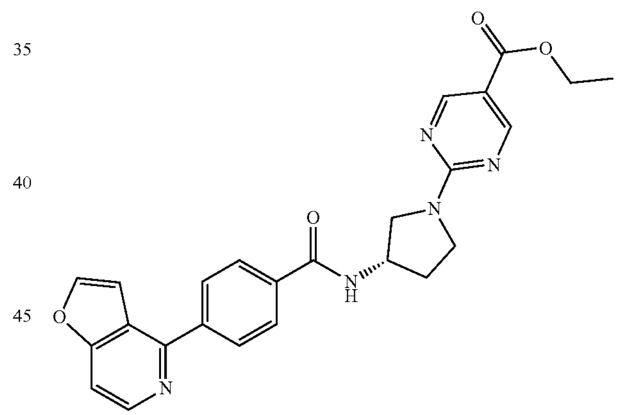

To a solution of the compound [191-2] (20 mg) in NMP (0.30 mL) were added potassium carbonate (29 mg) and ethyl 2-chloropyrimidine-5-carboxylate (24 mg) at room temperature, and the mixture was stirred at 120° C. for 3 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (31 mg) as a yellow solid.

ESI-MS: 458.4 $[M+H]^+$ (2) Synthesis of (S)-4-(furo[3,2-c]pyridin-4-yl)-N-{1-[5-(2-hydroxypropan-2-yl)pyrimidin-2-yl]pyrrolidin-3-yl}benzamide [200]

To a solution of the compound [200-1] (10 mg) in THE (0.20 mL) was added a solution of 3 M methylmagnesium bromide in diethyl ether (0.24 mL) at 0° C., and the mixture was stirred at room temperature for 3 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (3.8 mg) as a white solid.

$^1$H-NMR (400 MHz, DMSO-$d_6$) δ: 8.71 (d, J=6.9 Hz, 1H), 8.56 (d, J=5.9 Hz, 1H), 8.39 (s, 2H), 8.28-8.18 (m, 1H), 8.07 (d, J=8.2 Hz, 2H), 8.01 (d, J=8.2 Hz, 2H), 7.70 (d, J=5.5 Hz, 1H), 7.36-7.35 (m, 1H), 5.01 (s, 1H), 4.59-4.55 (m, 1H), 3.80-3.48 (m, 4H), 2.25-2.21 (m, 1H), 2.07-2.02 (m, 1H), 1.37 (s, 6H).

ESI-MS: 444.4 [M+H]$^+$

Example 201

Synthesis of (S)—N-[1-(5-cyanopyrimidin-2-yl) pyrrolidin-3-yl]-4-(furo[3,2-c]pyridin-4-yl)benzamide [201] (Hereinafter, Referred to as a Compound [201])

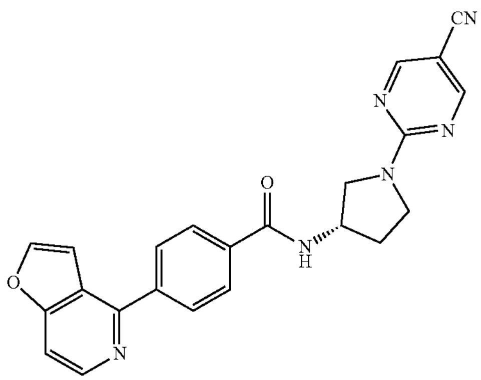 [SMILES: N#Cc1cnc(N2CC[C@H](NC(=O)c3ccc(-c4nccc5occc45)cc3)C2)nc1]

(1) Synthesis of (S)—N-[1-(5-bromopyrimidin-2-yl) pyrrolidin-3-yl]-4-(furo[3,2-c]pyridin-4-yl)benzamide [201-1] (Hereinafter, Referred to as a Compound [201-1])

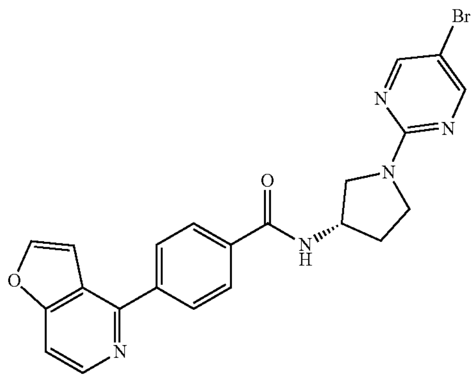 [SMILES: O=C(N[C@H]1CCN(c2ncc(Br)cn2)C1)c1ccc(-c2nccc3occc23)cc1]

To a solution of the compound [191-2] (30 mg) in NMP (0.30 mL) were added potassium carbonate (54 mg) and 5-bromo-2-chloropyrimidine (28 mg) at room temperature, and the mixture was stirred at 120° C. for 3 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (15 mg) as a yellow solid.

ESI-MS: 464.5 [M+H]$^+$

Synthesis of (S)—N-[1-(5-cyanopyrimidin-2-yl) pyrrolidin-3-yl]-4-(furo[3,2-c]pyridin-4-yl)benzamide [201]

To a solution of the compound [201-1] (13.4 mg) in DMF (0.60 mL) were added zinc cyanide (8.0 mg) and Pd $(PPh_3)_4$ (8.0 mg) at room temperature, and the mixture was stirred at 120° C. for 30 minutes using a microwave reactor under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (8.0 mg) as a white solid.

$^1$H-NMR (400 MHz, DMSO-$d_6$) δ: 8.81-8.76 (m, 3H), 8.59 (d, J=5.5 Hz, 1H), 8.24 (d, J=2.3 Hz, 1H), 8.10 (d, J=8.2 Hz, 2H), 8.03 (d, J=8.7 Hz, 2H), 7.72 (dd, J=5.5, 0.9 Hz, 1H), 7.36-7.35 (m, 1H), 4.66-4.62 (m, 1H), 3.88-3.64 (m, 4H), 2.32-2.24 (m, 1H), 2.16-2.08 (m, 1H).

ESI-MS: 411.3 [M+H]$^+$

Example 202

Synthesis of (S)-2-{3-[4-(furo[3,2-c]pyridin-4-yl) benzamide]pyrrolidin-1-yl}pyrimidine-5-carboxamide [202] (Hereinafter, Referred to as a Compound [202])

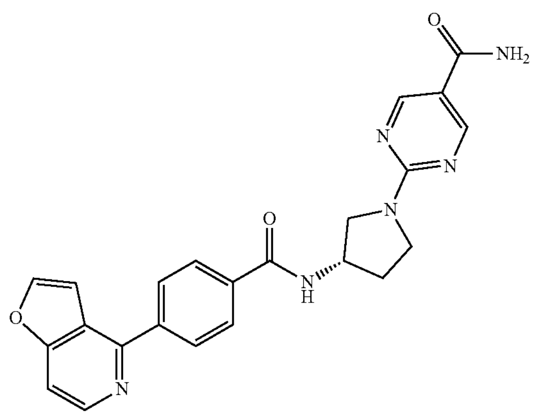 [SMILES: NC(=O)c1cnc(N2CC[C@H](NC(=O)c3ccc(-c4nccc5occc45)cc3)C2)nc1]

To a solution of the compound [201] (5.1 mg) in tert-butanol (0.30 mL) was added potassium tert-butoxide (16 mg) at room temperature, and the mixture was stirred at 80° C. for 6 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (1.5 mg) as a white solid.

ESI-MS: 429.3 [M+H]$^+$

Example 203

Synthesis of N-{(3R,4R)-4-fluoro-1-[5-(hydroxymethyl)pyrimidin-2-yl]pyrrolidin-3-yl}-4-(furo[3,2-c]pyridin-4-yl)benzamide [203] (Hereinafter, Referred to as a Compound [203])

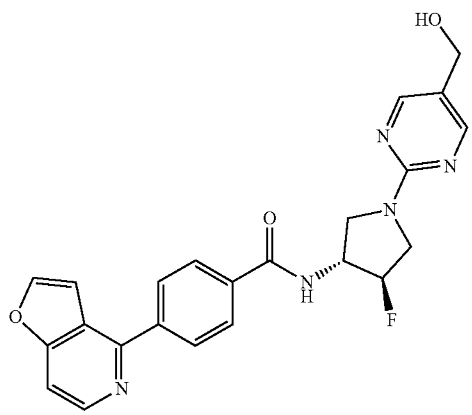 [SMILES: O=C(N[C@@H]1CN(c2ncc(CO)cn2)C[C@H]1F)c1ccc(-c2nccc3occc23)cc1]

(1) Synthesis of tert-butyl (3R,4R)-3-fluoro-4-[4-(furo[3,2-c]pyridin-4-yl)benzamide]pyrrolidine-1-carboxylate [203-1] (Hereinafter, Referred to as a Compound [203-1])

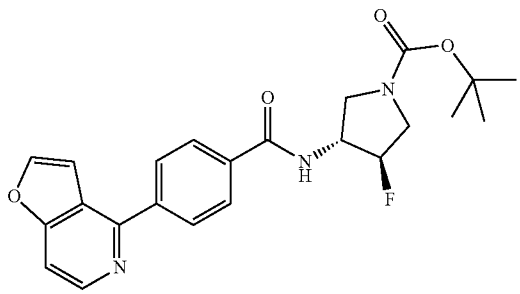 [SMILES: CC(C)(C)OC(=O)N1C[C@@H](F)[C@H](NC(=O)c2ccc(-c3nccc4occc34)cc2)C1]

To a solution of the compound [99-1] (176 mg) in dichloromethane (2.10 mL) were added 4-dimethylaminopyridine (63.0 mg), EDC (98.0 mg), and tert-butyl (3R,4R)-3-amino-4-fluoropyrrolidine-1-carboxylate (100 mg) at room temperature, and the mixture was stirred at room temperature for 7 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (208 mg) as a yellow oil.

ESI-MS: 426.4 $[M+H]^+$ (2) Synthesis of N-[(3R,4R)-4-fluoropyrrolidin-3-yl]-4-(furo[3,2-c]pyridin-4-yl)benzamide Dihydrochloride [203-2] (Hereinafter, Referred to as a Compound [203-2])

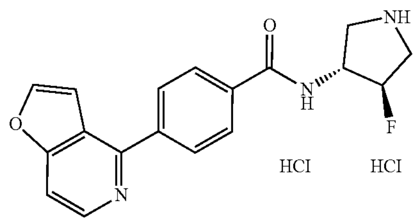

To a solution of the compound [203-1] (208 mg) in ethyl acetate (1.20 mL) was added a solution of 4 M hydrogen chloride in ethyl acetate (1.20 mL) at room temperature, and the mixture was stirred at room temperature for 15 minutes. The reaction mixture was concentrated under reduced pressure to give the title compound (170 mg) as a white solid.

ESI-MS: 326.3 $[M+H]^+$ (3) Synthesis of N-{(3R,4R)-4-fluoro-1-[5-(hydroxymethyl)pyrimidin-2-yl]pyrrolidin-3-yl}-4-(furo[3,2-c]pyridin-4-yl)benzamide [203]

To a solution of the compound [203-2] (49.0 mg) in NMP (500 μL) were added cesium carbonate (169 mg) and (2-chloropyrimidin-5-yl)methanol (15.0 mg) at room temperature, and the mixture was stirred at 120° C. for 19 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (15.2 mg) as a white solid.

$^1$H-NMR (400 MHz, $CD_3OD$) δ: 8.52 (d, J=5.9 Hz, 1H), 8.38 (s, 2H), 8.03-7.98 (m, 5H), 7.63 (d, J=5.9 Hz, 1H), 7.19 (d, J=2.1 Hz, 1H), 5.38-5.32 (m, 1H), 4.84-4.77 (m, 1H), 4.48 (s, 2H), 4.05-3.98 (m, 2H), 3.90-3.88 (m, 2H).

ESI-MS: 434.4 $[M+H]^+$

Example 204

Synthesis of N-{(3R,4S)-4-fluoro-1-[5-(hydroxymethyl)pyrimidin-2-yl]pyrrolidin-3-yl}-4-(furo[3,2-c]pyridin-4-yl)benzamide [204] (Hereinafter, Referred to as a Compound [204])

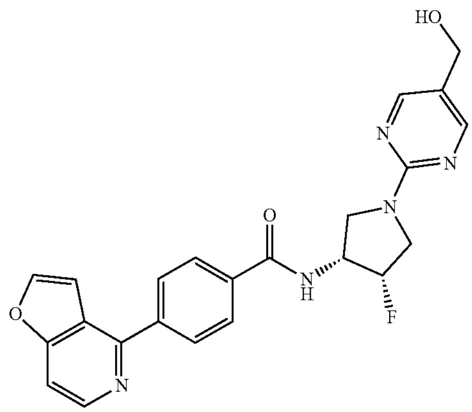 [SMILES: O=C(N[C@@H]1CN(c2ncc(CO)cn2)C[C@@H]1F)c1ccc(-c2nccc3occc23)cc1]

(1) Synthesis of tert-butyl (3S,4R)-3-fluoro-4-[4-(furo[3,2-c]pyridin-4-yl)benzamide]pyrrolidine-1-carboxylate [204-1] (Hereinafter, Referred to as a Compound [204-1])

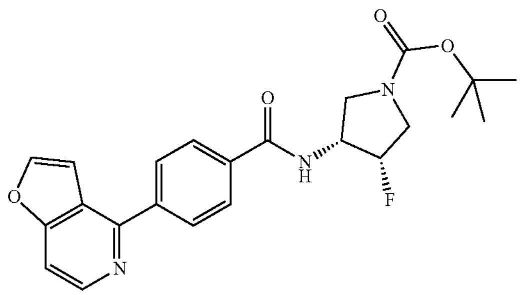 [SMILES: CC(C)(C)OC(=O)N1C[C@H](F)[C@H](NC(=O)c2ccc(-c3nccc4occc34)cc2)C1]

To a solution of the compound [99-1] (176 mg) in dichloromethane (2.10 mL) were added 4-dimethylaminopyridine (63.0 mg), EDC (98.0 mg), and tert-butyl (3S,4R)-3-amino-4-fluoropyrrolidine-1-carboxylate (100 mg) at room temperature, and the mixture was stirred at room temperature for 2 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (188 mg) as a yellow oil.

ESI-MS: 426.4 $[M+H]^+$ (2) Synthesis of N-{(3R,4S)-4-fluoro-1-[5-(hydroxymethyl)pyrimidin-2-yl]pyrrolidin-3-yl}-4-(furo[3,2-c]pyridin-4-yl)benzamide [204]

The title compound was synthesized from the compound [204-1] according to the methods of steps (2) and (3) in Example 203.

$^1$H-NMR (400 MHz, DMSO-$d_6$) δ: 8.81 (d, J=6.9 Hz, 1H), 8.57 (d, J=5.5 Hz, 1H), 8.31 (s, 2H), 8.22 (d, J=2.3 Hz, 1H), 8.15-8.09 (m, 4H), 7.71 (d, J=5.9 Hz, 1H), 7.36 (d, J=2.3 Hz, 1H), 5.44-5.26 (m, 1H), 5.05 (t, J=5.5 Hz, 1H), 4.81-4.74 (m, 1H), 4.32-4.30 (m, 2H), 3.96-3.60 (m, 4H).

ESI-MS: 434.3 $[M+H]^+$

Example 205

Synthesis of 4-(furo[3,2-c]pyridin-4-yl)-N-{(3R,4R)-1-[5-(hydroxymethyl)pyrimidin-2-yl]-4-methoxypyrrolidin-3-yl}benzamide [205] (Hereinafter, Referred to as a Compound [205])

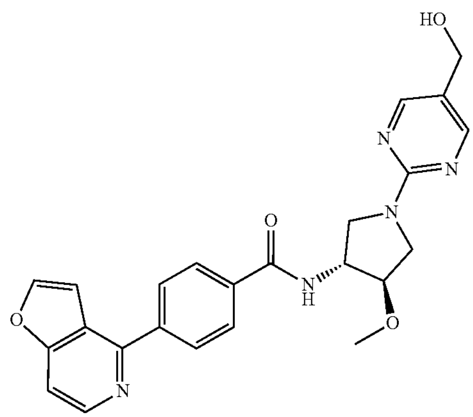 [SMILES: CO[C@@H]1CN(c2ncc(CO)cn2)C[C@H]1NC(=O)c1ccc(-c2nccc3occc23)cc1]

(1) Synthesis of tert-butyl (3R,4R)-3-[4-(furo[3,2-c]pyridin-4-yl)benzamide]-4-methoxypyrrolidine-1-carboxylate [205-1] (Hereinafter, Referred to as a Compound [205-1])

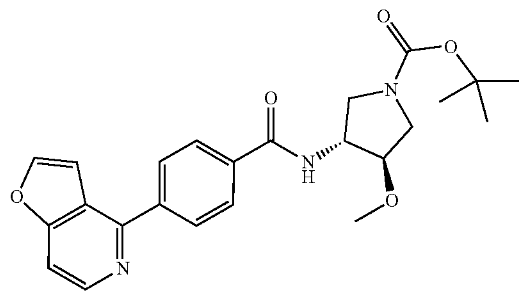 [SMILES: CO[C@@H]1CN(C(=O)OC(C)(C)C)C[C@H]1NC(=O)c1ccc(-c2nccc3occc23)cc1]

To a solution of the compound [99-1] (102 mg) in dichloromethane (1.00 mL) were added 4-dimethylaminopyridine (37.0 mg), EDC (58.0 mg), and tert-butyl (3R,4R)-3-amino-4-methoxypyrrolidine-1-carboxylate (62.0 mg) at room temperature, and the mixture was stirred at room temperature for 2 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (109 mg) as a colorless oil.

ESI-MS: 438.7 $[M+H]^+$ (2) Synthesis of 4-(furo[3,2-c]pyridin-4-yl)-N-{(3R, 4R)-1-[5-(hydroxymethyl)pyrimidin-2-yl]-4-methoxypyrrolidin-3-yl}benzamide [205]

The title compound was synthesized from the compound [205-1] according to the methods of steps (2) and (3) in Example 203.

$^1$H-NMR (400 MHz, DMSO-$d_6$) δ: 8.80 (d, J=6.4 Hz, 1H), 8.59-8.58 (m, 1H), 8.31 (s, 2H), 8.24-8.23 (m, 1H), 8.09 (d, J=8.7 Hz, 2H), 8.04 (d, J=8.7 Hz, 2H), 7.73-7.71 (m, 1H), 7.36-7.35 (m, 1H), 5.05 (t, J=5.7 Hz, 1H), 4.59-4.56 (m, 1H), 4.33-4.32 (m, 2H), 4.00-3.97 (m, 1H), 3.82-3.73 (m, 2H), 3.67-3.61 (m, 2H), 3.39 (s, 3H).

ESI-MS: 446.3 [M+H]$^+$

Example 206

Synthesis of 4-(furo[3,2-c]pyridin-4-yl)-N-{(3R, 4S)-1-[5-(hydroxymethyl)pyrimidin-2-yl]-4-methoxypyrrolidin-3-yl}benzamide [206] (Hereinafter, Referred to as a Compound [206])

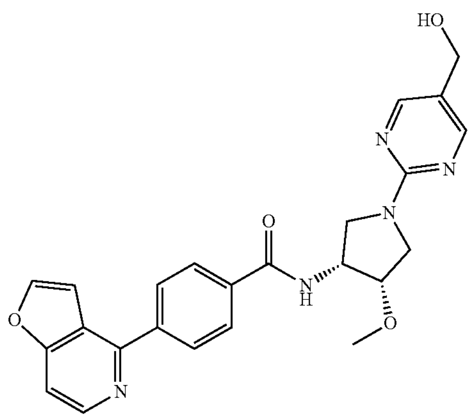 [SMILES: CO[C@H]1CN(c2ncc(CO)cn2)C[C@H]1NC(=O)c1ccc(-c2nccc3occc23)cc1]

(1) Synthesis of tert-butyl (3R,4S)-3-[4-(furo[3,2-c]pyridin-4-yl)benzamide]-4-methoxypyrrolidine-1-carboxylate [206-1] (Hereinafter, Referred to as a Compound [206-1])

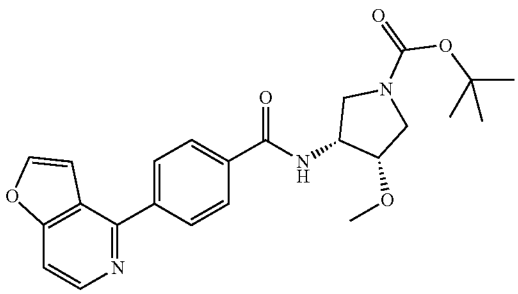 [SMILES: CO[C@H]1CN(C(=O)OC(C)(C)C)C[C@H]1NC(=O)c1ccc(-c2nccc3occc23)cc1]

To a solution of the compound [99-1] (85 mg) in dichloromethane (1.0 mL) were added 4-dimethylaminopyridine (29 mg), EDC (46 mg), and tert-butyl (3R,4S)-3-amino-4-methoxypyrrolidine-1-carboxylate (50 mg) at room temperature, and the mixture was stirred at room temperature for 2 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (96 mg) as a yellow oil.

ESI-MS: 438.4 [M+H]$^+$ (2) Synthesis of 4-(furo[3,2-c]pyridin-4-yl)-N-{(3R, 4S)-1-[5-(hydroxymethyl)pyrimidin-2-yl]-4-methoxypyrrolidin-3-yl}benzamide [206]

The title compound was synthesized from the compound [206-1] according to the methods of steps (2) and (3) in Example 203.

$^1$H-NMR (400 MHz, DMSO-$d_6$) δ: 8.68-8.52 (m, 2H), 8.31 (s, 2H), 8.24 (d, J=2.3 Hz, 1H), 8.12-8.07 (m, 4H), 7.73 (dd, J=5.5, 0.9 Hz, 1H), 7.39-7.38 (m, 1H), 5.05 (t, J=5.5 Hz, 1H), 4.75-4.72 (m, 1H), 4.33-4.31 (m, 2H), 4.12-4.09 (m, 1H), 3.86-3.77 (m, 2H), 3.65-3.57 (m, 2H), 3.32 (s, 3H).

ESI-MS: 446.3 [M+H]$^+$

Example 207

Synthesis of 4-(furo[3,2-c]pyridin-4-yl)-N-{(3R, 4R)-4-hydroxy-1-[5-(hydroxymethyl)pyrimidin-2-yl]pyrrolidin-3-yl}benzamide [207] (Hereinafter, Referred to as a Compound [207])

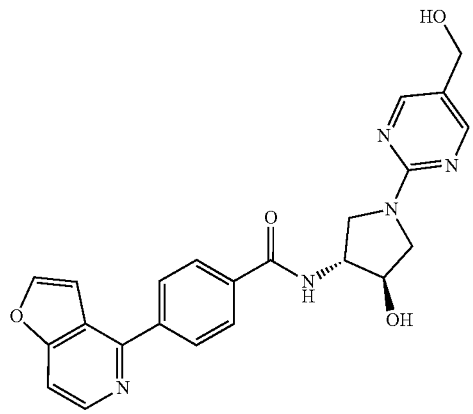 [SMILES: O=C(N[C@@H]1CN(c2ncc(CO)cn2)C[C@H]1O)c1ccc(-c2nccc3occc23)cc1]

(1) Synthesis of tert-butyl (3R,4R)-3-[4-(furo[3,2-c]pyridin-4-yl)benzamide]-4-hydroxypyrrolidine-1-carboxylate [207-1] (Hereinafter, Referred to as a Compound [207-1])

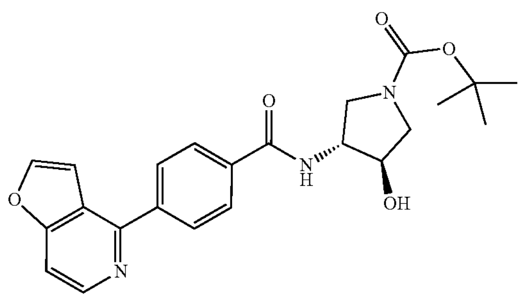 [SMILES: CC(C)(C)OC(=O)N1C[C@@H](O)[C@H](NC(=O)c2ccc(-c3nccc4occc34)cc2)C1]

To a solution of the compound [99-1] (176 mg) in dichloromethane (2.00 mL) were added 4-dimethylamino-pyridine (62.0 mg), EDC (98.0 mg), and tert-butyl (3R,4R)-3-amino-4-hydroxypyrrolidine-1-carboxylate (100 mg) at room temperature, and the mixture was stirred at room temperature for 5 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (91.0 mg) as a brown oil.

ESI-MS: 424.3 $[M+H]^+$ (2) Synthesis of 4-(furo[3,2-c]pyridin-4-yl)-N-{(3R,4R)-4-hydroxy-1-[5-(hydroxymethyl)pyrimidin-2-yl]pyrrolidin-3-yl}benzamide [207]

The title compound was synthesized from the compound [207-1] according to the methods of steps (2) and (3) in Example 203.

$^1$H-NMR (400 MHz, DMSO-$d_6$) δ: 8.68 (d, J=5.9 Hz, 1H), 8.58 (d, J=5.5 Hz, 1H), 8.30 (s, 2H), 8.24 (s, 1H), 8.09 (d, J=6.9 Hz, 2H), 8.03 (d, J=6.9 Hz, 2H), 7.72 (d, J=5.5 Hz, 1H), 7.36-7.34 (m, 1H), 5.43-5.42 (m, 1H), 5.05-5.03 (m, 1H), 4.45-4.28 (m, 4H), 3.86-3.72 (m, 2H), 3.61-3.58 (m, 1H), 3.49-3.46 (m, 1H).

ESI-MS: 432.3 $[M+H]^+$

Example 208

Synthesis of 4-(furo[3,2-c]pyridin-4-yl)-N-{(3R,4S)-4-hydroxy-1-[5-(hydroxymethyl)pyrimidin-2-yl]pyrrolidin-3-yl}benzamide [208] (Hereinafter, Referred to as a Compound [208])

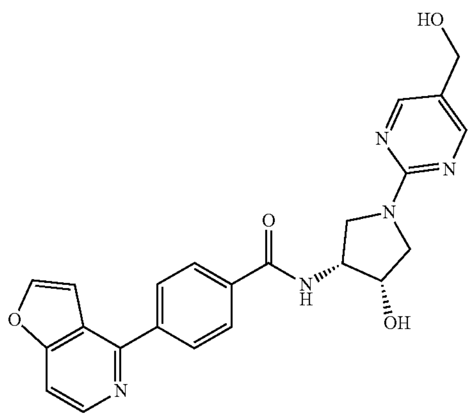 [SMILES: O=C(N[C@@H]1CN(c2ncc(CO)cn2)C[C@@H]1O)c1ccc(-c2nccc3occc23)cc1]

(1) Synthesis of tert-butyl (3R,4S)-3-[4-(furo[3,2-c]pyridin-4-yl)benzamide]-4-hydroxypyrrolidine-1-carboxylate [208-1] (Hereinafter, Referred to as a Compound [208-1])

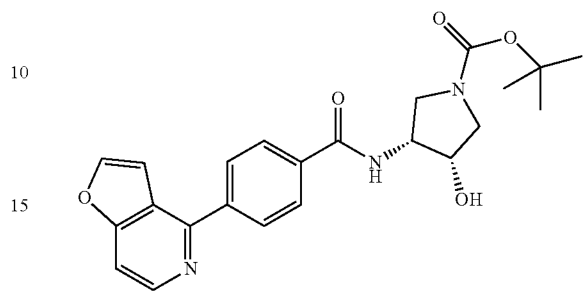

To a solution of the compound [99-1] (177 mg) in dichloromethane (2.00 mL) were added 4-dimethylamino-pyridine (63.0 mg), EDC (99.0 mg), and tert-butyl (3R,4S)-3-amino-4-hydroxypyrrolidine-1-carboxylate (100 mg) at room temperature, and the mixture was stirred at room temperature for 19 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (167 mg) as a colorless oil.

ESI-MS: 424.3 $[M+H]^+$ (2) Synthesis of 4-(furo[3,2-c]pyridin-4-yl)-N-{(3R,4S)-4-hydroxy-1-[5-(hydroxymethyl)pyrimidin-2-yl]pyrrolidin-3-yl}benzamide [208]

The title compound was synthesized from the compound [208-1] according to the methods of steps (2) and (3) in Example 203.

$^1$H-NMR (400 MHz, DMSO-$d_6$) δ: 8.60 (d, J=5.5 Hz, 1H), 8.39 (d, J=7.3 Hz, 1H), 8.30 (s, 2H), 8.25 (d, J=2.3 Hz, 1H), 8.14-8.08 (m, 4H), 7.73 (dd, J=5.7, 1.1 Hz, 1H), 7.39-7.38 (m, 1H), 5.36-5.34 (m, 1H), 5.03 (t, J=5.5 Hz, 1H), 4.61-4.49 (m, 1H), 4.40-4.37 (m, 1H), 4.32-4.31 (m, 2H), 3.87-3.83 (m, 1H), 3.63-3.52 (m, 3H).

ESI-MS: 432.3 $[M+H]^+$

Example 209

Synthesis of 4-(furo[3,2-c]pyridin-4-yl)-N-(2-azaspiro[3.3]heptan-6-yl)benzamide [209] (Hereinafter, Referred to as a Compound [209])

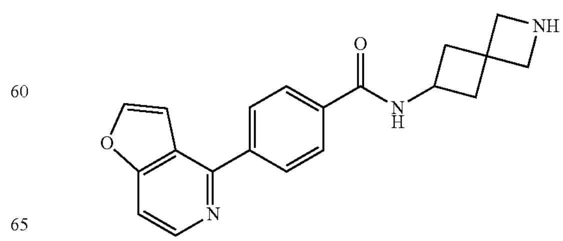

(1) Synthesis of tert-butyl 6-[4-(furo[3,2-c]pyridin-4-yl)benzamide]-2-azaspiro[3.3]heptane-2-carboxylate [209-1] (Hereinafter, Referred to as a Compound [209-1])

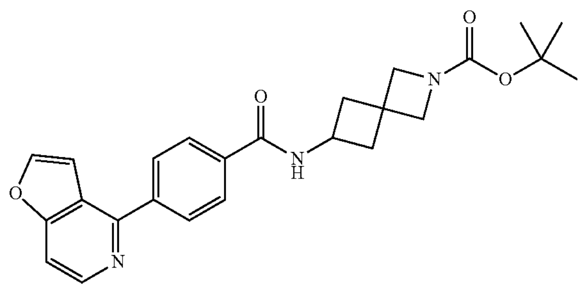 [SMILES: CC(C)(C)OC(=O)N1CC2(CC(NC(=O)c3ccc(-c4nccc5occc45)cc3)C2)C1]

To a solution of the compound [99-1] (200 mg) in dichloromethane (3.00 mL) were added 4-dimethylaminopyridine (110 mg), EDC (170 mg), and tert-butyl 6-amino-2-azaspiro[3.3]heptane-2-carboxylate (234 mg) at room temperature, and the mixture was stirred at room temperature for 24 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (317 mg) as a yellow solid.

ESI-MS: 434.5 $[M+H]^+$ (2) Synthesis of 4-(furo[3,2-c]pyridin-4-yl)-N-(2-azaspiro[3.3]heptan-6-yl)benzamide [209]

To a solution of the compound [209-1] (317 mg) in dichloromethane (2.00 mL) was added trifluoroacetic acid (3.00 mL) at room temperature, and the mixture was stirred at room temperature for 22 hours. To the reaction mixture was added a 5 M aqueous sodium hydroxide solution at 0° C., and the mixture was extracted with chloroform. The organic layer was dried over anhydrous sodium sulfate and concentrated under reduced pressure. The obtained residue was purified by silica gel column chromatography to give the title compound (100 mg) as a white solid.

ESI-MS: 334.4 $[M+H]^+$

Example 210

Synthesis of 4-(furo[3,2-c]pyridin-4-yl)-N-[2-(pyrimidin-2-yl)-2-azaspiro[3.3]heptan-6-yl]benzamide [210] (Hereinafter, Referred to as a Compound [210])

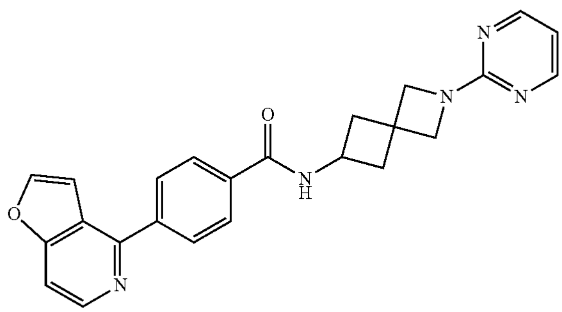 [SMILES: O=C(NC1CC2(C1)CN(c1ncccn1)C2)c1ccc(-c2nccc3occc23)cc1]

To a solution of the compound [209] (10 mg) in NMP (0.30 mL) were added potassium carbonate (12 mg) and 2-chloropyrimidine (4.5 mg) at room temperature, and the mixture was stirred at 140° C. for 2 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (3.0 mg) as a brown solid.

$^1$H-NMR (400 MHz, DMSO-$d_6$) δ: 8.76 (d, J=7.3 Hz, 1H), 8.59 (d, J=5.5 Hz, 1H), 8.33-8.30 (m, 2H), 8.24 (d, J=2.3 Hz, 1H), 8.10 (d, J=8.7 Hz, 2H), 8.02 (d, J=8.2 Hz, 2H), 7.76-7.68 (m, 1H), 7.38-7.37 (m, 1H), 6.64 (t, J=4.8 Hz, 1H), 4.42-4.36 (m, 1H), 4.11 (s, 2H), 4.00 (s, 2H), 2.61-2.57 (m, 2H), 2.38-2.34 (m, 2H).

ESI-MS: 412.4 $[M+H]^+$

Example 211

Synthesis of 4-(furo[3,2-c]pyridin-4-yl)-N-[(3R,6S)-6-(hydroxymethyl)tetrahydro-2H-pyran-3-yl]benzamide [211] (Hereinafter, Referred to as a Compound [211])

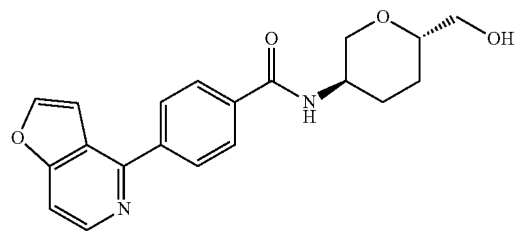 [SMILES: O=C(N[C@@H]1CC[C@@H](CO)OC1)c1ccc(-c2nccc3occc23)cc1]

To a solution of tert-butyl N-[(3R,6S)-6-(hydroxymethyl)oxan-3-yl]carbamate (200 mg) in ethyl acetate (650 μL) was added a solution of 4 M hydrogen chloride in ethyl acetate (650 μL) at room temperature, and the mixture was stirred at room temperature for 3 hours. The reaction mixture was concentrated under reduced pressure. To a solution of the obtained residue in dichloromethane (1.6 mL) were added 4-dimethylaminopyridine (62 mg), EDC (97 mg), and the compound [99-1] (120 mg) at room temperature, and the mixture was stirred at room temperature for 1 hour. To the reaction mixture was added a saturated aqueous sodium bicarbonate solution, and the mixture was extracted with chloroform. The organic layer was dried over anhydrous sodium sulfate and concentrated under reduced pressure. The obtained residue was purified by silica gel column chromatography to give the title compound (78 mg) as a white solid.

$^1$H-NMR (400 MHz, DMSO-$d_6$) δ: 8.60-8.57 (m, 1H), 8.34 (d, J=5.9 Hz, 1H), 8.25-8.23 (m, 1H), 8.10-8.08 (m, 2H), 8.02-8.00 (m, 2H), 7.74-7.72 (m, 1H), 7.36-7.35 (m, 1H), 4.65-4.63 (m, 1H), 3.92-3.90 (m, 2H), 3.40-3.24 (m,

3H), 3.19-3.12 (m, 1H), 1.99-1.96 (m, 1H), 1.75-1.58 (m, 2H), 1.36-1.27 (m, 1H).

ESI-MS: 353.3 [M+H]+

Example 212

Synthesis of 4-(furo[3,2-c]pyridin-4-yl)-N-[(3R,6S)-6-(1-hydroxyethyl)tetrahydro-2H-pyran-3-yl]benzamide [212] (Hereinafter, Referred to as a Compound [212])

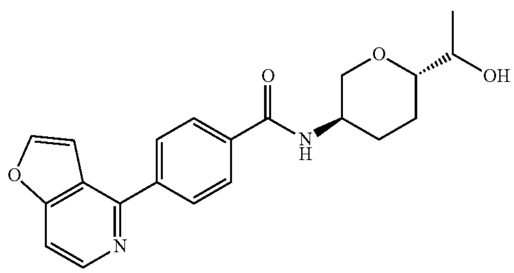

To a solution of the compound [211] (26.1 mg) in dichloromethane (600 μL) was added 1,1,1-triacetoxy-1,1-dihydro-1,2-benziodoxol-3(1H)-one (Dess-Martin periodinane) (47.0 mg) at room temperature, and the mixture was stirred at room temperature for 3 hours. To the reaction mixture was added water, and the mixture was extracted with ethyl acetate. The organic layer was dried over anhydrous sodium sulfate and concentrated under reduced pressure. To a solution of the obtained residue in THF (300 μL) was added a solution of 3 M methylmagnesium bromide in diethyl ether (114 μL) at 0° C., and the mixture was stirred at room temperature for 2 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (15.3 mg) as a white solid.

ESI-MS: 367.3 [M+H]+

Example 213

Synthesis of N-[(3R,6S)-6-acetyltetrahydro-2H-pyran-3-yl]-4-(furo[3,2-c]pyridin-4-yl)benzamide [213] (Hereinafter, Referred to as a Compound [213])

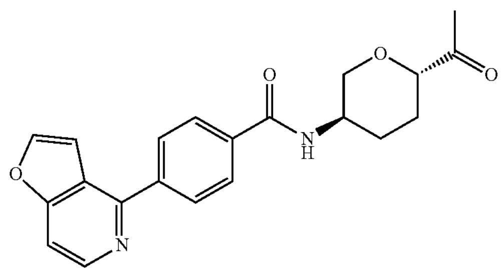 [SMILES: CC(=O)[C@@H]1CC[C@@H](NC(=O)c2ccc(-c3nccc4occc34)cc2)CO1]

To a solution of the compound [212] (11.0 mg) in dichloromethane (500 μL) was added 1,1,1-triacetoxy-1,1-dihydro-1,2-benziodoxol-3 (1H)-one (Dess-Martin periodinane) (19.0 mg) at room temperature, and the mixture was stirred at room temperature for 4 hours. To the reaction mixture was added a saturated aqueous sodium bicarbonate solution, and the mixture was extracted with chloroform. The organic layer was dried over anhydrous sodium sulfate and concentrated under reduced pressure. The obtained residue was purified by silica gel column chromatography to give the title compound (10.2 mg) as a white solid.

ESI-MS: 365.4 [M+H]+

Example 214

Synthesis of 4-(furo[3,2-c]pyridin-4-yl)-N-[(3R,6S)-6-(2-hydroxypropan-2-yl)tetrahydro-2H-pyran-3-yl]benzamide [214] (Hereinafter, Referred to as a Compound [214])

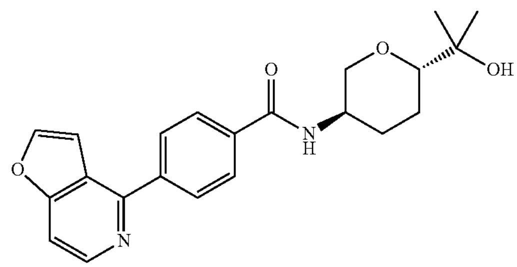 [SMILES: CC(C)(O)[C@@H]1CC[C@@H](NC(=O)c2ccc(-c3nccc4occc34)cc2)CO1]

To a solution of the compound [213] (9.0 mg) in THE (0.30 mL) was added a solution of 3 M methylmagnesium bromide in diethyl ether (246 μL) at 0° C., and the mixture was stirred at room temperature for 3 hours. To the reaction mixture was added a saturated aqueous ammonium chloride solution, and the mixture was extracted with ethyl acetate. The organic layer was dried over anhydrous sodium sulfate and concentrated under reduced pressure. The obtained residue was purified by preparative thin layer chromatography to give the title compound (1.6 mg) as a white solid.

$^1$H-NMR (400 MHz, $CD_3OD$) δ: 8.51 (d, J=5.5 Hz, 1H), 8.01-7.97 (m, 5H), 7.63 (d, J=5.9 Hz, 1H), 7.19-7.18 (m, 1H), 4.10-4.04 (m, 2H), 3.25-3.09 (m, 2H), 2.18-2.00 (m, 2H), 1.67-1.46 (m, 2H), 1.18 (s, 3H), 1.16 (s, 3H).

ESI-MS: 381.3 [M+H]+

Example 215

Synthesis of 4-(furo[3,2-c]pyridin-4-yl)-N-[(1R,3R)-3-(2-hydroxypropan-2-yl)cyclopentyl]benzamide [215] (Hereinafter, Referred to as a Compound [215])

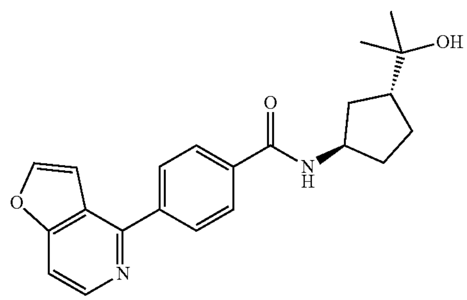 [SMILES: CC(C)(O)[C@@H]1CC[C@@H](NC(=O)c2ccc(-c3nccc4occc34)cc2)C1]

(1) Synthesis of methyl (1R,3R)-3-[4-(furo[3,2-c]pyridin-4-yl)benzamide]cyclopentane-1-carboxylate [215-1] (Hereinafter, Referred to as a Compound [215-1])

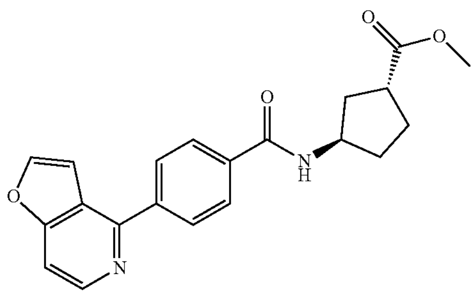 [SMILES: COC(=O)[C@@H]1CC[C@@H](NC(=O)c2ccc(-c3nccc4occc34)cc2)C1]

To a solution of the compound [99-1] (185 mg) in dichloromethane (2.00 mL) were added 4-dimethylaminopyridine (72.0 mg), EDC (113 mg), and (1R,3R)-3-aminocyclopentane-1-methyl carboxylate hydrochloride (100 mg) at room temperature, and the mixture was stirred at room temperature for 22 hours. To the reaction mixture was added a saturated aqueous sodium bicarbonate solution, and the mixture was extracted with chloroform. The organic layer was dried over anhydrous sodium sulfate and concentrated under reduced pressure. The obtained residue was purified by silica gel column chromatography to give the title compound (114 mg) as a white solid.

ESI-MS: 365.3 $[M+H]^+$ (2) Synthesis of 4-(furo[3,2-c]pyridin-4-yl)-N-[(1R,3R)-3-(2-hydroxypropan-2-yl)cyclopentyl]benzamide [215]

To a solution of the compound [215-1] (20.0 mg) in THF (300 μL) was added a solution of 3 M methylmagnesium bromide in diethyl ether (367 μL) at room temperature, and the mixture was stirred at room temperature for 24 hours. To the reaction mixture was added a saturated aqueous ammonium chloride solution, and the mixture was extracted with ethyl acetate. The organic layer was dried over anhydrous sodium sulfate and concentrated under reduced pressure. The obtained residue was purified by silica gel column chromatography to give the title compound (7.4 mg) as a yellow solid.

$^1$H-NMR (400 MHz, DMSO-$d_6$) δ: 8.59-8.58 (m, 1H), 8.35 (d, J=7.3 Hz, 1H), 8.21 (d, J=2.3 Hz, 1H), 8.10-8.03 (m, 2H), 8.02-8.00 (m, 2H), 7.69 (dd, J=6.2, 5.3 Hz, 1H), 7.36-7.35 (m, 1H), 4.26-4.20 (m, 1H), 4.06-4.05 (m, 1H), 2.17-1.40 (m, 7H), 1.08-1.00 (m, 6H).

ESI-MS: 365.3 $[M+H]^+$

Example 216

Synthesis of 4-(furo[3,2-c]pyridin-4-yl)-N-[(1S,3S)-3-(2-hydroxypropan-2-yl)cyclopentyl]benzamide [216] (Hereinafter, Referred to as a Compound [216])

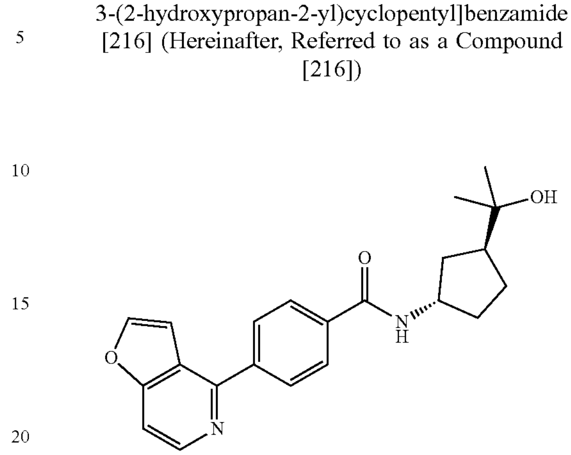

(1) Synthesis of methyl (1S,3S)-3-[4-(furo[3,2-c]pyridin-4-yl)benzamide]cyclopentane-1-carboxylate [216-1] (Hereinafter, Referred to as a Compound [216-1])

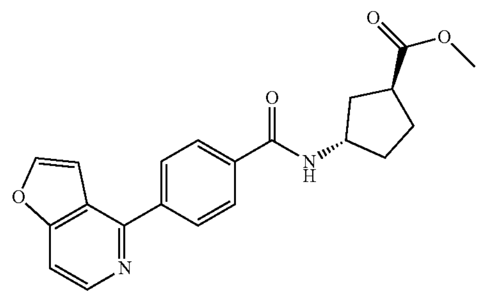 [SMILES: COC(=O)[C@H]1CC[C@H](NC(=O)c2ccc(-c3nccc4occc34)cc2)C1]

To a solution of the compound [99-1] (93 mg) in dichloromethane (1.0 mL) were added 4-dimethylaminopyridine (36 mg), EDC (57 mg), and (1S,3S)-3-aminocyclopentane-1-methyl carboxylate hydrochloride (50 mg) at room temperature, and the mixture was stirred at room temperature for 2 hours. To the reaction mixture was added a saturated aqueous sodium bicarbonate solution, and the mixture was extracted with chloroform. The organic layer was dried over anhydrous sodium sulfate and concentrated under reduced pressure. The obtained residue was purified by silica gel column chromatography to give the title compound (43 mg) as a white solid.

ESI-MS: 365.3 $[M+H]^+$ (2) Synthesis of 4-(furo[3,2-c]pyridin-4-yl)-N-[(1S,3S)-3-(2-hydroxypropan-2-yl)cyclopentyl]benzamide [216]

The title compound was synthesized from the compound [216-1] according to the method of the step (2) in Example 215.

$^1$H-NMR (400 MHz, $CDCl_3$) δ: 8.60-8.58 (m, 1H), 7.99 (d, J=8.2 Hz, 2H), 7.91-7.89 (m, 2H), 7.72 (d, J=1.8 Hz, 1H), 7.47-7.45 (m, 1H), 7.03 (d, J=2.3 Hz, 1H), 6.24 (d, J=7.3 Hz,

1H), 4.47-4.42 (m, 1H), 3.70-3.64 (m, 1H), 2.23-2.16 (m, 2H), 2.20-1.98 (m, 1H), 1.89-1.83 (m, 1H), 1.73-1.51 (m, 3H), 1.20 (s, 6H).

ESI-MS: 365.3 [M+H]$^+$

Example 217

Synthesis of 4-(furo[3,2-c]pyridin-4-yl)-N-[1-(pyrimidin-2-yl) azetidin-3-yl]benzamide [217] (Hereinafter, Referred to as a Compound [217])

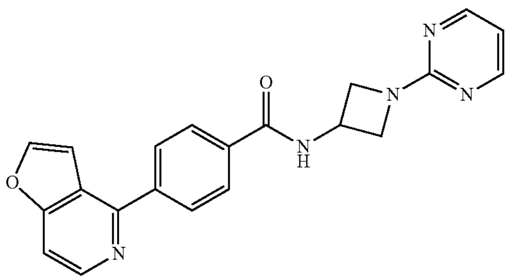 [SMILES: O=C(NC1CN(c2ncccn2)C1)c1ccc(-c2nccc3occc23)cc1]

To a solution of the compound [99-1] (20 mg) in dichloromethane (0.30 mL) were added 4-dimethylaminopyridine (11 mg), EDC (17 mg), and 1-(pyrimidin-2-yl)azetidine-3-amine dihydrochloride (25 mg) at room temperature, and the mixture was stirred at room temperature for 2 hours. To the reaction mixture was added a saturated aqueous sodium bicarbonate solution, and the mixture was extracted with chloroform. The organic layer was dried over anhydrous sodium sulfate and concentrated under reduced pressure. The obtained residue was purified by silica gel column chromatography to give the title compound (14 mg) as a white solid.

$^1$H-NMR (400 MHz, DMSO-d$_6$) δ: 9.19 (d, J=7.3 Hz, 1H), 8.59 (d, J=5.9 Hz, 1H), 8.37 (d, J=4.6 Hz, 2H), 8.24 (d, J=2.3 Hz, 1H), 8.12 (d, J=8.2 Hz, 2H), 8.06 (d, J=8.7 Hz, 2H), 7.73 (dd, J=5.5, 0.9 Hz, 1H), 7.39-7.38 (m, 1H), 6.69 (t, J=4.8 Hz, 1H), 4.94-4.84 (m, 1H), 4.38-4.34 (m, 2H), 4.07 (dd, J=9.1, 5.5 Hz, 2H).

ESI-MS: 372.4 [M+H]$^+$

Example 218

Synthesis of 4-(furo[3,2-c]pyridin-4-yl)-N-[(trans-3-hydroxycyclobutyl)methyl] benzamide [218] (Hereinafter, Referred to as a Compound [218])

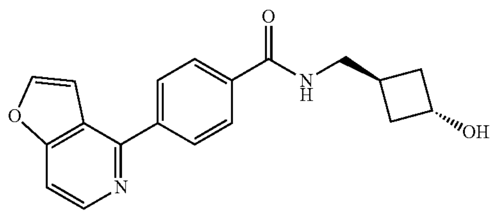 [SMILES: O=C(NC[C@H]1C[C@H](O)C1)c1ccc(-c2nccc3occc23)cc1]

The title compound was obtained as a white solid according to the method of Example 217.

$^1$H-NMR (400 MHz, DMSO-d$_6$) δ: 8.62-8.58 (m, 2H), 8.24 (d, J=2.3 Hz, 1H), 8.09 (dd, J=6.6, 2.1 Hz, 2H), 8.02-7.99 (m, 2H), 7.72 (dd, J=5.7, 1.1 Hz, 1H), 7.38-7.37 (m, 1H), 4.94 (d, J=6.4 Hz, 1H), 4.27-4.18 (m, 1H), 3.35-3.33 (m, 2H), 2.38-2.31 (m, 1H), 2.08-2.02 (m, 2H), 1.93-1.86 (m, 2H).

ESI-MS: 323.3 [M+H]$^+$

Example 219

Synthesis of 4-(furo[3,2-c]pyridin-4-yl)-N-[(cis-3-hydroxycyclobutyl)methyl] benzamide [219] (Hereinafter, Referred to as a Compound [219])

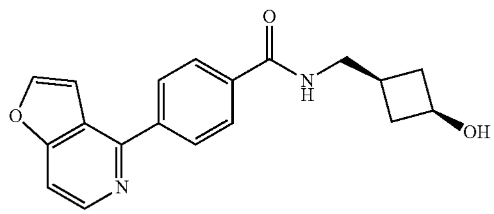 [SMILES: O=C(NC[C@H]1C[C@@H](O)C1)c1ccc(-c2nccc3occc23)cc1]

The title compound was obtained as a white solid according to the method of Example 217.

$^1$H-NMR (400 MHz, DMSO-d$_6$) δ: 8.59-8.56 (m, 2H), 8.24 (d, J=2.3 Hz, 1H), 8.09 (d, J=8.7 Hz, 2H), 8.02-8.00 (m, 2H), 7.72 (dd, J=5.5, 0.9 Hz, 1H), 7.37 (dd, J=1.1, 1.1 Hz, 1H), 4.93 (d, J=6.9 Hz, 1H), 3.93-3.84 (m, 1H), 3.29-3.27 (d, 2H), 2.27-2.21 (m, 2H), 1.99-1.90 (m, 1H), 1.58-1.51 (m, 2H).

ESI-MS: 323.4 [M+H]$^+$

Example 220

Synthesis of 4-(furo[3,2-c]pyridin-4-yl)-N-[2-hydroxy-1-(pyridin-2-yl)ethyl] benzamide [220] (Hereinafter, Referred to as a Compound [220])

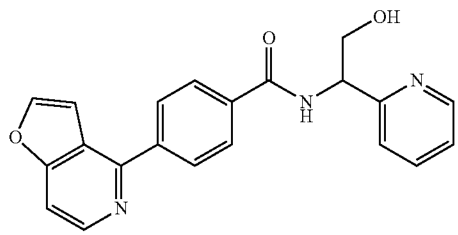 [SMILES: O=C(NC(CO)c1ccccn1)c1ccc(-c2nccc3occc23)cc1]

The title compound was obtained as a yellow solid according to the method of Example 217.

$^1$H-NMR (400 MHz, DMSO-d$_6$) δ: 8.81 (d, J=8.0 Hz, 1H), 8.60 (d, J=5.3 Hz, 1H), 8.54 (d, J=4.6 Hz, 1H), 8.25 (d, J=2.3 Hz, 1H), 8.18-8.06 (m, 4H), 7.80-7.70 (m, 2H), 7.44 (d, J=8.2 Hz, 1H), 7.38 (d, J=1.1 Hz, 1H), 7.29-7.25 (m, 1H), 5.18 (dd, J=12.8, 7.8 Hz, 1H), 4.96 (t, J=5.9 Hz, 1H), 3.89-3.77 (m, 2H).

ESI-MS: 360.3 [M+H]$^+$

Example 221

Synthesis of N-(chroman-3-ylmethyl)-4-(furo[3,2-c] pyridin-4-yl)benzamide [221] (Hereinafter, Referred to as a Compound [221])

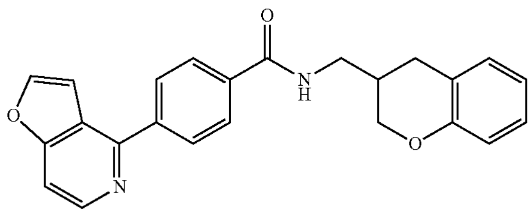 [SMILES: O=C(NCC1COc2ccccc2C1)c1ccc(-c2nccc3occc23)cc1]

To a solution of the compound [99-1] (358 mg) in dichloromethane (4.30 mL) were added 4-dimethylaminopyridine (128 mg), EDC (201 mg), and chroman-3-ylmethanamine hydrochloride (200 mg) at room temperature, and the mixture was stirred at room temperature for 16 hours. To the reaction mixture was added a saturated aqueous sodium bicarbonate solution, and the mixture was extracted with chloroform. The organic layer was dried over anhydrous sodium sulfate and concentrated under reduced pressure. The obtained residue was purified by silica gel column chromatography to give the title compound (313 mg) as a white solid.

$^1$H-NMR (400 MHz, DMSO-$d_6$) δ: 8.76-8.73 (m, 1H), 8.56 (d, J=5.5 Hz, 1H), 8.21 (d, J=2.3 Hz, 1H), 8.08 (d, J=8.2 Hz, 2H), 8.02 (d, J=8.7 Hz, 2H), 7.73-7.66 (m, 1H), 7.36-7.35 (m, 1H), 7.06-7.01 (m, 2H), 6.79 (t, J=7.3 Hz, 1H), 6.72 (d, J=8.2 Hz, 1H), 4.22-4.19 (m, 1H), 3.88-3.83 (m, 1H), 3.36-3.31 (m, 2H), 2.89-2.82 (m, 1H), 2.62-2.56 (m, 1H), 2.34-2.31 (m, 1H).

ESI-MS: 385.3 $[M+H]^+$

Example 222

Synthesis of 4-(furo[3,2-c]pyridin-4-yl)-N-{4-[4-(morpholine-4-carbonyl)piperidin-1-yl] phenyl}benzamide [222] (Hereinafter, Referred to as a Compound [222])

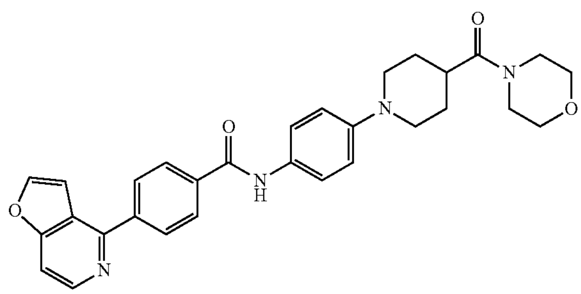 [SMILES: O=C(Nc1ccc(N2CCC(C(=O)N3CCOCC3)CC2)cc1)c1ccc(-c2nccc3occc23)cc1]

(1) Synthesis of 1-(4-nitrophenyl)piperidine-4-carboxylic Acid [222-1] (Hereinafter, Referred to as a Compound [222-1])

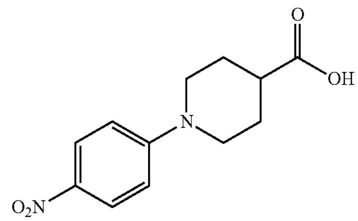 [SMILES: O=C(O)C1CCN(c2ccc([N+](=O)[O-])cc2)CC1]

To a solution of 4-fluoronitrobenzene (3.95 g) in acetonitrile (40 mL) were added ethyl 4-piperidinecarboxylate (4.75 mL) and potassium carbonate (9.70 g) at room temperature, and the mixture was stirred at 60° C. for 9 hours. Then, the mixture was stirred at room temperature for 20 hours. The reaction mixture was concentrated under reduced pressure, then water was added, and the mixture was extracted with ethyl acetate. The organic layer was dried over anhydrous sodium sulfate and concentrated under reduced pressure. To a solution of the obtained residue in ethanol (70 mL) was added a 2 M aqueous sodium hydroxide solution (28 mL) at room temperature, and the mixture was stirred at room temperature for 41 hours. Then, a 5 M aqueous sodium hydroxide solution (20 mL) was added at room temperature, and the mixture was stirred at 100° C. for 2 hours. The reaction mixture was cooled to 0° C., then concentrated hydrochloric acid was added, and the resulting solid was collected by filtration and dried under reduced pressure to give the title compound (6.78 g) as a yellow solid.

ESI-MS: 251.1 $[M+H]^+$ (2) Synthesis of morpholino [1-(4-nitrophenyl)piperidin-4-yl]methanone [222-2] (Hereinafter, Referred to as a Compound [222-2])

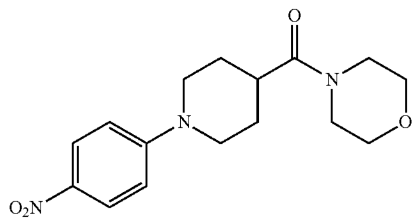 [SMILES: O=C(C1CCN(c2ccc([N+](=O)[O-])cc2)CC1)N1CCOCC1]

To a solution of the compound [222-1] (1.00 g) in DMF (15 mL) were added morpholine (522 μL), DIPEA (1.39 mL), and (1-cyano-2-ethoxy-2-oxoethylideneaminooxy)dimethylaminomorpholinocarbenium hexafluorophosphate (2.57 g) at 0° C., and the mixture was stirred at 0° C. for 1 hour. To the reaction mixture was added water, and the mixture was extracted with ethyl acetate. The organic layer was dried over anhydrous sodium sulfate and concentrated under reduced pressure. The obtained residue was suspended in ethyl acetate/diethyl ether, and the solid was collected by filtration to give the title compound (954 mg) as a yellow solid.

ESI-MS: 320.2 [M+H]$^+$ (3) Synthesis of [1-(4-aminophenyl)piperidin-4-yl](morpholino)methanone Dihydrochloride [222-3] (Hereinafter, Referred to as a Compound [222-3])

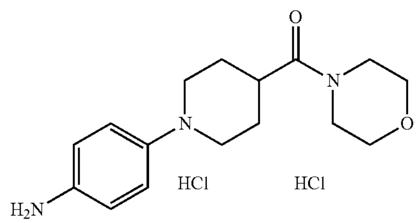 [SMILES: Nc1ccc(N2CCC(C(=O)N3CCOCC3)CC2)cc1 ; Cl ; Cl]

To a solution of the compound [222-2] (954 mg) in THF (25 mL)/methanol (20 mL) was added 10% palladium-activated carbon (320 mg) at room temperature, and the mixture was stirred at room temperature for 10 hours under a hydrogen atmosphere. The reaction mixture was filtered, and the filtrate was concentrated under reduced pressure. To a solution of the obtained residue in ethyl acetate (20 mL) was added a solution of 4 M hydrogen chloride in ethyl acetate (2.00 mL) at room temperature, and the mixture was stirred at room temperature for 15 minutes. The resulting solid was collected by filtration and dried under reduced pressure to give the title compound (1.04 g) as a white solid.

ESI-MS: 290.2 [M+H]$^+$ (4) Synthesis of 4-(furo[3,2-c]pyridin-4-yl)-N-{4-[4-(morpholine-4-carbonyl)piperidin-1-yl]phenyl}benzamide [222]

To a solution of the compound [99-1] (30 mg) in DMF (0.42 mL) were added DIPEA (85 μL), (1-cyano-2-ethoxy-2-oxoethylideneaminooxy)dimethylaminomorpholinocarbenium hexafluorophosphate (59 mg), and the compound [222-3] (59 mg) at room temperature, and the mixture was stirred at room temperature for 1 hour. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (41 mg) as a yellow solid.

ESI-MS: 511.2 [M+H]$^+$

Example 223

Synthesis of N-{3-fluoro-4-[4-(morpholine-4-carbonyl)piperidin-1-yl]phenyl}-4-(furo[3,2-c]pyridin-4-yl)benzamide [223] (Hereinafter, Referred to as a Compound [223])

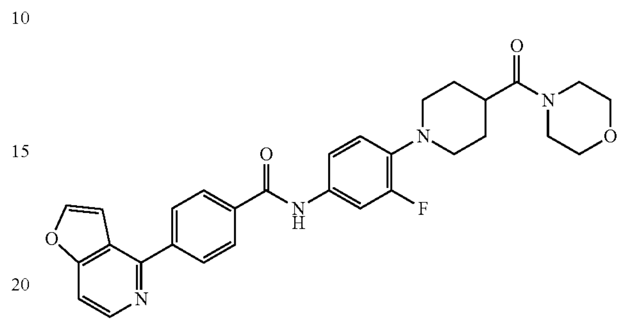

The title compound was synthesized from 3,4-difluoronitrobenzene according to the methods of steps (1), (2), (3), and (4) in Example 222.

ESI-MS: 529.2 [M+H]$^+$

Example 224

Synthesis of (S)-4-(furo[3,2-c]pyridin-4-yl)-N-[4-(pyrimidin-2-yl)-1,4-oxazepan-6-yl]benzamide [224] (Hereinafter, Referred to as a Compound [224])

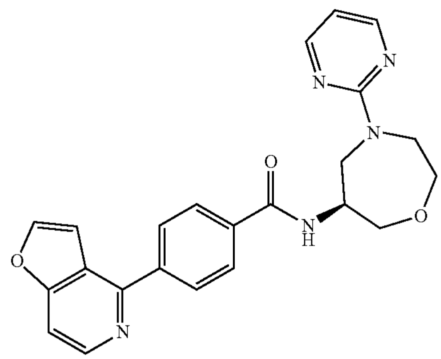 [SMILES: O=C(N[C@@H]1COCCN(c2ncccn2)C1)c1ccc(-c2nccc3occc23)cc1]

(1) Synthesis of tert-butyl (S)-6-[4-(furo[3,2-c]pyridin-4-yl)benzamide]-1,4-oxazepane-4-carboxylate [224-1] (Hereinafter, Referred to as a Compound [224-1])

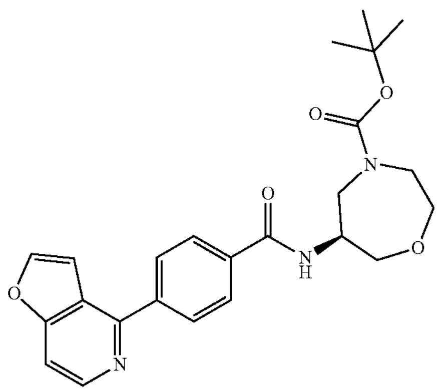 [SMILES: CC(C)(C)OC(=O)N1CCOC[C@@H](NC(=O)c2ccc(-c3nccc4occc34)cc2)C1]

To a solution of the compound [99-1] (100 mg) in dichloromethane (1.4 mL) were added 4-dimethylaminopyridine (56 mg), EDC (88 mg), and tert-butyl(S)-6-amino-1,4-oxazepane-6-carboxylate (108 mg) at room temperature, and the mixture was stirred at room temperature for 23 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (89 mg) as a colorless oil.

ESI-MS: 438.2 [M+H]$^+$ (2) Synthesis of (S)-4-(furo[3,2-c]pyridin-4-yl)-N-(1,4-oxazepan-6-yl)benzamide dihydrochloride [224-2] (Hereinafter, Referred to as a Compound [224-2])

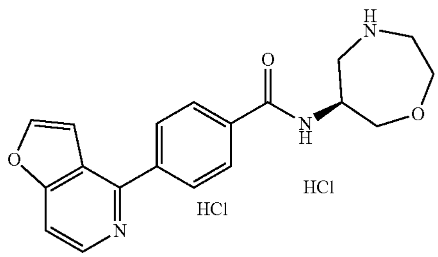 [SMILES: O=C(N[C@H]1CNCCOC1)c1ccc(-c2nccc3occc23)cc1 ; Cl ; Cl]

To a solution of the compound [224-1] (89 mg) in ethyl acetate (0.5 mL) was added a solution of 4 M hydrogen chloride in ethyl acetate (0.4 mL) at room temperature, and the mixture was stirred at room temperature for 4 hours. The reaction mixture was concentrated under reduced pressure to give the title compound (82 mg) as a yellow solid.

ESI-MS: 338.2 [M+H]$^+$ (3) Synthesis of (S)-4-(furo[3,2-c]pyridin-4-yl)-N-[4-(pyrimidin-2-yl)-1,4-oxazepan-6-yl]benzamide [224]

To a solution of the compound [224-2] (14.0 mg) in NMP (0.5 mL) were added cesium carbonate (139 mg) and 2-chloropyrimidine (15.0 mg) at room temperature, and the mixture was stirred at 120° C. for 4 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (6.70 mg) as a yellow solid.

ESI-MS: 416.3 [M+H]$^+$

Example 225

Synthesis of (R)-4-(furo[3,2-c]pyridin-4-yl)-N-[4-(pyrimidin-2-yl)-1,4-oxazepan-6-yl]benzamide [225] (Hereinafter, Referred to as a Compound [225])

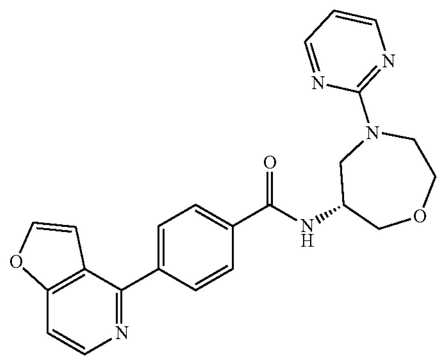 [SMILES: O=C(N[C@H]1COCCN(c2ncccn2)C1)c1ccc(-c2nccc3occc23)cc1]

The title compound was synthesized by a method according to Example 224, using tert-butyl (R)-6-amino-1,4-oxazepane-6-carboxylate in place of tert-butyl(S)-6-amino-1,4-oxazepane-6-carboxylate.

ESI-MS: 416.3 [M+H]$^+$

Example 226

Synthesis of (S)—N-[1-(6-fluoropyridin-2-yl)pyrrolidin-3-yl]-4-(furo[3,2-c]pyridin-4-yl)benzamide [226] (Hereinafter, Referred to as a Compound [226])

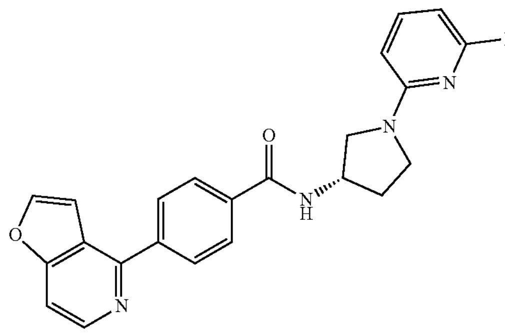

The title compound was synthesized by a method according to Example 193, using 2,6-difluoropyridine in place of (2-chloropyrimidin-5-yl)methanol.

ESI-MS: 403.2 [M+H]$^+$

Example 227

Synthesis of (S)—N-[1-(6-chloropyrimidin-4-yl) pyrrolidin-3-yl]-4-(furo[3,2-c]pyridin-4-yl)benzamide [227] (Hereinafter, Referred to as a Compound [227])

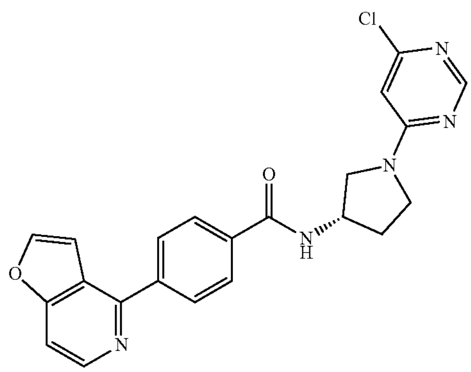 [SMILES: O=C(N[C@H]1CCN(c2cc(Cl)ncn2)C1)c1ccc(-c2nccc3occc23)cc1]

The title compound was synthesized by a method according to Example 193, using 4,6-dichloropyrimidine in place of (2-chloropyrimidin-5-yl)methanol.

ESI-MS: 420.1 $[M+H]^+$

Example 228

Synthesis of (S)—N-[1-(6-chloropyridazin-3-yl) pyrrolidin-3-yl]-4-(furo[3,2-c]pyridin-4-yl)benzamide [228] (Hereinafter, Referred to as a Compound [228])

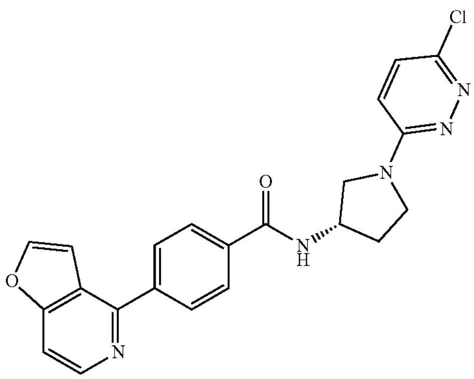 [SMILES: O=C(N[C@H]1CCN(c2ccc(Cl)nn2)C1)c1ccc(-c2nccc3occc23)cc1]

The title compound was synthesized by a method according to Example 193, using 3,6-dichloropyridazin in place of (2-chloropyrimidin-5-yl)methanol.

ESI-MS: 420.2 $[M+H]^+$

Example 229

Synthesis of (S)-4-(furo[3,2-c]pyridin-4-yl)-N-[1-(pyrimidin-4-yl)pyrrolidin-3-yl]benzamide [229] (Hereinafter, Referred to as a Compound [229])

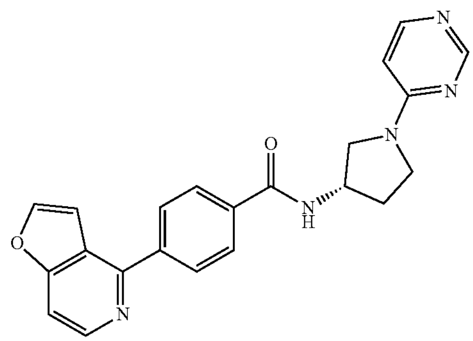 [SMILES: O=C(N[C@H]1CCN(c2ccncn2)C1)c1ccc(-c2nccc3occc23)cc1]

To a solution of the compound [227] (5.0 mg) in THE (0.3 mL) were added sodium borohydride (1.4 mg), N, N, N',N'-tetramethylethylenediamine (1.8 L), and $PdCl_2$(dppf) (9.0 mg) at room temperature, and the mixture was stirred at room temperature for 4 hours under an argon atmosphere. The reaction mixture was filtered, and the filtrate was concentrated under reduced pressure. The obtained residue was purified by silica gel column chromatography to give the title compound (3.2 mg) as a white solid.

ESI-MS: 386.2 $[M+H]^+$

Example 230

Synthesis of (S)-4-(furo[3,2-c]pyridin-4-yl)-N-[1-(pyridazin-3-yl)pyrrolidin-3-yl]benzamide [230] (Hereinafter, Referred to as a Compound [230])

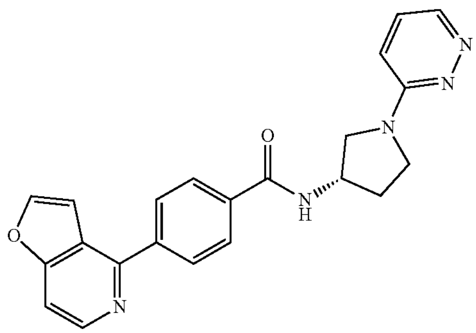 [SMILES: O=C(N[C@H]1CCN(c2cccnn2)C1)c1ccc(-c2nccc3occc23)cc1]

The title compound was synthesized from the compound according to the method of Example 229.

ESI-MS: 386.2 $[M+H]^+$

Example 231

Synthesis of (S)-4-(furo[3,2-c]pyridin-4-yl)-N-[1-(1-methyl-1H-tetrazol-5-yl)pyrrolidin-3-yl]benzamide [231] (Hereinafter, Referred to as a Compound [231])

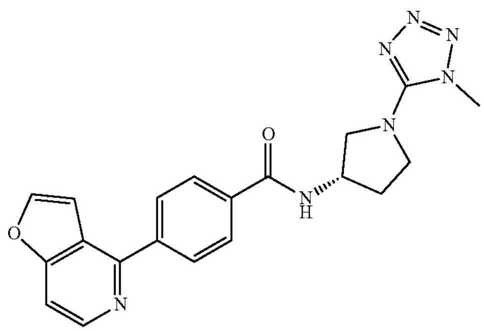 [SMILES: Cn1nnnc1N1CC[C@H](NC(=O)c2ccc(-c3nccc4occc34)cc2)C1]

To a solution of the compound [191-2] (40 mg) in acetonitrile (0.5 mL) were added methyl isothiocyanate (12 mg) and DIPEA (63 μL) at room temperature, the container was sealed, and then the mixture was stirred at 100° C. for 30 minutes. Then, 1,3-propane sultone (22 μL) and triethylamine (53 μL) were added at 100° C., the container was sealed, and then the mixture was stirred at 100° C. for 1 hour. Then, sodium azide (81 mg) was added at 100° C., the container was sealed, and then the mixture was stirred at 100° C. for 1 hour. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (2.3 mg) as a white solid.

ESI-MS: 390.2 $[M+H]^+$

Example 232

Synthesis of (S)-4-(furo[3,2-c]pyridin-4-yl)-N-[1-(1-ethyl-1H-tetrazol-5-yl)pyrrolidin-3-yl]benzamide [232] (Hereinafter, Referred to as a Compound [232])

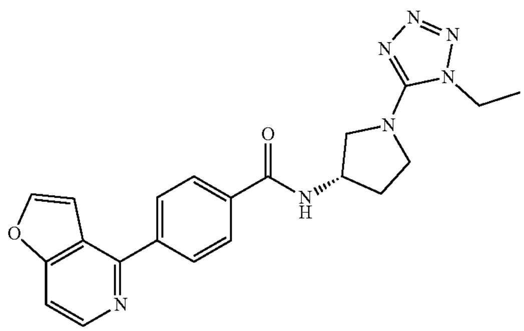 [SMILES: CCn1nnnc1N1CC[C@H](NC(=O)c2ccc(-c3nccc4occc34)cc2)C1]

The title compound was synthesized by a method according to Example 231, using ethyl isothiocyanate in place of methyl isothiocyanate.

ESI-MS: 404.2 $[M+H]^+$

Example 233

Synthesis of (S)-4-(furo[3,2-c]pyridin-4-yl)-N-[1-(6-oxo-1,6-dihydropyridin-2-yl)pyrrolidin-3-yl]benzamide [233] (Hereinafter, Referred to as a Compound [233])

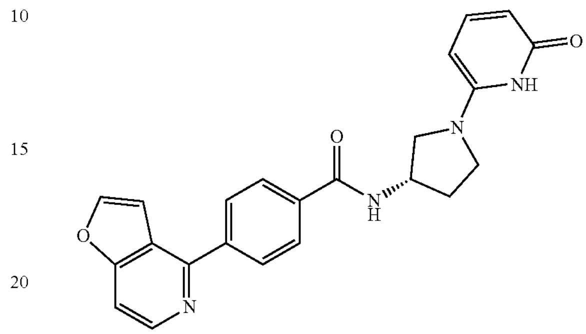

(1) Synthesis of 2-[(2,4-dimethoxybenzyl)oxy]-6-fluoropyridine [233-1] (Hereinafter, Referred to as a Compound [233-1])

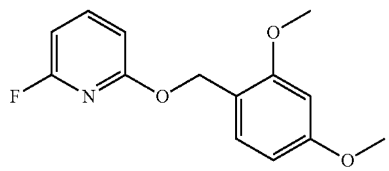 [SMILES: COc1ccc(COc2cccc(F)n2)c(OC)c1]

To a solution of 2,4-dimethoxybenzyl alcohol (1.46 g) in DMF (29 mL) were added 60% sodium hydride (382 mg) and 2,6-difluoropyridine (1.00 g) at room temperature, and the mixture was stirred at room temperature for 19 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (2.08 g) as a white solid.

$^1$H-NMR (400 MHz, $CDCl_3$) δ: 7.62 (dd, J=8.1, 8.1 Hz, 1H), 7.35 (d, J=8.7 Hz, 1H), 6.63 (dd, J=8.2, 1.4 Hz, 1H), 6.49-6.48 (m, 3H), 5.30 (s, 2H), 3.83 (s, 3H), 3.81 (s, 3H).

(2) Synthesis of (S)-4-(furo[3,2-c]pyridin-4-yl)-N-[1-(6-oxo-1,6-dihydropyridin-2-yl)pyrrolidin-3-yl]benzamide [233]

To a solution of the compound [191-2] (20 mg) in NMP (0.5 mL) were added cesium carbonate (101 mg) and the compound [233-1] (33 mg) at room temperature, and the mixture was stirred at 120° C. for 3 hours. To the reaction mixture was added water, and the mixture was extracted with ethyl acetate. The organic layer was dried over anhydrous sodium sulfate and concentrated under reduced pressure. To the obtained residue was added a solution of 4 M hydrogen chloride in ethyl acetate (4.0 mL) at room temperature, and the mixture was stirred at room temperature for 1 hour. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (5.2 mg) as a white solid.

ESI-MS: 401.2 [M+H]+

Example 234

Synthesis of 4-(furo[3,2-c]pyridin-4-yl)-N-(1-propionylpiperidin-4-yl)benzamide [234] (Hereinafter, Referred to as a Compound [234])

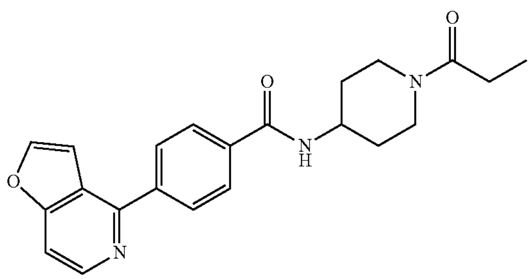 [SMILES: CCC(=O)N1CCC(NC(=O)c2ccc(-c3nccc4occc34)cc2)CC1]

To a solution of the compound [142] (30 mg) in DMF (0.5 mL) were added propionic acid (12 μL), DIPEA (78 μL), and (1-cyano-2-ethoxy-2-oxoethylideneaminooxy)dimethylaminomorpholinocarbenium hexafluorophosphate (65 mg) at room temperature, and the mixture was stirred at room temperature for 18 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (20 mg) as a pink solid.

$^1$H-NMR (400 MHz, DMSO-$d_6$) δ: 8.59 (d, J=5.5 Hz, 1H), 8.42 (d, J=7.8 Hz, 1H), 8.24-8.23 (m, 1H), 8.11-8.08 (m, 2H), 8.03-8.01 (m, 2H), 7.74-7.71 (m, 1H), 7.37-7.36 (m, 1H), 4.39-4.36 (m, 1H), 4.07-4.06 (m, 1H), 3.89-3.86 (m, 1H), 3.15-3.08 (m, 1H), 2.72-2.66 (m, 1H), 2.37-2.32 (m, 2H), 1.90-1.81 (m, 2H), 1.50-1.38 (m, 2H), 0.99 (t, J=7.4 Hz, 3H).

ESI-MS: 378.2 [M+H]+

Example 235

Synthesis of N-[1-(cyclopropanecarbonyl)piperidin-4-yl]-4-(furo[3,2-c]pyridin-4-yl)benzamide [235] (Hereinafter, Referred to as a Compound [235])

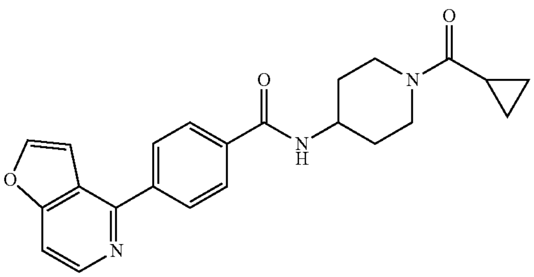 [SMILES: O=C(NC1CCN(C(=O)C2CC2)CC1)c1ccc(-c2nccc3occc23)cc1]

To a solution of the compound [142] (50 mg) in DMF (1.0 mL) were added cyclopropanecarboxylic acid (100 μL), DIPEA (100 μL), and (1-cyano-2-ethoxy-2-oxoethylideneaminooxy)dimethylaminomorpholinocarbenium hexafluorophosphate (100 mg) at room temperature, and the mixture was stirred at room temperature for 22 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (40 mg) as a white solid.

$^1$H-NMR (400 MHz, DMSO-$d_6$) δ: 8.59 (d, J=5.5 Hz, 1H), 8.43 (d, J=7.8 Hz, 1H), 8.26-8.22 (m, 1H), 8.10 (d, J=7.3 Hz, 2H), 8.02 (d, J=7.3 Hz, 2H), 7.74-7.71 (m, 1H), 7.37-7.36 (m, 1H), 4.36-4.25 (m, 2H), 4.11-4.07 (m, 1H), 3.26-3.19 (m, 1H), 2.79-2.65 (m, 1H), 2.05-1.82 (m, 3H), 1.52-1.42 (m, 2H), 0.73-0.69 (m, 4H).

ESI-MS: 390.2 [M+H]+

Example 236

Synthesis of 4-(furo[3,2-c]pyridin-4-yl)-N-[1-(oxetan-3-yl)piperidin-4-yl]benzamide [236] (Hereinafter, Referred to as a Compound [236])

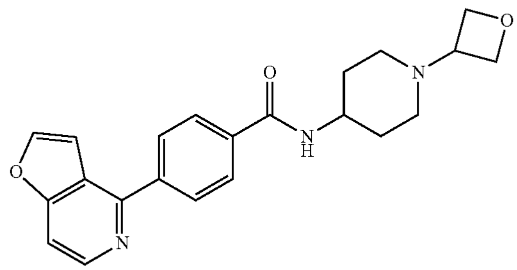 [SMILES: O=C(NC1CCN(C2COC2)CC1)c1ccc(-c2nccc3occc23)cc1]

To a solution of the compound [142] (60 mg) in THE (1.0 mL)/dichloromethane (1.5 mL) were added DIPEA (103 μL), sodium acetate (17 mg), 3-oxetanone (16 mg), and sodium cyanoborohydride (48 mg) at room temperature, and the mixture was stirred at 60° C. for 5 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (18 mg) as a white solid.

$^1$H-NMR (400 MHz, DMSO-$d_6$) δ: 8.59 (dd, J=5.6, 3.6 Hz, 1H), 8.40 (d, J=6.4 Hz, 1H), 8.24 (d, J=3.2 Hz, 1H), 8.09 (d, J=8.2 Hz, 2H), 8.01 (d, J=8.2 Hz, 2H), 7.73 (d, J=5.5 Hz, 1H), 7.37-7.36 (m, 1H), 4.53 (dd, J=6.4, 6.2 Hz, 2H), 4.42 (dd, J=6.4, 6.2 Hz, 2H), 3.88-3.75 (m, 1H), 3.41-3.35 (m, 1H), 2.73-2.65 (m, 2H), 1.89-1.80 (m, 4H), 1.64-1.54 (m, 2H).

ESI-MS: 378.2 [M+H]+

Example 237

Synthesis of N-[1-(1,3,4-thiadiazol-2-yl)piperidin-4-yl]-4-(furo[3,2-c]pyridin-4-yl)benzamide [237] (Hereinafter, Referred to as a Compound [237])

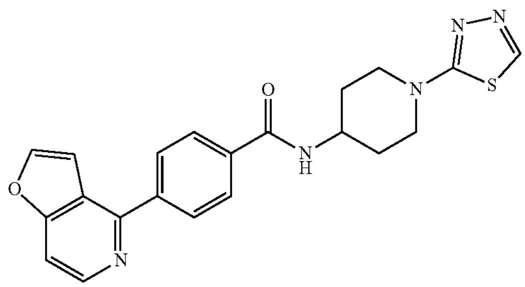 [SMILES: O=C(NC1CCN(c2nncs2)CC1)c1ccc(-c2nccc3occc23)cc1]

To a solution of the compound [142] (30 mg) in NMP (0.5 mL) were added cesium carbonate (124 mg) and 2-chloro-1,3,4-thiadiazole (30 mg) at room temperature, and the mixture was stirred at 90° C. for 20 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (4.2 mg) as a white solid.

$^1$H-NMR (400 MHz, DMSO-$d_6$) δ: 8.81 (s, 1H), 8.59 (d, J=5.5 Hz, 1H), 8.47 (d, J=7.8 Hz, 1H), 8.24 (d, J=2.3 Hz, 1H), 8.09 (d, J=8.7 Hz, 2H), 8.02 (d, J=8.7 Hz, 2H), 7.72 (dd, J=5.7, 1.1 Hz, 1H), 7.37-7.36 (m, 1H), 4.17-4.09 (m, 1H), 3.93-3.89 (m, 2H), 3.30-3.27 (m, 2H), 2.02-1.92 (m, 2H), 1.74-1.64 (m, 2H).

ESI-MS: 406.1 [M+H]$^+$

Example 238

Synthesis of 4-(furo[3,2-c]pyridin-4-yl)-N-[1-(imidazo[1,2-a]pyridin-5-yl)piperidin-4-yl]benzamide [238] (Hereinafter, Referred to as a Compound [238])

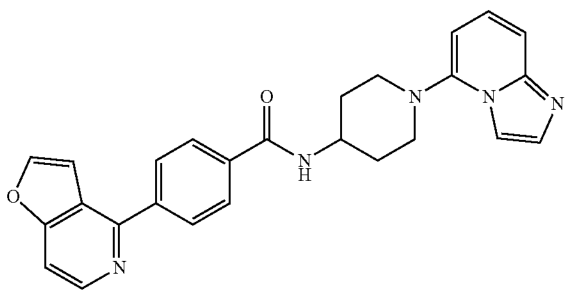 [SMILES: O=C(NC1CCN(c2cccc3nccn23)CC1)c1ccc(-c2nccc3occc23)cc1]

The title compound was synthesized by a method according to Example 237, using 5-chloroimidazo[1,2-a]pyridine in place of 2-chloro-1,3,4-thiadiazole.

ESI-MS: 438.2 [M+H]$^+$

Example 239

Synthesis of N-[1-(1-ethyl-1H-tetrazol-5-yl)piperidin-4-yl]-4-(furo[3,2-c]pyridin-4-yl)benzamide [239] (Hereinafter, Referred to as a Compound [239])

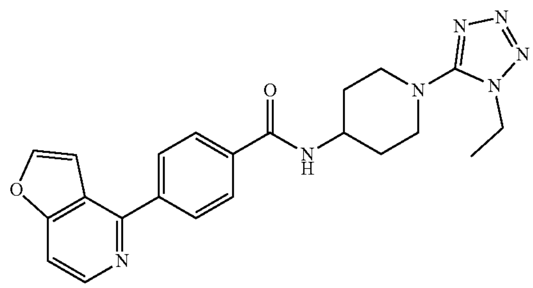 [SMILES: CCn1nnnc1N1CCC(NC(=O)c2ccc(-c3nccc4occc34)cc2)CC1]

To a solution of the compound [142] (100 mg) in acetonitrile (0.83 mL) were added ethyl isothiocyanate (28 μL) and DIPEA (127 μL) at room temperature, the container was sealed, and then the mixture was stirred at 100° C. for 30 minutes. Then, 1,3-propane sultone (44 μL) and triethylamine (104 μL) were added at 100° C., the container was sealed, and then the mixture was stirred at 100° C. for 1 hour. Then, sodium azide (163 mg) was added at 100° C., the container was sealed, and then the mixture was stirred at 100° C. for 1 hour. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (15 mg) as a white solid.

ESI-MS: 418.2 [M+H]$^+$

Examples 240 to 243

Each compound of Examples 240 to 243 shown in the following Tables was synthesized according to the method shown in Example 239. The structure, name, and ESI-MS of the compound of each Example are shown in the following Tables.

| Example | Structure | Name | ESI-MS |
|---|---|---|---|
| 240 | 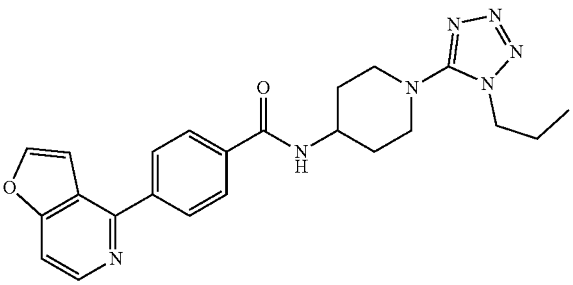 [SMILES: CCCn1nnnc1N1CCC(NC(=O)c2ccc(-c3nccc4occc34)cc2)CC1] | 4-(furo[3,2-c]pyridin-4-yl)-N-[1-(1-propyl-1H-tetrazol-5-yl)piperidin-4-yl]benzamide | 432.2 $[M + H]^+$ |
| 241 | 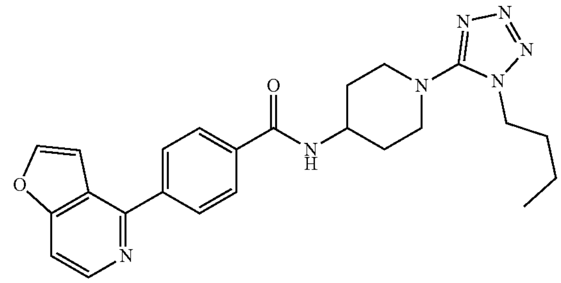 [SMILES: CCCCn1nnnc1N1CCC(NC(=O)c2ccc(-c3nccc4occc34)cc2)CC1] | N-[1-(1-butyl-1H-tetrazol-5-yl)piperidin-4-yl]-4-(furo[3,2-c]pyridin-4-yl)benzamide | 446.2[ $[M + H]^+$ |
| 242 | 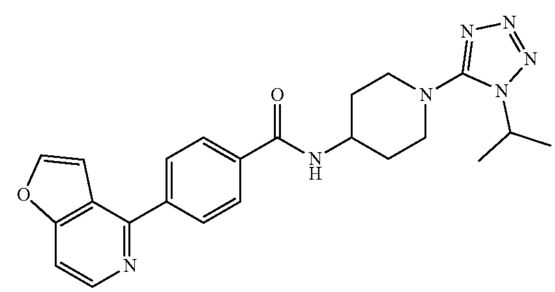 [SMILES: CC(C)n1nnnc1N1CCC(NC(=O)c2ccc(-c3nccc4occc34)cc2)CC1] | 4-(furo[3,2-c]pyridin-4-yl)-N-[1-(1-isopropyl-1H-tetrazol-5-yl)piperidin-4-yl]benzamide | 432.2 $[M + H]^+$ |
| 243 | 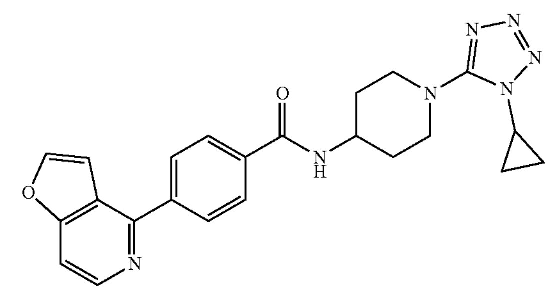 [SMILES: O=C(NC1CCN(c2nnnn2C2CC2)CC1)c1ccc(-c2nccc3occc23)cc1] | N-[1-(1-cyclopropyl-1H-tetrazol-5-yl) piperidin-4-yl]-4-(furo[3,2-c]pyridin-4-yl)benzamide | 430.2 $[M + H]^+$ |

Example 244

Synthesis of N-[1-(3-chloro-4-methoxybenzyl)piperidin-4-yl]-4-(furo[3,2-c]pyridin-4-yl)benzamide [244] (Hereinafter, Referred to as a Compound [244])

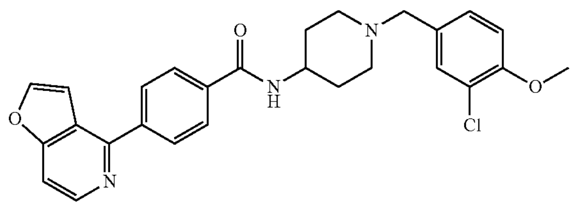 [SMILES: COc1ccc(CN2CCC(NC(=O)c3ccc(-c4nccc5occc45)cc3)CC2)cc1Cl]

To a solution of the compound [142] (20 mg) in dichloromethane (0.5 mL) were added 60% sodium hydride (3.0 mg) and 3-chloro-4-methoxybenzaldehyde (20 mg) at room temperature, and the mixture was stirred at room temperature for 10 minutes. Then, sodium triacetoxyborohydride (34 mg) was added at room temperature, and the mixture was stirred at room temperature for 30 minutes. To the reaction mixture was added water, and the mixture was extracted with chloroform. The organic layer was dried over anhydrous sodium sulfate and concentrated under reduced pressure. The obtained residue was purified by silica gel column chromatography to give the title compound (4.9 mg) as a yellow solid.

ESI-MS: 476.2 $[M+H]^+$

Example 245

Synthesis of 4-(furo[3,2-c]pyridin-4-yl)-N-[1-(2-hydroxy-2-methylpropanoyl)piperidin-4-yl]benzamide [245] (Hereinafter, Referred to as a Compound [245])

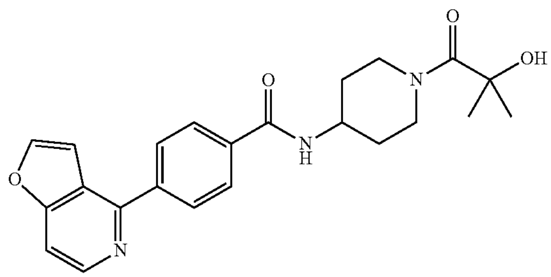 [SMILES: CC(C)(O)C(=O)N1CCC(NC(=O)c2ccc(-c3nccc4occc34)cc2)CC1]

To a solution of the compound [142] (21 mg) in DMF (0.5 mL) were added DIPEA (27 μL), 2-hydroxyisobutyric acid (7.5 mg), and (1-cyano-2-ethoxy-2-oxoethylideneaminooxy)dimethylaminomorpholinocarbenium hexafluorophosphate (31 mg) at room temperature, and the mixture was stirred at room temperature for 17 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (8.2 mg) as a white solid.

$^1$H-NMR (400 MHz, DMSO-$d_6$) δ: 8.56 (d, J=5.5 Hz, 1H), 8.40 (d, J=7.8 Hz, 1H), 8.21 (d, J=2.3 Hz, 1H), 8.06 (d, J=8.7 Hz, 2H), 8.02 (d, J=8.2 Hz, 2H), 7.69 (d, J=5.5 Hz, 1H), 7.37-7.36 (m, 1H), 5.35 (s, 1H), 4.84-4.34 (m, 2H), 4.12-4.04 (m, 1H), 3.20-2.66 (m, 2H), 1.87-1.84 (m, 2H), 1.52-1.44 (m, 2H), 1.33 (s, 6H).

ESI-MS: 408.2 $[M+H]^+$

Example 246

Synthesis of 4-(furo[3,2-c]pyridin-4-yl)-N-[1-(3,3,3-trifluoropropanoyl)piperidin-4-yl]benzamide [246] (Hereinafter, Referred to as a Compound [246])

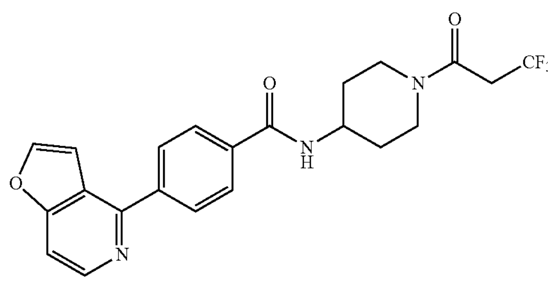 [SMILES: O=C(NC1CCN(C(=O)CC(F)(F)F)CC1)c1ccc(-c2nccc3occc23)cc1]

The title compound was synthesized by a method according to Example 245, using 3,3,3-trifluoropropionic acid in place of 2-hydroxyisobutyric acid.

ESI-MS: 432.2 $[M+H]^+$

Example 247

Synthesis of N-(1-cyanopiperidin-4-yl)-4-(furo[3,2-c]pyridin-4-yl)benzamide [247] (Hereinafter, Referred to as a Compound [247])

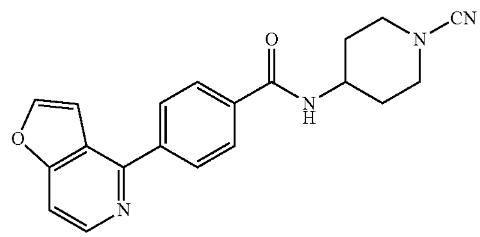 [SMILES: N#CN1CCC(NC(=O)c2ccc(-c3nccc4occc34)cc2)CC1]

To a solution of the compound [142] (100 mg) in dichloromethane (1.0 mL) were added DIPEA (255 μL) and cyanogen bromide (379 mg) at room temperature, and the mixture was stirred at room temperature for 16 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (92 mg) as a yellow solid.

ESI-MS: 347.1 $[M+H]^+$

Example 248

Synthesis of N-[1-(1H-tetrazol-5-yl)piperidin-4-yl]-4-(furo[3,2-c]pyridin-4-yl)benzamide [248] (Hereinafter, Referred to as a Compound [248])

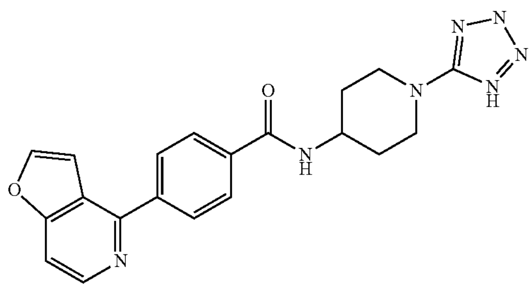 [SMILES: O=C(NC1CCN(c2nn[nH]n2)CC1)c1ccc(-c2nccc3occc23)cc1]

To a solution of the compound [247] (87 mg) in DMF (2.0 mL) were added sodium azide (253 mg) and triethylamine hydrochloride (253 mg) at room temperature, and the mixture was stirred at 100° C. for 1 hour. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (21 mg) as a white solid.

ESI-MS: 390.2 $[M+H]^+$

Example 249

Synthesis of 4-(furo[3,2-c]pyridin-4-yl)-N-[1-(2-methyl-2H-tetrazol-5-yl)piperidin-4-yl]benzamide [249] (Hereinafter, Referred to as a Compound [249])

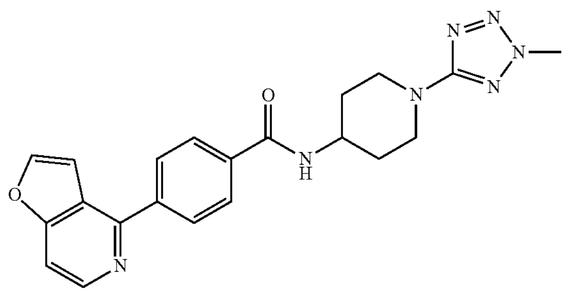 [SMILES: Cn1nnc(N2CCC(NC(=O)c3ccc(-c4nccc5occc45)cc3)CC2)n1]

To a solution of the compound [248] (19 mg) in DMF (0.5 mL) were added potassium carbonate (20 mg) and methyl iodide (5.0 μL) at room temperature, and the mixture was stirred at 60° C. for 1 hour. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (11 mg) as a white solid.

ESI-MS: 404.2 $[M+H]^+$

Example 250

Synthesis of 4-(furo[3,2-c]pyridin-4-yl)-N-[1-(1-methyl-1H-pyrazol-5-yl)piperidin-4-yl]benzamide [250] (Hereinafter, Referred to as a Compound [250])

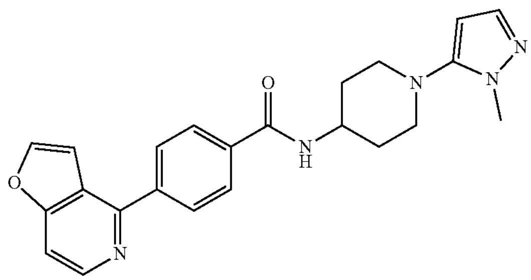 [SMILES: Cn1nccc1N1CCC(NC(=O)c2ccc(-c3nccc4occc34)cc2)CC1]

(1) Synthesis of N-[1-(4-formyl-1-methyl-1H-pyrazol-5-yl)piperidin-4-yl]-4-(furo[3,2-c]pyridin-4-yl) benzamide [250-1] (Hereinafter, Referred to as a Compound [250-1])

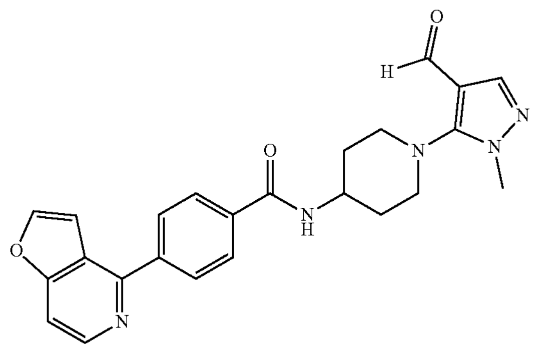 [SMILES: Cn1ncc(C=O)c1N1CCC(NC(=O)c2ccc(-c3nccc4occc34)cc2)CC1]

To a solution of the compound [142] (14 mg) in DMSO (0.2 mL) were added DIPEA (12 μL), cesium carbonate (10 mg), and 5-chloro-1-methyl-1H-pyrazole-4-carbaldehyde (10 mg) at room temperature, and the mixture was stirred at 150° C. for 6 hours using a microwave reactor. To the reaction mixture was added water, and the mixture was extracted with toluene. The organic layer was dried over anhydrous sodium sulfate and concentrated under reduced pressure. The obtained residue was purified by silica gel column chromatography to give the title compound (2.5 mg) as a brown oil.

ESI-MS: 430.2 $[M+H]^+$ (2) Synthesis of 4-(furo[3,2-c]pyridin-4-yl)-N-[1-(1-methyl-1H-pyrazol-5-yl)piperidin-4-yl]benzamide [250]

To a solution of the compound [250-1] (2.5 mg) in methanol (0.2 mL) was added p-toluenesulfonic acid monohydrate (0.1 mg) at room temperature, and the mixture was stirred at 120° C. for 20 minutes using a microwave reactor. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (2.0 mg) as a brown solid.

ESI-MS: 402.2 $[M+H]^+$

Example 251

Synthesis of 4-(furo[3,2-c]pyridin-4-yl)-N-[1-(1-methyl-1H-imidazol-2-yl)piperidin-4-yl]benzamide [251] (Hereinafter, Referred to as a Compound [251])

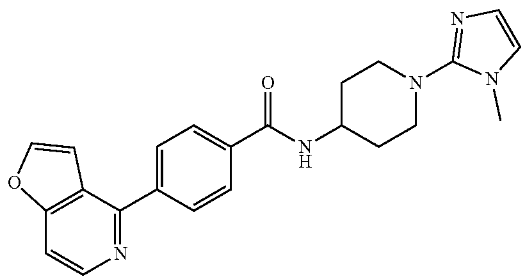 [SMILES: Cn1ccnc1N1CCC(NC(=O)c2ccc(-c3nccc4occc34)cc2)CC1]

(1) Synthesis of 4-azide-1-(1-methyl-1H-imidazol-2-yl)piperidine [251-1] (Hereinafter, Referred to as a Compound [251-1])

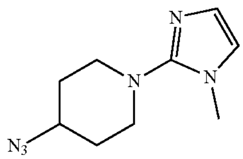

To a solution of 1-(1-methyl-1H-imidazol-2-yl)piperidin-4-ol (16 mg) obtained by a method described in the literature (WO 2011/143645) in dichloromethane (0.5 mL) were added triethylamine (23 μL) and methanesulfonyl chloride (33 μL) at room temperature, and the mixture was stirred at room temperature for 30 minutes. To the reaction mixture was added a saturated aqueous sodium bicarbonate solution, and the mixture was extracted with chloroform. The organic layer was dried over anhydrous sodium sulfate and concentrated under reduced pressure. To a solution of the obtained residue in DMF (0.3 mL)/THF (0.3 mL) was added sodium azide (28 mg) at room temperature, and the mixture was stirred at 100° C. for 2 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (9.3 mg) as a yellow oil.

ESI-MS: 207.2 $[M+H]^+$ (2) Synthesis of 1-(1-methyl-1H-imidazol-2-yl)piperidin-4-amine [251-2] (Hereinafter, Referred to as a Compound [251-2])

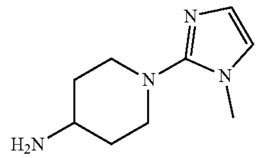

To a solution of the compound [251-1] (9.3 mg) in ethanol (0.5 mL) was added 10% palladium-activated carbon (4.8 mg) at room temperature, and the mixture was stirred at room temperature for 16 hours under a hydrogen atmosphere. The reaction mixture was filtered, and the filtrate was concentrated under reduced pressure to give the title compound (5.4 mg) as a colorless oil.

$^1H$-NMR (400 MHz, $CDCl_3$) δ: 6.76 (d, J=1.4 Hz, 1H), 6.65 (d, J=1.4 Hz, 1H), 3.72 (s, 3H), 3.23-3.20 (m, 2H), 2.95-2.84 (m, 3H), 2.68 (br, 2H), 1.96-1.93 (m, 2H), 1.62-1.54 (m, 2H).

(3) Synthesis of 4-(furo[3,2-c]pyridin-4-yl)-N-[1-(1-methyl-1H-imidazol-2-yl)piperidin-4-yl]benzamide [251]

The title compound was synthesized from the compound [251-2] according to the method of the step (2) in Example 99.

ESI-MS: 402.2 $[M+H]^+$

Example 252

Synthesis of 4-(furo[3,2-c]pyridin-4-yl)-N-[1-(1-methyl-1H-pyrazol-4-yl)piperidin-4-yl]benzamide [252] (Hereinafter, Referred to as a Compound [252])

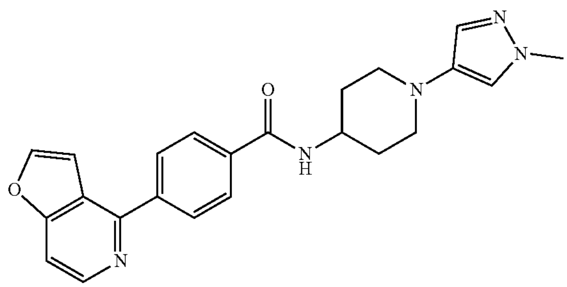 [SMILES: Cn1cc(N2CCC(NC(=O)c3ccc(-c4nccc5occc45)cc3)CC2)cn1]

To a solution of the compound [142] (113 mg) in DMSO (0.9 mL) were added 4-iodo-1-methylpyrazole (30.0 mg), DIPEA (98.0 μL), L-proline (13.0 mg), potassium carbonate (100 mg), and copper (I) iodide (11.0 mg) at room temperature, and the mixture was stirred at 100° C. for 23 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (10.7 mg) as an orange solid.

ESI-MS: 402.2 [M+H]$^+$

Example 253

Synthesis of 4-(furo[3,2-c]pyridin-4-yl)-N-{1-[4-(hydroxymethyl)-1-methyl-1H-imidazol-5-yl]piperidin-4-yl}benzamide [253] (Hereinafter, Referred to as a Compound [253])

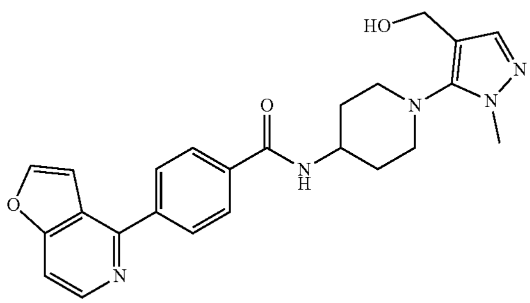 [SMILES: Cn1ncc(CO)c1N1CCC(NC(=O)c2ccc(-c3nccc4occc34)cc2)CC1]

(1) Synthesis of N-[1-(4-formyl-1-methyl-1H-imidazol-5-yl)piperidin-4-yl]-4-(furo[3,2-c]pyridin-4-yl)benzamide [253-1] (Hereinafter, Referred to as a Compound [253-1])

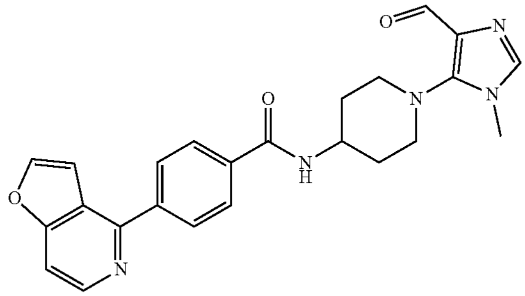 [SMILES: Cn1cnc(C=O)c1N1CCC(NC(=O)c2ccc(-c3nccc4occc34)cc2)CC1]

The title compound was synthesized by a method according to the step (1) in Example 250, using 5-chloro-1-methyl-1H-imidazole-4-carbaldehyde obtained by a method described in the literature (WO 2010/132999) in place of 5-chloro-1-methyl-1H-pyrazole-4-carbaldehyde.

ESI-MS: 430.2 [M+H]$^+$ (2) Synthesis of 4-(furo[3,2-c]pyridin-4-yl)-N-{1-[4-(hydroxymethyl)-1-methyl-1H-imidazol-5-yl]piperidin-4-yl}benzamide [253]

To a solution of the compound [253-1] (33 mg) in methanol (0.8 mL) was added sodium borohydride (12 mg) at room temperature, and the mixture was stirred at room temperature for 1 hour. The reaction mixture was concentrated under reduced pressure. The obtained residue was purified by silica gel column chromatography to give the title compound (13 mg) as a white solid.

ESI-MS: 432.2 [M+H]$^+$

Example 254

Synthesis of ethyl 2-{4-[4-(furo[3,2-c]pyridin-4-yl)benzamide]piperidin-1-yl]oxazole-5-carboxylate [254] (Hereinafter, Referred to as a Compound [254])

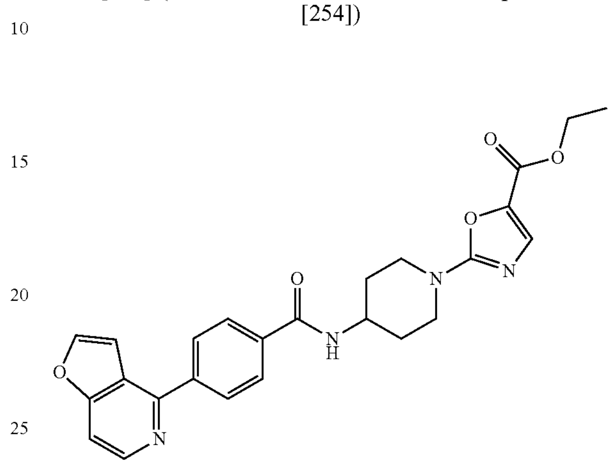

To a solution of the compound [142] (53 mg) in acetonitrile (0.65 mL) were added ethyl 2-chloro-1,3-oxazole-5-carboxylate (28 mg) and potassium carbonate (90 mg) at room temperature, and the mixture was stirred at 80° C. for 22 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (42 mg) as a yellow solid.

ESI-MS: 461.2 [M+H]$^+$

Example 255

Synthesis of 4-(furo[3,2-c]pyridin-4-yl)-N-{1-[5-(hydroxymethyl) oxazol-2-yl]piperidin-4-yl}benzamide [255] (Hereinafter, Referred to as a Compound [255])

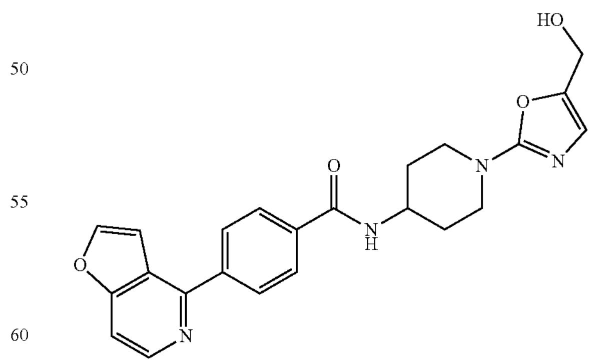

To a solution of the compound [254] (4.7 mg) in ethanol (0.3 mL) were added sodium borohydride (1.8 mg) and lithium chloride (2.2 mg) at room temperature, and the mixture was stirred at 70° C. for 19 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (1.9 mg) as a white solid.

ESI-MS: 419.2 [M+H]$^+$

Example 256

Synthesis of 4-(furo[3,2-c]pyridin-4-yl)-N-(trans-4-hydroxycyclohexyl)benzamide [256] (Hereinafter, Referred to as a Compound [256])

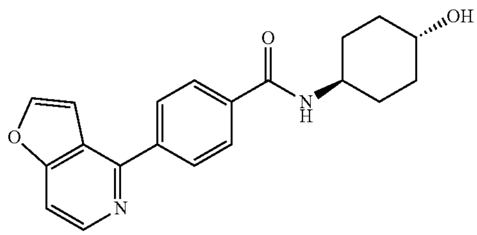 [SMILES: O=C(N[C@H]1CC[C@H](O)CC1)c1ccc(-c2nccc3occc23)cc1]

To a solution of the compound [99-1] (239 mg) in DMF (3.3 mL) were added DIPEA (680 μL), (1-cyano-2-ethoxy-2-oxoethylideneaminooxy)dimethylaminomorpholinocarbenium hexafluorophosphate (471 mg), and trans-4-aminocyclohexanol (150 mg) at room temperature, and the mixture was stirred at room temperature for 1 hour. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (206 mg) as a white solid.

$^1$H-NMR (400 MHz, DMSO-d$_6$) δ: 8.58 (d, J=5.9 Hz, 1H), 8.30 (d, J=7.8 Hz, 1H), 8.23 (d, J=2.3 Hz, 1H), 8.08 (dd, J=6.9, 1.8 Hz, 2H), 8.00 (dd, J=6.6, 2.1 Hz, 2H), 7.72 (dd, J=5.7, 1.1 Hz, 1H), 7.37-7.36 (m, 1H), 4.55 (d, J=4.1 Hz, 1H), 3.77-3.73 (m, 1H), 3.43-3.31 (m, 1H), 1.87-1.82 (m, 4H), 1.45-1.33 (m, 2H), 1.30-1.19 (m, 2H).

ESI-MS: 337.2 [M+H]$^+$

Example 257

Synthesis of 4-(furo[3,2-c]pyridin-4-yl)-N-[trans-4-(1-hydroxycyclopropyl)cyclohexyl]benzamide [257] (Hereinafter, Referred to as a Compound [257])

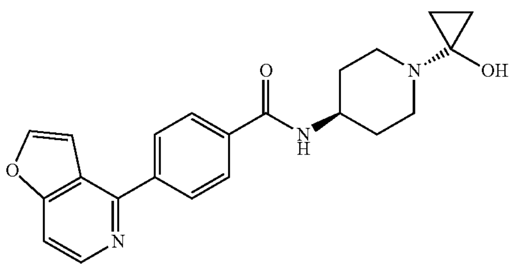

(1) Synthesis of methyl trans-4-(dibenzylamino)cyclohexane-1-carboxylate [257-1] (Hereinafter, Referred to as a Compound [257-1])

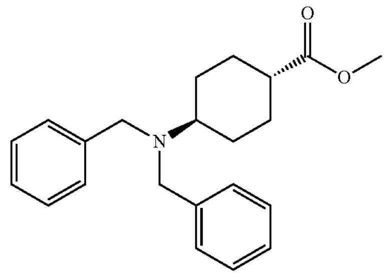 [SMILES: COC(=O)[C@H]1CC[C@H](N(Cc2ccccc2)Cc2ccccc2)CC1]

To a solution of methyl trans-4-aminocyclohexanecarboxylate hydrochloride (387 mg) in acetonitrile (6.7 mL) were added potassium carbonate (1.11 g) and benzyl bromide (598 μL) at room temperature, and the mixture was stirred at 80° C. for 9 hours. The reaction mixture was filtered, and the filtrate was concentrated under reduced pressure. The obtained residue was purified by reversed-phase silica gel column chromatography to give the title compound (344 mg) as a white solid.

$^1$H-NMR (400 MHz, $CDCl_3$) δ: 7.36-7.35 (m, 4H), 7.30-7.26 (m, 4H), 7.22-7.18 (m, 2H), 3.63-3.62 (m, 7H), 2.55-2.49 (m, 1H), 2.23-2.17 (m, 1H), 2.02-1.95 (m, 4H), 1.43-1.30 (m, 4H).

ESI-MS: 338.6 [M+H]$^+$ (2) Synthesis of 1-[trans-4-(dibenzylamino)cyclohexyl]cyclopropan-1-ol [257-2] (Hereinafter, Referred to as a Compound [257-2])

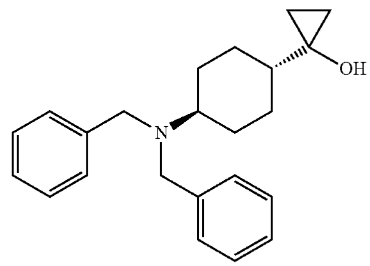 [SMILES: OC1([C@H]2CC[C@H](N(Cc3ccccc3)Cc3ccccc3)CC2)CC1]

To a solution of the compound [257-1] (238 mg) in THF (23.5 mL) was added titanium tetraisopropoxide (620 μL) at room temperature under an argon atmosphere. To this reaction mixture, a solution of 1 M ethyl magnesium bromide in THF (4.23 mL) was added dropwise over 5 minutes, and then the mixture was stirred at room temperature for 21 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (186 mg) as a white solid.

$^1$H-NMR (400 MHz, $CDCl_3$) δ: 7.38-7.36 (m, 4H), 7.30-7.26 (m, 4H), 7.22-7.18 (m, 2H), 3.62 (s, 4H), 2.54-2.47 (m, 1H), 1.99-1.95 (m, 2H), 1.83-1.80 (m, 2H), 1.62 (s, 1H), 1.42-1.32 (m, 2H), 1.26-1.16 (m, 2H), 0.93-0.85 (m, 1H), 0.68-0.66 (m, 2H), 0.42-0.39 (m, 2H).

ESI-MS: 336.1 $[M+H]^+$ (3) Synthesis of 1-(trans-4-aminocyclohexyl)cyclopropan-1-ol [257-3] (Hereinafter, Referred to as a Compound [257-3])

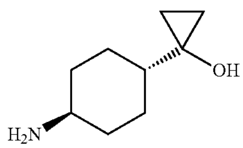

To a solution of the compound [257-2] (185 mg) in ethanol (6.9 mL) was added 20% palladium hydroxide-activated carbon (37.0 mg) at room temperature, and the mixture was stirred at room temperature for 17 hours under a hydrogen atmosphere. The reaction mixture was filtered, and the filtrate was concentrated under reduced pressure to give the title compound (81.8 mg) as a white solid.

$^1$H-NMR (400 MHz, $CDCl_3$) δ: 2.67-2.59 (m, 1H), 1.94-1.90 (m, 2H), 1.81-1.76 (m, 2H), 1.41-1.30 (m, 2H), 1.13-1.03 (m, 2H), 0.95-0.87 (m, 1H), 0.72-0.69 (m, 2H), 0.46-0.43 (m, 2H).

ESI-MS: 156.3 $[M+H]^+$ (4) Synthesis of 4-(furo[3,2-c]pyridin-4-yl)-N-[trans-4-(1-hydroxycyclopropyl)cyclohexyl]benzamide [257]

To a solution of the compound [99-1] (59 mg) in DMF (0.82 mL) were added DIPEA (209 μL), (1-cyano-2-ethoxy-2-oxoethylideneaminooxy)dimethylaminomorpholinocarbenium hexafluorophosphate (137 mg), and the compound [257-3] (38 mg) at room temperature, and the mixture was stirred at room temperature for 1 hour. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (18 mg) as an orange solid.

$^1$H-NMR (400 MHz, DMSO-$d_6$) δ: 8.58 (d, J=5.9 Hz, 1H), 8.33 (d, J=8.2 Hz, 1H), 8.24 (d, J=2.3 Hz, 1H), 8.10-8.08 (m, 2H), 8.01-7.99 (m, 2H), 7.72 (dd, J=5.5, 0.9 Hz, 1H), 7.37-7.36 (m, 1H), 4.87 (s, 1H), 3.74-3.72 (m, 1H), 1.93-1.88 (m, 2H), 1.75-1.70 (m, 2H), 1.36-1.31 (m, 4H), 0.94-0.89 (m, 1H), 0.50-0.47 (m, 2H), 0.36-0.33 (m, 2H).

ESI-MS: 377.2 $[M+H]^+$

Example 258

Synthesis of 4-(furo[3,2-c]pyridin-4-yl)-N-{trans-4-[(1-hydroxycyclopropyl)methoxy]cyclohexyl}benzamide [258] (Hereinafter, Referred to as a Compound [258])

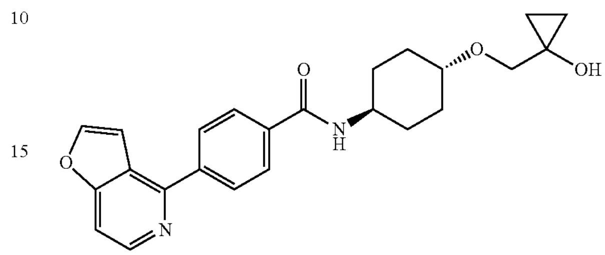

(1) Synthesis of 1-({[trans-4-(dibenzylamino)cyclohexyl]oxy}methyl)cyclopropan-1-ol [258-1] (Hereinafter, Referred to as a Compound [258-1])

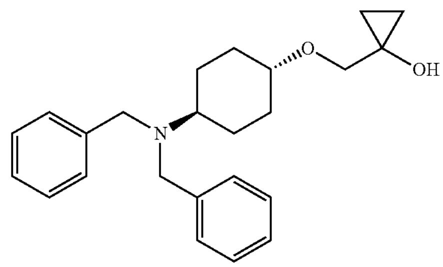 [SMILES: OC1(CO[C@H]2CC[C@H](N(Cc3ccccc3)Cc3ccccc3)CC2)CC1]

To a solution of the compound [64-1] (398 mg) in THE (32 mL) were added titanium tetraisopropoxide (852 L) and a solution of 1 M ethylmagnesium bromide in THF (5.82 mL) at room temperature, and the mixture was stirred at room temperature for 13 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (45.0 mg) as a white solid.

ESI-MS: 366.3 $[M+H]^+$ (2) Synthesis of 1-{[(trans-4-aminocyclohexyl)oxy]methyl}cyclopropan-1-ol [258-2] (Hereinafter, Referred to as a Compound [258-2])

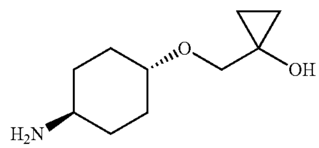 [SMILES: N[C@H]1CC[C@H](OCC2(O)CC2)CC1]

To a solution of the compound [258-1] (45 mg) in ethanol (0.5 mL) was added 20% palladium hydroxide-activated carbon (20 mg) at room temperature, and the mixture was stirred at room temperature for 18 hours under a hydrogen atmosphere. The reaction mixture was filtered, and the filtrate was concentrated under reduced pressure to give the title compound (25 mg) as a colorless oil.

$^1$H-NMR (400 MHz, $CD_3OD$) δ: 3.51 (s, 2H), 3.39-3.32 (m, 1H), 2.77-2.72 (m, 1H), 2.09-2.06 (m, 2H), 1.94-1.91 (m, 2H), 1.33-1.21 (m, 4H), 0.71-0.68 (m, 2H), 0.57-0.50 (m, 2H).

ESI-MS: 186.2 $[M+H]^+$ (3) Synthesis of 4-(furo[3,2-c]pyridin-4-yl)-N-{trans-4-[(1-hydroxycyclopropyl)methoxy]cyclohexyl}benzamide [258]

To a solution of the compound [99-1] (13 mg) in DMF (0.5 mL) were added (1-cyano-2-ethoxy-2-oxoethylideneaminooxy)dimethylaminomorpholinocarbenium hexafluorophosphate (23 mg), DIPEA (9.1 μL), and the compound [258-2] (9.0 mg) at room temperature, and the mixture was stirred at room temperature for 19 hours. To the reaction mixture was added a saturated aqueous sodium bicarbonate solution, and the mixture was extracted with ethyl acetate. The organic layer was washed sequentially with water and saturated saline. The organic layer was dried over anhydrous sodium sulfate and concentrated under reduced pressure. The obtained residue was purified by silica gel column chromatography to give the title compound (6.2 mg) as a white solid.

$^1$H-NMR (400 MHz, $CD_3OD$) δ: 8.53 (d, J=5.9 Hz, 1H), 7.99-7.98 (m, 5H), 7.63 (d, J=5.5 Hz, 1H), 7.19 (d, J=1.1 Hz, 1H), 3.94-3.88 (m, 1H), 3.54 (s, 2H), 3.47-3.43 (m, 1H), 2.17-2.14 (m, 2H), 2.07-2.04 (m, 2H), 1.52-1.35 (m, 4H), 0.71-0.68 (m, 2H), 0.59-0.56 (m, 2H).

ESI-MS: 407.3 $[M+H]^+$

Example 259

Synthesis of 4-(furo[3,2-c]pyridin-4-yl)-N-(trans-4-hydroxy-4-methylcyclohexyl)benzamide [259] (Hereinafter, Referred to as a Compound [259])

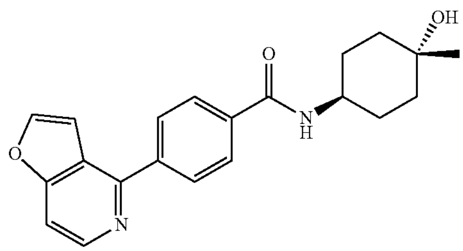 [SMILES: C[C@]1(O)CC[C@H](NC(=O)c2ccc(-c3nccc4occc34)cc2)CC1]

To a solution of the compound [99-1] (50 mg) in DMF (1.0 mL) were added (1-cyano-2-ethoxy-2-oxoethylideneaminooxy)dimethylaminomorpholinocarbenium hexafluorophosphate (116 mg), DIPEA (142 μL), and trans-4-amino-1-methylcyclohexanol (35 mg) at room temperature, and the mixture was stirred at room temperature for 22 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (30 mg) as a reddish brown solid.

$^1$H-NMR (400 MHz, DMSO-$d_6$) δ: 8.59 (d, J=5.5 Hz, 1H), 8.28 (d, J=7.8 Hz, 1H), 8.24 (d, J=2.3 Hz, 1H), 8.08 (d, J=8.2 Hz, 2H), 8.00 (d, J=8.2 Hz, 2H), 7.73-7.71 (m, 1H), 7.37-7.36 (m, 1H), 4.29 (br, 1H), 3.87-3.79 (m, 1H), 1.78-1.75 (m, 2H), 1.62-1.58 (m, 2H), 1.54-1.41 (m, 4H), 1.16 (s, 3H).

ESI-MS: 351.2 $[M+H]^+$

Example 260

Synthesis of 4-(furo[3,2-c]pyridin-4-yl)-N-(4-hydroxybicyclo[2.2.2]octan-1-yl)benzamide [260] (Hereinafter, Referred to as a Compound [260])

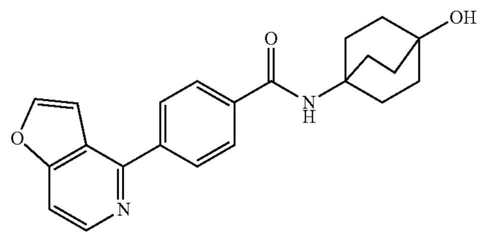 [SMILES: O=C(NC12CCC(O)(CC1)CC2)c1ccc(-c2nccc3occc23)cc1]

To a solution of the compound [99-1] (30 mg) in DMF (1.0 mL) were added (1-cyano-2-ethoxy-2-oxoethylideneaminooxy)dimethylaminomorpholinocarbenium hexafluorophosphate (160 mg), DIPEA (64 μL), and 4-aminobicyclo[2.2.2]octan-1-ol hydrochloride (49 mg) at room temperature, and the mixture was stirred at room temperature for 1 hour. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (31 mg) as a yellow solid.

$^1$H-NMR (400 MHz, DMSO-$d_6$) δ: 8.58 (d, J=5.9 Hz, 1H), 8.24 (d, J=2.3 Hz, 1H), 8.04 (d, J=8.2 Hz, 2H), 7.92 (d, J=8.2 Hz, 2H), 7.74-7.72 (m, 2H), 7.34-7.33 (m, 1H), 3.51 (br, 1H), 2.07-2.03 (m, 6H), 1.64-1.60 (m, 6H).

ESI-MS: 363.2 $[M+H]^+$

Examples 261 to 285

Each compound of Examples 261 to 285 shown in the following Tables was synthesized according to the method of Example 260. The structure, name, and ESI-MS of the compound of each Example are shown in the following Tables.

| Example | Structure | Name | ESI-MS |
|---|---|---|---|
| 261 | 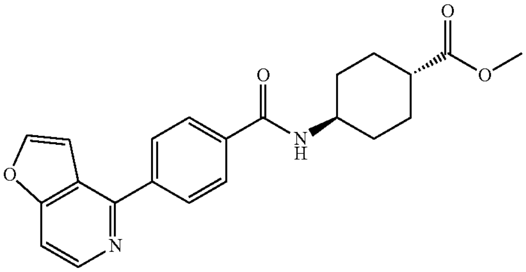 [SMILES: COC(=O)[C@H]1CC[C@H](NC(=O)c2ccc(-c3nccc4occc34)cc2)CC1] | Methyl trans-4-[4-(furo[3,2-c]pyridin-4-yl)benzamide]cyclohexane-1-carboxylate | 379.2 $[M + H]^+$ |
| 262 | 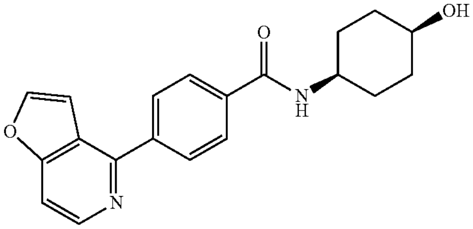 [SMILES: O=C(N[C@H]1CC[C@@H](O)CC1)c1ccc(-c2nccc3occc23)cc1] | 4-(furo[3,2-c]pyridin-4-yl)-N-(cis-4-hydroxycyclohexyl)benzamide | 337.2 $[M + H]^+$ |
| 263 | 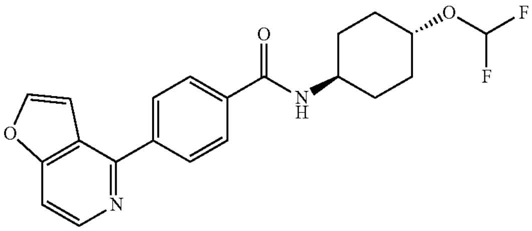 [SMILES: O=C(N[C@H]1CC[C@H](OC(F)F)CC1)c1ccc(-c2nccc3occc23)cc1] | N-[trans-4-(difluoromethoxy)cyclohexyl]-4-(furo[3,2-c]pyridin-4-yl)benzamide | 387.2 $[M + H]^+$ |
| 264 | 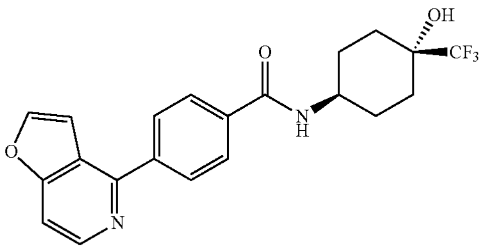 [SMILES: O=C(N[C@H]1CC[C@@](O)(C(F)(F)F)CC1)c1ccc(-c2nccc3occc23)cc1] | 4-(furo[3,2-c]pyridin-4-yl)-N-[trans-4-hydroxy-4-(trifluoromethyl)cyclohexyl]benzamide | 405.2 $[M + H]^+$ |
| 265 | 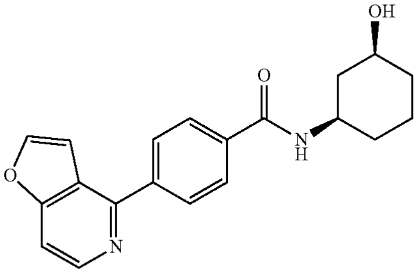 [SMILES: O=C(N[C@@H]1CCC[C@H](O)C1)c1ccc(-c2nccc3occc23)cc1] | 4-(furo[3,2-c]pyridin-4-yl)-N-(cis-3-hydroxycyclohexyl)benzamide | 337.2 $[M + H]^+$ |
| 266 | 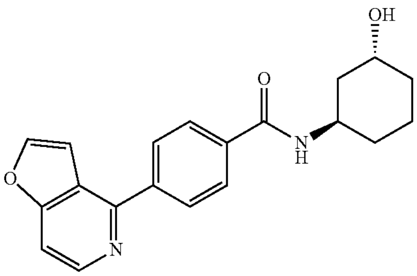 [SMILES: O=C(N[C@@H]1CCC[C@@H](O)C1)c1ccc(-c2nccc3occc23)cc1] | 4-(furo[3,2-c]pyridin-4-yl)-N-(trans-3-hydroxycyclohexyl)benzamide | 337.2 $[M + H]^+$ |

-continued

| Example | Structure | Name | ESI-MS |
| --- | --- | --- | --- |
| 267 | 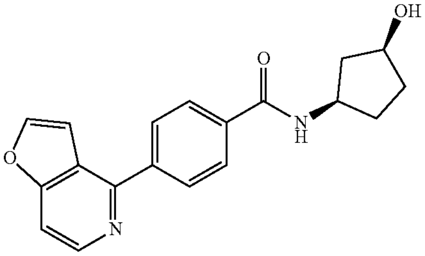 [SMILES: O=C(N[C@@H]1CC[C@H](O)C1)c1ccc(-c2nccc3occc23)cc1] | 4-(furo[3,2-c]pyridin-4-yl)-N-(cis-3-hydroxycyclopenthyl) benzamide | 323.2 $[M + H]^+$ |
| 268 | 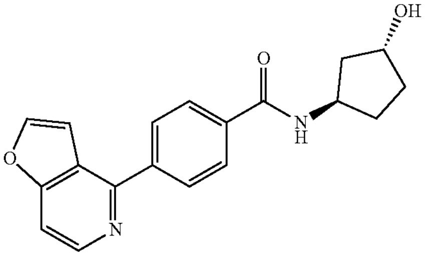 [SMILES: O=C(N[C@@H]1CC[C@@H](O)C1)c1ccc(-c2nccc3occc23)cc1] | 4-(furo[3,2-c]pyridin-4-yl)-N-(trans-3-hydroxycyclopenthyl) benzamide | 323.2 $[M + H]^+$ |
| 269 | 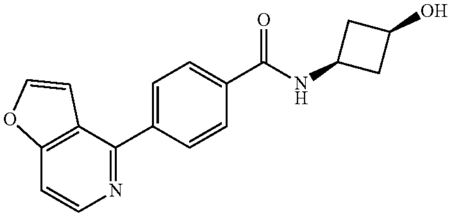 [SMILES: O=C(N[C@H]1C[C@@H](O)C1)c1ccc(-c2nccc3occc23)cc1] | 4-(furo[3,2-c]pyridin-4-yl)-N-(cis-3-hydroxycyclobutyl) benzamide | 309.2 $[M + H]^+$ |
| 270 | 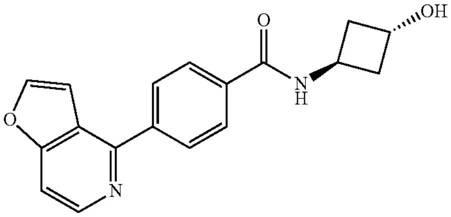 [SMILES: O=C(N[C@H]1C[C@H](O)C1)c1ccc(-c2nccc3occc23)cc1] | 4-(furo[3,2-c]pyridin-4-yl)-N-(trans-3-hydroxycyclobutyl) benzamide | 309.2 $[M + H]^+$ |
| 271 | 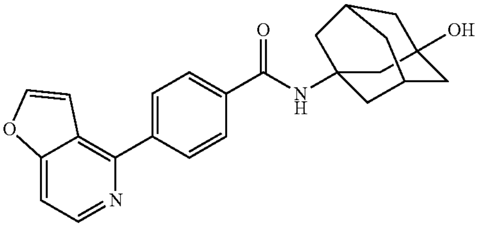 [SMILES: O=C(NC12CC3CC(CC(O)(C3)C1)C2)c1ccc(-c2nccc3occc23)cc1] | 4-(furo[3,2-c]pyridin-4-yl)-N-(3-hydroxyadamantan-1-yl)benzamide | 389.2 $[M + H]^+$ |
| 272 | 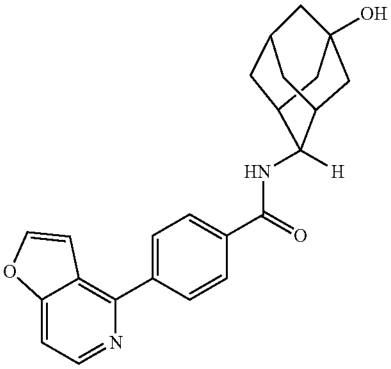 [SMILES: O=C(NC1C2CC3CC1CC(O)(C3)C2)c1ccc(-c2nccc3occc23)cc1] | 4-(furo[3,2-c]pyridin-4-yl)-N-(trans-5-hydroxyadamantan-2-yl)benzamide | 389.2 $[M + H]^+$ |

-continued

| Example | Structure | Name | ESI-MS |
|---|---|---|---|
| 273 | 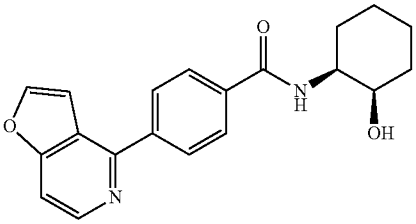 [SMILES: O=C(N[C@H]1CCCC[C@H]1O)c1ccc(-c2nccc3occc23)cc1] | 4-(furo[3,2-c]pyridin-4-yl)-N-(cis-2-hydroxycyclohexyl) benzamide | 337.2 $[M + H]^+$ |
| 274 | 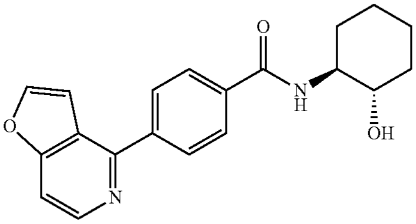 [SMILES: O=C(N[C@H]1CCCC[C@@H]1O)c1ccc(-c2nccc3occc23)cc1] | 4-(furo[3,2-c]pyridin-4-yl)-N-(trans-2-hydroxycyclohexyl) benzamide | 337.2 $[M + H]^+$ |
| 275 | 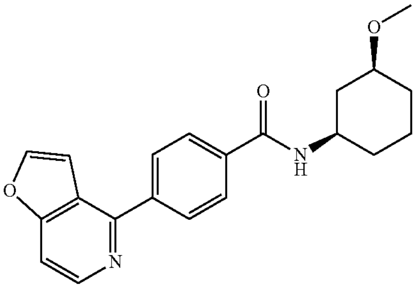 [SMILES: CO[C@H]1CCC[C@@H](NC(=O)c2ccc(-c3nccc4occc34)cc2)C1] | 4-(furo[3,2-c]pyridin-4-yl)-N-(cis-3-methoxycyclohexyl) benzamide | 351.2 $[M + H]^+$ |
| 276 | 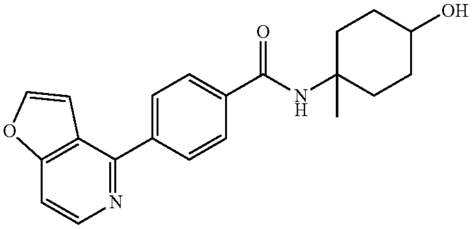 [SMILES: CC1(NC(=O)c2ccc(-c3nccc4occc34)cc2)CCC(O)CC1] | 4-(furo[3,2-c]pyridin-4-yl)-N-(4-hydroxy-1-methylcyclohexyl) benzamide | 351.2 $[M + H]^+$ |
| 277 | 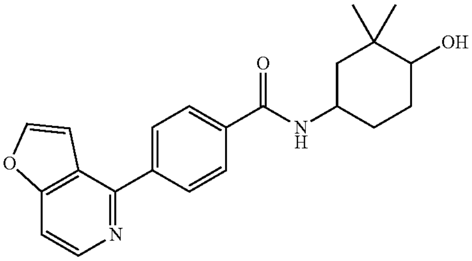 [SMILES: CC1(C)CC(NC(=O)c2ccc(-c3nccc4occc34)cc2)CCC1O] | 4-(furo[3,2-c]pyridin-4-yl)-N-(4-hydroxy-3,3-dimethylcyclohexyl) benzamide | 365.3 $[M + H]^+$ |
| 278 | 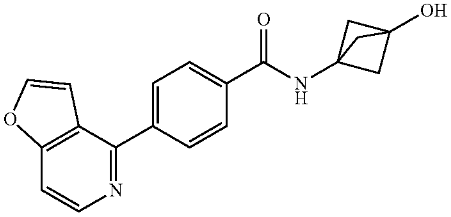 [SMILES: O=C(NC12CC(O)(C1)C2)c1ccc(-c2nccc3occc23)cc1] | 4-(furo[3,2-c]pyridin-4-yl)-N-(3-hydroxybicyclo [1.1.1]pentan-1-yl)benzamide | 321.2 $[M + H]^+$ |

-continued

| Example | Structure | Name | ESI-MS |
|---|---|---|---|
| 279 | 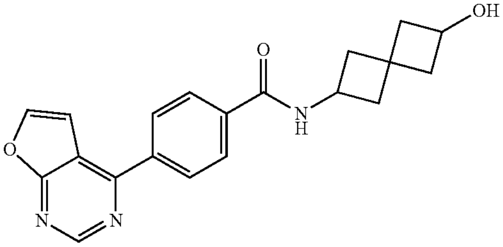 [SMILES: O=C(NC1CC2(CC(O)C2)C1)c1ccc(-c2ncnc3occc23)cc1] | 4-(furo[3,2-c]pyridin-4-yl)-N-[6-(2-hydroxypropan-2-yl)spiro[3.3]heptan-2-yl]benzamide | 349.2 $[M + H]^+$ |
| 280 | 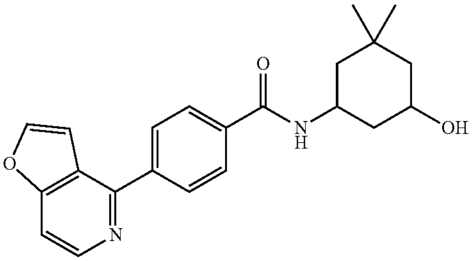 [SMILES: CC1(C)CC(O)CC(NC(=O)c2ccc(-c3nccc4occc34)cc2)C1] | 4-(furo[3,2-c]pyridin-4-yl)-N-(5-hydroxy-3,3-dimethylcyclohexyl)benzamide | 365.2 $[M + H]^+$ |
| 281 | 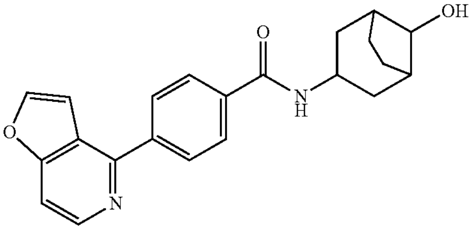 [SMILES: O=C(NC1CC2CCC(C1)C2O)c1ccc(-c2nccc3occc23)cc1] | 4-(furo[3,2-c]pyridin-4-yl)-N-(8-hydroxy-bicyclo[3.2.1]octan-3-yl)benzamide | 363.2 $[M + H]^+$ |
| 282 | 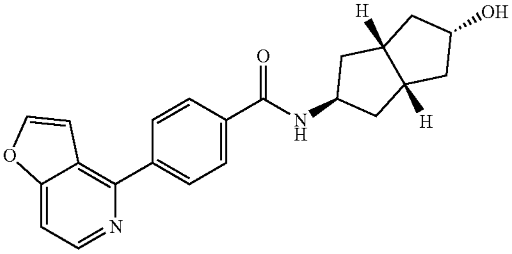 [SMILES: O=C(N[C@@H]1C[C@H]2C[C@@H](O)C[C@H]2C1)c1ccc(-c2nccc3occc23)cc1] | 4-(furo[3,2-c]pyridin-4-yl)-N-[(2r,3aR,5r,6aS)-5-hydroxyocta-hydropentalen-2-yl]benzamide | 363.2 $[M + H]^+$ |
| 283 | 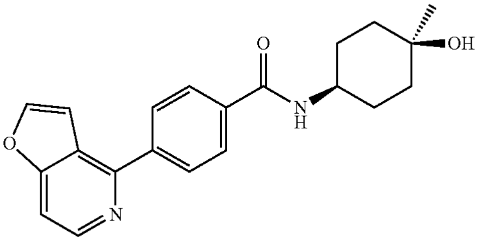 [SMILES: C[C@]1(O)CC[C@@H](NC(=O)c2ccc(-c3nccc4occc34)cc2)CC1] | 4-(furo[3,2-c]pyridin-4-yl)-N-(cis-4-hydroxy-4-methylcyclohexyl)benzamide | 351.2 $[M + H]^+$ |
| 284 | 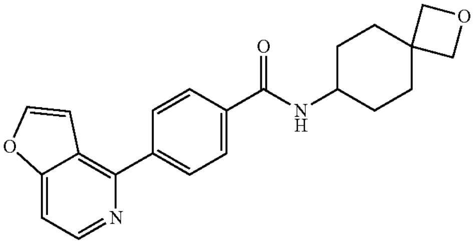 [SMILES: O=C(NC1CCC2(CC1)COC2)c1ccc(-c2nccc3occc23)cc1] | 4-(furo[3,2-c]pyridin-4-yl)-N-(2-oxaspiro[3.5]nonan-7-yl)benzamide | 363.2 $[M + H]^+$ |

-continued

| Example | Structure | Name | ESI-MS |
|---|---|---|---|
| 285 | 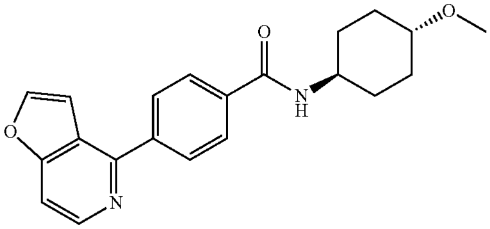 [SMILES: CO[C@H]1CC[C@H](NC(=O)c2ccc(-c3nccc4occc34)cc2)CC1] | 4-(furo[3,2-c]pyridin-4-yl)-N-(trans-4-methoxycyclohexyl) benzamide | 351.2 $[M+H]^+$ |

Example 286

Synthesis of 4-(furo[3,2-c]pyridin-4-yl)-N-[trans-4-(methoxy-$d_3$)cyclohexyl]benzamide [286] (Hereinafter, Referred to as a Compound [286])

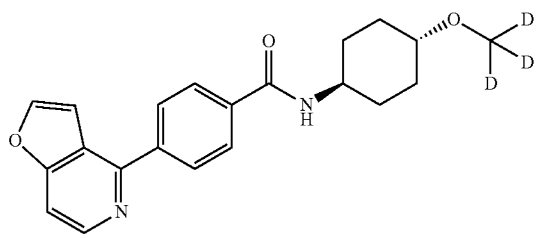 [SMILES: [2H]C([2H])([2H])O[C@H]1CC[C@H](NC(=O)c2ccc(-c3nccc4occc34)cc2)CC1]

(1) Synthesis of trans-N,N-dibenzyl-4-(methoxy-$d_3$) cyclohexane-1-amine [286-1] (Hereinafter, Referred to as a Compound [286-1])

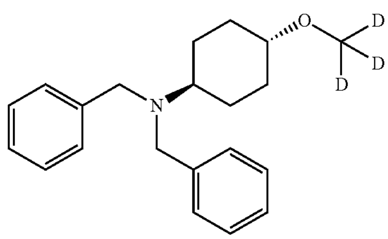 [SMILES: [2H]C([2H])([2H])O[C@H]1CC[C@H](N(Cc2ccccc2)Cc2ccccc2)CC1]

To a solution of the compound [64-1] (200 mg) in THE (3.4 mL) were added 60% sodium hydride (82 mg) and methyl iodide-$d_3$ (60 μL) at 0° C., and the mixture was stirred at room temperature for 1 hour. To the reaction mixture was added a saturated aqueous ammonium chloride solution, and the mixture was extracted with ethyl acetate. The organic layer was dried over anhydrous sodium sulfate and concentrated under reduced pressure. The obtained residue was purified by silica gel column chromatography to give the title compound (199 mg) as a colorless oil.

$^1$H-NMR (400 MHz, $CDCl_3$) δ: 7.37-7.18 (m, 10H), 3.61 (s, 4H), 3.10-3.00 (m, 1H), 2.58-2.47 (m, 1H), 2.09-2.03 (m, 2H), 1.96-1.90 (m, 2H), 1.41-1.37 (m, 2H), 1.13-1.02 (m, 2H).

ESI-MS: 313.3 $[M+H]^+$ (2) Synthesis of 4-(furo[3,2-c]pyridin-4-yl)-N-[trans-4-(methoxy-$d_3$)cyclohexyl]benzamide [286]

The title compound was synthesized from the compound [286-1] according to the methods of steps (3) and (4) in Example 257.

$^1$H-NMR (400 MHz, DMSO-$d_6$) δ: 8.58 (d, J=5.7 Hz, 1H), 8.34 (d, J=7.8 Hz, 1H), 8.24 (d, J=2.3 Hz, 1H), 8.08 (dd, J=6.4, 1.8 Hz, 2H), 8.00 (dd, J=6.9, 1.8 Hz, 2H), 7.72 (d, J=5.5 Hz, 1H), 7.36-7.35 (m, 1H), 3.82-3.76 (m, 1H), 3.13-3.03 (m, 1H), 2.07-2.02 (m, 2H), 1.90-1.86 (m, 2H), 1.45-1.32 (m, 2H), 1.26-1.19 (m, 2H).

ESI-MS: 354.2 $[M+H]^+$

Example 287

Synthesis of N-(trans-4-ethoxycyclohexyl)-4-(furo[3,2-c]pyridin-4-yl)benzamide [287] (Hereinafter, Referred to as a Compound [287])

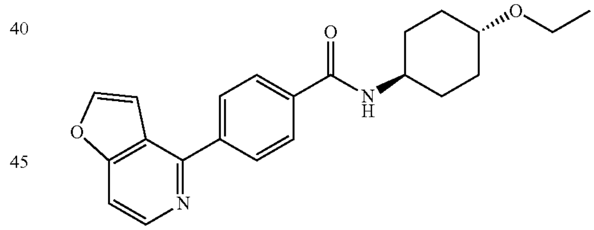

(1) Synthesis of trans-N,N-dibenzyl-4-ethoxycyclohexane-1-amine [287-1] (Hereinafter, Referred to as a Compound [287-1])

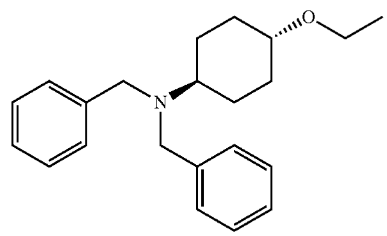 [SMILES: CCO[C@H]1CC[C@H](N(Cc2ccccc2)Cc2ccccc2)CC1]

The title compound was synthesized by a method according to the step (1) in Example 286, using ethyl iodide in place of methyl iodide-$d_3$.

ESI-MS: 324.3 $[M+H]^+$ (2) Synthesis of N-(trans-4-ethoxycyclohexyl)-4-(furo[3,2-c]pyridin-4-yl)benzamide [287]

The title compound was synthesized from the compound [287-1] according to the methods of steps (3) and (4) in Example 257.

ESI-MS: 365.2 $[M+H]^+$

Example 288

Synthesis of 4-(furo[3,2-c]pyridin-4-yl)-N-(trans-4-isopropoxycyclohexyl)benzamide [288] (Hereinafter, Referred to as a Compound [288])

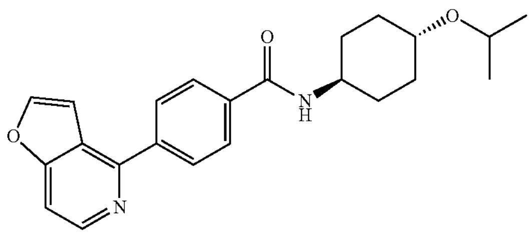 [SMILES: CC(C)O[C@H]1CC[C@H](NC(=O)c2ccc(-c3nccc4occc34)cc2)CC1]

(1) Synthesis of trans-N,N-dibenzyl-4-isopropoxy-cyclohexane-1-amine [288-1] (Hereinafter, Referred to as a Compound [288-1])

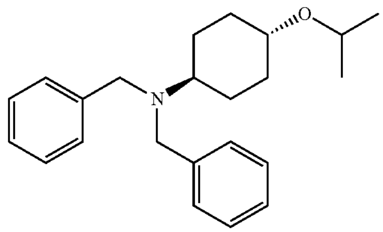 [SMILES: CC(C)O[C@H]1CC[C@H](N(Cc2ccccc2)Cc2ccccc2)CC1]

The title compound was synthesized by a method according to the step (1) in Example 286, using isopropyl iodide in place of methyl iodide-$d_3$.

ESI-MS: 338.3 $[M+H]^+$ (2) Synthesis of 4-(furo[3,2-c]pyridin-4-yl)-N-(trans-4-isopropoxycyclohexyl)benzamide [288]

The title compound was synthesized from the compound [288-1] according to the methods of steps (3) and (4) in Example 257.

$^1$H-NMR (400 MHz, $CD_3OD$) δ: 8.51 (d, J=5.9 Hz, 1H), 8.00-7.99 (m, 5H), 7.61 (dd, J=5.9, 0.9 Hz, 1H), 7.18 (d, J=0.9 Hz, 1H), 3.93-3.86 (m, 1H), 3.82-3.76 (m, 1H), 3.40-3.38 (m, 1H), 2.06-2.04 (m, 4H), 1.65-1.52 (m, 4H), 1.13 (d, J=5.9 Hz, 6H).

ESI-MS: 379.3 $[M+H]^+$

Example 289

Synthesis of N-(trans-4-ethyl-4-hydroxycyclohexyl)-4-(furo[3,2-c]pyridin-4-yl)benzamide [289] (Hereinafter, Referred to as a Compound [289])

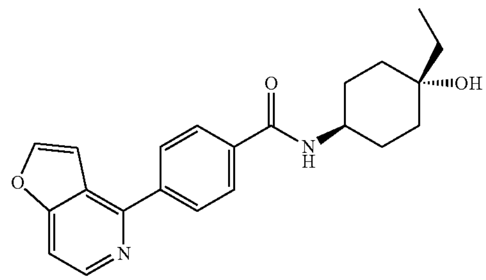 [SMILES: CC[C@]1(O)CC[C@H](NC(=O)c2ccc(-c3nccc4occc34)cc2)CC1]

(1) Synthesis of trans-4-(dibenzylamino)-1-ethylcyclohexan-1-ol [289-1-a] (Hereinafter, Referred to as a Compound [289-1-a]) and cis-4-(dibenzylamino)-1-ethylcyclohexan-1-ol [289-1-b] (Hereinafter, Referred to as a Compound [289-1-b])

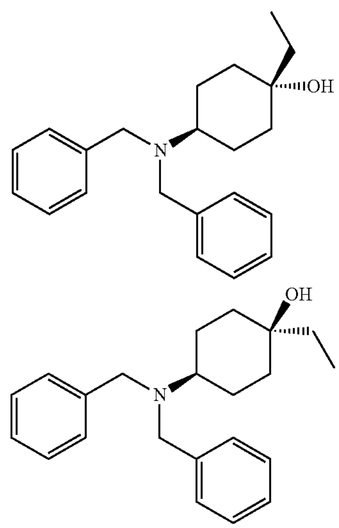

To a solution of 4-(dibenzylamino)cyclohexanone (1.0 g) in toluene (15 mL) was added a solution of 1.1 M triethylaluminum in toluene (6.8 mL) at room temperature, and the mixture was stirred at room temperature for 16 hours. A 2 M aqueous sodium hydroxide solution (4.5 mL) was added dropwise to the reaction mixture, and the mixture was extracted with ethyl acetate. The organic layer was dried over anhydrous sodium sulfate and concentrated under reduced pressure. The obtained residue was purified by silica gel column chromatography to give the title compound [289-1-a] (96 mg) and the title compound [289-1-b] (102 mg) as white solids.

Compound [289-1-a]

$^1$H-NMR (400 MHz, $CDCl_3$) δ: 7.35-7.17 (m, 10H), 3.63 (s, 4H), 2.57-2.53 (m, 1H), 1.77-1.75 (m, 4H), 1.54 (q, J=7.5 Hz, 2H), 1.47-1.37 (m, 2H), 1.31-1.23 (m, 2H), 0.87 (t, J=7.5 Hz, 3H).

ESI-MS: 324.2 $[M+H]^+$

Compound [289-1-b]

$^1$H-NMR (400 MHz, $CDCl_3$) δ: 7.38-7.18 (m, 10H), 3.66 (s, 4H), 2.48-2.44 (m, 1H), 1.80-1.58 (m, 6H), 1.39 (q, J=7.5 Hz, 2H), 1.28-1.18 (m, 2H), 0.86 (t, J=7.5 Hz, 3H).

ESI-MS: 324.2 $[M+H]^+$ (2) Synthesis of N-(trans-4-ethyl-4-hydroxycyclohexyl)-4-(furo[3,2-c]pyridin-4-yl)benzamide [289]

The title compound was synthesized from the compound [289-1-a] according to the methods of steps (3) and (4) in Example 257.

ESI-MS: 365.2 $[M+H]^+$

Example 290

Synthesis of N-(cis-4-ethyl-4-hydroxycyclohexyl)-4-(furo[3,2-c]pyridin-4-yl)benzamide [290] (Hereinafter, Referred to as a Compound [290])

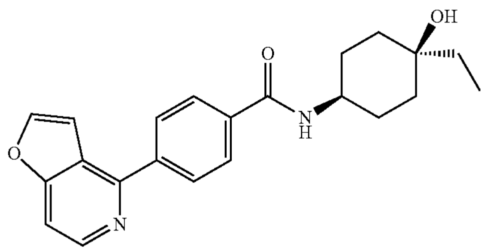 [SMILES: CC[C@]1(O)CC[C@@H](NC(=O)c2ccc(-c3nccc4occc34)cc2)CC1]

The title compound was synthesized from the compound [289-1-b] according to the methods of steps (3) and (4) in Example 257.

ESI-MS: 365.2 $[M+H]^+$

Example 291

Synthesis of N-(cis-4-cyclopropyl-4-hydroxycyclohexyl)-4-(furo[3,2-c]pyridin-4-yl)benzamide [291] (Hereinafter, Referred to as a Compound [291])

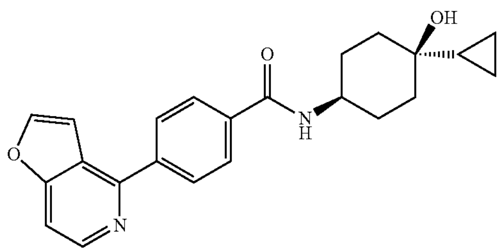 [SMILES: O=C(N[C@H]1CC[C@](O)(C2CC2)CC1)c1ccc(-c2nccc3occc23)cc1]

(1) Synthesis of cis-1-cyclopropyl-4-(dibenzylamino)cyclohexan-1-ol [291-1] (Hereinafter, Referred to as a Compound [291-1])

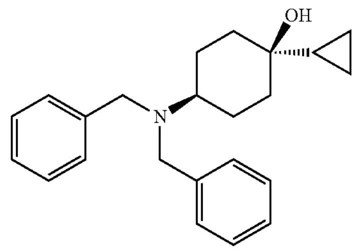 [SMILES: O[C@]1(C2CC2)CC[C@H](N(Cc2ccccc2)Cc2ccccc2)CC1]

To a solution of 4-(dibenzylamino)cyclohexanone (500 mg) in THF (57 mL) was added a solution of 0.7 M cyclopropylmagnesium bromide in THF (14.6 mL) at room temperature, and the mixture was stirred at room temperature for 4 hours. To the reaction mixture was added a saturated aqueous ammonium chloride solution, and the mixture was extracted with ethyl acetate. The organic layer was dried over anhydrous sodium sulfate and concentrated under reduced pressure. The obtained residue was purified by silica gel column chromatography to give the title compound (104 mg) as a white solid.

ESI-MS: 336.2 $[M+H]^+$ (2) Synthesis of N-(cis-4-cyclopropyl-4-hydroxycyclohexyl)-4-(furo[3,2-c]pyridin-4-yl)benzamide [291]

The title compound was synthesized from the compound [291-1] according to the methods of steps (3) and (4) in Example 257.

ESI-MS: 377.3 $[M+H]^+$

Example 292

Synthesis of 4-(furo[3,2-c]pyridin-4-yl)-N-(cis-4-hydroxy-4-isopropylcyclohexyl)benzamide [292] (Hereinafter, Referred to as a Compound [292])

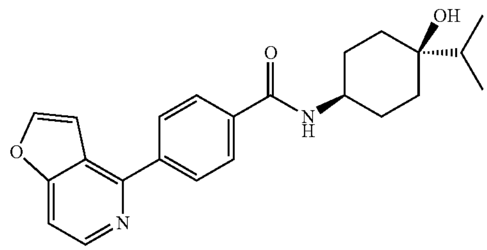 [SMILES: CC(C)[C@]1(O)CC[C@@H](NC(=O)c2ccc(-c3nccc4occc34)cc2)CC1]

(1) Synthesis of cis-4-(dibenzylamino)-1-isopropylcyclohexan-1-ol [292-1] (Hereinafter, Referred to as a Compound [292-1])

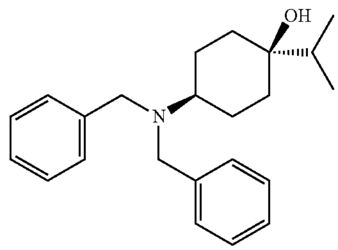 [SMILES: CC(C)[C@]1(O)CC[C@@H](N(Cc2ccccc2)Cc2ccccc2)CC1]

The title compound was synthesized by a method according to the step (1) in Example 291, using a solution of 2 M isopropylmagnesium chloride in THE in place of a solution of 0.7 M cyclopropylmagnesium bromide in THE.

ESI-MS: 338.3 [M+H]+

(2) Synthesis of 4-(furo[3,2-c]pyridin-4-yl)-N-(cis-4-hydroxy-4-isopropylcyclohexyl)benzamide [292]

The title compound was synthesized from the compound [292-1] according to the methods of steps (3) and (4) in Example 257.

ESI-MS: 379.3 [M+H]+

Example 293

Synthesis of 4-(furo[3,2-c]pyridin-4-yl)-N-(cis-4-hydroxycycloheptyl)benzamide [293] (Hereinafter, Referred to as a Compound [293])

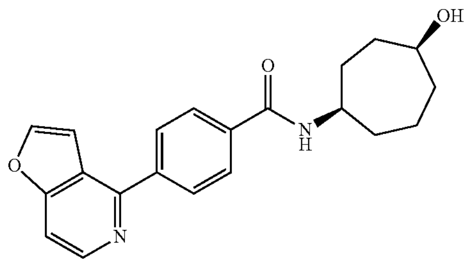 [SMILES: O=C(N[C@@H]1CCC[C@H](O)CC1)c1ccc(-c2nccc3occc23)cc1]

(1) Synthesis of cis-4-aminocycloheptan-1-ol hydrochloride [293-1] (Hereinafter, Referred to as a Compound [293-1])

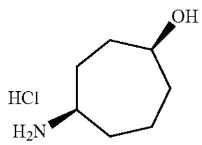

To a solution of tert-butyl N-(4-oxocycloheptyl) carbamate (120 mg) in methanol (5.4 mL) was added sodium borohydride (31 mg) at room temperature, and the mixture was stirred at room temperature for 1 hour. To the reaction mixture was added water, and the mixture was extracted with ethyl acetate. The organic layer was dried over anhydrous sodium sulfate and concentrated under reduced pressure. To the obtained residue was added a solution of 4 M hydrogen chloride in ethyl acetate (2.0 mL) at room temperature, and the mixture was stirred at room temperature for 4 hours. The reaction mixture was concentrated under reduced pressure to give the title compound (85 mg) as a yellow oil.

ESI-MS: 130.2 [M+H]+

(2) Synthesis of 4-(furo[3,2-c]pyridin-4-yl)-N-(cis-4-hydroxycycloheptyl)benzamide [293]

The title compound was synthesized from the compound [293-1] according to the method of Example 190.

ESI-MS: 351.2 [M+H]+

Example 294

Synthesis of N-{trans-4-[(2,2-difluoroethyl)amino]cyclohexyl}-4-(furo[3,2-c]pyridin-4-yl)benzamide [294] (Hereinafter, Referred to as a Compound [294])

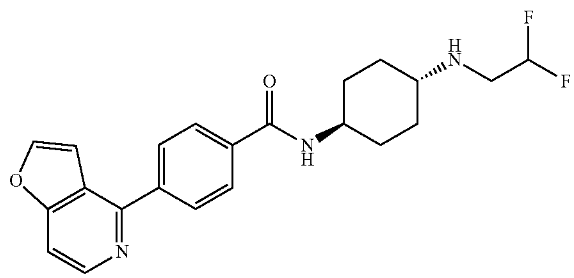 [SMILES: O=C(N[C@H]1CC[C@H](NCC(F)F)CC1)c1ccc(-c2nccc3occc23)cc1]

(1) Synthesis of N-(trans-4-aminocyclohexyl)-4-(furo[3,2-c]pyridin-4-yl)benzamide [294-1] (Hereinafter, Referred to as a Compound [294-1])

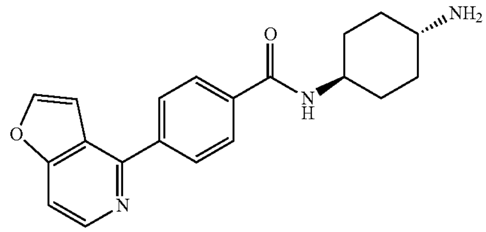 [SMILES: N[C@H]1CC[C@H](NC(=O)c2ccc(-c3nccc4occc34)cc2)CC1]

To a solution of the compound [99-1] (50 mg) in methanol (2.0 mL)/toluene (1.0 mL) were added 4-(4,6-dimethoxy-1,3,5-triazin-2-yl)-4-methylmorpholinium chloride (290 mg) and trans-1,4-cyclohexanediamine (150 mg) at room temperature, and the mixture was stirred at 110° C. for 17 hours. The reaction mixture was concentrated under reduced pressure. The obtained residue was purified by silica gel column chromatography to give the title compound (30 mg) as a white solid.

$^1$H-NMR (400 MHz, DMSO-$d_6$) δ: 8.55 (d, J=5.5 Hz, 1H), 8.29-8.28 (m, 1H), 8.21 (d, J=2.3 Hz, 1H), 8.04 (d,

J=8.2 Hz, 2H), 7.97 (d, J=8.2 Hz, 2H), 7.69 (d, J=5.5 Hz, 1H), 7.33-7.32 (m, 1H), 3.72-3.69 (m, 1H), 3.28 (br, 2H), 2.55-2.45 (m, 1H), 1.81-1.77 (m, 4H), 1.41-1.32 (m, 2H), 1.18-1.12 (m, 2H).

ESI-MS: 336.2 $[M+H]^+$ (2) Synthesis of N-{trans-4-[(2,2-difluoroethyl) amino]cyclohexyl}-4-(furo[3,2-c]pyridin-4-yl)benzamide [294]

To a solution of the compound [294-1] (14 mg) in 1,4-dioxane (0.5 mL) were added DIPEA (15 μL) and 2,2-difluoroethyl trifluoromethanesulfonate (40 μL) at room temperature, and the mixture was stirred at room temperature for 17 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (8.2 mg) as a white solid.

$^1$H-NMR (400 MHz, DMSO-$d_6$) δ: 8.56 (d, J=5.9 Hz, 1H), 8.32 (d, J=7.8 Hz, 1H), 8.21 (d, J=1.8 Hz, 1H), 8.06 (d, J=8.2 Hz, 2H), 7.98 (d, J=8.2 Hz, 2H), 7.70 (d, J=5.5 Hz, 1H), 7.37-7.36 (m, 1H), 5.96 (t, J=63.0 Hz, 1H), 3.80-3.70 (m, 1H), 3.10-2.85 (m, 2H), 2.44-2.38 (m, 1H), 1.97-1.83 (m, 5H), 1.40-1.31 (m, 2H), 1.15-1.10 (m, 2H).

ESI-MS: 400.3 $[M+H]^+$

Example 295

Synthesis of 4-(furo[3,2-c]pyridin-4-yl)-N-[trans-4-(oxetan-3-ylamino)cyclohexyl]benzamide [295] (Hereinafter, Referred to as a Compound [295])

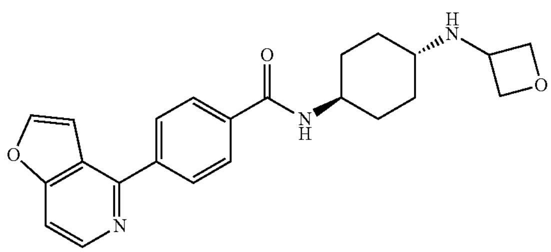 [SMILES: O=C(N[C@H]1CC[C@H](NC2COC2)CC1)c1ccc(-c2nccc3occc23)cc1]

To a solution of the compound [294-1] (53 mg) in dichloromethane (1.6 mL)/DMF (1.0 mL) were added sodium acetate (54 mg), 3-oxetanone (16 mg), and sodium cyanoborohydride (50 mg) at room temperature, and the mixture was stirred at 80° C. for 16 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (22 mg) as a white solid.

$^1$H-NMR (400 MHz, DMSO-$d_6$) δ: 8.58 (dd, J=5.7, 2.1 Hz, 1H), 8.32 (d, J=6.9 Hz, 1H), 8.23 (d, J=2.3 Hz, 1H), 8.08 (d, J=6.4 Hz, 2H), 8.00 (d, J=6.4 Hz, 2H), 7.72 (d, J=5.9 Hz, 1H), 7.37-7.36 (m, 1H), 4.62 (dd, J=6.2, 5.9 Hz, 2H), 4.30 (dd, J=6.2, 5.9 Hz, 2H), 3.97-3.94 (m, 1H), 3.76-3.68 (m, 1H), 3.46-3.40 (m, 1H), 2.40-2.36 (m, 1H), 1.89-1.75 (m, 4H), 1.40-1.31 (m, 2H), 1.15-1.06 (m, 2H).

ESI-MS: 392.2 $[M+H]^+$

Example 296

Synthesis of N-(trans-4-acetamidocyclohexyl)-4-(furo[3,2-c]pyridin-4-yl)benzamide [296] (Hereinafter, Referred to as a Compound [296])

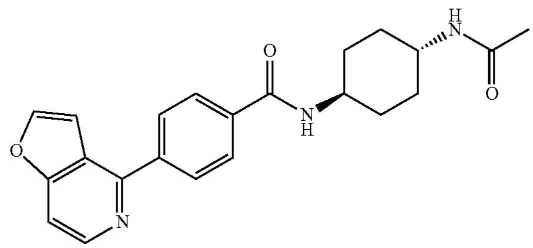 [SMILES: CC(=O)N[C@H]1CC[C@H](NC(=O)c2ccc(-c3nccc4occc34)cc2)CC1]

To a solution of the compound [294-1] (10 mg) in ethyl acetate (0.5 mL) were added acetic anhydride (36 μL) and DIPEA (65 μL) at room temperature, and the mixture was stirred at room temperature for 90 minutes. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (5.4 mg) as a white solid.

ESI-MS: 378.2 $[M+H]^+$

Example 297

Synthesis of 4-(furo[3,2-c]pyridin-4-yl)-N-[trans-4-(5-methyl-1H-tetrazol-1-yl)cyclohexyl]benzamide [297] (Hereinafter, Referred to as a Compound [297])

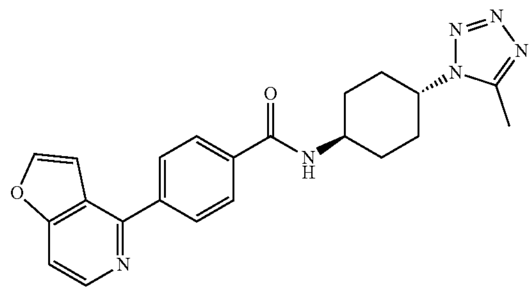 [SMILES: Cc1nnnn1[C@H]1CC[C@H](NC(=O)c2ccc(-c3nccc4occc34)cc2)CC1]

To a solution of the compound [296] (10 mg) in pyridine (0.2 mL) was added diphenylphosphate azide (72 μL) at room temperature, and the mixture was stirred at 115° C. for 6 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (5.0 mg) as a yellow solid.

ESI-MS: 403.2 $[M+H]^+$

Example 298

Synthesis of 4-(furo[3,2-c]pyridin-4-yl)-N-(trans-4-propionamidocyclohexyl)benzamide [298] (Hereinafter, Referred to as a Compound [298])

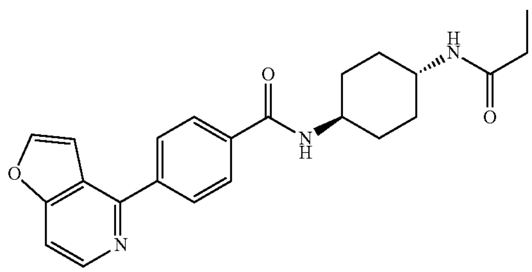 [SMILES: CCC(=O)N[C@H]1CC[C@H](NC(=O)c2ccc(-c3nccc4occc34)cc2)CC1]

To a solution of the compound [294-1] (20 mg) in THE (0.6 mL) were added pyridine (16 μL) and propionyl chloride (6.8 μL) at 0° C., and the mixture was stirred at room temperature for 24 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (5.2 mg) as a white solid.

ESI-MS: 392.2 $[M+H]^+$

Example 299

Synthesis of 4-(furo[3,2-c]pyridin-4-yl)-N-[trans-4-(2-oxopyrrolidin-1-yl)cyclohexyl]benzamide [299] (Hereinafter, Referred to as a Compound [299])

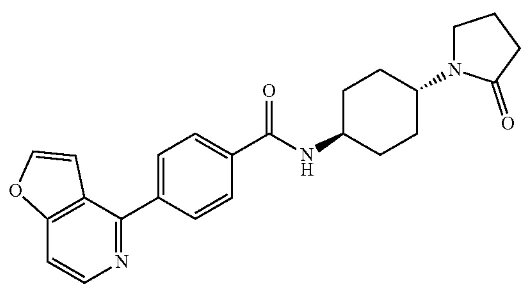 [SMILES: O=C(N[C@H]1CC[C@H](N2CCCC2=O)CC1)c1ccc(-c2nccc3occc23)cc1]

To a solution of the compound [294-1] (67 mg) in 1,4-dioxane (0.7 mL) were added 60% sodium hydride (21 mg) and 4-chlorobutyryl chloride (34 μL) at room temperature, and the mixture was stirred at 80° C. for 48 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (15 mg) as a white solid.

ESI-MS: 404.3 $[M+H]^+$

Example 300

Synthesis of 4-(furo[3,2-c]pyridin-4-yl)-N-[trans-4-(2-oxopiperidin-1-yl)cyclohexyl]benzamide [300] (Hereinafter, Referred to as a Compound [300])

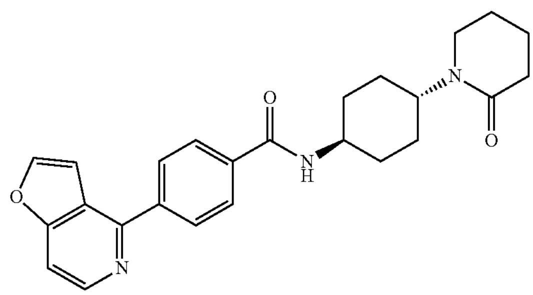 [SMILES: O=C(N[C@H]1CC[C@H](N2CCCCC2=O)CC1)c1ccc(-c2nccc3occc23)cc1]

The title compound was synthesized by a method according to Example 299, using 5-chloropentanoyl chloride in place of 4-chlorobutyryl chloride.

ESI-MS: 418.3 $[M+H]^+$

Example 301

Synthesis of 4-(furo[3,2-c]pyridin-4-yl)-N-{trans-4-[(2-methoxyethyl)amino]cyclohexyl}benzamide [301] (Hereinafter, Referred to as a Compound [301])

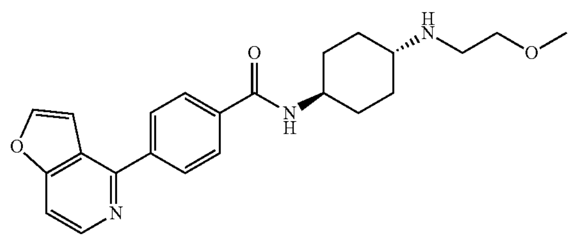 [SMILES: COCCN[C@H]1CC[C@H](NC(=O)c2ccc(-c3nccc4occc34)cc2)CC1]

To a solution of the compound [294-1] (35 mg) in 1,4-dioxane (1.0 mL) were added 2-bromoethyl methyl ether (12 μL) and potassium carbonate (43 mg) at room temperature, and the mixture was stirred at 100° C. for 8 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (3.2 mg) as a white solid.

ESI-MS: 394.2 $[M+H]^+$

Example 302

Synthesis of N-{trans-4-[(1,1-difluoropropan-2-yl)amino]cyclohexyl}-4-(furo[3,2-c]pyridin-4-yl)benzamide [302] (Hereinafter, Referred to as a Compound [302])

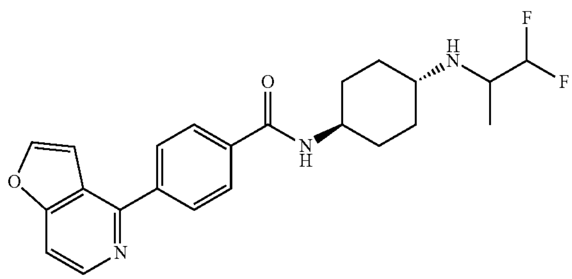 [SMILES: CC(N[C@H]1CC[C@H](NC(=O)c2ccc(-c3nccc4occc34)cc2)CC1)C(F)F]

To a solution of the compound [294-1] (17 mg) in dichloromethane (0.3 mL) were added 1,1-difluoroacetone (4.5 μL) and sodium cyanoborohydride (31 mg) at room temperature, and the mixture was stirred at 80° C. for 16 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (2.1 mg) as a white solid.

ESI-MS: 414.2 $[M+H]^+$

Example 303

Synthesis of 4-(furo[3,2-c]pyridin-4-yl)-N-(4-oxocyclohexyl)benzamide [303] (Hereinafter, Referred to as a Compound [303])

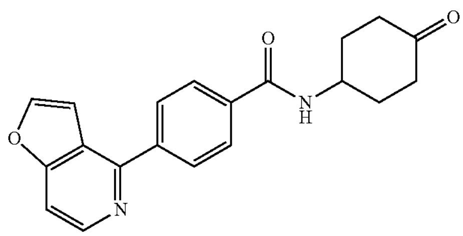 [SMILES: O=C1CCC(NC(=O)c2ccc(-c3nccc4occc34)cc2)CC1]

To a solution of the compound [256] (165 mg) in dichloromethane (5.0 mL) was added 1,1,1-triacetoxy-1,1-dihydro-1,2-benziodoxol-3(1H)-one (Dess-Martin periodinane) (270 mg) at room temperature, and the mixture was stirred for 5 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (104 mg) as a yellow solid.

$^1$H-NMR (400 MHz, DMSO-$d_6$) δ: 8.59 (d, J=5.9 Hz, 1H), 8.49 (d, J=7.3 Hz, 1H), 8.24 (d, J=2.3 Hz, 1H), 8.10 (d, J=8.2 Hz, 2H), 8.03 (d, J=8.2 Hz, 2H), 7.73 (d, J=5.5 Hz, 1H), 7.37-7.36 (m, 1H), 4.35-4.32 (m, 1H), 2.54-2.50 (m, 2H), 2.32-2.28 (m, 2H), 2.15-2.07 (m, 2H), 1.90-1.74 (m, 2H).

ESI-MS: 335.2 $[M+H]^+$

Example 304

Synthesis of N-[trans-4-(3,3-difluoroazetidin-1-yl)cyclohexyl]-4-(furo[3,2-c]pyridin-4-yl)benzamide [304] (Hereinafter, Referred to as a Compound [304])

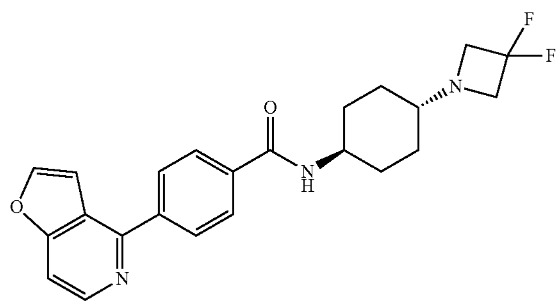 [SMILES: O=C(N[C@H]1CC[C@H](N2CC(F)(F)C2)CC1)c1ccc(-c2nccc3occc23)cc1]

To a solution of the compound [303] (6.1 mg) in dichloromethane (0.3 mL) were added 3,3-difluoroazetidine hydrochloride (3.2 mg) and sodium acetate (2.1 mg) at room temperature, and the mixture was stirred at room temperature for 1 hour. To the reaction mixture was added sodium triacetoxyborohydride (20 mg), and the mixture was stirred at room temperature for 18 hours. The reaction mixture was concentrated under reduced pressure, and the obtained residue was purified by preparative thin layer chromatography to give the title compound (2.1 mg) as a white solid.

ESI-MS: 412.3 $[M+H]^+$

Example 305

Synthesis of 4-(furo[3,2-c]pyridin-4-yl)-N-(trans-4-morpholinocyclohexyl)benzamide [305] (Hereinafter, Referred to as a Compound [305])

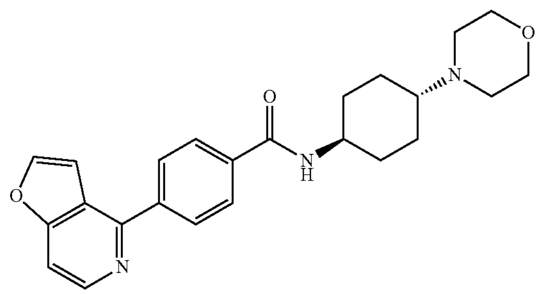 [SMILES: O=C(N[C@H]1CC[C@H](N2CCOCC2)CC1)c1ccc(-c2nccc3occc23)cc1]

To a solution of the compound [303] (10 mg) in dichloromethane (0.3 mL) were added morpholine (3.7 μL) and sodium acetate (3.4 mg) at room temperature, and the mixture was stirred at room temperature for 1 hour. To the reaction mixture was added sodium cyanoborohydride (20 mg), and the mixture was stirred at room temperature for 20 hours. The reaction mixture was concentrated under reduced pressure, and the obtained residue was purified by preparative thin layer chromatography to give the title compound (2.1 mg) as a white solid.

ESI-MS: 406.2 $[M+H]^+$

Example 306

Synthesis of N-[trans-4-(3,3-difluoropyrrolidin-1-yl) cyclohexyl]-4-(furo[3,2-c]pyridin-4-yl)benzamide [306] (Hereinafter, Referred to as a Compound [306])

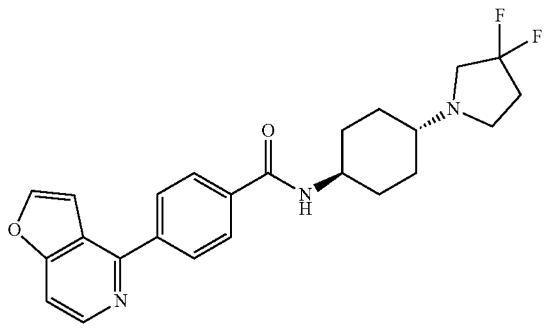 [SMILES: O=C(N[C@H]1CC[C@H](N2CCC(F)(F)C2)CC1)c1ccc(-c2nccc3occc23)cc1]

The title compound was synthesized by a method according to Example 305, using 3,3-difluoropyrrolidine hydrochloride in place of morpholine.

ESI-MS: 426.3 $[M+H]^+$

Example 307

Synthesis of N-[4-(4,4-difluoropiperidin-1-yl)cyclohexyl]-4-(furo[3,2-c]pyridin-4-yl)benzamide [307] (Hereinafter, Referred to as a Compound [307])

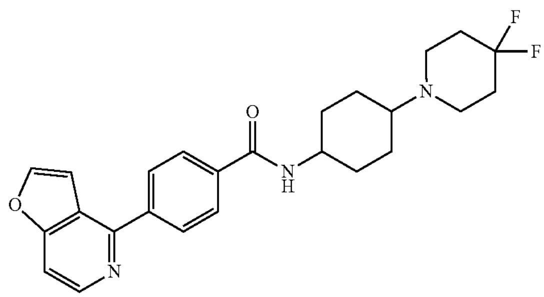 [SMILES: O=C(NC1CCC(N2CCC(F)(F)CC2)CC1)c1ccc(-c2nccc3occc23)cc1]

The title compound was synthesized by a method according to Example 305, using 4,4-difluoropiperidine hydrochloride in place of morpholine.

ESI-MS: 440.3 $[M+H]^+$

Example 308

Synthesis of 4-(furo[3,2-c]pyridin-4-yl)-N-[trans-4-(1-hydroxypropyl)cyclohexyl]benzamide [308] (Hereinafter, Referred to as a Compound [308])

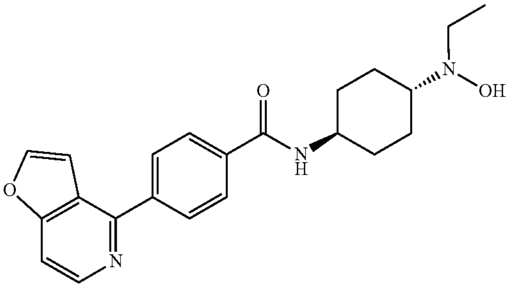 [SMILES: CCN(O)[C@H]1CC[C@H](NC(=O)c2ccc(-c3nccc4occc34)cc2)CC1]

(1) Synthesis of N-(trans-4-formylcyclohexyl)-4-(furo[3,2-c]pyridin-4-yl)benzamide [308-1] (Hereinafter, Referred to as a Compound [308-1])

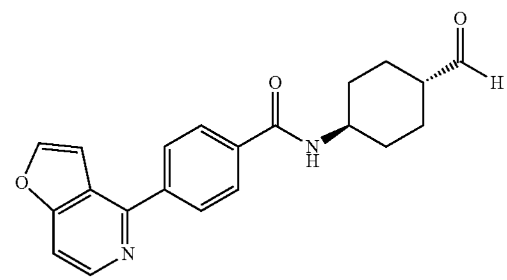 [SMILES: O=C[C@H]1CC[C@H](NC(=O)c2ccc(-c3nccc4occc34)cc2)CC1]

To a solution of the compound [120] (133 mg) in dichloromethane (1.3 mL) was added 1,1,1-triacetoxy-1,1-dihydro-1,2-benziodoxol-3 (1H)-one (Dess-Martin periodinane) (242 mg) at room temperature, and the mixture was stirred at room temperature for 3 hours. To the reaction mixture was added water, and the mixture was extracted with chloroform. The organic layer was dried over anhydrous sodium sulfate and concentrated under reduced pressure. The obtained residue was purified by silica gel column chromatography to give the title compound (101 mg) as a yellow oil.

$^1$H-NMR (400 MHz, DMSO-$d_6$) δ: 9.59 (s, 1H), 8.58 (d, J=5.7 Hz, 1H), 8.39 (d, J=8.2 Hz, 1H), 8.24 (d, J=2.3 Hz, 1H), 8.09 (d, J=8.7 Hz, 2H), 8.01 (d, J=8.2 Hz, 2H), 7.72 (d, J=5.5 Hz, 1H), 7.36-7.35 (m, 1H), 3.89-3.66 (m, 1H), 2.28-2.20 (m, 1H), 2.07-1.83 (m, 4H), 1.51-1.20 (m, 4H).

ESI-MS: 349.2 $[M+H]^+$ (2) Synthesis of 4-(furo[3,2-c]pyridin-4-yl)-N-[trans-4-(1-hydroxypropyl)cyclohexyl]benzamide [308]

To a solution of the compound [308-1] (45 mg) in THE (0.4 mL) was added a solution of 1 M ethylmagnesium bromide in diethyl ether (650 μL) at room temperature, and the mixture was stirred at room temperature for 15 minutes. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (11 mg) as a white solid.

ESI-MS: 379.2 [M+H]$^+$

Example 309

Synthesis of 4-(furo[3,2-c]pyridin-4-yl)-N-[trans-4-(2,2,2-trifluoro-1-hydroxyethyl)cyclohexyl]benzamide [309] (Hereinafter, Referred to as a Compound [309])

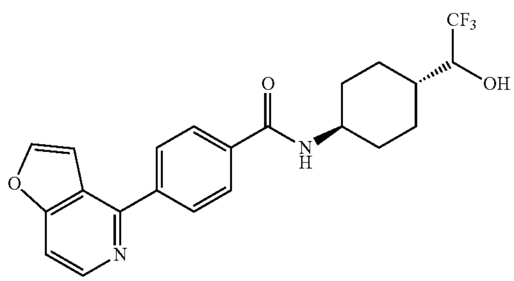 [SMILES: O=C(N[C@H]1CC[C@H](C(O)C(F)(F)F)CC1)c1ccc(-c2nccc3occc23)cc1]

To a solution of the compound [308-1] (20 mg) in THE (0.5 mL) were added (trifluoromethyl)trimethylsilane (34 μL) and cesium fluoride (35 mg) at room temperature, and the mixture was stirred at room temperature for 16 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (4.2 mg) as a white solid.

ESI-MS: 419.2 [M+H]$^+$

Example 310

Synthesis of N-[trans-4-(difluoromethyl)cyclohexyl]-4-(furo[3,2-c]pyridin-4-yl)benzamide [310] (Hereinafter, Referred to as a Compound [310])

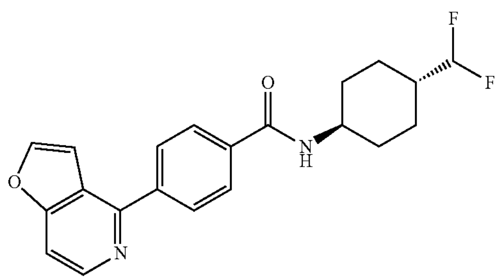 [SMILES: O=C(N[C@H]1CC[C@H](C(F)F)CC1)c1ccc(-c2nccc3occc23)cc1]

To a solution of the compound [308-1] (70 mg) in dichloromethane (2.0 mL) was added diethylaminosulfur trifluoride (39 μL) at room temperature, and the mixture was stirred at room temperature for 15 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (27 mg) as a white solid.

ESI-MS: 371.3 [M+H]$^+$

Example 311

Synthesis of 4-(furo[3,2-c]pyridin-4-yl)-N-[trans-4-(2-methoxyethoxy)cyclohexyl]benzamide [311] (Hereinafter, Referred to as a Compound [311])

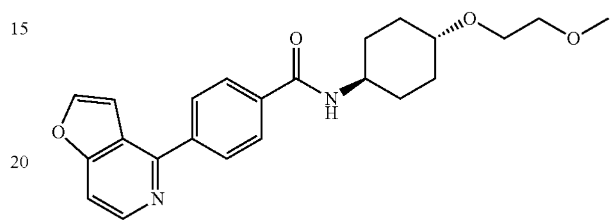

To a solution of the compound [256] (30 mg) in THE (0.5 mL) were added 60% sodium hydride (41 mg) and 2-bromoethyl methyl ether (62 μL) at room temperature, and the mixture was stirred at room temperature for 16 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (4.2 mg) as a white solid.

ESI-MS: 395.2 [M+H]$^+$

Example 312

Synthesis of 4-(6-chlorofuro[3,2-c]pyridin-4-yl)-N-[trans-4-(2-hydroxypropan-2-yl)cyclohexyl]benzamide [312] (Hereinafter, Referred to as a Compound [312])

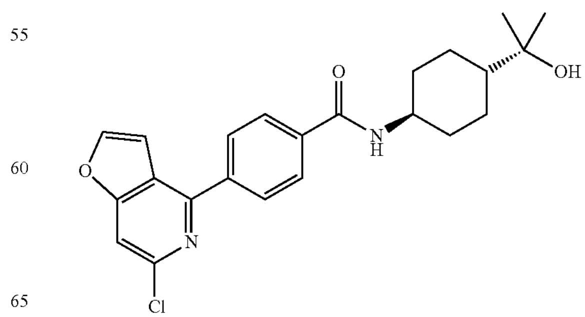

(1) Synthesis of 4-[4-(ethoxycarbonyl)phenyl] furo [3,2-c]pyridine=5-oxide [312-1] (Hereinafter, Referred to as a Compound [312-1])

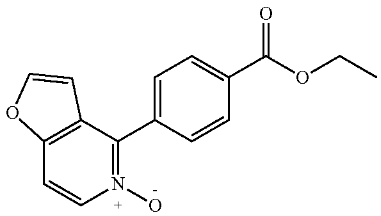

To a solution of the compound [64-5] (2.23 g) in chloroform (16.6 mL) was added m-chloroperbenzoic acid (2.16 g) at room temperature, and the mixture was stirred at room temperature for 24 hours. To the reaction mixture were added a saturated aqueous sodium bicarbonate solution and a saturated sodium thiosulfate solution, and the mixture was extracted with chloroform. The organic layer was dried over anhydrous sodium sulfate and concentrated under reduced pressure. The obtained residue was purified by silica gel column chromatography to give the title compound (2.06 g) as a white solid.

ESI-MS: 284.2 [M+H]$^+$ (2) Synthesis of ethyl 4-(6-chlorofuro[3,2-c]pyridin-4-yl)benzoate [312-2] (Hereinafter, Referred to as a Compound [312-2])

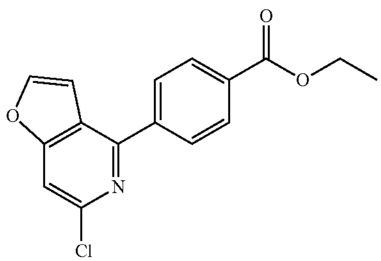 [SMILES: CCOC(=O)c1ccc(-c2nc(Cl)cc3occc23)cc1]

To the compound [312-1] (2.06 g) was added phosphoryl chloride (24.2 mL) at room temperature, and the mixture was heated under reflux for 24 hours. The reaction mixture was poured into an ice-cooled 5 M aqueous sodium hydroxide solution and extracted with ethyl acetate. The organic layer was dried over anhydrous sodium sulfate and concentrated under reduced pressure. The obtained residue was purified by silica gel column chromatography to give the title compound (752 mg) as a white solid.

$^1$H-NMR (400 MHz, $CDCl_3$) δ: 8.20 (d, J=8.4 Hz, 2H), 8.04 (d, J=8.4 Hz, 2H), 7.73 (d, J=2.0 Hz, 1H), 7.50 (s, 1H), 7.07 (d, J=2.0 Hz, 1H), 4.43 (q, J=7.2 Hz, 2H), 1.44 (t, J=7.2 Hz, 3H).

ESI-MS: 302.1 [M+H]$^+$ (3) Synthesis of 4-(6-chlorofuro[3,2-c]pyridin-4-yl) benzoic Acid [312-3] (Hereinafter, Referred to as a Compound [312-3])

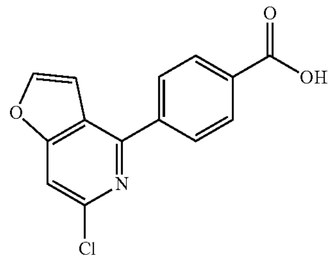 [SMILES: O=C(O)c1ccc(-c2nc(Cl)cc3occc23)cc1]

To a solution of the compound [312-2] (322 mg) in methanol (10.6 mL) was added a 2 M aqueous sodium hydroxide solution (5.3 mL) at room temperature, and the mixture was stirred at 60° C. for 1 hour. The reaction mixture was concentrated under reduced pressure, then 2 M hydrochloric acid (5.3 mL) was added, and the resulting solid was collected by filtration and dried under reduced pressure to give the title compound (285 mg) as a white solid.

ESI-MS: 274.2 [M+H]$^+$ (4) Synthesis of 4-(6-chlorofuro[3,2-c]pyridin-4-yl)-N-[trans-4-(2-hydroxypropan-2-yl)cyclohexyl]benzamide [312]

To a solution of the compound [312-3] (285 mg) in DMF (5.0 mL) were added DIPEA (195 μL) and (1-cyano-2-ethoxy-2-oxoethylideneaminooxy)dimethylaminomorpholinocarbenium hexafluorophosphate (490 mg) at room temperature, and the mixture was stirred at room temperature for 5 minutes. To the reaction mixture was added 2-(trans-4-aminocyclohexyl) propan-2-ol (213 mg) at room temperature, and the mixture was stirred at room temperature for 1 hour. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (414 mg) as a white solid.

$^1$H-NMR (400 MHz, DMSO-$d_6$) δ: 8.35 (d, J=7.6 Hz, 1H), 8.29 (d, J=2.4 Hz, 1H), 8.07-8.00 (m, 4H), 7.94 (s, 1H), 7.41 (d, J=2.4 Hz, 1H), 4.04 (s, 1H), 3.78-3.68 (m, 1H), 1.93-1.82 (m, 4H), 1.38-1.28 (m, 2H), 1.21-1.04 (m, 9H).

ESI-MS: 413.3 [M+H]$^+$

Example 313

Synthesis of N-[trans-4-(2-hydroxypropan-2-yl) cyclohexyl]-4-(6-vinylfuro[3,2-c]pyridin-4-yl)benzamide [313] (Hereinafter, Referred to as a Compound [313])

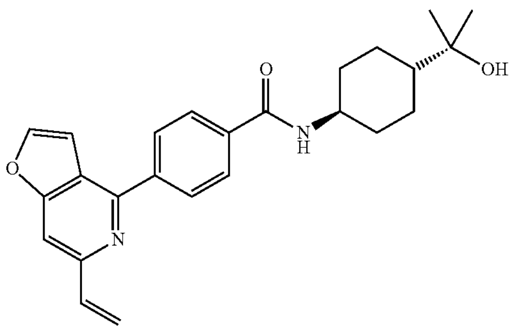

To a solution of the compound [312] (46 mg) in 1-propanol (1.1 mL) were added potassium vinyl trifluoroborate (30 mg), bis[di-tert-butyl (4-dimethylaminophenyl)phosphine]dichloropalladium (II) (7.9 mg), and triethylamine (31 μL) at room temperature, and the mixture was stirred at 110° C. for 1 hour under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (20 mg) as a white solid.

ESI-MS: 405.4 $[M+H]^+$

Example 314

Synthesis of 4-(6-ethylfuro[3,2-c]pyridin-4-yl)-N-[trans-4-(2-hydroxypropan-2-yl)cyclohexyl]benzamide [314] (Hereinafter, Referred to as a Compound [314])

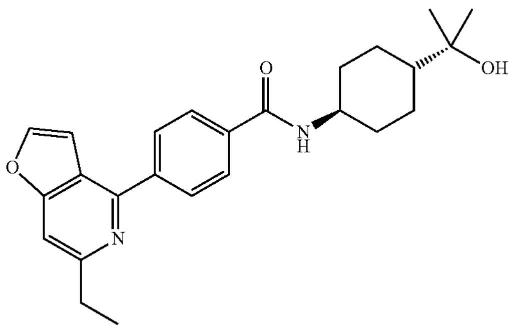

To a solution of the compound [313] (17 mg) in methanol (1.0 mL) was added 5% palladium-activated carbon (17 mg) at room temperature, and the mixture was stirred at room temperature for 40 minutes under a hydrogen atmosphere. The insoluble matter was filtered and concentrated under reduced pressure. The obtained residue was purified by reversed-phase silica gel column chromatography to give the title compound (3.0 mg) as a white solid.

ESI-MS: 407.4 $[M+H]^+$

Example 315

Synthesis of 4-(6-aminofuro[3,2-c]pyridin-4-yl)-N-[trans-4-(2-hydroxypropan-2-yl)cyclohexyl]benzamide [315] (Hereinafter, Referred to as a Compound [315])

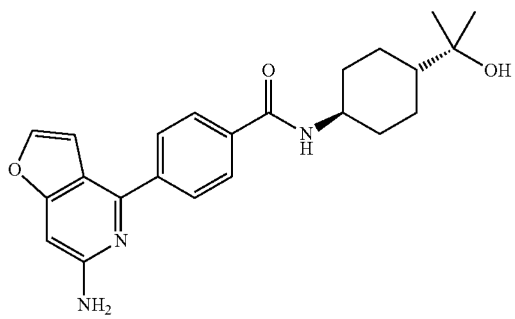

To a solution of the compound [312] (41 mg) in toluene (2.0 mL) were added benzophenone imine (34 μL), palladium (II) acetate (2.3 mg), 2,2'-bis(diphenylphosphino)-1,1'-binaphthyl (13 mg), and cesium carbonate (82 mg) at room temperature, and the mixture was stirred at 110° C. for 17 hours under an argon atmosphere. To the reaction mixture was added chloroform, and the mixture was purified by silica gel column chromatography to give a brown yellow oil (69 mg). Then, to a solution of the obtained oil in THF (2.0 mL) was added 1 M hydrochloric acid (100 μL) at room temperature, and the mixture was stirred at room temperature for 1 hour. To the reaction mixture was added a 1 M aqueous sodium hydroxide solution, and the mixture was extracted with ethyl acetate. The organic layer was dried over anhydrous sodium sulfate and concentrated under reduced pressure. The obtained residue was purified by silica gel column chromatography to give the title compound (26 mg) as a yellow solid.

$^1$H-NMR (400 MHz, DMSO-$d_6$) δ: 8.27 (d, J=8.4 Hz, 1H), 7.99-7.93 (m, 4H), 7.78 (d, J=2.4 Hz, 1H), 7.05 (d, J=2.4 Hz, 1H), 6.56 (s, 1H), 5.99 (br, 2H), 4.04 (s, 1H), 3.77-3.67 (m, 1H), 1.91-1.82 (m, 4H), 1.37-1.27 (m, 2H), 1.22-1.04 (m, 9H).

ESI-MS: 394.4 $[M+H]^+$

Example 316

Synthesis of 4-(6-fluorofuro[3,2-c]pyridin-4-yl)-N-[trans-4-(2-hydroxypropan-2-yl)cyclohexyl]benzamide [316] (Hereinafter, Referred to as a Compound [316])

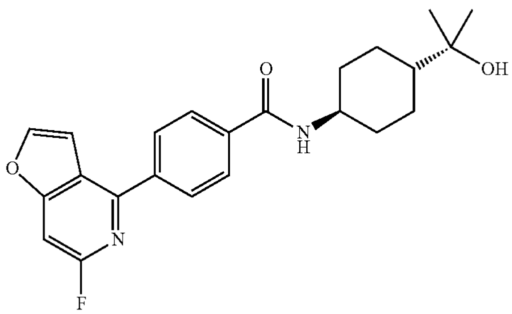

To a solution of the compound [312] (41 mg) in DMSO (2.0 mL) was added cesium fluoride (456 mg) at room temperature, and the mixture was stirred at 180° C. for 24 hours under an argon atmosphere. To the reaction mixture was added water, and the mixture was extracted with ethyl acetate. The organic layer was dried over anhydrous sodium sulfate and concentrated under reduced pressure. The obtained residue was purified by reversed-phase silica gel column chromatography to give the title compound (7.5 mg) as a white solid.

$^1$H-NMR (400 MHz, DMSO-$d_6$) δ: 8.35 (d, J=7.6 Hz, 1H), 8.26 (d, J=2.4 Hz, 1H), 8.08-8.06 (m, 2H), 8.02-8.00 (m, 2H), 7.56 (d, J=2.0 Hz, 1H), 7.43 (d, J=2.4 Hz, 1H), 4.04 (s, 1H), 3.78-3.68 (m, 1H), 1.92-1.82 (m, 4H), 1.37-1.28 (m, 2H), 1.21-1.04 (m, 9H).

ESI-MS: 397.4 $[M+H]^+$

Example 317

Synthesis of 4-(6-cyanofuro[3,2-c]pyridin-4-yl)-N-[trans-4-(2-hydroxypropan-2-yl)cyclohexyl]benzamide [317] (Hereinafter, Referred to as a Compound [317])

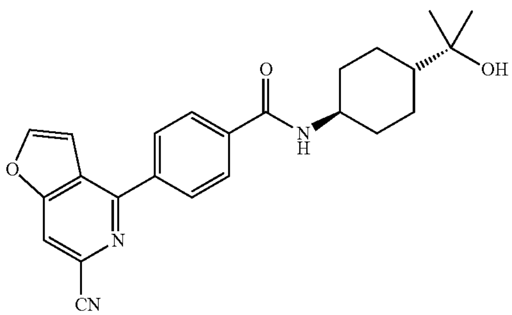

To a solution of the compound [312] (41 mg) in N,N-dimethylacetamide (2.0 mL) were added zinc cyanide (16 mg), tris (dibenzylideneacetone)dipalladium (0) (18 mg), and 2-dicyclohexylphosphino-2',4',6'-triisopropylbiphenyl (19 mg) at room temperature, and the mixture was stirred at 130° C. for 2 hours under an argon atmosphere. To the reaction mixture was added water, and the mixture was extracted with ethyl acetate. The organic layer was dried over anhydrous sodium sulfate and concentrated under reduced pressure. The obtained residue was purified by reversed-phase silica gel column chromatography to give the title compound (34 mg) as a white solid.

ESI-MS: 404.4 $[M+H]^+$

Example 318

Synthesis of 4-(4-{[trans-4-(2-hydroxypropan-2-yl)cyclohexyl]carbamoyl}phenyl)furo[3,2-c]pyridine-6-carboxamide (Hereinafter, Referred to as a Compound [318])

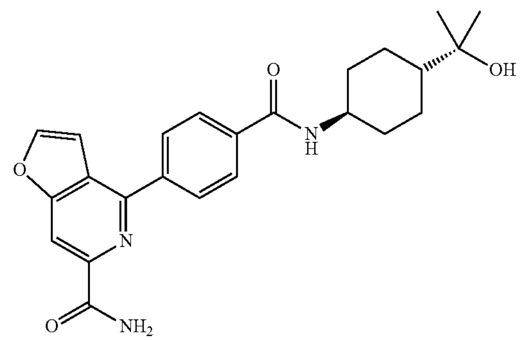

To a solution of the compound [317] (16 mg) in tert-butanol (1.3 mL) was added potassium tert-butoxide (67 mg) at room temperature, and the mixture was stirred at 40° C. for 2 hours under an argon atmosphere. To the reaction mixture was added water, and the mixture was extracted with ethyl acetate. The organic layer was dried over anhydrous sodium sulfate and concentrated under reduced pressure. The obtained residue was suspended in ethyl acetate/n-hexane and the solid was collected by filtration to give the title compound (6.5 mg) as a white solid.

ESI-MS: 422.4 $[M+H]^+$

Example 319

Synthesis of 4-[6-(hydroxymethyl)furo[3,2-c]pyridin-4-yl]-N-[trans-4-(2-hydroxypropan-2-yl)cyclohexyl]benzamide [319] (Hereinafter, Referred to as a Compound [319])

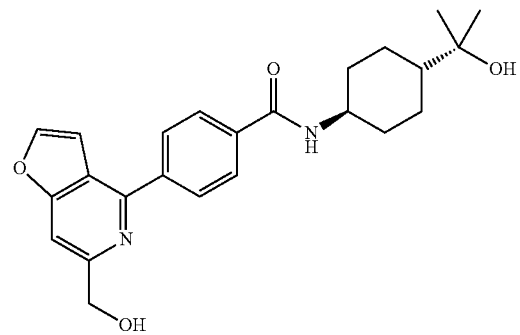

(1) Synthesis of ethyl 4-[6-(hydroxymethyl)furo[3,2-c]pyridin-4-yl]benzoate [319-1] (Hereinafter, Referred to as a Compound [319-1])

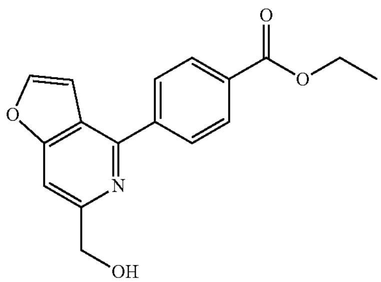 [SMILES: CCOC(=O)c1ccc(-c2nc(CO)cc3occc23)cc1]

To a solution of the compound [312-2] (30 mg) in 1,4-dioxane (1.8 mL)/water (0.20 mL) were added potassium (acetoxymethyl)trifluoroborate (54 mg), bis(dibenzylideneacetone)palladium (0) (5.8 mg), 2-dicyclohexylphosphino-2',6'-diisopropoxybiphenyl (11 mg), and cesium carbonate (98 mg) at room temperature, and the mixture was stirred at 110° C. for 6 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (6.9 mg) as a yellow white solid.

$^1$H-NMR (400 MHz, $CDCl_3$) δ: 8.22-8.20 (m, 2H), 8.06-8.04 (m, 2H), 7.73 (d, J=2.0 Hz, 1H), 7.42 (s, 1H), 7.07 (d, J=2.0 Hz, 1H), 4.93 (s, 2H), 4.43 (q, J=7.2 Hz, 2H), 3.76 (br, 1H), 1.44 (t, J=7.2 Hz, 3H).

ESI-MS: 298.3 [M+H]$^+$ (2) Synthesis of 4-[6-(hydroxymethyl)furo[3,2-c]pyridin-4-yl]benzoic acid [319-2] (Hereinafter, Referred to as a Compound [319-2])

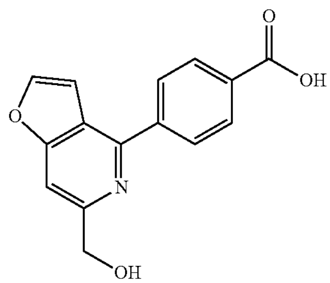 [SMILES: O=C(O)c1ccc(-c2nc(CO)cc3occc23)cc1]

To a solution of the compound [319-1] (6.9 mg) in methanol (1.0 mL) was added a 2 M aqueous sodium hydroxide solution (0.5 mL) at room temperature, and the mixture was stirred at room temperature for 1 hour. The reaction mixture was concentrated under reduced pressure, then 2 M hydrochloric acid (0.5 mL) was added, and the resulting solid was collected by filtration and dried under reduced pressure to give the title compound (6.3 mg) as a yellow solid.

$^1$H-NMR (400 MHz, DMSO-$d_6$) δ: 8.20 (d, J=2.4 Hz, 1H), 8.15-8.09 (m, 4H), 7.69 (s, 1H), 7.36 (d, J=2.4 Hz, 1H), 5.55 (br, 1H), 4.75 (s, 2H).

ESI-MS: 270.3 [M+H]$^+$ (3) Synthesis of 4-[6-(hydroxymethyl)furo[3,2-c]pyridin-4-yl]-N-[trans-4-(2-hydroxypropan-2-yl)cyclohexyl]benzamide [319]

To a solution of the compound [319-2] (5.9 mg) in DMF (1.0 mL) were added DIPEA (8.2 L) and (1-cyano-2-ethoxy-2-oxoethylideneaminooxy)dimethylaminomorpholinocarbenium hexafluorophosphate (21 mg) at room temperature, and the mixture was stirred at room temperature for 5 minutes. To the reaction mixture was added 2-(trans-4-aminocyclohexyl) propan-2-ol (9.0 mg) at room temperature, and the mixture was stirred at room temperature for 20 minutes. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (5.4 mg) as a white solid.

$^1$H-NMR (400 MHz, DMSO-$d_6$) δ: 8.30 (d, J=8.4 Hz, 1H), 8.18 (d, J=2.4 Hz, 1H), 8.07-8.05 (m, 2H), 8.01-7.98 (m, 2H), 7.67 (s, 1H), 7.31 (d, J=2.4 Hz, 1H), 5.54 (t, J=5.2 Hz, 1H), 4.74 (d, J=5.2 Hz, 2H), 4.03 (s, 1H), 3.78-3.68 (m, 1H), 1.92-1.82 (m, 4H), 1.38-1.29 (m, 2H), 1.22-1.04 (m, 9H).

ESI-MS: 409.4 [M+H]$^+$

Example 320

Synthesis of 4-[6-(hydroxymethyl-$d_2$)furo[3,2-c]pyridin-4-yl]-N-[trans-4-(2-hydroxypropan-2-yl)cyclohexyl]benzamide [320] (Hereinafter, Referred to as a Compound [320])

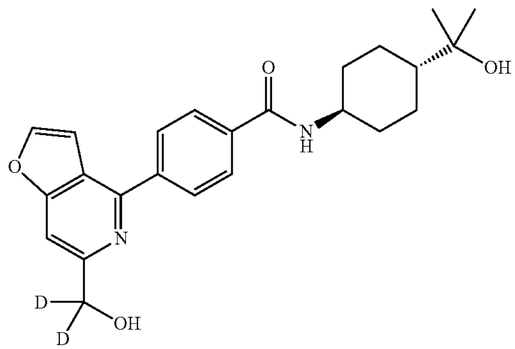 [SMILES: [2H]C([2H])(O)c1cc2occc2c(-c2ccc(C(=O)N[C@H]3CC[C@H](C(C)(C)O)CC3)cc2)n1]

(1) Synthesis of ethyl 4-(6-vinylfuro[3,2-c]pyridin-4-yl)benzoate [320-1] (Hereinafter, Referred to as a Compound [320-1])

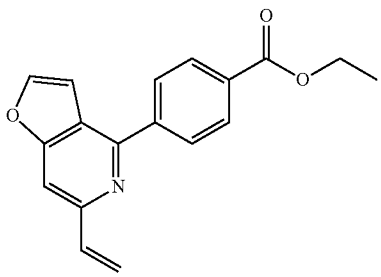 [SMILES: C=Cc1cc2occc2c(-c2ccc(C(=O)OCC)cc2)n1]

To a solution of the compound [312-2] (37 mg) in 1-propanol (1.2 mL) were added potassium vinyl trifluoroborate (33 mg), bis[di-tert-butyl (4-dimethylaminophenyl) phosphine]dichloropalladium (II) (8.7 mg), and triethylamine (34 μL) at room temperature, and the mixture was stirred at 110° C. for 1 hour under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (22 mg) as a yellow oil.

ESI-MS: 294.2 $[M+H]^+$ (2) Synthesis of ethyl 4-[6-(formyl-d)furo[3,2-c]pyridin-4-yl]benzoate [320-2] (Hereinafter, Referred to as a Compound [320-2])

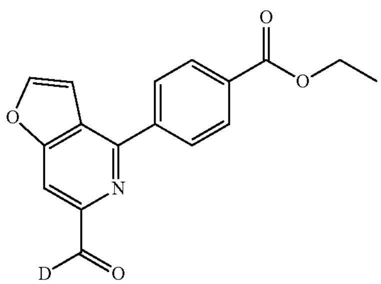 [SMILES: [2H]C(=O)c1cc2occc2c(-c2ccc(C(=O)OCC)cc2)n1]

To a solution of the compound [320-1] (22 mg) in acetone (0.60 mL)/water (0.20 mL) were added N-methylmorpholine N-oxide (13 mg) and a 4% aqueous osmium tetroxide solution (37 μL) at room temperature, and the mixture was stirred at room temperature for 30 minutes. To the reaction mixture were added 2,6-lutidine (17 μL) and sodium periodate (32 mg) at room temperature, and the mixture was stirred at room temperature for 20 minutes. To the reaction mixture was added water, and the mixture was extracted with ethyl acetate. The organic layer was dried over anhydrous sodium sulfate and concentrated under reduced pressure to give a yellow solid (27 mg). Subsequently, to a solution of the obtained solid in methanol (0.90 mL) was added sodium borodeuteride (6.0 mg) at room temperature, and the mixture was stirred at room temperature for 30 minutes. To the reaction mixture was added water, and the mixture was extracted with ethyl acetate. The organic layer was dried over anhydrous sodium sulfate and concentrated under reduced pressure to give a brown solid (33 mg). Then, to a solution of the obtained solid in dichloromethane (1.1 mL) was added 1,1,1-triacetoxy-1,1-dihydro-1,2-benziodoxol-3 (1H)-one (Dess-Martin periodinane) (72 mg) at room temperature, and the mixture was stirred for 2.5 hours. To the reaction mixture was added a saturated aqueous sodium bicarbonate solution, and the mixture was extracted with chloroform. The organic layer was dried over anhydrous sodium sulfate and concentrated under reduced pressure. The obtained residue was purified by silica gel column chromatography to give the title compound (13 mg) as a white solid.

$^1$H-NMR (400 MHz, DMSO-$d_6$) δ: 7.41-7.37 (m, 2H), 7.28 (dd, J=6.4, 1.8 Hz, 2H), 7.18-7.16 (m, 1H), 6.94 (d, J=0.9 Hz, 1H), 6.41-6.40 (m, 1H), 3.61-3.59 (m, 2H), 0.64-0.59 (m, 3H).

ESI-MS: 297.2 $[M+H]^+$ (3) Synthesis of 4-[6-(hydroxymethyl-$d_2$)furo[3,2-c]pyridin-4-yl]benzoic acid [320-3] (Hereinafter, Referred to as a Compound [320-3])

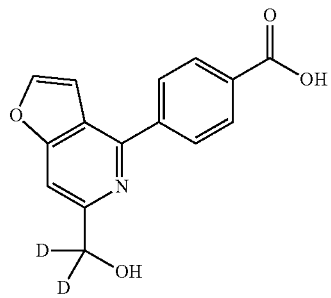 [SMILES: [2H]C([2H])(O)c1cc2occc2c(-c2ccc(C(=O)O)cc2)n1]

To a solution of the compound [320-2] (13 mg) in methanol (0.50 mL) was added sodium borodeuteride (2.2 mg) at room temperature, and the mixture was stirred at room temperature for 20 minutes. To the reaction mixture was added water, and the mixture was extracted with ethyl acetate. The organic layer was dried over anhydrous sodium sulfate and concentrated under reduced pressure to give a white solid (21 mg). Subsequently, to a solution of the obtained solid in methanol (0.70 mL) was added a 2 M aqueous sodium hydroxide solution (172 μL) at room temperature, and the mixture was stirred at 100° C. for 10 minutes. The reaction mixture was concentrated under reduced pressure, then 2 M hydrochloric acid was added, and the resulting solid was collected by filtration and dried under reduced pressure to give the title compound (9.3 mg) as a white solid.

$^1$H-NMR (400 MHz, $CD_3OD$) δ: 8.20 (d, J=7.8 Hz, 2H), 8.06 (d, J=7.8 Hz, 2H), 7.96-7.95 (m, 1H), 7.71 (s, 1H), 7.19-7.18 (m, 1H).

ESI-MS: 272.1 $[M+H]^+$ (4) Synthesis of 4-[6-(hydroxymethyl-$d_2$)furo[3,2-c]pyridin-4-yl]-N-[trans-4-(2-hydroxypropan-2-yl)cyclohexyl]benzamide [320]

To a solution of the compound [320-3] (4.0 mg) in DMF (0.50 mL) were added (1-cyano-2-ethoxy-2-oxoethylideneaminooxy)dimethylaminomorpholinocarbenium hexafluorophosphate (6.9 mg), DIPEA (2.7 μL), and 2-(trans-4-aminocyclohexyl) propan-2-ol (3.0 mg) at room temperature, and the mixture was stirred at room temperature for 1 hour. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (4.9 mg) as a white solid.

$^1$H-NMR (400 MHz, $CD_3OD$) δ: 8.04-7.94 (m, 5H), 7.69 (s, 1H), 7.17-7.16 (m, 1H), 3.92-3.84 (m, 1H), 2.12-2.05 (m, 2H), 1.98-1.95 (m, 2H), 1.48-1.17 (m, 11H).

ESI-MS: 411.2 $[M+H]^+$

Example 321

Synthesis of 3-fluoro-N-[trans-4-(2-hydroxypropan-2-yl)cyclohexyl]-4-(6-methylfuro[3,2-c]pyridin-4-yl) benzamide [321] (Hereinafter, Referred to as a Compound [321])

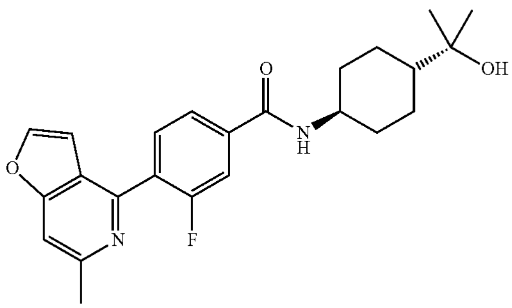

(1) Synthesis of methyl 4-(6-chlorofuro[3,2-c]pyridin-4-yl)-3-fluorobenzoate [321-1] (Hereinafter, Referred to as a Compound [321-1])

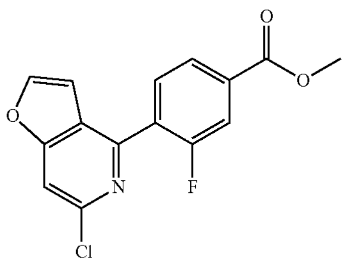 [SMILES: COC(=O)c1ccc(-c2nc(Cl)cc3occc23)c(F)c1]

The title compound was synthesized from the compound [125-1] according to the methods of steps (1) and (2) in Example 312.

$^1$H-NMR (400 MHz, $CDCl_3$) δ: 7.99-7.97 (m, 1H), 7.92-7.87 (m, 2H), 7.70 (d, J=2.0 Hz, 1H), 7.55 (d, J=1.2 Hz, 1H), 6.84-6.82 (m, 1H), 3.98 (s, 3H).

ESI-MS: 306.2 $[M+H]^+$ (2) Synthesis of methyl 3-fluoro-4-(6-methylfuro[3,2-c]pyridin-4-yl)benzoate [321-2] (Hereinafter, Referred to as a Compound [321-2])

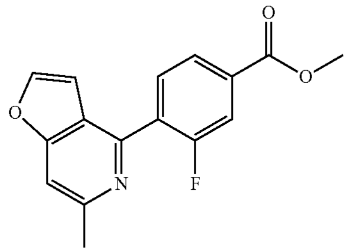 [SMILES: COC(=O)c1ccc(-c2nc(C)cc3occc23)c(F)c1]

To a solution of the compound [321-1] (100 mg) in 1,4-dioxane (6.50 mL) were added cesium carbonate (318 mg), bis[di-tert-butyl (4-dimethylaminophenyl)phosphine] dichloropalladium (II) (23.1 mg), and 2,4,6-trimethylboroxine (137 μL) at room temperature, and the mixture was stirred at 100° C. for 2 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (90.1 mg) as a white solid.

ESI-MS: 286.3 $[M+H]^+$ (3) Synthesis of 3-fluoro-N-[trans-4-(2-hydroxypropan-2-yl)cyclohexyl]-4-(6-methylfuro[3,2-c]pyridin-4-yl)benzamide [321]

The title compound was synthesized from the compound [321-2] according to the methods of steps (3) and (4) in Example 312.

ESI-MS: 411.5 $[M+H]^+$

Example 322

Synthesis of 3-fluoro-4-[6-(hydroxymethyl)furo[3,2-c]pyridin-4-yl]-N-[trans-4-(2-hydroxypropan-2-yl) cyclohexyl]benzamide [322] (Hereinafter, Referred to as a Compound [322])

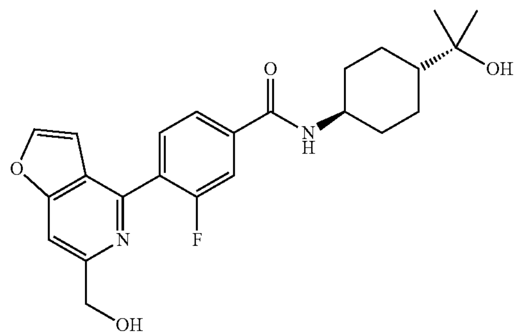

The title compound was synthesized from the compound [321-1] according to the methods of steps (1) to (3) in Example 319.

ESI-MS: 427.3 $[M+H]^+$

Example 323

Synthesis of 3-fluoro-4-(furo[3,2-c]pyridin-4-yl)-N-[1-(1-methyl-1H-tetrazol-5-yl)piperidin-4-yl]benzamide [323] (Hereinafter, Referred to as a Compound [323])

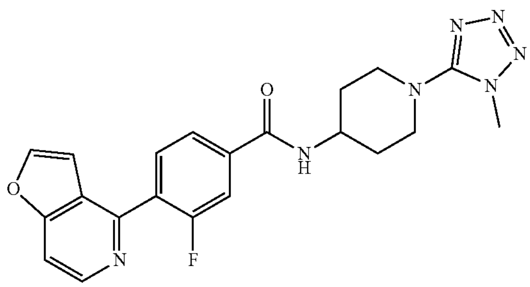 [SMILES: Cn1nnnc1N1CCC(NC(=O)c2ccc(-c3nccc4occc34)c(F)c2)CC1]

The title compound was synthesized from the compound [125-2] according to the method of the step (2) in Example 99.

ESI-MS: 422.3 $[M+H]^+$

Example 324

Synthesis of N-[1-(cyclopropanecarbonyl)piperidin-4-yl]-3-fluoro-4-(furo[3,2-c]pyridin-4-yl)benzamide [324] (Hereinafter, Referred to as a Compound [324])

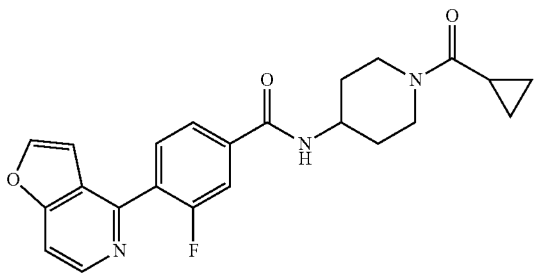 [SMILES: O=C(NC1CCN(C(=O)C2CC2)CC1)c1ccc(-c2nccc3occc23)c(F)c1]

To a solution of the compound [125-2] (26 mg) in DMF (1.0 mL) were added DIPEA (19 μL) and (1-cyano-2-ethoxy-2-oxoethylideneaminooxy)dimethylaminomorpholinocarbenium hexafluorophosphate (47 mg) at room temperature, and the mixture was stirred at room temperature for 5 minutes. To the reaction mixture was added 1-(cyclopropanecarbonyl)piperidin-4-amine (22 mg) at room temperature, and the mixture was stirred at room temperature for 20 minutes. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (39 mg) as a white solid.

ESI-MS: 408.3 $[M+H]^+$

Example 325

Synthesis of 3-fluoro-4-(furo[3,2-c]pyridin-4-yl)-N-(trans-4-hydroxycyclohexyl)benzamide [325] (Hereinafter, Referred to as a Compound [325])

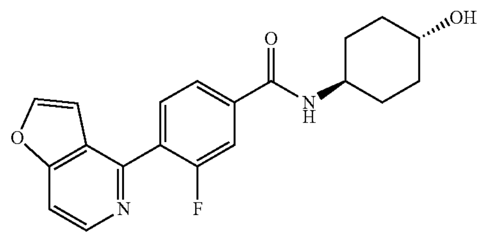 [SMILES: O=C(N[C@H]1CC[C@H](O)CC1)c1ccc(-c2nccc3occc23)c(F)c1]

The title compound was synthesized from the compound [125-2] according to the method of Example 256.

ESI-MS: 355.3 $[M+H]^+$

Example 326

Synthesis of N-{trans-4-[(2,2-difluoroethyl)amino]cyclohexyl}-3-fluoro-4-(furo[3,2-c]pyridin-4-yl)benzamide [326] (Hereinafter, Referred to as a Compound [326])

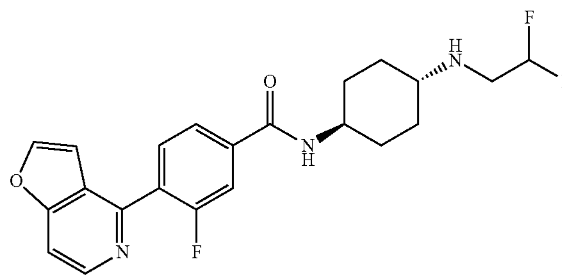

The title compound was synthesized from the compound [125-2] according to the methods of steps (1) and (2) in Example 294.

ESI-MS: 418.3 $[M+H]^+$

Example 327

Synthesis of 3-fluoro-4-(furo[3,2-c]pyridin-4-yl)-N-[trans-4-(1-hydroxycyclopropyl)cyclohexyl]benzamide [327] (Hereinafter, Referred to as a Compound [327])

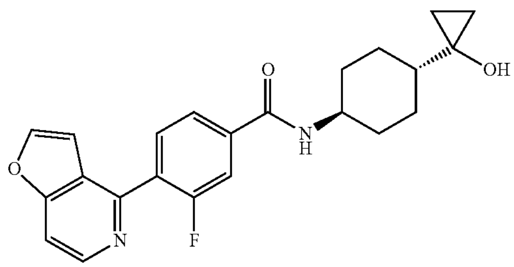 [SMILES: O=C(N[C@H]1CC[C@H](C2(O)CC2)CC1)c1ccc(-c2nccc3occc23)c(F)c1]

The title compound was synthesized from the compound [125-2] according to the method of the step (4) in Example 257.

ESI-MS: 395.3 [M+H]+

Example 328

Synthesis of (S)-3-fluoro-4-(furo[3,2-c]pyridin-4-yl)-N-[1-(pyrimidin-2-yl)pyrrolidin-3-yl]benzamide [328] (Hereinafter, Referred to as a Compound [328])

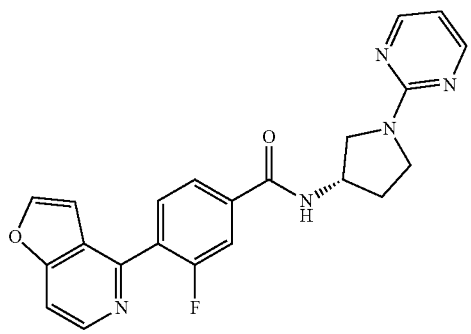 [SMILES: O=C(N[C@H]1CCN(c2ncccn2)C1)c1ccc(-c2nccc3occc23)c(F)c1]

(1) Synthesis of (S)-1-(pyrimidin-2-yl)pyrrolidine-3-amine dihydrochloride [328-1] (Hereinafter, Referred to as a Compound [328-1])

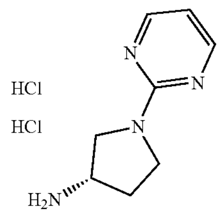 [SMILES: Cl ; Cl ; N[C@H]1CCN(c2ncccn2)C1]

To a solution of (3 S)-(−)-3-(tert-butoxycarbonylamino) pyrrolidine (186 mg) in DMF (2.0 mL) were added cesium carbonate (358 mg) and 2-chloropyrimidine (115 mg) at room temperature, and the mixture was stirred at 150° C. for 10 seconds using a microwave reactor. To the reaction mixture was added water, and the mixture was extracted with ethyl acetate. The organic layer was dried over anhydrous sodium sulfate and concentrated under reduced pressure. The obtained residue was purified by silica gel column chromatography to give a white solid (216 mg). Subsequently, to a solution of the obtained solid in ethyl acetate (4.1 mL) was added a solution of 4 M hydrogen chloride in ethyl acetate (4.1 mL) at room temperature. This solution was stirred at room temperature for 1.5 hours, then the resulting solid was collected by filtration and dried under reduced pressure to give the title compound (190 mg) as a white solid.

ESI-MS: 165.2 [M+H]+

(2) Synthesis of (S)-3-fluoro-4-(furo[3,2-c]pyridin-4-yl)-N-[1-(pyrimidin-2-yl)pyrrolidin-3-yl]benzamide [328]

To a solution of the compound [125-2] (26 mg) in DMF (1.0 mL) were added DIPEA (56 μL) and (1-cyano-2-ethoxy-2-oxoethylideneaminooxy)dimethylaminomorpholinocarbenium hexafluorophosphate (47 mg) at room temperature, and the mixture was stirred at room temperature for 5 minutes. To the reaction mixture was added the compound [328-1] (31 mg) at room temperature, and the mixture was stirred at room temperature for 30 minutes. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (20 mg) as a yellow white solid.

ESI-MS: 404.2 [M+H]+

Example 329

Synthesis of 3-fluoro-4-(furo[3,2-c]pyridin-4-yl)-N-[trans-4-(2-hydroxy-2-methylpropoxy)cyclohexyl]benzamide [329] (Hereinafter, Referred to as a Compound [329])

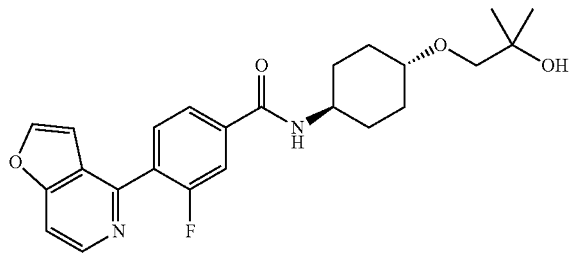 [SMILES: CC(C)(O)CO[C@H]1CC[C@H](NC(=O)c2ccc(-c3nccc4occc34)c(F)c2)CC1]

To a solution of the compound [125-2] (26 mg) in DMF (1.0 mL) were added DIPEA (19 μL) and (1-cyano-2-ethoxy-2-oxoethylideneaminooxy)dimethylaminomorpholinocarbenium hexafluorophosphate (47 mg) at room temperature, and the mixture was stirred at room temperature for 5 minutes. To the reaction mixture was added the compound [64-4] (24 mg) at room temperature, and the mixture was stirred at room temperature for 2 hours. Further, to the reaction mixture were added DIPEA (19 μL) and the compound [64-4] (24 mg) at room temperature, and the mixture was stirred at room temperature for 2 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (36 mg) as a white solid.

$^1$H-NMR (400 MHz, DMSO-$d_6$) δ: 8.61 (d, J=5.6 Hz, 1H), 8.41 (d, J=8.0 Hz, 1H), 8.19 (d, J=2.4 Hz, 1H), 7.86-7.77 (m, 4H), 6.97-6.96 (m, 1H), 4.21 (s, 1H), 3.83-3.74 (m, 1H), 3.27-3.17 (m, 3H), 2.03-2.01 (m, 2H), 1.90-1.87 (m, 2H), 1.44-1.35 (m, 2H), 1.30-1.20 (m, 2H), 1.06 (s, 6H).

ESI-MS: 427.3 [M+H]$^+$

Example 330

Synthesis of N-[1-(1-methyl-1H-tetrazol-5-yl)piperidin-4-yl]-4-(6-methylfuro[3,2-c]pyridin-4-yl)benzamide [330] (Hereinafter, Referred to as a Compound [330])

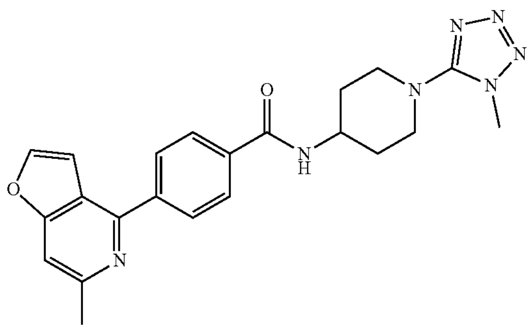 [SMILES: Cc1cc2occc2c(-c2ccc(C(=O)NC3CCN(c4nnnn4C)CC3)cc2)n1]

(1) Synthesis of ethyl 4-(6-methylfuro[3,2-c]pyridin-4-yl)benzoate [330-1] (Hereinafter, Referred to as a Compound [330-1])

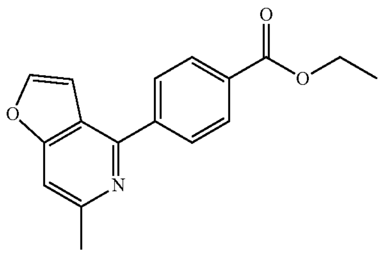 [SMILES: CCOC(=O)c1ccc(-c2nc(C)cc3occc23)cc1]

To a solution of the compound [312-2] (546 mg) in 1,4-dioxane (18.0 mL) were added cesium carbonate (1.77 g), bis[di-tert-butyl (4-dimethylaminophenyl)phosphine]dichloropalladium (II) (64.0 mg), and 2,4,6-trimethylboroxine (758 μL) at room temperature, and the mixture was stirred at 100° C. for 2 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (460 mg) as a white solid.

ESI-MS: 282.2 [M+H]$^+$ (2) Synthesis of 4-(6-methylfuro[3,2-c]pyridin-4-yl)benzoic acid [330-2] (Hereinafter, Referred to as a Compound [330-2])

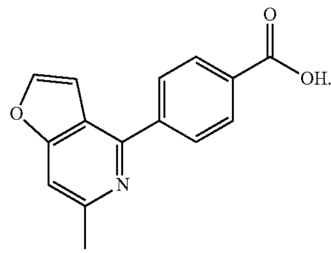 [SMILES: Cc1cc2occc2c(-c2ccc(C(=O)O)cc2)n1]

To a solution of the compound [330-1] (460 mg) in methanol (16 mL) was added a 2 M aqueous sodium hydroxide solution (8.0 mL) at room temperature, and the mixture was stirred at room temperature for 3 hours. The reaction mixture was concentrated under reduced pressure, then 2 M hydrochloric acid (8.0 mL) was added, and the resulting solid was collected by filtration and dried under reduced pressure to give the title compound (205 mg) as a white solid.

$^1$H-NMR (400 MHz, DMSO-$d_6$) δ: 8.18 (d, J=2.0 Hz, 1H), 8.13-8.09 (m, 4H), 7.63 (s, 1H), 7.33 (d, J=2.0 Hz, 1H), 2.66 (s, 3H).

ESI-MS: 254.2 [M+H]$^+$ (3) Synthesis of N-[1-(1-methyl-1H-tetrazol-5-yl)piperidin-4-yl]-4-(6-methylfuro[3,2-c]pyridin-4-yl)benzamide [330]

The title compound was synthesized from the compound [330-2] according to the method of the step (2) in Example 99.

ESI-MS: 418.3 [M+H]$^+$

Example 331

Synthesis of N-{trans-4-[(2,2-difluoroethyl)amino]cyclohexyl}-4-(6-methylfuro[3,2-c]pyridin-4-yl)benzamide [331] (Hereinafter, Referred to as a Compound [331])

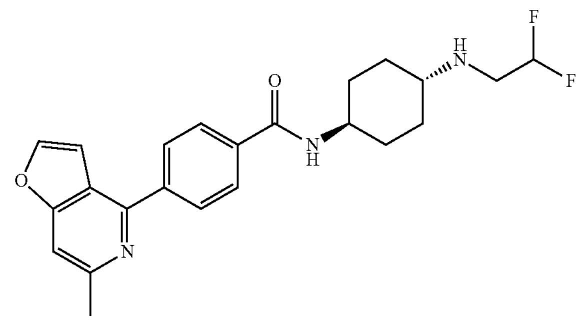 [SMILES: Cc1cc2occc2c(-c2ccc(C(=O)N[C@H]3CC[C@H](NCC(F)F)CC3)cc2)n1]

(1) Synthesis of trans-N1-(2,2-difluoroethyl)cyclohexane-1,4-diamine dihydrochloride [331-1] (Hereinafter, Referred to as a Compound [331-1])

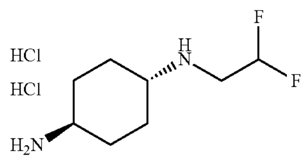 [SMILES: Cl ; Cl ; N[C@H]1CC[C@H](NCC(F)F)CC1]

To a solution of tert-butyl (trans-4-aminocyclohexyl) carbamate (214 mg) in 1,4-dioxane (3.3 mL) were added DIPEA (340 μL) and 2,2-difluoroethyl trifluoromethanesulfonate (159 μL) at room temperature, and the mixture was stirred at 70° C. for 2 hours. To the reaction mixture was added water, and the mixture was extracted with ethyl acetate. The organic layer was dried over anhydrous sodium sulfate and concentrated under reduced pressure to give a white solid (222 mg). Subsequently, to a solution of the obtained solid in methanol (4.0 mL) was added a solution of 4 M hydrogen chloride in 1,4-dioxane (4.0 mL) at room temperature, and the mixture was stirred at room temperature for 3 hours. The reaction mixture was concentrated under reduced pressure, then the obtained residue was suspended in ethyl acetate/methanol, and the solid was collected by filtration to give the title compound (158 mg) as a white solid.

$^1$H-NMR (400 MHz, DMSO-$d_6$) δ: 9.69 (br, 2H), 8.16 (br, 3H), 6.49 (t, J=54.8 Hz, 1H), 3.52-3.45 (m, 2H), 3.04-2.93 (m, 2H), 2.15 (d, J=10.8 Hz, 2H), 2.03 (d, J=10.8 Hz, 2H), 1.51-1.32 (m, 4H).

(2) Synthesis of N-{trans-4-[(2,2-difluoroethyl)amino]cyclohexyl}-4-(6-methylfuro[3,2-c]pyridin-4-yl)benzamide [331]

To a solution of the compound [330-2] (13 mg) in DMF (1.0 mL) were added DIPEA (28 μL) and (1-cyano-2-ethoxy-2-oxoethylideneaminooxy)dimethylaminomorpholinocarbenium hexafluorophosphate (24 mg) at room temperature, and the mixture was stirred at room temperature for 5 minutes. To the reaction mixture was added the compound [331-1] (16 mg) at room temperature, and the mixture was stirred at room temperature for 1.5 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (18 mg) as a white solid.

ESI-MS: 414.3 [M+H]$^+$

Example 332

Synthesis of (S)-4-(6-methylfuro[3,2-c]pyridin-4-yl)-N-[1-(pyrimidin-2-yl)pyrrolidin-3-yl]benzamide [332] (Hereinafter, Referred to as a Compound [332])

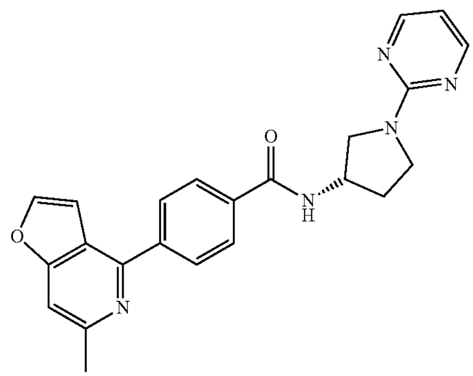

The title compound was synthesized from the compound [330-2] according to the method of the step (2) in Example 328.

ESI-MS: 400.3 [M+H]$^+$

Example 333

Synthesis of N-(trans-4-hydroxycyclohexyl)-4-(6-methylfuro[3,2-c]pyridin-4-yl)benzamide [333] (Hereinafter, Referred to as a Compound [333])

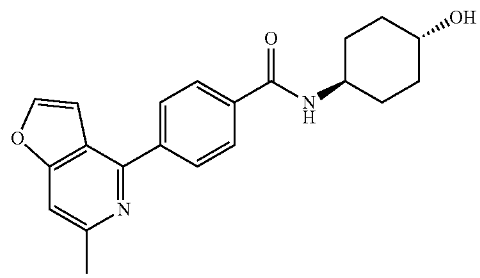 [SMILES: Cc1cc2occc2c(-c2ccc(C(=O)N[C@H]3CC[C@H](O)CC3)cc2)n1]

The title compound was synthesized from the compound [330-2] according to the method of Example 256.

ESI-MS: 351.4 [M+H]$^+$

Example 334

Synthesis of N-[trans-4-(1-hydroxycyclopropyl)cyclohexyl]-4-(6-methylfuro[3,2-c]pyridin-4-yl)benzamide [334] (Hereinafter, Referred to as a Compound [334])

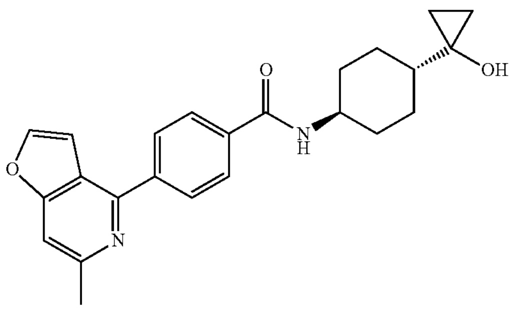 [SMILES: Cc1cc2occc2c(-c2ccc(C(=O)N[C@H]3CC[C@H](C4(O)CC4)CC3)cc2)n1]

The title compound was synthesized from the compound [330-2] according to the method of the step (4) in Example 257.

$^1$H-NMR (400 MHz, DMSO-$d_6$) δ: 8.32 (d, J=8.4 Hz, 1H), 8.13 (d, J=2.0 Hz, 1H), 8.06-8.04 (m, 2H), 8.00-7.98 (m, 2H), 7.56 (s, 1H), 7.29-7.28 (m, 1H), 4.87 (s, 1H), 3.78-3.68 (m, 1H), 2.64 (s, 3H), 1.91-1.86 (m, 2H), 1.74-1.69 (m, 2H), 1.39-1.29 (m, 4H), 0.95-0.85 (m, 1H), 0.50-0.47 (m, 2H), 0.36-0.33 (m, 2H).

ESI-MS: 391.4 $[M+H]^+$

Example 335

Synthesis of N-[1-(cyclopropanecarbonyl)piperidin-4-yl]-4-(6-methylfuro[3,2-c]pyridin-4-yl)benzamide [335] (Hereinafter, Referred to as a Compound [335])

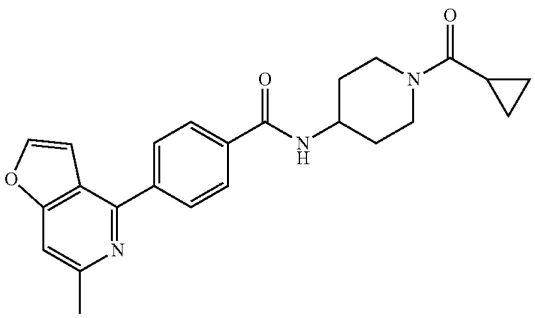 [SMILES: Cc1cc2occc2c(-c2ccc(C(=O)NC3CCN(C(=O)C4CC4)CC3)cc2)n1]

The title compound was synthesized from the compound [330-2] according to the method of Example 324.

ESI-MS: 404.4 $[M+H]^+$

Example 336

Synthesis of N-[1-(pyrimidin-2-yl)piperidin-4-yl]-4-(1H-pyrrolo[3,2-c]pyridin-4-yl)benzamide [336] (Hereinafter, Referred to as a Compound [336])

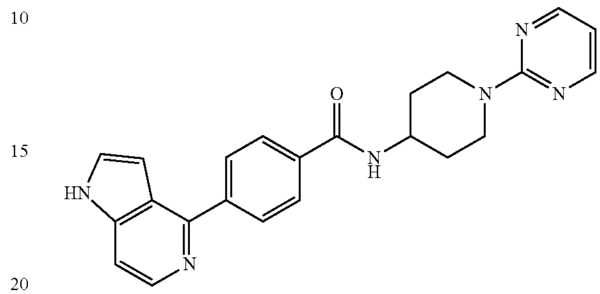

(1) Synthesis of ethyl 4-(1-{[2-(trimethylsilyl)ethoxy]methyl}-1H-pyrrolo[3,2-c]pyridin-4-yl)benzoate [336-1] (Hereinafter, Referred to as a Compound [336-1])

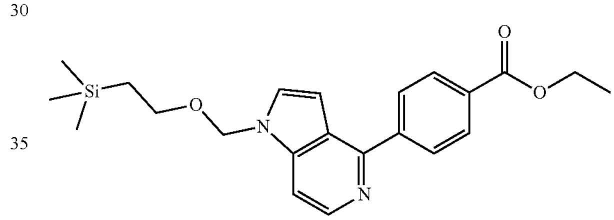

To a solution of the compound [5-1] (133 mg) in THF (2.5 mL) was added 60% sodium hydride (24 mg) at room temperature, and the mixture was stirred at room temperature for 5 minutes. To the reaction mixture was added 2-(trimethylsilyl) ethoxymethyl chloride (97 μL) at room temperature, and the mixture was stirred at room temperature for 30 minutes. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (140 mg) as a colorless oil.

$^1$H-NMR (400 MHz, $CDCl_3$) δ: 8.50 (d, J=6.0 Hz, 1H), 8.21-8.19 (m, 2H), 8.08-8.06 (m, 2H), 7.41 (d, J=6.0 Hz, 1H), 7.29 (d, J=3.2 Hz, 1H), 6.83 (d, J=3.2 Hz, 1H), 5.53 (s, 2H), 4.42 (q, J=7.2 Hz, 2H), 3.50 (t, J=8.4 Hz, 2H), 1.43 (t, J=7.2 Hz, 3H), 0.91 (t, J=8.4 Hz, 2H), −0.05 (s, 9H).

ESI-MS: 397.4 $[M+H]^+$ (2) Synthesis of 4-(1-{[2-(trimethylsilyl) ethoxy] methyl}-1H-pyrrolo[3,2-c]pyridin-4-yl)benzoic Acid [336-2] (Hereinafter, Referred to as a Compound [336-2])

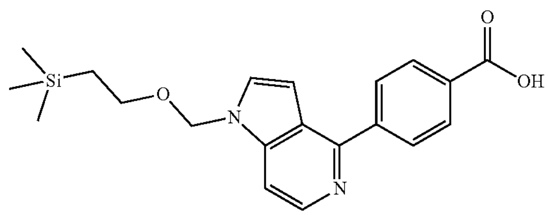 [SMILES: C[Si](C)(C)CCOCn1ccc2c(-c3ccc(C(=O)O)cc3)nccc21]

To a solution of the compound [336-1] (136 mg) in methanol (3.4 mL) was added a 2 M aqueous sodium hydroxide solution (1.7 mL) at room temperature, and the mixture was stirred at room temperature for 30 minutes. The reaction mixture was concentrated under reduced pressure, then 2 M hydrochloric acid (1.7 mL) was added, and the resulting solid was collected by filtration and dried under reduced pressure to give the title compound (114 mg) as a white solid.

$^1$H-NMR (400 MHz, $CD_3OD$) δ: 8.44 (d, J=6.4 Hz, 1H), 8.32-8.29 (m, 2H), 8.06-8.02 (m, 3H), 7.92 (d, J=3.6 Hz, 1H), 7.08 (d, J=3.6 Hz, 1H), 5.78 (s, 2H), 3.60 (t, J=8.0 Hz, 2H), 0.91 (t, J=8.0 Hz, 2H), −0.05 (s, 9H).

ESI-MS: 369.4 [M+H]$^+$ (3) Synthesis of N-[1-(pyrimidin-2-yl)piperidin-4-yl]-4-(1-{[2-(trimethylsilyl) ethoxy]methyl}-1H-pyrrolo[3,2-c]pyridin-4-yl)benzamide [336-3] (Hereinafter, Referred to as a Compound [336-3])

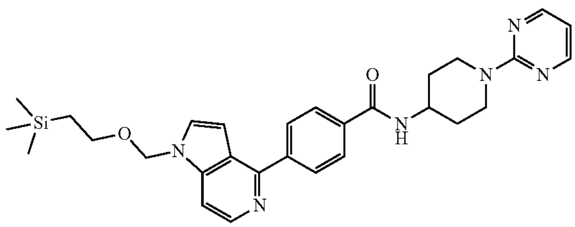 [SMILES: C[Si](C)(C)CCOCn1ccc2c(-c3ccc(C(=O)NC4CCN(c5ncccn5)CC4)cc3)nccc21]

To a solution of the compound [336-2] (37 mg) in DMF (1.0 mL) were added DIPEA (19 μL) and (1-cyano-2-ethoxy-2-oxoethylideneaminooxy)dimethylaminomorpholinocarbenium hexafluorophosphate (47 mg) at room temperature, and the mixture was stirred at room temperature for 5 minutes. To the reaction mixture was added 1-(pyrimidin-2-yl)piperidin-4-amine (23 mg) at room temperature, and the mixture was stirred at room temperature for 2 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (45 mg) as a white solid.

$^1$H-NMR (400 MHz, DMSO-$d_6$) δ: 8.39-8.36 (m, 4H), 8.07-8.05 (m, 2H), 8.00-7.98 (m, 2H), 7.69 (d, J=3.2 Hz, 1H), 7.61 (d, J=6.4 Hz, 1H), 6.85 (d, J=3.2 Hz, 1H), 6.60 (t, J=5.2 Hz, 1H), 5.63 (s, 2H), 4.68-4.64 (m, 2H), 4.20-4.10 (m, 1H), 3.48 (t, J=8.4 Hz, 2H), 3.07-3.01 (m, 2H), 1.91-1.87 (m, 2H), 1.56-1.46 (m, 2H), 0.82 (t, J=8.4 Hz, 2H), −0.10 (s, 9H).

ESI-MS: 529.5 [M+H]$^+$ (4) Synthesis of N-[1-(pyrimidin-2-yl)piperidin-4-yl]-4-(1H-pyrrolo[3,2-c]pyridin-4-yl)benzamide [336]

To the compound [336-3] (28 mg) was added a solution of 1 M tetrabutylammonium fluoride in THF (533 μL) at room temperature, and the mixture was stirred at 60° C. for 26 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (8.1 mg) as a white solid.

$^1$H-NMR (400 MHz, DMSO-$d_6$) δ: 11.71 (br, 1H), 8.39-8.36 (m, 3H), 8.28 (d, J=5.2 Hz, 1H), 8.08-8.06 (m, 2H), 7.99-7.97 (m, 2H), 7.56-7.55 (m, 1H), 7.41 (d, J=6.0 Hz, 1H), 6.79 (s, 1H), 6.61 (t, J=4.8 Hz, 1H), 4.68-4.64 (m, 2H), 4.19-4.10 (m, 1H), 3.06-3.00 (m, 2H), 1.91-1.87 (m, 2H), 1.56-1.46 (m, 2H).

ESI-MS: 399.4 [M+H]$^+$

Example 337

Synthesis of N-(trans-4-hydroxycyclohexyl)-4-(1H-pyrrolo[3,2-c]pyridin-4-yl)benzamide [337] (Hereinafter, Referred to as a Compound [337])

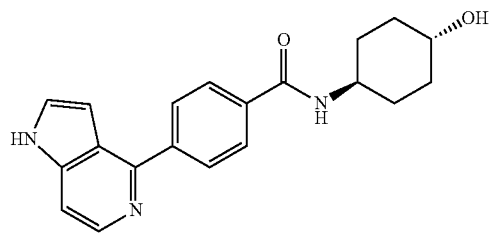 [SMILES: O=C(N[C@H]1CC[C@H](O)CC1)c1ccc(-c2nccc3[nH]ccc23)cc1]

(1) Synthesis of 4-(1H-pyrrolo[3,2-c]pyridin-4-yl) benzoic Acid [337-1] (Hereinafter, Referred to as a Compound [337-1])

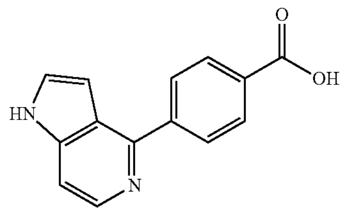 [SMILES: O=C(O)c1ccc(-c2nccc3[nH]ccc23)cc1]

To a solution of the compound [5-1] (533 mg) in methanol (20 mL) was added a 2 M aqueous sodium hydroxide solution (10 mL) at room temperature, and the mixture was stirred at room temperature for 1 hour. The reaction mixture was concentrated under reduced pressure, then 2 M hydrochloric acid (10 mL) was added, and the resulting solid was collected by filtration and dried under reduced pressure to give the title compound (427 mg) as a yellow white solid.

$^1$H-NMR (400 MHz, DMSO-$d_6$) δ: 8.38 (d, J=6.4 Hz, 1H), 8.18-8.16 (m, 2H), 8.12-8.10 (m, 2H), 7.87-7.86 (m, 1H), 7.79 (d, J=6.4 Hz, 1H), 6.99-6.98 (m, 1H).

ESI-MS: 239.3 [M+H]$^+$ (2) Synthesis of N-(trans-4-hydroxycyclohexyl)-4-(1H-pyrrolo[3,2-c]pyridin-4-yl)benzamide [337]

The title compound was synthesized from the compound [337-1] according to the method of Example 256.

$^1$H-NMR (400 MHz, DMSO-$d_6$) δ: 11.68 (s, 1H), 8.29-8.25 (m, 2H), 8.03 (d, J=8.7 Hz, 2H), 7.94 (d, J=8.2 Hz, 2H), 7.56-7.55 (m, 1H), 7.39 (d, J=5.5 Hz, 1H), 6.79-6.78 (m, 1H), 4.52 (d, J=4.1 Hz, 1H), 3.79-3.72 (m, 1H), 3.43-3.36 (m, 1H), 1.90-1.82 (m, 4H), 1.46-1.34 (m, 2H), 1.30-1.20 (m, 2H).

ESI-MS: 336.2 [M+H]$^+$

Example 338

Synthesis of N-[trans-4-(2-hydroxypropan-2-yl)cyclohexyl]-4-(6-methyl-1H-pyrrolo[3,2-c]pyridin-4-yl)benzamide [338] (Hereinafter, Referred to as a Compound [338])

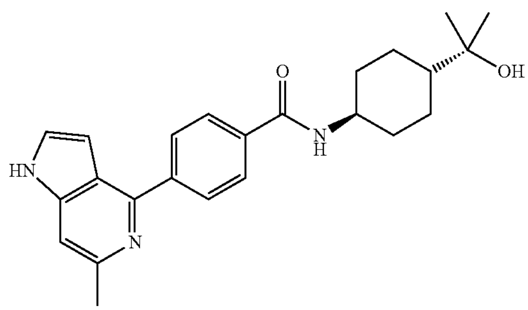

To a solution of 4-chloro-6-methyl-1H-pyrrolo[3,2-c]pyridine (33 mg) in ethanol (2.7 mL)/water (1.3 mL) were added the compound [2-1] (101 mg), potassium carbonate (36 mg), and [1,3-bis(2,6-diisopropylphenyl)-4,5-dihydroimidazol-2-ylidene]chloro[3-phenylallyl]palladium (II) (6.5 mg) at room temperature, and the mixture was stirred at 80° C. for 2 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (10 mg) as a white solid.

$^1$H-NMR (400 MHz, DMSO-$d_6$) δ: 11.50 (br, 1H), 8.26 (d, J=8.0 Hz, 1H), 8.05-8.03 (m, 2H), 7.97-7.95 (m, 2H), 7.45-7.44 (m, 1H), 7.23 (s, 1H), 6.71 (d, J=2.8 Hz, 1H), 4.03 (s, 1H), 3.78-3.68 (m, 1H), 2.58 (s, 3H), 1.92-1.82 (m, 4H), 1.38-1.29 (m, 2H), 1.22-1.01 (m, 9H).

ESI-MS: 392.4 [M+H]$^+$

Example 339

Synthesis of N-[trans-4-(2-hydroxypropan-2-yl)cyclohexyl]-4-(7-methyl-1H-pyrrolo[3,2-c]pyridin-4-yl)benzamide [339] (Hereinafter, Referred to as a Compound [339])

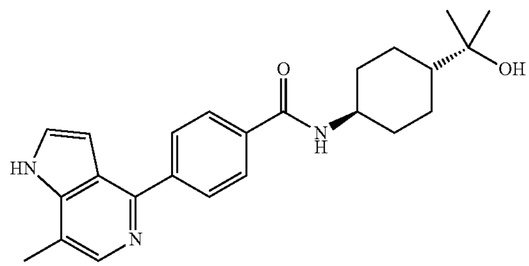

To a solution of 4-chloro-7-methy-1H-pyrrolo[3,2-c]pyridine (33 mg) in ethanol (2.7 mL)/water (1.3 mL) were added the compound [2-1] (101 mg), potassium carbonate (36 mg), and [1,3-bis(2,6-diisopropylphenyl)-4,5-dihydroimidazol-2-ylidene]chloro[3-phenylallyl]palladium (II) (6.5 mg) at room temperature, and the mixture was stirred at 80° C. for 3 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (14 mg) as a white solid.

$^1$H-NMR (400 MHz, $CD_3OD$) δ: 8.06 (s, 1H), 7.98-7.93 (m, 4H), 7.46-7.45 (m, 1H), 6.77 (d, J=3.2 Hz, 1H), 3.90-3.83 (m, 1H), 2.56 (s, 3H), 2.10-2.08 (m, 2H), 1.98-1.95 (m, 2H), 1.47-1.17 (m, 11H).

ESI-MS: 392.4 [M+H]$^+$

Example 340

Synthesis of 3-fluoro-N-[trans-4-(2-hydroxypropan-2-yl)cyclohexyl]-4-(1H-pyrrolo[3,2-c]pyridin-4-yl)benzamide [340] (Hereinafter, Referred to as a Compound [340])

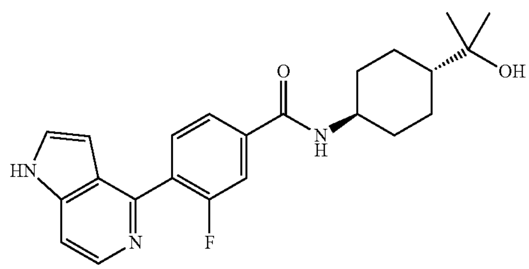 [SMILES: CC(C)(O)[C@H]1CC[C@H](NC(=O)c2ccc(-c3nccc4[nH]ccc34)c(F)c2)CC1]

(1) Synthesis of methyl 3-fluoro-4-(1H-pyrrolo[3,2-c]pyridin-4-yl)benzoate [340-1] (Hereinafter, Referred to as a Compound [340-1])

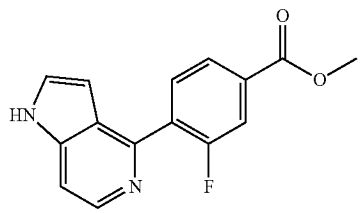 [SMILES: COC(=O)c1ccc(-c2nccc3[nH]ccc23)c(F)c1]

To a solution of 4-chloro-1H-pyrrolo[3,2-c]pyridine (153 mg) in methanol (6.6 mL)/water (3.3 mL) were added 2-fluoro-4-(methoxycarbonyl)phenylboronic acid (218 mg), potassium carbonate (152 mg), and [1,3-bis(2,6-diisopropylphenyl)-4,5-dihydroimidazol-2-ylidene]chloro[3-phenylallyl]palladium (II) (32.5 mg) at room temperature, and the mixture was stirred at 80° C. for 2 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (113 mg) as a white solid.

$^1$H-NMR (400 MHz, $CDCl_3$) δ: 8.60 (br, 1H), 8.48 (d, J=6.0 Hz, 1H), 7.99-7.96 (m, 1H), 7.91-7.83 (m, 2H), 7.38 (d, J=6.0 Hz, 1H), 7.31-7.30 (m, 1H), 6.60-6.59 (m, 1H), 3.97 (s, 3H).

ESI-MS: 271.3 [M+H]$^+$ (2) Synthesis of 3-fluoro-4-(1H-pyrrolo[3,2-c]pyridin-4-yl)benzoic acid [340-2] (Hereinafter, Referred to as a Compound [340-2])

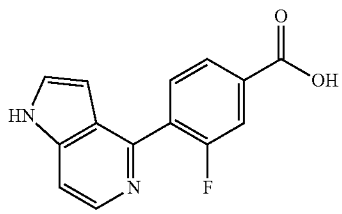 [SMILES: O=C(O)c1ccc(-c2nccc3[nH]ccc23)c(F)c1]

To a solution of the compound [340-1] (113 mg) in methanol (4.2 mL) was added a 2 M aqueous sodium hydroxide solution (2.1 mL) at room temperature, and the mixture was stirred at room temperature for 30 minutes. The reaction mixture was concentrated under reduced pressure and 2 M hydrochloric acid was added. The resulting solid was collected by filtration, washed with water, and then dried under reduced pressure to give the title compound (68.5 mg) as a white solid.

$^1$H-NMR (400 MHz, DMSO-$d_6$) δ: 8.45 (d, J=6.4 Hz, 1H), 8.01-7.86 (m, 5H), 6.72 (s, 1H).

ESI-MS: 257.2 [M+H]$^+$ (3) Synthesis of 3-fluoro-N-[trans-4-(2-hydroxypropan-2-yl)cyclohexyl]-4-(1H-pyrrolo[3,2-c]pyridin-4-yl)benzamide [340]

To a solution of 2-(trans-4-aminocyclohexyl) propan-2-ol (20 mg) in DMF (5.0 mL) were added DIPEA (19 μL), (1-cyano-2-ethoxy-2-oxoethylideneaminooxy)dimethylaminomorpholinocarbenium hexafluorophosphate (47 mg), and the compound [340-2] (26 mg) at room temperature, and the mixture was stirred at room temperature for 40 minutes. DIPEA (19 μL), (1-cyano-2-ethoxy-2-oxoethylideneaminooxy)dimethylaminomorpholinocarbenium hexafluorophosphate (47 mg), and 2-(trans-4-aminocyclohexyl) propan-2-ol (20 mg) were added at room temperature, and the mixture was stirred at room temperature for 40 minutes. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (4.0 mg) as a white solid.

$^1$H-NMR (400 MHz, DMSO-$d_6$) δ: 11.68 (br, 1H), 8.37 (d, J=8.0 Hz, 1H), 8.29 (d, J=5.6 Hz, 1H), 7.83-7.73 (m, 3H), 7.51-7.50 (m, 1H), 7.46-7.45 (m, 1H), 6.39 (s, 1H), 4.05 (s, 1H), 3.75-3.69 (m, 1H), 1.93-1.90 (m, 2H), 1.85-1.83 (m, 2H), 1.36-1.28 (m, 2H), 1.22-1.04 (m, 9H).

ESI-MS: 396.4 [M+H]$^+$

Example 341

Synthesis of N-(trans-4-hydroxycyclohexyl)-4-(thieno[3,2-c]pyridin-4-yl)benzamide [341] (Hereinafter, Referred to as a Compound [341])

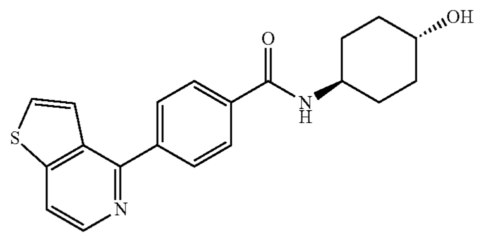 [SMILES: O=C(N[C@H]1CC[C@H](O)CC1)c1ccc(-c2nccc3sccc23)cc1]

(1) Synthesis of N-(trans-4-hydroxycyclohexyl)-4-(4,4,5,5-tetramethyl-1,3,2-dioxaborolan-2-yl)benzamide [341-1] (Hereinafter, Referred to as a Compound [341-1])

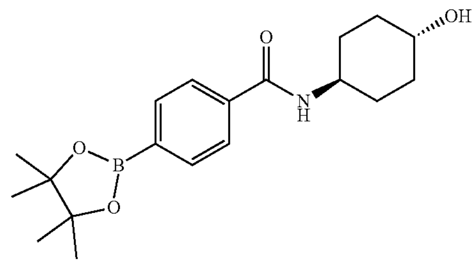 [SMILES: CC1(C)OB(c2ccc(C(=O)N[C@H]3CC[C@H](O)CC3)cc2)OC1(C)C]

The title compound was synthesized by a method according to step (1) in Example 2, using trans-4-aminocyclohexanol in place of 2-(trans-4-aminocyclohexyl) propan-2-ol.

ESI-MS: 346.4 $[M+H]^+$ (2) Synthesis of N-(trans-4-hydroxycyclohexyl)-4-(thieno[3,2-c]pyridin-4-yl)benzamide [341]

To a solution of 4-chlorothieno[3,2-c]pyridine (30 mg) in ethanol (0.75 mL)/water (0.75 mL) were added the compound [341-1] (92 mg), potassium carbonate (32 mg), and [1,3-bis(2,6-diisopropylphenyl)-4,5-dihydroimidazol-2-ylidene]chloro[3-phenylallyl]palladium (II) (34 mg) at room temperature, and the mixture was stirred at 120° C. for 30 minutes under an argon atmosphere using a microwave reactor. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (18 mg) as a white solid.

ESI-MS: 353.3 $[M+H]^+$

Example 342

Synthesis of N-[trans-4-(2-hydroxy-2-methylpropoxy)cyclohexyl]-4-(6-methylfuro[3,2-c]pyridin-4-yl)benzamide [342] (Hereinafter, Referred to as a Compound [342])

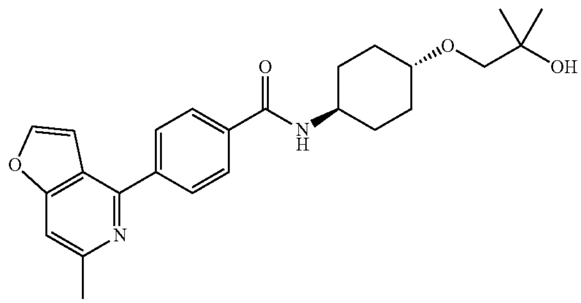 [SMILES: Cc1cc2occc2c(-c2ccc(C(=O)N[C@H]3CC[C@H](OCC(C)(C)O)CC3)cc2)n1]

To a solution of the compound [330-2] (9.7 mg) in DMF (0.80 mL) were added DIPEA (9.8 μL), the compound [64-4] (7.2 mg), and (1-cyano-2-ethoxy-2-oxoethylideneaminooxy)dimethylaminomorpholinocarbenium hexafluorophosphate (18 mg) at room temperature, and the mixture was stirred at room temperature for 4 hours. Then, to the reaction mixture was added triethylamine (10 μL) at room temperature, and the mixture was stirred at room temperature for 40 minutes. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (9.7 mg) as a white solid.

$^1$H-NMR (400 MHz, DMSO-$d_6$) δ: 8.32 (d, J=7.6 Hz, 1H), 8.13 (d, J=2.0 Hz, 1H), 8.07-8.05 (m, 2H), 8.00-7.97 (m, 2H), 7.56 (s, 1H), 7.28-7.27 (m, 1H), 4.22 (s, 1H), 3.84-3.74 (m, 1H), 3.28-3.17 (m, 3H), 2.64 (s, 3H), 2.03-2.01 (m, 2H), 1.89-1.86 (m, 2H), 1.45-1.35 (m, 2H), 1.29-1.20 (m, 2H), 1.06 (s, 6H).

ESI-MS: 423.4 $[M+H]^+$

Example 343

Synthesis of N-(4-hydroxybicyclo[2.2.2]octan-1-yl)-4-(6-methylfuro[3,2-c]pyridin-4-yl)benzamide [343] (Hereinafter, Referred to as a Compound [343])

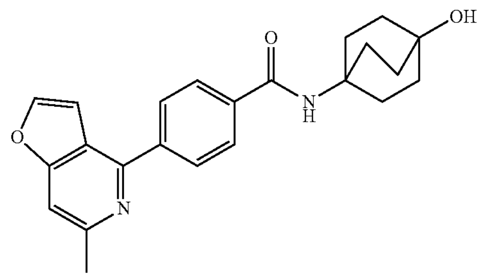 [SMILES: Cc1cc2occc2c(-c2ccc(C(=O)NC34CCC(O)(CC3)CC4)cc2)n1]

To a solution of the compound [330-2] (20 mg) in DMF (0.8 mL) were added (1-cyano-2-ethoxy-2-oxoethylideneaminooxy)dimethylaminomorpholinocarbenium hexafluorophosphate (37 mg), DIPEA (35 μL), and 4-aminobicyclo[2.2.2]octan-1-ol hydrochloride (18 mg) at room temperature, and the mixture was stirred at room temperature for 16 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (25 mg) as a white solid.

$^1$H-NMR (400 MHz, DMSO-$d_6$) δ: 8.12-8.11 (m, 1H), 8.04-8.00 (m, 2H), 7.92-7.90 (m, 2H), 7.72-7.71 (m, 1H), 7.55 (s, 1H), 7.26-7.25 (m, 1H), 4.29 (s, 1H), 2.63 (s, 3H), 2.05-2.03 (m, 6H), 1.62-1.59 (m, 6H).

ESI-MS: 377.3 $[M+H]^+$

Example 344

Synthesis of N-(trans-4-hydroxy-4-methylcyclohexyl)-4-(6-methylfuro[3,2-c]pyridin-4-yl)benzamide [344] (Hereinafter, Referred to as a Compound [344])

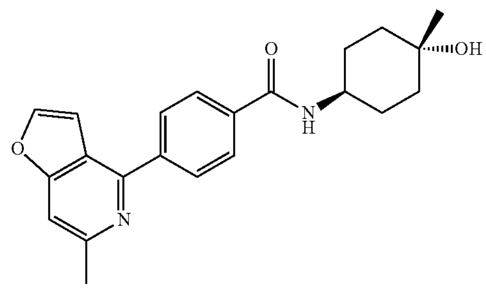 [SMILES: Cc1cc2occc2c(-c2ccc(C(=O)N[C@H]3CC[C@](C)(O)CC3)cc2)n1]

To a solution of the compound [330-2] (20 mg) in DMF (0.8 mL) were added (1-cyano-2-ethoxy-2-oxoethylideneaminooxy)dimethylaminomorpholinocarbenium hexafluorophosphate (37 mg), DIPEA (15 μL), and trans-4-amino-1-methylcyclohexanol (13 mg) at room temperature, and the mixture was stirred at room temperature for 16 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (11 mg) as a white solid.

$^1$H-NMR (400 MHz, DMSO-$d_6$) δ: 8.24 (d, J=7.8 Hz, 1H), 8.10 (d, J=2.3 Hz, 1H), 8.03 (d, J=8.2 Hz, 2H), 7.95 (d, J=8.2 Hz, 2H), 7.53 (s, 1H), 7.26-7.25 (m, 1H), 4.26 (s, 1H), 3.81-3.78 (m, 1H), 2.61 (s, 3H), 1.75-1.73 (m, 2H), 1.58-1.41 (m, 6H), 1.13 (s, 3H).

ESI-MS: 365.3 [M+H]$^+$

Example 345

Synthesis of 3-fluoro-4-(furo[3,2-c]pyridin-4-yl)-N-(4-hydroxybicyclo[2.2.2]octan-1-yl)benzamide [345] (Hereinafter, Referred to as a Compound [345])

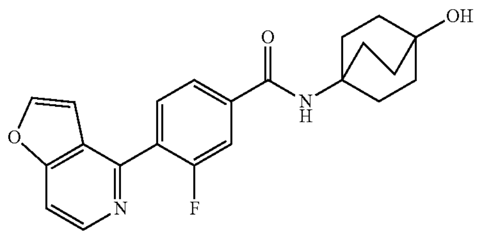 [SMILES: O=C(NC12CCC(O)(CC1)CC2)c1ccc(-c2nccc3occc23)c(F)c1]

To a solution of the compound [125-2] (20 mg) in DMF (0.8 mL) were added (1-cyano-2-ethoxy-2-oxoethylideneaminooxy)dimethylaminomorpholinocarbenium hexafluorophosphate (37 mg), DIPEA (32 μL), and 4-aminobicyclo[2.2.2]octan-1-ol hydrochloride (18 mg) at room temperature, and the mixture was stirred at room temperature for 19 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (25 mg) as a yellow white solid.

$^1$H-NMR (400 MHz, DMSO-$d_6$) δ: 8.60 (dd, J=5.7, 1.1 Hz, 1H), 8.18 (d, J=1.8 Hz, 1H), 7.83-7.77 (m, 5H), 6.94-6.93 (m, 1H), 4.31 (s, 1H), 2.07-2.03 (m, 6H), 1.64-1.60 (m, 6H).

ESI-MS: 381.2 [M+H]$^+$

Example 346

Synthesis of 3-fluoro-4-(furo[3,2-c]pyridin-4-yl)-N-(trans-4-hydroxy-4-methylcyclohexyl)benzamide [346] (Hereinafter, Referred to as a Compound [346])

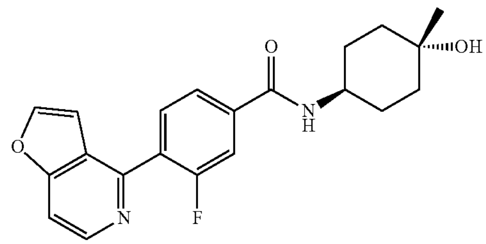 [SMILES: C[C@]1(O)CC[C@H](NC(=O)c2ccc(-c3nccc4occc34)c(F)c2)CC1]

To a solution of the compound [125-2] (20 mg) in DMF (0.8 mL) were added (1-cyano-2-ethoxy-2-oxoethylideneaminooxy)dimethylaminomorpholinocarbenium hexafluorophosphate (37 mg), DIPEA (15 μL), and trans-4-amino-1-methylcyclohexanol (13 mg) at room temperature, and the mixture was stirred at room temperature for 19 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (23 mg) as a white solid.

$^1$H-NMR (400 MHz, DMSO-$d_6$) δ: 8.62-8.59 (m, 1H), 8.36 (d, J=5.5 Hz, 1H), 8.19-8.18 (m, 1H), 7.84-7.78 (m, 4H), 6.96-6.95 (m, 1H), 4.30 (s, 1H), 3.86-3.80 (m, 1H), 1.76-1.41 (m, 8H), 1.16 (s, 3H).

ESI-MS: 369.3 [M+H]$^+$

Example 347

Synthesis of 3-fluoro-4-(furo[3,2-c]pyridin-4-yl)-N-{trans-4-[(1-hydroxycyclopropyl)methoxy]cyclohexyl}benzamide [347] (Hereinafter, Referred to as a Compound [347])

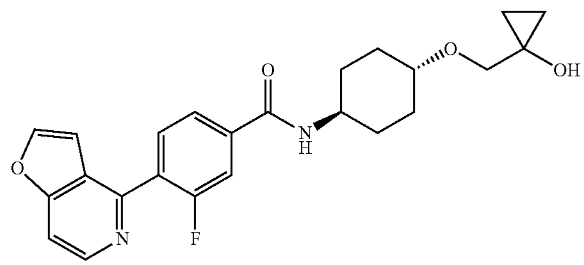 [SMILES: O=C(N[C@H]1CC[C@H](OCC2(O)CC2)CC1)c1ccc(-c2nccc3occc23)c(F)c1]

To a solution of the compound [125-2] (22 mg) in DMF (0.8 mL) were added (1-cyano-2-ethoxy-2-oxoethylideneaminooxy)dimethylaminomorpholinocarbenium hexafluorophosphate (37 mg), DIPEA (15 μL), and the compound [258-2] (12 mg) at room temperature, and the mixture was stirred at room temperature for 19 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (11 mg) as a yellow solid.

$^1$H-NMR (400 MHz, DMSO-$d_6$) δ: 8.61 (d, J=5.5 Hz, 1H), 8.41 (d, J=7.8 Hz, 1H), 8.19 (d, J=2.3 Hz, 1H), 7.90-7.76 (m, 4H), 6.92-6.90 (m, 1H), 5.24 (s, 1H), 3.84-3.71 (m, 1H), 3.42 (s, 2H), 3.29-3.27 (m, 1H), 2.05-2.02 (m, 2H), 1.90-1.87 (m, 2H), 1.45-1.33 (m, 2H), 1.27-1.20 (m, 2H), 0.55-0.52 (m, 2H), 0.46-0.43 (m, 2H).

ESI-MS: 425.3 [M+H]$^+$

Example 348

Synthesis of 4-(furo[3,2-c]pyridin-4-yl)-N-[cis-4-(2-hydroxy-2-methylpropoxy)cyclohexyl]benzamide [348] (Hereinafter, Referred to as a Compound [348])

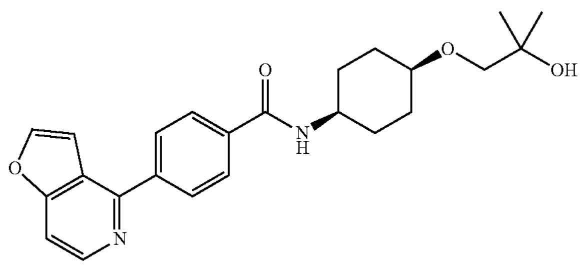 [SMILES: CC(C)(O)CO[C@H]1CC[C@@H](NC(=O)c2ccc(-c3nccc4occc34)cc2)CC1]

(1) Synthesis of cis-4-(dibenzylamino)cyclohexan-1-ol [348-1] (Hereinafter, Referred to as a Compound [348-1])

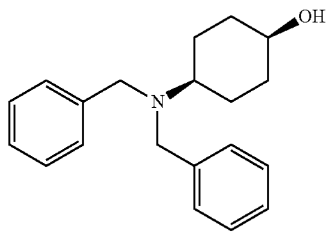 [SMILES: O[C@H]1CC[C@@H](N(Cc2ccccc2)Cc2ccccc2)CC1]

To a solution of cis-4-aminocyclohexan-1-ol hydrochloride (3.0 g) in acetonitrile (40 mL) were added benzyl bromide (5.2 mL) and potassium carbonate (11 g) at room temperature, and the mixture was heated under reflux for 6 hours. To the reaction mixture was added a saturated aqueous ammonium chloride solution, and the mixture was extracted with ethyl acetate. The organic layer was dried over anhydrous sodium sulfate and concentrated under reduced pressure. The obtained residue was purified by silica gel column chromatography to give the title compound (3.8 g) as a white solid.

ESI-MS: 296.4 [M+H]$^+$ (2) Synthesis of tert-butyl 2-{[cis-4-(dibenzylamino)cyclohexyl]oxy}acetate [348-2] (Hereinafter, Referred to as a Compound [348-2])

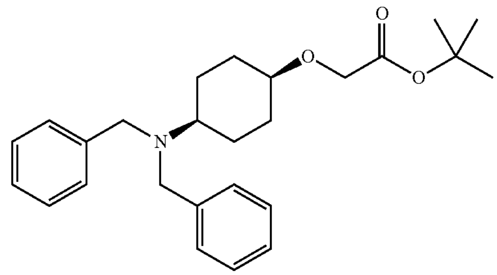 [SMILES: CC(C)(C)OC(=O)CO[C@H]1CC[C@@H](N(Cc2ccccc2)Cc2ccccc2)CC1]

To a solution of the compound [348-1] (1.0 g) in DMF (5.0 mL) were added tert-butyl bromoacetate (1.0 mL) and 60% sodium hydride (320 mg) at room temperature, and the mixture was stirred at room temperature for 5 minutes. Further, to the reaction mixture were added tert-butyl bromoacetate (1.0 mL) and 60% sodium hydride (320 mg) at room temperature, and the mixture was stirred at 55° C. for 90 minutes. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (550 mg) as a colorless oil.

ESI-MS: 410.4 [M+H]$^+$ (3) Synthesis of 1-{[cis-4-(dibenzylamino)cyclohexyl]oxy}-2-methylpropan-2-ol [348-3] (Hereinafter, Referred to as a Compound [348-3])

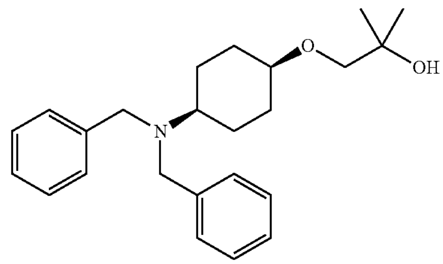 [SMILES: CC(C)(O)CO[C@H]1CC[C@@H](N(Cc2ccccc2)Cc2ccccc2)CC1]

To a solution of the compound [348-2] (400 mg) in THF (2.0 mL) was added a solution of 3 M methylmagnesium bromide in diethyl ether (3.2 mL) at room temperature, and the mixture was stirred at room temperature for 1 hour. To the reaction mixture was added a saturated aqueous ammonium chloride solution, and the mixture was extracted with ethyl acetate. The organic layer was dried over anhydrous sodium sulfate and concentrated under reduced pressure. The obtained residue was purified by silica gel column chromatography to give the title compound (134 mg) as a white solid.

ESI-MS: 368.4 [M+H]$^+$ (4) Synthesis of 1-[(cis-4-aminocyclohexyl)oxy]-2-methylpropan-2-ol [348-4] (Hereinafter, Referred to as a Compound [348-4])

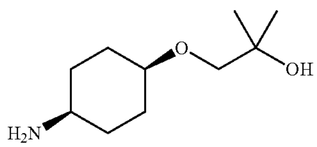

To a solution of the compound [348-3] (134 mg) in ethanol (1.0 mL) was added 20% palladium hydroxide-activated carbon (26.0 mg) at room temperature, and the mixture was stirred at room temperature for 4 hours under a hydrogen atmosphere. The reaction mixture was filtered and concentrated under reduced pressure to give the title compound (64.2 mg) as a black oil.

ESI-MS: 188.3 $[M+H]^+$ (5) Synthesis of 4-(furo[3,2-c]pyridin-4-yl)-N-[cis-4-(2-hydroxy-2-methylpropoxy)cyclohexyl]benzamide To a solution of the compound [99-1] (29 mg) in DMF (1.0 mL) were added (1-cyano-2-ethoxy-2-oxoethylideneaminooxy)dimethylaminomorpholinocarbenium hexafluorophosphate (51 mg), DIPEA (20 μL), and the compound [348-4] (20 mg) at room temperature, and the mixture was stirred at room temperature for 19 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (6.2 mg) as a white solid.

$^1$H-NMR (400 MHz, $CD_3OD$) δ: 8.53 (d, J=5.9 Hz, 1H), 8.01-7.98 (m, 5H), 7.63 (dd, J=5.5, 0.9 Hz, 1H), 7.21-7.20 (m, 1H), 3.98-3.95 (m, 1H), 3.58-3.54 (m, 1H), 3.25 (s, 2H), 2.03-2.00 (m, 2H), 1.80-1.75 (m, 4H), 1.62-1.55 (m, 2H), 1.23 (s, 6H).

ESI-MS: 409.4 $[M+H]^+$

Example 349

Synthesis of 4-(furo[3,2-c]pyridin-4-yl)-N-(4-hydroxybicyclo[2.2.1]heptan-1 yl)benzamide [349] (Hereinafter, Referred to as a Compound [349])

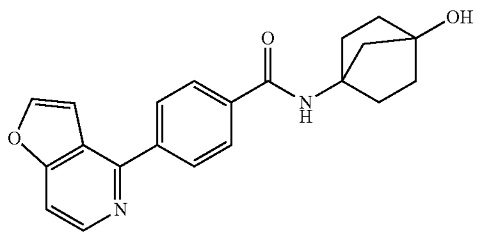 [SMILES: O=C(NC12CCC(O)(CC1)C2)c1ccc(-c2nccc3occc23)cc1]

To a solution of the compound [99-1] (48 mg) in DMF (1.8 mL) were added (1-cyano-2-ethoxy-2-oxoethylideneaminooxy)dimethylaminomorpholinocarbenium hexafluorophosphate (86 mg), DIPEA (68 μL), and 4-aminobicyclo[2.2.1]octan-1-ol hydrochloride (30 mg) at room temperature, and the mixture was stirred at room temperature for 22 hours. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (38 mg) as a red white solid.

$^1$H-NMR (400 MHz, DMSO-$d_6$) δ: 8.58 (dd, J=5.6, 3.2 Hz, 1H), 8.43-8.42 (m, 1H), 8.24-8.23 (m, 1H), 8.07 (d, J=8.2 Hz, 2H), 7.99 (d, J=8.2 Hz, 2H), 7.72 (d, J=5.5 Hz, 1H), 7.35-7.34 (m, 1H), 4.91 (s, 1H), 2.00-1.85 (m, 6H), 1.72-1.55 (m, 4H).

ESI-MS: 349.3 $[M+H]^+$

Example 350

Synthesis of 4-(furo[3,2-c]pyridin-4-yl)-N-[cis-4-hydroxy-4-(2-hydroxypropan-2-yl)cyclohexyl]benzamide [350] (Hereinafter, Referred to as a Compound [350])

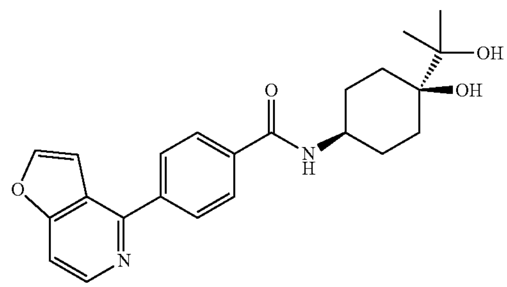 [SMILES: CC(C)(O)[C@]1(O)CC[C@@H](NC(=O)c2ccc(-c3nccc4occc34)cc2)CC1]

(1) Synthesis of cis-4-(dibenzylamino)-1-ethynylcyclohexan-1-ol [350-1] (Hereinafter, Referred to as a Compound [350-1])

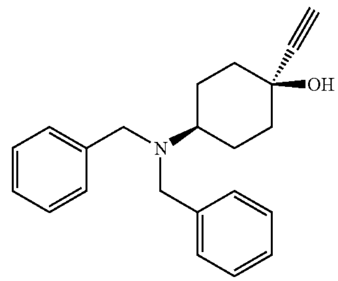 [SMILES: C#C[C@]1(O)CC[C@@H](N(Cc2ccccc2)Cc2ccccc2)CC1]

To a solution of trimethylsilylacetylene (2.1 mL) in THF (20 mL) was added a solution of 1.55 M n-butyllithium in hexane (9.9 mL) dropwise at −78° C., and the mixture was stirred at room temperature for 15 minutes. To the reaction mixture was added a solution of 4-(dibenzylamino)cyclohexanone (1.5 g) in THF (40 mL) dropwise at −78° C. over 10 minutes, and the mixture was stirred at room temperature for 18 hours. To the reaction mixture was added a saturated aqueous ammonium chloride solution, and the mixture was extracted with ethyl acetate. The organic layer was dried over anhydrous sodium sulfate and concentrated under reduced pressure to give a white solid (2.0 g). Subsequently, to a solution of the obtained solid in methanol (50 mL) was added potassium carbonate (1.1 g) at room temperature, and the mixture was stirred at room temperature for 1 hour. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (1.5 g) as a white solid.

ESI-MS: 320.3 [M+H]+

(2) Synthesis of cis-4-(dibenzylamino)-1-(2-hydroxypropan-2-yl)cyclohexan-1-ol [350-2] (Hereinafter, Referred to as a Compound [350-2])

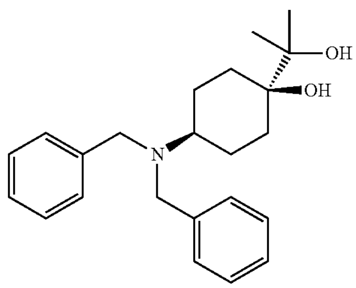 [SMILES: CC(C)(O)[C@]1(O)CC[C@@H](N(Cc2ccccc2)Cc2ccccc2)CC1]

To a solution of the compound [350-1] (290 mg) in THF (6.0 mL)/20% diluted sulfuric acid (3.0 mL) was added mercury (II) sulfate (53 mg) at room temperature, and the mixture was stirred at room temperature for 20 minutes. To the reaction mixture was added a 5 M aqueous sodium hydroxide solution, and the mixture was extracted with diethyl ether. The organic layer was dried over anhydrous sodium sulfate and concentrated under reduced pressure to give a white solid (304 mg). Subsequently, to the obtained solid was added a solution of 3 M methylmagnesium chloride in THF (6.0 mL) at room temperature, and the mixture was stirred at room temperature for 2 hours. To the reaction mixture was added a saturated aqueous ammonium chloride solution, and the mixture was extracted with ethyl acetate. The organic layer was dried over anhydrous sodium sulfate and concentrated under reduced pressure. The obtained residue was purified by silica gel column chromatography to give the title compound (236 mg) as a white solid.

ESI-MS: 354.4 [M+H]+

(3) Synthesis of 4-(furo[3,2-c]pyridin-4-yl)-N-[cis-4-hydroxy-4-(2-hydroxypropan-2-yl)cyclohexyl] benzamide [350]

The title compound was synthesized from the compound [350-2] according to the methods of steps (3) and (4) in Example 257.

ESI-MS: 395.3 [M+H]+

Example 351

Synthesis of N-(4-cyanobicyclo[2.2.2]octan-1-yl)-4-(furo[3,2-c]pyridin-4-yl)benzamide [351] (Hereinafter, Referred to as a Compound [351])

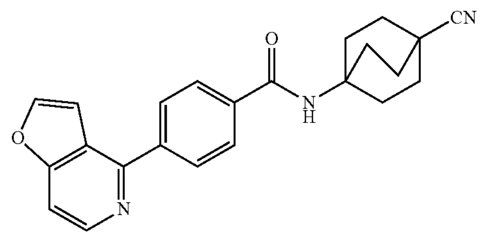 [SMILES: N#CC12CCC(NC(=O)c3ccc(-c4nccc5occc45)cc3)(CC1)CC2]

To a solution of the compound [99-1] (50 mg) in DMF (1.6 mL) were added (1-cyano-2-ethoxy-2-oxoethylideneaminooxy)dimethylaminomorpholinocarbenium hexafluorophosphate (103 mg), DIPEA (109 μL), and 4-aminobicyclo[2.2.2]octane-1-carbonitrile hydrochloride (30 mg) at room temperature, and the mixture was stirred at room temperature for 1 hour. To the reaction mixture was added a saturated aqueous sodium bicarbonate solution, and the mixture was extracted with ethyl acetate. The organic layer was dried over anhydrous sodium sulfate land concentrated under reduced pressure. The obtained residue was purified by silica gel column chromatography to give the title compound (46 mg) as an orange solid.

$^1$H-NMR (400 MHz, DMSO-$d_6$) δ: 8.58 (d, J=5.9 Hz, 1H), 8.23 (d, J=2.3 Hz, 1H), 8.06 (d, J=8.2 Hz, 2H), 7.94-7.89 (m, 3H), 7.72 (d, J=5.9 Hz, 1H), 7.34-7.33 (m, 1H), 2.05-1.98 (m, 12H).

ESI-MS: 372.3 [M+H]+

Example 352

Synthesis of 4-[4-(furo[3,2-c]pyridin-4-yl)benzamide] bicyclo[2.2.2]octane-1-carboxamide [352] (Hereinafter, Referred to as a Compound [352])

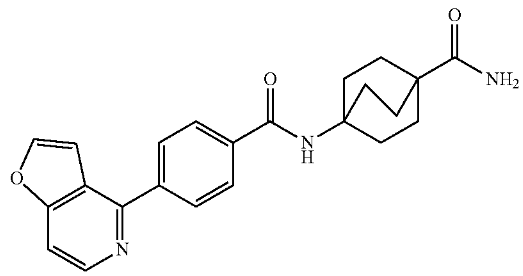 [SMILES: NC(=O)C12CCC(NC(=O)c3ccc(-c4nccc5occc45)cc3)(CC1)CC2]

To a solution of the compound [351] (20 mg) in tert-butanol (0.60 mL) was added potassium tert-butoxide (248 mg) at room temperature, and the mixture was stirred at 80° C. for 21 hours. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (11 mg) as a white solid.

$^1$H-NMR (400 MHz, DMSO-$d_6$) δ: 8.58 (d, J=5.9 Hz, 1H), 8.23 (d, J=2.3 Hz, 1H), 8.06-8.04 (m, 2H), 7.95-7.90 (m, 2H), 7.78-7.77 (m, 1H), 7.72 (dd, J=5.9, 0.9 Hz, 1H), 7.34-7.33 (m, 1H), 6.95 (s, 1H), 6.72 (s, 1H), 1.98-1.94 (m, 6H), 1.78-1.74 (m, 6H).

ESI-MS: 390.4 $[M+H]^+$

Example 353

Synthesis of 4-(furo[3,2-c]pyridin-4-yl)-N-{cis-4-[(1-hydroxycyclopropyl)methoxy]cyclohexyl}benzamide [353] (Hereinafter, Referred to as a Compound [353])

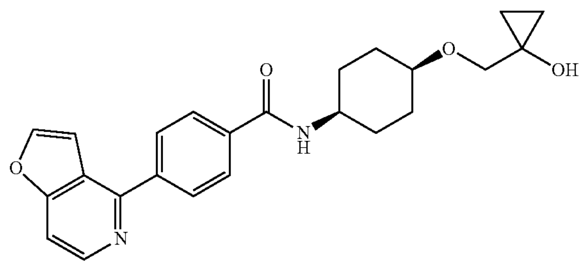 [SMILES: O=C(N[C@H]1CC[C@@H](OCC2(O)CC2)CC1)c1ccc(-c2nccc3occc23)cc1]

(1) Synthesis of 1-({[cis-4-(dibenzylamino)cyclohexyl]oxy}methyl)cyclopropan-1-ol [353-1] (Hereinafter, Referred to as a Compound [353-1])

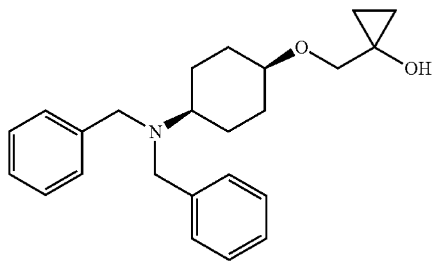 [SMILES: OC1(CO[C@H]2CC[C@@H](N(Cc3ccccc3)Cc3ccccc3)CC2)CC1]

To a solution of the compound [348-2] (1.06 g) in THF (30 mL) were added titanium tetraisopropoxide (7.70 mL) and a solution of 1 M ethylmagnesium bromide in THF (15.5 mL) at room temperature, and the mixture was stirred at room temperature for 3 hours under an argon atmosphere. To the reaction mixture was added water, and the mixture was extracted with ethyl acetate. The organic layer was dried over anhydrous sodium sulfate and concentrated under reduced pressure. The obtained residue was purified by silica gel column chromatography to give the title compound (160 mg) as a white solid.

ESI-MS: 366.4 $[M+H]^+$ (2) Synthesis of 4-(furo[3,2-c]pyridin-4-yl)-N-{cis-4-[(1-hydroxycyclopropyl)methoxy]cyclohexyl}benzamide [353]

To a solution of the compound [353-1] (160 mg) in ethanol (1.0 mL) was added 20% palladium hydroxide-activated carbon (40 mg) at room temperature, and the mixture was stirred at room temperature for 24 hours under a hydrogen atmosphere. The reaction mixture was filtered, and the filtrate was concentrated under reduced pressure. To a solution of the obtained residue in DMF (0.8 mL) were added the compound [99-1] (20 mg), (1-cyano-2-ethoxy-2-oxoethylideneaminooxy)dimethylaminomorpholinocarbenium hexafluorophosphate (39 mg), and DIPEA (16 μL) at room temperature, and the mixture was stirred at room temperature for 1 hour. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (9.2 mg) as a white solid.

$^1$H-NMR (400 MHz, DMSO-$d_6$) δ: 8.58 (dd, J=5.5, 2.1 Hz, 1H), 8.37 (d, J=7.8 Hz, 1H), 8.24-8.23 (m, 1H), 8.08-8.02 (m, 4H), 7.73-7.71 (m, 1H), 7.36-7.35 (m, 1H), 5.21 (s, 1H), 3.88-3.80 (m, 1H), 3.54-3.53 (m, 1H), 3.40 (s, 2H), 1.89-1.48 (m, 8H), 0.57-0.52 (m, 2H), 0.50-0.46 (m, 2H).

ESI-MS: 407.4 $[M+H]^+$

Example 354

Synthesis of 4-(furo[3,2-c]pyridin-4-yl)-N-[cis-4-(2-hydroxypropan-2-yl)cyclohexyl]benzamide [354] (Hereinafter, Referred to as a Compound [354])

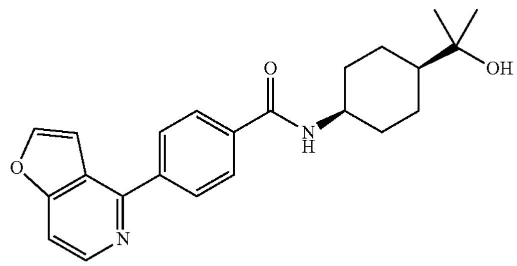 [SMILES: CC(C)(O)[C@H]1CC[C@@H](NC(=O)c2ccc(-c3nccc4occc34)cc2)CC1]

To a solution of the compound [99-1] (20 mg) in DMF (0.8 mL) were added (1-cyano-2-ethoxy-2-oxoethylideneaminooxy)dimethylaminomorpholinocarbenium hexafluorophosphate (39 mg), DIPEA (109 μL), and cis-2-(4-aminocyclohexyl) propan-2-ol hydrochloride (30 mg) at room temperature, and the mixture was stirred at room temperature for 1 hour. To the reaction mixture was added a saturated aqueous sodium bicarbonate solution, and the mixture was extracted with ethyl acetate. The organic layer was dried over anhydrous sodium sulfate and concentrated under reduced pressure. The obtained residue was purified by silica gel column chromatography to give the title compound (21 mg) as a white solid.

$^1$H-NMR (400 MHz, DMSO-$d_6$) δ: 8.59 (dd, J=5.7, 2.1 Hz, 1H), 8.24-8.23 (m, 1H), 8.10-8.07 (m, 3H), 8.01-7.98 (m, 2H), 7.72 (d, J=5.5 Hz, 1H), 7.36-7.35 (m, 1H), 4.07-3.99 (m, 2H), 1.96-1.93 (m, 2H), 1.60-1.37 (m, 6H), 1.23-1.15 (m, 1H), 1.05 (s, 6H).

ESI-MS: 379.4 $[M+H]^+$

Example 355

The H-PGDS inhibitory activity of each Example compound was measured according to the method reported by LIN, Jiang. et al. (WO 2007/041634).

Recombinant human H-PGDS (final concentration: 1.0 nM) expressed in *E. coli* was mixed in an assay buffer containing 20 mM Tris-HCl (pH 8.0), 2 mM magnesium chloride, 2 mM reduced glutathione, and 0.5 mg/mL Y-globulin, and 150 μL of the mixture was dispensed into a 8-strip PCR tube (BM Equipment Co., Ltd.). Test compounds (Example compounds) (16.5 μL) at various concentrations dissolved in DMSO were added and the mixture was preincubated for 15 minutes on ice.

Prostaglandin $H_2$ (final concentration: 25 μM) (Cayman Chemical) was dispensed into another 8-strip PCR tube, and the solvent was dried and solidified using a vacuum concentrator (Thermo Fisher Scientific). To the dried and solidified prostaglandin $H_2$ was added 50 μL of the assay buffer containing H-PGDS and each test compound after the preincubation, and the mixture was reacted on ice for 1 minute. 45 μL of this mixture was added to 45 μL of a stop solution (50 mM aqueous citric acid solution containing iron chloride at a final concentration of 4 mg/mL) to stop the reaction. Then, the reaction solution was deproteinized, added to a 96 square deep well plate (SHONANMARUHACHI STEC Co., Ltd.), and the prostaglandin $D_2$ concentration in the reaction solution was measured by LC-MS/MS. ACQUITY (registered trademark) TOD (Waters) was used as a measuring instrument.

Prostaglandin $D_2$ production activity (%) in the group with each test compound when a value obtained by subtracting the amount of production of prostaglandin $D_2$ in the group without enzyme, which is non-specific production of prostaglandin $D_2$, from the amount of production of prostaglandin $D_2$ in the group without test compound (DMSO-addition group) in each 8-strip PCR tube is 100% was calculated. From the calculated activity value, the test compound concentration that inhibits prostaglandin $D_2$ production by 50% ($IC_{50}$) was determined. The results are shown in Table 1 below.

TABLE 1

| Example No. of test compound | H-PGDS inhibitory activity ($IC_{50}$, nM) |
|---|---|
| [Table 6-1] | |
| Example 1 | 2.7 |
| Example 2 | 0.75 |
| Example 3 | 0.63 |
| Example 4 | 7.4 |
| Example 5 | 1.6 |
| Example 6 | 1.8 |
| Example 7 | 1.4 |
| Example 8 | 1.0 |
| Example 9 | 1.5 |
| Example 10 | 1.7 |
| Example 11 | 1.7 |
| Example 12 | 1.1 |
| Example 13 | 0.58 |
| Example 14 | 1.4 |
| Example 15 | 0.99 |
| Example 16 | 1.1 |
| Example 17 | 0.85 |
| Example 18 | 1.0 |
| Example 19 | 1.0 |
| Example 20 | 0.83 |
| Example 21 | 0.82 |
| Example 22 | 0.85 |
| Example 23 | 0.79 |
| Example 24 | 0.56 |
| Example 25 | 1.6 |
| Example 26 | 1.7 |
| Example 27 | 0.98 |
| Example 28 | 1.4 |
| Example 29 | 0.46 |

TABLE 1-continued

| Example No. of test compound | H-PGDS inhibitory activity ($IC_{50}$, nM) |
|---|---|
| Example 30 | 0.65 |
| Example 31 | 1.5 |
| Example 32 | 1.5 |
| [Table 6-2] | |
| Example 33 | 1.1 |
| Example 34 | 2.4 |
| Example 35 | 1.6 |
| Example 36 | 0.83 |
| Example 37 | 0.86 |
| Example 38 | 1.3 |
| Example 39 | 1.1 |
| Example 40 | 0.89 |
| Example 41 | 0.63 |
| Example 42 | 0.74 |
| Example 43 | 1.3 |
| Example 44 | 0.98 |
| Example 45 | 0.91 |
| Example 46 | 0.63 |
| Example 47 | 1.1 |
| Example 48 | 0.72 |
| Example 49 | 1.2 |
| Example 50 | 1.4 |
| Example 51 | 0.63 |
| Example 52 | 1.6 |
| Example 53 | 1.3 |
| Example 54 | 1.2 |
| Example 55 | 1.2 |
| Example 56 | 1.7 |
| Example 57 | 1.4 |
| Example 58 | 0.64 |
| Example 59 | 9.6 |
| Example 60 | 15 |
| Example 61 | 31 |
| Example 62 | 86 |
| Example 63 | 1.5 |
| Example 64 | 3.1 |
| [Table 6-3] | |
| Example 65 | 9.0 |
| Example 66 | 6.4 |
| Example 67 | 27 |
| Example 68 | 15 |
| Example 69 | 6.0 |
| Example 70 | 12 |
| Example 71 | 12 |
| Example 72 | 12 |
| Example 73 | 4.8 |
| Example 74 | 6.3 |
| Example 75 | 20 |
| Example 76 | 13 |
| Example 77 | 24 |
| Example 78 | 50 |
| Example 79 | 27 |
| Example 80 | 32 |
| Example 81 | 11 |
| Example 82 | 11 |
| Example 83 | 15 |
| Example 84 | 14 |
| Example 85 | 32 |
| Example 86 | 21 |
| Example 87 | 12 |
| Example 88 | 4.2 |
| Example 89 | 3.7 |
| Example 90 | 15 |
| Example 91 | 32 |
| Example 92 | 22 |
| Example 93 | 32 |
| Example 94 | 12 |
| Example 95 | 8.7 |
| Example 96 | 17 |
| [Table 6-4] | |
| Example 97 | 2.8 |
| Example 98 | 107 |
| Example 99 | 1.6 |

TABLE 1-continued

| Example No. of test compound | H-PGDS inhibitory activity ($IC_{50}$, nM) |
|---|---|
| Example 100 | 19 |
| Example 101 | 1.0 |
| Example 102 | 1.8 |
| Example 103 | 2.1 |
| Example 104 | 8.0 |
| Example 105 | 2.3 |
| Example 106 | 3.7 |
| Example 107 | 19 |
| Example 108 | 5.0 |
| Example 109 | 2.9 |
| Example 110 | 5.7 |
| Example 111 | 5.5 |
| Example 112 | 3.4 |
| Example 113 | 2.5 |
| Example 114 | 25 |
| Example 115 | 1.1 |
| Example 116 | 1.6 |
| Example 117 | 12 |
| Example 118 | 0.45 |
| Example 119 | 1.3 |
| Example 120 | 3.3 |
| Example 121 | 1.3 |
| Example 122 | 1.3 |
| Example 123 | 1.8 |
| Example 124 | 1.8 |
| Example 125 | 2.2 |
| Example 126 | 13 |
| Example 127 | 1.6 |
| Example 128 | 3.5 |

[Table 6-5]

| | |
|---|---|
| Example 129 | 2.4 |
| Example 130 | 6.8 |
| Example 131 | 26 |
| Example 132 | 74 |
| Example 133 | 16 |
| Example 134 | 6.6 |
| Example 135 | 14 |
| Example 136 | 9.0 |
| Example 137 | 12 |
| Example 138 | 15 |
| Example 139 | 251 |
| Example 140 | 224 |
| Example 141 | 160 |
| Example 142 | 3.4 |
| Example 143 | 0.78 |
| Example 144 | 1.5 |
| Example 145 | 1.2 |
| Example 146 | 1.0 |
| Example 147 | 1.0 |
| Example 148 | 1.8 |
| Example 149 | 1.8 |
| Example 150 | 1.7 |
| Example 151 | 1.4 |
| Example 152 | 2.3 |
| Example 153 | 4.1 |
| Example 154 | 6.3 |
| Example 155 | 1.5 |
| Example 156 | 1.6 |
| Example 157 | 3.0 |
| Example 158 | 0.69 |
| Example 159 | 1.3 |
| Example 160 | 2.1 |

[Table 6-6]

| | |
|---|---|
| Example 161 | 2.0 |
| Example 162 | 1.9 |
| Example 163 | 2.6 |
| Example 164 | 0.78 |
| Example 165 | 1.3 |
| Example 166 | 1.0 |
| Example 167 | 1.2 |
| Example 168 | 1.7 |
| Example 169 | 3.0 |
| Example 170 | 6.2 |
| Example 171 | 1.9 |

TABLE 1-continued

| Example No. of test compound | H-PGDS inhibitory activity ($IC_{50}$, nM) |
|---|---|
| Example 172 | 2.6 |
| Example 173 | 0.83 |
| Example 174 | 1.1 |
| Example 175 | 1.3 |
| Example 176 | 1.2 |
| Example 177 | 1.2 |
| Example 178 | 1.9 |
| Example 179 | 0.97 |
| Example 180 | 0.96 |
| Example 181 | 1.2 |
| Example 182 | 2.3 |
| Example 183 | 1.7 |
| Example 184 | 2.1 |
| Example 185 | 1.7 |
| Example 186 | 2.3 |
| Example 187 | 0.80 |
| Example 188 | 4.3 |
| Example 189 | 2.3 |
| Example 190 | 0.76 |
| Example 191 | 0.63 |
| Example 192 | 7.7 |

[Table 6-7]

| | |
|---|---|
| Example 193 | 1.0 |
| Example 194 | 0.94 |
| Example 195 | 1.7 |
| Example 196 | 1.5 |
| Example 197 | 6.1 |
| Example 198 | 2.3 |
| Example 199 | 9.7 |
| Example 200 | 1.1 |
| Example 201 | 1.2 |
| Example 202 | 1.5 |
| Example 203 | 1.9 |
| Example 204 | 1.1 |
| Example 205 | 5.6 |
| Example 206 | 39 |
| Example 207 | 6.7 |
| Example 208 | 14 |
| Example 209 | 39 |
| Example 210 | 3.5 |
| Example 211 | 2.5 |
| Example 212 | 3.8 |
| Example 213 | 4.3 |
| Example 214 | 3.4 |
| Example 215 | 4.8 |
| Example 216 | 3.6 |
| Example 217 | 2.4 |
| Example 218 | 21 |
| Example 219 | 12 |
| Example 220 | 68 |
| Example 221 | 4.9 |

[Table 6-8]

| | |
|---|---|
| Example 222 | 2.3 |
| Example 223 | 5.3 |
| Example 224 | 1.8 |
| Example 225 | 6.5 |
| Example 226 | 2.8 |
| Example 227 | 1.4 |
| Example 228 | 1.9 |
| Example 229 | 1.5 |
| Example 230 | 1.2 |
| Example 231 | 3.2 |
| Example 232 | 2.0 |
| Example 233 | 7.5 |
| Example 234 | 1.6 |
| Example 235 | 1.2 |
| Example 236 | 1.1 |
| Example 237 | 1.2 |
| Example 238 | 3.6 |
| Example 239 | 1.2 |
| Example 240 | 1.6 |
| Example 241 | 2.7 |
| Example 242 | 2.0 |
| Example 243 | 2.0 |

TABLE 1-continued

| Example No. of test compound | H-PGDS inhibitory activity ($IC_{50}$, nM) |
|---|---|
| Example 244 | 4.0 |
| Example 245 | 1.4 |
| Example 246 | 1.8 |
| Example 247 | 2.3 |
| Example 248 | 4.4 |
| Example 249 | 1.6 |
| Example 250 | 3.2 |
| Example 251 | 2.0 |
| Example 252 | 1.2 |
| Example 253 | 1.1 |

[Table 6-9]

| Example No. of test compound | H-PGDS inhibitory activity ($IC_{50}$, nM) |
|---|---|
| Example 254 | 4.0 |
| Example 255 | 1.5 |
| Example 256 | 2.6 |
| Example 257 | 1.6 |
| Example 258 | 0.93 |
| Example 259 | 2.0 |
| Example 260 | 1.9 |
| Example 261 | 1.6 |
| Example 262 | 2.5 |
| Example 263 | 4.2 |
| Example 264 | 3.5 |
| Example 265 | 4.8 |
| Example 266 | 3.8 |
| Example 267 | 3.1 |
| Example 268 | 6.4 |
| Example 269 | 5.2 |
| Example 270 | 6.4 |
| Example 271 | 1.2 |
| Example 272 | 2.4 |
| Example 273 | 2.8 |
| Example 274 | 13 |
| Example 275 | 1.8 |
| Example 276 | 12 |
| Example 277 | 3.5 |
| Example 278 | 3.3 |
| Example 279 | 2.0 |
| Example 280 | 2.2 |
| Example 281 | 2.0 |
| Example 282 | 1.3 |
| Example 283 | 1.7 |
| Example 284 | 1.7 |
| Example 285 | 2.0 |

[Table 6-10]

| Example No. of test compound | H-PGDS inhibitory activity ($IC_{50}$, nM) |
|---|---|
| Example 286 | 1.0 |
| Example 287 | 0.87 |
| Example 288 | 1.3 |
| Example 289 | 1.6 |
| Example 290 | 1.3 |
| Example 291 | 2.4 |
| Example 292 | 1.9 |
| Example 293 | 1.6 |
| Example 294 | 1.1 |
| Example 295 | 2.1 |
| Example 296 | 2.9 |
| Example 297 | 1.9 |
| Example 298 | 3.4 |
| Example 299 | 4.0 |
| Example 300 | 4.7 |
| Example 301 | 11 |
| Example 302 | 3.2 |
| Example 303 | 2.1 |
| Example 304 | 9.2 |
| Example 305 | 55 |
| Example 306 | 1.8 |
| Example 307 | 2.2 |
| Example 308 | 1.5 |
| Example 309 | 1.9 |
| Example 310 | 2.6 |
| Example 311 | 2.5 |
| Example 312 | 1.8 |
| Example 313 | 169 |
| Example 314 | 70 |
| Example 315 | 2.6 |
| Example 316 | 1.5 |
| Example 317 | 51 |

[Table 6-11]

| Example No. of test compound | H-PGDS inhibitory activity ($IC_{50}$, nM) |
|---|---|
| Example 318 | 367 |
| Example 319 | 1.6 |
| Example 320 | 0.90 |
| Example 321 | 5.5 |
| Example 322 | 3.2 |
| Example 323 | 1.1 |
| Example 324 | 1.3 |
| Example 325 | 2.3 |
| Example 326 | 1.3 |
| Example 327 | 1.1 |
| Example 328 | 0.74 |
| Example 329 | 2.0 |
| Example 330 | 1.7 |
| Example 331 | 1.8 |
| Example 332 | 1.6 |
| Example 333 | 2.3 |
| Example 334 | 2.0 |
| Example 335 | 1.2 |
| Example 336 | 0.94 |
| Example 337 | 0.44 |
| Example 338 | 2.4 |
| Example 339 | 1.4 |
| Example 340 | 1.0 |
| Example 341 | 2.4 |
| Example 342 | 3.0 |
| Example 343 | 1.2 |
| Example 344 | 1.7 |
| Example 345 | 1.2 |
| Example 346 | 2.0 |
| Example 347 | 2.0 |
| Example 348 | 1.7 |
| Example 349 | 1.5 |

[Table 6-12]

| Example No. of test compound | H-PGDS inhibitory activity ($IC_{50}$, nM) |
|---|---|
| Example 350 | 27 |
| Example 351 | 1.3 |
| Example 352 | 0.89 |
| Example 353 | 1.4 |
| Example 354 | 35 |

The test results indicate that the compound of the present invention exhibits H-PGDS inhibitory activity.

The correspondence relation between each compound of Examples 1 to 354 and Formula (I) is shown below.

| | $R^1$ | $R^2$ | $R^3$ | $R^4$ | $R^5$ | W | X |
|---|---|---|---|---|---|---|---|
| Example 1 | Hydrogen atom | Hydrogen atom | Hydrogen | Hydrogen atom | Hydrogen atom | —N($R^6$)— $R^6$ = Hydrogen atom | 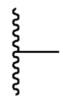 |
| Example 2 | Hydrogen atom | Hydrogen atom | Hydrogen atom | Hydrogen atom | Hydrogen atom | —N($R^6$)— $R^6$ = Hydrogen atom | 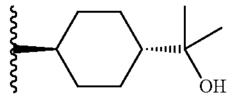 [SMILES: *[C@H]1CC[C@H](C(C)(C)O)CC1] |
| Example 3 | Hydrogen atom | Hydrogen atom | Hydrogen atom | Hydrogen atom | Hydrogen atom | —N($R^6$)— $R^6$ = Hydrogen atom | 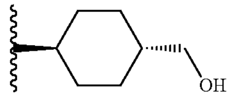 [SMILES: *[C@H]1CC[C@H](CO)CC1] |
| Example 4 | Hydrogen atom | Hydrogen atom | Hydrogen atom | Hydrogen atom | Hydrogen atom | —N($R^6$)— $R^6$ = Methyl | 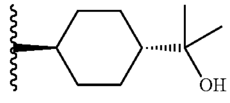 |
| Example 5 | Hydrogen atom | Hydrogen atom | Hydrogen atom | Hydrogen atom | Hydrogen atom | —N($R^6$)— $R^6$ = Hydrogen atom | 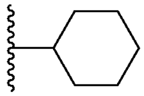 [SMILES: *C1CCCCC1] |
| Example 6 | Hydrogen atom | Hydrogen atom | Hydrogen atom | Hydrogen atom | Hydrogen atom | —N($R^6$)— $R^6$ = Hydrogen atom | 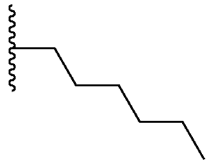 [SMILES: *CCCCCC] |
| Example 7 | Hydrogen atom | Hydrogen atom | Hydrogen atom | Hydrogen atom | Hydrogen atom | —N($R^6$)— $R^6$ = Hydrogen atom | 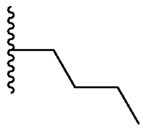 [SMILES: *CCCC] |
| Example 8 | Hydrogen atom | Hydrogen atom | Hydrogen atom | Hydrogen atom | Hydrogen atom | —N($R^6$)— $R^6$ = Hydrogen atom | 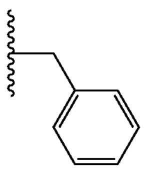 [SMILES: *Cc1ccccc1] |
| Example 9 | Hydrogen atom | Hydrogen atom | Hydrogen atom | Hydrogen atom | Hydrogen atom | —N($R^6$)— $R^6$ = Hydrogen atom | 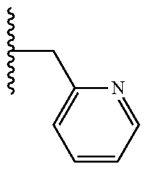 [SMILES: *Cc1ccccn1] |
| Example 10 | Hydrogen atom | Hydrogen atom | Hydrogen atom | Hydrogen atom | Hydrogen atom | —N($R^6$)— $R^6$ = Hydrogen atom | 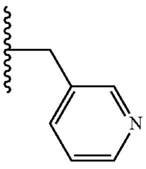 [SMILES: *Cc1cccnc1] |
| Example 11 | Hydrogen atom | Hydrogen atom | Hydrogen atom | Hydrogen atom | Hydrogen atom | —N($R^6$)— $R^6$ = Hydrogen atom | 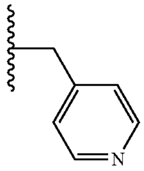 [SMILES: *Cc1ccncc1] |

-continued

| | $R^1$ | $R^2$ | $R^3$ | $R^4$ | $R^5$ | W | X |
|---|---|---|---|---|---|---|---|
| Example 12 | Hydrogen atom | Hydrogen atom | Hydrogen atom | Hydrogen atom | Hydrogen atom | —N($R^6$)— $R^6$ = Hydrogen atom | 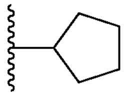 [SMILES: *C1CCCC1] |
| Example 13 | Hydrogen atom | Hydrogen atom | Hydrogen atom | Hydrogen atom | Hydrogen atom | —N($R^6$)— $R^6$ = Hydrogen atom | 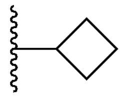 [SMILES: *C1CCC1] |
| Example 14 | Hydrogen atom | Hydrogen atom | Hydrogen atom | Hydrogen atom | Hydrogen atom | —N($R^6$)— $R^6$ = Hydrogen atom | 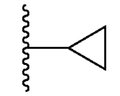 |
| Example 15 | Hydrogen atom | Hydrogen atom | Hydrogen atom | Hydrogen atom | Hydrogen atom | —N($R^6$)— $R^6$ = Hydrogen atom | 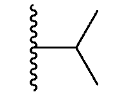 [SMILES: *C(C)C] |
| Example 16 | Hydrogen atom | Hydrogen atom | Hydrogen atom | Hydrogen atom | Hydrogen atom | —N($R^6$)— $R^6$ = Hydrogen atom | 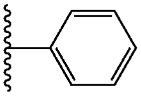 [SMILES: *c1ccccc1] |
| Example 17 | Hydrogen atom | Hydrogen atom | Hydrogen atom | Hydrogen atom | Hydrogen atom | —N($R^6$)— $R^6$ = Hydrogen atom | 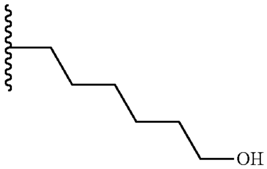 [SMILES: *CCCCCCO] |
| Example 18 | Hydrogen atom | Hydrogen atom | Hydrogen atom | Hydrogen atom | Hydrogen atom | —N($R^6$)— $R^6$ = Hydrogen atom | 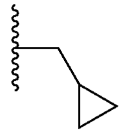 [SMILES: *CC1CC1] |
| Example 19 | Hydrogen atom | Hydrogen atom | Hydrogen atom | Hydrogen atom | Hydrogen atom | —N($R^6$)— $R^6$ = Hydrogen atom | 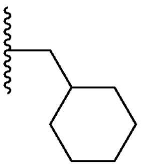 [SMILES: *CC1CCCCC1] |
| Example 20 | Hydrogen atom | Hydrogen atom | Hydrogen atom | Hydrogen atom | Hydrogen atom | —N($R^6$)— $R^6$ = Hydrogen atom | 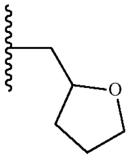 [SMILES: *CC1CCCO1] |
| Example 21 | Hydrogen atom | Hydrogen atom | Hydrogen atom | Hydrogen atom | Hydrogen atom | —N($R^6$)— $R^6$ = Hydrogen atom | 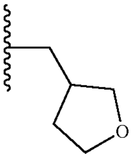 [SMILES: *CC1CCOC1] |
| Example 22 | Hydrogen atom | Hydrogen atom | Hydrogen atom | Hydrogen atom | Hydrogen atom | —N($R^6$)— $R^6$ = Hydrogen atom | 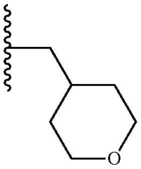 |

-continued

| | $R^1$ | $R^2$ | $R^3$ | $R^4$ | $R^5$ | W | X |
|---|---|---|---|---|---|---|---|
| Example 23 | Hydrogen atom | Hydrogen atom | Hydrogen atom | Hydrogen atom | Hydrogen atom | —N($R^6$)— $R^6$ = Hydrogen atom | 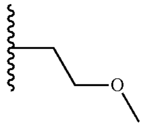 [SMILES: *CCOC] |
| Example 24 | Hydrogen atom | Hydrogen atom | Hydrogen atom | Hydrogen atom | Hydrogen atom | —N($R^6$)— $R^6$ = Hydrogen atom | 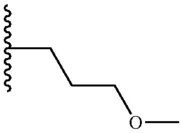 [SMILES: *CCCOC] |
| Example 25 | Hydrogen atom | Hydrogen atom | Hydrogen atom | Hydrogen atom | Hydrogen atom | —N($R^6$)— $R^6$ = Hydrogen atom | 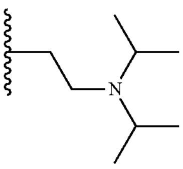 [SMILES: *CCN(C(C)C)C(C)C] |
| Example 26 | Hydrogen atom | Hydrogen atom | Hydrogen atom | Hydrogen atom | Hydrogen atom | —N($R^6$)— $R^6$ = Hydrogen atom | 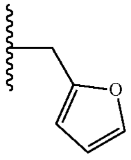 [SMILES: *Cc1ccco1] |
| Example 27 | Hydrogen atom | Hydrogen atom | Hydrogen atom | Hydrogen atom | Hydrogen atom | —N($R^6$)— $R^6$ = Hydrogen atom | 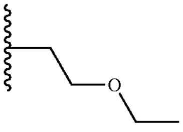 [SMILES: *CCOCC] |
| Example 28 | Hydrogen atom | Hydrogen atom | Hydrogen atom | Hydrogen atom | Hydrogen atom | —N($R^6$)— $R^6$ = Hydrogen atom | 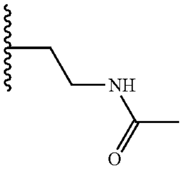 [SMILES: *CCNC(C)=O] |
| Example 29 | Hydrogen atom | Hydrogen atom | Hydrogen atom | Hydrogen atom | Hydrogen atom | —N($R^6$)— $R^6$ = Hydrogen atom | 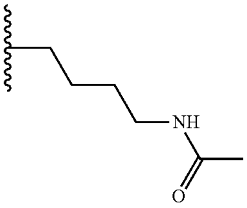 [SMILES: *CCCCNC(C)=O] |
| Example 30 | Hydrogen atom | Hydrogen atom | Hydrogen atom | Hydrogen atom | Hydrogen atom | —N($R^6$)— $R^6$ = Hydrogen atom | 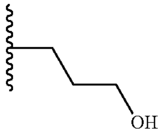 [SMILES: *CCCO] |
| Example 31 | Hydrogen atom | Hydrogen atom | Hydrogen atom | Hydrogen atom | Hydrogen atom | —N($R^6$)— $R^6$ = Hydrogen atom | 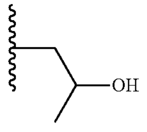 |
| Example 32 | Hydrogen atom | Hydrogen atom | Hydrogen atom | Hydrogen atom | Hydrogen atom | —N($R^6$)— $R^6$ = Hydrogen atom | 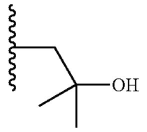 [SMILES: *CC(C)(C)O] |

-continued

| | $R^1$ | $R^2$ | $R^3$ | $R^4$ | $R^5$ | W | X |
|---|---|---|---|---|---|---|---|
| Example 33 | Hydrogen atom | Hydrogen atom | Hydrogen atom | Hydrogen atom | Hydrogen atom | —N($R^6$)— $R^6$ = Hydrogen atom | 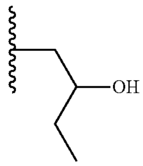 [SMILES: *CC(O)CC] |
| Example 34 | Hydrogen atom | Hydrogen atom | Hydrogen atom | Hydrogen atom | Hydrogen atom | —N($R^6$)— $R^6$ = Hydrogen atom | 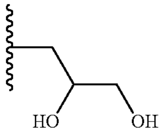 [SMILES: *CC(O)CO] |
| Example 35 | Hydrogen atom | Hydrogen atom | Hydrogen atom | Hydrogen atom | Hydrogen atom | —N($R^6$)— $R^6$ = Hydrogen atom | 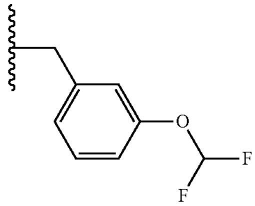 [SMILES: *Cc1cccc(OC(F)F)c1] |
| Example 36 | Hydrogen atom | Hydrogen atom | Hydrogen atom | Hydrogen atom | Hydrogen atom | —N($R^6$)— $R^6$ = Hydrogen atom | 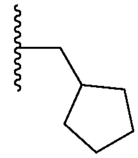 [SMILES: *CC1CCCC1] |
| Example 37 | Hydrogen atom | Hydrogen atom | Hydrogen atom | Hydrogen atom | Hydrogen atom | —N($R^6$)— $R^6$ = Hydrogen atom | 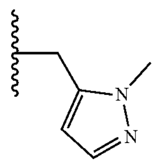 [SMILES: *Cc1ccnn1C] |
| Example 38 | Hydrogen atom | Hydrogen atom | Hydrogen atom | Hydrogen atom | Hydrogen atom | —N($R^6$)— $R^6$ = Hydrogen atom | 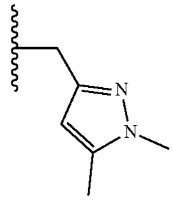 [SMILES: *Cc1cc(C)n(C)n1] |
| Example 39 | Hydrogen atom | Hydrogen atom | Hydrogen atom | Hydrogen atom | Hydrogen atom | —N($R^6$)— $R^6$ = Hydrogen atom | 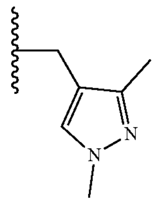 [SMILES: *Cc1cn(C)nc1C] |
| Example 40 | Hydrogen atom | Hydrogen atom | Hydrogen atom | Hydrogen atom | Hydrogen atom | —N($R^6$)— $R^6$ = Hydrogen atom | 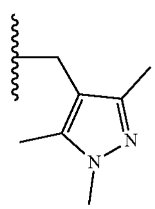 [SMILES: *Cc1c(C)nn(C)c1C] |

-continued

| | $R^1$ | $R^2$ | $R^3$ | $R^4$ | $R^5$ | W | X |
|---|---|---|---|---|---|---|---|
| Example 41 | Hydrogen atom | Hydrogen atom | Hydrogen atom | Hydrogen atom | Hydrogen atom | —N($R^6$)— $R^6$ = Hydrogen atom | 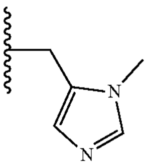 [SMILES: *Cc1cncn1C] |
| Example 42 | Hydrogen atom | Hydrogen atom | Hydrogen atom | Hydrogen atom | Hydrogen atom | —N($R^6$)— $R^6$ = Hydrogen atom | 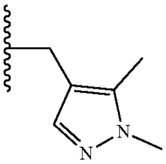 [SMILES: *Cc1cnn(C)c1C] |
| Example 43 | Hydrogen atom | Hydrogen atom | Hydrogen atom | Hydrogen atom | Hydrogen atom | —N($R^6$)— $R^6$ = Hydrogen atom | 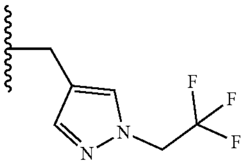 [SMILES: *Cc1cnn(CC(F)(F)F)c1] |
| Example 44 | Hydrogen atom | Hydrogen atom | Hydrogen atom | Hydrogen atom | Hydrogen atom | —N($R^6$)— $R^6$ = Hydrogen atom | 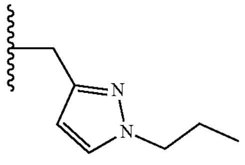 [SMILES: *Cc1ccn(CCC)n1] |
| Example 45 | Hydrogen atom | Hydrogen atom | Hydrogen atom | Hydrogen atom | Hydrogen atom | —N($R^6$)— $R^6$ = Hydrogen atom | 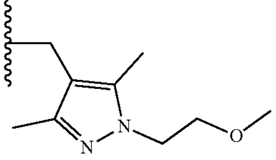 [SMILES: *Cc1c(C)nn(CCOC)c1C] |
| Example 46 | Hydrogen atom | Hydrogen atom | Hydrogen atom | Hydrogen atom | Hydrogen atom | —N($R^6$)— $R^6$ = Hydrogen atom | 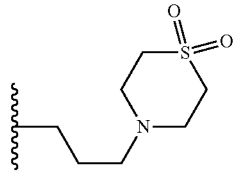 [SMILES: *CCCN1CCS(=O)(=O)CC1] |
| Example 47 | Hydrogen atom | Hydrogen atom | Hydrogen atom | Hydrogen atom | Hydrogen atom | —N($R^6$)— $R^6$ = Hydrogen atom | 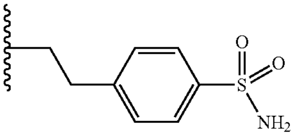 [SMILES: *CCc1ccc(S(N)(=O)=O)cc1] |
| Example 48 | Hydrogen atom | Hydrogen atom | Hydrogen atom | Hydrogen atom | Hydrogen atom | —N($R^6$)— $R^6$ = Hydrogen atom | 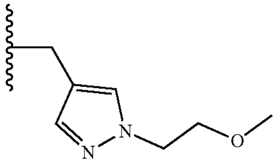 [SMILES: *Cc1cnn(CCOC)c1] |
| Example 49 | Hydrogen atom | Hydrogen atom | Hydrogen atom | Hydrogen atom | Hydrogen atom | —N($R^6$)— $R^6$ = Hydrogen atom | 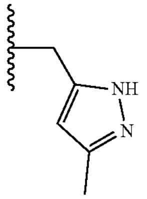 [SMILES: *Cc1cc(C)n[nH]1] |

-continued

| | $R^1$ | $R^2$ | $R^3$ | $R^4$ | $R^5$ | W | X |
|---|---|---|---|---|---|---|---|
| Example 50 | Hydrogen atom | Hydrogen atom | Hydrogen atom | Hydrogen atom | Hydrogen atom | —N($R^6$)— $R^6$ = Hydrogen atom | 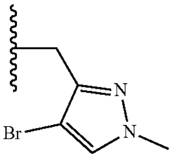 [SMILES: *Cc1nn(C)cc1Br] |
| Example 51 | Hydrogen atom | Hydrogen atom | Hydrogen atom | Hydrogen atom | Hydrogen atom | —N($R^6$)— $R^6$ = Hydrogen atom | 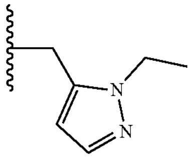 [SMILES: *Cc1ccnn1CC] |
| Example 52 | Hydrogen atom | Hydrogen atom | Hydrogen atom | Hydrogen atom | Hydrogen atom | —N($R^6$)— $R^6$ = Hydrogen atom | 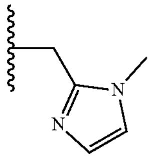 [SMILES: *Cc1nccn1C] |
| Example 53 | Hydrogen atom | Hydrogen atom | Hydrogen atom | Hydrogen atom | Hydrogen atom | —N($R^6$)— $R^6$ = Hydrogen atom | 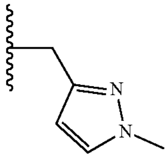 [SMILES: *Cc1ccn(C)n1] |
| Example 54 | Hydrogen atom | Hydrogen atom | Hydrogen atom | Hydrogen atom | Hydrogen atom | —N($R^6$)— $R^6$ = Hydrogen atom | 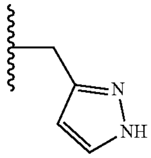 [SMILES: *Cc1cc[nH]n1] |
| Example 55 | Hydrogen atom | Hydrogen atom | Hydrogen atom | Hydrogen atom | Hydrogen atom | —N($R^6$)— $R^6$ = Hydrogen atom | 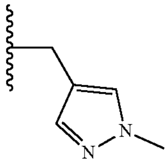 [SMILES: *Cc1cnn(C)c1] |
| Example 56 | Hydrogen atom | Hydrogen atom | Hydrogen atom | Hydrogen atom | Hydrogen atom | —N($R^6$)— $R^6$ = Hydrogen atom | 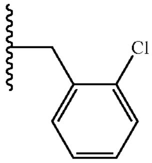 [SMILES: *Cc1ccccc1Cl] |
| Example 57 | Hydrogen atom | Hydrogen atom | Hydrogen atom | Hydrogen atom | Hydrogen atom | —N($R^6$)— $R^6$ = Hydrogen atom | 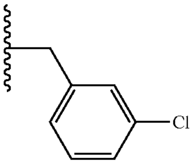 [SMILES: *Cc1cccc(Cl)c1] |

-continued

| | $R^1$ | $R^2$ | $R^3$ | $R^4$ | $R^5$ | W | X |
|---|---|---|---|---|---|---|---|
| Example 58 | Hydrogen atom | Hydrogen atom | Hydrogen atom | Hydrogen atom | Hydrogen atom | —N($R^6$)— $R^6$ = Hydrogen atom | 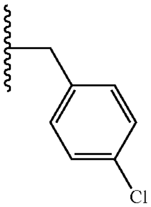 [SMILES: *Cc1ccc(Cl)cc1] |
| Example 59 | Hydrogen atom | Hydrogen atom | Hydrogen atom | Hydrogen atom | Hydrogen atom | Sulfur atom | 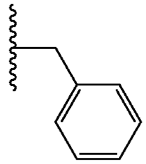 [SMILES: *Cc1ccccc1] |
| Example 60 | Hydrogen atom | Hydrogen atom | Hydrogen atom | Hydrogen atom | Hydrogen atom | Sulfur atom | 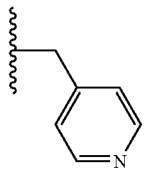 |
| Example 61 | Hydrogen atom | Hydrogen atom | Hydrogen atom | Hydrogen atom | Hydrogen atom | Sulfur atom | 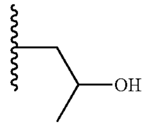 [SMILES: *CC(C)O] |
| Example 62 | Hydrogen atom | Hydrogen atom | Hydrogen atom | Hydrogen atom | Hydrogen atom | Sulfur atom | 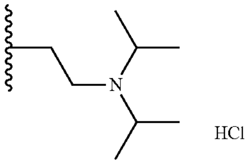 HCl |
| Example 63 | Hydrogen atom | Hydrogen atom | Hydrogen atom | Hydrogen atom | Hydrogen atom | Sulfur atom | 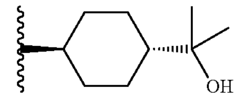 [SMILES: *[C@H]1CC[C@H](C(C)(C)O)CC1] |
| Example 64 | Hydrogen atom | Hydrogen atom | Hydrogen atom | Hydrogen atom | Hydrogen atom | Oxygen atom | 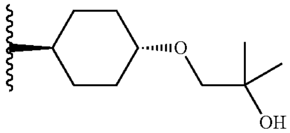 [SMILES: *[C@H]1CC[C@H](OCC(C)(C)O)CC1] |
| Example 65 | Hydrogen atom | Hydrogen atom | Hydrogen atom | Hydrogen atom | Hydrogen atom | Oxygen atom | 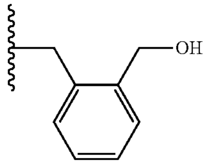 [SMILES: *Cc1ccccc1CO] |
| Example 66 | Hydrogen atom | Hydrogen atom | Hydrogen atom | Hydrogen atom | Hydrogen atom | Oxygen atom | 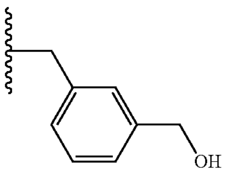 [SMILES: *Cc1cccc(CO)c1] |

-continued

| | $R^1$ | $R^2$ | $R^3$ | $R^4$ | $R^5$ | W | X |
|---|---|---|---|---|---|---|---|
| Example 67 | Hydrogen atom | Hydrogen atom | Hydrogen atom | Hydrogen atom | Hydrogen atom | Oxygen atom | 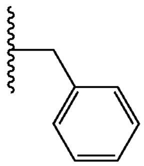 |
| Example 68 | Hydrogen atom | Hydrogen atom | Hydrogen atom | Hydrogen atom | Hydrogen atom | Oxygen atom | 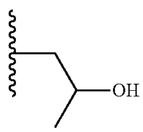 |
| Example 69 | Hydrogen atom | Hydrogen atom | Hydrogen atom | Hydrogen atom | Hydrogen atom | Oxygen atom | 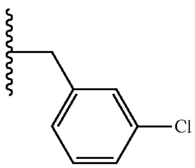 [SMILES: *Cc1cccc(Cl)c1] |
| Example 70 | Hydrogen atom | Hydrogen atom | Hydrogen atom | Hydrogen atom | Hydrogen atom | Oxygen atom | 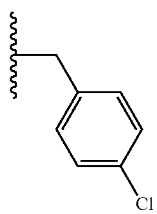 [SMILES: *Cc1ccc(Cl)cc1] |
| Example 71 | Hydrogen atom | Hydrogen atom | Hydrogen atom | Hydrogen atom | Hydrogen atom | Oxygen atom | 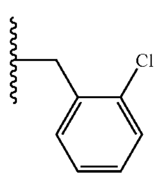 [SMILES: *Cc1ccccc1Cl] |
| Example 72 | Hydrogen atom | Hydrogen atom | Hydrogen atom | Hydrogen atom | Hydrogen atom | Oxygen atom | 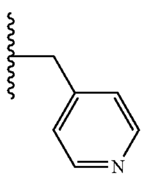 [SMILES: *Cc1ccncc1] |
| Example 73 | Hydrogen atom | Hydrogen atom | Hydrogen atom | Hydrogen atom | Hydrogen atom | Oxygen atom | 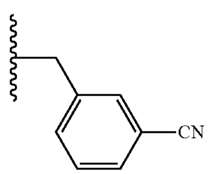 [SMILES: *Cc1cccc(C#N)c1] |
| Example 74 | Hydrogen atom | Hydrogen atom | Hydrogen atom | Hydrogen atom | Hydrogen atom | Oxygen atom | 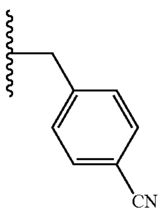 [SMILES: *Cc1ccc(C#N)cc1] |
| Example 75 | Hydrogen atom | Hydrogen atom | Hydrogen atom | Hydrogen atom | Hydrogen atom | Oxygen atom | 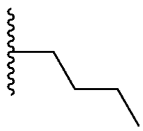 [SMILES: *CCCC] |

-continued

| | $R^1$ | $R^2$ | $R^3$ | $R^4$ | $R^5$ | W | X |
|---|---|---|---|---|---|---|---|
| Example 76 | Hydrogen atom | Hydrogen atom | Hydrogen atom | Hydrogen atom | Hydrogen atom | Oxygen atom | 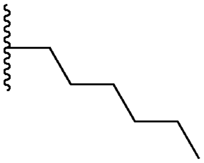 [SMILES: *CCCCCC] |
| Example 77 | Hydrogen atom | Hydrogen atom | Hydrogen atom | Hydrogen atom | Hydrogen atom | Oxygen atom | 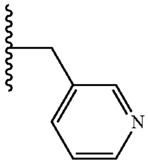 [SMILES: *Cc1cccnc1] |
| Example 78 | Hydrogen atom | Hydrogen atom | Hydrogen atom | Hydrogen atom | Hydrogen atom | Oxygen atom | 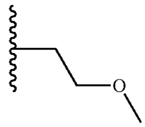 [SMILES: *CCOC] |
| Example 79 | Hydrogen atom | Hydrogen atom | Hydrogen atom | Hydrogen atom | Hydrogen atom | Oxygen atom | 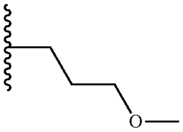 [SMILES: *CCCOC] |
| Example 80 | Hydrogen atom | Hydrogen atom | Hydrogen atom | Hydrogen atom | Hydrogen atom | Oxygen atom | 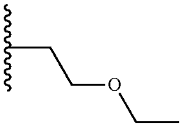 [SMILES: *CCOCC] |
| Example 81 | Hydrogen atom | Hydrogen atom | Hydrogen atom | Hydrogen atom | Hydrogen atom | Oxygen atom | 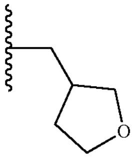 [SMILES: *CC1CCOC1] |
| Example 82 | Hydrogen atom | Hydrogen atom | Hydrogen atom | Hydrogen atom | Hydrogen atom | Oxygen atom | 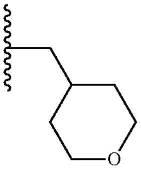 [SMILES: *CC1CCOCC1] |
| Example 83 | Hydrogen atom | Hydrogen atom | Hydrogen atom | Hydrogen atom | Hydrogen atom | Oxygen atom | 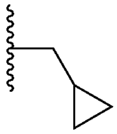 [SMILES: *CC1CC1] |
| Example 84 | Hydrogen atom | Hydrogen atom | Hydrogen atom | Hydrogen atom | Hydrogen atom | Oxygen atom | 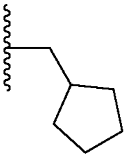 [SMILES: *CC1CCCC1] |

-continued

| | $R^1$ | $R^2$ | $R^3$ | $R^4$ | $R^5$ | W | X |
|---|---|---|---|---|---|---|---|
| Example 85 | Hydrogen atom | Hydrogen atom | Hydrogen atom | Hydrogen atom | Hydrogen atom | Oxygen atom | 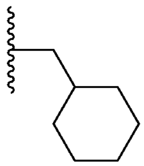 [SMILES: *CC1CCCCC1] |
| Example 86 | Hydrogen atom | Hydrogen atom | Hydrogen atom | Hydrogen atom | Hydrogen atom | Oxygen atom | 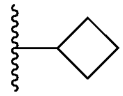 |
| Example 87 | Hydrogen atom | Hydrogen atom | Hydrogen atom | Hydrogen atom | Hydrogen atom | Oxygen atom | 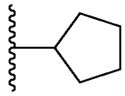 [SMILES: *C1CCCC1] |
| Example 88 | Hydrogen atom | Hydrogen atom | Hydrogen atom | Hydrogen atom | Hydrogen atom | Oxygen atom | 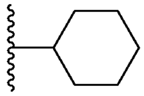 [SMILES: *C1CCCCC1] |
| Example 89 | Hydrogen atom | Hydrogen atom | Hydrogen atom | Hydrogen atom | Hydrogen atom | Oxygen atom | 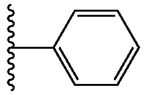 [SMILES: *c1ccccc1] |
| Example 90 | Hydrogen atom | Hydrogen atom | Hydrogen atom | Hydrogen atom | Hydrogen atom | Oxygen atom | 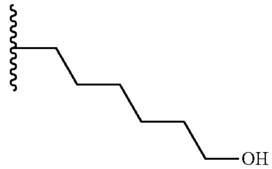 |
| Example 91 | Hydrogen atom | Hydrogen atom | Hydrogen atom | Hydrogen atom | Hydrogen atom | Oxygen atom | 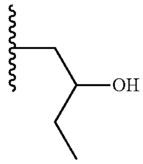 [SMILES: *CC(O)CC] |
| Example 92 | Hydrogen atom | Hydrogen atom | Hydrogen atom | Hydrogen atom | Hydrogen atom | Oxygen atom | 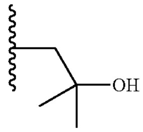 [SMILES: *CC(C)(C)O] |
| Example 93 | Hydrogen atom | Hydrogen atom | Hydrogen atom | Hydrogen atom | Hydrogen atom | Oxygen atom | 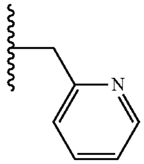 [SMILES: *Cc1ccccn1] |
| Example 94 | Hydrogen atom | Hydrogen atom | Hydrogen atom | Hydrogen atom | Hydrogen atom | Oxygen atom | 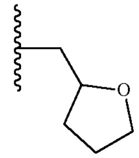 [SMILES: *CC1CCCO1] |
| Example 95 | Hydrogen atom | Hydrogen atom | Hydrogen atom | Hydrogen atom | Hydrogen atom | Oxygen atom | 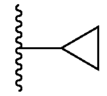 |

-continued

| | $R^1$ | $R^2$ | $R^3$ | $R^4$ | $R^5$ | W | X |
|---|---|---|---|---|---|---|---|
| Example 96 | Hydrogen atom | Hydrogen atom | Hydrogen atom | Hydrogen atom | Hydrogen atom | Oxygen atom | 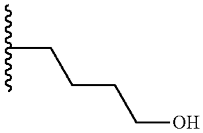 [SMILES: *CCCCO] |
| Example 97 | Hydrogen atom | Hydrogen atom | Hydrogen atom | Hydrogen atom | Hydrogen atom | Oxygen atom | 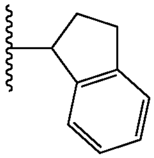 [SMILES: *C1CCc2ccccc21] |
| Example 98 | Hydrogen atom | Hydrogen atom | Hydrogen atom | Hydrogen atom | Hydrogen atom | Oxygen atom | 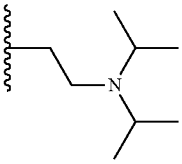 HCl |
| Example 99 | Hydrogen atom | Hydrogen atom | Hydrogen atom | Hydrogen atom | Hydrogen atom | Oxygen atom | 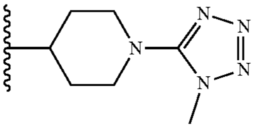 [SMILES: *C1CCN(c2nnnn2C)CC1] |
| Example 100 | Hydrogen atom | Hydrogen atom | Hydrogen atom | Hydrogen atom | Hydrogen atom | Oxygen atom | 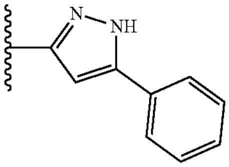 [SMILES: *c1cc(-c2ccccc2)[nH]n1] |
| Example 101 | Hydrogen atom | Hydrogen atom | Hydrogen atom | Hydrogen atom | Hydrogen atom | Oxygen atom | 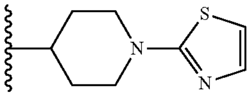 [SMILES: *C1CCN(c2nccs2)CC1] |
| Example 102 | Hydrogen atom | Hydrogen atom | Hydrogen atom | Hydrogen atom | Hydrogen atom | Oxygen atom | 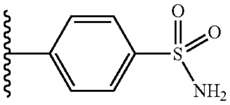 [SMILES: *c1ccc(S(N)(=O)=O)cc1] |
| Example 103 | Hydrogen atom | Hydrogen atom | Hydrogen atom | Hydrogen atom | Hydrogen atom | Oxygen atom | 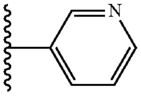 [SMILES: *c1cccnc1] |
| Example 104 | Hydrogen atom | Hydrogen atom | Hydrogen atom | Hydrogen atom | Hydrogen atom | Oxygen atom | 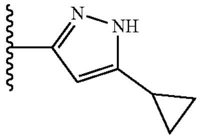 [SMILES: *c1cc(C2CC2)[nH]n1] |
| Example 105 | Hydrogen atom | Hydrogen atom | Hydrogen atom | Hydrogen atom | Hydrogen atom | Oxygen atom | 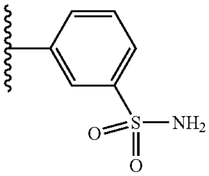 [SMILES: *c1cccc(S(N)(=O)=O)c1] |

-continued

| | $R^1$ | $R^2$ | $R^3$ | $R^4$ | $R^5$ | W | X |
|---|---|---|---|---|---|---|---|
| Example 106 | Hydrogen atom | Hydrogen atom | Hydrogen atom | Hydrogen atom | Hydrogen atom | Oxygen atom | 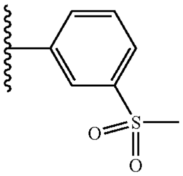 [SMILES: *c1cccc(S(C)(=O)=O)c1] |
| Example 107 | Hydrogen atom | Hydrogen atom | Hydrogen atom | Hydrogen atom | Hydrogen atom | Oxygen atom | 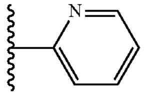 [SMILES: *c1ccccn1] |
| Example 108 | Hydrogen atom | Hydrogen atom | Hydrogen atom | Hydrogen atom | Hydrogen atom | Oxygen atom | 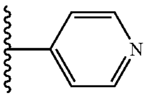 [SMILES: *c1ccncc1] |
| Example 109 | Hydrogen atom | Hydrogen atom | Hydrogen atom | Hydrogen atom | Hydrogen atom | Oxygen atom | 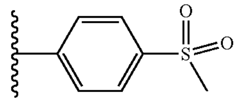 |
| Example 110 | Hydrogen atom | Hydrogen atom | Hydrogen atom | Hydrogen atom | Hydrogen atom | Oxygen atom | 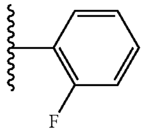 |
| Example 111 | Hydrogen atom | Hydrogen atom | Hydrogen atom | Hydrogen atom | Hydrogen atom | Oxygen atom | 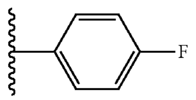 |
| Example 112 | Hydrogen atom | Hydrogen atom | Hydrogen atom | Hydrogen atom | Hydrogen atom | Oxygen atom | 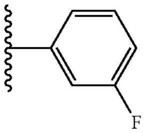 [SMILES: *c1cccc(F)c1] |
| Example 113 | Hydrogen atom | Hydrogen atom | Hydrogen atom | Hydrogen atom | Hydrogen atom | Oxygen atom | 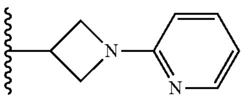 |
| Example 114 | Hydrogen atom | Hydrogen atom | Hydrogen atom | Hydrogen atom | Hydrogen atom | Oxygen atom | 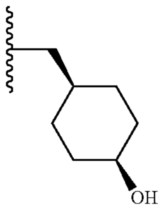 [SMILES: *C[C@H]1CC[C@@H](O)CC1] |
| Example 115 | Hydrogen atom | Hydrogen atom | Hydrogen atom | Hydrogen atom | Hydrogen atom | Oxygen atom | 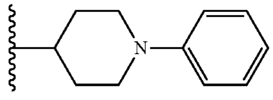 |
| Example 116 | Hydrogen atom | Hydrogen atom | Hydrogen atom | Hydrogen atom | Hydrogen atom | Oxygen atom | 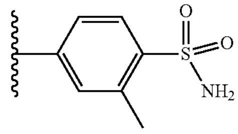 [SMILES: *c1ccc(S(N)(=O)=O)c(C)c1] |

-continued

| | $R^1$ | $R^2$ | $R^3$ | $R^4$ | $R^5$ | W | X |
|---|---|---|---|---|---|---|---|
| Example 117 | Hydrogen atom | Hydrogen atom | Hydrogen atom | Hydrogen atom | Hydrogen atom | Oxygen atom | 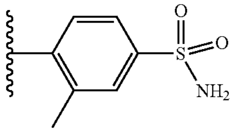 [SMILES: *c1ccc(S(N)(=O)=O)cc1C] |
| Example 118 | Hydrogen atom | Hydrogen atom | Hydrogen atom | Hydrogen atom | Hydrogen atom | Oxygen atom | 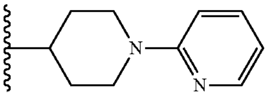 |
| Example 119 | Hydrogen atom | Hydrogen atom | Hydrogen atom | Hydrogen atom | Hydrogen atom | Oxygen atom | 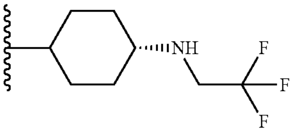 |
| Example 120 | Hydrogen atom | Hydrogen atom | Hydrogen atom | Hydrogen atom | Hydrogen atom | Oxygen atom | 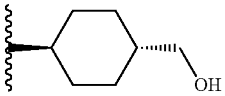 [SMILES: *[C@H]1CC[C@H](CO)CC1] |
| Example 121 | Hydrogen atom | Hydrogen atom | Hydrogen atom | Hydrogen atom | Hydrogen atom | Oxygen atom | 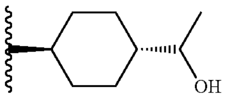 |
| Example 122 | Hydrogen atom | Hydrogen atom | Hydrogen atom | Hydrogen atom | Hydrogen atom | Oxygen atom | 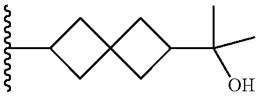 [SMILES: *C1CC2(C1)CC(C(C)(C)O)C2] |
| Example 123 | Hydrogen atom | Hydrogen atom | Hydrogen atom | Hydrogen atom | Hydrogen atom | Oxygen atom | 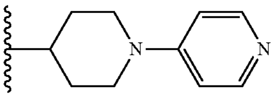 [SMILES: *C1CCN(c2ccncc2)CC1] |
| Example 124 | Hydrogen atom | Hydrogen atom | Hydrogen atom | Hydrogen atom | Hydrogen atom | Oxygen atom | 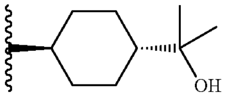 |
| Example 125 | Hydrogen atom | Hydrogen atom | Hydrogen atom | Hydrogen atom | Fluorine atom 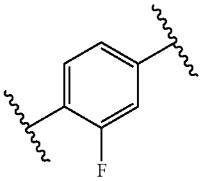 [SMILES: *c1ccc(*)c(F)c1] | Oxygen atom | 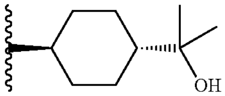 |
| Example 126 | Hydrogen atom | Hydrogen atom | Hydrogen atom | Hydrogen atom | Fluorine atom 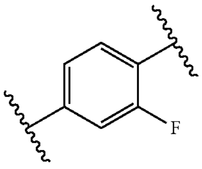 [SMILES: *c1ccc(*)c(F)c1] | Oxygen atom | 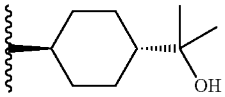 [SMILES: *[C@H]1CC[C@H](C(C)(C)O)CC1] |
| Example 127 | Hydrogen atom | Hydrogen atom | Methyl group | Hydrogen atom | Hydrogen atom | Oxygen atom | 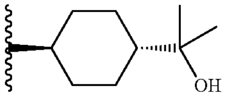 |

-continued

| | $R^1$ | $R^2$ | $R^3$ | $R^4$ | $R^5$ | W | X |
|---|---|---|---|---|---|---|---|
| Example 128 | Methyl group | Hydrogen atom | Hydrogen atom | Hydrogen atom | Hydrogen atom | Oxygen atom | 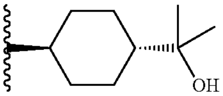 [SMILES: *[C@H]1CC[C@H](C(C)(C)O)CC1] |
| Example 129 | Hydrogen atom | Hydrogen atom | Hydrogen atom | Methyl group | Hydrogen atom | Oxygen atom | 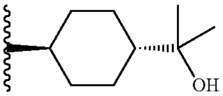 |
| Example 130 | Hydrogen atom | Methyl group | Hydrogen atom | Hydrogen atom | Hydrogen atom | Oxygen atom | 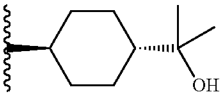 [SMILES: *[C@H]1CC[C@H](C(C)(C)O)CC1] |
| Example 131 | Hydrogen atom | Hydrogen atom | Hydrogen atom | Hydrogen atom | Chlorine atom<br>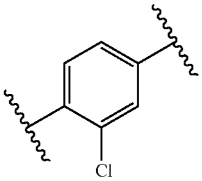 [SMILES: *c1ccc(*)c(Cl)c1] | Oxygen atom | 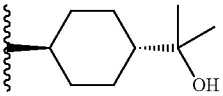 |
| Example 132 | Hydrogen atom | Hydrogen atom | Hydrogen atom | Hydrogen atom | Methyl group<br>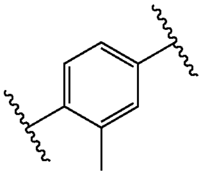 [SMILES: *c1ccc(*)c(C)c1] | Oxygen atom | 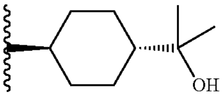 [SMILES: *[C@H]1CC[C@H](C(C)(C)O)CC1] |
| Example 133 | Hydrogen atom | Hydrogen atom | Hydrogen atom | Hydrogen atom | Cyano group<br>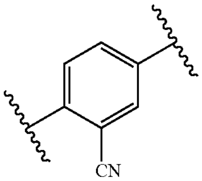 [SMILES: *c1ccc(*)c(C#N)c1] | Oxygen atom | 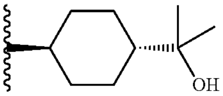 |
| Example 134 | Hydrogen atom | Hydrogen atom | Hydrogen atom | Hydrogen atom | Hydroxy group<br>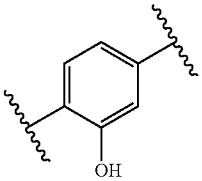 | Oxygen atom | 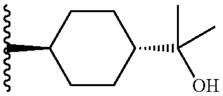 |
| Example 135 | Hydrogen atom | Hydrogen atom | Hydrogen atom | Hydroxy-methyl group | Hydrogen atom | Oxygen atom | 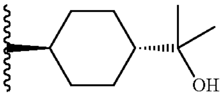 |
| Example 136 | Hydrogen atom | Hydrogen atom | Hydrogen atom | Fluorine atom | Hydrogen atom | Oxygen atom | 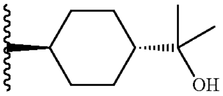 [SMILES: *[C@H]1CC[C@H](C(C)(C)O)CC1] |

-continued

| | $R^1$ | $R^2$ | $R^3$ | $R^4$ | $R^5$ | W | X |
|---|---|---|---|---|---|---|---|
| Example 137 | Hydrogen atom | Hydrogen atom | Hydrogen atom | Vinyl group | Hydrogen atom | Oxygen atom | 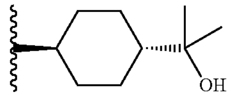 [SMILES: *[C@H]1CC[C@H](C(C)(C)O)CC1] |
| Example 138 | Hydrogen atom | Hydrogen atom | Hydrogen atom | Ethyl group | Hydrogen atom | Oxygen atom | 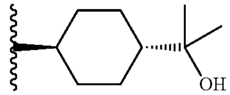 [SMILES: *[C@H]1CC[C@H](C(C)(C)O)CC1] |
| Example 139 | Hydrogen atom | Hydrogen atom | Hydrogen atom | Cyano group | Hydrogen atom | Oxygen atom | 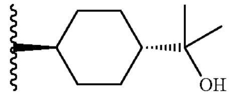 [SMILES: *[C@H]1CC[C@H](C(C)(C)O)CC1] |
| Example 140 | Hydrogen atom | Hydrogen atom | Hydrogen atom | Carbamoyl group | Hydrogen atom | Oxygen atom | 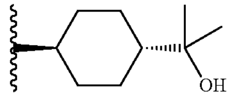 |
| Example 141 | Hydrogen atom | Hydrogen atom | Hydrogen atom | 1-Hydroxy-ethyl group | Hydrogen atom | Oxygen atom | 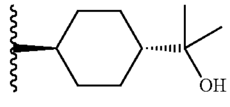 |
| Example 142 | Hydrogen atom | Hydrogen atom | Hydrogen atom | Hydrogen atom | Hydrogen atom | Oxygen atom | 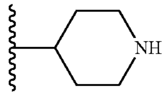 [SMILES: *C1CCNCC1] |
| Example 143 | Hydrogen atom | Hydrogen atom | Hydrogen atom | Hydrogen atom | Hydrogen atom | Oxygen atom | 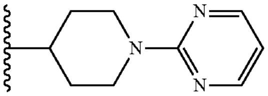 [SMILES: *C1CCN(c2ncccn2)CC1] |
| Example 144 | Hydrogen atom | Hydrogen atom | Hydrogen atom | Hydrogen atom | Hydrogen atom | Oxygen atom | 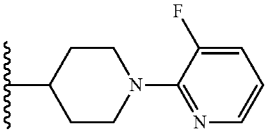 [SMILES: *C1CCN(c2ncccc2F)CC1] |
| Example 145 | Hydrogen atom | Hydrogen atom | Hydrogen atom | Hydrogen atom | Hydrogen atom | Oxygen atom | 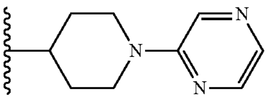 [SMILES: *C1CCN(c2cnccn2)CC1] |
| Example 146 | Hydrogen atom | Hydrogen atom | Hydrogen atom | Hydrogen atom | Hydrogen atom | Oxygen atom | 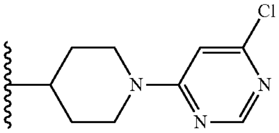 [SMILES: *C1CCN(c2cc(Cl)ncn2)CC1] |
| Example 147 | Hydrogen atom | Hydrogen atom | Hydrogen atom | Hydrogen atom | Hydrogen atom | Oxygen atom | 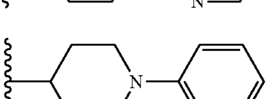 |
| Example 148 | Hydrogen atom | Hydrogen atom | Hydrogen atom | Hydrogen atom | Hydrogen atom | Oxygen atom | 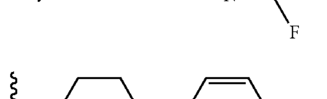 |
| Example 149 | Hydrogen atom | Hydrogen atom | Hydrogen atom | Hydrogen atom | Hydrogen atom | Oxygen atom | 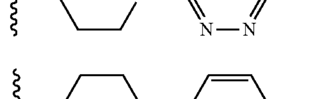 |

-continued

| | $R^1$ | $R^2$ | $R^3$ | $R^4$ | $R^5$ | W | X |
|---|---|---|---|---|---|---|---|
| Example 150 | Hydrogen atom | Hydrogen atom | Hydrogen atom | Hydrogen atom | Hydrogen atom | Oxygen atom | 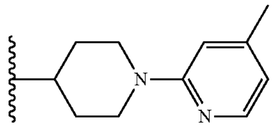 [SMILES: *C1CCN(c2cc(C)ccn2)CC1] |
| Example 151 | Hydrogen atom | Hydrogen atom | Hydrogen atom | Hydrogen atom | Hydrogen atom | Oxygen atom | 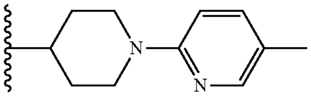 [SMILES: *C1CCN(c2ccc(C)cn2)CC1] |
| Example 152 | Hydrogen atom | Hydrogen atom | Hydrogen atom | Hydrogen atom | Hydrogen atom | Oxygen atom | 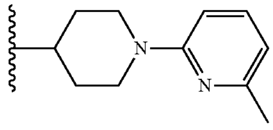 |
| Example 153 | Hydrogen atom | Hydrogen atom | Hydrogen atom | Hydrogen atom | Hydrogen atom | Oxygen atom | 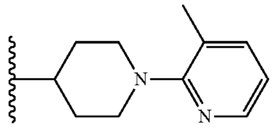 [SMILES: *C1CCN(c2ncccc2C)CC1] |
| Example 154 | Hydrogen atom | Hydrogen atom | Hydrogen atom | Hydrogen atom | Hydrogen atom | Oxygen atom | 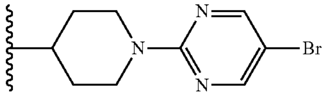 [SMILES: *C1CCN(c2ncc(Br)cn2)CC1] |
| Example 155 | Hydrogen atom | Hydrogen atom | Hydrogen atom | Hydrogen atom | Hydrogen atom | Oxygen atom | 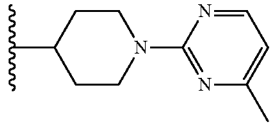 [SMILES: *C1CCN(c2nccc(C)n2)CC1] |
| Example 156 | Hydrogen atom | Hydrogen atom | Hydrogen atom | Hydrogen atom | Hydrogen atom | Oxygen atom | 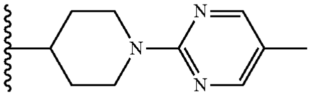 |
| Example 157 | Hydrogen atom | Hydrogen atom | Hydrogen atom | Hydrogen atom | Hydrogen atom | Oxygen atom | 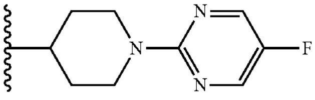 [SMILES: *C1CCN(c2ncc(F)cn2)CC1] |
| Example 158 | Hydrogen atom | Hydrogen atom | Hydrogen atom | Hydrogen atom | Hydrogen atom | Oxygen atom | 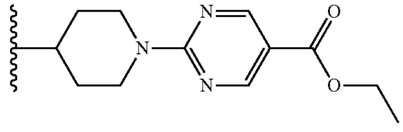 [SMILES: *C1CCN(c2ncc(C(=O)OCC)cn2)CC1] |
| Example 159 | Hydrogen atom | Hydrogen atom | Hydrogen atom | Hydrogen atom | Hydrogen atom | Oxygen atom | 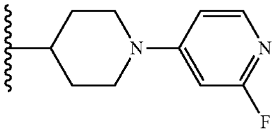 [SMILES: *C1CCN(c2ccnc(F)c2)CC1] |
| Example 160 | Hydrogen atom | Hydrogen atom | Hydrogen atom | Hydrogen atom | Hydrogen atom | Oxygen atom | 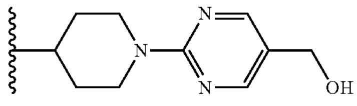 [SMILES: *C1CCN(c2ncc(CO)cn2)CC1] |
| Example 161 | Hydrogen atom | Hydrogen atom | Hydrogen atom | Hydrogen atom | Hydrogen atom | Oxygen atom | 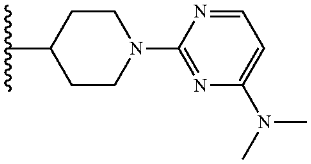 [SMILES: *C1CCN(c2nccc(N(C)C)n2)CC1] |

-continued

| | $R^1$ | $R^2$ | $R^3$ | $R^4$ | $R^5$ | W | X |
|---|---|---|---|---|---|---|---|
| Example 162 | Hydrogen atom | Hydrogen atom | Hydrogen atom | Hydrogen atom | Hydrogen atom | Oxygen atom | 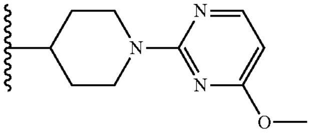 [SMILES: *C1CCN(c2nccc(OC)n2)CC1] |
| Example 163 | Hydrogen atom | Hydrogen atom | Hydrogen atom | Hydrogen atom | Hydrogen atom | Oxygen atom | 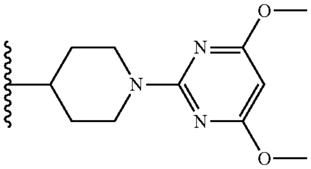 [SMILES: *C1CCN(c2nc(OC)cc(OC)n2)CC1] |
| Example 164 | Hydrogen atom | Hydrogen atom | Hydrogen atom | Hydrogen atom | Hydrogen atom | Oxygen atom | 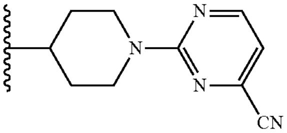 [SMILES: *C1CCN(c2nccc(C#N)n2)CC1] |
| Example 165 | Hydrogen atom | Hydrogen atom | Hydrogen atom | Hydrogen atom | Hydrogen atom | Oxygen atom | 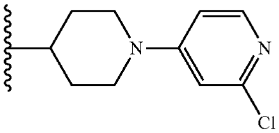 [SMILES: *C1CCN(c2ccnc(Cl)c2)CC1] |
| Example 166 | Hydrogen atom | Hydrogen atom | Hydrogen atom | Hydrogen atom | Hydrogen atom | Oxygen atom | 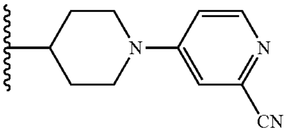 [SMILES: *C1CCN(c2ccnc(C#N)c2)CC1] |
| Example 167 | Hydrogen atom | Hydrogen atom | Hydrogen atom | Hydrogen atom | Hydrogen atom | Oxygen atom | 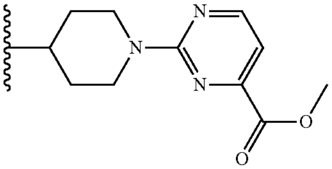 [SMILES: *C1CCN(c2nccc(C(=O)OC)n2)CC1] |
| Example 168 | Hydrogen atom | Hydrogen atom | Hydrogen atom | Hydrogen atom | Hydrogen atom | Oxygen atom | 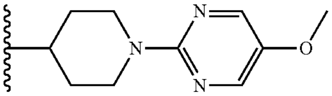 [SMILES: *C1CCN(c2ncc(OC)cn2)CC1] |
| Example 169 | Hydrogen atom | Hydrogen atom | Hydrogen atom | Hydrogen atom | Hydrogen atom | Oxygen atom | 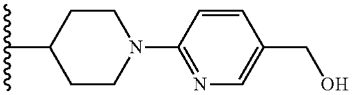 [SMILES: *C1CCN(c2ccc(CO)cn2)CC1] |
| Example 170 | Hydrogen atom | Hydrogen atom | Hydrogen atom | Hydrogen atom | Hydrogen atom | Oxygen atom | 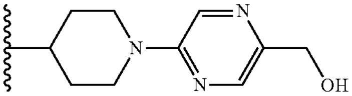 |
| Example 171 | Hydrogen atom | Hydrogen atom | Hydrogen atom | Hydrogen atom | Hydrogen atom | Oxygen atom | 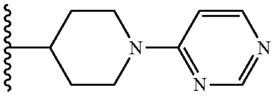 |
| Example 172 | Hydrogen atom | Hydrogen atom | Hydrogen atom | Hydrogen atom | Hydrogen atom | Oxygen atom | 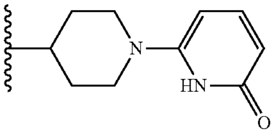 [SMILES: *C1CCN(c2cccc(=O)[nH]2)CC1] |

-continued

| | $R^1$ | $R^2$ | $R^3$ | $R^4$ | $R^5$ | W | X |
|---|---|---|---|---|---|---|---|
| Example 173 | Hydrogen atom | Hydrogen atom | Hydrogen atom | Hydrogen atom | Hydrogen atom | Oxygen atom | 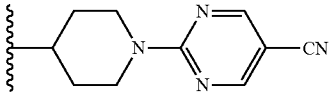 [SMILES: *C1CCN(c2ncc(C#N)cn2)CC1] |
| Example 174 | Hydrogen atom | Hydrogen atom | Hydrogen atom | Hydrogen atom | Hydrogen atom | Oxygen atom | 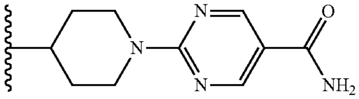 [SMILES: *C1CCN(c2ncc(C(N)=O)cn2)CC1] |
| Example 175 | Hydrogen atom | Hydrogen atom | Hydrogen atom | Hydrogen atom | Hydrogen atom | Oxygen atom | 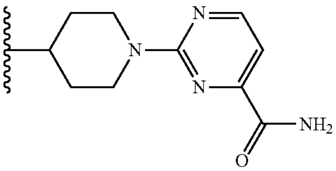 [SMILES: *C1CCN(c2nccc(C(N)=O)n2)CC1] |
| Example 176 | Hydrogen atom | Hydrogen atom | Hydrogen atom | Hydrogen atom | Hydrogen atom | Oxygen atom | 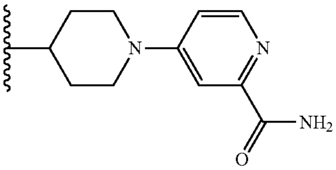 |
| Example 177 | Hydrogen atom | Hydrogen atom | Hydrogen atom | Hydrogen atom | Hydrogen atom | Oxygen atom | 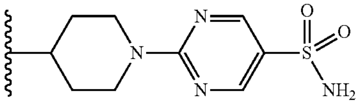 [SMILES: *C1CCN(c2ncc(S(N)(=O)=O)cn2)CC1] |
| Example 178 | Hydrogen atom | Hydrogen atom | Hydrogen atom | Hydrogen atom | Hydrogen atom | Oxygen atom | 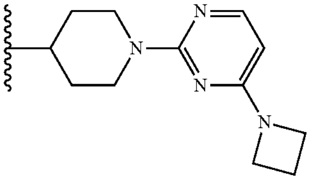 [SMILES: *C1CCN(c2nccc(N3CCC3)n2)CC1] |
| Example 179 | Hydrogen atom | Hydrogen atom | Hydrogen atom | Hydrogen atom | Hydrogen atom | Oxygen atom | 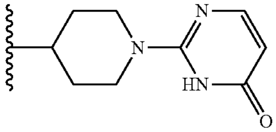 [SMILES: *C1CCN(c2nccc(=O)[nH]2)CC1] |
| Example 180 | Hydrogen atom | Hydrogen atom | Hydrogen atom | Hydrogen atom | Hydrogen atom | Oxygen atom | 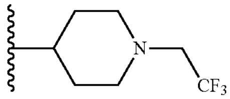 |
| Example 181 | Hydrogen atom | Hydrogen atom | Hydrogen atom | Hydrogen atom | Hydrogen atom | Oxygen atom | 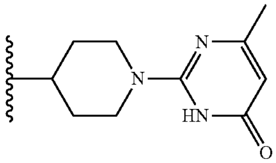 [SMILES: *C1CCN(c2nc(C)cc(=O)[nH]2)CC1] |
| Example 182 | Hydrogen atom | Hydrogen atom | Hydrogen atom | Hydrogen atom | Hydrogen atom | Oxygen atom | 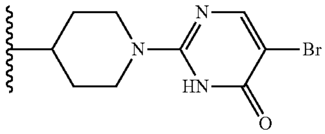 [SMILES: *C1CCN(c2ncc(Br)c(=O)[nH]2)CC1] |

-continued

| | $R^1$ | $R^2$ | $R^3$ | $R^4$ | $R^5$ | W | X |
|---|---|---|---|---|---|---|---|
| Example 183 | Hydrogen atom | Hydrogen atom | Hydrogen atom | Hydrogen atom | Hydrogen atom | Oxygen atom | 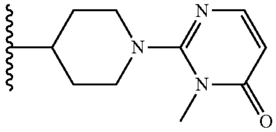 [SMILES: *C1CCN(c2nccc(=O)n2C)CC1] |
| Example 184 | Hydrogen atom | Hydrogen atom | Hydrogen atom | Hydrogen atom | Hydrogen atom | Oxygen atom | 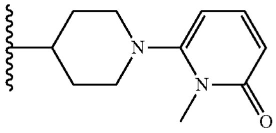 [SMILES: *C1CCN(c2cccc(=O)n2C)CC1] |
| Example 185 | Hydrogen atom | Hydrogen atom | Hydrogen atom | Hydrogen atom | Hydrogen atom | Oxygen atom | 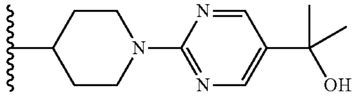 |
| Example 186 | Hydrogen atom | Hydrogen atom | Hydrogen atom | Hydrogen atom | Hydrogen atom | Oxygen atom | 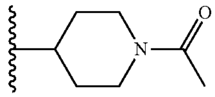 [SMILES: *C1CCN(C(C)=O)CC1] |
| Example 187 | Hydrogen atom | Hydrogen atom | Hydrogen atom | Hydrogen atom | Hydrogen atom | Oxygen atom | 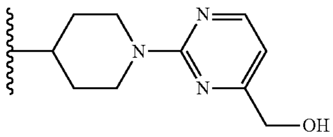 [SMILES: *C1CCN(c2nccc(CO)n2)CC1] |
| Example 188 | Hydrogen atom | Hydrogen atom | Hydrogen atom | Hydrogen atom | Hydrogen atom | Oxygen atom | 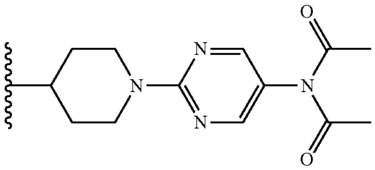 [SMILES: *C1CCN(c2ncc(N(C(C)=O)C(C)=O)cn2)CC1] |
| Example 189 | Hydrogen atom | Hydrogen atom | Hydrogen atom | Hydrogen atom | Hydrogen atom | Oxygen atom | 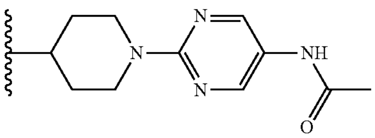 [SMILES: *C1CCN(c2ncc(NC(C)=O)cn2)CC1] |
| Example 190 | Hydrogen atom | Hydrogen atom | Hydrogen atom | Hydrogen atom | Hydrogen atom | Oxygen atom | 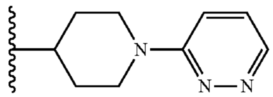 [SMILES: *C1CCN(c2cccnn2)CC1] |
| Example 191 | Hydrogen atom | Hydrogen atom | Hydrogen atom | Hydrogen atom | Hydrogen atom | Oxygen atom | 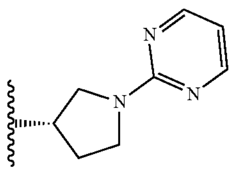 [SMILES: *[C@H]1CCN(c2ncccn2)C1] |
| Example 192 | Hydrogen atom | Hydrogen atom | Hydrogen atom | Hydrogen atom | Hydrogen atom | Oxygen atom | 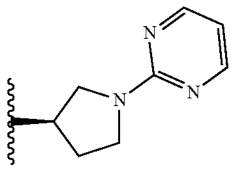 [SMILES: *[C@@H]1CCN(c2ncccn2)C1] |

-continued

| | $R^1$ | $R^2$ | $R^3$ | $R^4$ | $R^5$ | W | X |
|---|---|---|---|---|---|---|---|
| Example 193 | Hydrogen atom | Hydrogen atom | Hydrogen atom | Hydrogen atom | Hydrogen atom | Oxygen atom | 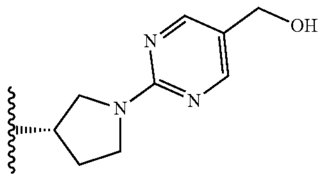 [SMILES: *[C@H]1CCN(c2ncc(CO)cn2)C1] |
| Example 194 | Hydrogen atom | Hydrogen atom | Hydrogen atom | Hydrogen atom | Hydrogen atom | Oxygen atom | 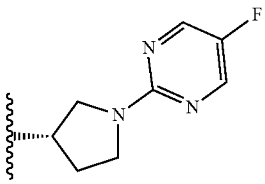 [SMILES: *[C@H]1CCN(c2ncc(F)cn2)C1] |
| Example 195 | Hydrogen atom | Hydrogen atom | Hydrogen atom | Hydrogen atom | Hydrogen atom | Oxygen atom | 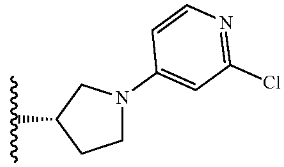 [SMILES: *[C@H]1CCN(c2ccnc(Cl)c2)C1] |
| Example 196 | Hydrogen atom | Hydrogen atom | Hydrogen atom | Hydrogen atom | Hydrogen atom | Oxygen atom | 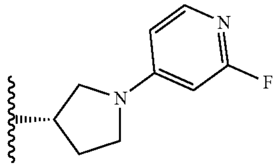 [SMILES: *[C@H]1CCN(c2ccnc(F)c2)C1] |
| Example 197 | Hydrogen atom | Hydrogen atom | Hydrogen atom | Hydrogen atom | Hydrogen atom | Oxygen atom | 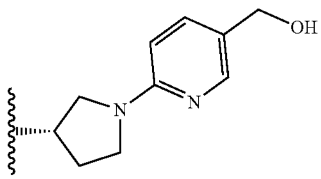 [SMILES: *[C@H]1CCN(c2ccc(CO)cn2)C1] |
| Example 198 | Hydrogen atom | Hydrogen atom | Hydrogen atom | Hydrogen atom | Hydrogen atom | Oxygen atom | 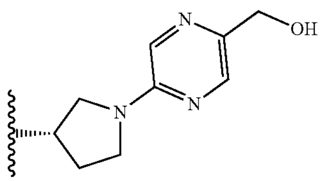 [SMILES: *[C@H]1CCN(c2cnc(CO)cn2)C1] |
| Example 199 | Hydrogen atom | Hydrogen atom | Hydrogen atom | Hydrogen atom | Hydrogen atom | Oxygen atom | 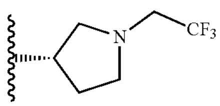 [SMILES: *[C@H]1CCN(CC(F)(F)F)C1] |
| Example 200 | Hydrogen atom | Hydrogen atom | Hydrogen atom | Hydrogen atom | Hydrogen atom | Oxygen atom | 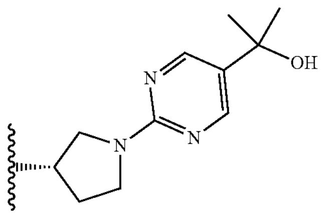 [SMILES: *[C@H]1CCN(c2ncc(C(C)(C)O)cn2)C1] |

-continued

| | $R^1$ | $R^2$ | $R^3$ | $R^4$ | $R^5$ | W | X |
|---|---|---|---|---|---|---|---|
| Example 201 | Hydrogen atom | Hydrogen atom | Hydrogen atom | Hydrogen atom | Hydrogen atom | Oxygen atom | 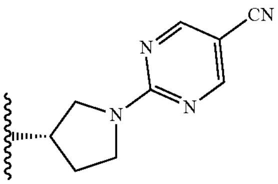 [SMILES: *[C@H]1CCN(c2ncc(C#N)cn2)C1] |
| Example 202 | Hydrogen atom | Hydrogen atom | Hydrogen atom | Hydrogen atom | Hydrogen atom | Oxygen atom | 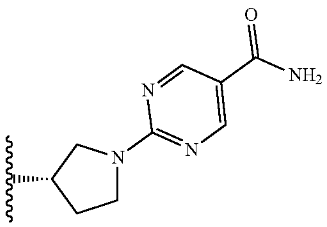 [SMILES: *[C@H]1CCN(c2ncc(C(N)=O)cn2)C1] |
| Example 203 | Hydrogen atom | Hydrogen atom | Hydrogen atom | Hydrogen atom | Hydrogen atom | Oxygen atom | 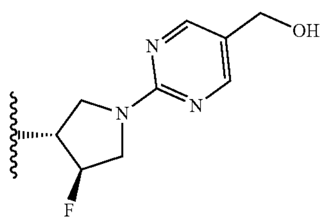 [SMILES: *[C@@H]1CN(c2ncc(CO)cn2)C[C@H]1F] |
| Example 204 | Hydrogen atom | Hydrogen atom | Hydrogen atom | Hydrogen atom | Hydrogen atom | Oxygen atom | 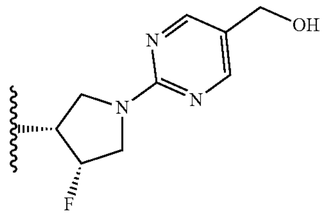 [SMILES: *[C@@H]1CN(c2ncc(CO)cn2)C[C@@H]1F] |
| Example 205 | Hydrogen atom | Hydrogen atom | Hydrogen atom | Hydrogen atom | Hydrogen atom | Oxygen atom | 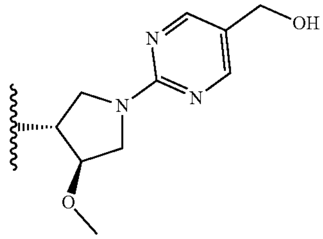 [SMILES: *[C@@H]1CN(c2ncc(CO)cn2)C[C@H]1OC] |
| Example 206 | Hydrogen atom | Hydrogen atom | Hydrogen atom | Hydrogen atom | Hydrogen atom | Oxygen atom | 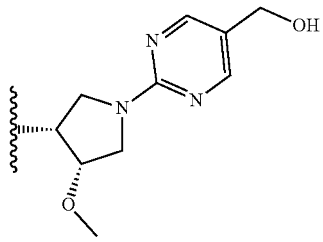 [SMILES: *[C@@H]1CN(c2ncc(CO)cn2)C[C@@H]1OC] |
| Example 207 | Hydrogen atom | Hydrogen atom | Hydrogen atom | Hydrogen atom | Hydrogen atom | Oxygen atom | 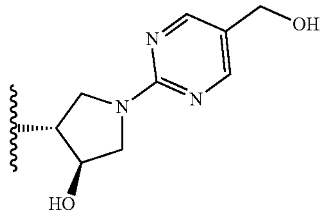 [SMILES: *[C@@H]1CN(c2ncc(CO)cn2)C[C@H]1O] |

-continued

| | $R^1$ | $R^2$ | $R^3$ | $R^4$ | $R^5$ | W | X |
|---|---|---|---|---|---|---|---|
| Example 208 | Hydrogen atom | Hydrogen atom | Hydrogen atom | Hydrogen atom | Hydrogen atom | Oxygen atom | 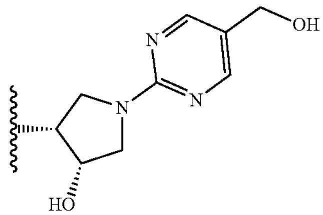 [SMILES: *[C@@H]1CN(c2ncc(CO)cn2)C[C@@H]1O] |
| Example 209 | Hydrogen atom | Hydrogen atom | Hydrogen atom | Hydrogen atom | Hydrogen atom | Oxygen atom | 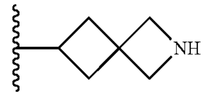 [SMILES: *C1CC2(CNC2)C1] |
| Example 210 | Hydrogen atom | Hydrogen atom | Hydrogen atom | Hydrogen atom | Hydrogen atom | Oxygen atom | 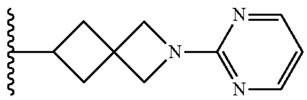 [SMILES: *C1CC2(C1)CN(c1ncccn1)C2] |
| Example 211 | Hydrogen atom | Hydrogen atom | Hydrogen atom | Hydrogen atom | Hydrogen atom | Oxygen atom | 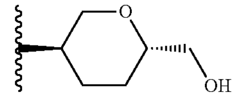 [SMILES: *[C@@H]1CC[C@@H](CO)OC1] |
| Example 212 | Hydrogen atom | Hydrogen atom | Hydrogen atom | Hydrogen atom | Hydrogen atom | Oxygen atom | 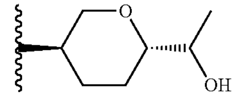 [SMILES: *[C@@H]1CC[C@@H](C(C)O)OC1] |
| Example 213 | Hydrogen atom | Hydrogen atom | Hydrogen atom | Hydrogen atom | Hydrogen atom | Oxygen atom | 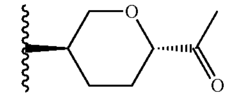 [SMILES: *[C@@H]1CC[C@@H](C(C)=O)OC1] |
| Example 214 | Hydrogen atom | Hydrogen atom | Hydrogen atom | Hydrogen atom | Hydrogen atom | Oxygen atom | 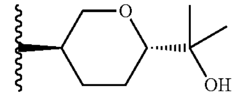 [SMILES: *[C@@H]1CC[C@@H](C(C)(C)O)OC1] |
| Example 215 | Hydrogen atom | Hydrogen atom | Hydrogen atom | Hydrogen atom | Hydrogen atom | Oxygen atom | 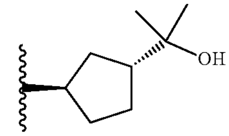 [SMILES: *[C@@H]1CC[C@@H](C(C)(C)O)C1] |
| Example 216 | Hydrogen atom | Hydrogen atom | Hydrogen atom | Hydrogen atom | Hydrogen atom | Oxygen atom | 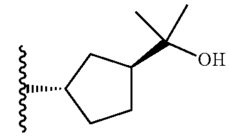 [SMILES: *[C@H]1CC[C@H](C(C)(C)O)C1] |
| Example 217 | Hydrogen atom | Hydrogen atom | Hydrogen atom | Hydrogen atom | Hydrogen atom | Oxygen atom | 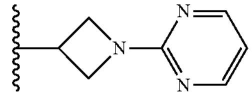 [SMILES: *C1CN(c2ncccn2)C1] |
| Example 218 | Hydrogen atom | Hydrogen atom | Hydrogen atom | Hydrogen atom | Hydrogen atom | Oxygen atom | 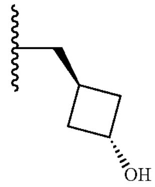 [SMILES: *C[C@H]1C[C@H](O)C1] |

-continued

| | $R^1$ | $R^2$ | $R^3$ | $R^4$ | $R^5$ | W | X |
|---|---|---|---|---|---|---|---|
| Example 219 | Hydrogen atom | Hydrogen atom | Hydrogen atom | Hydrogen atom | Hydrogen atom | Oxygen atom | 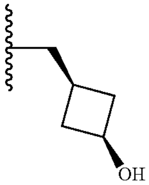 [SMILES: *C[C@H]1C[C@@H](O)C1] |
| Example 220 | Hydrogen atom | Hydrogen atom | Hydrogen atom | Hydrogen atom | Hydrogen atom | Oxygen atom | 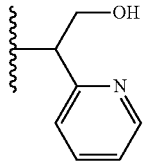 [SMILES: *C(CO)c1ccccn1] |
| Example 221 | Hydrogen atom | Hydrogen atom | Hydrogen atom | Hydrogen atom | Hydrogen atom | Oxygen atom | 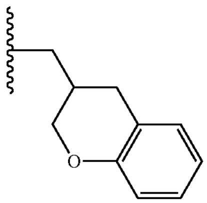 [SMILES: *CC1COc2ccccc2C1] |
| Example 222 | Hydrogen atom | Hydrogen atom | Hydrogen atom | Hydrogen atom | Hydrogen atom | Oxygen atom | 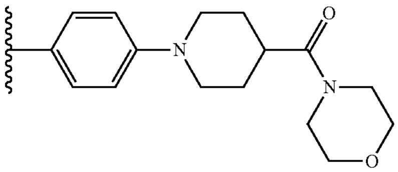 [SMILES: *c1ccc(N2CCC(C(=O)N3CCOCC3)CC2)cc1] |
| Example 223 | Hydrogen atom | Hydrogen atom | Hydrogen atom | Hydrogen atom | Hydrogen atom | Oxygen atom | 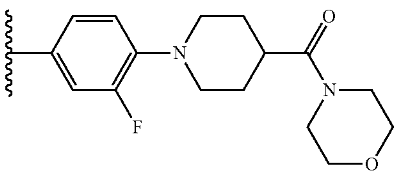 [SMILES: *c1ccc(N2CCC(C(=O)N3CCOCC3)CC2)c(F)c1] |
| Example 224 | Hydrogen atom | Hydrogen atom | Hydrogen atom | Hydrogen atom | Hydrogen atom | Oxygen atom | 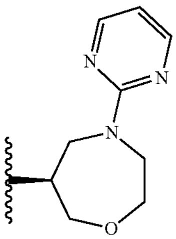 [SMILES: *[C@@H]1COCCN(c2ncccn2)C1] |
| Example 225 | Hydrogen atom | Hydrogen atom | Hydrogen atom | Hydrogen atom | Hydrogen atom | Oxygen atom | 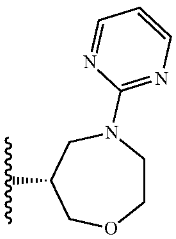 [SMILES: *[C@H]1COCCN(c2ncccn2)C1] |

-continued

| | R1 | R2 | R3 | R4 | R5 | W | X |
|---|---|---|---|---|---|---|---|
| Example 226 | Hydrogen atom | Hydrogen atom | Hydrogen atom | Hydrogen atom | Hydrogen atom | Oxygen atom | 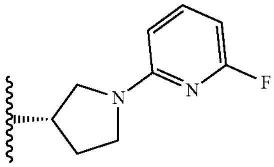 [SMILES: *[C@H]1CCN(c2cccc(F)n2)C1] |
| Example 227 | Hydrogen atom | Hydrogen atom | Hydrogen atom | Hydrogen atom | Hydrogen atom | Oxygen atom | 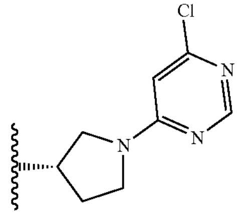 [SMILES: *[C@H]1CCN(c2cc(Cl)ncn2)C1] |
| Example 228 | Hydrogen atom | Hydrogen atom | Hydrogen atom | Hydrogen atom | Hydrogen atom | Oxygen atom | 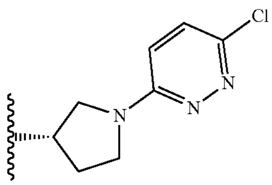 [SMILES: *[C@H]1CCN(c2ccc(Cl)nn2)C1] |
| Example 229 | Hydrogen atom | Hydrogen atom | Hydrogen atom | Hydrogen atom | Hydrogen atom | Oxygen atom | 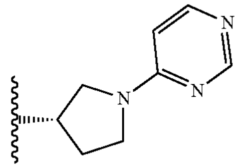 [SMILES: *[C@H]1CCN(c2ccncn2)C1] |
| Example 230 | Hydrogen atom | Hydrogen atom | Hydrogen atom | Hydrogen atom | Hydrogen atom | Oxygen atom | 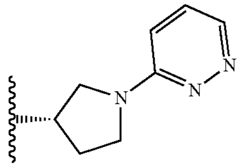 [SMILES: *[C@H]1CCN(c2cccnn2)C1] |
| Example 231 | Hydrogen atom | Hydrogen atom | Hydrogen atom | Hydrogen atom | Hydrogen atom | Oxygen atom | 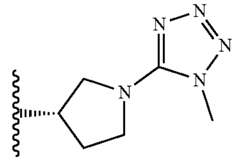 [SMILES: *[C@H]1CCN(c2nnnn2C)C1] |
| Example 232 | Hydrogen atom | Hydrogen atom | Hydrogen atom | Hydrogen atom | Hydrogen atom | Oxygen atom | 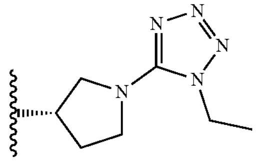 [SMILES: *[C@H]1CCN(c2nnnn2CC)C1] |
| Example 233 | Hydrogen atom | Hydrogen atom | Hydrogen atom | Hydrogen atom | Hydrogen atom | Oxygen atom | 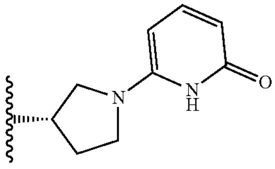 [SMILES: *[C@H]1CCN(c2cccc(=O)[nH]2)C1] |
| Example 234 | Hydrogen atom | Hydrogen atom | Hydrogen atom | Hydrogen atom | Hydrogen atom | Oxygen atom | 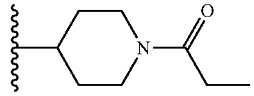 [SMILES: *C1CCN(C(=O)CC)CC1] |

-continued

| | R1 | R2 | R3 | R4 | R5 | W | X |
|---|---|---|---|---|---|---|---|
| Example 235 | Hydrogen atom | Hydrogen atom | Hydrogen atom | Hydrogen atom | Hydrogen atom | Oxygen atom | 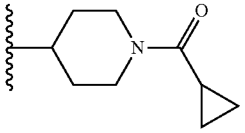 [SMILES: *C1CCN(C(=O)C2CC2)CC1] |
| Example 236 | Hydrogen atom | Hydrogen atom | Hydrogen atom | Hydrogen atom | Hydrogen atom | Oxygen atom | 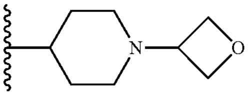 [SMILES: *C1CCN(C2COC2)CC1] |
| Example 237 | Hydrogen atom | Hydrogen atom | Hydrogen atom | Hydrogen atom | Hydrogen atom | Oxygen atom | 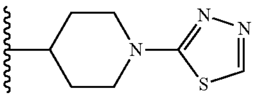 [SMILES: *C1CCN(c2nncs2)CC1] |
| Example 238 | Hydrogen atom | Hydrogen atom | Hydrogen atom | Hydrogen atom | Hydrogen atom | Oxygen atom | 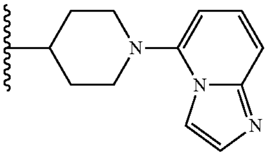 [SMILES: *C1CCN(c2cccc3nccn23)CC1] |
| Example 239 | Hydrogen atom | Hydrogen atom | Hydrogen atom | Hydrogen atom | Hydrogen atom | Oxygen atom | 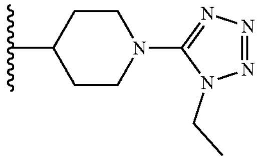 [SMILES: *C1CCN(c2nnnn2CC)CC1] |
| Example 240 | Hydrogen atom | Hydrogen atom | Hydrogen atom | Hydrogen atom | Hydrogen atom | Oxygen atom | 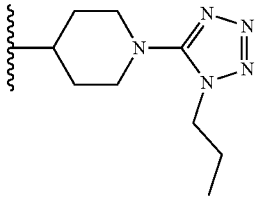 [SMILES: *C1CCN(c2nnnn2CCC)CC1] |
| Example 241 | Hydrogen atom | Hydrogen atom | Hydrogen atom | Hydrogen atom | Hydrogen atom | Oxygen atom | 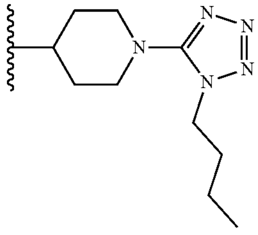 [SMILES: *C1CCN(c2nnnn2CCCC)CC1] |
| Example 242 | Hydrogen atom | Hydrogen atom | Hydrogen atom | Hydrogen atom | Hydrogen atom | Oxygen atom | 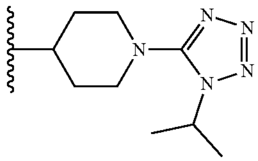 [SMILES: *C1CCN(c2nnnn2C(C)C)CC1] |
| Example 243 | Hydrogen atom | Hydrogen atom | Hydrogen atom | Hydrogen atom | Hydrogen atom | Oxygen atom | 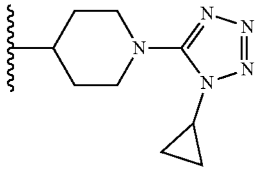 [SMILES: *C1CCN(c2nnnn2C2CC2)CC1] |

-continued

| | $R^1$ | $R^2$ | $R^3$ | $R^4$ | $R^5$ | W | X |
|---|---|---|---|---|---|---|---|
| Example 244 | Hydrogen atom | Hydrogen atom | Hydrogen atom | Hydrogen atom | Hydrogen atom | Oxygen atom | 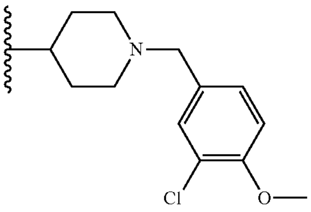 [SMILES: *C1CCN(Cc2ccc(OC)c(Cl)c2)CC1] |
| Example 245 | Hydrogen atom | Hydrogen atom | Hydrogen atom | Hydrogen atom | Hydrogen atom | Oxygen atom | 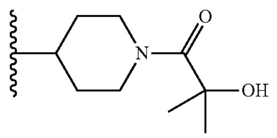 [SMILES: *C1CCN(C(=O)C(C)(C)O)CC1] |
| Example 246 | Hydrogen atom | Hydrogen atom | Hydrogen atom | Hydrogen atom | Hydrogen atom | Oxygen atom | 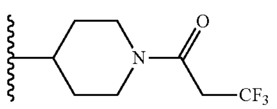 |
| Example 247 | Hydrogen atom | Hydrogen atom | Hydrogen atom | Hydrogen atom | Hydrogen atom | Oxygen atom | 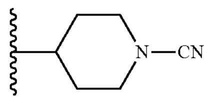 [SMILES: *C1CCN(C#N)CC1] |
| Example 248 | Hydrogen atom | Hydrogen atom | Hydrogen atom | Hydrogen atom | Hydrogen atom | Oxygen atom | 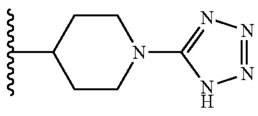 |
| Example 249 | Hydrogen atom | Hydrogen atom | Hydrogen atom | Hydrogen atom | Hydrogen atom | Oxygen atom | 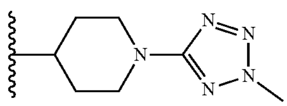 [SMILES: *C1CCN(c2nnn(C)n2)CC1] |
| Example 250 | Hydrogen atom | Hydrogen atom | Hydrogen atom | Hydrogen atom | Hydrogen atom | Oxygen atom | 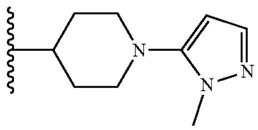 [SMILES: *C1CCN(c2ccnn2C)CC1] |
| Example 251 | Hydrogen atom | Hydrogen atom | Hydrogen atom | Hydrogen atom | Hydrogen atom | Oxygen atom | 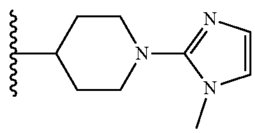 [SMILES: *C1CCN(c2nccn2C)CC1] |
| Example 252 | Hydrogen atom | Hydrogen atom | Hydrogen atom | Hydrogen atom | Hydrogen atom | Oxygen atom | 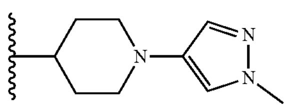 [SMILES: *C1CCN(c2cnn(C)c2)CC1] |
| Example 253 | Hydrogen atom | Hydrogen atom | Hydrogen atom | Hydrogen atom | Hydrogen atom | Oxygen atom | 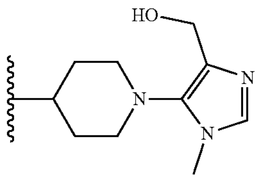 [SMILES: *C1CCN(c2c(CO)ncn2C)CC1] |
| Example 254 | Hydrogen atom | Hydrogen atom | Hydrogen atom | Hydrogen atom | Hydrogen atom | Oxygen atom | 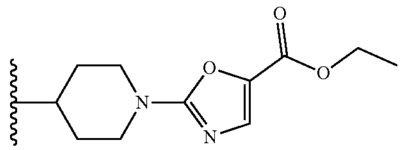 [SMILES: *C1CCN(c2ncc(C(=O)OCC)o2)CC1] |

-continued

| | R[1] | R[2] | R[3] | R[4] | R[5] | W | X |
|---|---|---|---|---|---|---|---|
| Example 255 | Hydrogen atom | Hydrogen atom | Hydrogen atom | Hydrogen atom | Hydrogen atom | Oxygen atom | 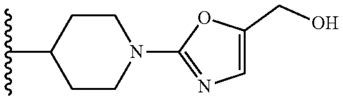 [SMILES: *C1CCN(c2ncc(CO)o2)CC1] |
| Example 256 | Hydrogen atom | Hydrogen atom | Hydrogen atom | Hydrogen atom | Hydrogen atom | Oxygen atom | 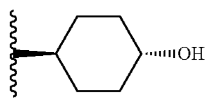 [SMILES: *[C@H]1CC[C@H](O)CC1] |
| Example 257 | Hydrogen atom | Hydrogen atom | Hydrogen atom | Hydrogen atom | Hydrogen atom | Oxygen atom | 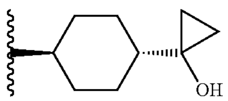 [SMILES: *[C@H]1CC[C@H](C2(O)CC2)CC1] |
| Example 258 | Hydrogen atom | Hydrogen atom | Hydrogen atom | Hydrogen atom | Hydrogen atom | Oxygen atom | 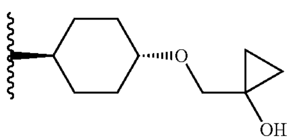 [SMILES: *[C@H]1CC[C@H](OCC2(O)CC2)CC1] |
| Example 259 | Hydrogen atom | Hydrogen atom | Hydrogen atom | Hydrogen atom | Hydrogen atom | Oxygen atom | 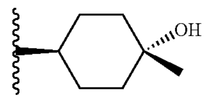 [SMILES: *[C@H]1CC[C@](C)(O)CC1] |
| Example 260 | Hydrogen atom | Hydrogen atom | Hydrogen atom | Hydrogen atom | Hydrogen atom | Oxygen atom | 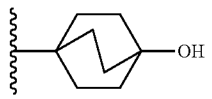 |
| Example 261 | Hydrogen atom | Hydrogen atom | Hydrogen atom | Hydrogen atom | Hydrogen atom | Oxygen atom | 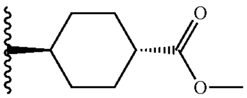 [SMILES: *[C@H]1CC[C@H](C(=O)OC)CC1] |
| Example 262 | Hydrogen atom | Hydrogen atom | Hydrogen atom | Hydrogen atom | Hydrogen atom | Oxygen atom | 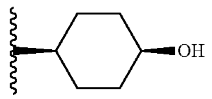 [SMILES: *[C@H]1CC[C@@H](O)CC1] |
| Example 263 | Hydrogen atom | Hydrogen atom | Hydrogen atom | Hydrogen atom | Hydrogen atom | Oxygen atom | 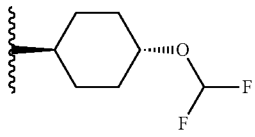 [SMILES: *[C@H]1CC[C@H](OC(F)F)CC1] |
| Example 264 | Hydrogen atom | Hydrogen atom | Hydrogen atom | Hydrogen atom | Hydrogen atom | Oxygen atom | 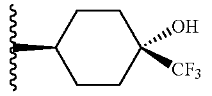 [SMILES: *[C@H]1CC[C@@](O)(C(F)(F)F)CC1] |
| Example 265 | Hydrogen atom | Hydrogen atom | Hydrogen atom | Hydrogen atom | Hydrogen atom | Oxygen atom | 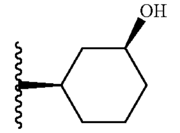 [SMILES: *[C@@H]1CCC[C@H](O)C1] |
| Example 266 | Hydrogen atom | Hydrogen atom | Hydrogen atom | Hydrogen atom | Hydrogen atom | Oxygen atom | 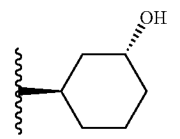 [SMILES: *[C@@H]1CCC[C@@H](O)C1] |
| Example 267 | Hydrogen atom | Hydrogen atom | Hydrogen atom | Hydrogen atom | Hydrogen atom | Oxygen atom | 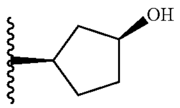 [SMILES: *[C@@H]1CC[C@H](O)C1] |

-continued

| | R1 | R2 | R3 | R4 | R5 | W | X |
|---|---|---|---|---|---|---|---|
| Example 268 | Hydrogen atom | Hydrogen atom | Hydrogen atom | Hydrogen atom | Hydrogen atom | Oxygen atom | 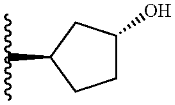 [SMILES: *[C@@H]1CC[C@@H](O)C1] |
| Example 269 | Hydrogen atom | Hydrogen atom | Hydrogen atom | Hydrogen atom | Hydrogen atom | Oxygen atom | 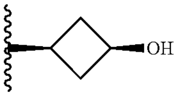 [SMILES: *[C@H]1C[C@@H](O)C1] |
| Example 270 | Hydrogen atom | Hydrogen atom | Hydrogen atom | Hydrogen atom | Hydrogen atom | Oxygen atom | 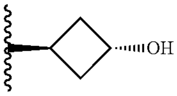 [SMILES: *[C@H]1C[C@H](O)C1] |
| Example 271 | Hydrogen atom | Hydrogen atom | Hydrogen atom | Hydrogen atom | Hydrogen atom | Oxygen atom | 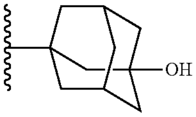 [SMILES: *C12CC3CC(C1)CC(O)(C3)C2] |
| Example 272 | Hydrogen atom | Hydrogen atom | Hydrogen atom | Hydrogen atom | Hydrogen atom | Oxygen atom | 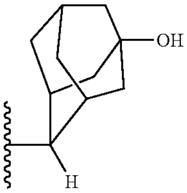 [SMILES: *C1C2CC3CC1CC(O)(C3)C2] |
| Example 273 | Hydrogen atom | Hydrogen atom | Hydrogen atom | Hydrogen atom | Hydrogen atom | Oxygen atom | 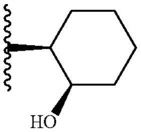 [SMILES: *[C@H]1CCCC[C@H]1O] |
| Example 274 | Hydrogen atom | Hydrogen atom | Hydrogen atom | Hydrogen atom | Hydrogen atom | Oxygen atom | 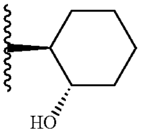 [SMILES: *[C@H]1CCCC[C@@H]1O] |
| Example 275 | Hydrogen atom | Hydrogen atom | Hydrogen atom | Hydrogen atom | Hydrogen atom | Oxygen atom | 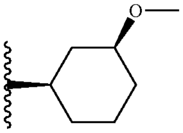 [SMILES: *[C@@H]1CCC[C@H](OC)C1] |
| Example 276 | Hydrogen atom | Hydrogen atom | Hydrogen atom | Hydrogen atom | Hydrogen atom | Oxygen atom | 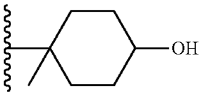 [SMILES: *C1(C)CCC(O)CC1] |
| Example 277 | Hydrogen atom | Hydrogen atom | Hydrogen atom | Hydrogen atom | Hydrogen atom | Oxygen atom | 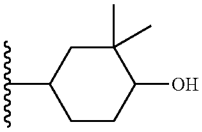 [SMILES: *C1CCC(O)C(C)(C)C1] |
| Example 278 | Hydrogen atom | Hydrogen atom | Hydrogen atom | Hydrogen atom | Hydrogen atom | Oxygen atom | 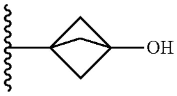 [SMILES: *C12CC(O)(C1)C2] |
| Example 279 | Hydrogen atom | Hydrogen atom | Hydrogen atom | Hydrogen atom | Hydrogen atom | Oxygen atom | 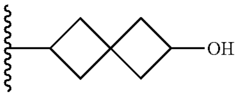 [SMILES: *C1CC2(C1)CC(O)C2] |

-continued

| | R1 | R2 | R3 | R4 | R5 | W | X |
|---|---|---|---|---|---|---|---|
| Example 280 | Hydrogen atom | Hydrogen atom | Hydrogen atom | Hydrogen atom | Hydrogen atom | Oxygen atom | 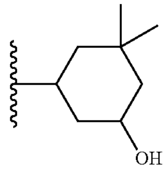 [SMILES: *C1CC(O)CC(C)(C)C1] |
| Example 281 | Hydrogen atom | Hydrogen atom | Hydrogen atom | Hydrogen atom | Hydrogen atom | Oxygen atom | 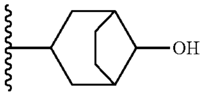 [SMILES: *C1CC2CCC(C1)C2O] |
| Example 282 | Hydrogen atom | Hydrogen atom | Hydrogen atom | Hydrogen atom | Hydrogen atom | Oxygen atom | 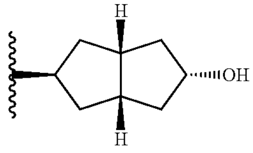 [SMILES: *[C@H]1C[C@@H]2C[C@H](O)C[C@@H]2C1] |
| Example 283 | Hydrogen atom | Hydrogen atom | Hydrogen atom | Hydrogen atom | Hydrogen atom | Oxygen atom | 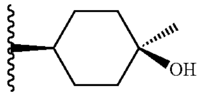 |
| Example 284 | Hydrogen atom | Hydrogen atom | Hydrogen atom | Hydrogen atom | Hydrogen atom | Oxygen atom | 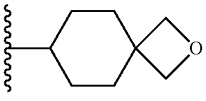 |
| Example 285 | Hydrogen atom | Hydrogen atom | Hydrogen atom | Hydrogen atom | Hydrogen atom | Oxygen atom | 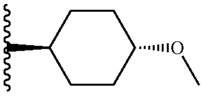 [SMILES: *[C@H]1CC[C@H](OC)CC1] |
| Example 286 | Hydrogen atom | Hydrogen atom | Hydrogen atom | Hydrogen atom | Hydrogen atom | Oxygen atom | 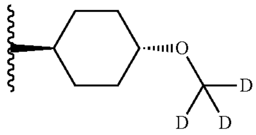 [SMILES: *[C@H]1CC[C@H](OC([2H])([2H])[2H])CC1] |
| Example 287 | Hydrogen atom | Hydrogen atom | Hydrogen atom | Hydrogen atom | Hydrogen atom | Oxygen atom | 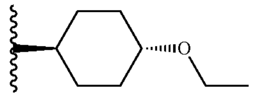 [SMILES: *[C@H]1CC[C@H](OCC)CC1] |
| Example 288 | Hydrogen atom | Hydrogen atom | Hydrogen atom | Hydrogen atom | Hydrogen atom | Oxygen atom | 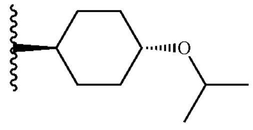 [SMILES: *[C@H]1CC[C@H](OC(C)C)CC1] |
| Example 289 | Hydrogen atom | Hydrogen atom | Hydrogen atom | Hydrogen atom | Hydrogen atom | Oxygen atom | 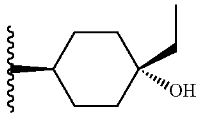 [SMILES: *[C@H]1CC[C@@](O)(CC)CC1] |
| Example 290 | Hydrogen atom | Hydrogen atom | Hydrogen atom | Hydrogen atom | Hydrogen atom | Oxygen atom | 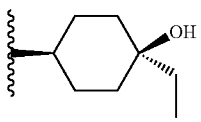 [SMILES: *[C@H]1CC[C@](O)(CC)CC1] |
| Example 291 | Hydrogen atom | Hydrogen atom | Hydrogen atom | Hydrogen atom | Hydrogen atom | Oxygen atom | 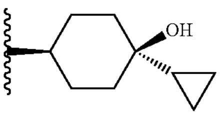 [SMILES: *[C@H]1CC[C@](O)(C2CC2)CC1] |

-continued

| | $R^1$ | $R^2$ | $R^3$ | $R^4$ | $R^5$ | W | X |
|---|---|---|---|---|---|---|---|
| Example 292 | Hydrogen atom | Hydrogen atom | Hydrogen atom | Hydrogen atom | Hydrogen atom | Oxygen atom | 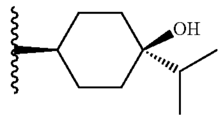 [SMILES: *[C@H]1CC[C@](O)(C(C)C)CC1] |
| Example 293 | Hydrogen atom | Hydrogen atom | Hydrogen atom | Hydrogen atom | Hydrogen atom | Oxygen atom | 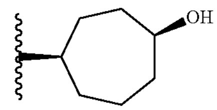 [SMILES: *[C@@H]1CCC[C@H](O)CC1] |
| Example 294 | Hydrogen atom | Hydrogen atom | Hydrogen atom | Hydrogen atom | Hydrogen atom | Oxygen atom | 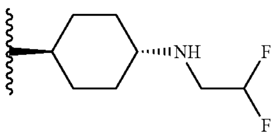 [SMILES: *[C@H]1CC[C@H](NCC(F)F)CC1] |
| Example 295 | Hydrogen atom | Hydrogen atom | Hydrogen atom | Hydrogen atom | Hydrogen atom | Oxygen atom | 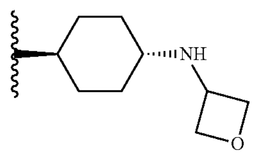 [SMILES: *[C@H]1CC[C@H](NC2COC2)CC1] |
| Example 296 | Hydrogen atom | Hydrogen atom | Hydrogen atom | Hydrogen atom | Hydrogen atom | Oxygen atom | 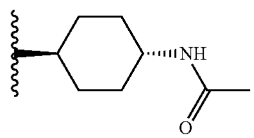 [SMILES: *[C@H]1CC[C@H](NC(C)=O)CC1] |
| Example 297 | Hydrogen atom | Hydrogen atom | Hydrogen atom | Hydrogen atom | Hydrogen atom | Oxygen atom | 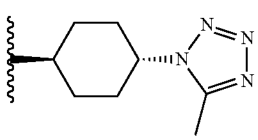 [SMILES: *[C@H]1CC[C@H](n2nnnc2C)CC1] |
| Example 298 | Hydrogen atom | Hydrogen atom | Hydrogen atom | Hydrogen atom | Hydrogen atom | Oxygen atom | 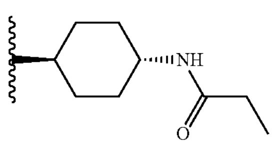 [SMILES: *[C@H]1CC[C@H](NC(=O)CC)CC1] |
| Example 299 | Hydrogen atom | Hydrogen atom | Hydrogen atom | Hydrogen atom | Hydrogen atom | Oxygen atom | 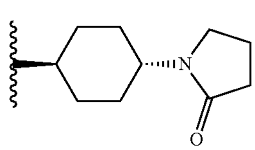 [SMILES: *[C@H]1CC[C@H](N2CCCC2=O)CC1] |
| Example 300 | Hydrogen atom | Hydrogen atom | Hydrogen atom | Hydrogen atom | Hydrogen atom | Oxygen atom | 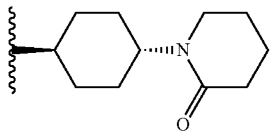 [SMILES: *[C@H]1CC[C@H](N2CCCCC2=O)CC1] |
| Example 301 | Hydrogen atom | Hydrogen atom | Hydrogen atom | Hydrogen atom | Hydrogen atom | Oxygen atom | 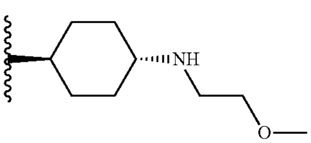 [SMILES: *[C@H]1CC[C@H](NCCOC)CC1] |
| Example 302 | Hydrogen atom | Hydrogen atom | Hydrogen atom | Hydrogen atom | Hydrogen atom | Oxygen atom | 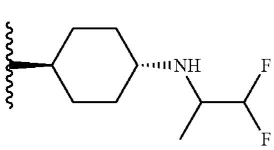 [SMILES: *[C@H]1CC[C@H](NC(C)C(F)F)CC1] |

-continued

| | $R^1$ | $R^2$ | $R^3$ | $R^4$ | $R^5$ | W | X |
|---|---|---|---|---|---|---|---|
| Example 303 | Hydrogen atom | Hydrogen atom | Hydrogen atom | Hydrogen atom | Hydrogen atom | Oxygen atom | 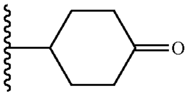 [SMILES: *C1CCC(=O)CC1] |
| Example 304 | Hydrogen atom | Hydrogen atom | Hydrogen atom | Hydrogen atom | Hydrogen atom | Oxygen atom | 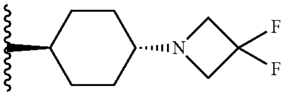 [SMILES: *[C@H]1CC[C@H](N2CC(F)(F)C2)CC1] |
| Example 305 | Hydrogen atom | Hydrogen atom | Hydrogen atom | Hydrogen atom | Hydrogen atom | Oxygen atom | 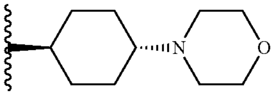 [SMILES: *[C@H]1CC[C@H](N2CCOCC2)CC1] |
| Example 306 | Hydrogen atom | Hydrogen atom | Hydrogen atom | Hydrogen atom | Hydrogen atom | Oxygen atom | 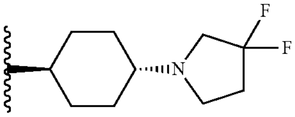 [SMILES: *[C@H]1CC[C@H](N2CCC(F)(F)C2)CC1] |
| Example 307 | Hydrogen atom | Hydrogen atom | Hydrogen atom | Hydrogen atom | Hydrogen atom | Oxygen atom | 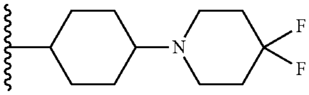 [SMILES: *C1CCC(N2CCC(F)(F)CC2)CC1] |
| Example 308 | Hydrogen atom | Hydrogen atom | Hydrogen atom | Hydrogen atom | Hydrogen atom | Oxygen atom | 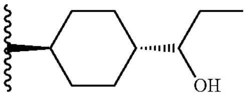 |
| Example 309 | Hydrogen atom | Hydrogen atom | Hydrogen atom | Hydrogen atom | Hydrogen atom | Oxygen atom | 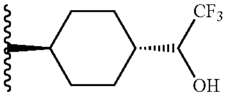 [SMILES: *[C@H]1CC[C@H](C(O)C(F)(F)F)CC1] |
| Example 310 | Hydrogen atom | Hydrogen atom | Hydrogen atom | Hydrogen atom | Hydrogen atom | Oxygen atom | 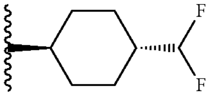 [SMILES: *[C@H]1CC[C@H](C(F)F)CC1] |
| Example 311 | Hydrogen atom | Hydrogen atom | Hydrogen atom | Hydrogen atom | Hydrogen atom | Oxygen atom | 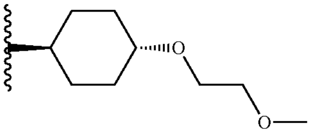 |
| Example 312 | Hydrogen atom | Hydrogen atom | Chlorine atom | Hydrogen atom | Hydrogen atom | Oxygen atom | 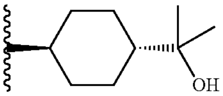 |
| Example 313 | Hydrogen atom | Hydrogen atom | Vinyl group | Hydrogen atom | Hydrogen atom | Oxygen atom | 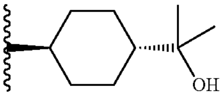 |
| Example 314 | Hydrogen atom | Hydrogen atom | Ethyl group | Hydrogen atom | Hydrogen atom | Oxygen atom | 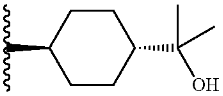 |
| Example 315 | Hydrogen atom | Hydrogen atom | Amino group | Hydrogen atom | Hydrogen atom | Oxygen atom | 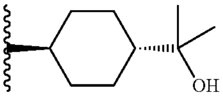 [SMILES: *[C@H]1CC[C@H](C(C)(C)O)CC1] |

-continued

| | $R^1$ | $R^2$ | $R^3$ | $R^4$ | $R^5$ | W | X |
|---|---|---|---|---|---|---|---|
| Example 316 | Hydrogen atom | Hydrogen atom | Fluorine atom | Hydrogen atom | Hydrogen atom | Oxygen atom | 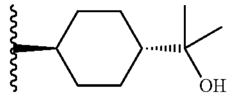 [SMILES: *[C@H]1CC[C@H](C(C)(C)O)CC1] |
| Example 317 | Hydrogen atom | Hydrogen atom | Cyano group | Hydrogen atom | Hydrogen atom | Oxygen atom | 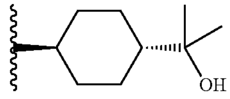 [SMILES: *[C@H]1CC[C@H](C(C)(C)O)CC1] |
| Example 318 | Hydrogen atom | Hydrogen atom | Carbamoyl group | Hydrogen atom | Hydrogen atom | Oxygen atom | 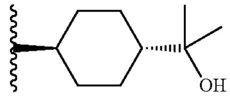 |
| Example 319 | Hydrogen atom | Hydrogen atom | Hydroxy-methyl group | Hydrogen atom | Hydrogen atom | Oxygen atom | 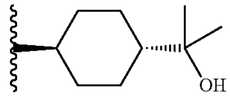 [SMILES: *[C@H]1CC[C@H](C(C)(C)O)CC1] |
| Example 320 | Hydrogen atom | Hydrogen atom | Hydroxy-methyl-$d_2$ group | Hydrogen atom | Hydrogen atom | Oxygen atom | 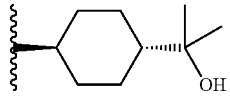 [SMILES: *[C@H]1CC[C@H](C(C)(C)O)CC1] |
| Example 321 | Hydrogen atom | Hydrogen atom | Methyl group | Hydrogen atom | Fluorine atom | Oxygen atom | 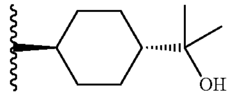 |
| | | | | | 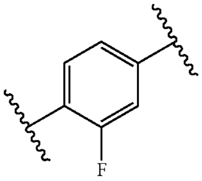 [SMILES: *c1ccc(*)c(F)c1] | | |
| Example 322 | Hydrogen atom | Hydrogen atom | Hydroxy-methyl group | Hydrogen atom | Fluorine atom | Oxygen atom | 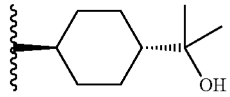 |
| | | | | | 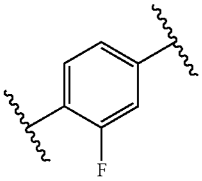 [SMILES: *c1ccc(*)c(F)c1] | | |
| Example 323 | Hydrogen atom | Hydrogen atom | Hydrogen atom | Hydrogen atom | Fluorine atom | Oxygen atom | 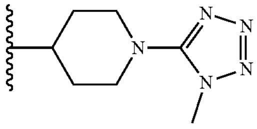 [SMILES: *C1CCN(c2nnnn2C)CC1] |
| | | | | | 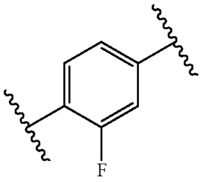 [SMILES: *c1ccc(*)c(F)c1] | | |
| Example 324 | Hydrogen atom | Hydrogen atom | Hydrogen atom | Hydrogen atom | Fluorine atom | Oxygen atom | 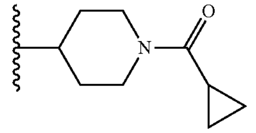 [SMILES: *C1CCN(C(=O)C2CC2)CC1] |
| | | | | | 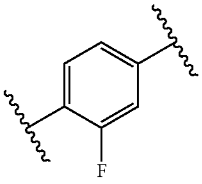 [SMILES: *c1ccc(*)c(F)c1] | | |

-continued

| | $R^1$ | $R^2$ | $R^3$ | $R^4$ | $R^5$ | W | X |
|---|---|---|---|---|---|---|---|
| Example 325 | Hydrogen atom | Hydrogen atom | Hydrogen atom | Hydrogen atom | Fluorine atom 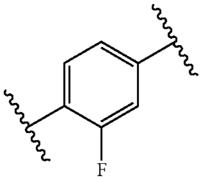 | Oxygen atom | 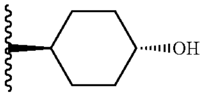 [SMILES: *[C@H]1CC[C@H](O)CC1] |
| Example 326 | Hydrogen atom | Hydrogen | Hydrogen | Hydrogen | Fluorine atom 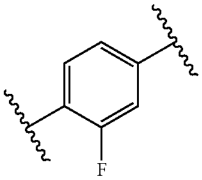 [SMILES: *c1ccc(*)c(F)c1] | Oxygen atom | 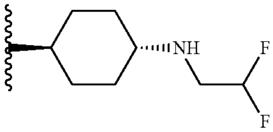 [SMILES: *[C@H]1CC[C@H](NCC(F)F)CC1] |
| Example 327 | Hydrogen atom | Hydrogen atom | Hydrogen atom | Hydrogen atom | Fluorine atom 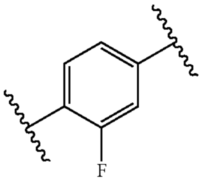 [SMILES: *c1ccc(*)c(F)c1] | Oxygen atom | 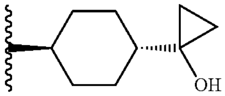 |
| Example 328 | Hydrogen atom | Hydrogen atom | Hydrogen atom | Hydrogen atom | Fluorine atom 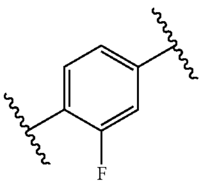 [SMILES: *c1ccc(*)c(F)c1] | Oxygen atom | 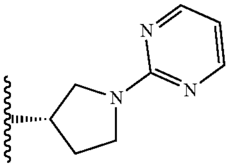 [SMILES: *[C@H]1CCN(c2ncccn2)C1] |
| Example 329 | Hydrogen atom | Hydrogen atom | Hydrogen atom | Hydrogen atom | Fluorine atom 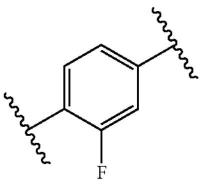 [SMILES: *c1ccc(*)c(F)c1] | Oxygen atom | 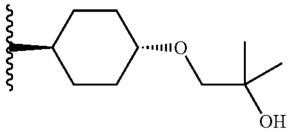 [SMILES: *[C@H]1CC[C@H](OCC(C)(C)O)CC1] |
| Example 330 | Hydrogen atom | Hydrogen atom | Methyl group | Hydrogen atom | Hydrogen atom | Oxygen atom | 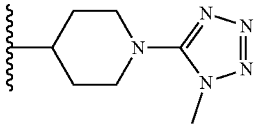 [SMILES: *C1CCN(c2nnnn2C)CC1] |
| Example 331 | Hydrogen atom | Hydrogen atom | Methyl group | Hydrogen atom | Hydrogen atom | Oxygen atom | 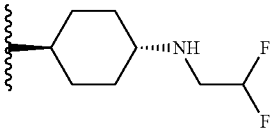 |

-continued

| | $R^1$ | $R^2$ | $R^3$ | $R^4$ | $R^5$ | W | X |
|---|---|---|---|---|---|---|---|
| Example 332 | Hydrogen atom | Hydrogen atom | Methyl group | Hydrogen atom | Hydrogen atom | Oxygen atom | 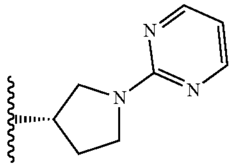 [SMILES: *[C@H]1CCN(c2ncccn2)C1] |
| Example 333 | Hydrogen atom | Hydrogen atom | Methyl group | Hydrogen atom | Hydrogen atom | Oxygen atom | 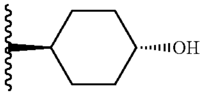 [SMILES: *[C@H]1CC[C@H](O)CC1] |
| Example 334 | Hydrogen atom | Hydrogen atom | Methyl group | Hydrogen atom | Hydrogen atom | Oxygen atom | 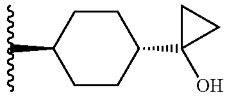 [SMILES: *[C@H]1CC[C@H](C2(O)CC2)CC1] |
| Example 335 | Hydrogen atom | Hydrogen atom | Methyl group | Hydrogen atom | Hydrogen atom | Oxygen atom | 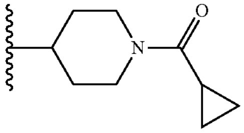 [SMILES: *C1CCN(C(=O)C2CC2)CC1] |
| Example 336 | Hydrogen atom | Hydrogen atom | Hydrogen atom | Hydrogen atom | Hydrogen atom | —N($R^6$)— $R^6$ = Hydrogen atom | 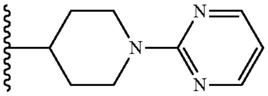 [SMILES: *C1CCN(c2ncccn2)CC1] |
| Example 337 | Hydrogen atom | Hydrogen atom | Hydrogen atom | Hydrogen atom | Hydrogen atom | —N($R^6$)— $R^6$ = Hydrogen atom | 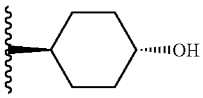 [SMILES: *[C@H]1CC[C@H](O)CC1] |
| Example 338 | Hydrogen atom | Hydrogen atom | Methyl group | Hydrogen atom | Hydrogen atom | —N($R^6$)— $R^6$ = Hydrogen atom | 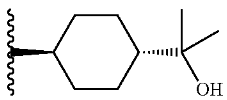 [SMILES: *[C@H]1CC[C@H](C(C)(C)O)CC1] |
| Example 339 | Hydrogen atom | Hydrogen atom | Hydrogen atom | Methyl group | Hydrogen atom | —N($R^6$)— $R^6$ = Hydrogen atom | 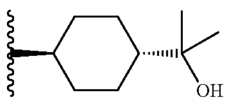 [SMILES: *[C@H]1CC[C@H](C(C)(C)O)CC1] |
| Example 340 | Hydrogen atom | Hydrogen atom | Hydrogen atom | Hydrogen atom | Fluorine atom 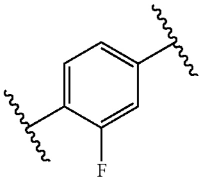 [SMILES: *c1ccc(*)c(F)c1] | —N($R^6$)— $R^6$ = Hydrogen atom | 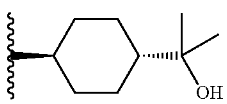 |
| Example 341 | Hydrogen atom | Hydrogen atom | Hydrogen atom | Hydrogen atom | Hydrogen atom | Sulfur atom | 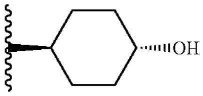 [SMILES: *[C@H]1CC[C@H](O)CC1] |
| Example 342 | Hydrogen atom | Hydrogen atom | Methyl group | Hydrogen atom | Hydrogen atom | Oxygen atom | 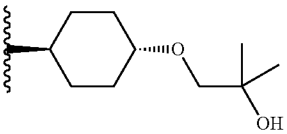 [SMILES: *[C@H]1CC[C@H](OCC(C)(C)O)CC1] |

-continued

| | R1 | R2 | R3 | R4 | R5 | W | X |
|---|---|---|---|---|---|---|---|
| Example 343 | Hydrogen atom | Hydrogen atom | Methyl group | Hydrogen atom | Hydrogen atom | Oxygen atom | 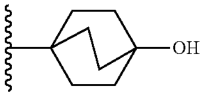 [SMILES: *C12CCC(O)(CC1)CC2] |
| Example 344 | Hydrogen atom | Hydrogen atom | Methyl group | Hydrogen atom | Hydrogen atom | Oxygen atom | 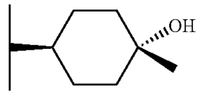 |
| Example 345 | Hydrogen atom | Hydrogen atom | Hydrogen atom | Hydrogen atom | Fluorine atom 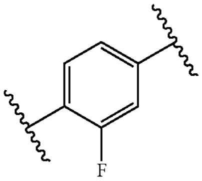 [SMILES: *c1ccc(*)c(F)c1] | Oxygen atom | 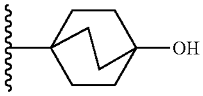 [SMILES: *C12CCC(O)(CC1)CC2] |
| Example 346 | Hydrogen atom | Hydrogen atom | Hydrogen atom | Hydrogen atom | Fluorine atom 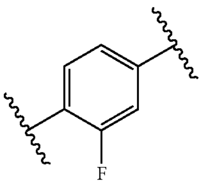 [SMILES: *c1ccc(*)c(F)c1] | Oxygen atom | 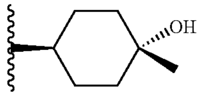 |
| Example 347 | Hydrogen atom | Hydrogen atom | Hydrogen atom | Hydrogen atom | Fluorine atom 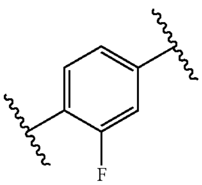 [SMILES: *c1ccc(*)c(F)c1] | Oxygen atom | 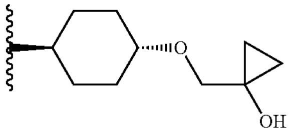 [SMILES: *[C@H]1CC[C@H](OCC2(O)CC2)CC1] |
| Example 348 | Hydrogen atom | Hydrogen atom | Hydrogen atom | Hydrogen atom | Hydrogen atom | Oxygen atom | 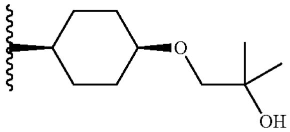 [SMILES: *[C@H]1CC[C@@H](OCC(C)(C)O)CC1] |
| Example 349 | Hydrogen atom | Hydrogen atom | Hydrogen atom | Hydrogen atom | Hydrogen atom | Oxygen atom | 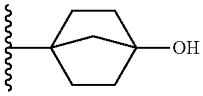 [SMILES: *C12CCC(O)(CC1)C2] |
| Example 350 | Hydrogen atom | Hydrogen atom | Hydrogen atom | Hydrogen atom | Hydrogen atom | Oxygen atom | 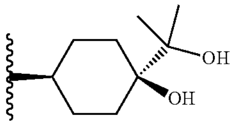 [SMILES: *[C@H]1CC[C@](O)(C(C)(C)O)CC1] |
| Example 351 | Hydrogen atom | Hydrogen atom | Hydrogen atom | Hydrogen atom | Hydrogen atom | Oxygen atom | 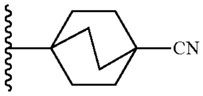 |
| Example 352 | Hydrogen atom | Hydrogen atom | Hydrogen atom | Hydrogen atom | Hydrogen atom | Oxygen atom | 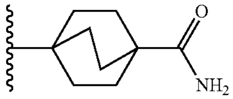 |

-continued

| | $R^1$ | $R^2$ | $R^3$ | $R^4$ | $R^5$ | W | X |
|---|---|---|---|---|---|---|---|
| Example 353 | Hydrogen atom | Hydrogen atom | Hydrogen atom | Hydrogen atom | Hydrogen atom | Oxygen atom | 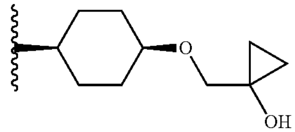 [SMILES: *[C@H]1CC[C@@H](OCC2(O)CC2)CC1] |
| Example 354 | Hydrogen atom | Hydrogen atom | Hydrogen atom | Hydrogen atom | Hydrogen atom | Oxygen atom | 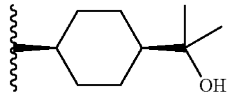 [SMILES: *[C@H]1CC[C@@H](C(C)(C)O)CC1] |

INDUSTRIAL APPLICABILITY

The compound of the present invention has H-PGDS inhibitory activity, and thus can be used as a therapeutic agent or a preventive agent for a disease involving H-PGDS.

The invention claimed is:

1. A compound represented by Formula (I):

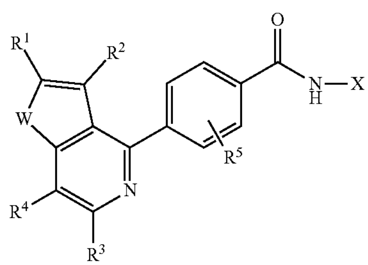

(I)

[wherein $R^1$ represents a hydrogen atom, a halogen atom, or a $C_{1-6}$ alkyl group;

$R^2$ represents a hydrogen atom, a halogen atom, a cyano group, a hydroxy group, a carbamoyl group, a $C_{1-6}$ alkyl group, a halo $C_{1-6}$ alkyl group, a hydroxy $C_{1-6}$ alkyl group, or a $C_{1-6}$ alkoxy group;

$R^3$ represents a hydrogen atom, a halogen atom, a cyano group, a hydroxy group, an amino group, a carbamoyl group, a sulfamoyl group, a carboxy group, a $C_{1-6}$ alkyl group, a $C_{2-6}$ alkenyl group, a halo $C_{1-6}$ alkyl group, a hydroxy $C_{1-6}$ alkyl group, a $C_{2-7}$ alkanoyl group, a $C_{1-6}$ alkylsulfonyl group, a $C_{1-6}$ alkoxy group, a halo $C_{1-6}$ alkoxy group, a $C_{1-6}$ alkylsulfonyloxy group, a halo $C_{1-6}$ alkylsulfonyloxy group, a mono $C_{1-6}$ alkylamino group, a di $C_{1-6}$ alkylamino group, a mono $C_{2-7}$ alkanoylamino group, a ($C_{2-7}$ alkanoyl) $C_{1-6}$ alkylamino group, a di $C_{2-7}$ alkanoylamino group, a mono $C_{1-6}$ alkylsulfonylamino group, a mono $C_{1-6}$ alkylcarbamoyl group, a di $C_{1-6}$ alkylcarbamoyl group, a mono $C_{1-6}$ alkylsulfamoyl group, a di $C_{1-6}$ alkylsulfamoyl group, a $C_{3-6}$ cycloalkyl group, a cyclic ether group, a cyclic amino group, or a halo cyclic amino group;

$R^4$ represents a hydrogen atom, a cyano group, a hydroxy group, an amino group, a carbamoyl group, a sulfamoyl group, a carboxy group, a $C_{1-6}$ alkyl group, a $C_{2-6}$ alkenyl group, a halo $C_{1-6}$ alkyl group, a hydroxy $C_{1-6}$ alkyl group, a $C_{1-6}$ alkoxy group, a halo $C_{1-6}$ alkoxy group, a mono $C_{1-6}$ alkylamino group, or a di $C_{1-6}$ alkylamino group;

$R^5$ represents a hydrogen atom, a halogen atom, a cyano group, a hydroxy group, a $C_{1-6}$ alkyl group, a halo $C_{1-6}$ alkyl group, or a hydroxy $C_{1-6}$ alkyl group;

W represents an oxygen atom, a sulfur atom, or a group represented by General Formula: —N($R^6$)—;

$R^6$ represents a hydrogen atom or a $C_{1-6}$ alkyl group; and

X represents a $C_{1-6}$ alkyl group, a $C_{2-6}$ alkenyl group, a halo $C_{1-6}$ alkyl group, a hydroxy $C_{1-6}$ alkyl group, a ($C_{1-6}$ alkoxy) $C_{1-6}$ alkyl group, a (halo $C_{1-6}$ alkoxy) $C_{1-6}$ alkyl group, an amino $C_{1-6}$ alkyl group, a (mono $C_{1-6}$ alkylamino) $C_{1-6}$ alkyl group, a (di $C_{1-6}$ alkylamino) $C_{1-6}$ alkyl group, a carbamoyl $C_{1-6}$ alkyl group, a (mono $C_{1-6}$ alkylcarbamoyl) $C_{1-6}$ alkyl group, a (di $C_{1-6}$ alkylcarbamoyl) $C_{1-6}$ alkyl group, a sulfamoyl $C_{1-6}$ alkyl group, a (mono $C_{1-6}$ alkylsulfamoyl) $C_{1-6}$ alkyl group, a (di $C_{1-6}$ alkylsulfamoyl) $C_{1-6}$ alkyl group, or a group represented by General Formula (II):

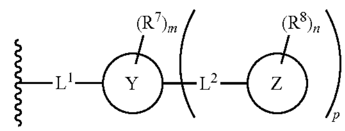

(wherein the wavy line represents the point of attachment to the nitrogen atom, $L^1$ represents a single bond, a $C_{1-6}$ alkanediyl group, or a hydroxy $C_{1-6}$ alkanediyl group;

ring Y represents a $C_{6-10}$ aryl group, a heteroaryl group, a $C_{3-10}$ cycloalkyl group, or a 4- to 10-membered heterocyclyl group (wherein the $C_{3-10}$ cycloalkyl group and the 4- to 10-membered heterocyclyl group are optionally condensed with a benzene ring or a heteroaryl ring to form a condensed ring group, or optionally form a bicyclo ring group or a spiro ring group);

each $R^7$ independently represents a halogen atom, a cyano group, a hydroxy group, a sulfanyl group, an amino group, a carbamoyl group, a sulfamoyl group, a carboxy group, a formyl group, an imino group, an azide group, a hydrazino group, a nitro group, an oxetanylamino group, a $C_{1-6}$ alkyl group, a $C_{2-6}$ alkenyl group, a halo $C_{1-6}$ alkyl group, a hydroxy $C_{1-6}$ alkyl group, a hydroxyhalo $C_{1-6}$ alkyl group, a ($C_{1-6}$ alkoxy) $C_{1-6}$ alkyl group, a $C_{2-7}$ alkanoyl group, a halo $C_{2-7}$ alkanoyl group, a hydroxy $C_{2-7}$ alkanoyl group, a $C_{1-6}$ alkylsulfonyl group, a $C_{1-6}$ alkoxy group, a halo $C_{1-6}$ alkoxy group, a hydroxy $C_{1-6}$ alkoxy group, a $C_{1-6}$ alkylthio group, a mono $C_{1-6}$ alkylamino group, a di $C_{1-6}$ alkylamino group, a mono (halo $C_{1-6}$ alkyl)amino group, a $C_{2-7}$ alkoxycarbonyl group, a mono $C_{1-6}$ alkylcarbamoyl group, a di $C_{1-6}$ alkylcarbamoyl group, a $C_{1-6}$ alkylsulfonyloxy group, a halo $C_{1-6}$ alkylsulfonyloxy group, a mono $C_{1-6}$ alkylsulfamoyl group, a di $C_{1-6}$ alkylsulfamoyl group, a mono $C_{2-7}$ alkanoylamino group, a ($C_{2-7}$ alkanoyl) $C_{1-6}$ alkylamino group, a di $C_{2-7}$ alkanoylamino group, a mono $C_{1-6}$ alkylsulfonylamino group, a mono ($C_{2-7}$ alkoxycarbonyl)amino group, a $C_{3-6}$ cycloalkyl group, a hydroxy $C_{3-6}$ cycloalkyl group, a (hydroxy $C_{3-6}$ cycloalkyl) $C_{1-6}$ alkoxy group, a $C_{3-6}$ cycloalkylcarbonyl group, a cyclic ether group, a cyclic amino group, a halo cyclic amino group, or an oxo group;

$L^2$ represents a single bond, a $C_{1-6}$ alkanediyl group, a hydroxy $C_{1-6}$ alkanediyl group, a carbonyl group, or a sulfonyl group;

ring Z represents a phenyl group, a heteroaryl group, or a 4- to 10-membered heterocyclyl group (the 4- to 10-membered heterocyclyl group is optionally condensed with a benzene ring or a heteroaryl ring to form a condensed ring group, or optionally forms a bicyclo ring group or a spiro ring group);

each $R^8$ independently represents a halogen atom, a cyano group, a hydroxy group, a sulfanyl group, an amino group, a carbamoyl group, a sulfamoyl group, a carboxy group, a morpholinocarbonyl group, a $C_{1-6}$ alkyl group, a $C_{2-6}$ alkenyl group, a halo $C_{1-6}$ alkyl group, a hydroxy $C_{1-6}$ alkyl group, a ($C_{1-6}$ alkoxy) $C_{1-6}$ alkyl group, a $C_{2-7}$ alkanoyl group, a $C_{1-6}$ alkylsulfonyl group, a $C_{1-6}$ alkoxy group, a halo $C_{1-6}$ alkoxy group, a mono $C_{1-6}$ alkylamino group, a di $C_{1-6}$ alkylamino group, a $C_{2-7}$ alkoxycarbonyl group, a mono $C_{1-6}$ alkylcarbamoyl group, a di $C_{1-6}$ alkylcarbamoyl group, a $C_{1-6}$ alkylsulfonyloxy group, a halo $C_{1-6}$ alkylsulfonyloxy group, a mono $C_{1-6}$ alkylsulfamoyl group, a di $C_{1-6}$ alkylsulfamoyl group, a mono $C_{2-7}$ alkanoylamino group, a ($C_{2-7}$ alkanoyl) $C_{1-6}$ alkylamino group, a di $C_{2-7}$ alkanoylamino group, a mono $C_{1-6}$ alkylsulfonylamino group, a mono ($C_{2-7}$ alkoxycarbonyl)amino group, a $C_{3-6}$ cycloalkyl group, a cyclic ether group, a cyclic amino group, a halo cyclic amino group, or an oxo group;

m represents 0, 1, 2, or 3;

n represents 0, 1, or 2; and p represents 0 or 1)]

or a pharmaceutically acceptable salt thereof.

2. The compound or a pharmaceutically acceptable salt thereof according to claim 1, wherein X is a group represented by General Formula (II):

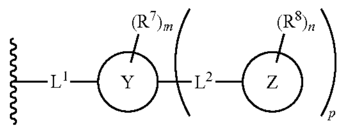

(wherein the wavy line represents the point of attachment to the nitrogen atom, and $L^1$, ring Y, $R^7$, $L^2$, ring Z, $R^8$, m, n, and p are as defined above).

3. The compound or a pharmaceutically acceptable salt thereof according to claim 1, wherein $L^1$ is a single bond or a methylene group.

4. The compound or a pharmaceutically acceptable salt thereof according to claim 1, wherein p is 1.

5. The compound or a pharmaceutically acceptable salt thereof according to claim 4, wherein ring Y is a group represented by General Formula (III):

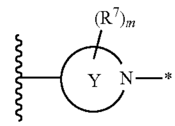

(wherein the wavy line represents the point of attachment to $L^1$,

* represents the point of attachment to $L^2$, $R^7$ and m are as defined above, and ring A is a 4- to 10-membered nitrogen-containing heterocyclyl group).

6. The compound or a pharmaceutically acceptable salt thereof according to claim 4, wherein ring Y is a group represented by General Formula:

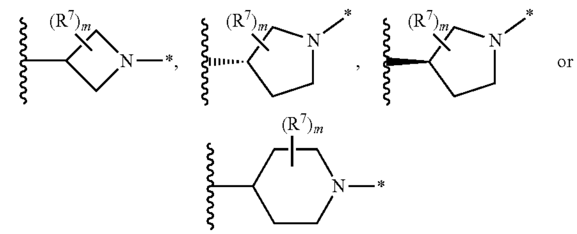

(wherein the wavy line represents the point of attachment to $L^1$,

* represents the point of attachment to $L^2$, and $R^7$ and m are as defined above).

7. The compound or a pharmaceutically acceptable salt thereof according to claim 4, wherein m is 0.

8. The compound or a pharmaceutically acceptable salt thereof according to claim 4, wherein $L^2$ is a single bond.

9. The compound or a pharmaceutically acceptable salt thereof according to claim 4, wherein ring Z is a phenyl group or a heteroaryl group.

10. The compound or a pharmaceutically acceptable salt thereof according to claim 4, wherein ring Z is a phenyl group or a 5- or 6-membered nitrogen-containing heteroaryl group.

11. The compound or a pharmaceutically acceptable salt thereof according to claim 4, wherein ring Z is a group represented by General Formula:

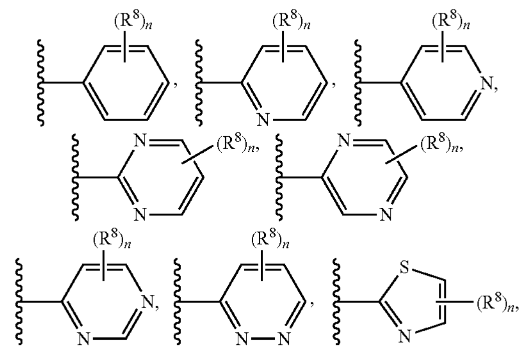

-continued

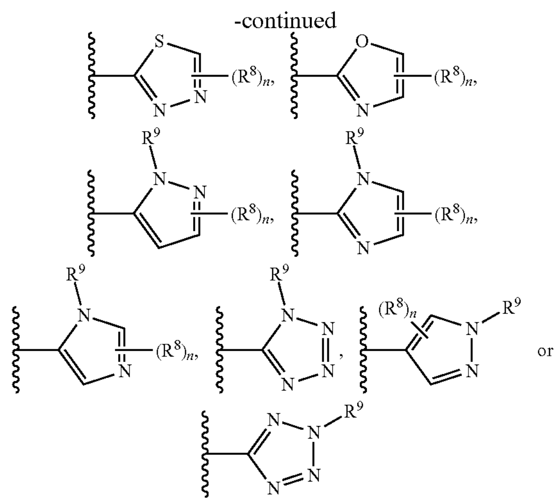

or (wherein the wavy line represents the point of attachment to $L^2$, $R^8$ and n are as defined above, and $R^9$ is a $C_{1-6}$ alkyl group, a halo $C_{1-6}$ alkyl group, a hydroxy $C_{1-6}$ alkyl group, a ($C_{1-6}$ alkoxy) $C_{1-6}$ alkyl group, or a $C_{3-6}$ cycloalkyl group.

12. The compound or a pharmaceutically acceptable salt thereof according to claim 1, wherein p is 0.

13. The compound or a pharmaceutically acceptable salt thereof according to claim 12, wherein ring Y is a $C_{3-10}$ cycloalkyl group (the $C_{3-10}$ cycloalkyl group is optionally condensed with a benzene ring or a heteroaryl ring to form a condensed ring group, or optionally forms a bicyclo ring group or a spiro ring group), or a 4- to 10-membered heterocyclyl group (the 4- to 10-membered heterocyclyl group is optionally condensed with a benzene ring or a heteroaryl ring to form a condensed ring group, or optionally forms a bicyclo ring group or a spiro ring group).

14. The compound or a pharmaceutically acceptable salt thereof according to claim 12, wherein ring Y is a $C_{3-10}$ cycloalkyl group (the $C_{3-10}$ cycloalkyl group is optionally condensed with a benzene ring or a heteroaryl ring to form a condensed ring group, or optionally forms a bicyclo ring group or a spiro ring group).

15. The compound or a pharmaceutically acceptable salt thereof according to claim 12, wherein ring Y is a group represented by General Formula:

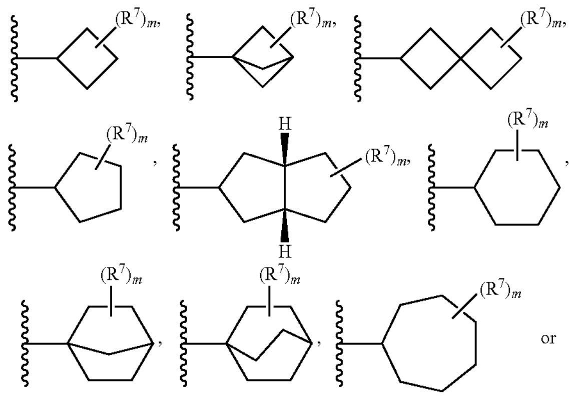

or

-continued

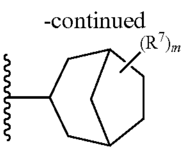

(wherein the wavy line represents the point of attachment to $L^1$, and $R^7$ and m are as defined above).

16. The compound or a pharmaceutically acceptable salt thereof according to claim 12, wherein ring Y is a group represented by General Formula:

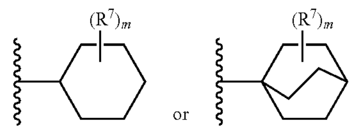

(wherein the wavy line represents the point of attachment to $L^1$, and $R^7$ and m are as defined above).

17. The compound or a pharmaceutically acceptable salt thereof according to claim 12, wherein ring Y is a group represented by General Formula:

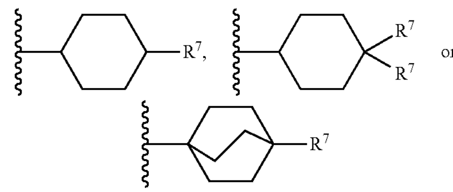

(wherein the wavy line represents the point of attachment to $L^1$, and $R^7$ is as defined above).

18. The compound or a pharmaceutically acceptable salt thereof according to claim 12, wherein m is 1 or 2.

19. The compound or a pharmaceutically acceptable salt thereof according to claim 1, wherein W is an oxygen atom or a group represented by General Formula: —N($R^6$)— (wherein $R^6$ is as defined above).

20. The compound or a pharmaceutically acceptable salt thereof according to claim 1, wherein W is an oxygen atom.

21. The compound or a pharmaceutically acceptable salt thereof according to claim 1, wherein W is a group represented by General Formula: —N($R^6$)— (wherein $R^6$ is as defined above).

22. The compound or a pharmaceutically acceptable salt thereof according to claim 1, wherein W is —NH—.

23. The compound or a pharmaceutically acceptable salt thereof according to claim 1, wherein $R^5$ is a hydrogen atom or a fluorine atom.

24. The compound or a pharmaceutically acceptable salt thereof according to claim 1, wherein $R^1$, $R^2$, and $R^4$ are each independently a hydrogen atom, a halogen atom, or a $C_{1-6}$ alkyl group.

25. The compound or a pharmaceutically acceptable salt thereof according to claim 1, wherein $R^3$ is a hydrogen atom, a halogen atom, a $C_{1-6}$ alkyl group, or a hydroxy $C_{1-6}$ alkyl group.

26. The compound or a pharmaceutically acceptable salt thereof according to claim 1, which is selected from (1) to (49) below:

(1) N-[trans-4-(2-hydroxypropan-2-yl)cyclohexyl]-4-(1H-pyrrolo[3,2-c]pyridin-4-yl)benzamide;
(2) N-[trans-4-(2-hydroxypropan-2-yl)cyclohexyl]-4-(thieno[3,2-c]pyridin-4-yl)benzamide;
(3) 4-(furo[3,2-c]pyridin-4-yl)-N-[trans-4-(2-hydroxy-2-methylpropoxy)cyclohexyl]benzamide;
(4) 4-(furo[3,2-c]pyridin-4-yl)-N-[1-(1-methyl-1H-tetrazol-5-yl)piperidin-4-yl]benzamide;
(5) 4-(furo[3,2-c]pyridin-4-yl)-N-{trans-4-[(2,2,2-trifluoroethyl)amino]cyclohexyl}benzamide;
(6) 4-(furo[3,2-c]pyridin-4-yl)-N-[trans-4-(2-hydroxypropan-2-yl)cyclohexyl]benzamide;
(7) 3-fluoro-4-(furo[3,2-c]pyridin-4-yl)-N-[trans-4-(2-hydroxypropan-2-yl)cyclohexyl]benzamide;
(8) N-[trans-4-(2-hydroxypropan-2-yl)cyclohexyl]-4-(6-methylfuro[3,2-c]pyridin-4-yl)benzamide;
(9) N-[trans-4-(2-hydroxypropan-2-yl)cyclohexyl]-4-(7-methylfuro[3,2-c]pyridin-4-yl)benzamide;
(10) 4-(furo[3,2-c]pyridin-4-yl)-N-[1-(pyrimidin-2-yl)piperidin-4-yl]benzamide;
(11) 4-(furo[3,2-c]pyridin-4-yl)-N-[1-(2,2,2-trifluoroethyl)piperidin-4-yl]benzamide;
(12) (S)-4-(furo[3,2-c]pyridin-4-yl)-N-[1-(pyrimidin-2-yl)pyrrolidin-3-yl]benzamide;
(13) (S)-4-(furo[3,2-c]pyridin-4-yl)-N-{1-[5-(hydroxymethyl)pyrimidin-2-yl]pyrrolidin-3-yl}benzamide;
(14) N-(chroman-3-ylmethyl)-4-(furo[3,2-c]pyridin-4-yl)benzamide;
(15) 4-(furo[3,2-c]pyridin-4-yl)-N-(1-propionylpiperidin-4-yl)benzamide;
(16) N-[1-(cyclopropanecarbonyl)piperidin-4-yl]-4-(furo[3,2-c]pyridin-4-yl)benzamide;
(17) 4-(furo[3,2-c]pyridin-4-yl)-N-[1-(oxetan-3-yl)piperidin-4-yl]benzamide;
(18) N-[1-(1,3,4-thiadiazol-2-yl)piperidin-4-yl]-4-(furo[3,2-c]pyridin-4-yl)benzamide;
(19) 4-(furo[3,2-c]pyridin-4-yl)-N-[1-(2-hydroxy-2-methylpropanoyl)piperidin-4-yl]benzamide;
(20) 4-(furo[3,2-c]pyridin-4-yl)-N-(trans-4-hydroxycyclohexyl)benzamide;
(21) 4-(furo[3,2-c]pyridin-4-yl)-N-[trans-4-(1-hydroxycyclopropyl)cyclohexyl]benzamide;
(22) 4-(furo[3,2-c]pyridin-4-yl)-N-{trans-4-[(1-hydroxycyclopropyl)methoxy]cyclohexyl}benzamide;
(23) 4-(furo[3,2-c]pyridin-4-yl)-N-(trans-4-hydroxy-4-methylcyclohexyl)benzamide;
(24) 4-(furo[3,2-c]pyridin-4-yl)-N-(4-hydroxybicyclo[2.2.2]octan-1-yl)benzamide;
(25) 4-(furo[3,2-c]pyridin-4-yl)-N-[trans-4-(methoxy-$d_3$)cyclohexyl]benzamide;
(26) 4-(furo[3,2-c]pyridin-4-yl)-N-(trans-4-isopropoxycyclohexyl)benzamide;
(27) N-{trans-4-[(2,2-difluoroethyl)amino]cyclohexyl}-4-(furo[3,2-c]pyridin-4-yl)benzamide;
(28) 4-(furo[3,2-c]pyridin-4-yl)-N-[trans-4-(oxetan-3-ylamino)cyclohexyl]benzamide;
(29) 4-[6-(hydroxymethyl)furo[3,2-c]pyridin-4-yl]-N-[trans-4-(2-hydroxypropan-2-yl)cyclohexyl]benzamide;
(30) 4-[6-(hydroxymethyl-$d_2$)furo[3,2-c]pyridin-4-yl]-N-[trans-4-(2-hydroxypropan-2-yl)cyclohexyl]benzamide;
(31) 3-fluoro-4-(furo[3,2-c]pyridin-4-yl)-N-[trans-4-(2-hydroxy-2-methylpropoxy)cyclohexyl]benzamide;
(32) N-[trans-4-(1-hydroxycyclopropyl)cyclohexyl]-4-(6-methylfuro[3,2-c]pyridin-4-yl)benzamide;
(33) N-[1-(pyrimidin-2-yl)piperidin-4-yl]-4-(1H-pyrrolo[3,2-c]pyridin-4-yl)benzamide;
(34) N-(trans-4-hydroxycyclohexyl)-4-(1H-pyrrolo[3,2-c]pyridin-4-yl)benzamide;
(35) N-[trans-4-(2-hydroxypropan-2-yl)cyclohexyl]-4-(6-methyl-1H-pyrrolo[3,2-c]pyridin-4-yl)benzamide;
(36) N-[trans-4-(2-hydroxypropan-2-yl)cyclohexyl]-4-(7-methyl-1H-pyrrolo[3,2-c]pyridin-4-yl)benzamide;
(37) 3-fluoro-N-[trans-4-(2-hydroxypropan-2-yl)cyclohexyl]-4-(1H-pyrrolo[3,2-c]pyridin-4-yl)benzamide;
(38) N-[trans-4-(2-hydroxy-2-methylpropoxy)cyclohexyl]-4-(6-methylfuro[3,2-c]pyridin-4-yl)benzamide;
(39) N-(4-hydroxybicyclo[2.2.2]octan-1-yl)-4-(6-methylfuro[3,2-c]pyridin-4-yl)benzamide;
(40) N-(trans-4-hydroxy-4-methylcyclohexyl)-4-(6-methylfuro[3,2-c]pyridin-4-yl)benzamide;
(41) 3-fluoro-4-(furo[3,2-c]pyridin-4-yl)-N-(4-hydroxybicyclo[2.2.2]octan-1-yl)benzamide;
(42) 3-fluoro-4-(furo[3,2-c]pyridin-4-yl)-N-(trans-4-hydroxy-4-methylcyclohexyl)benzamide;
(43) 3-fluoro-4-(furo[3,2-c]pyridin-4-yl)-N-{trans-4-[(1-hydroxycyclopropyl)methoxy]cyclohexyl}benzamide;
(44) 4-(furo[3,2-c]pyridin-4-yl)-N-[cis-4-(2-hydroxy-2-methylpropoxy)cyclohexyl]benzamide;
(45) 4-(furo[3,2-c]pyridin-4-yl)-N-(4-hydroxybicyclo[2.2.1]heptan-1-yl)benzamide;
(46) N-(4-cyanobicyclo[2.2.2]octan-1-yl)-4-(furo[3,2-c]pyridin-4-yl)benzamide;
(47) 4-[4-(furo[3,2-c]pyridin-4-yl)benzamide] bicyclo[2.2.2]octane-1-carboxamide;
(48) 4-(furo[3,2-c]pyridin-4-yl)-N-{cis-4-[(1-hydroxycyclopropyl)methoxy]cyclohexyl}benzamide; and
(49) 4-(furo[3,2-c]pyridin-4-yl)-N-[cis-4-(2-hydroxypropan-2-yl)cyclohexyl]benzamide.

27. A method for treating a disease involving H-PGDS, comprising:

administering the compound or a pharmaceutically acceptable salt thereof according to claim 1 to a subject in need thereof, wherein the disease involving H-PGDS is selected from the group consisting of asthma, chronic obstructive pulmonary disease, allergic rhinitis, sinusitis, eosinophilic pneumonia, atherosclerosis, rheumatoid arthritis, cystic fibrosis, actinic keratosis, chronic urticaria, dermatitis, muscular dystrophy, sarcopenia, disuse muscle atrophy, muscle damage, wounds, dermatomyositis, amyotrophic lateral sclerosis, cerebral infarction, myocardial infarction, ischemic bowel disease, ischemic renal disease, ischemic stomach disease, ischemic liver disease, diabetic ischemic limb, and Buerger's disease.

28. A method for inhibiting H-PGDS activity in a subject, comprising: administering the compound or a pharmaceutically acceptable salt thereof according to claim 1 to a subject in need thereof.

* * * * *